United States Patent
Finlay et al.

(10) Patent No.: US 9,050,345 B2
(45) Date of Patent: Jun. 9, 2015

(54) PYRROLOTRIAZINES AS POTASSIUM ION CHANNEL INHIBITORS

(71) Applicant: BRISTOL-MYERS SQUIBB COMPANY, Princeton, NJ (US)

(72) Inventors: Heather Finlay, Skillman, NJ (US); Ashok Kumar Adisechan, Pondicherry (IN); Naveen Kumar Dhondi, Secunderabad (IN); Kavitha Govindrajulu, Bangalore (IN); Prashantha Gunaga, Bangalore (IN); John Lloyd, Yardley, PA (US); Pothukanuri Srinivasu, Bangalore (IN)

(73) Assignee: Bristol-Myers Squibb Company, Princeton, NJ (US)

(*) Notice: Subject to any disclaimer, the term of this patent is extended or adjusted under 35 U.S.C. 154(b) by 0 days.

(21) Appl. No.: 14/200,055

(22) Filed: Mar. 7, 2014

(65) Prior Publication Data

US 2014/0256719 A1    Sep. 11, 2014

Related U.S. Application Data

(60) Provisional application No. 61/775,731, filed on Mar. 11, 2013.

(51) Int. Cl.

| | | |
|---|---|---|
| *C07D 487/04* | (2006.01) | |
| *C07D 401/04* | (2006.01) | |
| *C07D 401/14* | (2006.01) | |
| *C07D 403/04* | (2006.01) | |
| *C07D 403/14* | (2006.01) | |
| *A61K 31/53* | (2006.01) | |
| *A61P 9/06* | (2006.01) | |
| *A61P 9/04* | (2006.01) | |
| *C07D 405/04* | (2006.01) | |
| *C07D 405/14* | (2006.01) | |
| *C07D 413/04* | (2006.01) | |
| *C07D 413/14* | (2006.01) | |
| *C07D 417/04* | (2006.01) | |
| *A61K 31/5377* | (2006.01) | |
| *C07D 519/00* | (2006.01) | |

(52) U.S. Cl.
CPC .............. *A61K 31/5377* (2013.01); *A61K 31/53* (2013.01); *C07D 487/04* (2013.01); *C07D 519/00* (2013.01)

(58) Field of Classification Search
CPC .. C07D 487/04; C07D 401/04; C07D 401/14; C07D 403/04; C07D 403/14; C07D 405/04; C07D 405/14; C07D 413/04; C07D 413/14; C07D 417/04; C07D 417/14; A61K 31/53; A61K 31/5377
USPC .......................................... 544/183; 514/243
See application file for complete search history.

(56) References Cited

U.S. PATENT DOCUMENTS

| 6,867,300 B2 | 3/2005 | Godfrey, Jr. et al. |
|---|---|---|
| 7,034,151 B2 | 4/2006 | Chen et al. |
| 7,504,521 B2 | 3/2009 | Lobben |
| 8,263,765 B2 * | 9/2012 | Wittman et al. ............... 544/183 |
| 8,445,676 B2 * | 5/2013 | Purandare et al. ............ 544/183 |
| 8,575,184 B2 | 11/2013 | Johnson et al. |
| 2003/0186982 A1 | 10/2003 | Godfrey, Jr. et al. |
| 2004/0157846 A1 | 8/2004 | Chen et al. |
| 2006/0084650 A1 | 4/2006 | Dong et al. |
| 2008/0064718 A1 | 3/2008 | Saavedra et al. |
| 2012/0077814 A1 | 3/2012 | Wang et al. |
| 2012/0232068 A1 | 9/2012 | Johnson et al. |
| 2014/0031345 A1 | 1/2014 | Johnson et al. |

FOREIGN PATENT DOCUMENTS

| CN | 103373996 A | 10/2013 |
|---|---|---|
| WO | WO 00/71129 | 11/2000 |
| WO | WO 02/40486 | 5/2002 |
| WO | WO 2004/009601 | 1/2004 |
| WO | WO 2004/009784 | 1/2004 |
| WO | WO 2004/013145 | 2/2004 |
| WO | WO 2006/035061 | 4/2006 |
| WO | WO 2007/103839 | 9/2007 |
| WO | WO 2008/005956 | 1/2008 |
| WO | WO 2008/021924 | 2/2008 |
| WO | WO 2008/057402 | 5/2008 |
| WO | WO 2008/131050 | 10/2008 |
| WO | WO 2009/026254 | 2/2009 |
| WO | WO 2009/111531 | 9/2009 |
| WO | WO 2010/002472 | 1/2010 |
| WO | WO 2010/051042 | 5/2010 |

OTHER PUBLICATIONS

Finlay et al., U.S. Appl. No. 14/200,063, filed Mar. 7, 2014.
Finlay et al., U.S. Appl. No. 61/775,735, filed Mar. 11, 2013.
Finlay et al., U.S. Appl. No. 61/775,742, filed Mar. 11, 2013.
Finlay et al., U.S. Appl. No. 61/775,750, filed Mar. 11, 2013.

* cited by examiner

*Primary Examiner* — Venkataraman Balasubramanian
(74) *Attorney, Agent, or Firm* — Mary K. VanAtten

(57) ABSTRACT

A compound of formula (I)

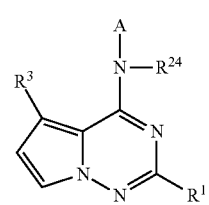

(I)

wherein A, $R^1$, $R^3$, and $R^{24}$ are described herein. The compounds are useful as inhibitors of potassium channel function and in the treatment of arrhythmia, maintaining normal sinus rhythm, $I_{Kur}$-associated disorders, and other disorders mediated by ion channel function.

19 Claims, No Drawings

PYRROLOTRIAZINES AS POTASSIUM ION CHANNEL INHIBITORS

CROSS-REFERENCE TO RELATED APPLICATIONS

This application claims the benefit of U.S. Provisional Application No. 61/775,731 filed Mar. 11, 2013, whose contents are hereby incorporated by reference.

FIELD OF THE INVENTION

The present invention provides for pyrrolotriazines useful as inhibitors of potassium channel function (especially inhibitors of the $K_v1$ subfamily of voltage gated $K^+$ channels, more especially inhibitors of $K_v1.5$ (which have been linked to the ultra-rapidly activating delayed rectifier $K^+$ current $I_{Kur}$), and/or $K_v1.3$ channels, and/or $K_v1.1$ channels) and to pharmaceutical compositions containing such compounds. The present invention further provides for methods of using such compounds in the treatment and prevention of arrhythmia, $I_{Kur}$-associated disorders, and other disorders mediated by ion channel function.

BACKGROUND OF THE INVENTION

The ultra-rapidly activating delayed rectifier $K^+$ current $(I_{Kur})$ is believed to represent the native counterpart to a cloned potassium channel designated $K_v1.5$ and, while present in human atrium, it appears to be absent in human ventricle. Furthermore, because of its rapidity of activation and limited slow inactivation, $I_{Kur}$ is believed to contribute significantly to repolarization in human atrium. Consequently, a specific blocker of $I_{Kur}$, that is a compound which blocks $K_v1.5$, would overcome the short coming of other compounds by prolonging refractoriness by retarding repolarization in the human atrium without causing the delays in ventricular repolarization that underlie arrhythmogenic after depolarizations and acquired long QT syndrome observed during treatment with current Class III antiarrhythmic agents. (Antiarrhythmic agents of Class III are drugs that cause a selective prolongation of the duration of the action potential without significant cardiac depression.)

Immunoregulatory abnormalities have been shown to exist in a wide variety of autoimmune and chronic inflammatory diseases, including systemic lupus erythematosis, chronic rheumatoid arthritis, type I and II diabetes mellitus, inflammatory bowel disease, biliary cirrhosis, uveitis, multiple sclerosis and other disorders such as Crohn's disease, ulcerative colitis, bullous pemphigoid, sarcoidosis, psoriasis, ichthyosis, Graves' ophthalmopathy and asthma. Although the underlying pathogenesis of each of these conditions may vary, they have in common the appearance of a variety of auto-antibodies and self-reactive lymphocytes. Such self-reactivity may be due, in part, to a loss of the homeostatic controls under which the normal immune system operates. Similarly, following a bone-marrow or an organ transplantation, lymphocytes recognize the foreign tissue antigens and begin to produce immune mediators which lead to graft rejection or graft-vs-host rejection.

One end result of an autoimmune or a rejection process is tissue destruction caused by inflammatory cells and the mediators they release. Anti-inflammatory agents such as NSAIDs act principally by blocking the effect or secretion of these mediators but do nothing to modify the immunologic basis of the disease. On the other hand, cytotoxic agents, such as cyclophosphamide, act in such a nonspecific fashion in which both the normal and autoimmune responses are shut off. Indeed, patients treated with such nonspecific immunosuppressive agents are as likely to succumb to infection as they are to their autoimmune disease.

Cyclosporin A, which was approved by the US FDA in 1983 is currently the leading drug used to prevent rejection of transplanted organs. In 1993, FK-506 (PROGRAF®) was approved by the US FDA for the prevention of rejection in liver transplantation. Cyclosporin A and FK-506 act by inhibiting the body's immune system from mobilizing its vast arsenal of natural protecting agents to reject the transplant's foreign protein. In 1994, Cyclosporin A was approved by the US FDA for the treatment of severe psoriasis and has been approved by European regulatory agencies for the treatment of atopic dermatitis. Though these agents are effective in fighting transplant rejection, Cyclosporin A and FK-506 are known to cause several undesirable side effects including nephrotoxicity, neurotoxicity, and gastrointestinal discomfort. Therefore, a selective immunosuppressant without these side effects still remains to be developed. Potassium channel inhibitors as described here promise to be the solution to this problem, since inhibitors of $K_v1.3$, for example, are immunosuppressive. See Wulff et al., "Potassium channels as therapeutic targets for autoimmune disorders", *Curr. Opin. Drug Discov. Devel.*, 6(5):640-647 (September 2003); Shah et al., "Immunosuppressive effects of a $K_v1.3$ inhibitor", *Cell Immunol.*, 221(2):100-106 (February 2003); Hanson et al., "UK-78,282, a novel piperidine compound that potently blocks the $K_v1.3$ voltage-gated potassium channel and inhibits human T cell activation", *Br. J. Pharmacol.*, 126(8):1707-1716 (April 1999).

Inhibitors of $K_v1.5$ and other $K_v1.x$ channels stimulate gastrointestinal motility. Thus, the compounds of the invention are believed to be useful in treating motility disorders such as reflux esophagitis. See Frey et al., "Blocking of cloned and native delayed rectifier K channels from visceral smooth muscles by phencyclidine", *Neurogastroenterol. Motil.*, 12(6):509-516 (December 2000); Hatton et al., "Functional and molecular expression of a voltage-dependent K(+) channel ($K_v1.1$) in interstitial cells of Cajal", *J. Physiol.*, 533(Pt 2):315-327 (Jun. 1, 2001); Vianna-Jorge et al., "Shaker-type $K_v1$ channel blockers increase the peristaltic activity of guinea-pig ileum by stimulating acetylcholine and tachykinins release by the enteric nervous system", *Br. J. Pharmacol.*, 138(1):57-62 (January 2003); Koh et al., "Contribution of delayed rectifier potassium currents to the electrical activity of murine colonic smooth muscle", *J. Physiol.*, 515(Pt. 2):475-487 (Mar. 1, 1999).

Inhibitors of $K_v1.5$ relax pulmonary artery smooth muscle. Thus, the compounds of the invention are believed to be useful in treating hypertension and otherwise improving vascular health. See Davies et al., "$K_v$ channel subunit expression in rat pulmonary arteries", *Lung*, 179(3):147-161 (2001), Epub. Feb. 4, 2002; Pozeg et al., "In vivo gene transfer of the O2-sensitive potassium channel $K_v1.5$ reduces pulmonary hypertension and restores hypoxic pulmonary vasoconstriction in chronically hypoxic rats", *Circulation*, 107(15):2037-2044 (Apr. 22, 2003), Epub. Apr. 14, 2003.

Inhibitors of $K_v1.3$ increase insulin sensitivity. Hence, the compounds of the invention are believed to be useful in treating diabetes. See Xu et al., "The voltage-gated potassium channel $K_v1.3$ regulates peripheral insulin sensitivity", *Proc. Natl. Acad. Sci. U.S.A.*, 101(9):3112-3117 (Mar. 2, 2004), Epub. Feb. 23, 2004; MacDonald et al., "Members of the $K_v1$ and $K_v2$ voltage-dependent K(+) channel families regulate insulin secretion", *Mol. Endocrinol.*, 15(8):1423-1435 (August 2001); MacDonald et al., "Voltage-dependent K(+)

channels in pancreatic beta cells: role, regulation and potential as therapeutic targets", *Diabetologia*, 46(8): 1046-1062 (August 2003), Epub. Jun. 27, 2003.

Stimulation of $K_v1.1$ is believed to reduce seizure activity by hyperpolarizing neurons. Thus, the compounds of the invention are believed to be useful in treating seizures, including seizures associated with epilepsy and other neurological diseases. See Rho et al., "Developmental seizure susceptibility of kv1.1 potassium channel knockout mice", *Dev. Neurosci.*, 21(3-5):320-327 (November 1999); Coleman et al., "Subunit composition of $K_v1$ channels in human CNS", *J. Neurochem.*, 73(2):849-858 (August 1999); Lopantsev et al., "Hyperexcitability of CA3 pyramidal cells in mice lacking the potassium channel subunit $K_v1.1$", *Epilepsia*, 44(12): 1506-1512 (December 2003); Wickenden, "Potassium channels as anti-epileptic drug targets", *Neuropharmacology*, 43(7):1055-1060 (December 2002).

Inhibition of $K_v1.x$ channels improves cognition in animal models. Thus, the compounds of the invention are believed to be useful in improving cognition and/or treating cognitive disorders. See Cochran et al., "Regionally selective alterations in local cerebral glucose utilization evoked by charybdotoxin, a blocker of central voltage-activated K+-channels", *Eur. J. Neurosci.*, 14(9):1455-1463 (November 2001); Kourrich et al., "Kaliotoxin, a $K_v1.1$ and $K_v1.3$ channel blocker, improves associative learning in rats", *Behav. Brain Res.*, 120(1):35-46 (Apr. 8, 2001).

SUMMARY OF THE INVENTION

In accordance with the present invention, compounds are provided that have the general structure of formula (I):

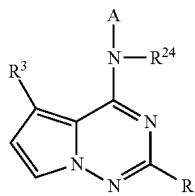

(I)

wherein A, $R^1$, $R^3$, and $R^{24}$ are defined below.

By use of a respective effective amount of at least one compound described herein, provided are methods of treating (including ameliorating), reducing the risk of, or preventing arrhythmias, atrial fibrillation, atrial flutter, supraventricular arrhythmias, gastrointestinal disorders (such as reflux esophagitis or a motility disorder), inflammatory or immunological disease (such as chronic obstructive pulmonary disease), diabetes, cognitive disorders, migraine, epilepsy, hypertension, or treating $I_{Kur}$-associated conditions, or controlling heart rate.

Also provided are pharmaceutical compositions comprising a therapeutically effective amount of at least one compound described herein and a pharmaceutically acceptable vehicle or carrier thereof. Such compositions can further comprise one or more other agent(s). For example, at least one other anti-arrhythmic agent (such as sotalol, dofetilide, diltiazem or Verapamil), or at least one calcium channel blocker, or at least one anti-platelet agent (such as clopidogrel, cangrelor, ticlopidine, CS-747, ifetroban and aspirin), or at least one anti-hypertensive agent (such as a beta adrenergic blocker, ACE inhibitor (e.g., captopril, zofenopril, fosinopril, enalapril, ceranopril, cilazopril, delapril, pentopril, quinapril, ramipril, or lisinopril), A II antagonist, ET antagonist, Dual ET/A II antagonist, or vasopepsidase inhibitor (e.g., omapatrilat or gemopatrilat)), or at least one anti thrombotic/anti thrombolytic agent (such as tPA, recombinant tPA, TNK, nPA, factor VIIa inhibitors, factor Xa inhibitors (such as apixaban), factor XIa inhibitors or thrombin inhibitors), or at least one anti coagulant (such as warfarin or a heparin), or at least one HMG-CoA reductase inhibitor (pravastatin, lovastatin, atorvastatin, simvastatin, NK-104 or ZD-4522), or at least one anti diabetic agent (such as a biguanide or a biguanide/glyburide combination), or at least one thyroid mimetic, or at least one mineralocorticoid receptor antagonist (such as spironolactone or eplerinone), or at least one cardiac glycoside (such as digitalis or ouabain).

Another aspect of this invention is directed to methods of treating, inhibiting, or ameliorating the symptoms of a disease or disorder that is modulated or otherwise affected by inhibitors of potassium channel function (especially inhibitors of the $K_v1$ subfamily of voltage gated K+ channels, more especially inhibitors of $K_v1.5$ (which have been linked to the ultra-rapidly activating delayed rectifier K+ current $I_{Kur}$), and/or $K_v1.3$ channels, and/or $K_v1.1$ channels), comprising administering to a subject in need thereof a therapeutically effective amount of a compound of the present invention or an individual isomer or mixture of isomers or a pharmaceutically acceptable salt thereof.

Another aspect of this invention is directed to methods of treating, inhibiting, or ameliorating arrhythmia, or maintaining normal sinus rhythm, comprising administering to a subject in need thereof a therapeutically effective amount of a compound of the present invention or an individual isomer or mixture of isomers or a pharmaceutically acceptable salt thereof.

Another aspect of this invention is directed to methods of controlling heart rate, comprising administering to a subject in need thereof a therapeutically effective amount of a compound of the present invention or an individual isomer or mixture of isomers or a pharmaceutically acceptable salt thereof.

DEFINITIONS

The terms "alk" or "alkyl" refer to straight or branched chain hydrocarbon groups having 1 to 12 carbon atoms, or 1 to 8 carbon atoms, 1 to 6 carbon atoms, 1 to 4 carbon atoms, or 1 to 3 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described above in the definition of $R^{10}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocyclic ring groups of 3 to 15 carbon atoms which are, respectively, fully saturated and partially unsaturated. The rings of multi-ring cycloalkyl groups may be fused, bridged and/or joined through one or more spiro unions. The term "substituted cycloalkyl" refers to a cycloalkyl group substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The term "haloalkyl" is intended to include both branched and straight-chain saturated aliphatic hydrocarbon groups, for example $CF_3$, having the specified number of carbon atoms, substituted with 1 or more halogen, up to and including perhalo alkyls (where all hydrogen atoms are replaced with a halogen).

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl,

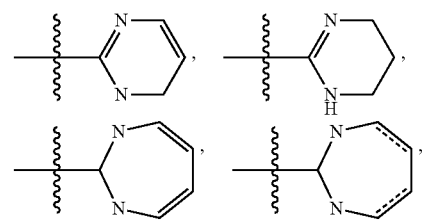

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

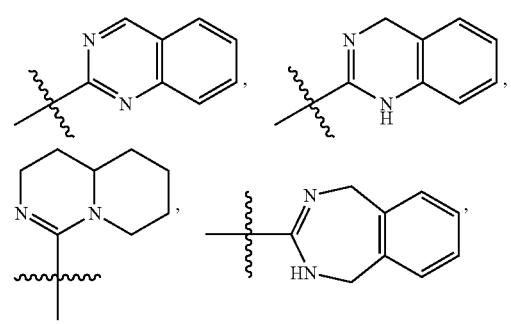

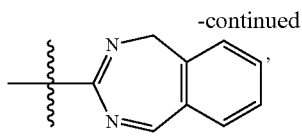

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups (such as by groups described above in the definition of $R^{10}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

The term "alkanoyl" refers to alkyl group (which may be optionally substituted as described above) linked to a carbonyl group (i.e., —C(O)-alkyl). Similarly, the term "aroyl" refers to an aryl group (which may be optionally substituted as described above) linked to a carbonyl group (i.e., —C(O)-aryl).

Throughout the specification, groups and substituents thereof may be chosen to provide stable moieties and compounds.

Compounds described herein may form salts or solvates which are also within the scope of this invention. Reference to a compound described herein is understood to include reference to salts thereof, unless otherwise indicated. The term "salt(s)", as employed herein, denotes acidic and/or basic salts formed with inorganic and/or organic acids and bases. In addition, when a compound described herein contains both a basic moiety and an acidic moiety, zwitterions ("inner salts") may be formed and are included within the term "salt(s)" as used herein. In one embodiment, the salts are pharmaceutically acceptable (i.e., non-toxic, physiologically acceptable), although other salts are also useful, e.g., in isolation or purification steps which may be employed during preparation. Salts of the compounds described herein may be formed, for example, by reacting a compound with an amount of acid or base, such as an equivalent amount, in a medium such as one in which the salt precipitates or in an aqueous medium followed by lyophilization.

The present invention is intended to cover the compounds in their neutral state, salts of those compounds, or mixtures of the compounds in their neutral state with one or more salt forms, or mixtures of salt forms.

The compounds described herein which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds described herein which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Any compound that can be converted in vivo to provide the bioactive agent (i.e., the compound of formula (I)) is a prodrug within the scope and spirit of the invention.

The term "prodrugs" as employed herein includes esters and carbonates formed by reacting one or more hydroxyls of compounds of formula (I) with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, H. Bundgaard, ed., Elsevier (1985);

c) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991); and d) Testa, B. et al., *Hydrolysis in Drug and Prodrug Metabolism*, Wiley-VCH (2003).

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problems or complications commensurate with a reasonable benefit/risk ratio or which have otherwise been approved by the United States Food and Drug Administration as being acceptable for use in humans or domestic animals.

The various compounds described herein, or their pharmaceutically acceptable salts, may contain one or more asymmetric centers and may thus give rise to isomers, such as enantiomers, diastereomers, and other stereoisomeric forms. Such forms may be defined, in terms of absolute stereochemistry, as (R)- or (S)-, or as (D)- or (L)- for amino acids. The present invention is meant to include all such possible individual stereoisomers and mixtures thereof, including their racemic and optically pure enantiomeric or diastereomeric forms. The compounds may be prepared as racemates and can conveniently be used as such, or optically active (+) and (−), (R)- and (S)-, or (D)- and (L)-isomers or corresponding diastereomers may be prepared using chiral synthons or chiral reagents, or they may be resolved from racemic mixtures using conventional techniques, such as chiral chromatography or reverse phase HPLC. When the compounds described herein contain olefinic double bonds or other centers of geometric asymmetry, and unless specified otherwise, it is intended that the compounds include both E and Z geometric isomers.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H or D and $^3$H or T, carbon such as $^{11}$C, $^{13}$C, and $^{14}$C, chlorine, such as $^{36}$Cl, fluorine such as $^{18}$F, iodine, such as $^{123}$I and $^{125}$I, nitrogen, such as $^{13}$N and $^{15}$N, oxygen, such as $^{15}$O, $^{17}$O, and $^{18}$O, phosphorus, such as $^{32}$P, and sulfur, such as $^{35}$S. Certain isotopically-labeled compounds of the invention, for example, those incorporating a radioactive isotope, are useful in drug and/or substrate tissue distribution studies. The radioactive isotopes tritium, $^3$H, and carbon-14, $^{14}$C, are particularly useful for this purpose in view of their ease of incorporation and ready means of detection. Substitution with heavier isotopes such as deuterium, $^2$H or D, may afford certain therapeutic advantages resulting from greater metabolic stability, for example, increase in vivo half-life or reduced dosage requirements, and hence may be preferred in some circumstances. Substitution with positron emitting isotopes, such as $^1$C, F, $^{15}$O, and $^{13}$N, can be useful in Positron Emission Topography (PET) studies for examining substrate receptor occupancy.

To the extent that compounds described herein, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms are contemplated within the scope of this invention. Individual stereoisomers of the compounds of the invention may, for example, be substantially free of other isomers, or may be admixed, for example, as racemates or with all other, or other selected, stereoisomers.

"Stable compound" and "stable structure" are meant to indicate a compound that is sufficiently robust to survive isolation to a useful degree of purity from a reaction mixture, and formulation into an efficacious therapeutic agent. The present invention is intended to cover stable compounds.

When any variable (e.g., $R^{13}$) occurs more than one time in any constituent or formula for a compound, its definition at each occurrence is independent of its definition at every other occurrence. Thus, for example, if a group is shown to be substituted with 0-2 $R^{13}$, then said group may optionally be substituted with up to two $R^{13}$ groups and $R^{13}$ at each occurrence is selected independently from the definition of $R^{13}$. Also, combinations of substituents and/or variables are permissible only if such combinations result in stable compounds.

"Therapeutically effective amount" refers to that amount of a compound which, when administered to a subject, is sufficient to effect treatment for a disease or disorder described herein. The amount of a compound which constitutes a "therapeutically effective amount" will vary depending on the compound, the disorder and its severity, and the age of the subject to be treated, but can be determined routinely by one of ordinary skill in the art.

"Treating" or "treatment" as used herein covers the treatment, prophylaxis, and/or reducing the risk, of a disease or disorder described herein, or treatment, prophylaxis, or reducing the risk of a symptom of a disease or disorder, in a subject, such as a human, and includes:

i. inhibiting a disease or disorder, i.e., arresting its development; or ii. relieving a disease or disorder, i.e., causing regression of the disorder.

"Subject" refers to a warm blooded animal such as a mammal, such as a human, or a human child, which is afflicted with, or has the potential to be afflicted with one or more diseases and disorders described herein.

The terms "including", "such as", "for example" and the like are intended to refer to exemplary embodiments and not to limit the scope of the present invention.

DETAILED DESCRIPTION OF THE INVENTION

In accordance with the present invention, compounds of formula (I) are provided

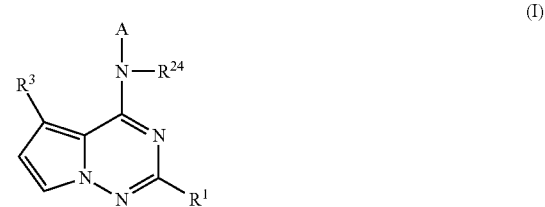

(I)

or enantiomers, diastereomers, tautomers, prodrugs or salts thereof wherein:

A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

$R^1$ is C$_{1-10}$ alkyl substituted with 1-2 —OH, haloC$_{1-10}$ alkyl, C$_{2-12}$ alkenyl, or C$_{3-10}$ cycloalkyl, wherein the cycloalkyl may be substituted with 0-2 R$^{13}$; or $R^1$ is

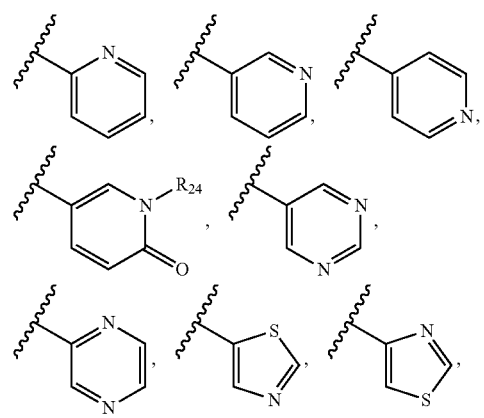

-continued

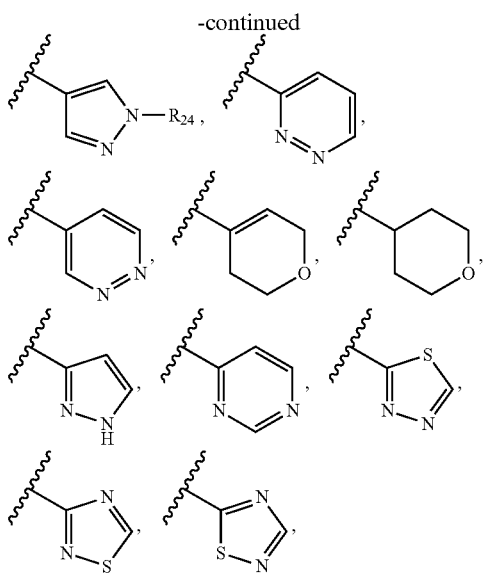

or

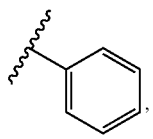

any of which may be substituted with 0-2 $R^{13}$;

$R^2$ is phenyl, cyclopentyl, cyclohexyl, pyridinyl, pyrazinyl, pyridazinyl, pyrimidinyl, piperidinyl, pyridinone, pyrrolidinyl, tetrahydropyranyl, or thiazolyl, any of which are substituted with 0-2 $R^{2a}$;

$R^{2a}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$ aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, NR$^{14}$CONR$^{14}$R$^{14}$, —C(=NOR$^{14}$)NR$^{14}$R$^{14}$, —CONR$^{14}$OR$^{14}$ or —NCOR$^{14}$, wherein the alkyl, cycloalkyl, alkenyl, alkoxy, aryl, heteroaryl and heterocyclyl may be substituted with 0-2 $R^{14a}$ and the heteroaryl and heterocyclyl consist of carbon atoms and 1, 2, 3, or 4 heteroatoms independently selected from the group consisting of N, S, or O;

$R^3$ is phenyl, pyridinyl, pyrimidinyl, dihydropyran, or tetrahydropyran any of which may be substituted with 0-1 $R^{3a}$;

$R^{3a}$ is halo, CN, NH$_2$, —O—C$_{1-3}$alkyl, or morpholinyl;

$R^{13}$, at each occurrence, is independently H, —OH, F, Cl, Br, I, CN, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, NR$^{14}$CONR$^{14}$R$^{14}$, —C(=NOR$^{14}$)NR$^{14}$R$^{14}$, —CONR$^{14}$OR$^{14}$—NCOR$^{14}$, or —OR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-10}$ alkyl, $C_{3-10}$ cycloalkyl, $C_{6-10}$ aryl, or a 4- to 12-membered heteroaryl, or a 4- to 12-membered heterocyclyl, wherein the alkyl, cycloalkyl, aryl, heteroaryl and heterocyclyl may be substituted with 0-3 $R^{14a}$ and the heteroaryl and heterocyclyl consist of carbon atoms and 1, 2, 3, or 4 heteroatoms independently selected from the group consisting of N, S, or O; or alternatively, two $R^{14}$'s are taken together with the atoms to which they are attached to form a cyclic ring, wherein the cyclic ring may be substituted with 0-1 $R^{14a}$ and optionally contain 1, 2, 3, or 4 heteroatoms independently selected from the group consisting of N, S, or O;

$R^{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$R$^{26}$, —CO$_2$NR$^{24}$R$^{24}$, —OCF$_3$, —OR$^{25}$, =O, —CONR$^{24}$R$^{24}$, —COR$^{24}$, —SO$_2$R$^{24}$, —NR$^{24}$R$^{24}$, —NR$^{24}$CO$_2$R$^{24}$, —SO$_2$NR$^{24}$R$^{24}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R^{24}$, at each occurrence, is independently selected from hydrogen, $C_{1-10}$alkyl, $C_{3-6}$cycloalkyl, or phenyl;

$R^{25}$, at each occurrence, is independently selected from hydrogen, $C_{1-10}$alkyl, $C_{3-6}$cycloalkyl, or phenyl;

$R^{26}$, at each occurrence, is independently selected from hydrogen, $C_{1-10}$alkyl, $C_{3-6}$cycloalkyl, or phenyl;

m is 0 to 4;

n is 0 to 4; and n–1 is 2 to 4.

In another aspect, the present invention provides compound of formula (I), or enantiomers, diastereomers, tautomers, prodrugs or salts thereof wherein:

A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

$R^1$ is $C_{1-10}$ alkyl substituted with 1-2 —OH, halo$C_{1-10}$ alkyl, $C_{2-12}$ alkenyl, or $C_{3-10}$ cycloalkyl, wherein the cycloalkyl may be substituted with 0-2 $R^{13}$; or $R^1$ is

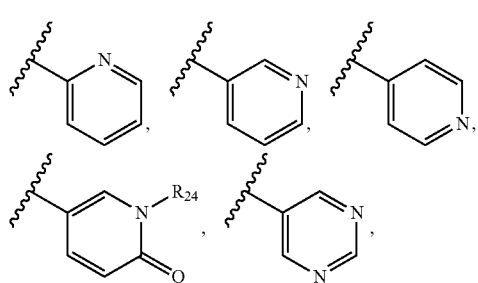

-continued

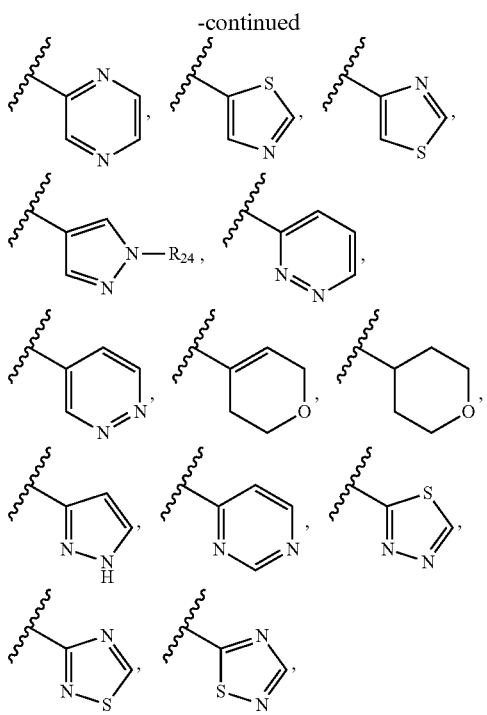

or

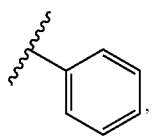

any of which may be substituted with 0-2 $R^{13}$;

$R^2$ is phenyl, cyclopentyl, cyclohexyl, pyridinyl, pyrazinyl, pyridazinyl, pyrimidinyl, piperidinyl, pyridinone, pyrrolidinyl, tetrahydropyranyl, or thiazolyl, any of which are substituted with 0-2 $R^{2a}$;

$R^{2a}$, at each occurrence, is independently H, —OH, F, Cl, Br, I, $C_{1-10}$ alkyl, $C_{1-10}$ alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, NR$^{14}$CONR$^{14}$R$^{14}$, —C(=NOR$^{14}$)NR$^{14}$R$^{14}$, —CONR$^{14}$OR$^{14}$ or —NR$^{14}$COR$^{14}$, wherein the alkyl, cycloalkyl, alkenyl, alkoxy, aryl, heteroaryl and heterocyclyl may be substituted with 0-2 $R^{14a}$ and the heteroaryl and heterocyclyl consist of carbon atoms and 1, 2, 3, or 4 heteroatoms independently selected from the group consisting of N, S, or O;

$R^3$ is phenyl, pyridinyl, pyrimidinyl, dihydropyran, or tetrahydropyran any of which may be substituted with 0-1 $R^{3a}$;

$R^{3a}$ is halo, CN, NH$_2$, —O—$C_{1-3}$alkyl, or morpholinyl;

$R^{13}$, at each occurrence, is independently H, —OH, F, Cl, Br, I, CN, $C_{1-10}$ alkyl, $C_{1-10}$-alkoxy, halo$C_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, NR$^{14}$CONR$^{14}$R$^{14}$, —C(=NOR$^{14}$)NR$^{14}$R$^{14}$, —CONR$^{14}$OR$^{14}$—NR$^{14}$COR$^{14}$, or —OR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be substituted with 0-3 $R^{14a}$ and the heteroaryl and heterocyclyl consist of carbon atoms and 1, 2, 3, or 4 heteroatoms independently selected from the group consisting of N, S, or O; or alternatively, two $R^{14}$'s are taken together with the atoms to which they are attached to form a cyclic ring, wherein the cyclic ring may be substituted with 0-1 $R^{14a}$ and optionally contain 1, 2, 3, or 4 heteroatoms independently selected from the group consisting of N, S, or O;

$R^{14a}$, at each occurrence, is independently selected from F, Cl, Br, I, $C_{1-10}$ alkyl, halo$C_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$R$^{26}$, —CO$_2$NR$^{24}$R$^{24}$, —OCF$_3$, —OR$^{25}$, =O, —CONR$^{24}$R$^{24}$, —COR$^{24}$, —SO$_2$R$^{24}$, —NR$^{24}$R$^{24}$, —NR$^{24}$CO$_2$R$^{24}$, —SO$_2$NR$^{24}$R$^{24}$, or $C_{6-10}$aryl$C_{1-10}$alkyl, wherein the heteroaryl and heterocyclyl consist of carbon atoms and 1, 2, 3, or 4 heteroatoms independently selected from the group consisting of N, S, or O;

$R^{24}$, at each occurrence, is independently selected from hydrogen, $C_{1-10}$alkyl, $C_{3-6}$cycloalkyl, or phenyl;

$R^{25}$, at each occurrence, is independently selected from hydrogen, $C_{1-10}$alkyl, $C_{3-6}$cycloalkyl, or phenyl;

$R^{26}$, at each occurrence, is independently selected from hydrogen, $C_{1-10}$alkyl, $C_{3-6}$cycloalkyl, or phenyl;

m is 0 to 4;

n is 0 to 4; and n–1 is 2 to 4.

In another aspect, the present invention provides compound of formula (I), or enantiomers, diastereomers, tautomers, prodrugs or salts thereof wherein:

A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, CH(R$^{26}$)CO$_2$—R$^2$, or —(CH$_2$)$_{n-1}$—NR$^{25}$—CO$_2$—R$^2$;

A and $R^{24}$, along with the nitrogen to which they are attached, combine to form

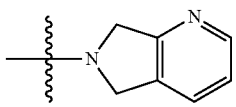 [SMILES: *N1Cc2cccnc2C1]

or

[structure: isoindoline attached via N]

either of which may be substituted with 0-2 $R^{2a}$;

$R^1$ is $C_{1-10}$ alkyl substituted with 1-2 —OH, haloC$_{1-10}$ alkyl, $C_{2-12}$ alkenyl, or $C_{3-10}$ cycloalkyl, wherein the cycloalkyl may be substituted with 0-2 $R^{13}$; or $R^1$ is

[structures: 2-pyridyl, 3-pyridyl, 4-pyridyl, N-$R_{24}$-pyridinone, pyrimidinyl, pyrazinyl, thiazolyl, thiazolyl, N-$R_{24}$-pyrazolyl, pyrazolyl, pyridazinyl, pyridazinyl, tetrahydropyranyl (O), tetrahydropyranyl, pyrazolyl-NH, pyrimidinyl, thiadiazolyl]

[structures: thiadiazolyl, thiadiazolyl]

or

[structure: phenyl], any of which may be substituted with 0-2 $R^{13}$; or $R^1$ is —C(O)—$R^{1a}$;

$R^{1a}$ is —NH-phenyl, —NH—$C_{1-6}$alkyl-phenyl, —NH—$C_{3-6}$cycloalkyl, -piperidinyl, piperazinyl, or —NH-pyrimidinyl, wherein the phenyl, alkyl, cycloalkyl, piperidinyl, piperazinyl, or pyrimidinyl may be substituted with 0-2 $R^{13}$;

$R^2$ is phenyl, cyclopentyl, cyclohexyl, pyridinyl, pyrazinyl, pyridazinyl, pyrimidinyl, piperidinyl, pyridinone, pyrrolidinyl, tetrahydropyranyl, thiazolyl, imidazolyl, isoxazolyl, oxazolyl, morpholinyl, benzothiazolyl, or tetrahydronaphthalenyl, any of which are substituted with 0-2 $R^{2a}$;

$R^{2a}$, at each occurrence, is independently H, —OH, F, Cl, Br, I, $C_{1-10}$ alkyl, $C_{1-10}$ alkoxy, haloC$_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, CONR$^{14}$R$^{14}$, (CH$_2$)$_m$—SO$_2$NR$^{14}$R$^{14}$, —(CH$_2$)$_m$—NR$^{14}$SO$_2$R$^{14}$, (CH$_2$)$_n$NR$^{14}$SO$_2$NR$^{14}$R$^{14}$, NR$^{14}$SO$_2$NR$^{14}$R$^{14}$, —CO$_2$NR$^{14}$R$^{14}$, —NR$^{14}$CO$_2$NR$^{14}$R$^{14}$, NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, NR$^{14}$R$^{14}$, —NR$^{14}$CONR$^{14}$R$^{14}$, C(=NOR$^{14}$)NR$^{14}$R$^{14}$, —CONR$^{14}$OR$^{14}$ or —NR$^{14}$COR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^3$ is phenyl, pyridinyl, pyrimidinyl, dihydropyran, or tetrahydropyran any of which may be substituted with 0-1 $R^{3a}$;

$R^{3a}$ is halo, CN, NH$_2$, —O—$C_{1-3}$alkyl, or morpholinyl;

$R^{13}$, at each occurrence, is independently H, —OH, F, Cl, Br, I, CN, $C_{1-10}$ alkyl, $C_{1-10}$ alkoxy, haloC$_{1-10}$ alkyl, $C_{3-10}$ cycloalkyl, $C_{2-12}$ alkenyl, $C_{2-12}$ alkynyl, $C_{6-10}$aryl, a 4- to 12-membered heteroaryl, a 4- to 12-membered heterocyclyl, a 4- to 12-membered heteroaryl-$C_{1-10}$ alkyl, —CN, —NO$_2$, —(CH$_2$)$_m$—SO$_2$R$^{14}$, —NR$^{14}$SO$_2$R$^{14}$, =O, CONR$^{14}$R$^{14}$, (CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, NR$^{14}$SO$_2$NR$^{14}$R$^{14}$, —CO$_2$NR$^{14}$R$^{14}$, —NR$^{14}$CO$_2$NR$^{14}$R$^{14}$, NR$^{14}$COR$^{14}$, SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, NR$^{14}$R$^{14}$, NR$^{14}$CONR$^{14}$R$^{14}$, NR$^{14}$—CO—CO—NR$^{14}$R$^{14}$, C(=NOR$^{14}$)NR$^{14}$R$^{14}$, —CONR$^{14}$OR$^{14}$ or —NR$^{14}$COR$^{14}$, OR$^{14}$, wherein the alkyl, cycloalkyl, alkenyl, alkoxy, aryl, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O; or $R^{13}$ is SO$_2$NHP(O)(OH)$_2$;

$R^{14}$, at each occurrence, is independently selected from hydrogen, $C_{1-10}$ alkyl, $C_{3-10}$ cycloalkyl, $C_{6-10}$ aryl, a 4- to 12-membered heteroaryl or a 4- to 12-membered heterocyclyl, wherein the alkyl, cycloalkyl, aryl, heteroaryl and heterocyclyl may be substituted with 0-3 $R^{14a}$ and the heteroaryl and heterocyclyl consist of carbon atoms and 1, 2, 3, or 4 heteroatoms independently selected from the group consisting of N, S, or O; or alternatively, two $R^{14}$'s are taken together with the atoms to which they are attached to form a cyclic ring, wherein the cyclic ring may be substituted with 0-1 $R^{14a}$ and optionally contain 1, 2, 3, or 4 heteroatoms independently selected from the group consisting of N, S, or O;

$R^{14a}$, at each occurrence, is independently selected from F, Cl, Br, I, $C_{1-10}$-alkyl, $haloC_{1-10}$alkyl, $C_{6-10}$aryl, $C_{3-10}$cycloalkyl, a 4- to 12-membered heteroaryl, a 4- to 12-membered heterocyclyl, F, Cl, Br, I, —CN, —NO$_2$, —CO$_2$R$_{26}$, —CO$_2$NR$_{24}$R$^{24}$, OCF$_3$, —OR$_{25}$, =O, —CONR$^{24}$R$^{24}$, —COR$^{24}$, —SO$_2$R$^{24}$, —NR$^{24}$R$^{24}$, —NR$^{24}$CO$_2$R$^{24}$, SO$_2$NR$^{24}$R$^{24}$, or $C_{6-10}$arylC$_{1-10}$alkyl, wherein the heteroaryl and heterocyclyl consist of carbon atoms and 1, 2, 3, or 4 heteroatoms independently selected from the group consisting of N, S, or O;

$R^{24}$, at each occurrence, is independently selected from hydrogen, $C_{1-10}$alkyl, $C_{36}$cycloalkyl, or phenyl;

$R^{25}$, at each occurrence, is independently selected from hydrogen, $C_{1-10}$alkyl, $C_{36}$cycloalkyl, or phenyl;

$R_{26}$, at each occurrence, is independently selected from hydrogen, $C_{1-10}$alkyl, $C_{110}$alkyl-OH, $C_{1-6}$haloalkyl, $C_{3-6}$cycloalkyl, or phenyl;

m is 0 to 4;

n is 0 to 4; and n–1 is 2 to 4.

In another aspect, the present invention provides compound of formula (Ia) or enantiomers, diastereomers, tautomers, prodrugs or salts thereof, wherein:

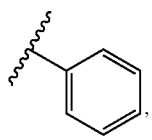 [SMILES: *c1ccccc1]

(Ia)

In another aspect, the present invention provides compound of formula (I) or (Ia), or enantiomers, diastereomers, tautomers, prodrugs or salts thereof, wherein:

A is —(CH$_2$)$_m$—R$^2$, —CH(R$^{26}$)—R$^2$, or —(CH$_2$)$_{n-1}$—O—R$^2$;

$R^1$ is $C_{1-6}$ alkyl substituted with 1-2 —OH, $C_{2-6}$alkenyl, or $C_{3-6}$cycloalkyl, wherein the cycloalkyl may be substituted with 0-2 $R^{13}$; or $R^1$ is

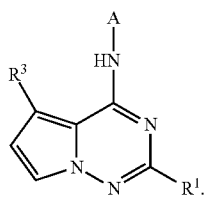

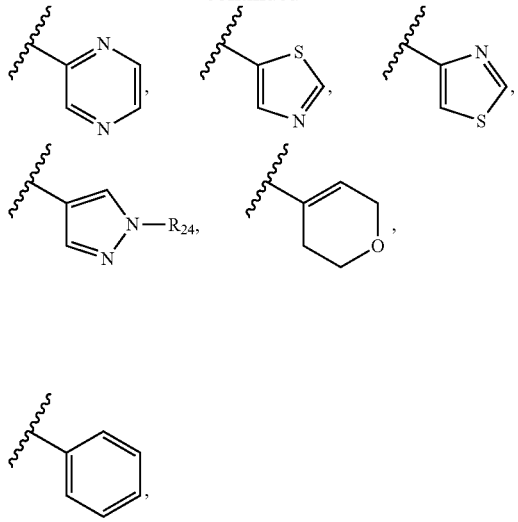

or

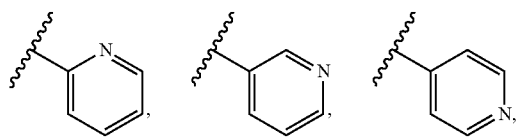

any of which may be substituted with 0-2 $R^{13}$;

$R^2$ is phenyl, cyclohexyl, pyridinyl, pyridazinyl, or tetrahydropyran, any of which are substituted with 0-2 $R^{2a}$;

$R^{2a}$, at each occurrence, is independently H, —OH, F, Cl, Br, I, or SO$_2$NH$_2$;

$R^3$ is phenyl, or pyridinyl, either of which may be substituted with 0-1 $R^{3a}$;

$R^{3a}$ is halo, CN, NH$_2$, —O—C$_{1-3}$alkyl, or morpholinyl;

$R^{13}$, at each occurrence, is independently H, —OH, F, Cl, Br, I, CN, $C_{1-6}$alkyl, $C_{1-6}$ alkoxy, $haloC_{1-6}$ alkyl, $C_{2-12}$ alkenyl, a 4- to 6-membered heteroaryl, a 4- to 6-membered heterocyclyl, —NR$^{14}$SO$_2$R$^{14}$, —CONR$^{14}$R$^{14}$, —SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —CO$_2$R$^{14}$, —NR$^{14}$R$^{14}$, or OR$^{14}$, wherein the alkyl, cycloalkyl, alkenyl, alkoxy, heteroaryl and heterocyclyl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-6}$ alkyl, $C_{3-6}$ cycloalkyl, phenyl, or a 4- to 6-membered heterocyclyl, wherein the alkyl, cycloalkyl, aryl, heteroaryl and heterocyclyl may be substituted with 0-3 $R^{14a}$ and the heterocyclyl is pyrrolidinyl, or dioxanyl; or alternatively, two $R^{14}$'s are taken together with the atoms to which they are attached to form a cyclic ring, wherein the cyclic ring may be substituted with 0-1 $R^{14a}$ the cyclic ring is selected from morpholinyl, piperidinyl, or piperazinyl;

$R^{14a}$, at each occurrence, is independently selected from F, Cl, Br, I, $C_{1-6}$alkyl, phenyl, $C_{3-6}$cycloalkyl, —CO$_2$R$^{26}$, —CO$_2$NR$^{24}$R$^{24}$—OR$^{25}$—COR$^{24}$, —NR$^{24}$R$^{24}$, or —NR$^{24}$CO$_2$R$^{24}$;

$R^{24}$, at each occurrence, is independently selected from hydrogen, $C_{1-10}$alkyl, $C_{3-6}$cycloalkyl, or phenyl;

$R^{25}$, at each occurrence, is independently selected from hydrogen, $C_{1-10}$alkyl, $C_{3-6}$cycloalkyl, or phenyl;

$R^{26}$, at each occurrence, is independently selected from hydrogen, $C_{1-10}$alkyl, $C_{3-6}$cycloalkyl, or phenyl;

m is 0 to 4;

n is 0 to 4; and n–1 is 2 to 4.

In another aspect, the present invention provides compound of formula (I) or (Ia), or enantiomers, diastereomers, tautomers, prodrugs or salts thereof, wherein:

$R^1$ is $C_{1-10}$ alkyl substituted with 1-2 —OH, halo$C_{1-10}$ alkyl, or $C_{3-10}$ cycloalkyl, wherein the cycloalkyl may be substituted with 0-2 $R^{13}$; or $R^1$ is

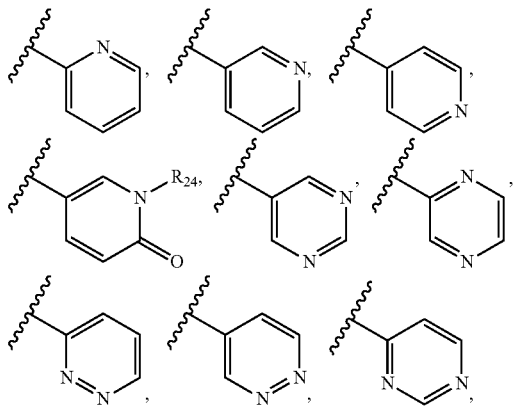

or

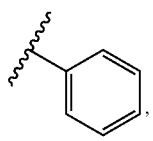 [SMILES: *c1ccccc1]

any of which may be substituted with 0-2 $R^{13}$.

In another aspect, the present invention provides compound of formula (I) or (Ia), or enantiomers, diastereomers, tautomers, prodrugs or salts thereof, wherein:

$R^1$ is $C_{1-10}$ alkyl substituted with 1-2 —OH, halo$C_{1-10}$ alkyl, or $C_{3-10}$ cycloalkyl, wherein the cycloalkyl may be substituted with 0-1 $R^{13}$; or $R^1$ is

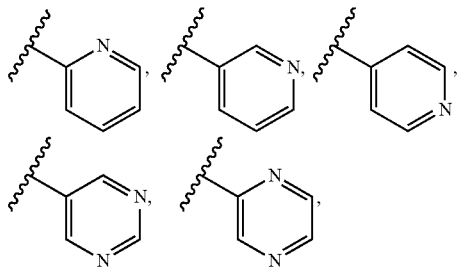

or

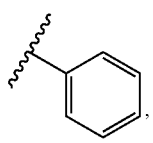

any of which may be substituted with 0-2 $R^{13}$.

In another aspect, the present invention provides compound of formula (I) or (Ia), or enantiomers, diastereomers, tautomers, prodrugs or salts thereof, wherein:

$R^1$ is $C_{1-10}$ alkyl substituted with 1-2 —OH, halo$C_{1-10}$ alkyl, or $C_{3-10}$ cycloalkyl, wherein the cycloalkyl may be substituted with 0-1 $R^{13}$; or $R^1$ is

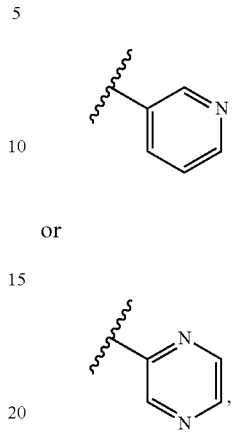

any of which may be substituted with 0-2 $R^{13}$.

In another aspect, the present invention provides compound of formula (I) or (Ia), or enantiomers, diastereomers, tautomers, prodrugs or salts thereof, wherein:

$R^1$ is

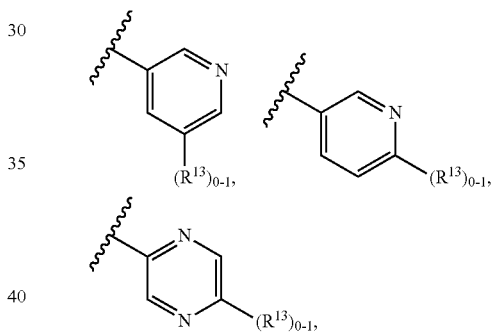

or

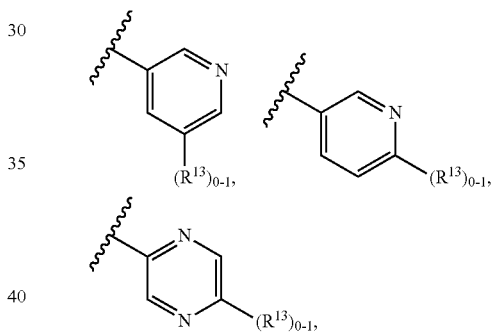

In another aspect, the present invention provides compound of formula (I) or (Ia), or enantiomers, diastereomers, tautomers, prodrugs or salts thereof, wherein:

$R^{13}$, at each occurrence, is independently H, —OH, F, Cl, Br, I, $C_{1-6}$alkyl, $C_{1-6}$ alkoxy, halo$C_{1-6}$ alkyl, $C_{3-6}$cycloalkyl, phenyl, or a 4- to 12-membered heteroaryl, wherein the heteroaryl is selected from tetrazolyl, —CN, —NO$_2$, —(CH$_2$)$_m$—SO$_2$R$^{14}$, —NR$^{14}$SO$_2$R$^{14}$, —CONR$^{14}$R$^{14}$, —(CH$_2$)$_m$—SO$_2$NR$^{14}$R$^{14}$, —NR$^{14}$CO$_2$NR$^{14}$R$^{14}$, —NR$^{14}$CO$_2$NR$^{14b}$R$^{14b}$, —NR$^{14}$COR$^{14}$, —NR$^{14}$CO$_2$R$^{14}$, —CO$_2$R$^{14}$, or —NR$^{14}$R$^{14}$, wherein the alkyl, cycloalkyl, phenyl, and heteroaryl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-6}$ alkyl, $C_{3-6}$ cycloalkyl, or phenyl, wherein the alkyl, cycloalkyl, and phenyl, may be substituted with 0-3 $R^{14a}$; or alternatively, two $R^{14b}$'s are taken together with the atoms to which they are attached to form a cyclic ring, wherein the cyclic ring is morpholinyl, piperidinyl, or piperazinyl, and may be substituted with 0-1 $C_{1-6}$alkyl; and $R^{14a}$, at each occurrence, is independently selected from F, Cl, Br, I, $C_{1-6}$alkyl, halo$C_{1-6}$alkyl, phenyl, or $C_{3-6}$cycloalkyl.

In another aspect, the present invention provides compound of formula (I) or (Ia), or enantiomers, diastereomers, tautomers, prodrugs, or salts thereof, wherein:

$R^{13}$, at each occurrence, is independently H, $C_{1-6}$alkyl, or a 4- to 12-membered heteroaryl, wherein the heteroaryl is selected from tetrazolyl, —CN, —$NR^{14}SO_2R^{14}$, —$CONR^{14}R^{14}$, —$SO_2NR^{14}R^{14}$, —$NR^{14}CO_2NR^{14}R^{14}$, —$NR^{14}CO_2NR^{14b}R^{14b}$, —$NR^{14}COR^{14}$, —$CO_2R^{14}$, or —$NR^{14}R^{14}$, wherein the alkyl, and heteroaryl may be substituted with 0-2 $R^{14a}$;

$R^{14}$, at each occurrence, is independently selected from hydrogen, $C_{1-6}$ alkyl, $C_{3-6}$ cycloalkyl, or phenyl, wherein the alkyl, cycloalkyl, and phenyl, may be substituted with 0-3 $R^{14a}$; or two $R^{14b}$'s are taken together with the atoms to which they are attached to form a cyclic ring, wherein the cyclic ring is morpholinyl, and may be substituted with 0-1 $C_{1-6}$alkyl; and $R^{14a}$, at each occurrence, is independently selected from F, Cl, Br, I, $C_{1-6}$alkyl, halo$C_{1-6}$alkyl, phenyl, or $C_{3-6}$cycloalkyl.

In another aspect, the present invention provides compound of formula (I) or (Ia), wherein:

$R^{13}$, at each occurrence, is independently H, —OH, F, Cl, Br, I, $C_{1-6}$alkyl, $C_{1-6}$ alkoxy, halo$C_{1-6}$ alkyl, $C_{3-6}$ cycloalkyl, phenyl, or a 4- to 12-membered heteroaryl, wherein the heteroaryl is selected from tetrazolyl, —CN, —$NO_2$, —$(CH_2)_m$—$SO_2R^{14}$, —$NR^{14}SO_2R^{14}$, —$CONR^{14}R^{14}$, —$(CH_2)_m$—$SO_2NR^{14}R^{14}$, —$NR^{14}CO_2NR^{14}R^{14}$, —$NR^{14}CO_2NR^{14}R^{1b}$, —$NR^{14}COR^{14}$, —$NR^{14}CO_2R^{14}$, —$CO_2R^{14}$, or —$NR^{14}R^{14}$, wherein the alkyl, cycloalkyl, phenyl, and heteroaryl may be substituted with 0-2 $R^{14a}$, and the heteroaryl and heterocyclyl consist of carbon atoms and 1, 2, 3, or 4 heteroatoms independently selected from the group consisting of N, S, or O;

$R^{14}$, at each occurrence, is independently selected from hydrogen, $C_{1-6}$ alkyl, $C_{3-6}$ cycloalkyl, or phenyl, wherein the alkyl, cycloalkyl, and phenyl, may be substituted with 0-3 $R^{14a}$; or alternatively, two $R^{14}$'s are taken together with the atoms to which they are attached to form a cyclic ring, wherein the cyclic ring is morpholinyl, piperidinyl, or piperazinyl, and may be substituted with 0-1 $C_{1-6}$alkyl; and $R^{14a}$, at each occurrence, is independently selected from F, Cl, Br, I, $C_{1-6}$ alkyl, halo$C_{1-6}$alkyl, phenyl, or $C_{3-6}$cycloalkyl.

In another aspect, the present invention provides compound of formula (I) or (Ia), or enantiomers, diastereomers, tautomers, prodrugs, or salts thereof, wherein:

$R^{13}$, at each occurrence, is independently H, —CN, —$NHSO_2R^{14}$, —$CONH_2$, —$SO_2NR^{14}R^{14}$, —$NHCO_2NR^{14b}R^{14b}R^{14b}$, —$NHCOR^{14}$, or —$NH_2$; and $R^{14}$, at each occurrence, is independently selected from hydrogen or methyl.

In another aspect, the present invention provides compound of formula (I) or (Ia), or enantiomers, diastereomers, tautomers, prodrugs, or salts thereof, wherein:

$R^{13}$, at each occurrence, is —$SO_2NH_2$.

In another aspect, the present invention provides compound of formula (I) or (Ia), or enantiomers, diastereomers, tautomers, prodrugs, or salts thereof, wherein:

A is —$(CH_2)_m$—$R^2$, —$CH(R^{26})$—$R_2$, —$(CH_2)_{n-1}$—O—$R_2$, —$(CH_2)_{n-1}$—$NR^{25}$—$R_2$, —$CH(R^{26})$—$CO_2$—$R^2$, or —$(CH_2)_{n-1}$—$NR^{25}$—$CO_2$—$R^2$;

$R^2$ is phenyl, pyridinyl, pyrazinyl, pyrimidinyl, piperidinyl, or pyridinone, any of which are substituted with 0-2 $R^{2a}$; and $R^{2a}$, at each occurrence, is independently H, —OH, F, $C_{1-6}$ alkyl, $C_{1-6}$ alkoxy, or 6-$SO_2NR^{14}R^{14}$.

In another aspect, the present invention provides compound of formula (I) or (Ia), or enantiomers, diastereomers, tautomers, prodrugs, or salts thereof, wherein:

A is —$(CH_2)$—$R^2$;

$R^2$ is phenyl,

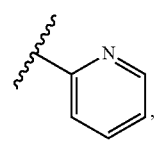

or

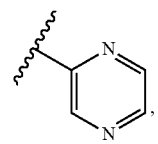 [SMILES: *c1cnccn1]

any of which are substituted with 0-1 $R^{2a}$; and $R^{2a}$, at each occurrence, is independently H, —OH, F, $C_{1-6}$ alkyl, $C_{1-6}$ alkoxy, $C_{1-6}$ haloalkoxy, or $SO_2NR^{14}R^{14}$.

In another aspect, the present invention provides compound of formula (I) or (Ia), or enantiomers, diastereomers, tautomers, prodrugs, or salts thereof, wherein:

A is —$(CH_2)$—$R^2$; and $R^2$ is phenyl or

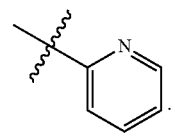

In another aspect, the present invention provides compound of formula (I) or (Ia), or enantiomers, diastereomers, tautomers, prodrugs, or salts thereof, wherein:

A is —$(CH_2)$—$R^2$ or —$CH(R^{26})$—$R^2$;

$R^2$ is phenyl,

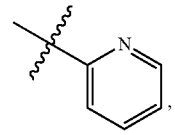 [SMILES: *c1ccccn1]

or $C_{1-6}$alkyl, any of which are substituted with 0-1 $R^{2a}$; and $R^{2a}$, at each occurrence, is independently H or F.

In another aspect, the present invention provides compound of formula (I) or (Ia), or enantiomers, diastereomers, tautomers, prodrugs, or salts thereof, wherein:

$R^3$ is phenyl.

In another aspect, the present invention provides compound of formula (I) or (Ia), or enantiomers, diastereomers, tautomers, prodrugs, or salts thereof, wherein:

$R^{24}$, at each occurrence, is independently selected from hydrogen, $C_{1-6}$alkyl, $C_{3-6}$cycloalkyl, or phenyl;

$R^{25}$, at each occurrence, is independently selected from hydrogen, $C_{1-6}$alkyl, $C_{3-6}$cycloalkyl, or phenyl; and $R^{2}{}_{6}$, at each occurrence, is independently selected from hydrogen, $C_{1-6}$alkyl, $C_{3-6}$cycloalkyl, or phenyl.

In another aspect, the present invention provides compound of formula (I) or (Ia), or enantiomers, diastereomers, tautomers, prodrugs, or salts thereof, wherein:

$R^{24}$, at each occurrence, is independently selected from hydrogen, methyl or ethyl;

$R^{25}$, at each occurrence, is independently selected from hydrogen methyl or ethyl; and $R^{26}$, at each occurrence, is independently selected from hydrogen, methyl or ethyl.

In another aspect, the present invention provides compound of formula (I) or (Ia), or enantiomers, diastereomers, tautomers, prodrugs, or salts thereof, wherein:

m is 0-2; and
n–1 is 1-2.

In another aspect, the present invention provides compound of formula (I) or (Ia), or enantiomers, diastereomers, tautomers, prodrugs, or salts thereof, wherein:

m is 1 or 2;
n–1 is 2; and
n is 1.

In another aspect, the present invention provides compound of formula (I) or (Ia), or salts thereof, wherein:

$R^{13}$ is $SO_2NHP(O)(OH)_2$.

In another aspect, the present invention provides compound of formula (I) or (Ia), or salts thereof, wherein:

$R^1$ pyridinyl, substituted with 1 $R^{13}$; and
$R^{13}$ is $SO_2NHP(O)(OH)_2$.

In another aspect, the present invention provides compound of formula (I) or (Ia), or salts thereof, wherein:
$R^1$ is

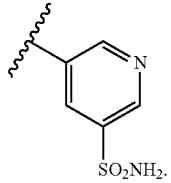 [SMILES: *c1cncc(S(N)(=O)=O)c1]

$SO_2NH_2$.

In another aspect, the present invention provides compound of formula (I) or (Ia), or salts thereof, wherein:
$R^1$ is

$SO_2NHP(O)(OH)_2$.

In another embodiment, compounds, enantiomers, diastereomers, tautomers, or salt thereof, of the present invention are selected from the compounds exemplified in the examples.

In one embodiment, pharmaceutical compositions comprising a therapeutically effective amount of at least one compound of formula (I), (Ia), and/or compounds exemplified in the examples.

In another embodiment, pharmaceutical compositions comprising a therapeutically effective amount of at least one compound of formula (I), (Ia), and/or compounds exemplified in the examples, and at least one other therapeutic agent, for example, anti-arrhythmic agents, calcium channel blockers, anti-platelet agents, anti-hypertensive agents, anti thrombotic/anti thrombolytic agents, anti coagulants, HMG-CoA reductase inhibitors, anti diabetic agents, thyroid mimetics, mineralocorticoid receptor antagonists, and cardiac glycosides, are provided.

In yet another embodiment, pharmaceutical compositions comprising a therapeutically effective amount of at least one compound of formula (I), (Ia), or compounds exemplified in the examples, and at least one other therapeutic agent, for example, sotalol, dofetilide, diltiazem, verapamil, clopidogrel, cangrelor, ticlopidine, CS-747, ifetroban, aspirin, a beta adrenergic blocker, an ACE inhibitor, an A II antagonist, an ET antagonist, a dual ET/A II antagonist, a vasopepsidase inhibitor, tPA, recombinant tPA, TNK, nPA, a factor VIIa inhibitor, a factor Xa inhibitor, a factor XIa inhibitor, a thrombin inhibitor, warfarin, a heparin, pravastatin, lovastatin, atorvastatin, simvastatin, NK-104, ZD-4522, a biguanide, a biguanide/glyburide combination, spironolactone, eplerinone, digitalis and ouabain, are provided.

In still yet another embodiment, pharmaceutical compositions comprising a therapeutically effective amount of at least one compound of formula (I), (Ia), or compounds exemplified in the examples, and at least one other therapeutic agent, for example, captopril, zofenopril, fosinopril, enalapril, ceranopril, cilazopril, delapril, pentopril, quinapril, ramipril, lisinopril, omapatrilat, gemopatrilat, and apixaban, are provided.

In one embodiment, methods of treating or preventing arrhythmia comprising administering to a patient in need thereof an effective amount of at least one compound of formula (I), (Ia), or compounds exemplified in the examples, are provided.

In another embodiment, methods of treating or preventing supraventricular arrhythmia, for example, atrial fibrillation and atrial flutter, comprising administering to a patient in need thereof an effective amount of at least one compound of formula (I), (Ia), or compounds exemplified in the examples, are provided.

In one embodiment, a method of controlling heart rate comprising administering to a patient in need thereof an effective amount of at least one compound of formula (I), (Ia), or compounds exemplified in the examples, is provided.

In another embodiment, methods of treating an $I_{Kur}$-associated conditions, for example, gastrointestinal disorders, such as reflux esophagitis and a motility disorder; inflammatory and/or immunological diseases, such as chronic obstructive pulmonary disease; diabetes; cognitive disorders; migraines; epilepsy; and hypertension, comprising administering to a patient in need thereof an effective amount of at least one compound of formula (I), (Ia), or compounds exemplified in the examples, are provided.

Another aspect of this invention is directed to a composition comprising a compound of the invention together with a pharmaceutically acceptable carrier, diluent, or excipient. When water is a carrier or diluent, the composition optionally further comprises another pharmaceutically acceptable carrier or diluent and/or a pharmaceutically acceptable excipient. Within this aspect are such compositions for pharmaceutical use.

Another aspect of this invention is directed to a composition comprising a compound of the invention together with a pharmaceutically acceptable carrier, diluent, or excipient. When water is a carrier or diluent, the composition optionally further comprises another pharmaceutically acceptable carrier or diluent and/or a pharmaceutically acceptable excipient. Within this aspect are such compositions for pharmaceutical use.

Another aspect of this invention is directed to treatment of diseases or disorders associated with inhibition of potassium channel function, wherein the disease or disorder is atrial fibrillation, controlling heart rate, and/or prophylactically treating arrhythmia, comprising administering a therapeutically effective amount of a compound of the present invention or an individual isomer or mixture of isomers or a pharmaceutically acceptable salt thereof.

The compounds of the invention may be useful in therapy.

The compounds of the invention may be used for the manufacture of a medicament for the treatment and/or prophylaxis of diseases or disorders associated with inhibition of potassium channel function, of the $K_v1$ subfamily of voltage gated $K^+$ channels, of $K_v1.5$ (which have been linked to the ultra-rapidly activating delayed rectifier $K^+$ current $I_{Kur}$, and/or $K_v1.3$ channels, and/or $K_v1.1$ channels.

The compounds of the invention can be used alone, in combination with other compounds of the present invention, or in combination with one or more, preferably one to two other agent(s).

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

SYNTHESIS

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

The compounds of the present invention may be prepared by the exemplary processes described in the following schemes and working examples, as well as relevant published literature procedures that are used by one skilled in the art. Exemplary reagents and procedures for these reactions appear hereinafter and in the working examples. Protection and de-protection of functional groups in the processes below may be carried out by procedures generally known in the art (see, for example, Greene, T. W. et al., *Protecting Groups in Organic Synthesis*, Third Edition, Wiley (1999). General methods of organic synthesis and functional group transformations are found in: Trost, B. M. et al., eds., *Comprehensive Organic Synthesis: Selectivity, Strategy & Efficiency in Modern Organic Chemistry*, Pergamon Press, New York, N.Y. (1991); March, J., *Advanced Organic Chemistry: Reactions, Mechanisms, and Structure*, Fourth Edition, Wiley & Sons, New York, N.Y. (1992); Katritzky, A. R. et al., eds., *Comprehensive Organic Functional Groups Transformations*, First Edition, Elsevier Science Inc., Tarrytown, N.Y. (1995); Larock, R. C., *Comprehensive Organic Transformations*, VCH Publishers, Inc., New York, N.Y. (1989); and references therein.

ABBREVIATIONS

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "nM" for nanomolar, "mol" for mole or moles, "mmol" for millimole or millimoles, "min" for minute or minutes, "h" for hour or hours, "rt" for room temperature, "Rt" for retention time, "atm" for atmosphere, "psi" for pounds per square inch, "conc." for concentrate, "sat" or "sat'd" for saturated, "MW" for molecular weight, "mp" for melting point, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Solvents, temperatures, pressures, and other reaction conditions may readily be selected by one of ordinary skill in the art. Starting materials are commercially available or can be readily prepared by one of ordinary skill in the art using known methods. For all of the schemes and compounds described below $X^1$, $X^2$, A and $R^1$ are as described for a compound of Formula (I). The following are the definitions of symbols used in the Examples:

Ar Aryl
Me Methyl
AcOH or HOAc acetic acid
$BF_3.OEt_2$ Boron trifluoride etherate
Et Ethyl
Pr Propyl
i-Pr Isopropyl
Bu Butyl i-Bu Isobutyl
t-Bu tert-butyl
Ph Phenyl
Bn Benzyl
Boc tert-butyloxycarbonyl
BOP (Benzotriazol1yloxy)tris(dimethylamino) phosphoniumhexafluorophosphate
$CH_2Cl_2$ dichloromethane
$CH_3CN$ or ACN Acetonitrile
$CDCl_3$ deutero-chloroform
$CHCl_3$ Chloroform
$Cs_2CO_3$ cesium carbonate
DCM dichloromethane
DEA Diethylamine
DIPEA or Hunig's base diisopropylethylamine
DMSO dimethyl sulfoxide
Dppp (R)-(+)-1,2-bis(diphenylphosphino)propane
EDC N-(3-dimthylaminopropyl)-N'-ethylcarbodiimide
$Et_3N$ or TEA Triethylamine
EtOAc ethyl acetate
$Et_2O$ diethyl ether
EtOH Ethanol
HATU (Dimethylamino)-N,N-dimethyl(3H-[1,2,3]triazolo[4,5-b]pyridin-3-yloxy)methaniminium hexafluorophosphate
HCl hydrochloric acid
HOBt 1-hydroxybenzotriazole
$H_2SO_4$ sulfuric acid
$K_2CO_3$ potassium carbonate
KOAc potassium acetate
$K_3PO_4$ potassium phosphate
LiOH lithium hydroxide
MeOH Methanol
$MgSO_4$ magnesium sulfate
MsOH or MSA methylsulfonic acid
MTBE methyl tertiary-butyl ether
NaCl sodium chloride
NaH sodium hydride
$NaHCO_3$ sodium bicarbonate
$Na_2CO_3$ sodium carbonate
NaOH sodium hydroxide
$Na_2SO_3$ sodium sulfite
$Na_2SO_4$ sodium sulfate
$NH_3$ Ammonia
$NH_4Cl$ ammonium chloride
$NH_4OH$ ammonium hydroxide
$Pd(OAc)_2$ palladium(II) acetate
Pd/C palladium on carbon
$Pd_2(dba)_3$ Tris(dibenzylideneacetone)dipalladium (0)
$Pd(dppf)Cl_2$ [1,1'-bis(diphenylphosphino)-ferrocene]dichloropalladium(II)
$Pd(TPP)_2Cl_2$ Bis(triphenylphosphine)palladium(II) dichloride
$Ph_3PCl_2$ triphenylphosphine dichloride
$POCl_3$ phosphorus oxychloride
i-PrOH or IPA Isopropanol
PyBOP (Benzotriazol-1-yloxy)tripyrrolidinophosphonium hexafluorophosphate
PyBrop Bromo-tris-pyrrolidino phosphoniumhexafluorophosphate
TFA Trifluoroacetic acid
THF Tetrahydrofuran
XPHOS Chloro(2-dicyclohexylphosphino-2',4',6'-triisopropyl-1,1'-biphenyl)[2-(2'-amino-1,1'-biphenyl)]palladium (II)

SYNTHESIS

A particularly useful compendium of synthetic methods which may be applicable to the preparation of compounds of the present invention may be found in Larock, R. C., *Comprehensive Organic Transformations*, VCH, New York (1989). Preferred methods include, but are not limited to, those described below. All references cited herein are hereby incorporated in their entirety herein by reference.

The novel compounds of this invention may be prepared using the reactions and techniques described in this section. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. Restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Wiley and Sons (1991)).

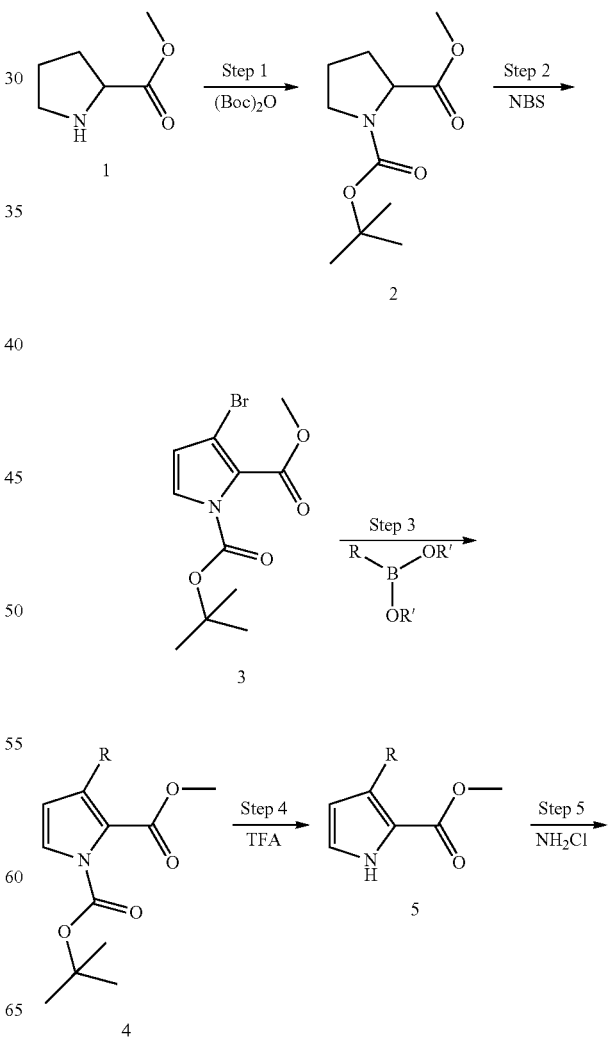

Scheme 1

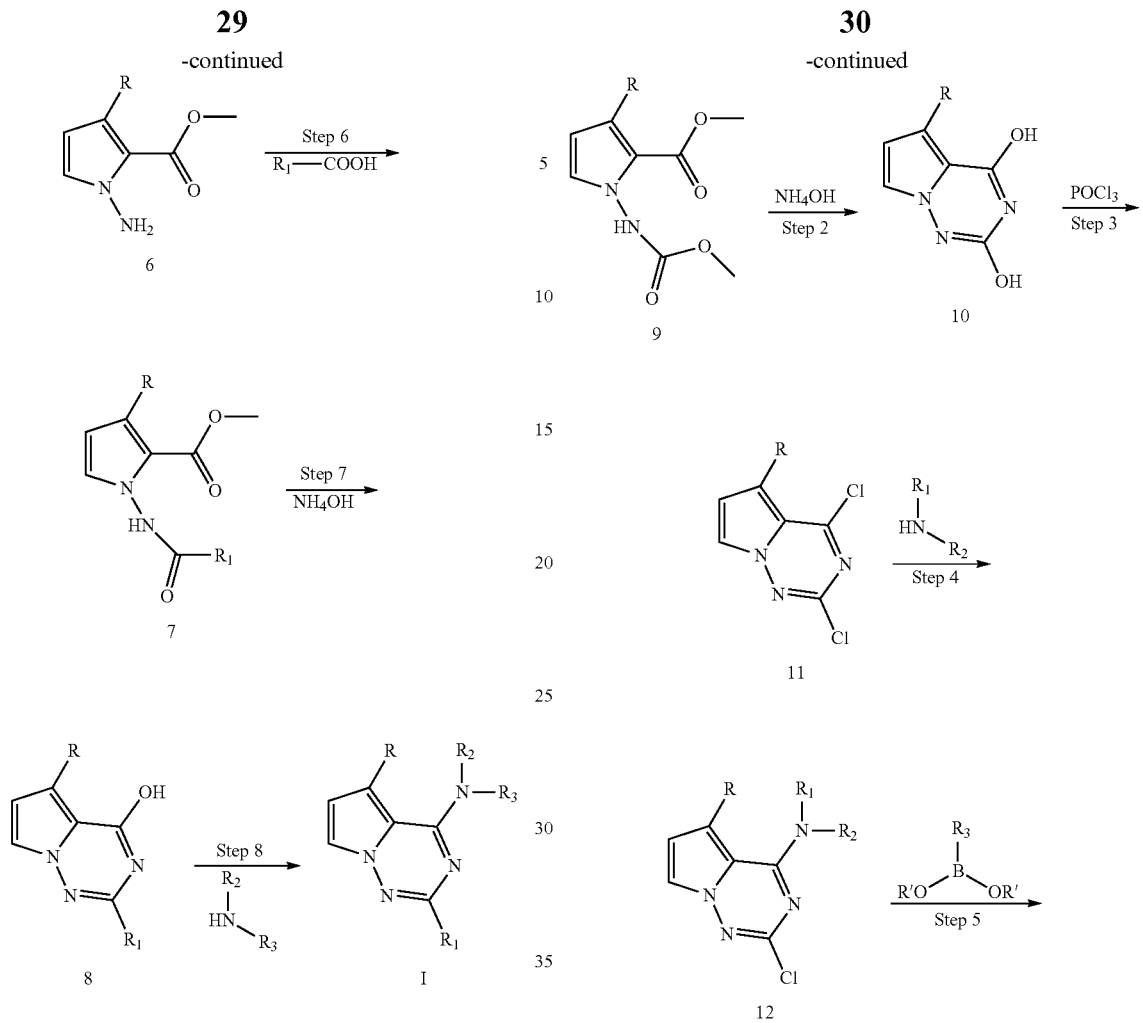

Compounds of formula (I) may be synthesized according to Scheme 1. Commercially available methylpyrrolidine-2-carboxylate 1 was protected using a protecting group, for example, Boc and 2 was converted to 1-tert-butyl 2-methyl 3-bromo-1H-pyrrole-1,2-dicarboxylate 3 using NBS which acts as a brominating as well as oxidizing agent (*Aust. J. Chem.*, 62(7):683-691 (2009)). Palladium mediated Suzuki cross-coupling with boronic acids or esters (R is optionally substituted aryl, heteroaryl, alkyl or cycloalkyl) followed by deprotection gave the aryl pyrrole derivative 5. N-amination of 5 gave compounds of general formula 6 which on acylation gave corresponding compounds 7. When treated with ammonia under pressure, 7 undergoes cyclization to form the pyrrolotriazine core 8. Subsequent displacement at C4 by amines using activating agents for example, BOP reagent yield compounds of general formula (I).

Alternatively, compounds of formula (I) can be synthesized by the general sequence shown in Scheme 2. N-amino derivative 6 was treated with methylchloroformate and the resulting acyl derivative 9 was subjected to ring closure with ammonia under pressure to yield the pyrrolotriazine core 10. Intermediate 10 was converted to the corresponding dichloro derivative 11 using chlorinating agents for example, phosphorous oxychloride. Sequential displacement of chloro of 11 at the 4 position followed by transition metal mediated cross coupling or displacement of the C2 chloride of 12 formed compounds of general formula (I).

Scheme 2

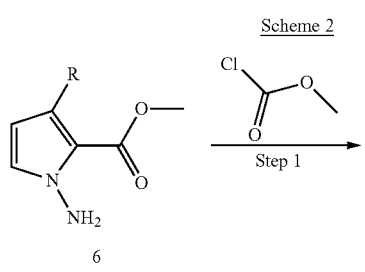

Scheme 3

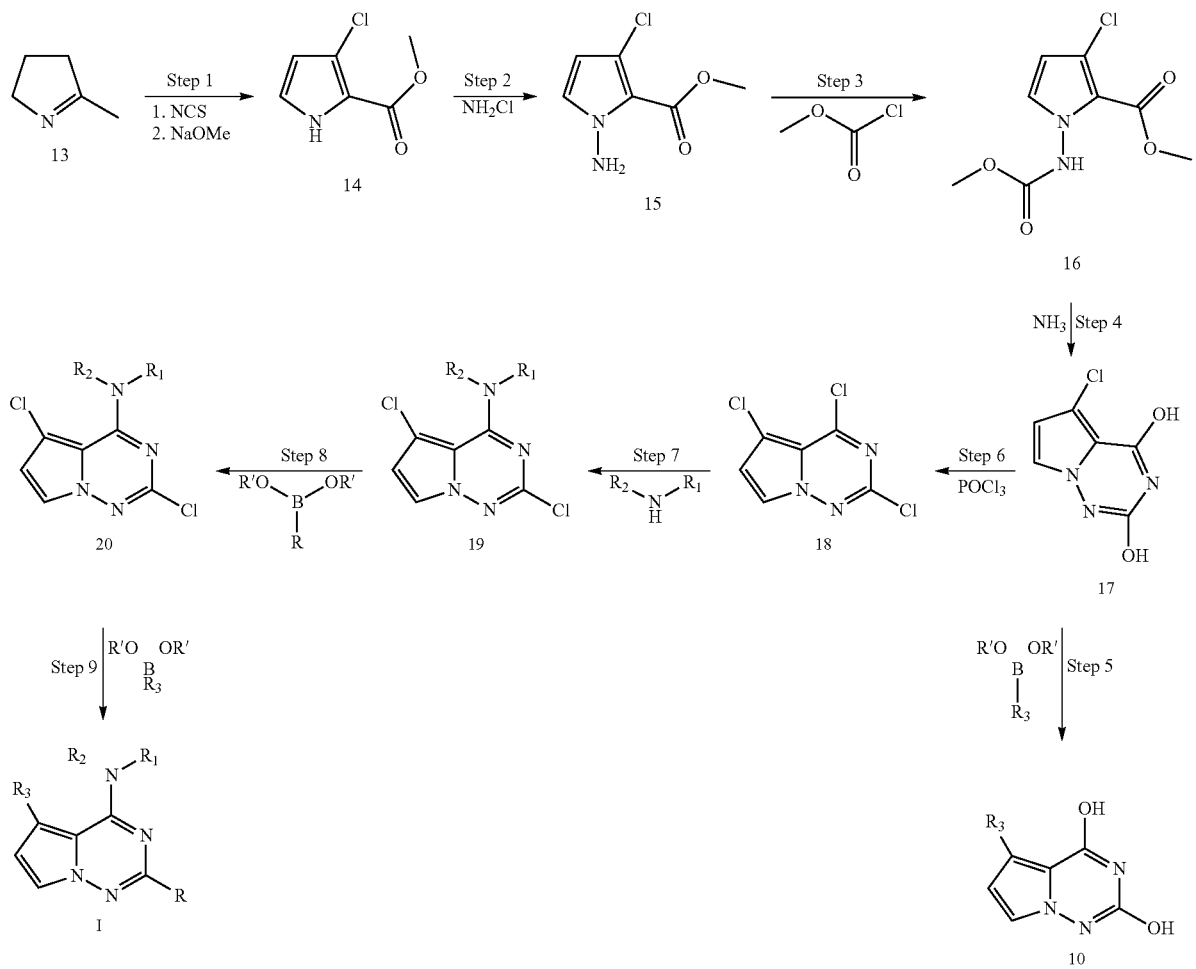

Alternately, compounds of formula (I) can be synthesized by the general sequence shown in Scheme 3. Commercially available 5-methyl-3,4-dihydro-2H-pyrrole 13 was treated with N-chlorosuccinimide followed by sodium methoxide to generate methyl 3-chloro-1H-pyrrole-2-carboxylate 14. Compound 14 was N-aminated and the product 15 was acylated to yield methyl 3-chloro-1-(methoxycarbonylamino)-1H-pyrrole-2-carboxylate 16. Compound 16 was treated with ammonia to yield 5-chloropyrrolo[1,2-f][1,2,4]triazine-2,4-diol 17. Compound 10 can be obtained from 17 by transition metal mediated Suzuki cross-coupling reactions with boronic acids or esters. Compound 17 gave 2,4,5-trichloropyrrolo[1,2-f][1,2,4]triazine 18 on treatment with chlorinating agents for example, $POCl_3$ and then displacement of the C4 chloro with amines gave regioselectively 19. Using different palladium reagent/ligand combinations we could achieve regioselective Suzuki cross-couplings at C2 and C5 to generate compounds of general formula (I).

EXAMPLES

The following Examples are offered to better illustrate, but not limit, some of the preferred embodiments of the application and are not meant to be limiting of the scope of the invention. Abbreviations and chemical symbols have their usual and customary meanings unless otherwise indicated. Unless otherwise indicated, the compounds described herein have been prepared, isolated and characterized using the schemes and other methods disclosed herein or may be prepared using the same.

General Methods

The following methods were used in the working Examples, except where noted otherwise.
Analytical HPLC and HPLC/MS Methods Employed in Characterization of Examples Preparative HPLC was carried on AGILENT® 1200 series, Shimadzu prominence or Waters systems. Preparative SFC was performed on Thar instrument. Reverse phase analytical HPLC/MS was performed on AGILENT® 1200 systems coupled with Mass Spectrometers. LCMS was performed on AGILENT® 1200 or Waters AQUITY® system coupled with Mass Spectrometer. Chiral analytical LC was performed on a Thar Analytical SFC instrument.
Condition B-1:
Column=XBridge Phenyl, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100

Gradient time=12 min; Stop time=23 min
Isocratic time=3 min
Flow Rate=1 mL/min; Wavelength=220 and 254 nm
Condition B-2:
Column=SunFire C18, 4.6×150 mm, 3.5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=23 min
Isocratic time=3 min
Flow Rate=1 mL/min; Wavelength=220 and 254 nm
Condition B-3:
Column=YMC Triart, 4.6×150 mm, 5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=15 min
Isocratic time=3 min
Flow Rate=1 mL/min; Wavelength=220 and 254 nm
Condition B-4:
Column=SunFire C18, 4.6×150 mm, 3.5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=0; Final % B=50
Gradient time-1=15 min
Final % B=100
Gradient time-2=3 min
Isocratic time=5 min
Stop time=28 min
Flow Rate=1 mL/min; Wavelength=220 and 254 nm
Condition B-5:
Column=SunFire C18, 4.6×150 mm, 3.5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=25 min; Stop time=30 min
Isocratic time=5 min
Flow Rate=1 mL/min; Wavelength=220 and 254 nm
Condition B-6:
Column=XBridge Phenyl, 4.6×150 mm, 3.5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=25 min; Stop time=30 min
Isocratic time=5 min
Flow Rate=1 mL/min; Wavelength=220 and 254 nm
Condition B-7:
Column=Eclipse XDB C18, 4.6×150 mm, 3.5 μm
Solvent A=20 mM NH$_4$OAc in H$_2$O
Solvent B=CH$_3$CN
Start % B=10; Final % B=100
Gradient time=25 min; Stop time=36 min
Isocratic time=5 min
Flow Rate=1 mL/min; Wavelength=220 and 254 nm
Condition B-8:
Column=Eclipse XDB C18, 4.6×150 mm, 3.5 μm
Solvent A=20 mM NH$_4$OAc in H$_2$O
Solvent B=CH$_3$CN
Start % B=10; Final % B=100
Gradient time=12 min; Stop time=26 min
Isocratic time=8 min
Flow Rate=1 mL/min; Wavelength=220 and 254 nm
Condition B-9:
Column=ZORBAX® SB C18, 4.6×50 mm, 5 μm
Solvent A=MeOH (10%)+0.1% TFA in H$_2$O (90%)
Solvent B=MeOH (90%)+0.1% TFA in H$_2$O (10%)
Start % B=0; Final % B=100
Gradient time=2 min; Stop time=3 min
Flow Rate=5 mL/min; Wavelength=220 nm
Condition B-10:
Column=PUROSPHER® STAR RP-18, 4.0×55 mm, 3 μm
Solvent A=CH$_3$CN (10%)+20 mM NH$_4$OAc in H$_2$O (90%)
Solvent B=CH$_3$CN (90%)+20 mM NH$_4$OAc in H$_2$O (10%)
Start % B=0; Final % B=100
Gradient time=2 min; Stop time=3 min
Isocratic time=0.5 min
Flow Rate=2.5 mL/min; Wavelength=220 nm
Condition B-11:
Column=PUROSPHER® STAR RP-18, 4.0×55 mm, 3 μm
Solvent A=CH$_3$CN (10%)+20 mM NH$_4$OAc in H$_2$O (90%)
Solvent B=CH$_3$CN (90%)+20 mM NH$_4$OAc in H$_2$O (10%)
Start % B=0; Final % B=100
Gradient time=1.8 min; Stop time=4 min
Isocratic time=1.5 min
Flow Rate=2.5 mL/min; Wavelength=220 nm
Condition B-12:
Column=Ascentis Express C18, 2.1×50 mm, 2.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.4 min; Stop time=4 min
Isocratic time=1.6 min
Flow Rate=1 mL/min; Wavelength=220 nm
Condition B-13:
Column=Ascentis Express C8, 2.1×50 mm, 2.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.5 min; Stop time=4 min
Isocratic time=1.7 min
Flow Rate=1 mL/min; Wavelength=220 nm
Condition B-14:
Column=Ascentis Express C8, 2.1×50 mm, 2.7 μm
Solvent A=CH$_3$CN (10%)+10 mM NH$_4$COOH in H$_2$O (90%)
Solvent B=CH$_3$CN (90%)+10 mM NH$_4$COOH in H$_2$O (10%)
Start % B=0; Final % B=100
Gradient time=1.6 min; Stop time=4 min
Isocratic time=1.6 min
Flow Rate=1 mL/min; Wavelength=220 nm
Condition B-15:
Column=Ascentis Express C18 2.1×50 mm, 2.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.5 min; Stop time=4 min
Isocratic time=1.7 min
Flow Rate=1 mL/min; Wavelength=220 nm
Condition B-16:
Column=Acquity BEH C18, 2.1×50 mm, 3 μm
Solvent A=CH$_3$CN (5%)+5 mM NH$_4$OAc in H$_2$O (95%)
Solvent B=CH$_3$CN (95%)+5 mM NH$_4$OAc in H$_2$O (5%)
Start % B=5; Final % B=95
Gradient time=1.1 min; Stop time=2.4 min
Isocratic time=0.6 min
Flow Rate=0.8 mL/min; Wavelength=220 nm Condition B-17:
Column=ACE Excel 2 C18, 3.0×50 mm, 2.0 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=5; Final % B=100
Gradient time=1.8 min; Stop time=4 min
Isocratic time=0.8 min
Flow Rate=1.2 mL/min; Wavelength=220 nm
Condition B-18:
Column=BEH C18, 3.0×50 mm, 5.0 μm
Solvent A=CH$_3$CN (5%)+10 mM NH$_4$OAc in H$_2$O (95%)
Solvent B=CH$_3$CN (95%)+10 mM NH$_4$OAc in H$_2$O (5%)
Start % B=5; Final % B=100
Gradient time=1.8 min; Stop time=4 min
Isocratic time=1.4 min
Flow Rate=1.2 mL/min; Wavelength=220 nm
Condition B-19:
Column=XBridge C18, 2.1×50 mm, 2.5 μm
Solvent A=CH$_3$CN (5%)+10 mM NH$_4$HCO$_3$ in H$_2$O (95%)
Solvent B=CH$_3$CN (95%)+10 mM NH$_4$HCO$_3$ in H$_2$O (5%)
Start % B=0; Final % B=100
Gradient time=1.7 min; Stop time=4 min
Isocratic time=1.5 min
Flow Rate=1 mL/min; Wavelength=220 nm
Condition B-20:
Column=ZORBAX® SB-Aq, 4.6×50 mm, 3.5 μm
Solvent A=CH$_3$CN (5%)+10 mM NH$_4$COOH in H$_2$O (95%)
Solvent B=CH$_3$CN (95%)+10 mM NH$_4$COOH in H$_2$O (5%)
Start % B=5; Final % B=95
Gradient time=1.7 min; Stop time=4 min
Isocratic time=1.5 min
Flow Rate=1 mL/min; Wavelength=220 nm
Condition B-21:
Column=Ascentis Express C18, 2.1×50 mm, 2.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.6 min; Stop time=4 min
Isocratic time=1.6 min
Flow Rate=1 mL/min; Wavelength=220 nm
Condition B-22:
Column=Ascentis Express C8, 2.1×50 mm, 2.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.5 min; Stop time=4 min
Isocratic time=1.7 min
Flow Rate=1 mL/min; Wavelength=220 nm
Condition B-23:
Column=ZORBAX® SB C18, 4.6×50 mm, 3.5 μm
Solvent A=CH$_3$CN (10%)+20 mM NH$_4$OAc in H$_2$O (90%)
Solvent B=CH$_3$CN (90%)+20 mM NH$_4$OAc in H$_2$O (10%)
Start % B=0; Final % B=100
Gradient time=2.5 min; Stop time=3 min
Flow Rate=2.5 mL/min; Wavelength=220 nm
Condition B-24:
Column=ZORBAX® SB C18, 2.1×30 mm, 3.5 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=6; Final % B=100
Gradient time=1.5 min; Stop time=3 min
Isocratic time=1.7 min
Flow Rate=2.5 mL/min; Wavelength=220 nm
Condition B-25:
Column=ZORBAX® SB-Aq, 4.6×50 mm, 3.5 μm
Solvent A=CH$_3$CN (10%)+0.1% HCOOH in H$_2$O (90%)
Solvent B=CH$_3$CN (90%)+0.1% HCOOH in H$_2$O (10%)
Start % B=0; Final % B=20
Gradient time-1=1.5 min;
Final % B=95
Gradient time-2=2.5 min; Stop time=4 min
Flow Rate=1 mL/min; Wavelength=220 nm
Condition B-26:
Column=XBridge BEH C18, 2.1×50 mm, 2.5 μm
Solvent A=0.1% HCOOH in H$_2$O
Solvent B=0.07% HCOOH in CH$_3$CN
Start % B=10; Final % B=100
Gradient time=2.0 min; Stop time=4.0 min
Isocratic time=1. min
Flow Rate=1.2 mL/min; Wavelength=220 nm
Condition B-27:
Column=ZORBAX® SB C18, 2.1×30 mm, 3.5 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=6; Final % B=100
Gradient time=1.5 min; Stop time=3 min
Isocratic time=0.7 min
Flow Rate=1.5 mL/min; Wavelength=220 nm
Condition B-28:
Column=Ascentis Express C18, 4.6×50 mm, 2.7 μm
Solvent A=CH$_3$CN (5%)+10 mM NH$_4$COOH in H$_2$O (95%)
Solvent B=CH$_3$CN (95%)+10 mM NH$_4$COOH in H$_2$O (5%)
Start % B=0; Final % B=100
Gradient time=4 min; Stop time=5 min
Flow Rate=4 mL/min; Wavelength=220 nm
Condition B-29:
Column=XBridge C18, 2.1×50 mm, 2.5 μm
Solvent A=10 mM NH$_4$HCO$_3$
Solvent B=CH$_3$CN
Start % A=100; Final % B=100
Gradient time=1.7 min; Stop time=4 min
Isocratic time=1.5 min
Flow Rate=1 mL/min; Wavelength=220 nm
Condition B-30:
Column=SunFire C18, 4.6×150 mm, 3.5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=18 min
Isocratic time=3 min
Flow Rate=1 mL/min; Wavelength=220 and 254 nm
Condition B-31:
Column=XBridge, 4.6×150 mm, 3.5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=18 min
Isocratic time=3 min
Flow Rate=1 mL/min; Wavelength=220 and 254 nm
Condition B-32:
Column=SunFire C18, 4.6×150 mm, 3.5 μm
Solvent A=Buffer: CH$_3$CN (95:5)
Solvent B=Buffer: CH$_3$CN (5:95)
Buffer=0.05% TFA in H$_2$O (pH 2.5, adjusted with dilute ammonia)
Start % B=10; Final % B=100
Gradient time=12 min; Stop time=15 min
Isocratic time=3 min
Flow Rate=1 mL/min; Wavelength=220 and 254 nm Condition B-33:
Column=ZORBAX®-SB-CN, 4.6×150 mm, 5.0 μm
Solvent A=$CH_3CN$ (10%)+10 mM $NH_4COOH$ in $H_2O$ (90%)
Solvent B=$CH_3CN$ (90%)+10 mM $NH_4COOH$ in $H_2O$ (10%)
Start % B=10; Final % B=100
Gradient time=20 min; Stop time=27 min
Isocratic time=5 min
Flow Rate=1 mL/min; Wavelength=220 and 254 nm
Condition B-34:
Column=Kinetex C-18, 2.1×50 mm, 2.6 μm
Solvent A=$CH_3CN$ (2%)+0.1% $NH_4COOH$ in $H_2O$ (98%)
Solvent B=$CH_3CN$ (98%)+0.1% $NH_4COOH$ in $H_2O$ (2%)
Start % B=0; Final % B=100
Gradient time=1.7 min; Stop time=4 min
Isocratic time=1.5 min
Flow Rate=1 mL/min; Wavelength=220 nm
Condition B-35:
Column=XBridge Phenyl, 4.6×150 mm, 3.5 μm
Solvent A=Buffer: $CH_3CN$ (95:5)
Solvent B=Buffer: $CH_3CN$ (5:95)
Buffer=0.05% TFA in $H_2O$ (pH 2.5, adjusted with dilute ammonia)
Start % B=10; Final % B=100
Gradient time=12 min; Stop time=18 min
Isocratic time=3 min
Flow Rate=1 mL/min; Wavelength=220 and 254 nm
Condition B-36:
Column=Eclipse XDB C18, 4.6×150 mm, 3.5 μm
Solvent A=10 mM $NH_4OAc$ in $H_2O$
Solvent B=$CH_3CN$
Start % B=10; Final % B=100
Gradient time=12 min; Stop time=17 min
Isocratic time=3 min
Flow Rate=1 mL/min; Wavelength=220 and 254 nm
Condition B-37:
Column=ZORBAX® SB C18, 4.6×50 mm, 3.5 μm
Solvent A=$CH_3CN$ (10%)+20 mM $NH_4OAc$ in $H_2O$ (90%)
Solvent B=$CH_3CN$ (90%)+20 mM $NH_4OAc$ in $H_2O$ (10%)
Start % B=10; Final % B=100
Gradient time=2.0 min; Stop time=3 min
Flow Rate=2.5 mL/min; Wavelength=220 nm
Condition B-38:
Column=Ascentis Express C18, 5×2.1 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.5 min; Stop time=4 min
Flow Rate=1 mL/min; Wave length=220 nm
Condition B-39:
Column=Ascentis Express C18, 5×2.1 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.5 min; Stop time=4 min
Isocratic time=1.7 min
Flow Rate=1 mL/min; Wave length=220 nm
Condition B-40:
Column=Acquity BEH C18, 2.1×50 mm, 1.7 μm
Solvent A=Buffer: $CH_3CN$ (95:5)
Solvent B=Buffer: $CH_3CN$ (5:95)
Buffer=10 mM $NH_4OAc$ in $H_2O$ (pH 5, adjusted with HCOOH)
Start % B=5; Final % B=95
Gradient time=1.1 min; Stop time=2.4 min
Isocratic time=0.6 min
Flow Rate=0.8 mL/min; Wave length=220 nm Condition B-41:
Column: Acquity BEH C18, 2.1×50 mm, 1.7 μm
Solvent A=0.1% TFA in $H_2O$
Solvent B=0.1% TFA in $CH_3CN$
Start % B=2; Final % B=98
Gradient time=1 min; Stop time=2.2 min
Isocratic time=0.6 min
Flow Rate=0.8 mL/min; Wave length=220 nm
Condition B-42:
Column=ZORBAX® SB C18, 4.6×50 mm, 3.5 μm
Solvent A=MeOH (10%)+0.1% TFA in $H_2O$ (90%)
Solvent B=MeOH (90%)+0.1% TFA in $H_2O$ (10%)
Start % B=10; Final % B=100
Gradient time=1.8 min; Stop time=3 min
Isocratic time=0.5 min
Flow Rate=4 mL/min; Wave length=220 nm
Condition B-43:
Column=XBridge BEH C18, 2.1×50 mm, 2.5 μm
Solvent A=$CH_3CN$ (2%)+0.1% TFA in $H_2O$ (98%)
Solvent B=$CH_3CN$ (98%)+0.1% TFA in $H_2O$ (2%)
Start % B=3; Final % B=100
Gradient time=1.3 min; Stop time=3 min
Isocratic time=0.5 min
Flow Rate=1.1 mL/min; Wave length=220 nm
Condition B-44:
Column=POROSHELL® 120, 50×3.0 mm, 2.7 μm
Solvent A=Buffer: $CH_3CN$ (90:10)
Solvent B=Buffer: $CH_3CN$ (10:90)
Buffer=10 mM $NH_4OAc$ in $H_2O$ (pH 5, adjusted with HCOOH)
Start % B=5; Final % B=100
Gradient time=1.5 min; Stop time=3 min
Isocratic time=0.7 min
Flow Rate=1.5 mL/min; Wave length=220 nm
Condition B-45:
Column=Ascentis Express C18, 5×2.1 mm, 2.7 μm
Solvent A=10 mM $NH_4HCO_3$
Solvent B=$CH_3CN$
Start % B=0; Final % B=100
Gradient time=1.7 min; Stop time=4 min
Isocratic time=1.5 min
Flow Rate=1 mL/min; Wave length=220 nm
Condition B-46:
Column=Ascentis Express C18, 5×2.1 mm, 2.7 μm
Solvent A=0.1% HCOOH in $H_2O$
Solvent B=0.07% HCOOH in $CH_3CN$
Start % B=10; Final % B=100
Gradient time=2 min; Stop time=4 min
Isocratic time=1 min
Flow Rate=1.2 mL/min; Wave length=220 nm
Condition B-47:
Column=XBridge BEH C18, 2.1×50 mm, 2.5 μm
Solvent A=$CH_3CN$ (2%)+0.1% TFA in $H_2O$ (98%)
Solvent B=$CH_3CN$ (98%)+0.05% TFA in $H_2O$ (2%)
Start % B=2; Final % B=100
Gradient time=2.6 min; Stop time=4.1 min
Isocratic time=0.6 min
Flow Rate=1.2 mL/min; Wave length=220 nm
Condition B-48:
Column=Inertsil 3 V ODS C18, 20×250 mm, 5 μm
Solvent A=10 mM $NH_4OAc$ in $H_2O$
Solvent B=$CH_3CN$
Start % B=70; Final % B=90
Gradient time=16 min; Stop time=30 min
Isocratic time=9 min
Flow Rate=16 mL/min; Wave length=220 nm Condition B-49:
Column=XBridge Phenyl, 4.6×150 mm, 3.5 μm
Solvent A=10 mM NH$_4$OAc in H$_2$O (pH 5.0)
Solvent B=Methanol
Buffer: 10 mM NH$_4$OAc in H$_2$O
Start % B=20; Final % B=70
Gradient time-1=8 min;
Start % B=70; Final % B=100
Gradient time-2=4 min; Stop time=20 min
Isocratic time=3 min
Flow Rate=1 mL/min; Wave length=220 nm
Condition B-50:
Column=CHIRALCEL® OJH, 250×4.6 mm, 5 μm
Solvent A=n-Hexane
Solvent B=Ethanol
Isocratic=A:B (50:50)
Flow=1 mL/min; Wave length=220 nm
Condition B-51:
Column=SunFire C18, 20×250 mm, 5.0 μm
Solvent A=10 mM NH$_4$OAc in H$_2$O (pH 4.6, adjusted with AcOH)
Solvent B=CH$_3$CN
Start % B=20; Final % B=90
Gradient time=15 min; Stop time=35 min
Flow=15 mL/min; Wave length=220 nm
Condition B-52:
Column=CHIRALCEL® OJH, 250×4.6 mm, 5 μm
Solvent A=CO$_2$
Solvent B=0.3% DEA in MeOH
Isocratic=A:B (40:60)
Flow=3 mL/min; Wave length=220 nm
Condition B-53:
Column=Inertsil ods, 20×250 mm, 5.0 μm
Solvent A=10 mM NH$_4$OAc in H$_2$O
Solvent B=CH$_3$CN
Start % B=15; Final % B=95
Gradient time=14 min; Stop time=25 min
Flow=15 mL/min; Wave length=220 nm
Condition B-54:
Column=Atlantis C18, 19×250 mm, 5.0 μm
Solvent A=10 mM NH$_4$OAc in H$_2$O (pH 4.6, adjusted with AcOH)
Solvent B=CH$_3$CN
Start % B=10; Final % B=80
Gradient time=20 min; Stop time=35 min
Flow=17 mL/min; Wave length=220 nm
Condition B-55:
Column=XSelect C18, 19×250 mm, 5.0 μm
Solvent A=10 mM NH$_4$OAc in H$_2$O (pH 4.6, adjusted with AcOH)
Solvent B=CH$_3$CN
Start % B=20; Final % B=90
Gradient time=15 min; Stop time=25 min
Flow=17 mL/min; Wave length=220 nm
Condition B-56:
Column=XBridge BEH C18, 2.1×50 mm, 2.5 μm
Solvent A=1% HCOOH in H$_2$O
Solvent B=CH$_3$CN
Start % B=5; Final % B=100
Gradient time=2.5 min; Stop time=4 min
Flow=1 mL/min; Wave length=220 nm
Condition B-57:
Column=PHENOMENEX® C18, 19×250 mm, 5 μm
Solvent A=10 mM NH$_4$OAc in H$_2$O (pH 4.5, adjusted with AcOH)
Solvent B=CH$_3$CN
Start % B=6; Final % B=60
Gradient time=20 min; Stop time=35 min
Flow=16 mL/min; Wave length=220 nm
Condition B-58:
Column=SunFire C18, 20×250 mm, 5 μm
Solvent A=10 mM NH$_4$OAc in H$_2$O (pH 4.5, adjusted with AcOH)
Solvent B=CH$_3$CN
Start % B=50; Final % B=90
Gradient time=10 min; Stop time=20 min
Isocratic time=5 min
Flow=16 mL/min; Wave length=220 nm
Condition B-59:
Column=YMC C18, 150×20 mm, 5 μm
Solvent A=10 mM NH$_4$OAc in H$_2$O (pH 4.6, adjusted with AcOH)
Solvent B=CH$_3$CN
Start % B=30; Final % B=70
Gradient time-1=10 min;
Start % B=70; Final % B=100
Gradient time-2=7.1 min; Stop time=20 min
Isocratic time=5 min
Flow=15 mL/min; Wave length=220 nm
Condition B-60:
Column=SYMMETRY® C18, 21.2×250 mm, 7 μm
Solvent A=10 mM NH$_4$OAc in H$_2$O (pH 4.5, adjusted with AcOH)
Solvent B=CH$_3$CN
Start % B=30; Final % B=65
Gradient time=5 min; Stop time=25 min
Flow=16 mL/min; Wave length=220 nm
Condition B-61:
Column=Luna C18, 19×250 mm, 7 μm
Solvent A=10 mM NH$_4$OAc in H$_2$O
Solvent B=CH$_3$CN
Start % B=30; Final % B=100
Gradient time=8 min; Stop time=20 min
Isocratic time=7 min
Flow=16 mL/min; Wave length=220 nm
Condition B-62:
Column=SYMMETRY® C18, 300×19 mm, 7 μm
Solvent A=10 mM NH$_4$OAc in H$_2$O
Solvent B=CH$_3$CN
Start % B=20; Final % B=60
Gradient time=10 min; Stop time=24 min
Flow=16 mL/min; Wave length=220 nm
Condition B-63:
Column=XBridge Phenyl, 4.6×150 mm, 3.5 μm
Solvent A=10 mM NH$_4$HCO$_3$ (pH 9.5, adjusted with dilute NH$_3$)
Solvent B=Methanol
Start % B=10; Final % B=100
Gradient time=25 min; Stop time=30 min
Isocratic time=5 min
Flow=1 mL/min; Wave length=220 nm
Condition B-64:
Column=XTERRA® C18, 250×19 mm, 10 μm
Solvent A=10 mM NH$_4$OAc in H$_2$O (pH 4.5, adjusted with AcOH)
Solvent B=CH$_3$CN
Start % B=30; Final % B=50
Gradient time-1=10 min;
Isocratic time=7 min
Start % B=50; Final % B=100
Gradient time-2=1 min; Stop time=22 min
Flow=16 mL/min; Wave length=220 nm Condition B-65:
Column=CHIRALPAK® OJH, 19×250 mm, 5 μm
Solvent A=n-Hexane
Solvent B=EtOH
Isocratic=A:B (80:20)
Flow=15 mL/min; Wave length=220 nm
Condition B-66:
Column=YMC triat C18, 150×19 mm, 5 μm
Solvent A=10 mM $NH_4OAc$ in $H_2O$
Solvent B=$CH_3CN$
Start % B=60; Final % B=90
Gradient time=10 min; Stop time=19 min
Flow=15 mL/min; Wave length=220 nm
Condition B-67:
Column=Atlantis DC18, 250×19 mm, 10 μm
Solvent A=10 mM $NH_4OAc$ in $H_2O$
Solvent B=$CH_3CN$
Start % B=20; Final % B=75
Gradient time-1=10 min;
Isocratic time=4 min
Start % B=75; Final % B=100
Gradient time=0.2 min; Stop time=23 min
Isocratic time=3.8 min
Flow=15 mL/min; Wave length=220 nm
Condition B-68:
Column=SYMMETRY® C18, 250×19 mm, 7 μm
Solvent A=10 mM $NH_4OAc$ in $H_2O$ (pH 4.5, adjusted with AcOH)
Solvent B=$CH_3CN$
Start % B=50; Final % B=90
Gradient time=10 min; Stop time=19 min
Isocratic time=5 min
Flow=17 mL/min; Wave length=220 nm
Condition B-69:
Column=SunFire C18, 19×150 mm, 5 μm
Solvent A=10 mM $NH_4OAc$ in $H_2O$ (pH 4.5, adjusted with AcOH)
Solvent B=$CH_3CN$
Isocratic=A:B (20:80)
Flow=16 mL/min; Wave length=220 nm
Condition B-70:
Column=Atlantis C18, 19×250 mm, 5 μm
Solvent A=10 mM $NH_4OAc$ in $H_2O$ (pH 4.5, adjusted with AcOH)
Solvent B=$CH_3CN$
Isocratic=A:B (30:70)
Flow=16 mL/min; Wave length=220 nm
Condition B-71:
Column=XSelect C18, 19×150 mm, 5 μm
Solvent A=10 mM $NH_4OAc$ in $H_2O$
Solvent B=$CH_3CN$
Start % B=30; Final % B=70
Gradient time-1=12 min;
Start % B=70; Final % B=100
Gradient time=3 min; Stop time=19 min
Flow=16 mL/min; Wave length=220 nm
Condition B-72:
Column=XBridge C18, 19×150 mm, 5 μm
Solvent A=10 mM $NH_4OAc$ in $H_2O$ (pH 4.5, adjusted with AcOH)
Solvent B=$CH_3CN$
Start % B=30; Final % B=70
Gradient time-1=8 min;
Start % B=70; Final % B=100
Gradient time=7 min; Stop time=19 min
Flow=17 mL/min; Wave length=220 nm Condition B-73:
Column=ODS(19×150 mm), 5.0μ
Solvent A=10 mM ammonium acetate (pH 4.6 adjusted by acetic acid)
Solvent B=$CH_3CN$
Flow=16 mL/min
Start % B=40; Final % B=90
Gradient time=10 min: Stop time=20 min
Condition B-74:
Column=SunFire C18, 4.6×250 mm, 5 μm
Solvent A=Buffer: $CH_3CN$ (90:10)
Solvent B=$CH_3CN$
Buffer=0.05% TFA in $H_2O$
Start % B=10; Final % B=100
Gradient time=21 min; Stop time=27 min
Isocratic time=6 min
Flow=1 mL/min; Wave length=220 nm
Condition B-75:
Column: XBridge prep OBD C18, 19×150 mm, 5 μm
Solvent A=10 mM ammonium acetate in water,
Solvent B=Methanol
Start % B=10; 16 min % B=100: Final % B=10
Gradient time=16 min; Stop time=20 min
Flow: 15 mL/min flow
Condition B-76:
Column=Ascentis Express C18, 2.1×50 mm, 2.7 μm
Solvent A=5% $CH_3CN$-95% $H_2O$ 10 mM $NH_4OAc$,
Solvent B=95% $CH_3CN$-5% $H_2O$ 10 mM $NH_4OAc$
3 min gradient from 0% B to 100% B
UV detection at 220 nm; and a column heater set at 50° C.
Flow=1.1 mL/min flow
Condition B-77:
Column=SYMMETRY® C18, 300×19 mm, 7 μm
Solvent A=10 mM $NH_4OAc$ in $H_2O$ (pH 4.5, adjusted with AcOH)
Solvent B=$CH_3CN$
Start % B=30; Final % B=70
Gradient time-1=10 min;
Start % B=70; Final % B=100
Gradient time-2=10 min;
Isocratic time=5 min
Flow=16 mL/min; Wave length=220 nm
Condition B-78:
Column=Ascentis Express C18, 5×2.1 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.7 min; Stop time=4 min
Isocratic time=1.7 min
Flow Rate=1 mL/min; Wave length=220 nm
Condition B-79:
Column=Ascentis Express C18, 2.1×50 mm, 2.7 g
Solvent A=$CH_3CN$ (5%)+10 mM $NH_4OAc$ in $H_2O$ (95%)
Solvent B=$CH_3CN$ (95%)+10 mM $NH_4OAc$ in $H_2O$ (5%)
Start % B=0; Final % B=100
Gradient time=3.0 min; Stop time=4 min
Flow Rate=1.1 mL/min; Wavelength=220 nm
Condition B-80:
Column=Ascentis Express C18, 2.1×50 mm, 2.7 μm
Solvent A=$CH_3CN$ (2%)+10 mM $NH_4COOH$ in $H_2O$ (98%)
Solvent B=$CH_3CN$ (98%)+10 mM $NH_4COOH$ in $H_2O$ (2%)
Start % B=0; Final % B=100
Gradient time=1.7 min; Stop time=4 min
Isocratic time=1.5 min
Flow Rate=1 mL/min; Wavelength=220 nm Condition B-81:
Column=Ascentis Express C18, 2.1×50 mm, 2.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.7 min; Stop time=4 min
Isocratic time=1.3 min
Flow Rate=1 mL/min; Wavelength=220 nm
Condition B-82:
Column=Ascentis Express C18, 5×2.1 mm, 2.7 μm
Solvent A=0.1% HCOOH in H$_2$O
Solvent B=CH$_3$CN
Start % B=0; Final % B=100
Gradient time=1.7 min; Stop time=4 min
Isocratic time=1.5 min
Flow Rate=1 mL/min; Wave length=220 nm
Condition B-83:
Column=Ascentis Express C18, 2.1×50 mm, 2.7μ
Solvent A=CH$_3$CN (5%)+0.1% TFA in H$_2$O (95%)
Solvent B=CH$_3$CN (95%)+0.1% TFA in H$_2$O (5%)
Start % B=0; Final % B=100
Gradient time=3.0 min; Stop time=4 min
Flow Rate=1.1 mL/min; Wavelength=220 nm
Condition B-84:
Column=Ascentis Express C18, 2.1×50 mm, 1.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=0; Final % B=100
Gradient time=1.5 min; Stop time=4 min
Isocratic time=2.1 min
Flow Rate=1 mL/min; Wavelength=254 nm
Condition B-85:
Column=ZORBAX® SB C18, 3.0×50 mm, 5 μm
Solvent A=10 mM NH$_4$COOH in H$_2$O
Solvent B=CH$_3$CN
Start % B=0; Final % B=100
Gradient time=1.7 min; Stop time=4 min
Isocratic time=2.3 min
Flow Rate=2 mL/min; Wavelength=254 nm
Condition B-86:
Column=Ascentis Express C18, 2.1×50 mm, 1.7 μm
Solvent A=CH$_3$CN (2%)+10 mM NH$_4$COOH in H$_2$O (98%)
Solvent B=CH$_3$CN (98%)+10 mM NH$_4$COOH in H$_2$O (2%)
Start % B=50; Final % B=100
Gradient time=1.7 min; Stop time=4 min
Isocratic time=2.3 min
Flow Rate=1 mL/min; Wavelength=220 nm
Condition B-87:
Column=Ascentis Express C18, 2.1×50 mm, 1.7 μm
Solvent A=10 mM NH$_4$COOH in H$_2$O
Solvent B=CH$_3$CN
Start % B=20; Final % B=100
Gradient time=1.0 min; Stop time=4 min
Isocratic time=2.0 min
Flow Rate=1 mL/min; Wavelength=220 nm
Condition B-88:
Column=XSelect C18, 19×150 mm, 5 μm
Solvent A=10 mM NH$_4$OAc in H$_2$O
Solvent B=CH$_3$CN
Start % B=10; Final % B=70
Gradient time=10 min;
Flow=15 mL/min; Wave length=220 nm
Condition B-89:
Column=XBridge C18, 150×19 mm, 5 μm
Guard Column=XBridge C18, 10×19 mm, 5 μm
Solvent A=Buffer: CH$_3$CN (95:5)
Solvent B=Buffer: CH$_3$CN (5:95)
Buffer=10 mM NH$_4$OAc in H$_2$O
Start % B=10; Final % B=50
Gradient time-1=25 min;
Isocratic time=10 min
Start % B=50; Final % B=100
Gradient time-2=1 min;
Isocratic time=5 min
Flow Rate=15 mL/min; Wave length=220 nm
Condition B-90:
Column=XBridge C18, 150×19 mm, 5 μm
Guard Column=XBridge C18, 10×19 mm, 5 μm
Solvent A=Buffer: CH$_3$CN (95:5)
Solvent B=Buffer: CH$_3$CN (5:95)
Buffer=10 mM NH$_4$OAc in H$_2$O
Start % B=15; Final % B=40
Gradient time-1=25 min;
Isocratic time=10 min
Start % B=40; Final % B=100
Gradient time-2=1 min;
Isocratic time=5 min
Flow Rate=15 mL/min; Wave length=220 nm
Condition B-91:
Column=XBridge C18, 150×19 mm, 5 μm
Guard Column=XBridge C18, 10×19 mm, 5 μm
Solvent A=Buffer: CH$_3$CN (95:5)
Solvent B=Buffer: CH$_3$CN (5:95)
Buffer=10 mM NH$_4$OAc in H$_2$O
Start % B=15; Final % B=70
Gradient time-1=25 min;
Isocratic time=10 min
Start % B=70; Final % B=100
Gradient time-2=1 min;
Isocratic time=5 min
Flow Rate=15 mL/min; Wave length=220 nm
Condition B-92:
Column=CHIRALPAK® ADH, 21.2×250 mm, 5 μm
Solvent A=CO$_2$
Solvent B=0.25% diethylamine in MeOH
Isocratic=A:B (70:30)
Flow=60 g/min; Wave length=210 nm
Condition B-93:
Column=SYMMETRY® C18, 250×19 mm, 7 μm
Solvent A=10 mM NH$_4$OAc in H$_2$O (pH 4.5, adjusted with AcOH)
Solvent B=CH$_3$CN
Start % B=20; Final % B=50
Gradient time=10 min;
Flow=16 mL/min; Wave length=220 nm
Condition B-94:
Column=SYMMETRY® C18, 300×19 mm, 7 μm
Solvent A=10 mM NH$_4$OAc in H$_2$O (pH 4.5, adjusted with AcOH)
Solvent B=CH$_3$CN
Start % B=30; Final % B=70
Gradient time-1=10 min;
Start % B=70; Final % B=100
Gradient time-2=5 min;
Flow=16 mL/min; Wave length=220 nm
Condition B-95:
Column=XBridge C18, 150×19 mm, 5 μm
Guard Column=XBridge C18, 10×19 mm, 5 μm
Solvent A=Buffer: CH$_3$CN (95:5)
Solvent B=Buffer: CH$_3$CN (5:95)
Buffer=10 mM NH$_4$OAc in H$_2$O
Start % B=15; Final % B=50
Gradient time-1=25 min;
Isocratic time=10 min Start % B=70; Final % B=100
Gradient time-2=1 min;
Isocratic time=5 min
Flow Rate=15 mL/min; Wave length=220 nm
Condition B-96:
Column=YMC, 50×19 mm, 5 μm
Solvent A=10 mM $NH_4OAc$ in $H_2O$
Solvent B=$CH_3CN$
Start % B=30; Final % B=70
Gradient time-1=8 min;
Start % B=70; Final % B=100
Gradient time-1=7 min;
Flow=16 mL/min; Wave length=220 nm
Condition B-97:
Column=XBridge C18, 150×19 mm, 5 μm
Guard Column=XBridge C18, 10×19 mm, 5 μm
Solvent A=Buffer: $CH_3CN$ (95:5)
Solvent B=Buffer: $CH_3CN$ (5:95)
Buffer=10 mM $NH_4OAc$ in $H_2O$
Start % B=20; Final % B=80
Gradient time-1=25 min;
Isocratic time=10 min
Start % B=80; Final % B=100
Gradient time-2=1 min;
Isocratic time=5 min
Flow Rate=15 mL/min; Wave length=220 nm
Condition B-98:
Column=SunFire C18, 150×19 mm, 7 μm
Solvent A=10 mM $NH_4OAc$ in $H_2O$ (pH 4.5, adjusted with AcOH)
Solvent B=$CH_3CN$
Start % B=30; Final % B=90
Gradient time=9 min;
Flow=16 mL/min; Wave length=220 nm
Condition B-99:
Column=Gemini C18, 300×19 mm, 7 μm
Solvent A=10 mM $NH_4OAc$ in $H_2O$ (pH 4.5, adjusted with AcOH)
Solvent B=$CH_3CN$
Start % B=50; Final % B=95
Gradient time=15 min;
Flow=16 mL/min; Wave length=220 nm
Condition B-100:
Column=KROMASIL® C18, 19×250 mm, 5 μm
Solvent A=10 mM $NH_4OAc$ in $H_2O$ (pH 4.5, adjusted with AcOH)
Solvent B=$CH_3CN$
Start % B=40; Final % B=80
Gradient time-1=12 min;
Start % B=80; Final % B=100
Gradient time-2=3 min;
Flow=16 mL/min; Wave length=220 nm
Condition B-101:
Column=SunFire C18, 150×20 mm, 5 μm
Solvent A=10 mM $NH_4OAc$ in $H_2O$ (pH 4.5, adjusted with AcOH)
Solvent B=MeOH
Start % B=30; Final % B=70
Gradient time-1=10 min;
Start % B=70; Final % B=100
Gradient time-2=10 min;
Flow=16 mL/min; Wave length=220 nm
Condition B-102:
Column=XBridge C18, 150×19 mm, 5 μm
Solvent A=10 mM $NH_4OAc$ in $H_2O$ (pH 4.5, adjusted with AcOH)
Solvent B=$CH_3CN$
Start % B=30; Final % B=70
Gradient time-1=14 min;
Start % B=70; Final % B=100
Gradient time-2=1 min;
Flow=16 mL/min; Wave length=220 nm
Condition B-103:
Column=XBridge C18, 150×19 mm, 5 μm
Solvent A=10 mM $NH_4OAc$ in $H_2O$ (pH 4.5, adjusted with AcOH)
Solvent B=$CH_3CN$
Start % B=30; Final % B=70
Gradient time-1=10 min;
Start % B=70; Final % B=100
Gradient time-2=5 min;
Flow=16 mL/min; Wave length=220 nm
Condition B-104:
Column=CHIRALPAK® ADH, 4.6×250 mm, 5 μm
Solvent A=$CO_2$
Solvent B=0.3% diethylamine in MeOH
Isocratic=A:B (70:30)
Flow=3 mL/min; Wave length=250 nm
Condition B-105:
Column=CHIRALCEL® ADH, 4.6×250 mm, 5 μm
Solvent A=$CO_2$
Solvent B=0.2% diethylamine in EtOH
Isocratic=A:B (60:40)
Stop time=30 min
Flow=1.0 mL/min; Wave length=220 nm
Condition B-106:
Column=CHIRALPAK® ADH, 4.6×250 mm, 5 μm
Solvent A=$CO_2$
Solvent B=0.2% diethylamine in EtOH
Isocratic=A:B (60:40)
Stop time=30 min
Flow=1.0 mL/min; Wave length=220 nm
Condition B-107:
Column=Kinetex C8, 4.6×150 mm, 2.8 μm
Solvent A=10 mM $NH_4OAc$ in $H_2O$
Solvent B=$CH_3CN$
Start % B=10; Final % B=100
Gradient time=12 min; Stop time=16 min
Isocratic time=3 min
Flow Rate=1 mL/min; Wavelength=220 and 254 nm
Condition B-108:
Column=KROMASIL® packed C18, 19×250 mm, 5 μm
Solvent A=10 mM $NH_4OAc$ in $H_2O$ (pH 4.5, adjusted with AcOH)
Solvent B=$CH_3CN$
Start % B=40; Final % B=70
Gradient time-1=12 min;
Start % B=70; Final % B=100
Gradient time-2=3 min;
Flow=16 mL/min; Wave length=220 nm
Condition B-109:
Column=CHIRALCEL® OJH, 21×250 mm, 5 μm
Solvent A=$CO_2$
Solvent B=0.3% diethylamine in EtOH
Isocratic=A:B (85:15)
Stop time=30 min
Flow=60.0 g/min; Wave length=220 nm
Condition B-110:
Column=CHIRALCEL® OJH, 4.6×250 mm, 5 μm
Solvent A=$CO_2$
Solvent B=0.2% diethylamine in EtOH
Isocratic=A:B (80:20)
Stop time=14 min
Flow=3.0 mL/min; Wave length=220 nm Condition B-111:
Column=YMC Triart, 12×250 mm, 5 μm
Solvent A=10 mM NH$_4$OAc in H$_2$O (pH 4.5, adjusted with AcOH)
Solvent B=CH$_3$CN
Start % B=0; Final % B=50
Gradient time-1=15 min;
Start % B=50; Final % B=100
Gradient time-2=5 min;
Flow=1 mL/min; Wave length=220 nm
Condition B-112:
Column=Atlantis C18, 19×250 mm, 5 μm
Solvent A=10 mM NH$_4$OAc in H$_2$O (pH 4.5, adjusted with AcOH)
Solvent B=CH$_3$CN
Start % B=10; Final % B=50
Gradient time=10 min;
Flow=17 mL/min; Wave length=220 nm
NMR Employed in Characterization of Examples.

$^1$H NMR spectra were obtained with Bruker or JEOL® Fourier transform spectrometers operating at frequencies as follows: $^1$H NMR: 400 MHz or 300 MHz (Bruker) $^{13}$C NMR: 100 MHz or 75 MHz (Bruker). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for CD$_2$HSOCD$_3$, 3.30 ppm for CD$_2$HOD, and 7.24 ppm for CHCl$_3$, and which in $^{13}$C NMR spectra appear at 39.7 ppm for CD$_3$SOCD$_3$, 49.0 ppm for CD$_3$OD, and 77.0 ppm for CDCl$_3$. All $^{13}$C NMR spectra were proton decoupled.

Example 1

5-(4-(Benzylamino)-5-phenylpyrrolo[1,2-f][1,2,4]triazin-2-yl)pyridine-3-sulfonamide

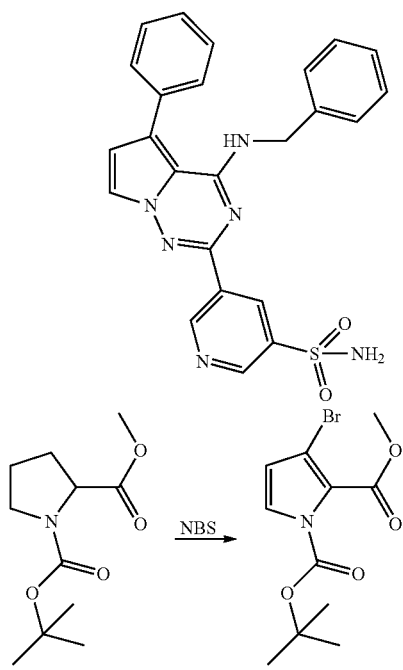

Synthesis was carried out according to the procedure reported: Hasse et al., *Aust. J. Chem.*, 62(7):683-691 (2009). N-Bromo succinimide was recrystallized from water and (100 g, 564 mmol) was added to a solution of 1-tert-butyl 2-methyl pyrrolidine-1,2-dicarboxylate (34.0 g, 148 mmol) in carbon tetrachloride (17 L). The resulting suspension was heated at 85° C. for 2 h. The reaction mixture was cooled to 0° C. and the precipitated succinimide removed by filtration. The filtrate was concentrated under reduced pressure. The oil obtained was subjected to column chromatography (REDISEP®, silica gel, 120 g, 10% EtOAc/hexanes), gave 1-tert-butyl 2-methyl 3-bromo-1H-pyrrole-1,2-dicarboxylate (18.0 g, 39.1%) as an orange liquid. $^1$H NMR (400 MHz, CD$_3$OD) δ ppm 1.53 (s, 9H), 3.32 (s, 3H), 6.46 (d, J=3.6 Hz, 1H), 7.44 (d, J=3.6 Hz, 1H).

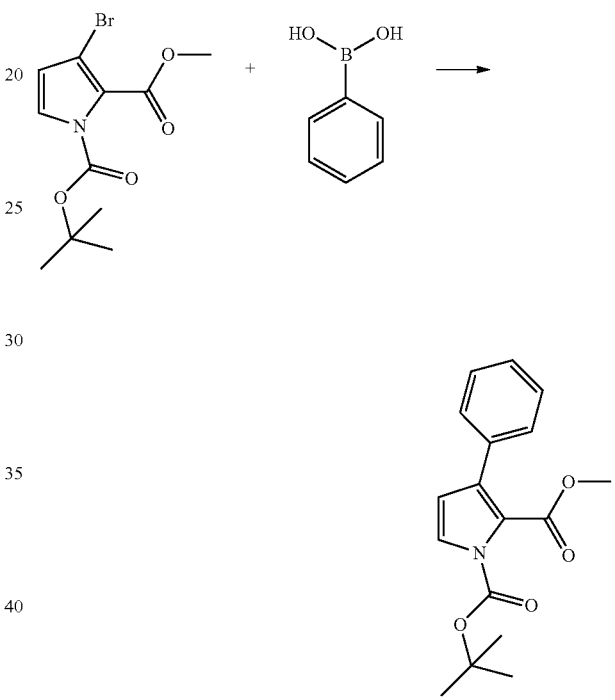

To a solution of 1-tert-butyl 2-methyl 3-bromo-1H-pyrrole-1,2-dicarboxylate (17.6 g, 57.9 mmol) in toluene (200 mL) and water (200 mL) was added K$_2$CO$_3$ (64.0 g, 463 mmol), followed by phenylboronic acid (10.6 g, 87.0 mmol) and tetrabutylammonium bromide (1.68 g, 5.21 mmol). The reaction mixture degassed for 10 min with nitrogen and then tetrakis(triphenylphosphine)palladium (1.34 g, 1.16 mmol) was added. The resulting slurry was degassed with nitrogen for 30 min and then heated to reflux for 16 h. The reaction mixture was concentrated under reduced pressure to remove water and toluene. Water was then added to the residue and the mixture extracted by ethyl acetate. The combined organic layers were dried over sodium sulfate, filtered and concentrated under reduced pressure. The residue was purified by column chromatography using CombiFlash (REDISEP®, silica gel, 80 g, 20% EtOAc/hexanes) to obtain 1-tert-butyl 2-methyl 3-phenyl-1H-pyrrole-1,2-dicarboxylate (11.5 g, 65.9%) as a tan solid. $^1$H NMR (400 MHz, CD$_3$OD) δ ppm 1.60 (s, 9H), 3.79 (s, 3H), 6.40 (d, J=3.4 Hz, 1H), 7.37 (m, 6H).

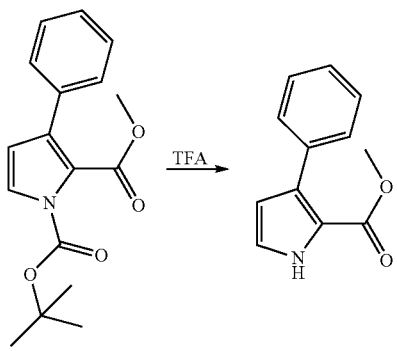 [SMILES: COC(=O)c1c(-c2ccccc2)ccn1C(=O)OC(C)(C)C ; COC(=O)c1[nH]ccc1-c1ccccc1 ; "TFA"]

1-tert-Butyl 2-methyl 3-phenyl-1H-pyrrole-1,2-dicarboxylate (18.0 g, 59.7 mmol) was dissolved in CH$_2$Cl$_2$ (20 mL) and cooled to 0° C. TFA (23.0 mL, 0.299 mmol) was added to the reaction mixture and the solution stirred at room temperature for 14 h. The reaction mixture was concentrated under reduced pressure to remove excess of TFA. To the resulting residue was added 10% sodium bicarbonate solution (50 mL) and the aqueous portion extracted with CH$_2$Cl$_2$. The organic layer was separated, dried over sodium sulfate, filtered and concentrated under reduced pressure. The residue was purified by column chromatography using CombiFlash (REDISEP®, silica gel, 40 g, 30% EtOAc/hexanes) to obtain methyl 3-phenyl-1H-pyrrole-2-carboxylate (7.50 g, 62.4%). $^1$H NMR (400 MHz, DMSO-d$_6$) δ ppm 3.69 (s, 3H), 6.29 (t, J=2.8 Hz, 1H), 7.02 (d, J=2.8 Hz, 1H), 7.03 (m, 5H), 12.0 (s, 1H).

Synthesis of Monochloramine Reagent

Ammonium chloride (3.00 g, 56.1 mmol) was dissolved in ether (110 mL) and the solution cooled to −5° C. Concentrated ammonium hydroxide (28.0 M, 4.70 mL, 120 mmol) was added dropwise. Commercial bleach that is sodium hypochorite (2M, 72.0 mL, 0.144 mol) was added via addition funnel over 15 min. The reaction mixture was stirred for 15 min, the layers were separated and the organic layer was washed with brine. The organic layer was dried over powdered CaCl$_2$ in a freezer for 1 h and stored at −40° C. The approximate concentration of monochloramine is 0.15 M.

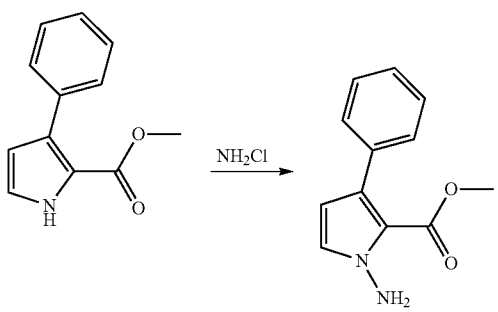

To a solution of methyl 3-phenyl-1H-pyrrole-2-carboxylate (2.50 g, 12.4 mmol) in DMF (25 mL) was added NaH (0.358 g, 14.9 mmol) and the reaction mixture was stirred for 45 min at room temperature. Monochloramine (0.15 M, 150 mL, 0.225 g, 4.40 mmol) was added via syringe. The reaction was stirred for 2 h and was quenched by the addition of saturated aqueous sodium thiosulfite. The reaction mixture was diluted with water and the aqueous portion extracted with ethyl acetate. The organic layer dried over anhydrous sodium sulfate, filtered and concentrated under reduced pressure. The residue was purified by column chromatography using CombiFlash (REDISEP®, neutral alumina, 40 g, 25% EtOAc/hexanes) to afford methyl 5-amino-2-phenylcyclopenta-1,3-dienecarboxylate (2.20 g, 82.0%). LCMS Condition B-38: retention time 1.79 min, [M+1]=217.0. $^1$H NMR (400 MHz, DMSO-d$_6$) δ ppm 3.63 (s, 3H), 6.07 (d, J=2.8 Hz, 1H), 6.28 (s, 2H), 7.05 (d, J=2.8 Hz, 1H), 7.33-7.35 (m, 5H).

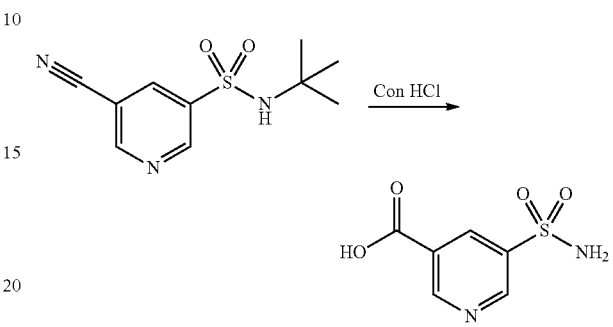

To N-(tert-butyl)-5-cyanopyridine-3-sulfonamide (10.0 g, 41.8 mmol) (Johnson et al., WO 2011/28741) was added concentrated HCl (100 mL, 3.29 mol). The reaction mixture was heated to 110° C. for 14 h and concentrated under reduced pressure to remove HCl. Water (10 mL) was added to the residue and the slurry was filtered. The solid obtained was washed with diethyl ether and dried under vacuum. (5-Sulfamoyl)nicotinic acid, (5.50 g, 65.1%) was further dried and used without further purification in the next step. LCMS Condition B-12: retention time 0.75 min, [M+1]=202.7. $^1$H NMR (400 MHz, DMSO-d$_6$) δ ppm 7.72 (s, 2H), 8.62 (dd, J=2.2 Hz, J=2.0 Hz, 1H), 9.16 (d, J=2.2 Hz, 1H), 9.25 (d, J=2 Hz, 1H), 13.9 (s, 1H).

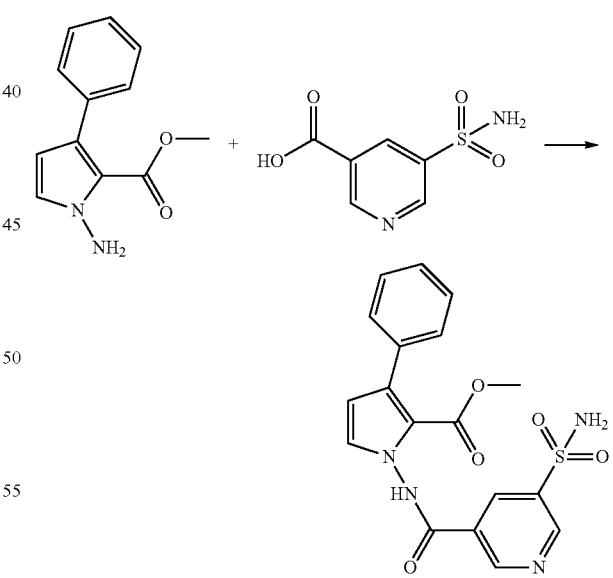

To a stirred solution of methyl 1-amino-3-phenyl-1H-pyrrole-2-carboxylate (2.00 g, 9.25 mmol) in DMF (20 mL) was added DMAP (3.39 g, 27.7 mmol) and HATU (10.6 g, 27.7 mmol). The reaction mixture was stirred for 15 minutes and a solution of 5-sulfamoylnicotinic acid (3.74 g, 18.5 mmol) dissolved in DMF was added. The reaction mixture was stirred at room temperature for 14 h. The reaction mixture was concentrated under reduced pressure to remove DMF and saturated solution of citric acid was added to the residue until the pH was 3. The solution was extracted with CH$_2$Cl$_2$ and the organic layer was separated, dried over sodium sulfate, filtered and concentrated under reduced pressure. The residue was purified by column chromatography using CombiFlash (REDISEP®, neutral alumina, 40 g, 13% methanol in CH$_2$Cl$_2$) to afford methyl 3-phenyl-1-(5-sulfamoylnicotinamido)-1H-pyrrole-2-carboxylate (1.20 g, 32.4%). LCMS Condition B-39: retention time 1.79 min, [M−1]=399.0. $^1$H NMR (400 MHz, DMSO-d$_6$) δ ppm 3.54 (s, 3H), 6.34 (d, J=3.2 Hz, 1H), 7.32-7.44 (m, 7H), 7.80 (br s, 2H), 8.68 (t, J=2.0 Hz, 1H), 9.20 (d, J=2.0 Hz, 1H), 9.30 (d, J=2.0 Hz, 1H).

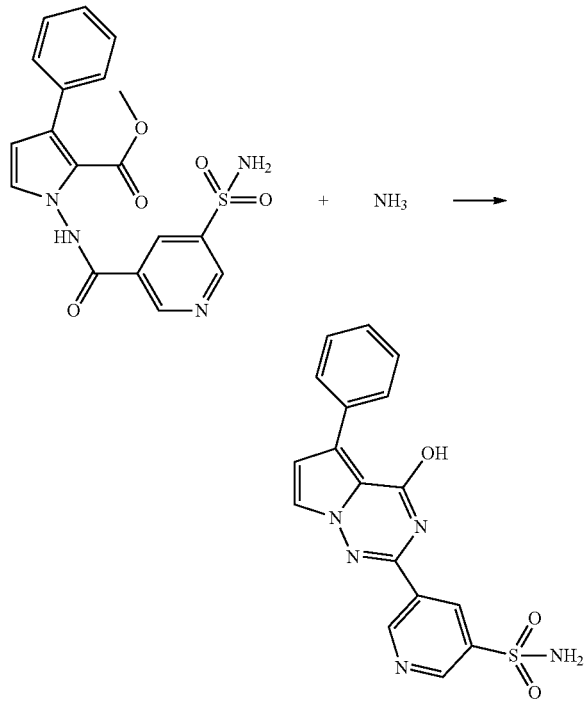

Methyl 3-phenyl-1-(5-sulfamoylnicotinamido)-1H-pyrrole-2-carboxylate (1.20 g, 4.30 mmol) was taken in a pressure tube and NH$_4$OH (100 mL, 3.00 mol) solution was added. Then the reaction mixture was heated to 110° C. for 48 h. The reaction mixture was concentrated under reduced pressure to remove water and then azeotroped 3 times with toluene. The crude solid was triturated successively with ethyl acetate (5 mL) and methanol (2 mL). The solid was dried under vacuum to afford 3-(4-oxo-5-phenyl-1,2,3,4-tetrahydropyrrolo[2,1-f][1,2,4]triazin-2-yl)benzenesulfonamide (0.300 g, 27.0%). The crude compound was taken as such for the next step. LCMS Condition B-39: retention time 1.81 min, [M−1]=368.0.

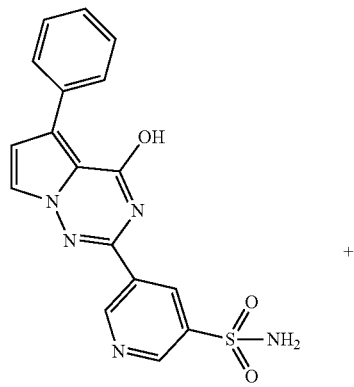

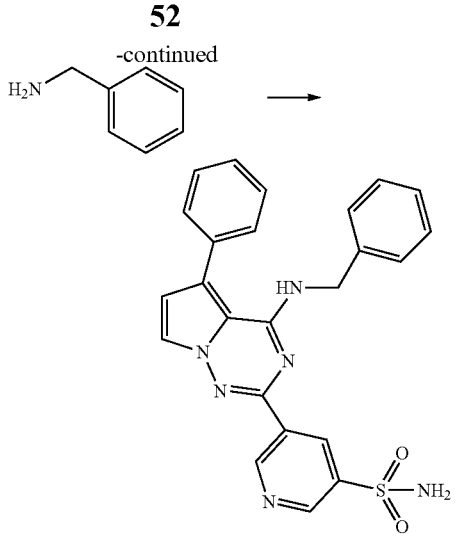

5-(4-Hydroxy-5-phenylpyrrolo[2,1-f][1,2,4]triazin-2-yl)pyridine-3-sulfonamide (0.100 g, 0.272 mmol) was dissolved in THF (10 mL) and BOP reagent (0.181 g, 0.408 mmol) and DIPEA (0.143 mL, 0.817 mmol) were added. The reaction mixture was stirred at room temperature for 30 min. Benzylamine (0.0440 g, 0.408 mmol) in THF (3 mL) was added and the reaction mixture was stirred at room temperature for 14 h. The reaction mixture was concentrated under reduced pressure and water was added (30 mL). The resulting aqueous solution was extracted with ethyl acetate. The organic layer was separated, dried over anhydrous sodium sulfate, filtered and concentrated under reduced pressure. The residue was purified by prep HPLC (Condition B-61 as described in general methods) to obtain 5-(4-(benzylamino)-5-phenylpyrrolo[2,1-f][1,2,4]triazin-2-yl)pyridine-3-sulfonamide (0.0250 g, 20.1%). LCMS Condition B-38: retention time 2.08 min, [M+1]=457.2. HPLC Condition B-5: retention time 20.11 min, Purity 97.00%. $^1$H NMR (400 MHz, DMSO-d$_6$) δ ppm 4.84 (d, J=5.6 Hz, 2H), 6.76 (t, J=5.6 Hz, 1H), 6.84 (d, J=2.8 Hz, 1H), 7.30 (t, J=7.2 Hz, 1H), 7.34 (t, J=7.6 Hz, 2H), 7.40-7.45 (m, 3H), 7.48 (t, J=7.6 Hz, 2H), 7.55 (dd, J=1.6, J=3.4 Hz, 2H), 7.68 (br s, 2H), 7.95 (d, J=2.4 Hz, 1H), 8.94 (t, J=2.2 Hz, 1H), 9.05 (d, J=2.4 Hz, 1H), 9.53 (d, J=1.6 Hz, 1H).

Example 2

5-(5-Phenyl-4-(pyridin-2-ylmethylamino)pyrrolo[1,2-f][1,2,4]triazin-2-yl)pyridine-3-sulfonamide

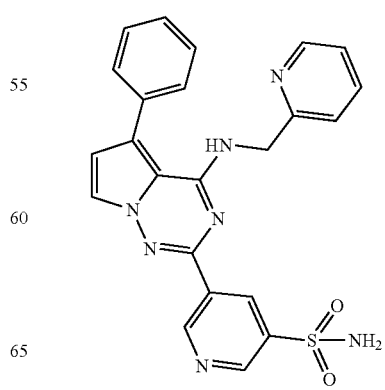

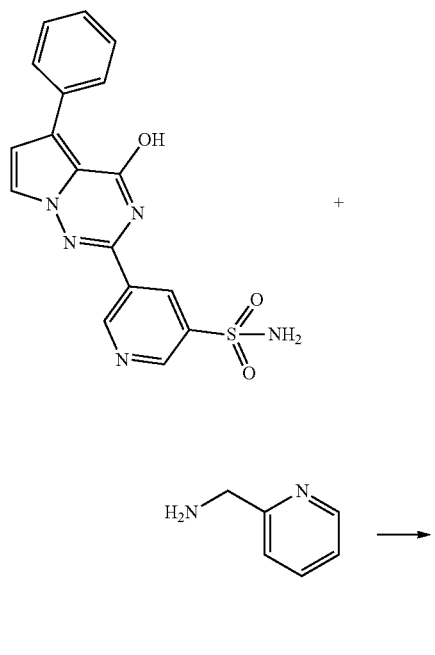

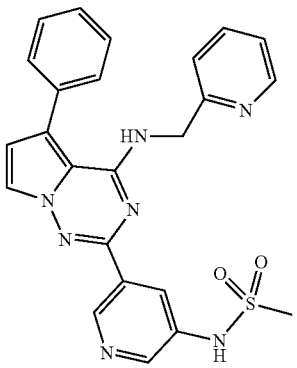

5-(4-Hydroxy-5-phenylpyrrolo[2,1-f][1,2,4]triazin-2-yl)pyridine-3-sulfonamide (0.150 g, 0.408 mmol) was dissolved in THF (10 mL) and BOP reagent (0.271 g, 0.612 mmol) and DIPEA (0.214 mL, 1.23 mmol) were added. The reaction mixture was stirred at room temperature for 30 min. Pyridin-2-ylmethanamine (0.0660 g, 0.612 mmol) in THF (3 mL) was added to the reaction mixture and the resulting mixture was stirred at room temperature for 14 h. The reaction mixture was concentrated under reduced pressure and water was added to the residue. The aqueous layer was extracted with ethyl acetate (25×2 mL). The organic layer was dried (with anhydrous sodium sulfate), filtered and concentrated under reduced pressure. The residue was purified by CombiFlash (REDISEP®, silica gel, 40 g, 3% methanol in CH$_2$Cl$_2$) to afford 5-(5-phenyl-4-((pyridin-2-ylmethyl)amino)pyrrolo[2,1-f][1,2,4]triazin-2-yl)pyridine-3-sulfonamide (0.0400 g, 21.4%). LCMS Condition B-38: retention time 1.99 min, [M+1]=458.2. HPLC Condition B-32: retention time 7.75 min, Purity 98.90%. $^1$H NMR (400 MHz, DMSO-d$_6$) δ ppm 4.94 (d, J=4.4 Hz, 2H), 6.85 (d, J=2.8 Hz, 1H), 7.29 (dd, J=5.2 Hz, J=6.8 Hz, 1H), 7.42 (t, J=4.6 Hz, 1H), 7.46-7.50 (m, 2H), 7.52-7.56 (m, 2H), 7.60 (dd, J=2.0 Hz, J=6.8 Hz, 2H), 7.75 (s, 2H), 7.79 (dt, J=1.6 Hz, J=7.6 Hz, 1H), 7.96 (d, J=2.8 Hz, 1H), 8.39 (dd, J=0.8 Hz, J=1.6 Hz, 1H), 8.94 (t, J=2.0 Hz, 1H), 9.07 (d, J=2.4 Hz, 1H), 9.58 (d, J=2.0 Hz, 1H).

Example 3

N-(5-(5-Phenyl-4-(pyridin-2-ylmethylamino)pyrrolo[1,2-f][1,2,4]triazin-2-yl)pyridin-3-yl)methanesulfonamide

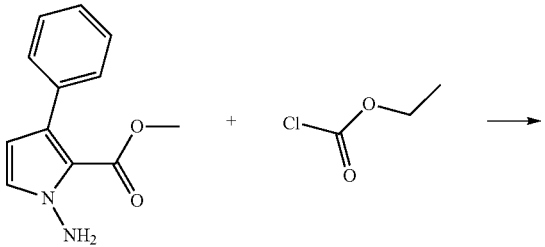

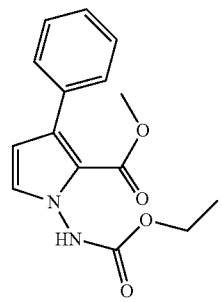

Methyl 1-amino-3-phenyl-1H-pyrrole-2-carboxylate (0.200 g, 0.925 mmol) was dissolved in CH$_2$Cl$_2$ (20 mL) and then was added TEA (0.387 mL, 2.77 mmol), followed by ethylchloroformate (0.0890 mL, 0.925 mmol). The reaction mixture was stirred at room temperature for overnight. Water (50 mL) was added to reaction mixture and the aqueous mixture was extracted with CH$_2$Cl$_2$ (25×2 mL). The organic layer separated and dried over anhydrous sodium sulfate and concentrated under reduced pressure. The residue was purified by silica gel column chromatography using CombiFlash (REDISEP®, silica gel, 24 g, 15% EtOAc/hexanes) to afford methyl 1-((ethoxycarbonyl)amino)-3-phenyl-1H-pyrrole-2-carboxylate (0.100 g, 37.5%). LCMS Condition B-39: retention time 2.14 min, [M+1]=289.0.

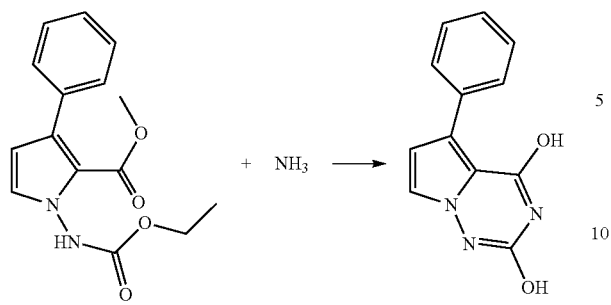 + NH₃ →

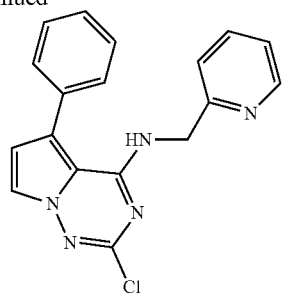

Methyl 1-((ethoxycarbonyl)amino)-3-phenyl-1H-pyrrole-2-carboxylate (1.00 g, 3.47 mmol) was taken in a pressure tube and ammonium hydroxide (30%, 67.5 mL, 1.73 mol) was added and sealed. The reaction mixture was stirred at 110° C. for 30 h and transferred to a round bottomed flask and concentrated under reduced pressure. Toluene was added to it and azeotroped to remove trace amount of water (3 times). Then residue obtained was triturated with ethyl acetate (50×2 mL) to afford 5-phenylpyrrolo[2,1-f][1,2,4]triazine-2,4(1H,3H)-dione (0.300 g, 38.1%). LCMS Condition B-39: retention time 1.49 min, [M+1]=228.0.

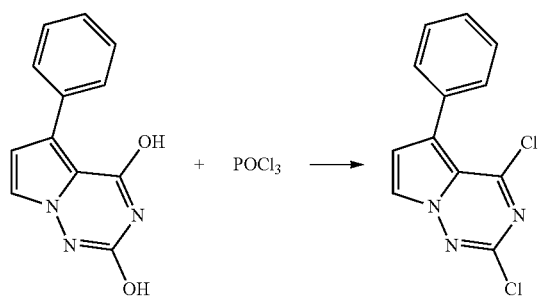

5-Phenylpyrrolo[2,1-f][1,2,4]triazine-2,4(1H,3H)-dione (0.250 g, 1.10 mmol) dissolved in toluene (5 mL) and was taken in a pressure tube. To this mixture was added DIPEA (0.384 mL, 2.20 mmol), followed by the addition of POCl₃ (0.308 mL, 3.30 mmol). The pressure tube was closed tightly and was heated to 125° C. and maintained at the same temperature for 24 h. The reaction mass was cooled to room temperature and the contents were slowly added to the ice cold solution of sodium bicarbonate and extracted with CH₂Cl₂ (25×2 mL). The organic layer dried over anhydrous sodium sulfate and concentrated under reduced pressure. The residue was purified by column chromatography using CombiFlash (REDISEP®, silica gel, 24 g, 0.5% methanol in CH₂Cl₂) to afford 2,4-dichloro-5-phenylpyrrolo[2,1-f][1,2,4]triazine (0.0850 g, 29.3%). LCMS Condition B-9: retention time 2.11 min, [M+1]=264.0.

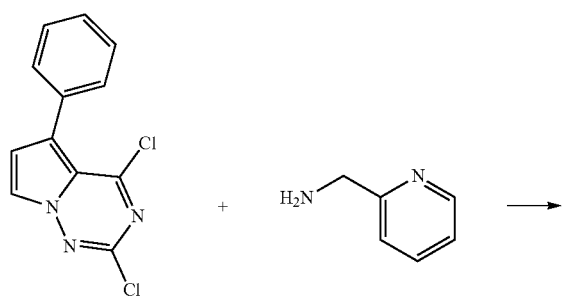

2,4-Dichloro-5-phenylpyrrolo[2,1-f][1,2,4]triazine (0.560 g, 2.12 mmol) was dissolved in THF (15 mL) and then DIPEA (1.85 mL, 10.6 mmol) was added followed by the addition of pyridin-2-ylmethanamine (0.688 g, 6.36 mmol). Then the reaction mixture was stirred at room temperature for 14 h. The reaction mixture was concentrated under reduced pressure to remove THF and to this residue water (10 mL) added. The aqueous solution was extracted with CH₂Cl₂ (25×3 mL) and the organic layer was separated, dried over anhydrous sodium sulfate and was concentrated under reduced pressure. The residue was purified by column chromatography using CombiFlash (REDISEP®, silica gel, 40 g, 20% EtOAc/hexanes) to afford 2-chloro-5-phenyl-N-(pyridin-2-ylmethyl)pyrrolo[2,1-f][1,2,4]triazin-4-amine (0.250 g, 35.1%). LCMS Condition B-39: retention time 2.10 min, [M+1]=336.0.

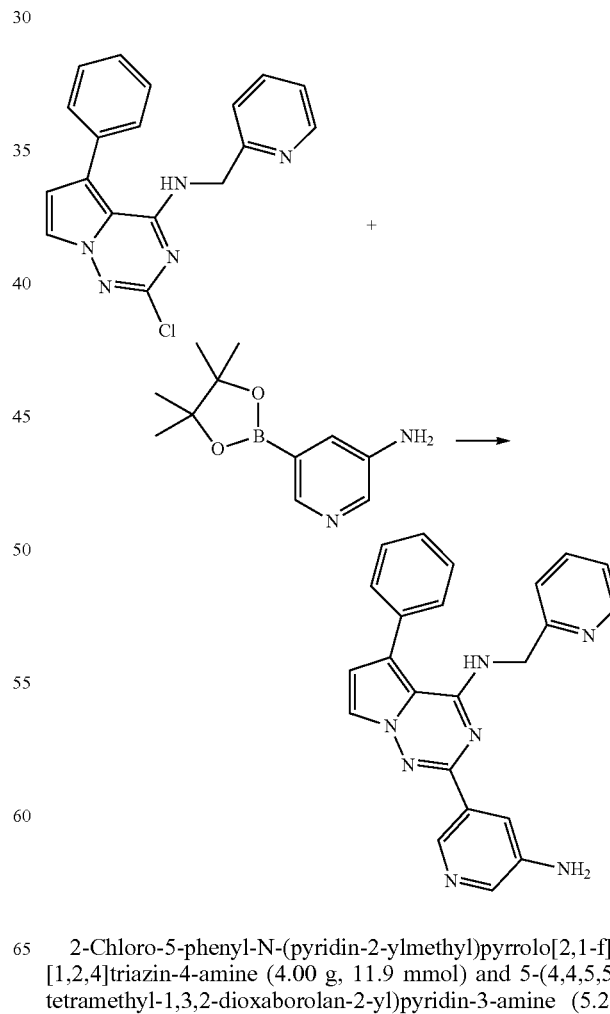

2-Chloro-5-phenyl-N-(pyridin-2-ylmethyl)pyrrolo[2,1-f][1,2,4]triazin-4-amine (4.00 g, 11.9 mmol) and 5-(4,4,5,5-tetramethyl-1,3,2-dioxaborolan-2-yl)pyridin-3-amine (5.24 g, 23.8 mmol, commercial) were dissolved in dioxane (50 mL) and water (3 mL). To the reaction mixture was added K$_2$CO$_3$ (6.59 g, 47.6 mmol) and the reaction mixture was degassed with nitrogen for 15 minutes.
Bis(diphenylphosphino)ferrocene-palladium(II)dichloride dichloromethane complex (0.973 g, 1.19 mmol) was added and the resulting reaction mixture degassed with nitrogen for 20 minutes then heated to reflux at 110° C. for 14 h. The reaction mixture was cooled and concentrated under reduced pressure. The residue was diluted with CH$_2$Cl$_2$ and filtered through CELITE®. The filtrate was dried over anhydrous sodium sulfate, filtered and concentrated under reduced pressure. The residue was purified by column chromatography using CombiFlash (REDISEP®, silica gel, 24 g, 0.5% methanol in CH$_2$Cl$_2$) to afford 5.0 g of impure 2-(5-aminopyridin-3-yl)-5-phenyl-N-(pyridin-2-ylmethyl)pyrrolo[2,1-f][1,2,4] triazin-4-amine which was further purified by preparative HPLC (Condition B-61 as described in general methods) to afford 2-(5-aminopyridin-3-yl)-5-phenyl-N-(pyridin-2-ylmethyl)pyrrolo[2,1-f][1,2,4]triazin-4-amine (3.00 g, 64.0%). LCMS Condition B-12: retention time 1.92 min, [M+1]=394.4. HPLC Condition B-32: retention time 5.87 min, Purity 97.80%. $^1$H NMR (400 MHz, DMSO-d$_6$) δ ppm 4.91 (d, J=4.8 Hz, 2H), 5.46 (s, 2H), 6.79 (d, J=2.4 Hz, 1H), 7.24 (t, J=2.8 Hz, 1H), 7.27-7.31 (m, 1H), 7.44-7.60 (m, 6H), 7.75 (dd, J=2.0 Hz, J=2.8 Hz, 1H), 7.79 (dt, J=2.0 Hz, J=7.6 Hz, 1H), 7.85 (d, J=2.8 Hz, 1H), 8.01 (d, J=2.4 Hz, 1H), 8.39 (ddd, J=1.2 Hz, J=2.8 Hz, J=5.2 Hz, 1H), 8.60 (d, J=1.6 Hz, 1H).

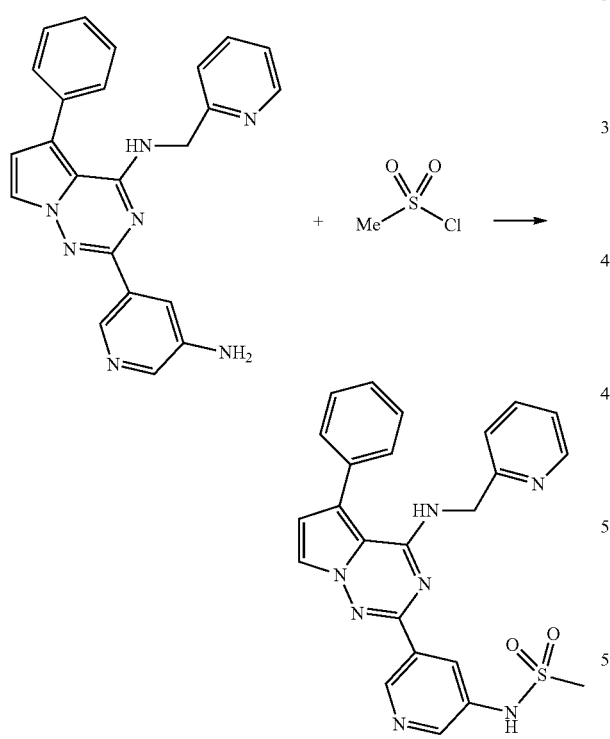

2-(5-Aminopyridin-3-yl)-5-phenyl-N-(pyridin-2-ylmethyl)pyrrolo[2,1-f][1,2,4]triazin-4-amine (80.0 mg, 0.201 mmol) was dissolved in CH$_2$Cl$_2$ (10 mL) and pyridine (0.0500 mL, 0.610 mmol) was added, followed by methanesulfonyl chloride (26.0 mg, 0.221 mmol). The reaction mixture was stirred at room temperature for 3 h then diluted with water (10 mL) and the aqueous solution was extracted with CH$_2$Cl$_2$ (25×2 mL). The combined organic layer was dried over sodium sulfate, filtered and concentrated under reduced pressure. The residue was purified by preparative HPLC (Condition B-64 as described in general methods) to obtain N-(5-(5-phenyl-4-((pyridin-2-ylmethyl)amino)pyrrolo[2,1-f][1,2,4]triazin-2-yl)pyridin-3-yl)methanesulfonamide (20.0 mg, 20.0%). LCMS Condition B-39: retention time 2.02 min, [M+1]=471.80. HPLC Condition B-32: retention time 6.96 min, Purity 99.40%. $^1$H NMR (400 MHz, DMSO-d$_6$) δ ppm 3.11 (s, 3H), 4.92 (d, J=4.8 Hz, 2H), 6.82 (d, J=2.8 Hz, 1H), 7.31 (dd, J=4.4 Hz, J=8.8 Hz, 2H), 7.46-7.61 (m, 8H), 7.79 (dt, J=2.0 Hz, J=7.6 Hz, 1H), 7.92 (d, J=2.8 Hz, 1H), 8.40 (d, J=4.0 Hz, 1H), 8.44 (t, J=2.4 Hz, 1H), 9.15 (d, J=2.0 Hz, 1H).

Example 4

N1-(5-(4-(Benzylamino)-5-phenylpyrrolo[1,2-f][1,2,4]triazin-2-yl)pyridin-3-yl)malonamide

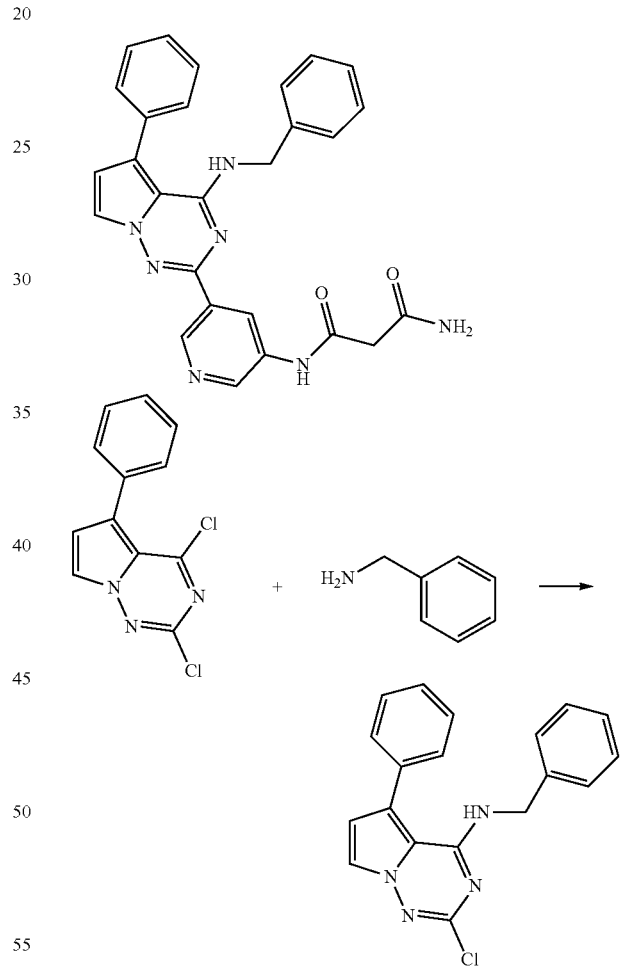

2,4-Dichloro-5-phenylpyrrolo[2,1-f][1,2,4]triazine (0.500 g, 1.89 mmol) was dissolved in THF (10 mL) then was added DIPEA (1.65 mL, 9.47 mmol), followed by benzylamine (0.406 g, 3.79 mmol). Then the reaction mixture was stirred at room temperature for 2 h. The reaction mixture was concentrated under reduced pressure to remove THF. To this residue, water (10 mL) was added and the aqueous solution was extracted with CH$_2$Cl$_2$ (25×3 mL). The organic layer was separated and dried over anhydrous sodium sulfate and concentrated under reduced pressure. The residue was purified by column chromatography using CombiFlash (REDISEP®, silica gel, 24 g, 11% EtOAc/hexanes) to afford N-benzyl-2-chloro-5-phenylpyrrolo[2,1-f][1,2,4]triazin-4-amine (0.400 g, 63.1%). LCMS Condition B-47: retention time 2.70 min, [M+1]=335.0.

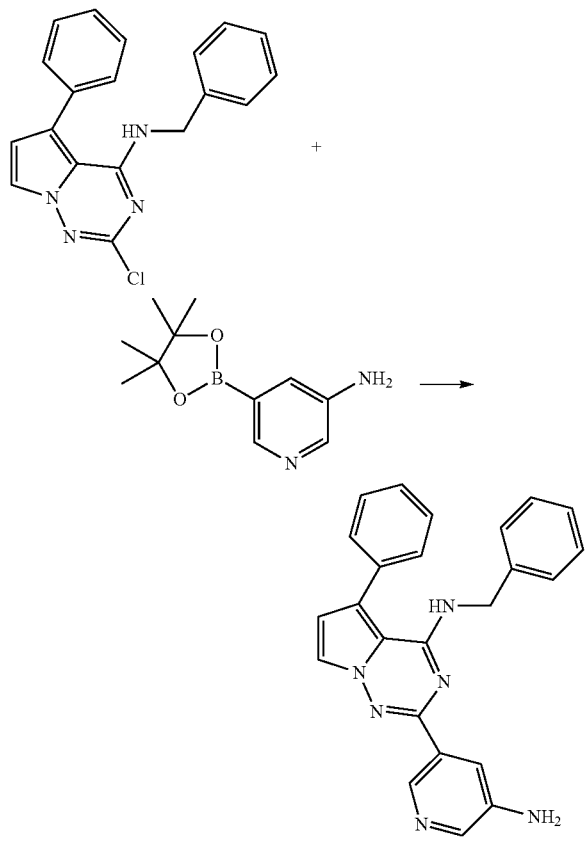

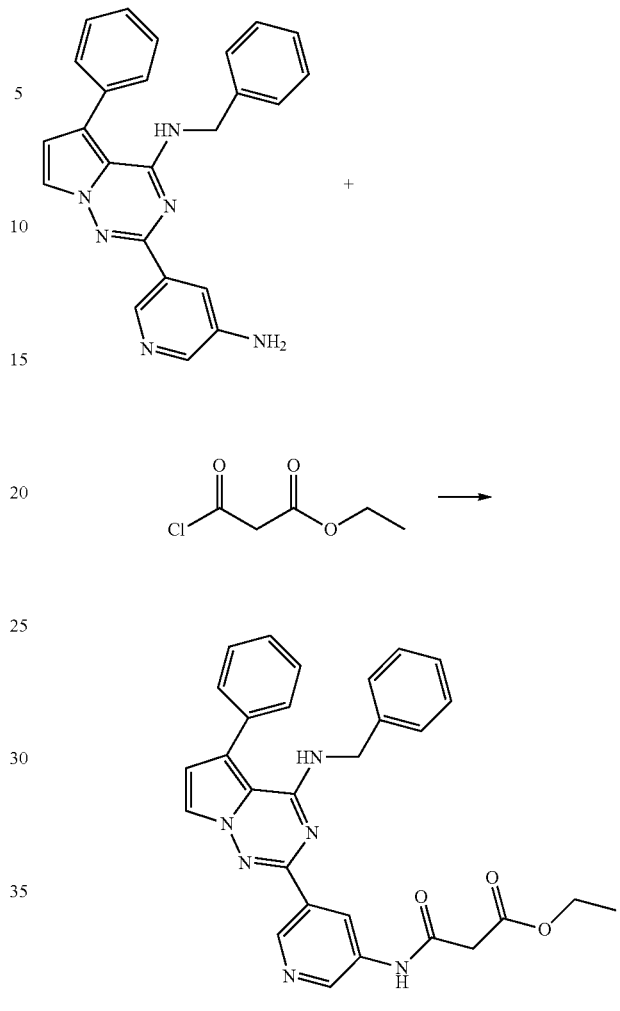

N-Benzyl-2-chloro-5-phenylpyrrolo[2,1-f][1,2,4]triazin-4-amine (0.200 g, 0.597 mmol) and 5-(4,4,5,5-tetramethyl-1,3,2-dioxaborolan-2-yl)pyridin-3-amine (0.263 g, 1.20 mmol, commercial) were dissolved in dioxane (10 mL) and water (2 mL). To the above solution was added $K_2CO_3$ (0.248 g, 1.79 mmol) and the reaction mixture was degassed with nitrogen for 15 minutes then $PdCl_2(dppf)\text{-}CH_2Cl_2$ (0.0490 g, 0.0600 mmol) was added. The resulting reaction mixture was degassed for 20 minutes and heated to reflux at 110° C. for 14 h. The reaction mixture was allowed to cool, concentrated under reduced pressure and diluted with $CH_2Cl_2$ (10 mL). The resulting solid was filtered through a CELITE® bed and the filtrate dried over anhydrous sodium sulfate, filtered and concentrated under reduced pressure. The residue was purified by preparative HPLC (Condition B-62 as described in general methods) to afford 2-(5-aminopyridin-3-yl)-N-benzyl-5-phenylpyrrolo[2,1-f][1,2,4]triazin-4-amine (20.0 mg, 8.53%). $^1$H NMR (400 MHz, DMSO-$d_6$) δ ppm 4.81 (d, J=6.0 Hz, 2H), 5.46 (s, 2H), 6.54 (t, J=6.0 Hz, 1H), 6.78 (d, J=2.8 Hz, 1H), 7.26-7.54 (m, 10H), 7.75 (dd, J=2.0 Hz, J=2.8 Hz, 1H), 7.85 (d, J=2.4 Hz, 1H), 8.01 (d, J=2.8 Hz, 1H), 8.58 (d, J=1.6 Hz, 1H). LCMS Condition B-47: retention time 2.20 min, [M+1]=393.2. HPLC Condition B-63: retention time 24.18 min, Purity 97.00%.

2-(5-Aminopyridin-3-yl)-N-benzyl-5-phenylpyrrolo[2,1-f][1,2,4]triazin-4-amine (0.500 g, 1.27 mmol) was dissolved in $CH_2Cl_2$ (10 mL) and pyridine (0.103 mL, 1.27 mmol) was added, followed by the addition of ethyl 3-chloro-3-oxopropanoate (0.192 g, 1.27 mmol). The reaction mixture was stirred at room temperature for 14 h. Water (10 mL) was added to the reaction mixture followed by addition of $CH_2Cl_2$ (10×4 mL). The combined organic extracts were dried over sodium sulfate, filtered and concentrated under reduced pressure. The residue was purified by column chromatography using CombiFlash (REDISEP®, silica gel, 24 g, 3% methanol in $CH_2Cl_2$) to afford ethyl 3-((5-(4-(benzylamino)-5-phenylpyrrolo[2,1-f][1,2,4]triazin-2-yl)pyridin-3-yl)amino)-3-oxopropanoate (0.400 g, 62.0%). $^1$H NMR (400 MHz, DMSO-$d_6$) δ ppm 1.23 (t, J=7.2 Hz, 3H), 3.54 (s, 2H), 4.15 (q, J=7.2 Hz, 2H), 4.82 (d, J=5.6 Hz, 2H), 6.66 (t, J=5.6 Hz, 1H), 6.81 (d, J=2.8 Hz, 1H), 7.27-7.55 (m, 10H), 7.91 (d, J=2.8 Hz, 1H), 8.81 (d, J=2.4 Hz, 1H), 8.87 (dd, J=2.4 Hz, J=1.6 Hz, 1H), 9.09 (d, J=1.6 Hz, 1H), 10.52 (s, 1H). LCMS Condition B-49: retention time 1.91 min, [M+1]=507.2. HPLC Condition B-32: retention time 10.36 min, Purity 98.80%.

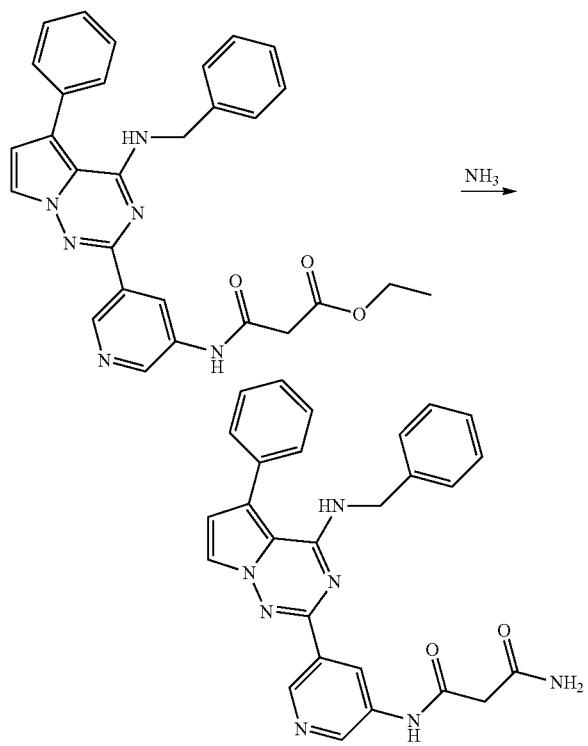

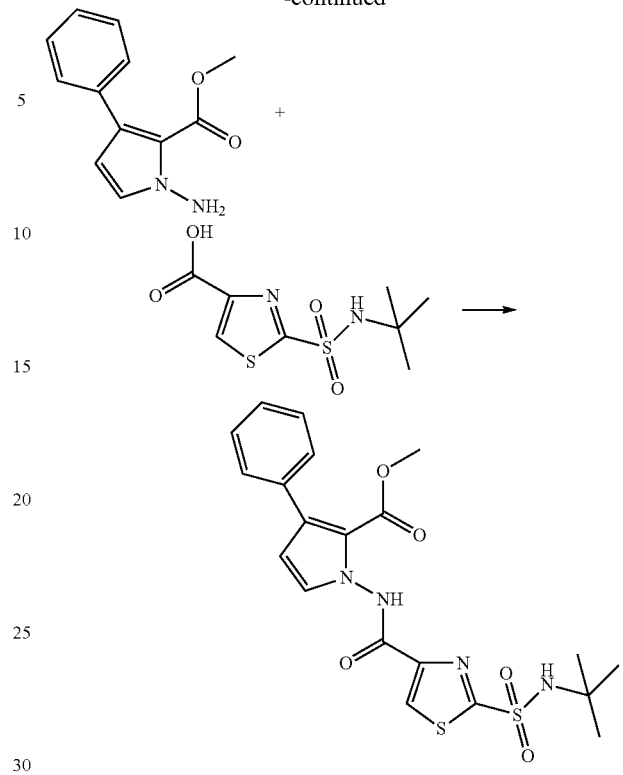

Ethyl 3-((5-(4-(benzylamino)-5-phenylpyrrolo[2,1-f][1,2,4]triazin-2-yl)pyridin-3-yl)amino)-3-oxopropanoate (0.200 g, 0.395 mmol) was dissolved in ethanol (10 mL) and transferred to a pressure tube, then cooled to −80° C. The reaction mixture was purged with ammonia gas for 15 minutes, then the pressure tube was tightly closed and heated to 85° C. for 24 h. The reaction mixture was allowed to cool and transferred in to a round bottomed flask and concentrated under reduced pressure to remove ethanol completely. The residue was purified by preparative HPLC (by the Condition B-64 as described in general methods) to obtain N1-(5-(4-(benzylamino)-5-phenylpyrrolo[2,1-f][1,2,4]triazin-2-yl)pyridin-3-yl)malonamide (0.100 g, 53.1%). $^1$H NMR (400 MHz, DMSO-$d_6$) δ ppm 3.29 (s, 2H), 4.82 (d, J=5.6 Hz, 2H), 6.65 (t, J=5.6 Hz, 1H), 6.80 (d, J=2.8 Hz, 1H), 7.15-7.56 (m, 12H), 7.90 (d, J=2.8 Hz, 1H), 8.83 (d, J=2.4 Hz, 1H), 8.87 (dd, J=1.6 Hz, J=2.4 Hz, 1H), 9.07 (d, J=1.6 Hz, 1H), 10.47 (s, 1H). LCMS Condition B-39: retention time 1.97 min, [M+1]=477.8. HPLC Condition B-31: retention time 8.85 min, Purity 99.80%.

Example 5

4-(5-Phenyl-4-(pyridin-2-ylmethylamino)pyrrolo[1,2-f][1,2,4]triazin-2-yl)thiazole-2-sulfonamide

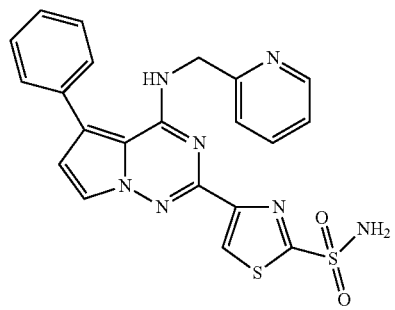

Methyl 1-amino-3-phenyl-1H-pyrrole-2-carboxylate (0.400 g, 1.85 mmol) and 2-(N-(tert-butyl)sulfamoyl)thiazole-4-carboxylic acid (0.733 g, 2.77 mmol) (Johnson et al., WO 2011/28741) were dissolved in DMF (10 mL) and cooled to 0° C. HATU (1.41 g, 3.70 mmol) was added slowly, followed by DIPEA (1.29 mL, 7.40 mmol). The reaction mixture was allowed to reach ambient temperature over 14 h and was diluted with water (25 mL) and extracted with ethylacetate (3×20 mL). The organic layer was separated and the combined organic portions dried over anhydrous sodium sulfate, filtered and concentrated under reduced pressure. The residue was purified by column chromatography using CombiFlash (REDISEP®, silica gel, 40 g, 38% EtOAc/hexanes) to afford methyl 1-(2-(N-(tert-butyl)sulfamoyl)thiazole-5-carboxamido)-3-phenyl-1H-pyrrole-2-carboxylate (0.250 g, 29.2%). $^1$H NMR (400 MHz, DMSO-$d_6$) δ ppm 1.26 (s, 9H), 3.50 (s, 3H), 6.31 (d, J=3.2 Hz, 1H), 7.25-7.43 (m, 6H), 8.39 (s, 1H), 8.77 (s, 1H), 11.83 (s, 1H).

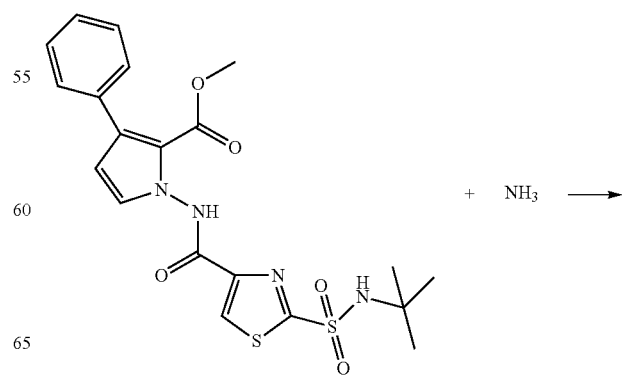

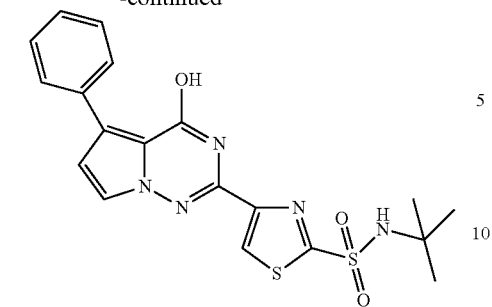

Methyl 1-(2-(N-(tert-butyl)sulfamoyl)thiazole-5-carboxamido)-3-phenyl-1H-pyrrole-2-carboxylate (0.250 g, 0.540 mmol) was dissolved in aqueous ammonium hydroxide (30 M, 5.00 mL, 0.150 mol) and heated to 100° C. in a sealed tube for 16 h. The reaction mixture was allowed to cool and evaporated under reduced pressure. The crude residue was purified by preparative HPLC (Condition B-53 as described in general methods) to afford N-(tert-butyl)-4-(4-hydroxy-5-phenylpyrrolo[2,1-f][1,2,4]triazin-2-yl)thiazole-2-sulfonamide (0.0650 g, 28.0%). LCMS Condition B-13: retention time 2.06 min, [M−1]=428.2.

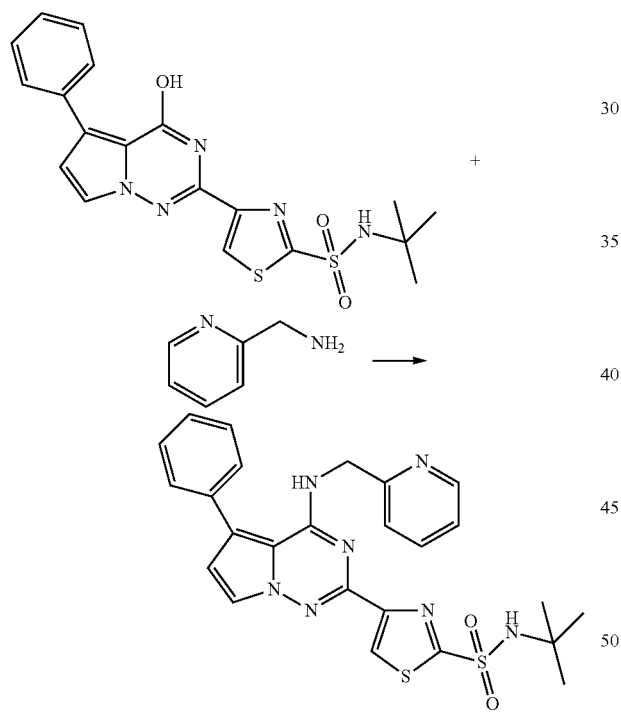

N-(tert-Butyl)-4-(4-hydroxy-5-phenylpyrrolo[2,1-f][1,2,4]triazin-2-yl)thiazole-2-sulfonamide (0.0600 g, 0.140 mmol) was dissolved in acetonitrile (5 mL) and cooled to 0° C. BOP reagent (0.0620 g, 0.140 mmol) was added slowly, followed by DBU (0.0210 mL, 0.140 mmol). The reaction mixture was allowed to reach ambient temperature for 1 h then cooled to 0° C. Pyridin-2-ylmethanamine was added, (0.0150 g, 0.140 mmol). The reaction mixture was allowed to reach ambient temperature and stir for 14 h and diluted with water. The aqueous mixture was extracted with ethyl acetate (3×10 mL). The combined organic extracts were dried with anhydrous sodium sulfate, filtered and evaporated under reduced pressure. The residue was purified by column chromatography using CombiFlash (REDISEP®, silica gel, 40 g, 1.2% methanol in CH$_2$Cl$_2$) to afford N-(tert-butyl)-4-(5-phenyl-4-((pyridin-2-ylmethyl)amino)pyrrolo[2,1-f][1,2,4]triazin-2-yl)thiazole-2-sulfonamide (0.0400 g, 55.0%). The impure compound was taken to the next step as such. LCMS Condition B-13: retention time 2.13 min, [M+1]=520.2.

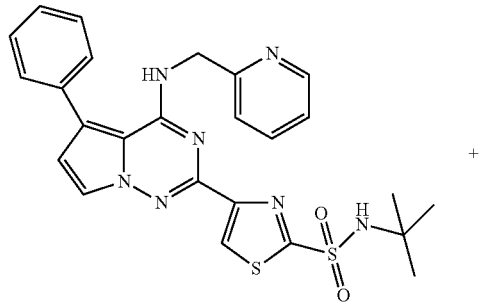

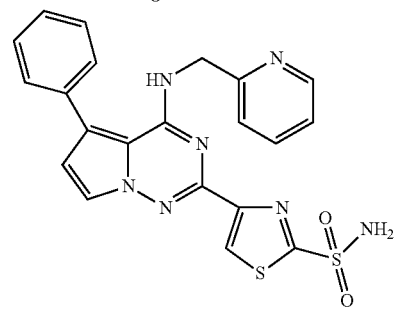

N-(tert-Butyl)-4-(5-phenyl-4-((pyridin-2-ylmethyl)amino)pyrrolo[2,1-f][1,2,4]triazin-2-yl)thiazole-2-sulfonamide (40.0 mg, 0.0770 mmol) and TFA (3 mL) were stirred at ambient temperature for 14 h. The excess TFA was evaporated under reduced pressure and the residue purified by preparative HPLC (Condition B-33 as described in general methods) to obtain 4-(5-phenyl-4-((pyridin-2-ylmethyl)amino)pyrrolo[2,1-f][1,2,4]triazin-2-yl)thiazole-2-sulfonamide (9.00 mg, 26.0%). LCMS Condition B-13: retention time 1.94 min, [M+1]=464.0. HPLC Condition B-32: retention time 7.06 min, Purity 97.62%. $^1$H NMR (400 MHz, DMSO-d$_6$): δ ppm 4.91 (d, J=4.4 Hz, 2H), 6.82 (d, J=2.8 Hz, 1H), 7.27-7.31 (m, 2H), 7.43-7.61 (m, 6H), 7.79 (dt, J=2.0 Hz, J=8.0 Hz, 1H), 7.90 (d, J=2.8 Hz, 1H), 8.24 (s, 2H), 8.39-8.40 (m, 1H), 8.63 (s, 1H).

Example 6

5-(5-(4-Fluorophenyl)-4-(pyridin-2-ylmethylamino)pyrrolo[1,2-f][1,2,4]triazin-2-yl)pyridine-3-sulfonamide

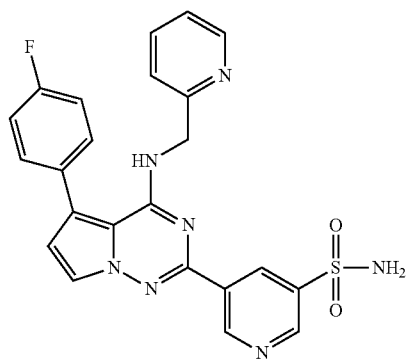

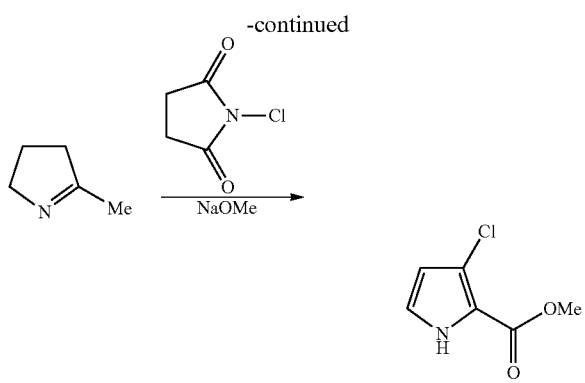

The commercially available methyl 3-chloro-1H-pyrrole-2-carboxylate (1.50 g, 94.0%, yellow solid) was synthesized according to Fang et al., *J. Med. Chem.*, 53:7967-7978 (2010) using 2-methyl-1-pyrroline (0.831 g, 10.0 mmol, commercial), NCS (10.7 g, 80.0 mmol) and NaOMe in MeOH (3M, 20 mL, 60.0 mmol). LCMS Condition B-41: retention time 1.71 min, [M+1]=160.10. $^1$H NMR (400 MHz, CDCl$_3$) δ 3.90 (s, 3H), 6.25 (t, J=3.0 Hz, 1H), 6.86 (t, J=3.0 Hz, 1H), 9.17 (br s, 1H).

Synthesis of Monochloramine Reagent

Ammonium chloride (3.00 g, 60.0 mmol) was dissolved in ether (110 mL) and the solution cooled to −5° C. Concentrated ammonium hydroxide (28 M, 4.70 mL, 120 mmol) was added dropwise. Commercial bleach that is sodium hypochlorite (2M, 72.0 mL, 0.144 mol) was added via addition funnel over 15 min. The reaction mixture was stirred for 15 min, the layers were separated and the organic layer was washed with brine. The organic layer was dried over powdered CaCl$_2$ in a freezer for 1 h and stored at −40° C. The approximate concentration of monochloramine is 0.15 M.

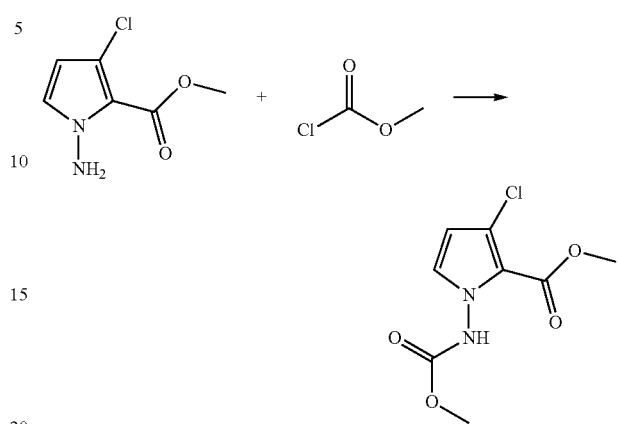

NMR (400 MHz, DMSO-d$_6$) δ 3.80 (s, 3H), 6.11 (d, J=2.8 Hz, 1H), 6.28 (s, 2H), 7.06 (d, J=2.8 Hz, 1H).

To a stirred solution of methyl 1-amino-3-phenyl-1H-pyrrole-2-carboxylate (1.00 g, 4.62 mmol) in DCM (25 mL) was added pyridine (0.450 mL, 5.55 mmol). The contents were stirred at ambient temperature for 5 min. Methyl chloroformate (0.390 mL, 5.09 mmol) was added dropwise to the reaction mixture and stirring continued for 1 h. The reaction mixture was washed with 1.5 N HCl and the organic layer was separated, dried over anhydrous Na$_2$SO$_4$ filtered and concentrated to give a brown oil (1.10 g, 84.0%), which was then taken to the next step without further purification. LCMS Condition B-23: retention time 0.73 min, [M+1]=233.0. $^1$H NMR (400 MHz, DMSO-d$_6$) δ ppm 3.76 (s, 3H), 3.79 (s, 3H), 6.28 (d, J=3.2 Hz, 1H), 7.23 (d, J=3.2 Hz, 1H), 10.69 (br s, 1H).

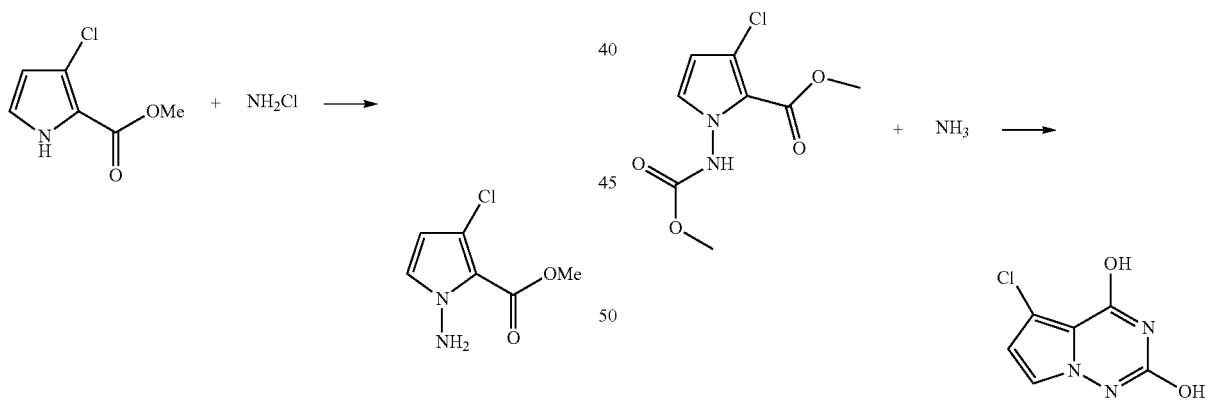

To a stirred solution of methyl 3-chloro-1H-pyrrole-2-carboxylate (1.00 g, 6.30 mmol) in DMF (15 mL) was added NaH (0.45 g, 18.80 mmol, 99%, dry) and the contents were stirred for 1 h at ambient temperature. NH$_2$Cl (42.0 mL, 0.327 g, 6.30 mmol) was added at −10° C. to the reaction mixture and the contents were stirred for another 30 min at −10° C. The solvents were removed under reduced pressure and the residue was extracted with MTBE. The MTBE layer was passed through anhydrous Na$_2$SO$_4$ and concentrated under reduced pressure to give a brown solid. The crude residue was purified by CombiFlash (REDISEP®, silica gel, 40 g, 20% EtOAc/hexanes) to give a methyl 1-amino-3-chloro-1H-pyrrole-2-carboxylate (0.750 g, 69.0%) as a yellow solid. LCMS Condition B-23: retention time 0.68 min, [M+1]=175.1. $^1$H Methyl 3-chloro-1-((methoxycarbonyl)amino)-1H-pyrrole-2-carboxylate (5.00 g, 21.5 mmol) in MeOH (15 mL)/water (35 mL) was taken in a pressure tube and the reaction mixture was cooled to −80° C. The reaction mixture was purged with NH$_3$ gas for 5-10 min. The pressure tube was closed and heated at 120° C. for 12 h. The solvents were removed under reduced pressure to give a brown solid which was recrystallized with MeOH to gave 5-chloropyrrolo[1,2-f][1,2,4]triazine-2,4-diol (2.65 g, 65.0%) as a white solid. LCMS Condition B-23: retention time 0.56 min, [M+1]=186.0. $^1$H NMR (400 MHz, DMSO-d$_6$) δ ppm 6.87 (d, J=2.6 Hz, 1H), 7.10 (d, J=2.8 Hz, 1H), 7.32 (br s, 2H).

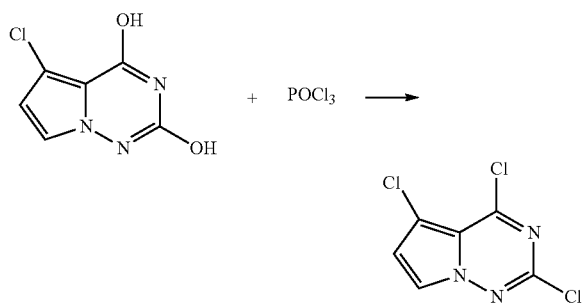

To a stirred solution of 5-chloropyrrolo[2,1-f][1,2,4]triazine-2,4(1H,3H)-dione (0.500 g, 2.69 mmol) in toluene (15 mL) was added POCl$_3$ (1.01 mL, 10.8 mmol) and DIPEA (0.941 mL, 5.39 mmol). The contents were stirred at 120° C. for 24 h. The reaction mixture was concentrated under reduced pressure, redissolved in CH$_2$Cl$_2$ (50 mL) and washed with 10% NaHCO$_3$ (2×25 mL). The organic layer was separated and dried over anhydrous Na$_2$SO$_4$, filtered and concentrated under reduced pressure to give a yellow solid. The residue was purified by column chromatography using CombiFlash (REDISEP®, silica gel, 24 g, 20% EtOAc/hexanes) to give 2,4,5-trichloropyrrolo[2,1-f][1,2,4]triazine (0.320 g, 53.0%) as yellow solid. LCMS Condition B-23: retention time 1.67, [M+1]=220.0. $^1$H NMR (400 MHz, DMSO-d$_6$) δ ppm 7.63 (d, J=3.2 Hz, 1H), 8.34 (d, J=3.2 Hz, 1H).

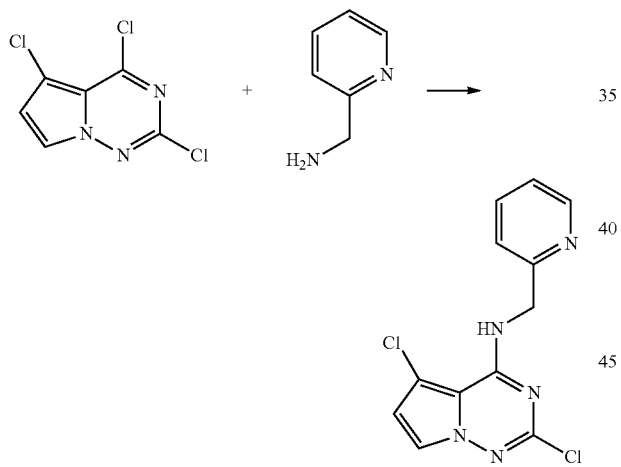

To a stirred solution of 2,4,5-trichloropyrrolo[2,1-f][1,2,4]triazine (0.530 g, 2.38 mmol) in CH$_2$Cl$_2$ (20 mL) was added DIPEA (0.832 mL, 4.76 mmol) and pyridin-2-ylmethanamine (0.283 g, 2.62 mmol) and the contents were stirred for 10 min at room temperature. The reaction mixture was washed with water and the organic layer was separated, dried over anhydrous Na$_2$SO$_4$, filtered and concentrated under reduced pressure to give a brown solid. The residue was purified by column chromatography using CombiFlash (REDISEP®, silica gel, 24 g, 20% EtOAc/hexanes) to give 2,5-dichloro-N-(pyridin-2-ylmethyl)pyrrolo[2,1-f][1,2,4]triazin-4-amine (0.400 g, 57.0%) as an off-white solid. LCMS Condition B-12: retention time 2.20, [M+1]=294.2. $^1$H NMR (400 MHz, DMSO-d$_6$) δ ppm 4.87 (d, J=5.7 Hz, 2H), 6.81 (d, J=2.8 Hz, 1H), 7.32 (t, J=1.6 Hz, 1H), 7.42 (d, J=8.0 Hz, 1H), 7.81 (d, J=2.8 Hz, 1H), 7.83 (t, J=1.6 Hz, 1H), 8.48 (t, J=5.2 Hz, 1H), 8.57 (d, J=1.2 Hz, 1H).

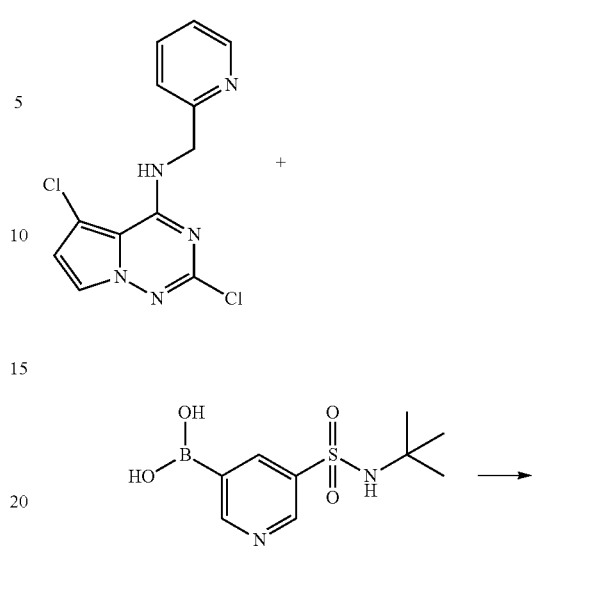

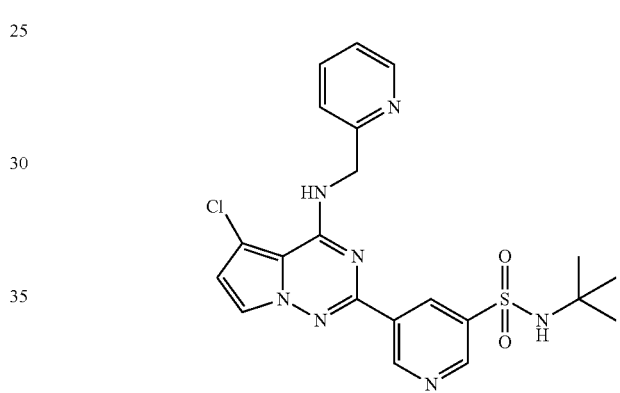

2,5-Dichloro-N-(pyridin-2-ylmethyl)pyrrolo[2,1-f][1,2,4]triazin-4-amine (0.120 g, 0.408 mmol) was converted to N-(tert-butyl)-5-(5-chloro-4-((pyridin-2-ylmethyl)amino)pyrrolo[2,1-f][1,2,4]triazin-2-yl)pyridine-3-sulfonamide via Suzuki cross-coupling using the conditions mentioned in Example 3. Following reagents were used for the conversion; (5-(N-(tert-butyl)sulfamoyl)pyridin-3-yl)boronic acid (0.158 g, 0.612 mmol), K$_2$CO$_3$ (0.169 g, 1.22 mmol) and 1,1'-bis(diphenylphosphino)ferrocene-palladium(II)dichloride dichloromethane complex (90.0 mg, 0.122 mmol) at 95° C. for 5 h. The residue was purified by column chromatography using CombiFlash (REDISEP®, silica gel, 12 g, 50% EtOAc/hexanes) to give the product as yellow solid. The product was further purified by recrystallization using 30% CH$_2$Cl$_2$ in hexane to afford N-(tert-butyl)-5-(5-chloro-4-((pyridin-2-ylmethyl)amino)pyrrolo[2,1-f][1,2,4]triazin-2-yl)pyridine-3-sulfonamide (65.0 mg, 33.8%) as an off-white solid. LCMS Condition B-23: retention time 2.00 min, [M+1]=572.2. $^1$H NMR (400 MHz, DMSO-d$_6$) δ ppm 1.16 (s, 9H), 5.02 (d, J=5.2 Hz, 2H), 6.87 (d, J=2.9 Hz, 1H), 7.29-7.31 (m, 2H), 7.78 (t, J=5.6 Hz, 1H), 7.91-7.98 (m, 2H), 8.36 (t, J=5.2 Hz, 1H), 8.57 (m, 1H), 8.82 (s, 1H), 9.05 (d, J=2.0 Hz, 1H), 9.31 (d, J=1.8 Hz, 1H).

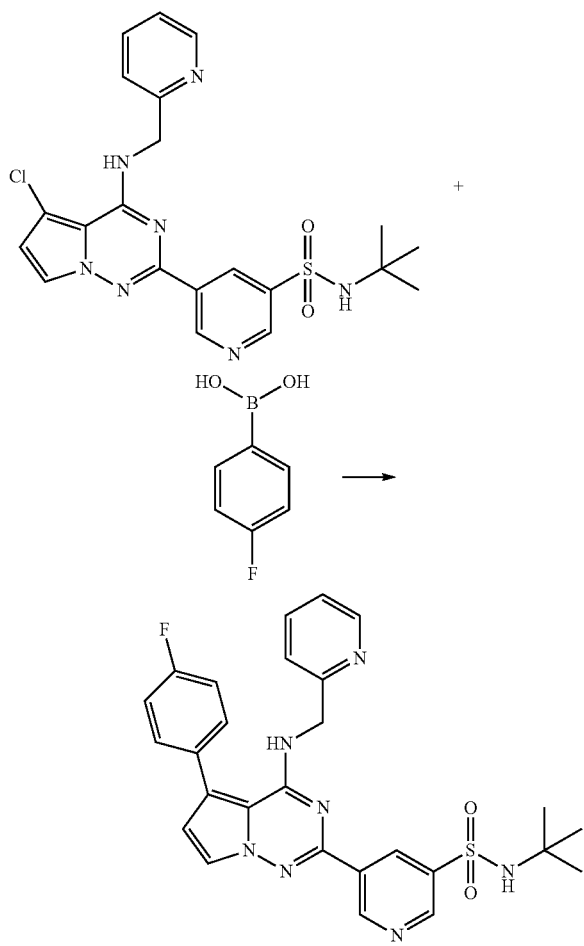

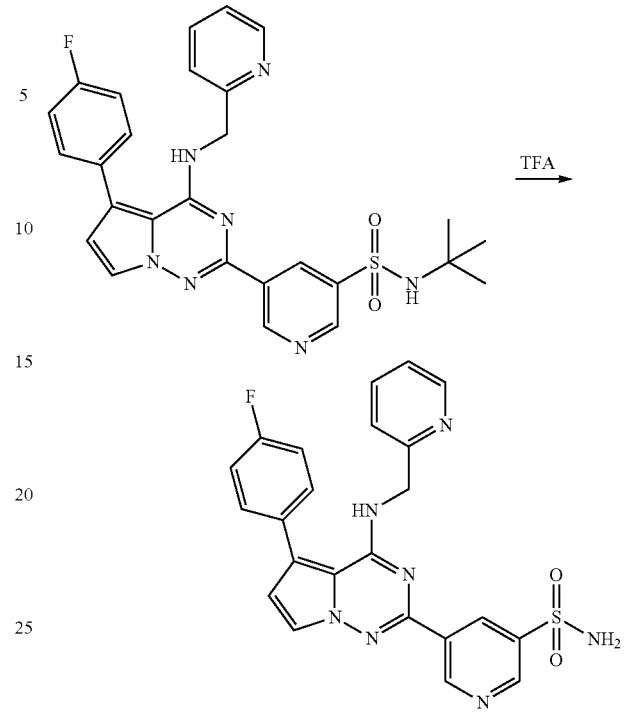

To a stirred solution of N-(tert-butyl)-5-(5-chloro-4-((pyridin-2-ylmethyl)amino)pyrrolo[2,1-f][1,2,4]triazin-2-yl)pyridine-3-sulfonamide (50.0 mg, 0.106 mmol) in dioxane (10 mL)/water (4 mL) was added (4-fluorophenyl)boronic acid (14.8 mg, 0.106 mmol, commercial), $K_2CO_3$ (43.9 mg, 0.318 mmol) and X-PHOS (15.2 mg, 0.0320 mmol). The contents were purged with nitrogen for 5 min. Palladium(II) acetate (2.38 mg, 0.0106 mmol) was added to the reaction mixture and the contents were heated to 95° C. for a period of 5 h. The reaction was allowed to cool, filtered through a pad of CELITE® and the filtrate was concentrated under reduced pressure to give a brown solid. The residue was purified by silica gel column chromatography using Combi-Flash (REDISEP®, silica gel, 12 g, 20% methanol in $CH_2Cl_2$) to give product as a pale yellow solid. The solid was further purified by recrystallization using $CH_2Cl_2$/hexane (3:7) to give N-tert-butyl-5-(5-(4-fluorophenyl)-4-(pyridin-2-ylmethylamino)pyrrrol[1,2-f][1,2,4]triazin-2-yl)pyridine-3-sulfonamide (32.0 mg, 54.0%) as a pale yellow solid. LCMS Condition B-23: retention time 2.32, [M+1]=532.2. $^1$H NMR (400 MHz, DMSO-$d_6$) δ ppm 1.55 (s, 9H), 4.93 (d, J=4.0 Hz, 2H), 6.84 (d, J=2.8 Hz, 1H), 7.28-7.47 (m, 5H), 7.59-7.60 (m, 1H), 7.61-7.64 (m, 2H), 7.77 (t, J=1.80 Hz, 1H), 7.91 (d, J=2.7 Hz, 1H), 8.39-8.41 (m, 1H), 8.91 (s, 1H), 9.05 (d, J=2.6 Hz, 1H), 9.56 (d, J=2.0 Hz, 1H).

To a stirred solution of N-(tert-butyl)-5-(5-(4-fluorophenyl)-4-((pyridin-2-ylmethyl)amino)pyrrolo[2,1-f][1,2,4]triazin-2-yl)pyridine-3-sulfonamide (30.0 mg, 0.0560 mmol) in dioxane (5 mL) was added 2 mL of 5 N HCl in dioxane. The contents were heated at 50° C. for 12 h. The solvents were removed under reduced pressure to give a white solid. The solid was purified by preparative HPLC (Condition B-61 as described in general methods) to give 5-(5-(4-fluorophenyl)-4-((pyridin-2-ylmethyl)amino)pyrrolo[2,1-f][1,2,4]triazin-2-yl)pyridine-3-sulfonamide (19.0 mg, 44.0%) as an off-white solid. LCMS Condition B-23: retention time 1.91 min, [M+1]=476.2. HPLC Condition B-1: retention time 8.03 min, Purity=98.30%. $^1$H NMR (400 MHz, DMSO-$d_6$) δ ppm 4.93 (d, J=4.8 Hz, 2H), 6.84 (d, J=2.8 Hz, 1H), 7.25-7.52 (m, 5H), 7.52-7.62 (m, 4H) 7.79 (t, J=1.6 Hz, 1H), 7.88 (d, J=2.8 Hz, 1H), 8.35 (s, 1H), 8.92 (s, 1H), 9.05 (s, 1H), 9.65 (s, 1H).

Example 7

2,5-Bis(6-methoxypyridin-3-yl)-N-(pyridin-2-ylmethyl)pyrrolo[1,2-f][1,2,4]triazin-4-amine

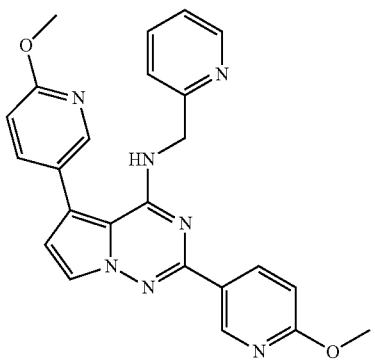

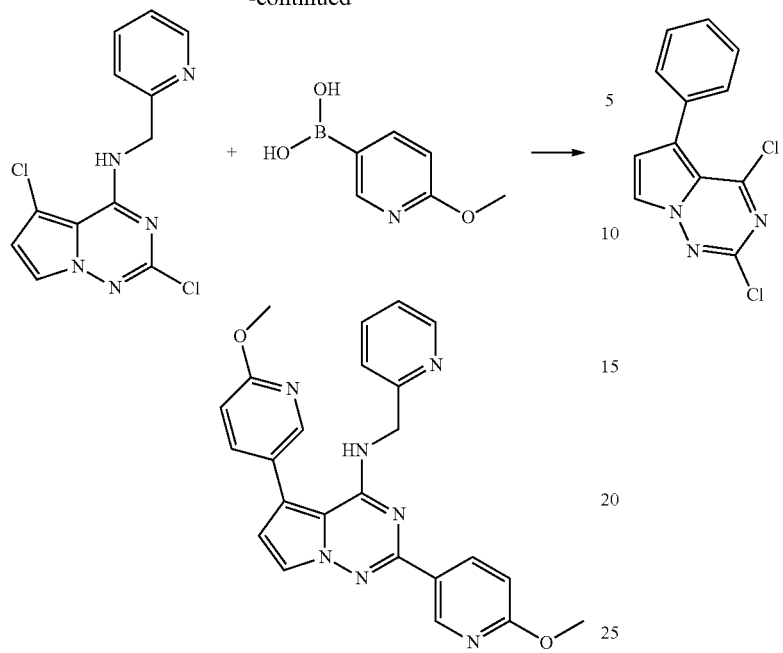

2,5-Dichloro-N-(pyridin-2-ylmethyl)pyrrolo[2,1-f][1,2,4]triazin-4-amine (0.100 g, 0.340 mmol) (prepared as in Example 6) was converted into 2-(6-methoxypyridin-3-yl)-5-(2-methoxypyridin-4-yl)-N-(pyridin-2-ylmethyl)pyrrolo[2,1-f][1,2,4]triazin-4-amine using the procedure described in Example 6 via Suzuki cross-coupling. Following reagents were used for the conversion; (6-methoxypyridin-3-yl)boronic acid (0.130 g, 0.850 mmol), K$_2$CO$_3$ (0.206 mg, 0.149 mmol), X-PHOS (0.0486 g, 0.102 mmol) and palladium(II) acetate (7.60 mg, 0.0340 mmol) at 95° C. for 12 h. The residue was purified by column chromatography using CombiFlash (REDISEP®, silica gel, 40 g, 20% methanol in chloroform) to yield a yellow solid which was further purified by recrystallization using DCM:MeOH (9:1) to give 2-(6-methoxypyridin-3-yl)-5-(2-methoxypyridin-4-yl)-N-(pyridin-2-ylmethyl)pyrrolo[2,1-f][1,2,4]triazin-4-amine (0.0680 mg, 43.2%) as a white solid. LCMS Condition B-12: retention time 2.20 min, [M+1]=440.2. HPLC Condition B-2: retention time 9.80 min, purity 99.20%. $^1$H NMR (400 MHz, DMSO-d$_6$) δ ppm 3.95 (s, 3H), 3.98 (s, 3H), 4.89 (d, J=4.8 Hz, 2H), 6.78 (d, J=2.8 Hz, 1H), 6.91-7.00 (m, 2H), 7.25-7.40 (m, 2H), 7.55-7.60 (m, 1H), 7.80 (t, J=2.8 Hz, 1H), 7.85-7.89 (m, 2H), 8.32-8.52 (m, 3H), 8.95 (s, 1H).

Example 8

5-(5-Phenyl-4-(1-phenylethylamino)pyrrolo[1,2-f][1,2,4]triazin-2-yl)pyridine-3-sulfonamide

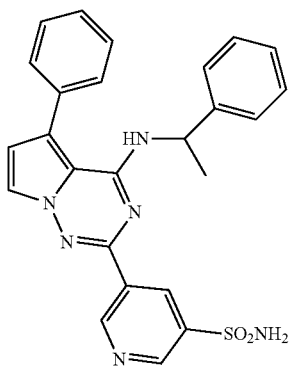

2,4-Dichloro-5-phenylpyrrolo[2,1-f][1,2,4]triazine (1.00 g, 3.79 mmol) (prepared as in Example 3) was converted to 2-chloro-5-phenyl-N-(1-phenylethyl)pyrrolo[2,1-f][1,2,4]triazin-4-amine using DIPEA (3.31 mL, 18.9 mmol) and 1-phenylethanamine (0.918 g, 7.57 mmol) in THF at room temperature for 14 h. The residue was purified by column chromatography using CombiFlash (REDISEP®, silica gel, 24 g, 18% EtOAc/hexanes) to obtain 2-chloro-5-phenyl-N-(1-phenylethyl)pyrrolo[2,1-f][1,2,4]triazin-4-amine (0.750 g, 56.8%). LCMS Condition B-39: retention time 2.34 min, [M+1]=349.2.

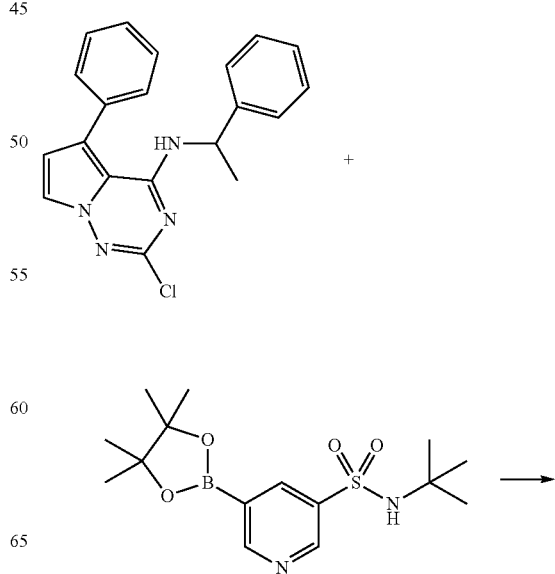

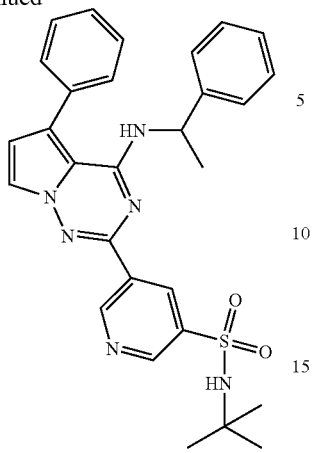

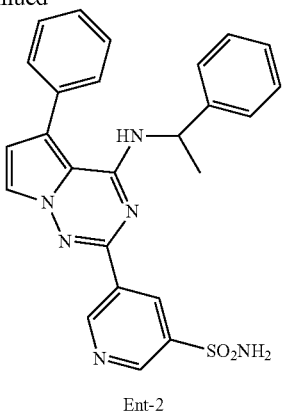

2-Chloro-5-phenyl-N-(1-phenylethyl)pyrrolo[2,1-f][1,2,4]triazin-4-amine (0.700 g, 2.01 mmol) was converted to N-(tert-butyl)-5-(5-phenyl-4-((1-phenylethyl)amino)pyrrolo[2,1-f][1,2,4]triazin-2-yl)pyridine-3-sulfonamide via Suzuki cross-coupling using the conditions mentioned in Example 3. Following reagents were used for the conversion; N-(tert-butyl)-5-(4,4,5,5-tetramethyl-1,3,2-dioxaborolan-2-yl)pyridine-3-sulfonamide (1.37 g, 4.01 mmol), $K_2CO_3$ (1.11 g, 8.03 mmol) and 1,1'-bis(diphenylphosphino)ferrocene-palladium (II)dichloride dichloromethane complex (0.164 g, 0.201 mmol) at 110° C. for 14 h. The residue was purified by column chromatography using CombiFlash (REDISEP®, silica gel, 24 g, 3% methanol in chloroform) to give N-(tert-butyl)-5-(5-phenyl-4-((1-phenylethyl)amino)pyrrolo[2,1-f][1,2,4]triazin-2-yl)pyridine-3-sulfonamide (0.500 g, 47.3%). LCMS Condition B-39: retention time 2.45 min, [M+1]=527.2.

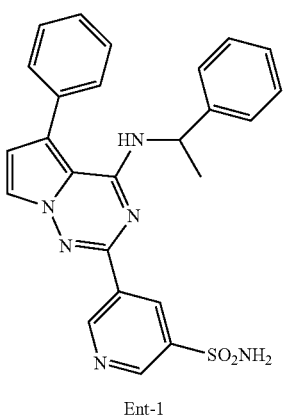

N-(tert-Butyl)-5-(5-phenyl-4-((1-phenylethyl)amino)pyrrolo[2,1-f][1,2,4]triazin-2-yl)pyridine-3-sulfonamide (0.500 g, 0.949 mmol) was converted to 5-(5-phenyl-4-((1-phenylethyl)amino)pyrrolo[2,1-f][1,2,4]triazin-2-yl)pyridine-3-sulfonamide by following the procedure reported in Example 5 using TFA (0.366 mL, 4.75 mmol) at room temperature for 24 h. The residue was purified by column chromatography using CombiFlash (REDISEP®, silica gel, 24 g, 6% methanol in chloroform) to give a solid which was further purified by chiral preparative HPLC purification (Condition B-65 as described in general methods).

Ent-1: 5-(5-Phenyl-4-((1-phenylethyl)amino)pyrrolo[2,1-f][1,2,4]triazin-2-yl)pyridine-3-sulfonamide (0.0450 g, 10.1%). Chiral HPLC Condition B-50: retention time 7.19 min, Purity 100.00%.

Ent-2: 5-(5-Phenyl-4-((1-phenylethyl)amino)pyrrolo[2,1-f][1,2,4]triazin-2-yl)pyridine-3-sulfonamide (0.0650 g, 14.6%). Chiral HPLC Condition B-50: retention time 9.79 min, Purity 99.70%.

$^1$H NMR (400 MHz, DMSO-$d_6$) δ ppm 1.47 (d, J=6.8 Hz, 3H), 5.50-5.60 (m, 1H), 6.29 (d, J=7.2 Hz, 1H), 6.86 (d, J=2.8 Hz, 1H), 7.24-7.61 (m, 10H), 7.95 (br s, 2H), 7.95 (d, J=2.8 Hz, 1H), 8.90 (dd, J=1.6 Hz, J=2.4 Hz, 1H), 9.05 (d, J=2.4 Hz, 1H), 9.47 (d, J=1.6 Hz, 1H). LCMS Condition B-39: retention time 2.98 min, [M+1]=471.2.

Example 9

5-(5-Phenyl-4-(pyridin-2-ylmethylamino)pyrrolo[1,2-f][1,2,4]triazin-2-yl)nicotinamide

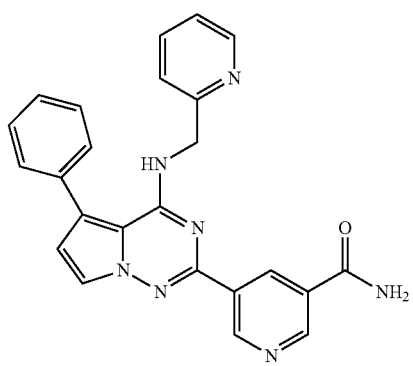

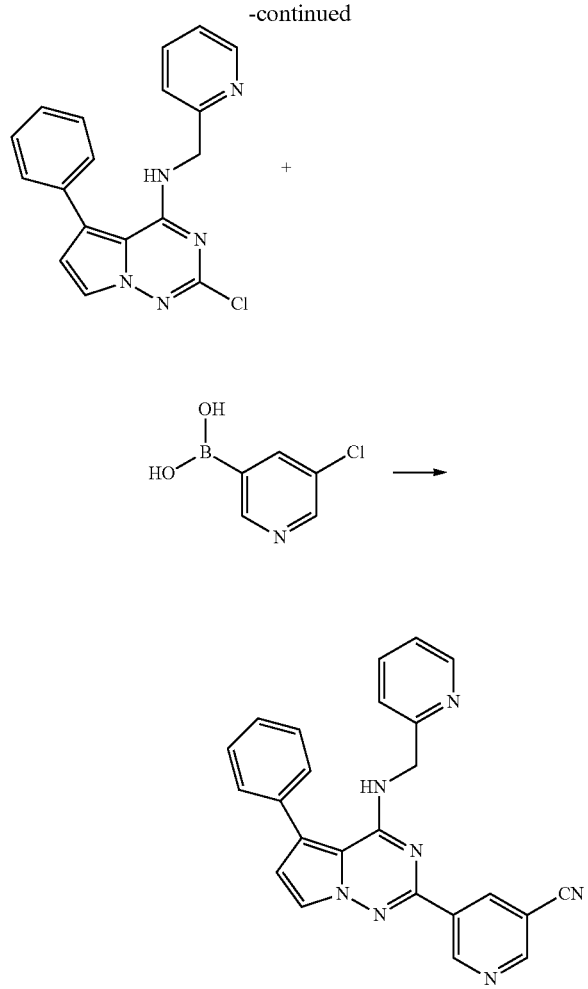

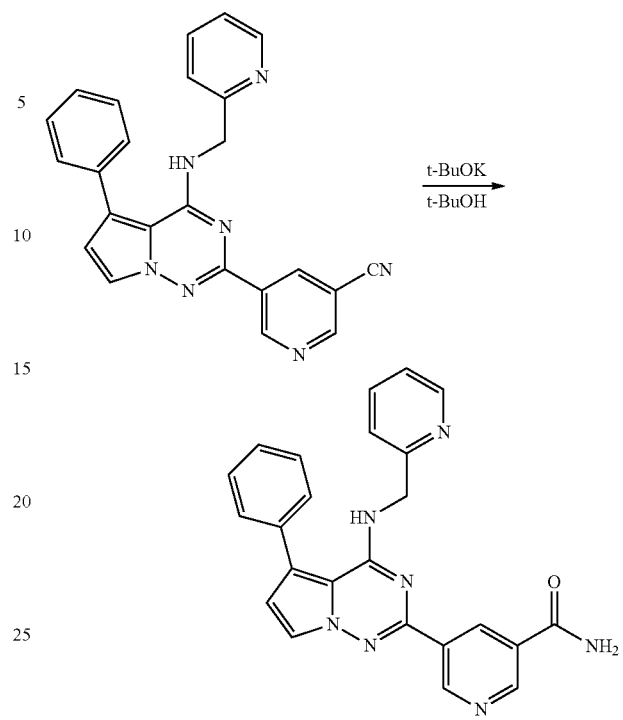

2-Chloro-5-phenyl-N-(pyridin-2-ylmethyl)pyrrolo[2,1-f][1,2,4]triazin-4-amine (0.100 g, 0.298 mmol) (prepared as in Example 3) was converted to 5-(5-phenyl-4-((pyridin-2-ylmethyl)amino)pyrrolo[2,1-f][1,2,4]triazin-2-yl)nicotinonitrile via Suzuki cross-coupling using the conditions mentioned in Example 3. Following reagents were used for the conversion; (5-cyanopyridin-3-yl)boronic acid (0.0529 g, 0.357 mmol), $K_2CO_3$ (0.123 g, 0.893 mmol) and 1,1'-bis(diphenylphosphino)ferrocene-palladium(II)dichloride dichloromethane complex (0.0218 mg, 0.0300 mmol) at 95° C. for 12 h. The residue was purified by column chromatography using CombiFlash (REDISEP®, silica gel, 24 g, 20% EtOAc/hexanes) to obtain the product as brown solid. The brown solid was further purified by recrystallization using DCM:hexane (2:8) to give the 5-(5-phenyl-4-((pyridin-2-ylmethyl)amino)pyrrolo[2,1-f][1,2,4]triazin-2-yl)nicotinonitrile (0.0680 g, 53.8%) as a brown solid. LCMS Condition B-12: retention time 2.10 min, [M+1]=404.2. HPLC Condition B-1: retention time=8.12 min, Purity=95.30%. $^1$H NMR (400 MHz, DMSO-$d_6$) δ ppm 4.96 (d, J=4.4 Hz, 2H), 6.86 (d, J=2.8 Hz, 1H), 7.29 (t, J=1.7 Hz, 1H), 7.30-7.50 (m, 7H), 7.79-7.84 (m, 1H), 7.93 (d, J=2.8 Hz, 1H), 8.31 (s, 1H), 8.92 (s, 1H), 9.15 (s, 1H), 9.52 (s, 1H).

To a solution of 5-(5-phenyl-4-((pyridin-2-ylmethyl)amino)pyrrolo[2,1-f][1,2,4]triazin-2-yl)nicotinonitrile (45.0 mg, 0.112 mmol) in t-butanol (5.00 mL, 502 mmol) was added potassium tert-butoxide (125 mg, 1.12 mmol) and the contents were heated to 90° C. for 12 h. The reaction mixture was allowed to cool and the solvents were removed under reduced pressure. The residue was dissolved in $CH_2Cl_2$ (25 mL) and washed with 1.5 N HCl (20 mL). The organic layer was separated and dried over anhydrous $Na_2SO_4$, filtered and concentrated under reduced pressure to give a brown solid. The solid was purified by preparative HPLC (Condition B-64 as described in general methods) to give 5-(5-phenyl-4-((pyridin-2-ylmethyl)amino)pyrrolo[2,1-f][1,2,4]triazin-2-yl)nicotinamide (21.0 mg, 44.7%) as a brown solid. LCMS Condition B-12: retention time 2.07 min, [M+1]=422.2. HPLC Condition B-1: retention time=6.85 min, Purity=96.30%. $^1$H NMR (400 MHz, DMSO-$d_6$) δ ppm 4.96 (d, J=4.4 Hz, 2H), 6.84 (d, J=2.8 Hz, 1H), 7.25-7.53 (m, 8H), 7.58-7.72 (m, 3H), 7.93 (d, J=2.8 Hz, 1H), 8.31 (s, 1H), 8.92 (s, 1H), 9.12 (s, 1H), 9.51 (s, 1H).

Example 10

5-(5-Phenyl-4-(pyridin-2-ylmethylamino)pyrrolo[1,2-f][1,2,4]triazin-2-yl)nicotinic acid

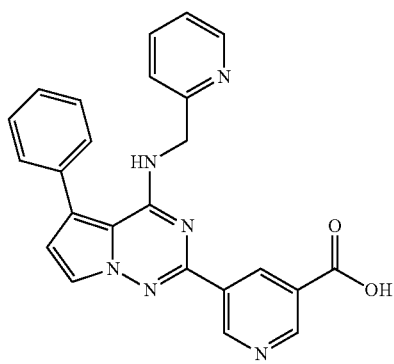

77

-continued

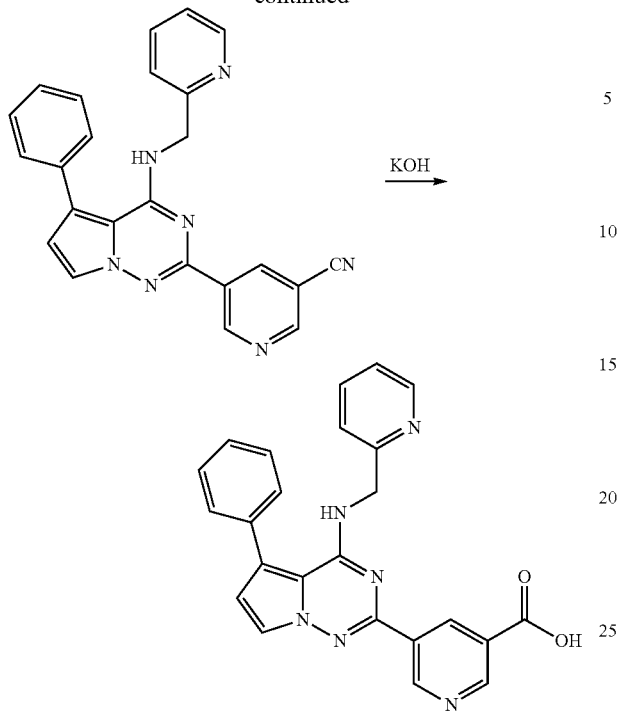

To a stirred solution of 5-(5-phenyl-4-((pyridin-2-ylmethyl)amino)pyrrolo[2,1-f][1,2,4]triazin-2-yl)nicotinonitrile (50.0 mg, 0.124 mmol) in dioxane (5 mL)/MeOH (2 mL) was added KOH (34.8 mg, 0.620 mmol) dissolved in water (2 mL) in a pressure tube. The contents were heated at 95° C. for 12 h. The reaction mixture was allowed to cool and concentrated under reduced pressure to give a white solid. The solid was dissolved in CHCl$_3$ and washed with 1.5 N HCl (5 mL) and the organic layer was separated and dried over anhydrous Na$_2$SO$_4$, filtered and concentrated to give 5-(5-phenyl-4-((pyridin-2-ylmethyl)amino)pyrrolo[2,1-f][1,2,4]triazin-2-yl)nicotinic acid (24.0 mg, 49.0%) as an off-white solid. LCMS Condition B-23: retention time 1.64, [M+1]=423.2. HPLC Condition B-1: retention time 5.80 min, purity 98.80%. $^1$H NMR (400 MHz, DMSO-d$_6$) δ ppm 4.94 (d, J=4.4 Hz, 2H), 6.83 (d, J=2.8 Hz, 1H), 7.21-7.52 (m, 8H), 7.89 (t, J=1.7 Hz, 1H), 7.96 (d, J=2.8 Hz, 1H), 8.38 (br s, 1H), 8.98 (s, 1H), 9.19 (s, 1H), 9.52 (s, 1H).

Example 11

2-(5-(1H-Tetrazol-5-yl)pyridin-3-yl)-N-benzyl-5-phenylpyrrolo[1,2-f][1,2,4]triazin-4-amine

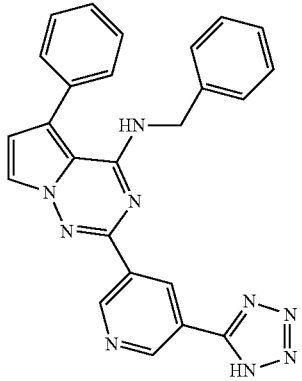

78

-continued

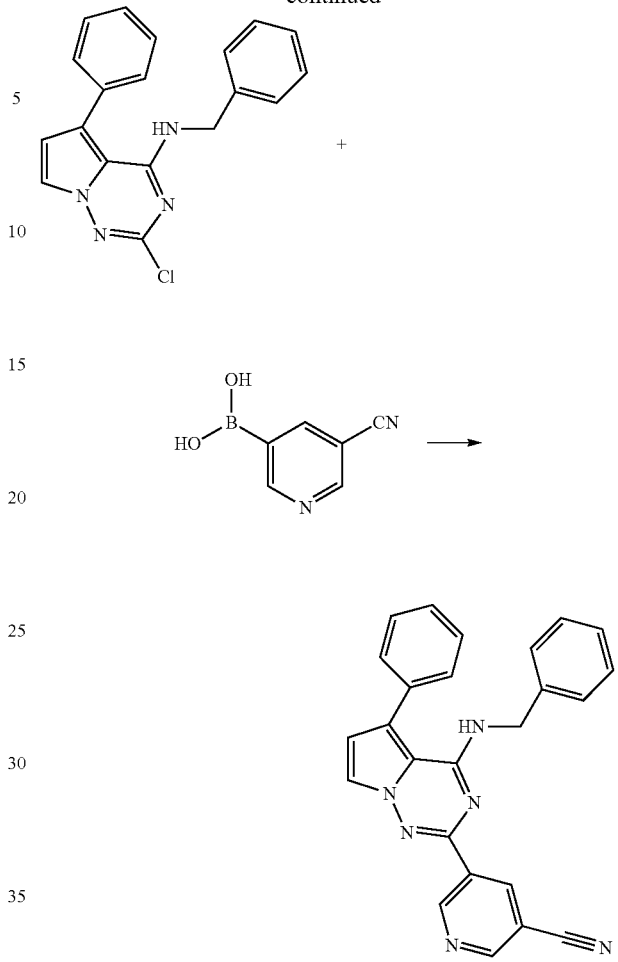

N-Benzyl-2-chloro-5-phenylpyrrolo[2,1-f][1,2,4]triazin-4-amine (1.00 g, 32.9 mmol) (prepared as in Example 4) was converted to 5-(4-(benzylamino)-5-phenylpyrrolo[2,1-f][1,2,4]triazin-2-yl)nicotinonitrile via Suzuki cross-coupling using the conditions mentioned in Example 3. Following reagents were used for the conversion; (5-cyanopyridin-3-yl) boronic acid (0.884 g, 5.97 mmol, commercial), K$_2$CO$_3$ (1.65 g, 11.9 mmol) and 1,1'-bis(diphenylphosphino)ferrocenepalladium(II)dichloride dichloromethane complex (0.244 g, 0.299 mmol) at 110° C. for 18 h. The residue was purified by column chromatography using CombiFlash (REDISEP®, silica gel, 24 g, 40% EtOAc/hexanes) to obtain a residue which was further purified by preparative HPLC (Condition B-53 as described in general methods) to obtain 5-(4-(benzylamino)-5-phenylpyrrolo[2,1-f][1,2,4]triazin-2-yl)nicotinonitrile (0.700 g, 58.2%). $^1$H NMR (400 MHz, DMSO-d$_6$) δ ppm 4.84 (d, J=5.6 Hz, 2H), 6.75 (t, J=5.6 Hz, 1H), 6.83 (d, J=2.8 Hz, 1H), 7.25-7.55 (m, 10H), 7.92 (d, J=2.8 Hz, 1H), 8.87 (t, J=2.0 Hz, 1H), 9.11 (d, J=2.0 Hz, 1H), 9.57 (d, J=2.0 Hz, 1H). LCMS Condition B-39: retention time 2.50 min, [M+1]=402.8. HPLC Condition B-5: retention time 24.30 min, Purity 98.30%.

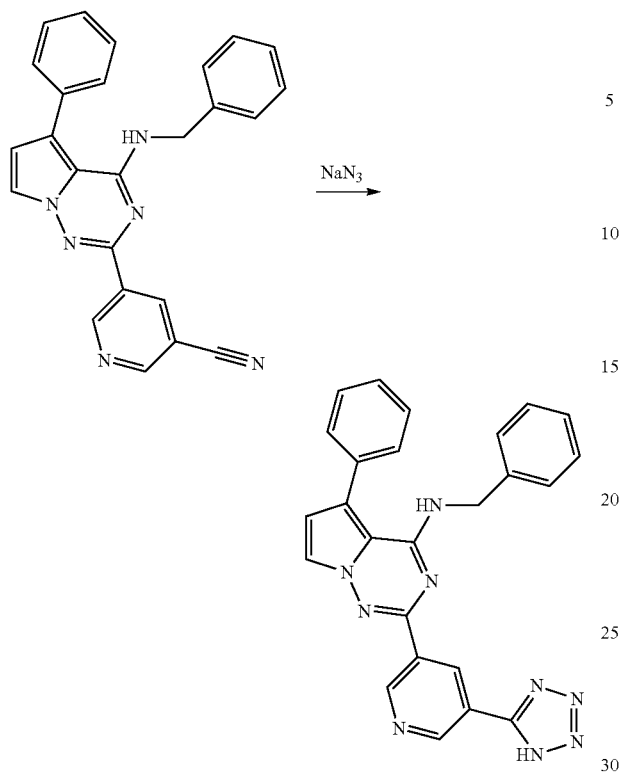

5-(4-(Benzylamino)-5-phenylpyrrolo[2,1-f][1,2,4]triazin-2-yl)nicotinonitrile (0.120 g, 0.298 mmol) was dissolved in DMF (2 mL) and sodium azide (0.116 g, 1.79 mmol) was added. The reaction mixture was heated to 100° C. for 16 h. The reaction mixture was concentrated under reduced pressure to remove DMF. The residue was purified by preparative HPLC (Condition B-66 as described in general methods) to obtain 5-(4-(benzylamino)-5-phenylpyrrolo[2,1-f][1,2,4]triazin-2-yl)nicotinonitrile (70.0 mg, 52.7%). $^1$H NMR (400 MHz, DMSO-$d_6$) δ ppm 4.85 (d, J=5.6 Hz, 2H), 6.64 (t, J=5.6 Hz, 1H), 6.81 (d, J=2.8 Hz, 1H), 7.09 (br s, 1H), 7.24-7.57 (m, 10H), 7.97 (d, J=2.8 Hz, 1H), 9.10 (t, J=2.0 Hz, 1H), 9.22 (d, J=1.6 Hz, 1H), 9.26 (d, J=2.0 Hz, 1H). LCMS Condition B-23: retention time 1.64 min, [M+1]=446.4. HPLC Condition B-31: retention time 10.6 min, Purity 98.90%.

Example 12

5-(4-(Benzylamino)-5-phenylpyrrolo[1,2-f][1,2,4]triazin-2-yl)nicotinic acid

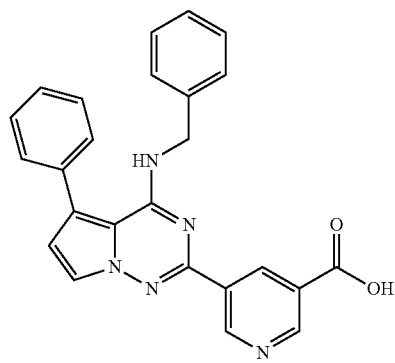

5-(4-(Benzylamino)-5-phenylpyrrolo[2,1-f][1,2,4]triazin-2-yl)nicotinonitrile (prepared as in Example 11) (0.800 g, 1.99 mmol) was dissolved in dioxane (3 mL), and KOH (0.892 g, 15.9 mmol) was added. The reaction mixture was heated to 100° C. for 14 h. The reaction mixture was allowed to cool and concentrated under reduced pressure to remove dioxane. The residue obtained was diluted with water (10 mL) and neutralized with dilute HCl to pH 6. The solid was filtered and air dried. The solid was purified by preparative HPLC (Condition B-67 as described in general methods) to obtain 5-(4-(benzylamino)-5-phenylpyrrolo[2,1-f][1,2,4]triazin-2-yl)nicotinic acid (0.500 g, 59.7%). $^1$H NMR (400 MHz, DMSO-$d_6$) δ ppm 4.83 (d, J=5.6 Hz, 2H), 6.66 (t, J=5.6 Hz, 1H), 6.83 (d, J=2.8 Hz, 1H), 7.26-7.56 (m, 10H), 7.96 (d, J=2.8 Hz, 1H), 8.99 (dd, J=1.6 Hz, J=2.0 Hz, 1H), 9.14 (d, J=2.0 Hz, 1H), 9.53 (d, J=1.6 Hz, 1H), 13.61 (br s, 1H). LCMS Condition B-44: retention time 1.54 min, [M+1]=422.2. HPLC Condition B-31: retention time 10.72 min, Purity 97.70%.

Example 13

5-(4-(Benzylamino)-5-phenylpyrrolo[1,2-f][1,2,4]triazin-2-yl)nicotinamide

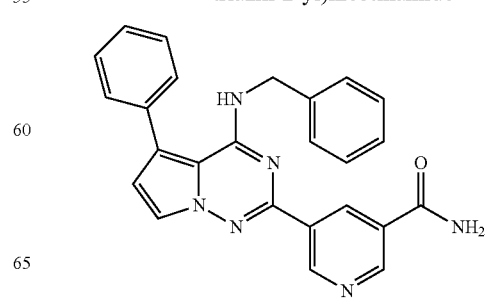

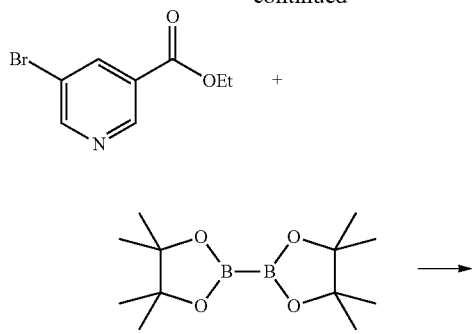

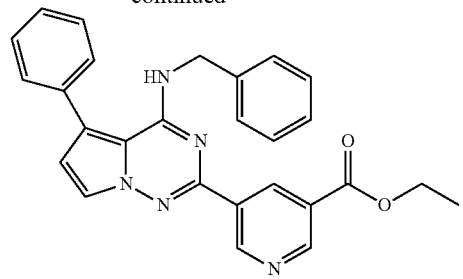

N-Benzyl-2-chloro-5-phenylpyrrolo[2,1-f][1,2,4]triazin-4-amine (0.100 g, 0.299 mmol) was converted to ethyl 5-(4-(benzylamino)-5-phenylpyrrolo[2,1-f][1,2,4]triazin-2-yl)nicotinate via Suzuki cross-coupling using the conditions mentioned in Example 3. Following reagents were used for the conversion; ethyl 5-(4,4,5,5-tetramethyl-1,3,2-dioxaborolan-2-yl)nicotinate (0.0990 g, 0.358 mmol), $K_2CO_3$ (0.124 g, 0.896 mmol) and 1,1'-bis(diphenylphosphino)ferrocene-palladium(II)dichloride dichloromethane complex (0.0240 g, 0.0300 mmol) at 80° C. for 14 h in a sealed tube. The residue was purified by silica gel column chromatography using CombiFlash (REDISEP®, silica gel, 40 g, 25% EtOAc/hexanes) to obtain ethyl 5-(4-(benzylamino)-5-phenylpyrrolo[2,1-f][1,2,4]triazin-2-yl)nicotinate (0.100 g, 74.5%). LCMS Condition B-39: retention time 2.55 min, [M+1]=449.6.

To the solution of 4,4,5,5-tetramethyl-2-(4,4,5,5-tetramethyl (1,3,2-dioxaborolan-2-yl))-1,3,2-dioxaborolane (1.54 g, 6.09 mmol) and tricyclohexylphosphonium tetrafluoroborate (0.112 g, 0.304 mmol) in 1,4-dioxane (20 mL) at ambient temperature was added potassium acetate (1.71 g, 17.4 mmol) and the reaction mixture was purged with nitrogen gas for 10 min. The reaction mixture was heated to 80° C. $Pd_2(dba)_3$ (0.199 g, 0.217 mmol) was added to the reaction mixture and again nitrogen was passed through for 10 min at 80° C. The reaction mixture was heated to 90° C. and a solution of ethyl 5-bromonicotinate (1.00 g, 4.35 mmol) in 1,4-dioxane (5 mL) was added. The resulting mixture was stirred at 100° C. for 16 h. The reaction mixture was allowed to cool, filtered through CELITE® and the filtrate was concentrated under reduced pressure to obtain ethyl 5-(4,4,5,5-tetramethyl-1,3,2-dioxaborolan-2-yl)nicotinate (1.5 g, 115%). The residue was taken to the next step without further purification. (Leblanc et al., *Synth Comm.*, 38:2775-2781 (2008) and Bard et al., US 2012/184577, p 5). LCMS Condition B-40: retention time 0.52 min, [M+1]=196.1. $^1$H NMR (400 MHz, DMSO-$d_6$) δ 1.16 (s, 12H), 1.35 (t, J=7.2 Hz, 3H), 4.36 (q, J=7.2 Hz, 2H), 8.43 (dd, J=1.6 Hz, J=2.0 Hz, 1H), 8.95 (d, J=1.6 Hz, 1H), 9.16 (br s, 1H).

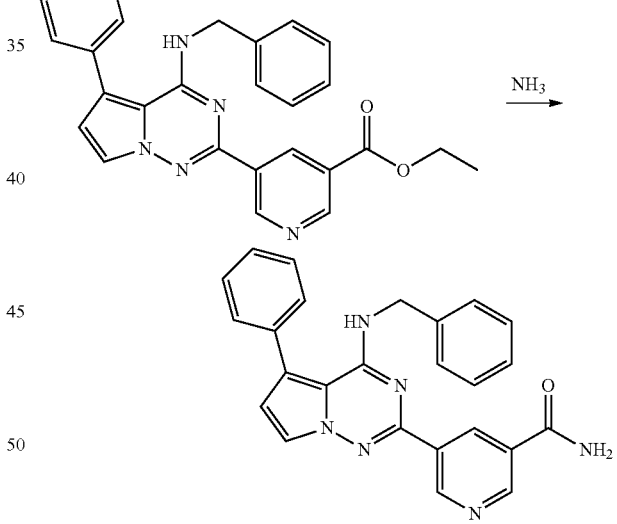

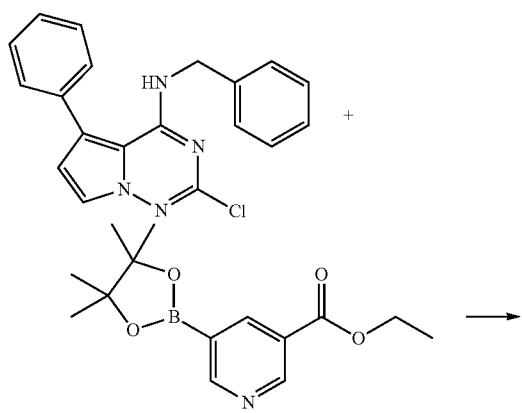

A solution of ethyl 5-(4-(benzylamino)-5-phenylpyrrolo[2,1-f][1,2,4]triazin-2-yl)nicotinate (0.100 g, 0.222 mmol) in ethanol (10 mL) was purged with ammonia gas at −40° C. in a sealed tube for 15 min. The tube was sealed and the reaction mixture was stirred at ambient temperature for 14 h. The sealed tube was opened at −40° C. and allowed to rise to ambient temperature. The solvent was evaporated under reduced pressure to give a residue which was purified by preparative HPLC (Condition B-58 as described in general methods) to get 5-(4-(benzylamino)-5-phenylpyrrolo[2,1-f][1,2,4]triazin-2-yl)nicotinamide (80.0 mg, 86.0%) as a white solid. LCMS Condition B-26: retention time 2.28 min, [M+1]=421.2. HPLC Condition B-6: retention time 7.62 min, purity 99.33%. ¹H NMR (400 MHz, DMSO-d₆) δ ppm 4.84 (d, J=4.0 Hz, 2H), 6.68 (t, J=4.0 Hz, 1H), 6.82 (d, J=2.4 Hz, 1H), 7.25-7.32 (m, 1H), 7.34-7.41 (m, 5H), 7.45-7.48 (m, 2H), 7.52-7.54 (m, 2H), 7.67 (s, 1H), 7.93 (d, J=4.0 Hz, 1H), 8.32 (s, 1H), 8.95 (t, J=4.0 Hz, 1H), 9.11 (d, J=2.4 Hz, 1H), 9.46 (d, J=2.0 Hz, 1H).

Example 14

1-(5-(4-(Benzylamino)-5-phenylpyrrolo[1,2-f][1,2,4]triazin-2-yl)pyridin-3-yl)ethane-1,2-diol

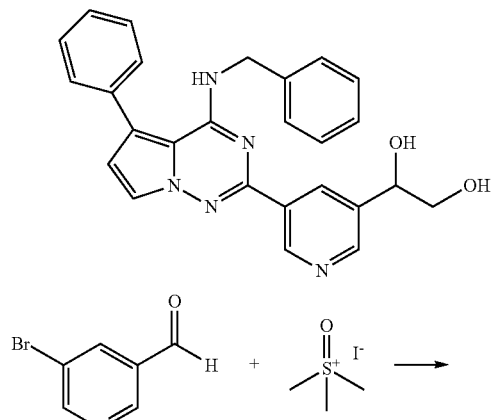

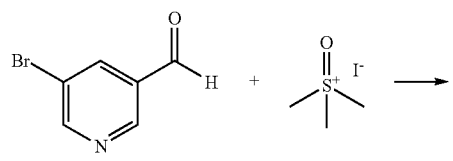

To a solution of trimethylsulfoxonium iodide (7.10 g, 32.3 mmol) in DMSO (25 mL) were added, sodium hydride (0.774 g, 32.3 mmol, 95%) (portionwise) at ambient temperature, followed by 5-bromonicotinaldehyde (3.00 g, 16.1 mmol) in DMSO (15 mL). The reaction mixture was quenched by the addition of cold ice water (200 mL) and the resulting mixture extracted with ethyl acetate (2×150 mL). The combined organic layer was dried over anhydrous sodium sulfate, filtered and evaporated under reduced pressure to give the residue which was purified by column chromatography using CombiFlash (REDISEP®, silica gel, 40 g, 25% EtOAc/hexanes) to obtain 3-bromo-5-(oxiran-2-yl)pyridine (1.00 g, 31.0%). LCMS Condition B-26: retention time 1.83, [M+2]=202.2. ¹H NMR (400 MHz, CDCl₃) δ 2.79 (dd, J=2.4 Hz, J=5.2 Hz, 1H), 3.20 (dd, J=4.0 Hz, J=5.2 Hz, 1H), 3.87 (dd, J=2.4 Hz, J=4.0 Hz, 1H), 7.69 (dd, J=1.6 Hz, J=2.0 Hz, 1H), 8.50 (d, J=1.6 Hz, 1H), 8.62 (d, J=2.0 Hz, 1H).

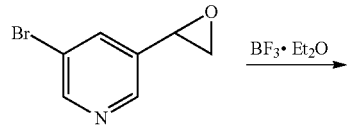

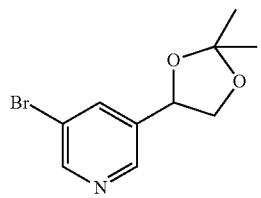

To a solution of 3-bromo-5-(oxiran-2-yl)pyridine (1.00 g, 5.00 mmol) in acetone (25 mL) was added BF₃.OEt₂ (0.950 mL, 7.50 mmol) dropwise and the reaction mixture was stirred at ambient temperature for 14 h. The reaction mixture was diluted with water (15 mL) and the resulting mixture extracted with ethyl acetate (2×50 mL). The combined organic layer was dried over anhydrous sodium sulfate, filtered and evaporated under reduced pressure to give a residue which was purified by column chromatography using CombiFlash (REDISEP®, silica gel, 40 g, 25% EtOAc/hexanes) to obtain 3-bromo-5-(2,2-dimethyl-1,3-dioxolan-4-yl)pyridine (0.700 g, 54.2%). LCMS Condition B-26: retention time 2.17, [M+2]=260.0. ¹H NMR (400 MHz, CDCl₃) δ 1.48 (s, 3H), 1.55 (s, 3H), 3.72 (dd, J=7.6 Hz, J=8.4 Hz, 1H), 4.36 (dd, J=6.4 Hz, J=8.4 Hz, 1H), 5.08 (dd, J=6.4 Hz, J=7.6 Hz, 1H), 7.85-7.86 (m, 1H), 8.49 (d, J=1.6 Hz, 1H), 8.62 (d, J=2.0 Hz, 1H).

A solution of 3-bromo-5-(2,2-dimethyl-1,3-dioxolan-4-yl)pyridine (100 mg, 0.387 mmol), bis(pinacolato)diboron (148 mg, 0.581 mmol) and KOAc (114 mg, 1.16 mmol) in 1,4-dioxane (10 mL) was purged with nitrogen for 30 min. 1,1'-Bis(diphenylphosphino)ferrocene-palladium(II)dichloride dichloromethane complex (32.0 mg, 0.0390 mmol) was added and the reaction mixture was heated at 100° C. in a sealed tube for 14 h. The reaction mixture was allowed to cool and filtered through CELITE® and the filtrate was evaporated under reduced pressure to remove dioxane to yield 3-(2,2-dimethyl-1,3-dioxolan-4-yl)-5-(4,4,5,5-tetramethyl-1,3,2-dioxaborolan-2-yl)pyridine (90.0 mg, 76.0%) which was used without further purification. LCMS Method B40: retention time 0.95 min, [M+1]=306.1.

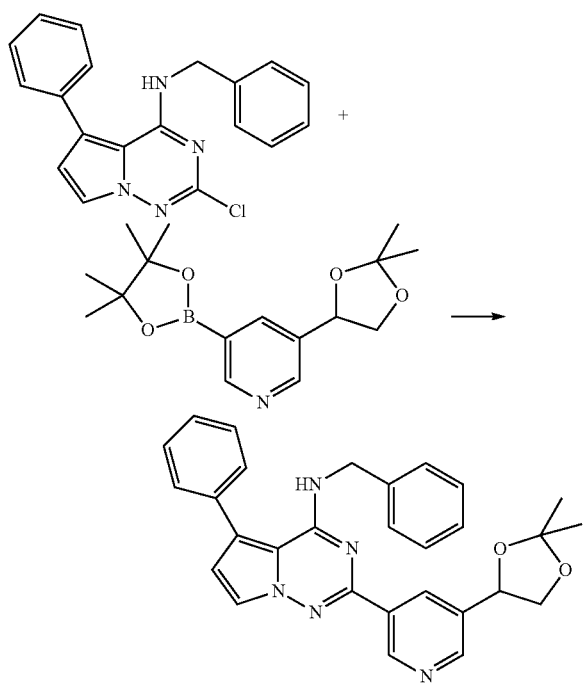

N-Benzyl-2-chloro-5-phenylpyrrolo[2,1-f][1,2,4]triazin-4-amine (0.100 g, 0.299 mmol) (prepared as in Example 4), converted to N-benzyl-2-(5-(2,2-dimethyl-1,3-dioxolan-4-yl)pyridin-3-yl)-5-phenylpyrrolo[2,1-f][1,2,4]triazin-4-amine via Suzuki cross-coupling using the conditions mentioned in Example 3. Following reagents were used for the conversion; 3-(2,2-dimethyl-1,3-dioxolan-4-yl)-5-(4,4,5,5-tetramethyl-1,3,2-dioxaborolan-2-yl)pyridine (0.137 g, 0.448 mmol), $K_2CO_3$ (0.124 g, 0.896 mmol) and 1,1'-bis(diphenylphosphino)ferrocene-palladium(II)dichloride dichloromethane complex (24.0 mg, 0.0300 mmol) at 100° C. for 14 h in a sealed tube. The residue was purified by preparative HPLC (Condition B-51 as described in general methods) to get N-benzyl-2-(5-(2,2-dimethyl-1,3-dioxolan-4-yl)pyridin-3-yl)-5-phenylpyrrolo[2,1-f][1,2,4]triazin-4-amine (50.0 mg, 35.0%). LCMS Condition B-27: retention time, 1.85, [M+1]=478.2. HPLC Condition B-5: retention time 19.75, purity 99.34%. $^1$H NMR (400 MHz, DMSO-$d_6$) δ ppm 1.46 (s, 6H), 3.69-3.73 (m, 1H), 4.39-4.43 (m, 1H), 4.82 (d, J=5.6 Hz, 2H), 5.24 (t, J=6.4 Hz, 1H), 6.70-6.76 (m, 1H), 6.80-6.81 (m, 1H), 7.25-7.27 (m, 1H), 7.32-7.41 (m, 5H), 7.45-7.49 (m, 2H), 7.49-7.55 (m, 2H), 7.91 (d, J=2.8 Hz, 1H), 8.52 (t, J=2.0 Hz, 1H), 8.65 (d, J=2.0 Hz, 1H), 9.30 (d, J=2.0 Hz, 1H).

N-Benzyl-2-(5-(2,2-dimethyl-1,3-dioxolan-4-yl)pyridin-3-yl)-5-phenylpyrrolo[2,1-f][1,2,4]triazin-4-amine (0.150 g, 0.314 mmol) was dissolved in TFA (10 mL) and stirred for 1 h at 60° C. TFA was removed under reduced pressure and the reaction mixture was diluted with saturated sodium bicarbonate (100 mL) and extracted with ethyl acetate (3×30 mL). The combined organic extracts were dried over sodium sulfate, filtered and evaporated under reduced pressure to a residue which was purified by preparative HPLC (Condition B-53 as described in general methods) to get 1-(5-(4-(benzylamino)-5-phenylpyrrolo[2,1-f][1,2,4]triazin-2-yl)pyridin-3-yl)ethane-1,2-diol (90.0 mg, 65.5%). The enantiomers of 1-(5-(4-(benzylamino)-5-phenylpyrrolo[2,1-f][1,2,4]triazin-2-yl)pyridin-3-yl)ethane-1,2-diol were separated by SFC (Condition B-52 as described in general methods).

Ent-1: 1-(5-(4-(Benzylamino)-5-phenylpyrrolo[2,1-f][1,2,4]triazin-2-yl)pyridin-3-yl)ethane-1,2-diol (18.0 mg, 32.7%). LCMS Condition B-22: retention time 2.55, [M+1]=438.2. Chiral HPLC Condition B-52: retention time 5.39 min, Purity 98.32%.

Ent-2: 1-(5-(4-(Benzylamino)-5-phenylpyrrolo[2,1-f][1,2,4]triazin-2-yl)pyridin-3-yl)ethane-1,2-diol (20.0 mg, 36.4%). LCMS Condition B-22: retention time 2.56, [M+1]=438.2. Chiral HPLC Condition B-52: retention time 6.22 min, Purity 97.88%.

$^1$H NMR (400 MHz, DMSO-$d_6$) δ ppm 3.50-3.51 (m, 1H), 3.57-3.58 (m, 1H), 4.68-4.69 (m, 1H), 4.79-4.85 (m, 3H), 5.53 (d, J=4.0 Hz, 1H), 6.80 (t, J=5.6 Hz, 1H), 6.79 (d, J=2.8 Hz, 1H), 7.23-7.55 (m, 10H), 7.91 (d, J=2.8 Hz, 1H), 8.50 (t, J=2.0 Hz, 1H), 8.60 (d, J=2.0 Hz, 1H), 9.24 (d, J=2.0 Hz, 1H).

Example 15

6-(4-(Benzylamino)-5-phenylpyrrolo[1,2-f][1,2,4]triazin-2-yl)pyrazine-2-sulfonamide

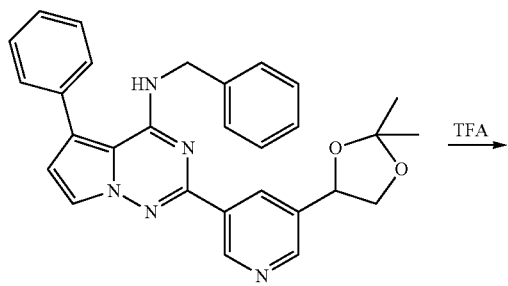

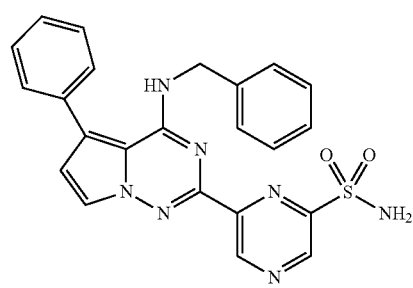

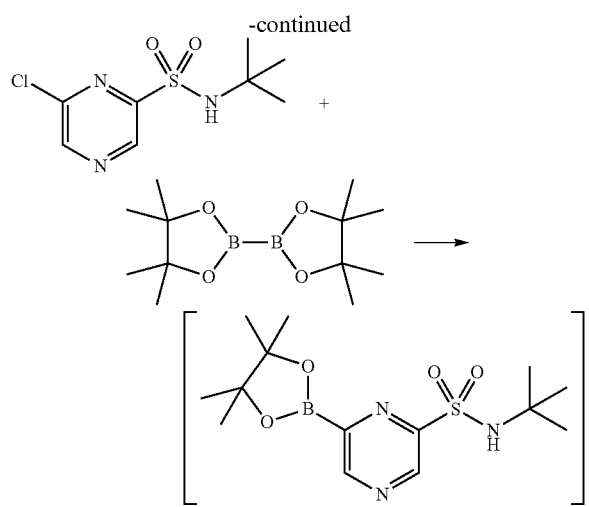

N-(tert-Butyl)-6-chloropyrazine-2-sulfonamide (0.500 g, 2.00 mmol) (Johnson et al., WO 2011/28741) was converted to N-(tert-butyl)-6-(4,4,5,5-tetramethyl-1,3,2-dioxaborolan-2-yl)pyrazine-2-sulfonamide following the procedure as in Example 14 and by using bis(pinacolato)diboron (0.763 g, 3.00 mmol), KOAc (0.786 g, 8.01 mmol) and 1,1'-bis(diphenylphosphino)ferrocene-palladium(II)dichloride dichloromethane complex (0.164 g, 0.200 mmol) at 100° C. in a sealed tube for 14 h. The reaction mixture was allowed to cool, filtered through CELITE®, washed with dioxane. The filtrate was evaporated under reduced pressure to get N-(tert-butyl)-6-(4,4,5,5-tetramethyl-1,3,2-dioxaborolan-2-yl)pyrazine-2-sulfonamide (0.500 g, 73.2%) which was used without further purification.

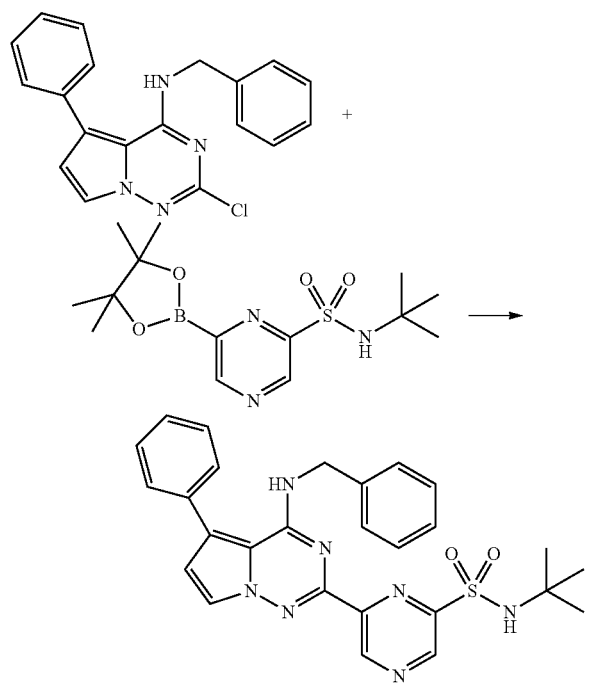

N-Benzyl-2-chloro-5-phenylpyrrolo[2,1-f][1,2,4]triazin-4-amine (0.300 g, 0.896 mmol) (prepared as in Example 4), was converted to 6-(4-(benzylamino)-5-phenylpyrrolo[2,1-f][1,2,4]triazin-2-yl)-N-(tert-butyl)pyrazine-2-sulfonamide via Suzuki cross-coupling using the conditions mentioned in Example 3. Following reagents were used for the conversion; N-(tert-butyl)-6-(4,4,5,5-tetramethyl-1,3,2-dioxaborolan-2-yl)pyrazine-2-sulfonamide (0.306 g, 0.896 mmol), $K_2CO_3$ (0.248 g, 1.79 mmol) and 1,1'-bis(diphenylphosphino)ferrocene-palladium(II)dichloride dichloromethane complex (0.0730 g, 0.0900 mmol) at 95° C. for 14 h. The residue was purified by column chromatography using CombiFlash (REDISEP®, silica gel, 24 g, 42% EtOAc/hexanes) to obtain the impure product and the sample was further purified by preparative HPLC (Condition B-48 as described in general methods) to obtain 6-(4-(benzylamino)-5-phenylpyrrolo[2,1-f][1,2,4]triazin-2-yl)-N-(tert-butyl)pyrazine-2-sulfonamide (35.0 mg, 7.60%). $^1$H NMR (400 MHz, DMSO-$d_6$) δ ppm 1.18 (s, 9H), 4.85 (d, J=5.6 Hz, 2H), 6.74 (t, J=5.6 Hz, 1H), 6.88 (d, J=2.8 Hz, 1H), 7.25-7.55 (m, 11H), 7.97 (d, J=2.8 Hz, 1H), 9.22 (s, 1H), 9.58 (s, 1H). LCMS Condition B-29: retention time 2.31, [M−1]=511.9. HPLC Condition B-5: retention time 24.91 min, Purity 97.81%.

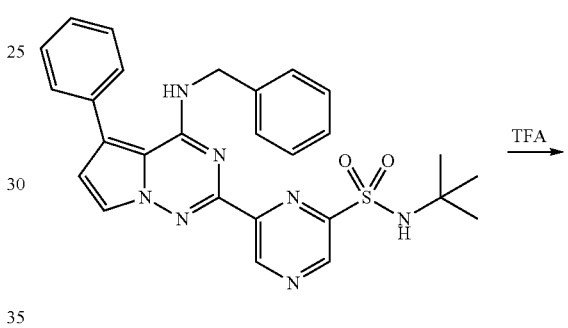

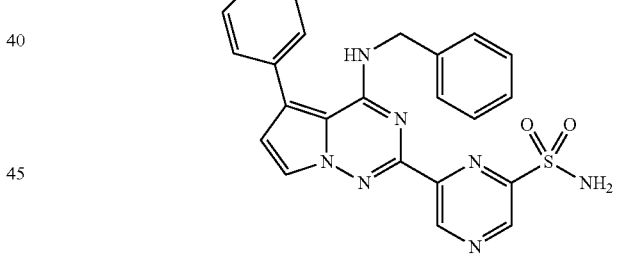

6-(4-(Benzylamino)-5-phenylpyrrolo[2,1-f][1,2,4]triazin-2-yl)-N-(tert-butyl)pyrazine-2-sulfonamide (0.0300 g, 0.0580 mmol) was converted to 6-(4-(benzylamino)-5-phenylpyrrolo[2,1-f][1,2,4]triazin-2-yl)pyrazine-2-sulfonamide following the Example 5 by treating with TFA (2 mL) at ambient temperature. The residue was purified by preparative HPLC (Condition B-51 as described in general methods) to obtain 6-(4-(benzylamino)-5-phenylpyrrolo[2,1-f][1,2,4]triazin-2-yl)pyrazine-2-sulfonamide (8.00 mg, 29.9%). $^1$H NMR (400 MHz, DMSO-$d_6$) δ ppm 4.82 (d, J=4.8 Hz, 2H), 6.76 (t, J=5.6 Hz, 1H), 6.87 (d, J=2.8 Hz, 1H), 7.22-7.52 (m, 10H), 7.82-7.87 (m, 2H), 7.97 (d, J=2.8 Hz, 1H), 9.18 (s, 1H), 9.58 (s, 1H). LCMS Condition B-29: retention time 2.08, [M−1]=455.8. HPLC Condition B-32: retention time 11.55 min, Purity 99.7%.

Example 16

5-(4-(Benzylamino)-5-phenylpyrrolo[1,2-f][1,2,4]triazin-2-yl)-2-hydroxypyridine-3-sulfonamide

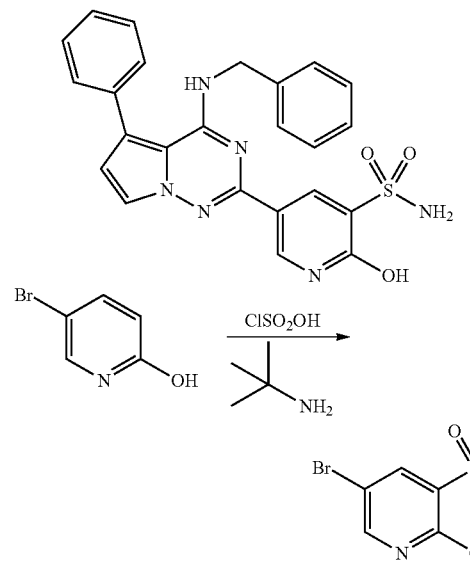

A solution of 5-bromopyridin-2-ol (1.00 g, 5.75 mmol) in chlorosulfonic acid (15.0 mL, 224 mmol) was heated to 150° C. for 14 h. The reaction mixture was added dropwise to tert-butyl amine (25 mL) in THF (25 mL) at 0° C. and was evaporated under reduced pressure to give a brown residue. The residue was dissolved in water (100 mL) and acidified with saturated citric acid solution (pH=6) and extracted with ethyl acetate (2×100 mL). The combined organic layers were dried over anhydrous sodium sulfate, filtered and evaporated under reduced pressure to a residue which was purified by column chromatography using CombiFlash (REDISEP®, silica gel, 24 g, 60% EtOAc/hexanes) to obtain 5-bromo-N-(tert-butyl)-2-hydroxypyridine-3-sulfonamide (0.260 g, 14.6%). LCMS Condition B-24: retention time 1.10 min, [M+2]=309.0.

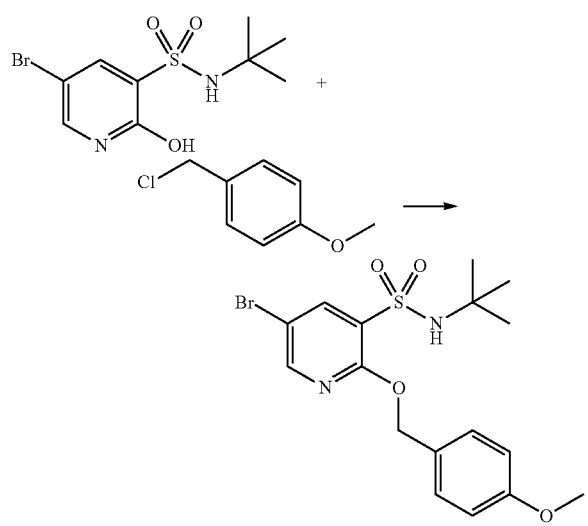

To a solution of 5-bromo-N-(tert-butyl)-2-hydroxypyridine-3-sulfonamide (2.00 g, 6.47 mmol) in DMF (40 mL) was added 4-methoxybenzyl chloride (1.76 mL, 12.9 mmol) followed by $K_2CO_3$ (1.78 g, 12.9 mmol) at ambient temperature. The reaction mixture was heated to 100° C. for 14 h, diluted with cold water (100 mL). The aqueous mixture was extracted with ethyl acetate (2×50 mL). The combined organic layers were dried over anhydrous sodium sulfate, filtered and evaporated under reduced pressure to give a residue which was purified by column chromatography using CombiFlash (REDISEP®, silica gel, 40 g, 50% EtOAc/hexanes) to obtain 5-bromo-N-(tert-butyl)-2-((4-methoxybenzyl)oxy)pyridine-3-sulfonamide (1.50 g, 54.0%). LCMS Condition B-39: retention time 2.53 min, [M+1]=429.0. $^1$H NMR (400 MHz, CDCl$_3$) 1.25 (s, 9H), 3.81 (s, 3H), 6.88-6.91 (m, 2H), 7.24-7.30 (m, 4H), 7.55 (d, J=2.8 Hz, 1H), 8.11 (d, J=2.8 Hz, 1H).

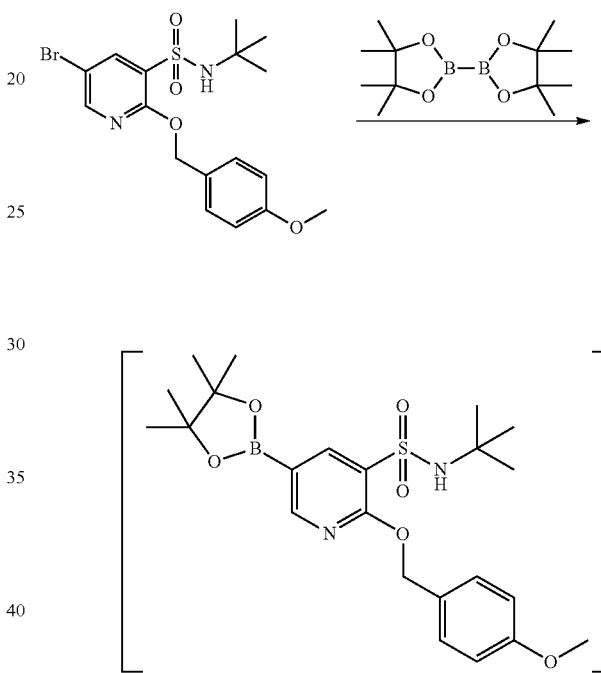

5-Bromo-N-(tert-butyl)-2-((4-methoxybenzyl)oxy)pyridine-3-sulfonamide (0.500 g, 1.17 mmol) was converted to N-(tert-butyl)-2-((4-methoxybenzyl)oxy)-5-(4,4,5,5-tetramethyl-1,3,2-dioxaborolan-2-yl)pyridine-3-sulfonamide using the bis(pinacolato)diboron (0.444 g, 1.75 mmol), KOAc (0.343 g, 3.49 mmol) and 1,1'-bis(diphenylphosphino)ferrocene-palladium(II)dichloride dichloromethane complex (0.0950 g, 0.116 mmol) as in Example 14, to get N-(tert-butyl)-2-((4-methoxybenzyl)oxy)-5-(4,4,5,5-tetramethyl-1,3,2-dioxaborolan-2-yl)pyridine-3-sulfonamide (0.450 g, 81.0%) which was used without further purification.

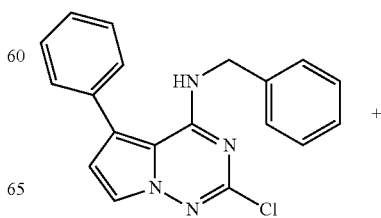

-continued

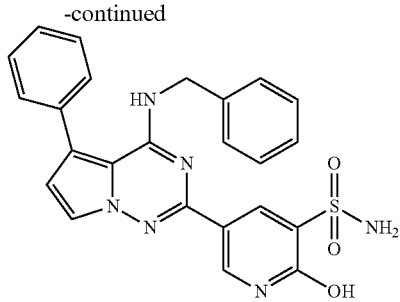

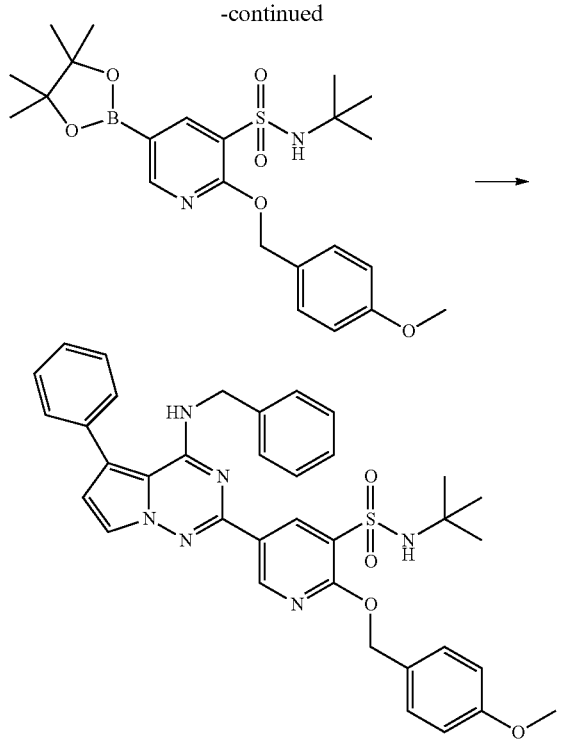

N-Benzyl-2-chloro-5-phenylpyrrolo[2,1-f][1,2,4]triazin-4-amine (0.200 g, 0.597 mmol) (prepared as in Example 4) was converted to 5-(4-(benzylamino)-5-phenylpyrrolo[2,1-f][1,2,4]triazin-2-yl)-N-(tert-butyl)-2-((4-methoxybenzyl)oxy)pyridine-3-sulfonamide via Suzuki cross-coupling using the conditions mentioned in Example 3. Following reagents were used for the conversion; N-(tert-butyl)-2-((4-methoxybenzyl)oxy)-5-(4,4,5,5-tetramethyl-1,3,2-dioxaborolan-2-yl)pyridine-3-sulfonamide (0.427 g, 0.896 mmol), KOAc (0.248 g, 1.79 mmol) and 1,1'-bis(diphenylphosphino)ferrocene-palladium(II)dichloride dichloromethane complex (0.0240 g, 0.0300 mmol) at 80° C. overnight in a sealed tube. The residue obtained, was purified by preparative HPLC (Condition B-69 as described in general methods) to get 5-(4-(benzylamino)-5-phenylpyrrolo[2,1-f][1,2,4]triazin-2-yl)-N-(tert-butyl)-2-((4-methoxybenzyl)oxy)pyridine-3-sulfonamide (0.150 g, 38.7%). LCMS Condition B-38: retention time 3.10 min, [M+1]=649.2. HPLC Condition B-6: retention time 21.99 min, Purity 98.43%. $^1$H NMR (400 MHz, DMSO-$d_6$) δ ppm 1.12 (s, 9H), 3.71 (s, 3H), 4.76 (d, J=5.6 Hz, 2H), 5.29 (s, 2H), 6.68 (t, J=5.6 Hz, 1H), 6.93 (d, J=2.8 Hz, 1H), 6.94-7.00 (m, 3H), 7.23-7.52 (m, 12H), 7.87 (d, J=2.8 Hz, 1H), 8.78 (d, J=2.4 Hz, 1H), 8.88 (d, J=2.4 Hz, 1H).

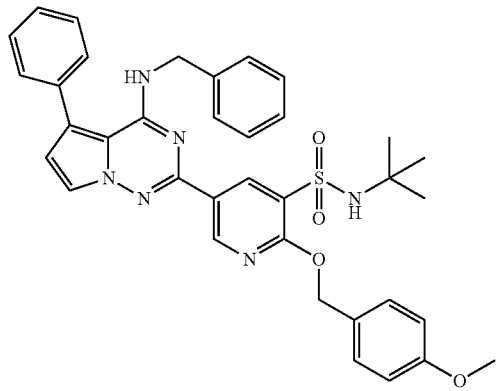

TFA →

-continued

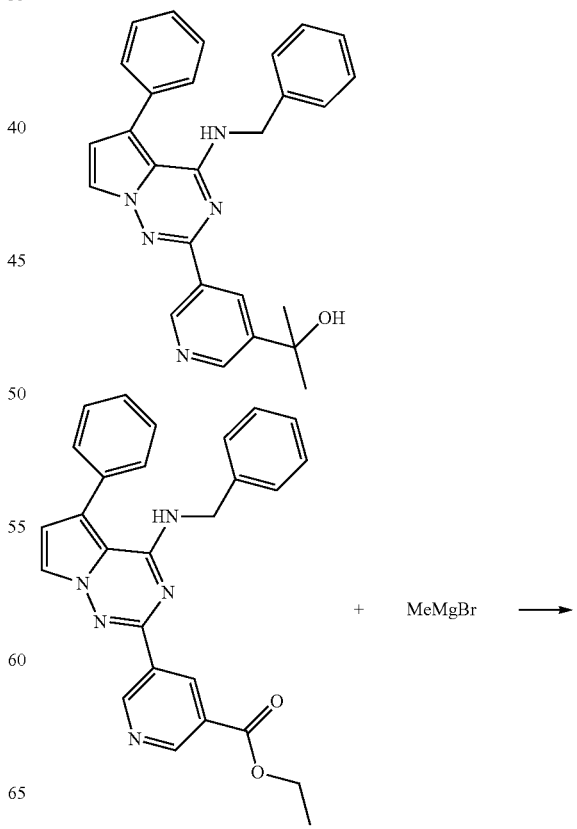

5-(4-(Benzylamino)-5-phenylpyrrolo[2,1-f][1,2,4]triazin-2-yl)-N-(tert-butyl)-2-((4-methoxybenzyl)oxy)pyridine-3-sulfonamide (0.100 g, 0.154 mmol) was dissolved in TFA (25 mL) and stirred for 6 h at 60° C. TFA was removed under reduced pressure and reaction mixture was diluted with saturated sodium bicarbonate (100 mL) and extracted with ethyl acetate (3×30 mL). The combined organic extracts were dried over sodium sulfate, filtered and evaporated under reduced pressure to give a residue which was purified by preparative HPLC (Condition B-70 as described in general methods) to get 5-(4-(benzylamino)-5-phenylpyrrolo[2,1-f][1,2,4]triazin-2-yl)-2-hydroxypyridine-3-sulfonamide (20.0 mg, 27.5%). LCMS Condition B-38: retention time 2.48 min, [M−1]=471.0. HPLC Condition B-6: retention time 15.64 min, Purity 99.67%. $^1$H NMR (400 MHz, DMSO-$d_6$) δ 4.75 (d, J=8.0 Hz, 2H), 6.61 (t, J=8.0 Hz, 1H), 6.74 (d, J=4.0 Hz, 1H), 7.03 (s, 2H), 7.24-7.28 (m, 1H), 7.32-7.39 (m, 5H), 7.44-7.52 (m, 4H), 7.87 (d, J=2.8 Hz, 1H), 8.42 (d, J=4.0 Hz, 1H), 8.77 (d, J=4.0 Hz, 1H), 12.70 (s, 1H).

Example 17

2-(5-(4-(Benzylamino)-5-phenylpyrrolo[1,2-f][1,2,4]triazin-2-yl)pyridin-3-yl)propan-2-ol + MeMgBr →

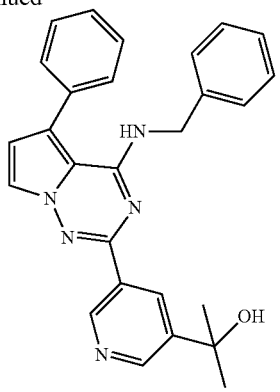

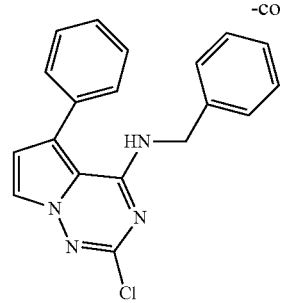

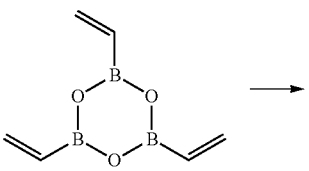

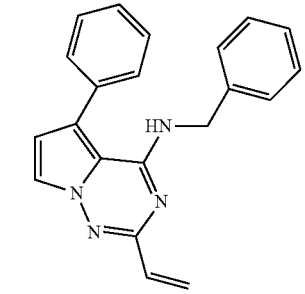

Ethyl 5-(4-(benzylamino)-5-phenylpyrrolo[2,1-f][1,2,4]triazin-2-yl)nicotinate (0.100 g, 0.222 mmol) (prepared as in Example 13) was dissolved in THF (5 mL) and cooled to 0° C. Methylmagnesium bromide solution in THF (1.6 M, 2.11 mL, 3.37 mmol) was added and the reaction mixture was stirred at room temperature for 14 h. Reaction mixture was diluted with water (20 mL) and the aqueous mixture extracted with ethyl acetate (20×3 mL). The organic layer was dried over anhydrous sodium sulfate, filtered and concentrated under reduced pressure. The residue was purified by preparative HPLC (Condition B-48 as described in general methods) to obtain 2-(5-(4-(benzylamino)-5-phenylpyrrolo[2,1-f][1,2,4]triazin-2-yl)pyridin-3-yl)propan-2-ol (30.0 g, 31.0%). LCMS Condition B-21: retention time 2.28 min, [M+1]=436.2. HPLC Condition B-63: retention time 14.04 min, Purity 98.70%. $^1$H NMR (400 MHz, DMSO-$d_6$) δ ppm 1.51 (s, 6H), 4.81 (d, J=5.6 Hz, 2H), 5.34 (s, 1H), 6.69 (t, J=5.6 Hz, 1H), 6.80 (d, J=2.8 Hz, 1H), 7.23-7.55 (m, 10H), 7.91 (d, J=2.8 Hz, 1H), 8.60 (dd, J=2.0 Hz, J=2.4 Hz, 1H), 8.76 (d, J=2.4 Hz, 1H), 9.21 (d, J=2.0 Hz, 1H).

Example 18

1-(4-(Benzylamino)-5-phenylpyrrolo[1,2-f][1,2,4]triazin-2-yl)ethane-1,2-diol

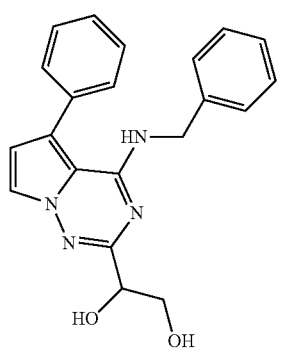

N-Benzyl-2-chloro-5-phenylpyrrolo[2,1-f][1,2,4]triazin-4-amine (0.300 g, 0.896 mmol) (as in Example 4) and 2,4,6-trivinyl cyclotriboroxane pyridine complex (0.323 g, 1.34 mmol) were dissolved in dioxane (15 mL) and then cesium carbonate (0.584 g, 1.79 mmol) dissolved in water (2 mL) was added. The reaction mixture was degassed with nitrogen for 15 minutes, then tetrakistriphenylphosphine palladium (0.0520 g, 0.0450 mmol) was added and the resulting reaction mixture degassed for 15 minutes. The reaction mixture was then heated to 110° C. for 14 h, allowed to cool, concentrated under reduced pressure and $CH_2Cl_2$ (25 mL) was added. The residue was filtered through a CELITE® bed and the filtrate dried over sodium sulfate, filtered and concentrated under reduced pressure. The residue was purified by column chromatography using CombiFlash (REDISEP®, silica gel, 24 g, 3% methanol in chloroform) to yield N-benzyl-5-phenyl-2-vinylpyrrolo[2,1-f][1,2,4]triazin-4-amine (0.200 g, 34.2%). LCMS Condition B-25: retention time 3.12 min, [M+1]=327.2. $^1$H NMR (400 MHz, DMSO-$d_6$) δ ppm 4.72 (d, J=5.6 Hz, 2H), 5.60 (d, J=2.4 Hz, J=10.4 Hz, 1H), 6.36-6.56 (m, 3H), 6.72 (d, J=2.8 Hz, 1H), 7.30-7.37 (m, 5H), 7.42-7.52 (m, 5H), 7.74 (d, J=2.8 Hz, 1H).

-continued

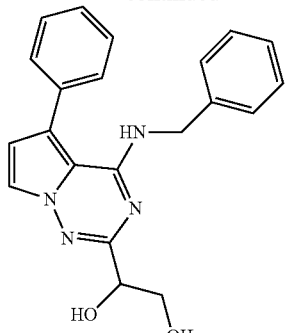
Ent 1

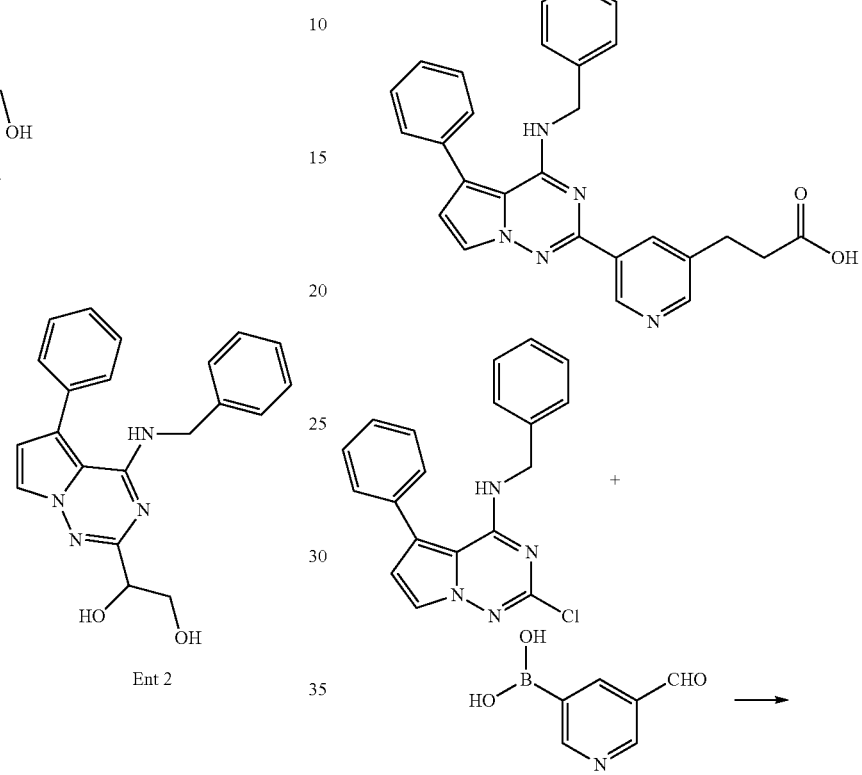
Ent 2

N-Benzyl-5-phenyl-2-vinylpyrrolo[2,1-f][1,2,4]triazin-4-amine (0.150 g, 0.460 mmol) was dissolved in 3:1 ratio of dioxane (15 mL) and water (5 mL) and N-methylmorpholine N-oxide monohydrate (0.0620 g, 0.460 mmol) was added, followed by the addition of osmium tetroxide (0.0430 mL, 0.138 mmol). The reaction mixture was stirred at room temperature for 14 h then filtered through a CELITE® bed and the filtrate was extracted by $CH_2Cl_2$ (25×2 mL). The organic layer was dried over anhydrous sodium sulfate, filtered and concentrated under reduced pressure and the residue resolved into individual enantiomers by chiral HPLC (Condition B-52 as described in general methods).

Ent-1: 1-(4-(Benzylamino)-5-phenylpyrrolo[2,1-f][1,2,4]triazin-2-yl)ethane-1,2-diol (0.0250 g, 15.1%). Chiral HPLC Condition B-52: retention time 5.05 min, Purity 99.10%.

Ent-2: 1-(4-(Benzylamino)-5-phenylpyrrolo[2,1-f][1,2,4]triazin-2-yl)ethane-1,2-diol (20.0 mg, 12.1%). Chiral HPLC Condition B-52: retention time 6.10 min, Purity 98.10%.

LCMS Condition B-25: retention time 1.97 min, [M+1]=360.6. $^1$H NMR (400 MHz, DMSO-$d_6$) δ ppm 3.62 (dt, J=6.0 Hz, J=10.8 Hz, 1H), 3.73 (dt, J=6.0 Hz, J=10.8 Hz, 1H), 4.35 (dt, J=5.6 Hz, J=6.0 Hz, 1H), 4.56 (t, J=6.0 Hz, 1H), 4.70 (t, J=5.6 Hz, 2H), 5.01 (d, J=6.0 Hz, 1H), 6.31 (t, J=6.0 Hz, 1H), 6.71 (d, J=2.8 Hz, 1H), 7.24-7.48 (m, 10H), 7.74 (d, J=2.8 Hz, 1H).

Example 19

3-(5-(4-(Benzylamino)-5-phenylpyrrolo[1,2-f][1,2,4]triazin-2-yl)pyridin-3-yl)propanoic acid

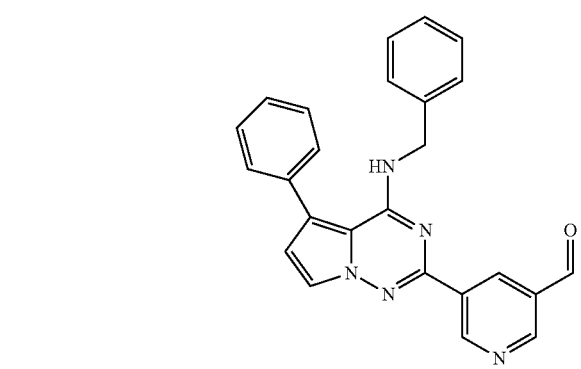

N-Benzyl-2-chloro-5-phenylpyrrolo[1,2-f][1,2,4]triazin-4-amine (0.300 g, 0.900 mmol) (prepared as in Example 4) was converted to 5-(4-(benzylamino)-5-phenylpyrrolo[1,2-f][1,2,4]triazin-2-yl)nicotinaldehyde via Suzuki cross-coupling using the conditions mentioned in Example 3. Following reagents were used for the conversion; potassium carbonate (0.320 g, 270 mmol), 5-(4,4,5,5-tetramethyl-1,3,2-dioxaborolan-2-yl)nicotinaldehyde (0.250 g, 1.08 mmol, commercial) and 1,1'-bis(diphenylphosphino) ferrocene-palladium(II)dichloride dichloromethane complex (27.0 mg, 0.0330 mmol) at 95° C. for 12 h. The residue obtained was purified by column chromatography using CombiFlash (RE-DISEP®, silica gel, 12 g, 50% EtOAc/hexanes) to obtain 5-(4-(benzylamino)-5-phenylpyrrolo[1,2-f][1,2,4]triazin-2-yl)nicotinaldehyde (0.210 g, 57.0%) as pale yellow solid. LCMS Condition B-12: retention time 2.30 min, [M+1]=406.2. $^1$H NMR (400 MHz, DMSO-d$_6$) δ ppm 4.81 (d, J=5.7 Hz, 2H), 6.71 (t, J=1.6 Hz, 1H), 6.73 (d, J=2.8 Hz, 1H), 7.15-7.62 (m, 10H), 7.92 (d, J=2.7 Hz, 1H), 8.91 (s, 1H), 9.18 (br s, 1H), 9.65 (br s, 1H), 10.22 (s, 1H).

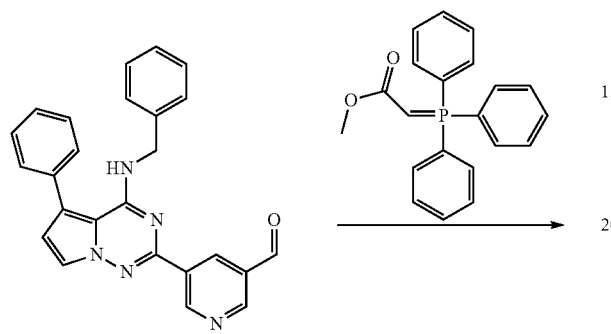

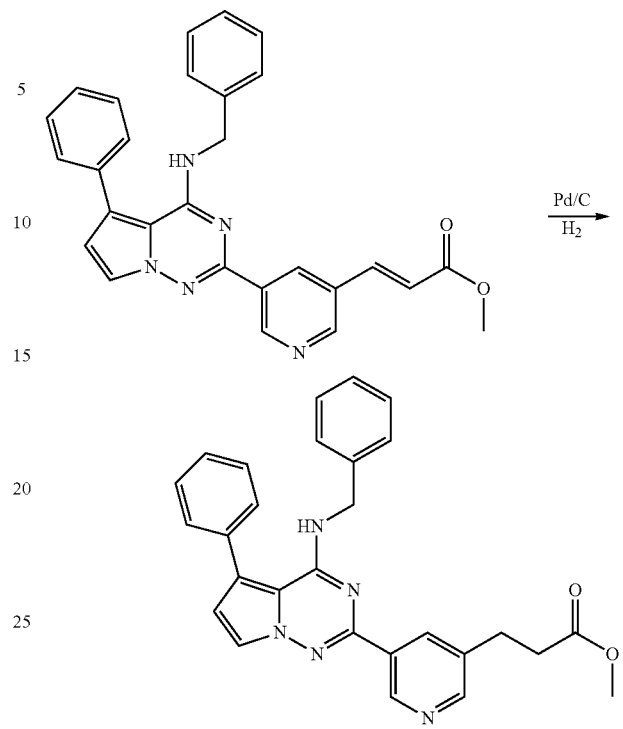

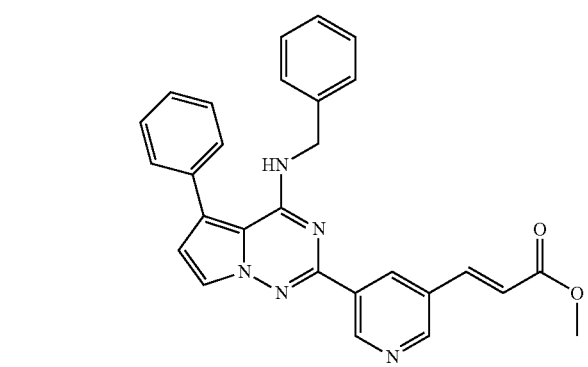

To a stirred solution of 5-(4-(benzylamino)-5-phenylpyrrolo[1,2-f][1,2,4]triazin-2-yl)nicotinaldehyde (0.200 g, 0.500 mmol) in THF was added methyl (triphenylphosphoranylidene)acetate (0.250 g 0.750 mmol, commercial) and the contents were heated to reflux for 12 h. The reaction mixture was allowed to cool and was concentrated under reduced pressure to give a brown solid residue which was purified by column chromatography using CombiFlash (REDISEP®, silica gel, 12 g, 50% EtOAc/hexanes) to obtain (E)-methyl 3-(5-(4-(benzylamino)-5-phenylpyrrolo[1,2-f][1,2,4]triazin-2-yl)pyridin-3-yl)acrylate (0.185 g, 84.0%) as off-white solid. LCMS Condition B-12: retention time 2.49 min, [M+1]=462.2. HPLC Condition B-1: retention time 19.4 min, Purity 99.60%. $^1$H NMR (300 MHz, DMSO-d$_6$) δ ppm 3.59 (s, 3H), 4.81 (d, J=5.7 Hz, 2H), 6.70 (t, J=1.8 Hz, 1H), 6.73 (d, J=2.7 Hz, 1H), 6.81 (d, J=2.7 Hz, 1H), 7.15-7.62 (m, 10H), 7.72-7.84 (m, 1H) 8.65 (s, 1H), 8.53 (br s, 1H), 9.01 (br s, 1H), 9.32 (br s, 1H).

To a stirred solution of (E)-methyl 3-(5-(4-(benzylamino)-5-phenylpyrrolo[1,2-f][1,2,4]triazin-2-yl)pyridin-3-yl)acrylate (50.0 mg, 0.100 mmol) in MeOH (20 mL) was added catalytic amount (5.00 mg) of 10% Pd/C. The contents were stirred at room temperature under hydrogen atmosphere (2 kg) for 3 h. The reaction mixture was filtered through a pad of CELITE®. The filtrate was concentrated under reduced pressure to give a residue which was purified by column chromatography using CombiFlash (REDISEP®, silica gel, 40 g, 20% methanol in chloroform) to give methyl 3-(5-(4-(benzylamino)-5-phenylpyrrolo[1,2-f][1,2,4]triazin-2-yl)pyridin-3-yl)propanoate (34.2 g, 53.0%) as a white solid. LCMS Condition B-12: retention time 2.37 min, [M+1]=464.2. HPLC Condition B-1: retention time 16.50 min, Purity 96.80%. $^1$H NMR (300 MHz, DMSO-d$_6$) δ ppm 2.74 (t, J=7.2 Hz, 2H), 2.96 (t, J=7.2 Hz, 2H), 3.59 (s, 3H), 4.81 (d, J=5.7 Hz, 2H), 6.67 (t, J=1.8 Hz, 1H), 6.81 (d, J=2.7 Hz, 1H), 7.15-7.52 (m, 10H), 7.89 (d, J=3.0 Hz, 1H), 8.15 (br s, 1H), 8.53 (br s, 1H), 9.19 (br s, 1H).

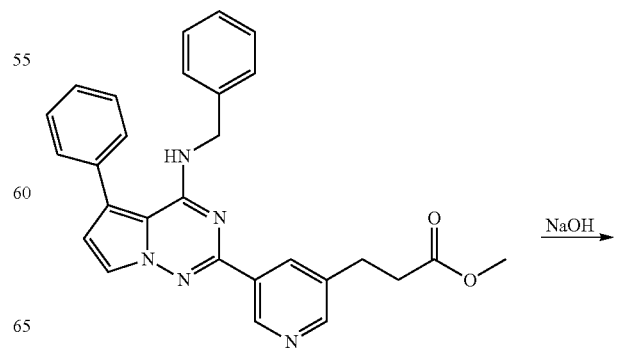

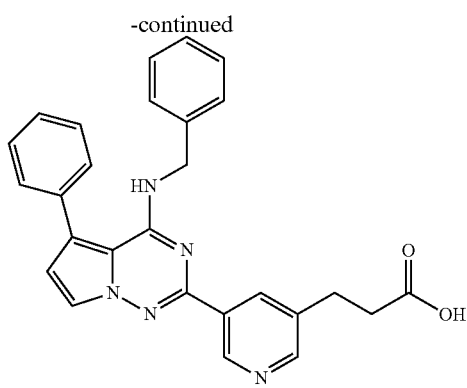

To a stirred solution of methyl 3-(5-(4-(benzylamino)-5-phenylpyrrolo[1,2-f][1,2,4]triazin-2-yl)pyridin-3-yl)propanoate (28.0 mg, 0.0600 mmol) in MeOH was added NaOH (30.0 mg, 0.180 mmol). The contents were stirred at ambient temperature for 3 h. The reaction solution was acidified with 1.5 N HCl to pH 3 and concentrated under reduced pressure to give a brown solid. The residue was purified by column chromatography using CombiFlash (REDISEP®, silica gel, 12 g, 20% methanol in chloroform) to give 3-(5-(4-(benzylamino)-5-phenylpyrrolo[1,2-f][1,2,4]triazin-2-yl)pyridin-3-yl)propanoic acid (18.0 mg, 66.0%) as a white solid. LCMS Condition B-12: retention time 2.00, [M+1]=450.2. HPLC Condition B-1: retention time 14.60 min, purity 98.10%. $^1$H NMR (300 MHz, DMSO-$d_6$) δ ppm 2.64 (t, J=7.2 Hz, 2H), 2.95 (t, J=7.2 Hz, 2H), 4.81 (d, J=5.7 Hz, 2H), 6.68 (t, J=1.8 Hz, 1H), 6.79 (d, J=2.7 Hz, 1H), 7.15-7.52 (m, 10H), 7.89 (d, J=2.7 Hz, 1H), 8.35 (br s, 1H), 8.53 (br s, 1H), 9.19 (br s, 1H).

Example-20

(5-(4-(Benzylamino)-5-phenylpyrrolo[1,2-f][1,2,4]triazin-2-yl)pyridin-3-yl)methanol

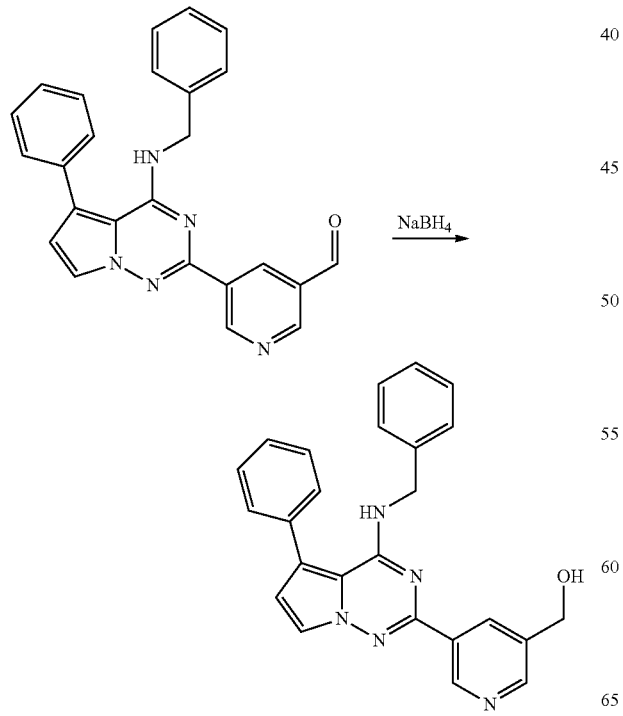

To a solution of 5-(4-(benzylamino)-5-phenylpyrrolo[2,1-f][1,2,4]triazin-2-yl)nicotinaldehyde (30.0 mg, 0.0740 mmol) in methanol (25 mL) was added NaBH$_4$ (8.40 mg, 0.220 mmol). Reaction mixture was stirred at room temperature for 3 h and diluted with cold water (50 mL). The aqueous solution was extracted with ethyl acetate (2×50 mL). The combined organic layer was washed with saturated brain solution, dried over anhydrous sodium sulfate, filtered and evaporated under reduced pressure to give a residue which was purified by column chromatography using CombiFlash (REDISEP®, silica gel, 12 g, 40% EtOAc/hexanes) to get (5-(4-(benzylamino)-5-phenylpyrrolo[2,1-f][1,2,4]triazin-2-yl)pyridin-3-yl)methanol (15.0 mg, 50.0%). LCMS Condition B-12: retention time 2.15 min, [M+1]=406.2. HPLC Condition B-2: retention time 9.20 min, Purity 98.03%. $^1$H NMR (400 MHz, DMSO-$d_6$) δ ppm 4.64 (d, J=5.7 Hz, 2H), 4.82 (d, J=5.7 Hz, 2H), 5.45 (t, J=5.7 Hz, 1H), 6.64 (t, J=5.2 Hz, 1H), 6.80 (d, J=2.7 Hz, 1H), 7.22-7.55 (m, 10H), 7.90 (d, J=2.7 Hz, 1H), 8.49 (t, J=2.1 Hz, 1H), 8.59 (d, J=2.0 Hz, 1H), 9.24 (d, J=2.0 Hz, 1H).

Example-21

1-(5-(4-(Benzylamino)-5-phenylpyrrolo[1,2-f][1,2,4]triazin-2-yl)pyridin-3-yl)ethanol

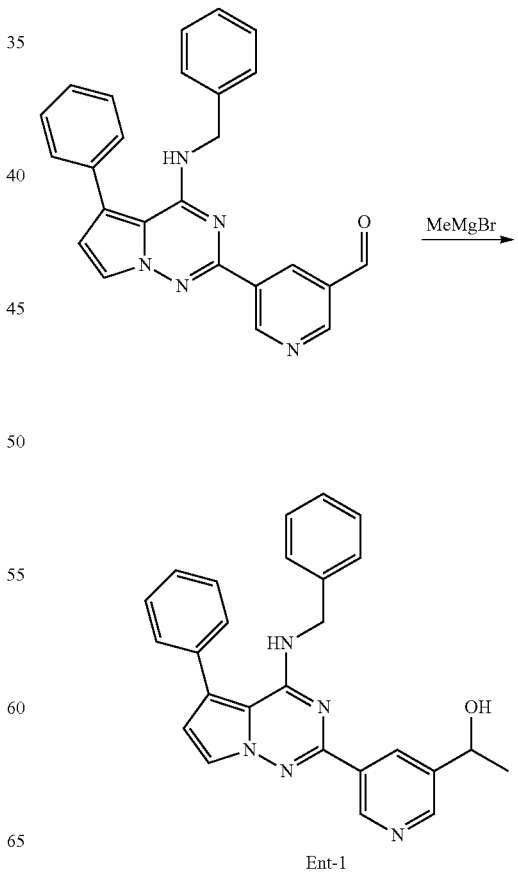

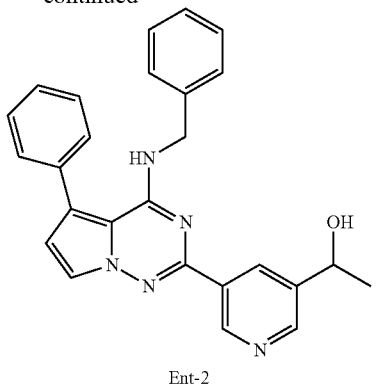

Ent-2

To a solution of 5-(4-(benzylamino)-5-phenylpyrrolo[2,1-f][1,2,4]triazin-2-yl)nicotinaldehyde (0.100 mg, 0.247 mmol) in THF (50 mL) was added methylmagnesium bromide (1.6 M in THF, 0.230 mL, 0.370 mmol) at −10° C. Reaction mixture was allowed to stir at −10° C. for 30 min, and was quenched by the addition of saturated ammonium chloride solution (50 mL) at 0° C. The aqueous mixture was extracted with ethyl acetate (2×50 mL). The combined organic layer was dried over sodium sulfate, filtered and concentrated under reduced pressure to give a residue. The resulting residue was purified by preparative HPLC (Condition B-66 as described in general methods) and the racemate was separated into the enantiomers by SFC (Condition B-52 as described in general methods).

Enantiomer-I: 1-(5-(4-(Benzylamino)-5-phenylpyrrolo[2,1-f][1,2,4]triazin-2-yl)pyridin-3-yl)ethanol (30.0 mg, 28.0%). LCMS Condition B-12: retention time 2.19 min, [M+1]=422.2. HPLC Condition B-6: retention time 13.61 min, Purity 96.13%.

Enantiomer-II: 1-(5-(4-(Benzylamino)-5-phenylpyrrolo[2,1-f][1,2,4]triazin-2-yl)pyridin-3-yl)ethanol (20.0 g, 25.0%). LCMS Condition B-12: retention time 2.19 min, [M+1]=422.2. HPLC Condition B-6: retention time 13.61 min, Purity 96.13%.

$^1$H NMR (400 MHz, DMSO-$d_6$) δ ppm 1.43 (d, J=6.3 Hz, 3H), 4.88-4.90 (m, 3H), 5.43 (d, J=4.2 Hz, 1H), 6.67 (t, J=5.7 Hz, 1H), 6.80 (d, J=2.7 Hz, 1H), 7.22-7.55 (m, 10H), 7.90 (d, J=2.7 Hz, 1H), 8.50 (t, J=2.1 Hz, 1H), 8.62 (d, J=2.0 Hz, 1H), 9.32 (d, J=2.0 Hz, 1H).

Example 22

Methyl 1-(5-(4-(benzylamino)-5-phenylpyrrolo[1,2-f][1,2,4]triazin-2-yl)nicotinoyl)pyrrolidine-2-carboxylate

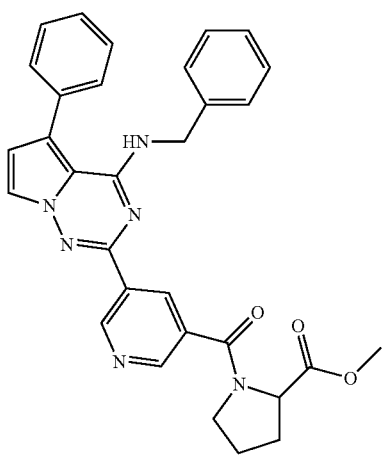

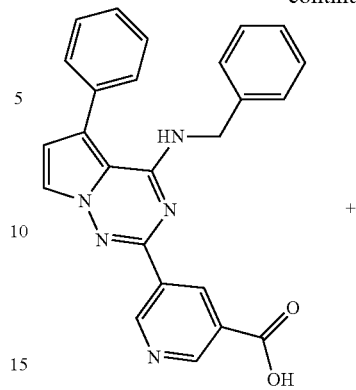

+

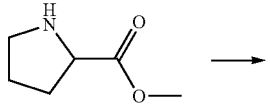

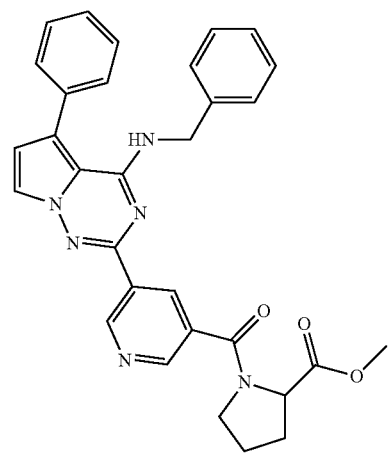

To a stirred solution of 5-(4-(benzylamino)-5-phenylpyrrolo[2,1-f][1,2,4]triazin-2-yl)nicotinic acid (80.0 mg, 0.190 mmol) (prepared as in Example 12) in DMF (2 mL), were added DMAP (35.0 mg, 0.285 mmol) and HATU (108 mg, 0.285 mmol) and the reaction mixture was stirred for 10 minutes. Methyl pyrrolidine-2-carboxylate (12.0 g, 0.0950 mmol) was added and the reaction mixture was stirred at room temperature for 14 h. The reaction mixture concentrated under reduced pressure to remove DMF and to the resulting residue water (10 mL) was added. The aqueous mixture was extracted with $CH_2Cl_2$ (15×2 mL). The combined organic layers were dried over anhydrous sodium sulfate and concentrated under reduced pressure. The residue was purified by preparative HPLC (Condition B-68 as described in general methods) to obtain methyl 1-(5-(4-(benzylamino)-5-phenylpyrrolo[2,1-f][1,2,4]triazin-2-yl)nicotinoyl)pyrrolidine-2-carboxylate (30.0 mg, 59.3%). LCMS Condition B-14: retention time 2.31 min, [M−1]=531.2. HPLC Condition B-63: retention time 16.30 min, Purity 99.70%. $^1$H NMR (400 MHz, DMSO-$d_6$) δ ppm 1.87-1.98/2.30-2.35 (m, 4H), 3.44/3.70 (s, 3H), 3.55/3.67 (dd, J=6.0 Hz, J=6.8 Hz, 2H), 4.47-4.49/4.56-4.58 (m, 1H), 4.54/4.82 (d, J=5.6 Hz, 2H), 6.71/6.76 (t, J=5.6 Hz, 1H), 6.82 (d, J=2.8 Hz, 1H), 7.23-7.56 (m, 10H), 7.91/7.94 (d, J=2.8 Hz, 1H), 8.44/8.58 (t, J=2.0 Hz, 1H), 8.65/8.81 (d, J=2.0 Hz, 1H), 9.39/9.44 (d, J=2.0 Hz, 1H). Molecule exists as two rotomers with ratio 70/30.

Example 23

5-(5-Phenyl-4-((2-(pyrazin-2-yloxy)ethyl)amino) pyrrolo[2,1-f][1,2,4]triazin-2-yl)pyridine-3-sulfonamide

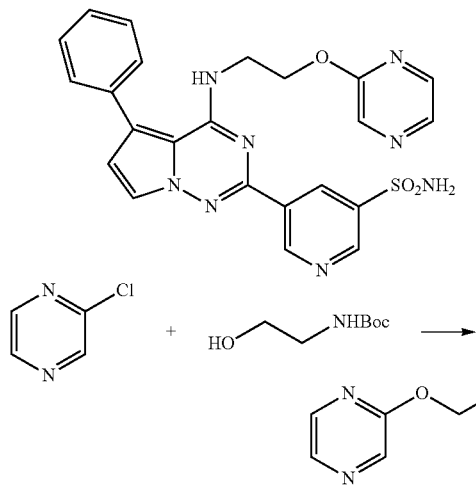

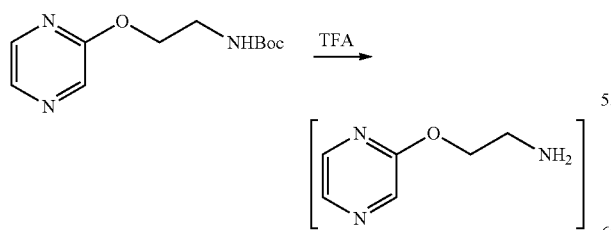

To a stirred solution of NaH (0.126 g, 5.24 mmol, 95%) in THF (10 mL) was added dropwise tert-butyl (2-hydroxyethyl)carbamate (0.281 g, 1.75 mmol) and the resulting mixture stirred for 60 min at room temperature. To the above solution, a solution of 2-chloropyrazine (0.200 g, 1.75 mmol) in THF (9 mL) was added dropwise at ambient temperature and the mixture was heated for 4 h at 80° C. The reaction mixture was allowed to cool and quenched by the addition of saturated ammonium chloride solution (6 mL). The aqueous mixture extracted with EtOAc (2×25 mL) and the combined organic phases were washed with brine, dried over anhydrous sodium sulfate, filtered and concentrated under reduced pressure. tert-Butyl (2-(pyrazin-2-yloxy)ethyl)carbamate (80.0 mg, 19.2%) generated was taken to the next step without further purification. LCMS Condition B-13: retention time 2.11, [M+1]=240.2. $^1$H NMR (400 MHz, CDCl$_3$) δ ppm 1.39 (s, 9H), 3.27-3.31 (m, 2H), 3.53-3.56 (m, 2H), 4.92 (s, 1H), 8.06 (dd, J=1.2 Hz, J=2.8 Hz, 1H), 8.14 (d, J=2.8 Hz, 1H), 8.24 (d, J=1.2 Hz, 1H).

To a solution of tert-butyl (2-(pyrazin-2-yloxy)ethyl)carbamate (0.100 g, 0.418 mmol) in CH$_2$Cl$_2$ (5 mL) was added TFA (0.0640 mL, 0.836 mmol) and the reaction mixture was stirred for 16 h at ambient temperature. TFA was removed under reduced pressure and the residue carried in to the next step without further purification (120 mg).

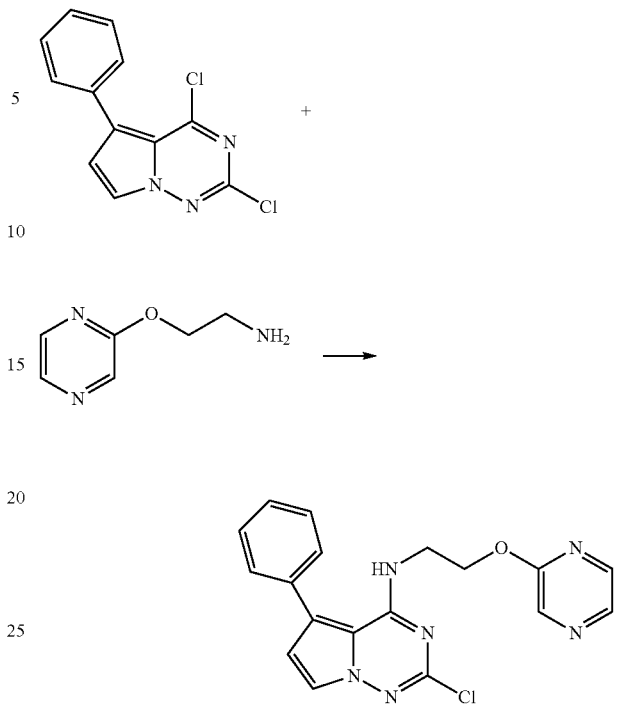

2,4-Dichloro-5-phenylpyrrolo[2,1-f][1,2,4]triazine (0.500 g, 1.89 mmol) (prepared as in Example 3) was converted to 2-chloro-5-phenyl-N-(2-(pyrazin-2-yloxy)ethyl)pyrrolo[2,1-f][1,2,4]triazin-4-amine by following the procedure in Example 3 in THF (20 mL) using DIPEA (0.661 mL, 3.79 mmol) and 2-(pyrazin-2-yloxy)ethanamine (0.395 g, 2.84 mmol). The residue obtained was purified by column chromatography using CombiFlash (REDISEP®, silica gel, 24 g, 18% EtOAc/hexanes) to obtain 2-chloro-5-phenyl-N-(2-(pyrazin-2-yloxy)ethyl)pyrrolo[2,1-f][1,2,4]triazin-4-amine (0.300 g, 43.2%). LCMS Condition B-21: retention time 2.08, [M+1]=367.2. $^1$H NMR (400 MHz, DMSO-d$_6$) δ ppm 3.88 (q, J=5.6 Hz, 2H), 4.48 (t, J=5.6 Hz, 2H), 6.62 (t, J=5.6 Hz, 1H), 6.74 (t, J=2.8 Hz, 1H), 7.32-7.47 (m, 5H), 7.80 (d, J=2.4 Hz, 1H), 8.16 (dd, J=1.6 Hz, J=2.8 Hz, 1H), 8.22 (dd, J=1.6 Hz, J=4.8 Hz, 2H).

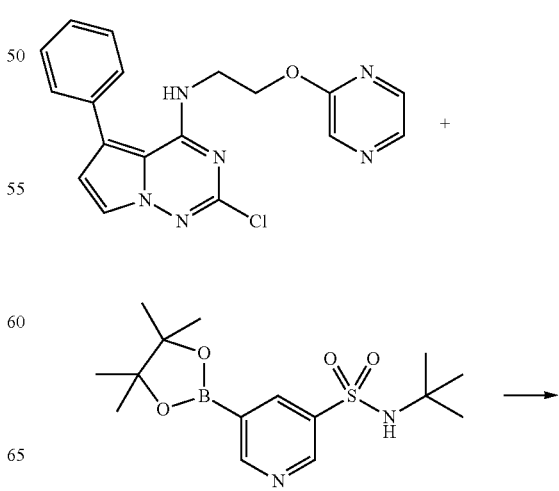

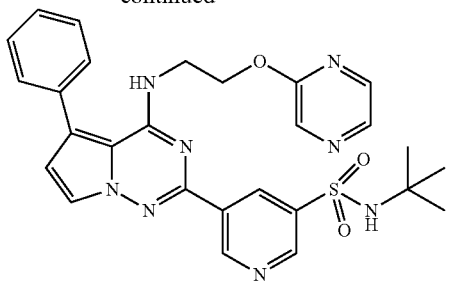

2-Chloro-5-phenyl-N-(2-(pyrazin-2-yloxy)ethyl)pyrrolo[2,1-f][1,2,4]triazin-4-amine (0.200 g, 0.545 mmol) was converted to N-(tert-butyl)-5-(5-phenyl-4-((2-(pyrazin-2-yloxy)ethyl)amino)pyrrolo[2,1-f][1,2,4]triazin-2-yl)pyridine-3-sulfonamide via Suzuki cross-coupling using the conditions mentioned in Example 3. Following reagents were used for the conversion; N-(tert-butyl)-5-(4,4,5,5-tetramethyl-1,3,2-dioxaborolan-2-yl)pyridine-3-sulfonamide (0.241 g, 0.709 mmol), $K_2CO_3$ (0.226 g, 1.64 mmol)) and 1,1'-bis(diphenylphosphino)ferrocene-palladium(II)dichloride dichloromethane complex (40.0 mg, 0.0550 mmol) heated for 18 h in a sealed tube at 100° C. The residue obtained was purified by column chromatography using CombiFlash (REDISEP®, silica gel, 12 g, 1.8% methanol in chloroform) to obtain the product with 93% purity. It was further purified by preparative HPLC (Condition B-72 as described in general methods) to obtain N-(tert-butyl)-5-(5-phenyl-4-((2-(pyrazin-2-yloxy)ethyl)amino)pyrrolo[2,1-f][1,2,4]triazin-2-yl)pyridine-3-sulfonamide (0.130 g, 43.8%). LCMS Condition B-39: retention time 2.73, [M+1]=546.2. $^1$H NMR (400 MHz, DMSO-$d_6$) δ ppm 1.60 (s, 9, H), 4.06 (q, J=5.2 Hz, 2H), 4.56 (t, J=5.2 Hz, 2H), 6.49 (t, J=5.6 Hz, 1H), 6.83 (d, J=2.8 Hz, 1H), 7.34-7.52 (m, 5H), 7.95 (d, J=2.4 Hz, 1H), 7.97 (s, 1H), 8.17-8.21 (m, 3H), 8.91 (t, J=2.0 Hz, 1H), 9.07 (d, J=2.4 Hz, 1H), 9.56 (d, J=2.0 Hz, 1H).

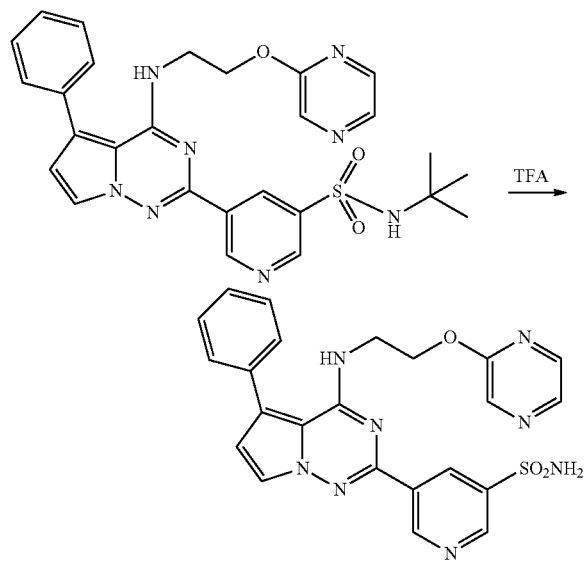

N-(tert-Butyl)-5-(5-phenyl-4-((2-(pyrazin-2-yloxy)ethyl)amino)pyrrolo[2,1-f][1,2,4]triazin-2-yl)pyridine-3-sulfonamide (80.0 mg, 0.147 mmol) was converted to 5-(5-phenyl-4-((2-(pyrazin-2-yloxy)ethyl)amino)pyrrolo[2,1-f][1,2,4]triazin-2-yl)pyridine-3-sulfonamide using TFA (0.0210 mL, 0.278 mmol) as per the procedure in Example 5. The residue obtained, was purified by column chromatography using CombiFlash (REDISEP®, silica gel, 12 g, 2% methanol in chloroform). Finally the product was further purified with preparative HPLC (Condition B-72 as described in general methods) to obtain 5-(5-phenyl-4-((2-(pyrazin-2-yloxy)ethyl)amino)pyrrolo[2,1-f][1,2,4]triazin-2-yl)pyridine-3-sulfonamide (30.0 mg, 41.8%). LCMS Condition B-19: retention time 2.02, [M+1]=489.6. HPLC Condition B-4: retention time 10.71, purity 99.02%. $^1$H NMR (400 MHz, DMSO-$d_6$) δ ppm 4.07-4.10 (m, 2H), 4.57 (t, J=5.2 Hz, 2H), 6.47 (t, J=5.2 Hz, 1H), 6.83 (d, J=2.8 Hz, 1H), 7.34-7.54 (m, 5H), 7.68 (s, 2H), 7.95 (d, J=2.8 Hz, 2H), 8.17-8.21 (m, 2H), 8.92 (dd, J=1.6 Hz, J=2.4 Hz, 1H), 9.06 (d, J=2.4 Hz, 1H), 9.56 (d, J=1.6 Hz, 1H).

Example 24

2-(5-(4-(Benzylamino)-5-phenylpyrrolo[1,2-f][1,2,4]triazin-2-yl)pyridin-3-yl)propane-1,3-diol

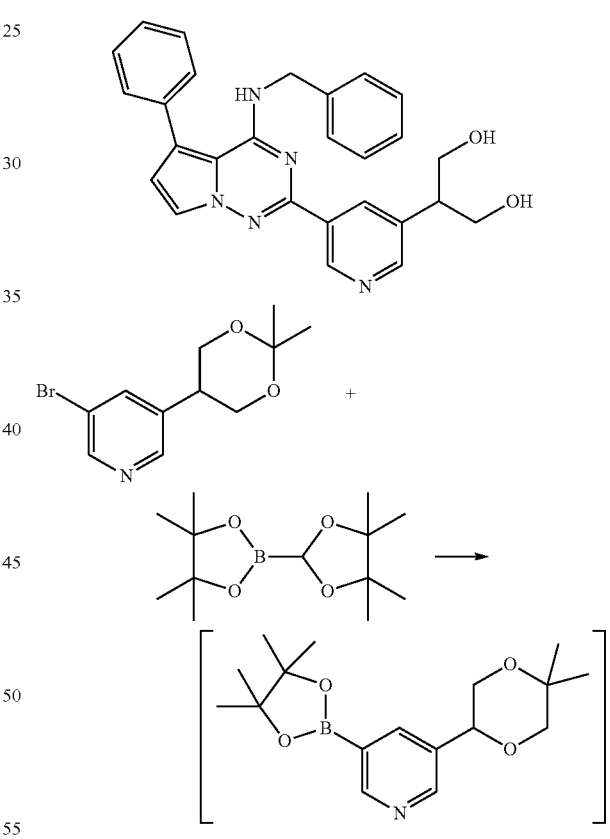

3-Bromo-5-(2,2-dimethyl-1,3-dioxan-5-yl)pyridine (0.140 g, 0.514 mmol) ((Johnson et al., WO 2011/28741) was converted to 3-(2,2-dimethyl-1,3-dioxan-5-yl)-5-(4,4,5,5-tetramethyl-1,3,2-dioxaborolan-2-yl)pyridine using bis-pinacolatodiboron (0.196 g, 0.772 mmol), potassium acetate (0.151 g, 1.54 mmol) and 1,1'-bis(diphenylphosphino) ferrocene-palladium(ii) dichloride dichloromethane complex (42.0 mg, 0.0510 mmol) as per the procedure in Example 13 at 100° C. in a microwave for 1.5 h. On removal of dioxane, 3-(2,2-dimethyl-1,3-dioxan-5-yl)-5-(4,4,5,5-tetramethyl-1,3,2-dioxaborolan-2-yl)pyridine was obtained (0.140 g, 85.0%). It was used as such for the next step without further purification (Johnson et al., WO 2011/28741). LCMS Condition B-12: retention time 1.91 [M+1]=320.2.

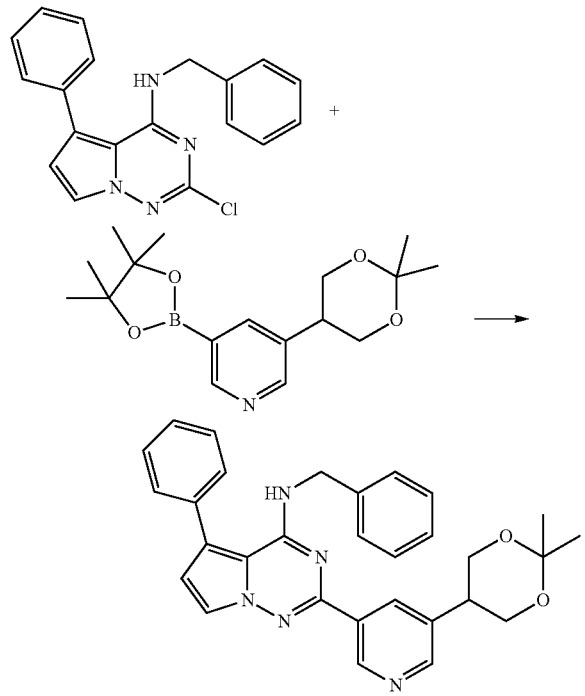

N-Benzyl-2-chloro-5-phenylpyrrolo[2,1-f][1,2,4]triazin-4-amine (50.0 mg, 0.149 mmol) (prepared as in Example 4) was converted to N-benzyl-2-(5-(2,2-dimethyl-1,3-dioxan-5-yl)pyridin-3-yl)-5-phenylpyrrolo[2,1-f][1,2,4]triazin-4-amine via Suzuki cross-coupling using the conditions mentioned in Example 3. Following reagents were used for the conversion; 3-(2,2-dimethyl-1,3-dioxan-5-yl)-5-(4,4,5,5-tetramethyl-1,3,2-dioxaborolan-2-yl)pyridine (57.0 mg, 0.179 mmol), potassium carbonate (62.0 mg, 0.448 mmol) and 1,1' bis(diphenylphosphino)ferrocene-palladium(ii) dichloride dichloromethane complex (6.10 mg, 0.00747 mmol). Residue obtained was purified by preparative HPLC (Condition B-73 as described in general methods) to get N-benzyl-2-(5-(2,2-dimethyl-1,3-dioxan-5-yl)pyridin-3-yl)-5-phenylpyrrolo[2,1-f][1,2,4]triazin-4-amine (25.0 mg, 34.1%). LCMS Condition B-40: retention time 1.32, [M+1]=492.3. $^1$H NMR (400 MHz, DMSO-d$_6$) δ ppm 1.39 (s, 3H), 1.46 (s, 3H), 3.07-3.12 (m, 1H), 3.93-4.07 (m, 4H), 4.80 (d, J=5.6 Hz, 2H), 6.67 (t, J=5.6 Hz, 1H), 6.78 (d, J=2.8 Hz, 1H), 7.22-7.29 (m, 1H), 7.31-7.38 (m, 5H), 7.43-7.53 (m, 4H), 7.87 (d, J=2.8 Hz, 1H), 8.51 (t, J=2.0 Hz, 1H), 8.66 (d, J=2.4 Hz, 1H), 9.21 (d, J=2.4 Hz, 1H).

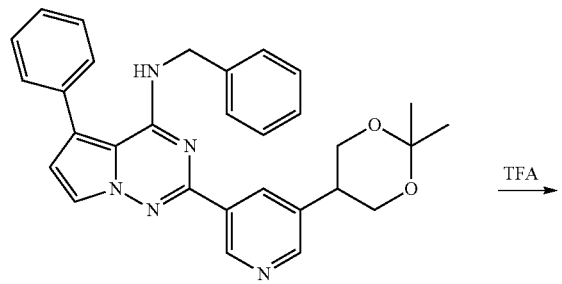

TFA

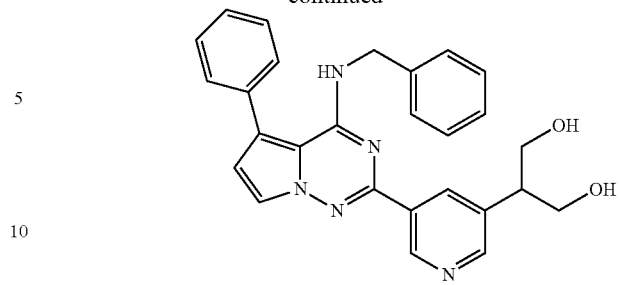

To a solution of N-benzyl-2-(5-(2,2-dimethyl-1,3-dioxan-5-yl)pyridin-3-yl)-5-phenylpyrrolo[2,1-f][1,2,4]triazin-4-amine (60.0 mg, 0.122 mmol) in methanol (15 mL) was added p-toluenesulfonic acid monohydrate (12.0 mg, 0.0610 mmol) and stirred at ambient temperature for 2 h. Reaction mixture was diluted with saturated sodium bicarbonate solution (50 mL) and extracted into DCM (2×50 mL). The combined organic layer was dried over anhydrous sodium sulfate, filtered and evaporated under reduced pressure. The resulting residue was purified by preparative HPLC (Condition B-73 as described in general methods) to get 2-(5-(4-(benzylamino)-5-phenylpyrrolo[2,1-f][1,2,4]triazin-2-yl)pyridin-3-yl)propane-1,3-diol (35.0 mg, 63.5%). LCMS Condition B-12: retention time 2.00, [M+1]=452.2. HPLC Condition B-4: retention time 7.22, purity 97.89%. $^1$H NMR (400 MHz, DMSO-d$_6$) δ ppm 2.93-2.96 (m, 1H), 3.68-3.77 (m, 4H), 4.69 (br s, 2H), 4.80 (d, J=5.6 Hz, 2H), 6.69 (t, J=5.6 Hz, 1H), 6.79 (d, J=2.8 Hz, 1H), 7.23-7.27 (m, 1H), 7.32-7.41 (m, 5H), 7.46-7.55 (m, 4H), 7.90 (d, J=2.8 Hz, 1H), 8.36 (t, J=2.4 Hz, 1H), 8.51 (d, J=2.0 Hz, 1H), 9.19 (d, J=2.0 Hz, 1H).

Example 25

1-(5-(5-Phenyl-4-(pyridin-2-ylmethylamino)pyrrolo[1,2-f][1,2,4]triazin-2-yl)pyridin-3-yl)urea

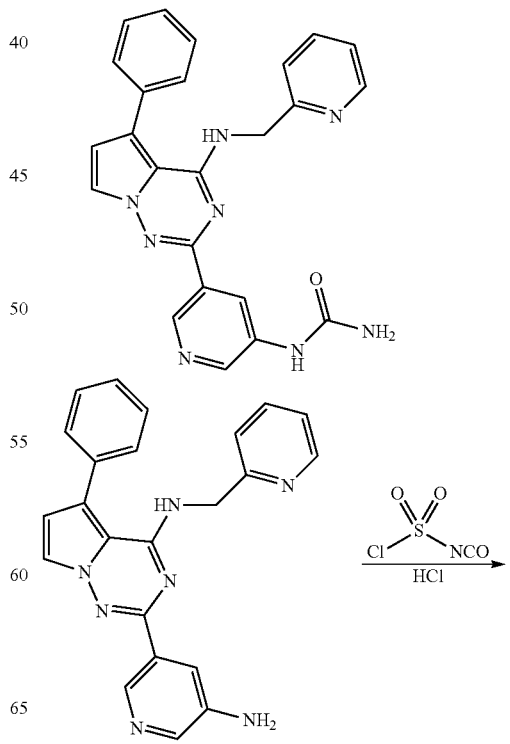

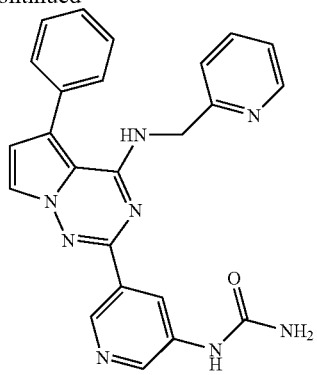

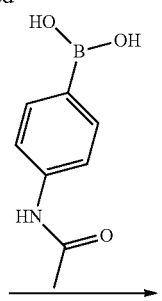

2-(5-Aminopyridin-3-yl)-5-phenyl-N-(pyridin-2-ylmethyl)pyrrolo[2,1-f][1,2,4]triazin-4-amine (0.100 g, 0.254 mmol) (prepared as in Example 3) was dissolved in $CH_2Cl_2$ (10 mL) and chlorosulfonyl isocyanate (0.0330 mL, 0.381 mmol) was added. The reaction mixture was stirred at room temperature for 3 h. Concentrated hydrochloric acid was added until the reaction mixture forms a clear solution. The aqueous mixture was extracted with $CH_2Cl_2$ (30 mL) and the organic layer was separated. The aqueous layer was adjusted to pH 11 using saturated solution of sodium hydroxide. The aqueous solution was extracted with $CH_2Cl_2$ (20×3 mL). The combined organic layer was dried over sodium sulfate, filtered and concentrated under reduced pressure. The residue was purified by preparative HPLC (Condition B-62 as described in general methods) to obtain 1-(5-(5-phenyl-4-((pyridin-2-ylmethyl)amino)pyrrolo[2,1-f][1,2,4]triazin-2-yl)pyridin-3-yl)urea (30.0 mg, 27.0%). LCMS Condition B-14: retention time 1.831 min, [M+1]=437.2. HPLC Condition B-30: retention time 5.48 min, Purity 95.9%. $^1$H NMR (400 MHz, DMSO-$d_6$) δ ppm 4.91 (d, J=4.8 Hz, 2H), 6.05 (br s, 2H), 6.81 (d, J=2.4 Hz, 1H), 7.27 (t, J=4.8 Hz, 2H), 7.46-7.61 (m, 7H), 7.76 (dt, J=1.6 Hz, J=7.6 Hz, 1H), 7.90 (d, J=2.8 Hz, 1H), 8.38-8.39 (m, 1H), 8.66-8.68 (m, 1H), 8.88 (s, 1H), 8.96 (d, J=1.6 Hz, 1H).

Example-26

N-(4-(5-Phenyl-4-(pyridin-2-ylmethylamino)pyrrolo[1,2-f][1,2,4]triazin-2-yl)phenyl)acetamide

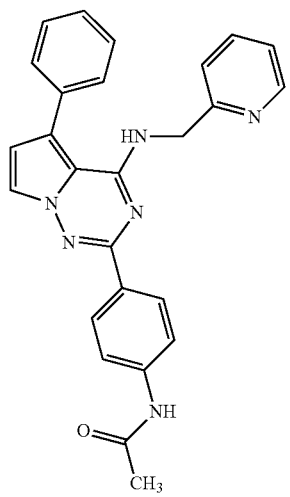

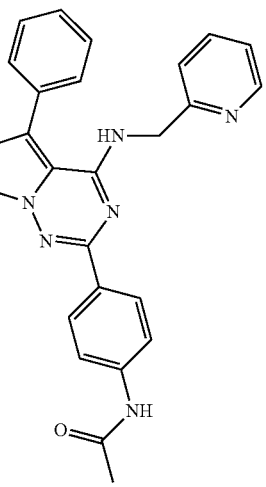

2-Chloro-5-phenyl-N-(pyridin-2-ylmethyl)pyrrolo[2,1-f][1,2,4]triazin-4-amine (75.0 mg, 0.223 mmol) (prepared as per Example 3) was converted to N-(4-(5-phenyl-4-((pyridin-2-ylmethyl)amino)pyrrolo[2,1-f][1,2,4]triazin-2-yl)phenyl)acetamide via Suzuki cross-coupling using the conditions mentioned in Example 3. Following reagents were used for the conversion; (4-acetamidophenyl)boronic acid (44.0 mg, 0.246 mmol), $K_2CO_3$ (93.0 mg, 0.670 mmol) and 1,1'-bis(diphenylphosphino)ferrocene-palladium(II)dichloride dichloromethane complex (18.0 mg, 0.0220 mmol) at 110° C. for 16 h. The residue was purified by column chromatography using CombiFlash (REDISEP®, silica gel, 40 g, 7% methanol in chloroform) to afford 90% pure compound which was further purified by preparative HPLC (Condition B-54 as described in general methods) to obtain N-(4-(5-phenyl-4-((pyridin-2-ylmethyl)amino)pyrrolo[2,1-f][1,2,4]triazin-2-yl)phenyl)acetamide (12.0 mg, 12.4%). LCMS Condition B-39: retention time, 2.05 min, [M+1]=435.2. HPLC Condition B-2: retention time 8.84 min, Purity 98.20%. $^1$H NMR (400 MHz, DMSO-$d_6$) δ ppm 2.08 (s, 3H), 4.91 (d, J=4.4 Hz, 2H), 6.76 (d, J=2.8 Hz, 1H), 7.20 (t, J=4.0 Hz, 1H), 7.30 (dd, J=4.8 Hz, J=6.8 Hz, 1H), 7.45-7.59 (m, 7H), 7.69 (d, J=8.8

Hz, 2H), 7.78 (dt, J=1.6 Hz, J=7.6 Hz, 1H), 7.82 (d, J=2.8 Hz, 1H), 8.19 (d, J=8.8 Hz, 2H), 8.38 (d, J=4.0 Hz, 1H).

Example-27

4-(Benzylamino)-N-(3-(methylsulfonamido)phenyl)-5-phenylpyrrolo[1,2-f][1,2,4]triazine-2-carboxamide

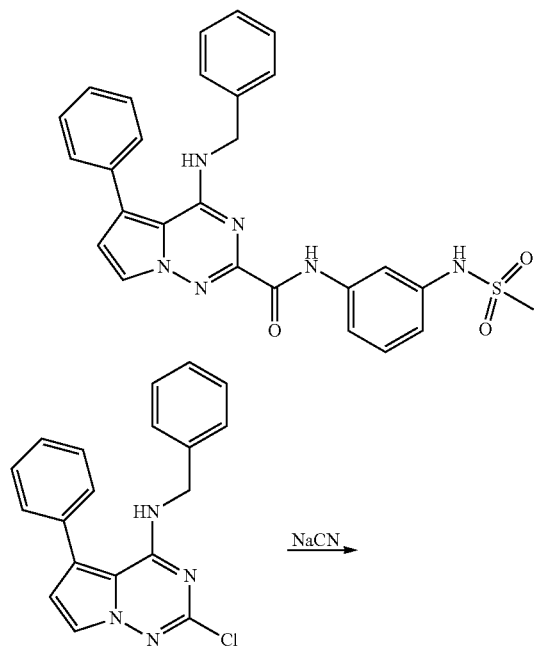

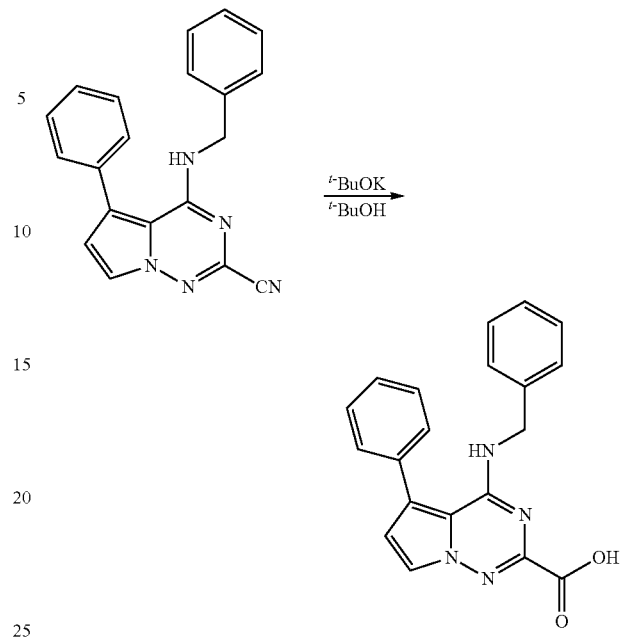

To a stirred solution of 4-(benzylamino)-5-phenylpyrrolo[2,1-f][1,2,4]triazine-2-carbonitrile (0.100 g, 0.307 mmol) dissolved in tert-butanol (15.0 mL, 157 mmol) and water (15 mL) was added potassium tert-butoxide (0.138 g, 1.23 mmol). The reaction mixture was heated in a pressure tube to 95° C. for 16 h and concentrated under reduced pressure. To the resulting residue, was added water (100 mL) and the aqueous solution was neutralized with dilute HCl to pH 7. The solid precipitated, was filtered and further purified by preparative HPLC (Condition B-74 as described in general methods) to afford 4-(benzylamino)-5-phenylpyrrolo[2,1-f][1,2,4]triazine-2-carboxylic acid (30.0 mg, 28.3%). LCMS Condition B-15: retention time 1.66 min, [M+1]=345.2. HPLC Condition B-1: retention time 14.64 min, Purity 99.30%. $^1$H NMR (400 MHz, DMSO-$d_6$) δ ppm 4.71 (s, 2H), 6.29 (br s, 1H), 6.77 (d, J=2.8 Hz, 1H), 7.24-7.48 (m, 10H), 7.77 (d, J=2.8 Hz, 1H).

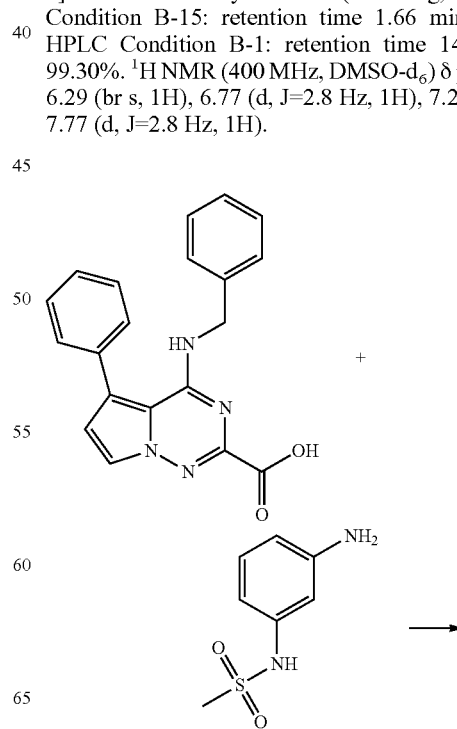

To a stirred solution of N-benzyl-2-chloro-5-phenylpyrrolo[2,1-f][1,2,4]triazin-4-amine (0.500 g, 1.49 mmol) dissolved in DMF (5 mL) was added sodium cyanide (0.366 g, 7.47 mmol). The reaction mixture was heated to 100° C. for 24 h and cooled. Reaction was quenched by adding ice cold water (100 mL) and was extracted with EtOAc (50×3 mL). The organic layer was separated and dried over anhydrous sodium sulfate and concentrated under reduced pressure. The residue was purified by column chromatography using CombiFlash (REDISEP®, silica gel, 24 g, 10% EtOAc/hexanes) to afford 4-(benzylamino)-5-phenylpyrrolo[2,1-f][1,2,4]triazine-2-carbonitrile (0.200 g, 41.2%). LCMS Condition B-45: retention time 2.95 min, [M−1]=324.2. HPLC Condition B-2: retention time 25.49 min, Purity 98.76%. $^1$H NMR (400 MHz, DMSO-$d_6$) δ ppm 4.68 (s, 2H), 6.92-6.96 (m, 2H), 7.26 (m, 10H), 7.86 (d, J=2.8 Hz, 1H).

-continued

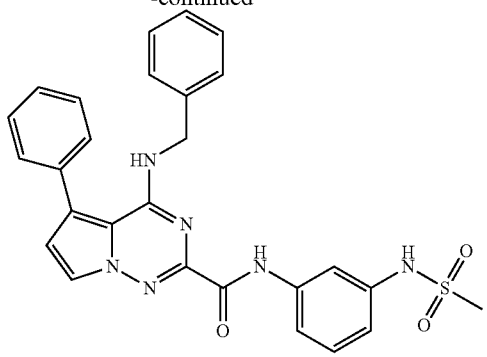

In a 8 mL glass reaction vial, 4-(benzylamino)-5-phenylpyrrolo[2,1-f][1,2,4]triazine-2-carboxylic acid (10.0 mg, 0.0290 mmol), HATU (16.6 mg, 0.0440 mmol) and N-(3-aminophenyl)methane sulfonamide (5.93 mg, 0.0320 mmol, commercial) were taken. To this, DMF (0.5 mL) and DIPEA (0.0150 mL, 0.0870 mmol) were added and the reaction mixture was stirred for 5 h at room temperature. The reaction mixture was diluted with methanol. The crude compound was purified by reverse phase prep HPLC (Condition B-75 as described in general methods). The multiple fractions of the sample were combined and evaporated to dryness using Genevac to afford 4-(benzylamino)-N-(3-(methylsulfonamido)phenyl)-5-phenylpyrrolo[1,2-f][1,2,4]triazine-2-carboxamide (6.40 mg, 42.7%) as a white solid. LCMS Condition B-76: retention time 2.00 min, [M+1]=513.0; purity=99.30%. $^1$H NMR (400 MHz, DMSO-d$_6$) δ ppm 3.03 (s, 3H), 4.85 (d, J=5.6 Hz, 2H), 6.79 (t, J=5.6 Hz, 1H), 6.89 (d, J=2.8 Hz, 1H), 7.00 (dt, J=1.2 Hz, J=6.8 Hz, 1H), 7.23-7.54 (m, 12H), 7.73 (t, J=2.0 Hz, 1H), 7.91 (d, J=2.8 Hz, 1H), 9.80 (br s, 1H), 10.25 (s, 1H).

Example 28

2-(5-(5-Phenyl-4-(pyridin-2-ylmethylamino)pyrrolo[1,2-f][1,2,4]triazin-2-yl)pyridine-3-sulfonamido)acetamide

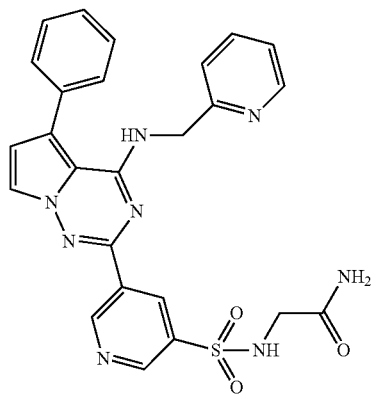

-continued

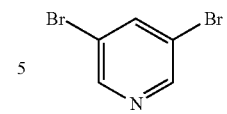 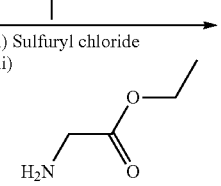

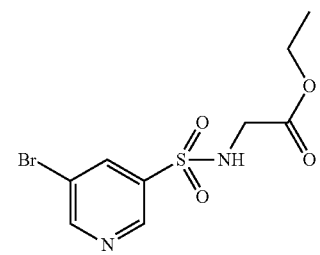

3,5-Dibromopyridine (3.00 g, 12.7 mmol) was dissolved in THF (20 mL) and the solution cooled to −20° C. Isopropyl magnesium chloride-lithium chloride complex (2.76 g, 19.0 mmol) was added to the solution under the nitrogen atmosphere. The reaction mixture was stirred for 45 minutes and sulfuryl chloride (1.55 mL, 19.0 mmol) was added (at −20° C.). Stirring continued for additional 30 minutes and to this mixture was added THF (10 mL) solution containing ethylglycinate (7.07 g, 50.7 mmol) and DIPEA (11.1 mL, 63.3 mmol) at −20° C. The reaction mixture was allowed to reach room temperature and stirred for 20 minutes before quenching with the addition of aqueous solution of ammonium chloride. The aqueous solution was extracted with ethyl acetate (2×25 mL). The combined organic portion was dried over anhydrous sodium sulfate, filtered and concentrated under reduced pressure. The residue was purified by column chromatography using CombiFlash (REDISEP®, silica gel, 40 g, 35% ethyl acetate/pet ether) to obtain ethyl 2-(5-bromopyridine-3-sulfonamido)acetate (1.50 g, 21.3%). LCMS Condition B-39: retention time 1.95 min, [M+1]=322.8. $^1$H NMR (400 MHz, DMSO-d$_6$) δ ppm 1.10 (t, J=7.2 Hz, 3H), 3.89 (d, J=6.0 Hz, 2H), 3.98 (q, J=7.2 Hz, 2H), 8.39 (t, J=2.0 Hz, 1H), 8.62 (t, J=6.0 Hz, 1H), 8.92 (d, J=2.0 Hz, 1H), 8.98 (d, J=2.0 Hz, 1H).

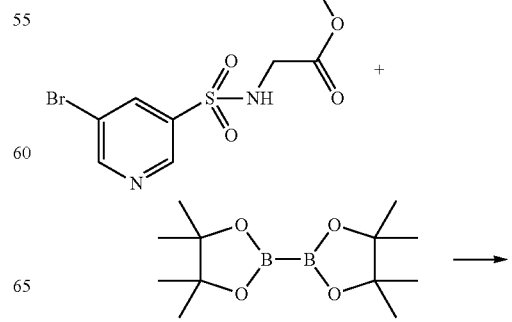

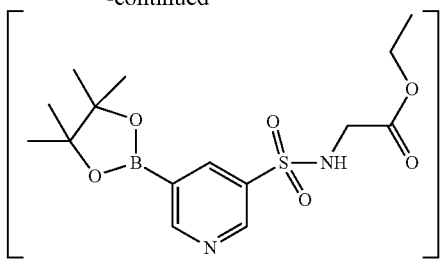

Ethyl 2-(5-bromopyridine-3-sulfonamido)acetate (0.300 g, 0.928 mmol) was converted to ethyl 2-(5-(4,4,5,5-tetramethyl-1,3,2-dioxaborolan-2-yl)pyridine-3-sulfonamido)acetate following the general procedure described for Example 14 using bis(pinacolato)diboron (0.350 g, 1.39 mmol), KOAc (0.0910 g, 0.928 mmol) and 1,1'-bis(diphenylphosphino)ferrocene-palladium(II)dichloride dichloromethane complex (0.758 g, 0.928 mmol) in dioxane at 110° C. in a sealed tube for 14 h. The reaction mixture was allowed to cool, filtered through CELITE®, washed with dioxane. The filtrate was evaporated under reduced pressure and the residue (0.450 g) used without further purification. LCMS Condition B-34: retention time 1.69 min, [M+1]=287.0.

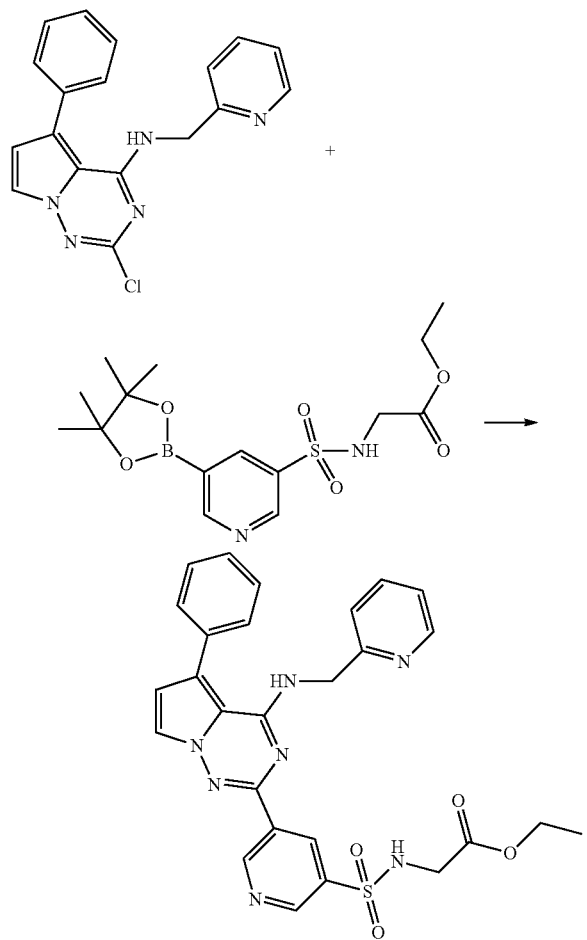

2-Chloro-5-phenyl-N-(pyridin-2-ylmethyl)pyrrolo[2,1-f][1,2,4]triazin-4-amine (0.200 g, 0.596 mmol) was converted to ethyl 2-(5-(5-phenyl-4-((pyridin-2-ylmethyl)amino)pyrrolo[2,1-f][1,2,4]triazin-2-yl)pyridine-3-sulfonamido)acetate via Suzuki cross-coupling using the general procedure described in Example 3. The following reagents were used for the conversion; ethyl 2-(5-(4,4,5,5-tetramethyl-1,3,2-dioxaborolan-2-yl)pyridine-3-sulfonamido)acetate (0.441 g, 1.19 mmol), K₂CO₃ (0.247 g, 1.79 mmol) and 1,1'-bis(diphenylphosphino)ferrocene-palladium(II)dichloride dichloromethane complex (0.0490 g, 0.0600 mmol) at 110° C. for 16 h. The reaction mixture was concentrated and the residue was purified by preparative HPLC (Condition B-77 as described in general methods) to obtain ethyl 2-(5-(5-phenyl-4-((pyridin-2-ylmethyl)amino)pyrrolo[2,1-f][1,2,4]triazin-2-yl)pyridine-3-sulfonamido)acetate (0.0800 g. 46.0%). LCMS Condition B-34: retention time 2.41 min, [M+1]=544.0. ¹H NMR (300 MHz, DMSO-d₆) δ ppm 0.96-1.12 (m, 3H), 3.94 (q, J=7.2 Hz, 4H), 4.94 (d, J=4.5 Hz, 2H), 6.86 (d, J=2.6 Hz, 1H), 7.23-7.31 (m, 1H), 7.40-7.66 (m, 8H), 7.79 (td, J=7.7 Hz, J=1.7 Hz, 1H), 7.98 (d, J=3.0 Hz, 1H), 8.39 (d, J=4.2 Hz, 1H), 8.85 (d, J=2.3 Hz, 1H), 9.02 (s, 1H), 9.58 (d, J=1.9 Hz, 1H).

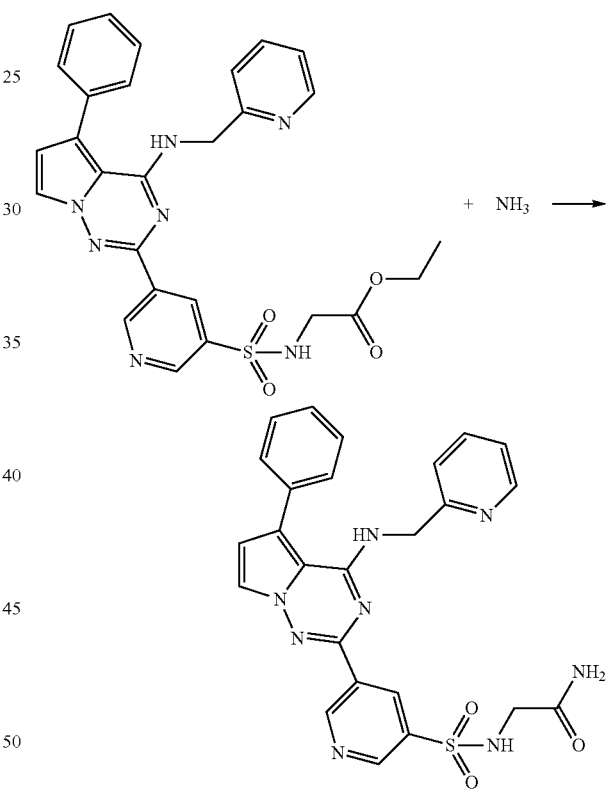

Ethyl 2-(5-(5-phenyl-4-((pyridin-2-ylmethyl)amino)pyrrolo[2,1-f][1,2,4]triazin-2-yl)pyridine-3-sulfonamido)acetate (0.0800 g, 0.147 mmol) was dissolved in ethanol (5 mL) and the reaction mixture cooled to −75° C. and ammonia gas purged for 10 minutes. The closed pressure tube reaction mixture was heated to 85° C. for 14 h. The reaction mixture was allowed to cool and concentrated under reduced pressure. The residue was purified by preparative HPLC (Condition B-88 as described in general methods) to obtain 2-(5-(5-phenyl-4-(pyridin-2-ylmethylamino)pyrrolo[1,2-f][1,2,4]triazin-2-yl)pyridine-3-sulfonamido)acetamide (15.0 mg, 19.6%). LCMS Condition B-39: retention time 2.08 min, [M+1]=514.8. HPLC Condition B-30: retention time 6.93 min, Purity 99.0%. ¹H NMR (400 MHz, DMSO-d₆) δ ppm 3.54 (s, 2H), 4.94 (d, J=4.5 Hz, 2H), 6.85 (d, J=3.0 Hz, 1H), 7.04 (br s, 1H), 7.27-7.35 (m, 3H), 7.38-7.42 (m, 1H), 7.43-7.49 (m, 2H), 7.51-7.55 (m, 2H), 7.57-7.64 (m, 2H), 7.75-7.84 (m, 1H), 7.97 (d, J=2.5 Hz, 1H), 8.34-8.43 (m, 1H), 8.87 (t, J=2.3 Hz, 1H), 9.01 (s, 1H), 9.56 (d, J=2.0 Hz, 1H).

Example 30

N1-(5-(5-Phenyl-4-(pyridin-2-ylmethylamino)pyrrolo[1,2-f][1,2,4]triazin-2-yl)pyridin-3-yl)succinamide

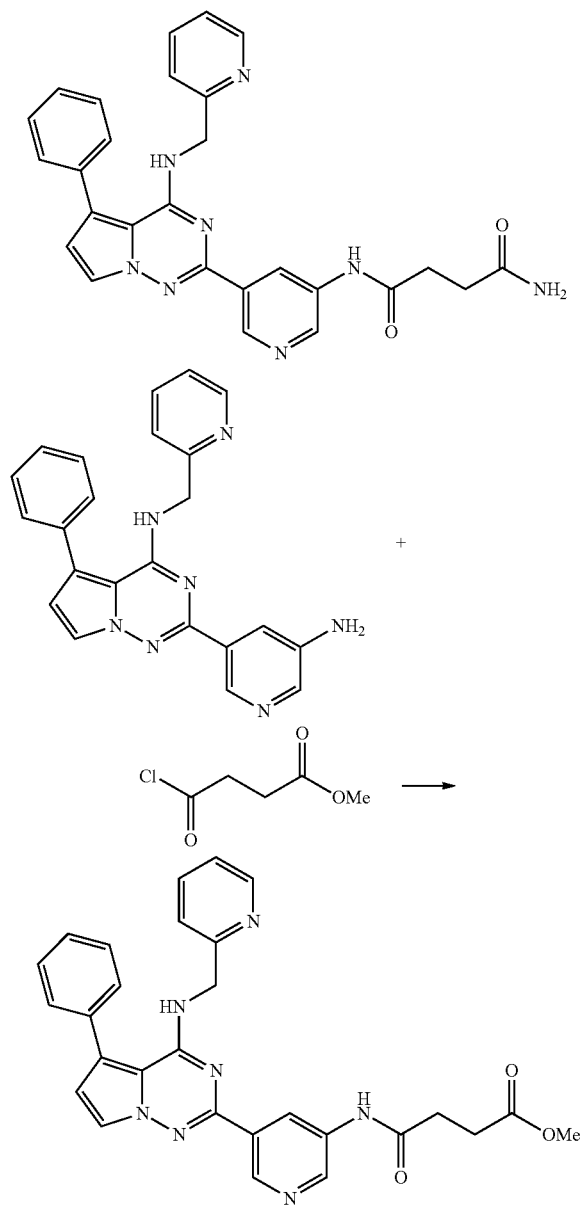

2-(5-Aminopyridin-3-yl)-5-phenyl-N-(pyridin-2-ylmethyl)pyrrolo[2,1-f][1,2,4]triazin-4-amine (0.200 g, 0.508 mmol, synthesized as described in Example 3) was dissolved in DCM (10 mL) and pyridine (0.0820 mL, 1.02 mmol) was added, followed by the addition of methyl 4-chloro-4-oxobutanoate (77.0 mg, 0.508 mmol). The reaction mixture was stirred at room temperature for 30 min. Water (10 mL) was added to the reaction mixture followed by addition of CH$_2$Cl$_2$ (4×10 mL). The combined organic extracts were separated, dried over sodium sulfate, filtered and concentrated under reduced pressure to afford methyl 4-oxo-4-((5-(5-phenyl-4-((pyridin-2-ylmethyl)amino) pyrrolo[2,1-f][1,2,4]triazin-2-yl)pyridin-3-yl)amino)butanoate (0.170 g, 65.9%). 60 mg of the residue was further purified by preparative HPLC (Condition B-89 as described in general methods) to obtain methyl 4-oxo-4-(5-(5-phenyl-4-(pyridin-2-ylmethylamino) pyrrolo[1,2-f][1,2,4]triazin-2-yl)pyridin-3-ylamino)butanoate.

LCMS Condition B-79: retention time 1.88 min, [M+1]=508.0. $^1$H NMR (400 MHz, DMSO-d$_6$) δ ppm 2.62-2.78 (m, 4H), 3.62 (s, 3H), 4.93 (s, 2H), 6.81 (d, J=2.4 Hz, 1H), 7.23-7.34 (m, 2H), 7.41-7.64 (m, 6H), 7.72-7.82 (m, 1H), 7.90-7.93 (m, 1H), 8.33-8.44 (m, 1H), 8.79-8.89 (m, 2H), 9.04-9.12 (m, 1H), 10.37 (s, 1H).

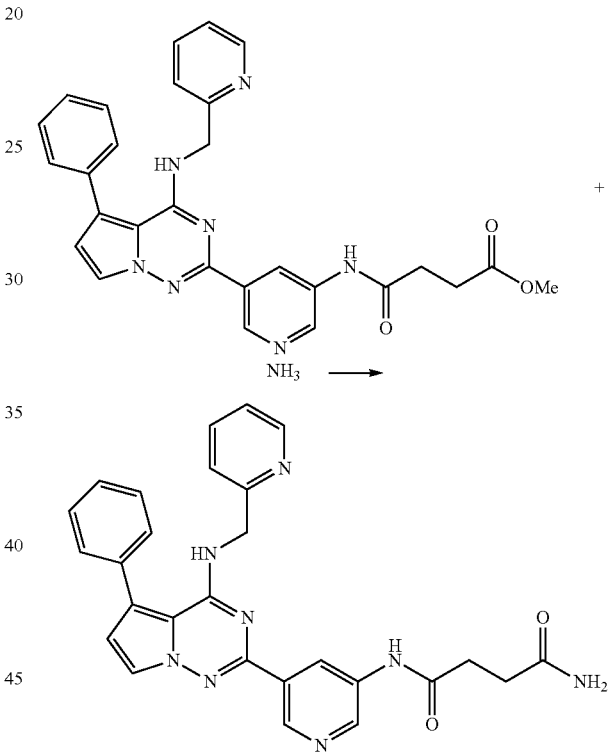

Methyl 4-oxo-4-((5-(5-phenyl-4-((pyridin-2-ylmethyl)amino)pyrrolo[2,1-f][1,2,4]triazin-2-yl)pyridin-3-yl)amino)butanoate (0.150 g, 0.296 mmol) was converted into N1-(5-(5-phenyl-4-((pyridin-2-ylmethyl)amino)pyrrolo[2,1-f][1,2,4]triazin-2-yl)pyridin-3-yl)succinamide using the general procedure described in Example 4. Methyl 4-oxo-4-((5-(5-phenyl-4-((pyridin-2-ylmethyl)amino)pyrrolo[2,1-f][1,2,4]triazin-2-yl)pyridin-3-yl)amino)butanoate (0.150 g, 0.296 mmol) was dissolved in methanol (20 mL) and cooled to −78° C. The reaction mixture was purged with ammonia gas for 15 minutes and transferred to a miniclave and heated to 65° C. for 14 h. The reaction mixture was cooled to 0° C. and transferred in to a round bottomed flask. The solution was concentrated under reduced pressure to obtain a brown residue. The residue was further purified by preparative HPLC (Condition B-90 as described in general methods) to obtain N1-(5-(5-phenyl-4-((pyridin-2-ylmethyl)amino)pyrrolo[2,1-f][1,2,4]triazin-2-yl)pyridin-3-yl)succinamide (0.0250 g, 17.0%).

HPLCMS Condition B-79: retention time 1.53 min, [M+1]=493.0, Purity 99.59%. ¹H NMR (400 MHz, DMSO-d₆) δ ppm 2.42-2.49 (m, 2H), 2.57-2.67 (m, 2H), 4.92 (d, J=4.5 Hz, 2H), 6.78 (s, 1H), 6.81 (d, J=2.8 Hz, 1H), 7.26-7.35 (m, 3H), 7.44-7.64 (m, 6H), 7.79 (td, J=7.8 Hz, J=2.0 Hz, 1H), 7.89-7.95 (m, 1H), 8.39 (dt, J=5.6 Hz, J=1.2 Hz, 1H), 8.81-8.91 (m, 2H), 9.09 (s, 1H), 10.31 (s, 1H).

Example 31

N1-(5-(5-Phenyl-4-(pyridin-2-ylmethylamino)pyrrolo[1,2-f][1,2,4]triazin-2-yl)pyridin-3-yl)oxalamide

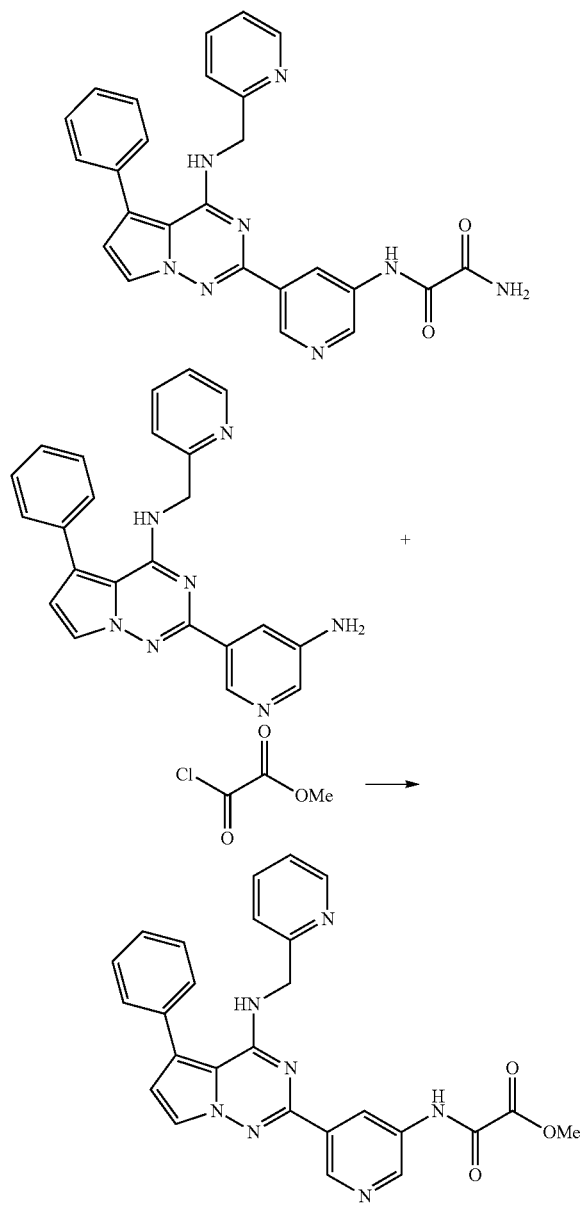

2-(5-Aminopyridin-3-yl)-5-phenyl-N-(pyridin-2-ylmethyl)pyrrolo[2,1-f][1,2,4]triazin-4-amine (0.200 g, 0.508 mmol) was dissolved in DCM (5 mL) and pyridine (0.0820 mL, 1.02 mmol) was added, followed by the addition of methyl 2-chloro-2-oxoacetate (0.0620 g, 0.508 mmol). The reaction mixture was stirred at room temperature for 30 min. The reaction mixture was quenched by the addition of water (10 mL) and the mixture extracted with CH₂Cl₂ (4×10 mL). The combined organic layer was separated, dried over sodium sulfate, filtered and concentrated under reduced pressure to afford methyl 2-oxo-2-((5-(5-phenyl-4-((pyridin-2-ylmethyl)amino)pyrrolo[2,1-f][1,2,4]triazin-2-yl)pyridin-3-yl)amino)acetate (0.180 g, 70.2%). The residue was taken for the next step without further purification. LCMS Condition B-80: retention time 2.32 min, [M+1]=480.2. ¹H NMR (400 MHz, DMSO-d₆) δ ppm 3.90 (s, 3H), 4.93 (d, J=4.7 Hz, 2H), 6.83 (d, J=2.8 Hz, 1H), 7.25-7.39 (m, 2H), 7.44-7.63 (m, 6H), 7.79 (td, J=7.7 Hz, J=1.8 Hz, 1H), 7.92 (d, J=2.8 Hz, 1H), 8.36-8.41 (m, 1H), 8.95-9.05 (m, 2H), 9.19 (d, J=1.8 Hz, 1H), 11.20 (s, 1H).

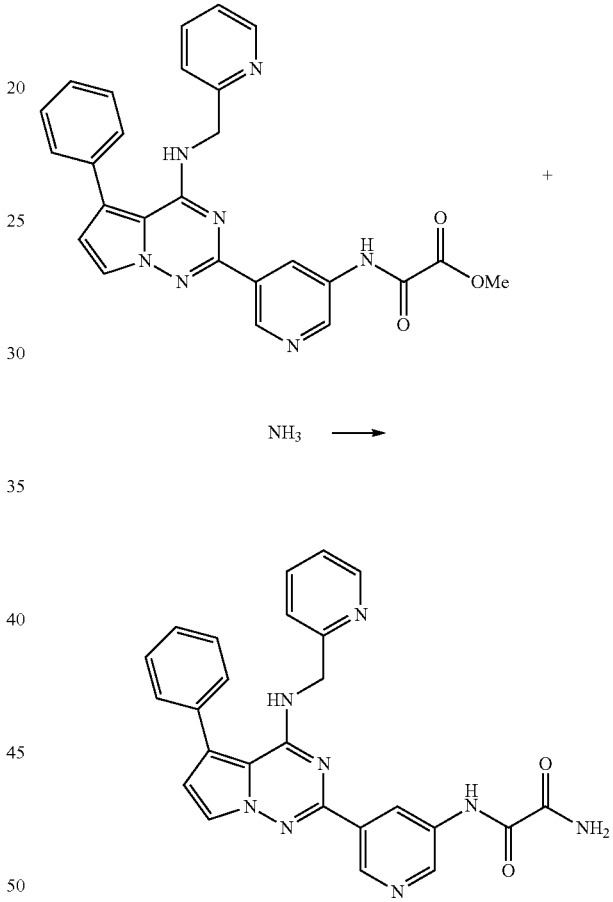

Methyl 2-oxo-2-((5-(5-phenyl-4-((pyridin-2-ylmethyl)amino)pyrrolo[2,1-f][1,2,4]triazin-2-yl)pyridin-3-yl)amino) acetate (0.160 g, 0.334 mmol) was converted into N1-(5-(5-phenyl-4-((pyridin-2-ylmethyl)amino)pyrrolo[2,1-f][1,2,4]triazin-2-yl)pyridin-3-yl)oxalamide by the general procedures described in Example 4. The residue was purified using reverse phase HPLC (Condition B-91 as described in general methods) to afford N1-(5-(5-phenyl-4-((pyridin-2-ylmethyl)amino)pyrrolo[2,1-f][1,2,4]triazin-2-yl)pyridin-3-yl)oxalamide (8.00 mg, 5.11%). HPLCMS Condition B-79: retention time 1.72 min, [M+1]=465.0, Purity 99.03%. ¹H NMR (400 MHz, DMSO-d₆) δ ppm 4.94 (d, J=4.5 Hz, 2H), 6.83 (d, J=3.0 Hz, 1H), 7.24-7.36 (m, 2H), 7.43-7.65 (m, 6H), 7.80 (td, J=7.7 Hz, J=1.76 Hz, 1H), 7.92 (d, J=3.0 Hz, 1H), 8.07 (br s, 1H), 8.40 (d, J=2.5 Hz, 2H), 9.04-9.13 (m, 2H), 9.18 (d, J=2.0 Hz, 1H), 11.01 (br s, 1H).

Example 32

5-(4-((2-Methylthiazol-4-yl)methylamino)-5-phenylpyrrolo[1,2-f][1,2,4]triazin-2-yl)pyridine-3-sulfonamide

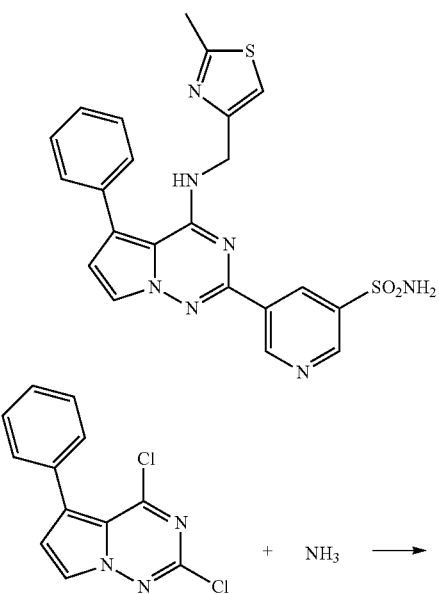

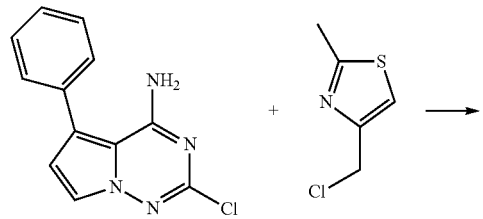

To a solution of 2,4-dichloro-5-phenylpyrrolo[2,1-f][1,2,4]triazine (0.500 g, 1.89 mmol) in THF (5 mL), NH₃ gas was bubbled at −20° C. for 15 min. The reaction mixture was stirred at RT for 1 h. The reaction mixture was concentrated under reduced pressure to remove THF and water (30 mL) was added to the resulting residue. The aqueous solution was extracted with EtOAc (3×100 mL). The combined organic layer was dried over anhydrous sodium sulfate, filtered and concentrated under reduced pressure. The residue was purified by CombiFlash (REDISEP®, silica gel, 40 g, 45% EtOAc/petroleum ether) to afford 2-chloro-5-phenylpyrrolo[2,1-f][1,2,4]triazin-4-amine (0.300 g, 64.8%). LCMS Condition B-81: retention time 2.14 min, [M+1]=245.0. ¹H NMR (400 MHz, DMSO-d₆) δ ppm 5.98 (br s, 1H), 6.75 (d, J=2.4 Hz, 1H), 7.38-7.43 (m, 2H), 7.46-7.52 (m, 3H), 7.80 (d, J=2.4 Hz, 1H), 8.40 (br s, 1H).

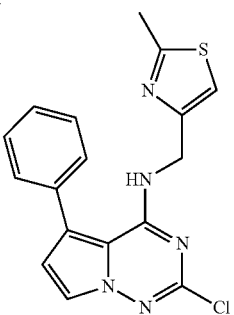

Potassium tert-butoxide (92.0 mg, 0.817 mmol) was added to a stirred solution of 2-chloro-5-phenylpyrrolo[2,1-f][1,2,4]triazin-4-amine (100 mg, 0.409 mmol) in DMF (2 mL) followed by the addition of 4-(chloromethyl)-2-methylthiazole (66.0 mg, 0.450 mmol). The reaction mixture was stirred at room temperature for 14 h. The reaction mixture was concentrated under reduced pressure to remove DMF and to this residue ice water (10 mL) was added. The aqueous solution was extracted with CH₂Cl₂ (3×10 mL) and the combined organic layer was dried over anhydrous sodium sulfate and was concentrated under reduced pressure to afford a residue that was used without further purification (45.0 mg, 30.6%). LCMS Condition B-79: retention time 2.03 min, [M+1]=356.0. ¹H NMR (400 MHz, DMSO-d₆) δ ppm 2.56-2.63 (m, 3H), 4.62-4.72 (m, 2H), 6.76 (s, 1H), 6.87 (t, J=5.3 Hz, 1H), 7.33 (s, 1H), 7.38-7.52 (m, 5H), 7.78-7.84 (m, 1H).

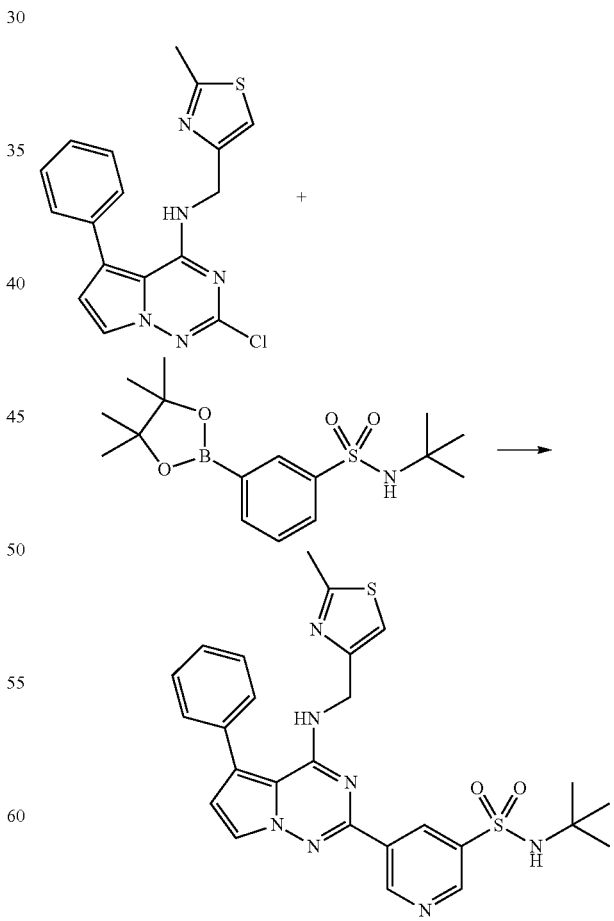

2-Chloro-N-((2-methylthiazol-4-yl)methyl)-5-phenylpyrrolo[2,1-f][1,2,4]triazin-4-amine (0.300 g, 0.843 mmol) and N-(tert-butyl)-5-(4,4,5,5-tetramethyl-1,3,2-dioxaborolan-2-yl)pyridine-3-sulfonamide (0.574 g, 1.69 mmol) were dissolved in dioxane (25 mL) and water (3 mL). To the reaction mixture was added $K_2CO_3$ (0.350 g, 2.53 mmol) and the reaction mixture was degassed with nitrogen for 15 minutes. $PdCl_2$(dppf)-$CH_2Cl_2$ (69.0 mg, 0.0840 mmol) was added and the resulting reaction mixture degassed with nitrogen for 20 minutes then heated to reflux at 110° C. for 14 h. The reaction mixture was allowed to cool and concentrated under reduced pressure. The residue was diluted with $CH_2Cl_2$ (2×25 mL) and filtered through CELITE®. The filtrate was dried over anhydrous sodium sulfate, filtered and concentrated under reduced pressure. The residue was purified by column chromatography using CombiFlash (REDISEP®, silica gel, 40 g, 25% EtOAc/hexanes) to afford N-(tert-butyl)-5-(4-(((2-methylthiazol-4-yl)methyl)amino)-5-phenylpyrrolo[2,1-f][1,2,4]triazin-2-yl)pyridine-3-sulfonamide (0.150 g, 28.0%). LCMS Condition B-82: retention time 2.35 min, [M+1]=534.2. $^1$H NMR (400 MHz, DMSO-$d_6$) δ ppm 1.15 (s, 9H), 2.62 (m, 3H), 4.88 (d, J=4.8 Hz, 2H), 6.75 (t, J=5.2 Hz, 1H), 6.85 (d, J=2.8 Hz, 1H), 7.36 (s, 1H), 7.42-7.57 (m, 5H), 7.94-7.97 (m, 2H) 8.91 (dd, J=2.0 Hz, J=2.4 Hz, 1H), 9.06 (d, J=2.4 Hz, 1H), 9.57 (d, J=2.0 Hz, 1H).

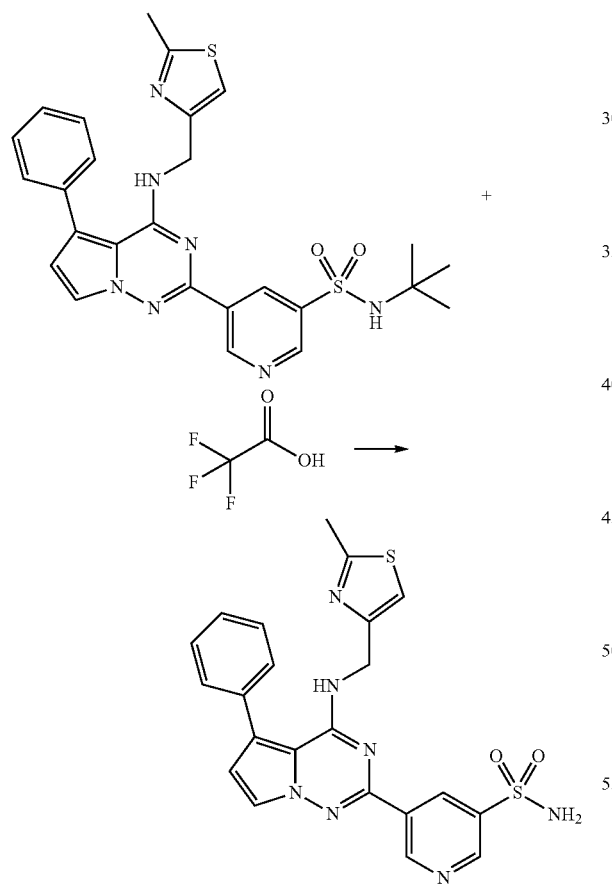

To N-(tert-Butyl)-5-(4-(((2-methylthiazol-4-yl)methyl)amino)-5-phenylpyrrolo[2,1-f][1,2,4]triazin-2-yl)pyridine-3-sulfonamide (90.0 mg, 0.169 mmol) was added TFA (1.00 mL, 11.0 mmol) and the reaction mixture stirred at room temperature for 12 h. The volatile components were removed under reduced pressure and water (5 mL) was added to the residue. The aqueous solution neutralized to pH 7 using 10% solution of sodium bicarbonate. The resulting precipitate was filtered and dried under high vacuum to obtain a residue which was purified by preparative HPLC (Condition B-89 as described in general methods) to obtain 5-(4-((2-methylthiazol-4-yl)methylamino)-5-phenylpyrrolo[1,2-f][1,2,4]triazin-2-yl)pyridine-3-sulfonamide (20.0 mg, 24.3%). LCMS Condition B-79: retention time 1.71 min, [M+1]=477.0, Purity 98.7%. $^1$H NMR (400 MHz, DMSO-$d_6$) δ ppm 2.61-2.67 (m, 3H), 4.88 (d, J=4.6 Hz, 2H), 6.75 (t, J=5.2 Hz, 1H), 6.85 (d, J=2.8 Hz, 1H), 7.38 (s, 1H), 7.42-7.60 (m, 5H), 7.76 (s, 2H), 7.92-8.03 (m, 1H) 8.95 (t, J=2.2 Hz, 1H), 9.07 (d, J=2.3 Hz, 1H), 9.60 (d, J=2.0 Hz, 1H).

Example 33

5-(4-((2-Hydroxy-1-(pyridin-2-yl)ethyl)amino)-5-phenylpyrrolo[2,1-f][1,2,4]triazin-2-yl)pyridine-3-sulfonamide

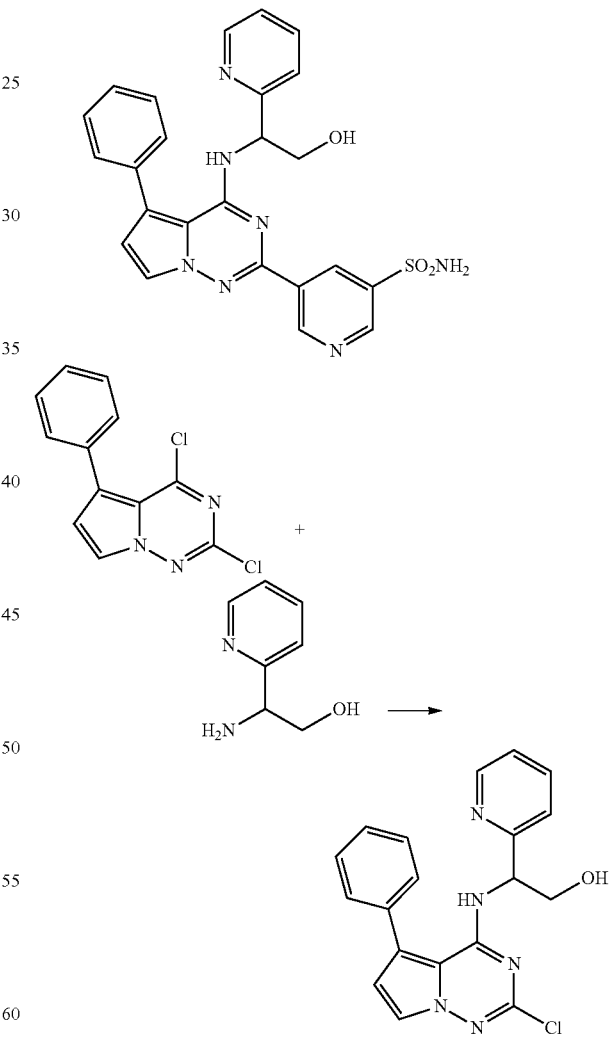

2,4-Dichloro-5-phenylpyrrolo[2,1-f][1,2,4]triazine (50.0 mg, 0.189 mmol) was converted to 2-((2-chloro-5-phenylpyrrolo[2,1-f][1,2,4]triazin-4-yl)amino)-2-(pyridin-2-yl)ethanol by the general procedure utilized in Example 4. The following reagents were utilized for conversion: DIPEA (0.132 mL, 0.757 mmol), 2-amino-2-(pyridin-2-yl)ethanol (52.0 mg, 0.379 mmol) at room temperature for 14 h. The reaction mixture was concentrated under reduced pressure and the residue was diluted with water (5 mL) and extracted with CH$_2$Cl$_2$ (3×5 mL). The combined organic layer was concentrated under reduced pressure. The residue was purified by column chromatography using CombiFlash (REDISEP®, silica gel, 12 g, 45% EtOAc/hexanes) to afford 2-((2-chloro-5-phenylpyrrolo[2,1-f][1,2,4]triazin-4-yl)amino)-2-(pyridin-2-yl)ethanol (0.0350 g, 50.0%). LCMS Condition B-79: retention time 1.80 min, [M+1]=366.0. $^1$H NMR (400 MHz, DMSO-d$_6$) δ ppm 3.65-3.85 (m, 2H) 4.92 (t, J=5.5 Hz, 1H), 5.32 (d, J=4.0 Hz, 1H), 6.74-6.83 (m, 1H), 7.30 (ddd, J=7.5 Hz, J=4.5 Hz, J=1.0 Hz, 1H), 7.42 (d, J=8.0 Hz, 1H), 7.46-7.60 (m, 6H), 7.74-7.80 (m, 1H), 7.82-7.85 (m, 1H), 8.33 (dd, J=6.5 Hz, J=1.0 Hz, 1H).

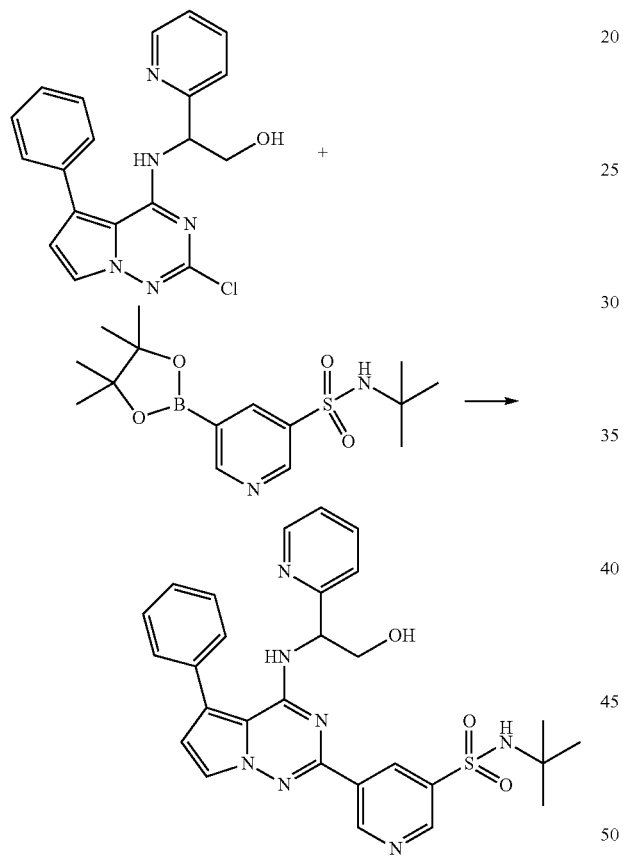

2-((2-Chloro-5-phenylpyrrolo[2,1-f][1,2,4]triazin-4-yl)amino)-2-(pyridin-2-yl)ethanol (0.500 g, 1.37 mmol) was converted to N-(tert-butyl)-5-(4-((2-hydroxy-1-(pyridin-2-yl)ethyl)amino)-5-phenylpyrrolo[2,1-f][1,2,4]triazin-2-yl)pyridine-3-sulfonamide via Suzuki cross-coupling using the general procedures described for Example 3. The following reagents were used for the conversion; N-(tert-butyl)-5-(4,4,5,5-tetramethyl-1,3,2-dioxaborolan-2-yl)pyridine-3-sulfonamide (0.930 g, 2.73 mmol), K$_2$CO$_3$ (0.567 g, 4.10 mmol), 1,1' bis(diphenylphosphino)ferrocene-palladium(II)dichloride dichloromethane complex (0.112 g, 0.137 mmol) in dioxane (35 mL) and water (5 mL) at 110° C. for 14 h. The residue was purified by column chromatography using CombiFlash (REDISEP®, silica gel, 24 g, 2% methanol/chloroform) to give N-(tert-butyl)-5-(4-((2-hydroxy-1-(pyridin-2-yl)ethyl)amino)-5-phenylpyrrolo[2,1-f][1,2,4]triazin-2-yl)pyridine-3-sulfonamide (0.480 g, 64.0%). LCMS Condition B-79: retention time 2.03 min, [M+1]=544.0. $^1$H NMR (400 MHz, DMSO-d$_6$) δ ppm 1.16 (s, 9H), 3.76-3.92 (m, 2H), 4.98 (t, J=5.6 Hz, 1H), 5.55 (d, J=6.5 Hz, 1H), 6.87 (d, J=2.7 Hz, 1H), 7.26-7.36 (m, 2H), 7.45-7.60 (m, 4H), 7.62-7.67 (m, 2H), 7.77 (td, J=7.7 Hz, J=1.8 Hz, 1H), 7.97 (d, J=2.8 Hz, 1H), 8.37-8.46 (m, 1H), 8.89 (t, J=2.1 Hz, 1H), 9.07 (d, J=2.3 Hz, 1H), 9.53 (d, J=2.0 Hz, 1H).

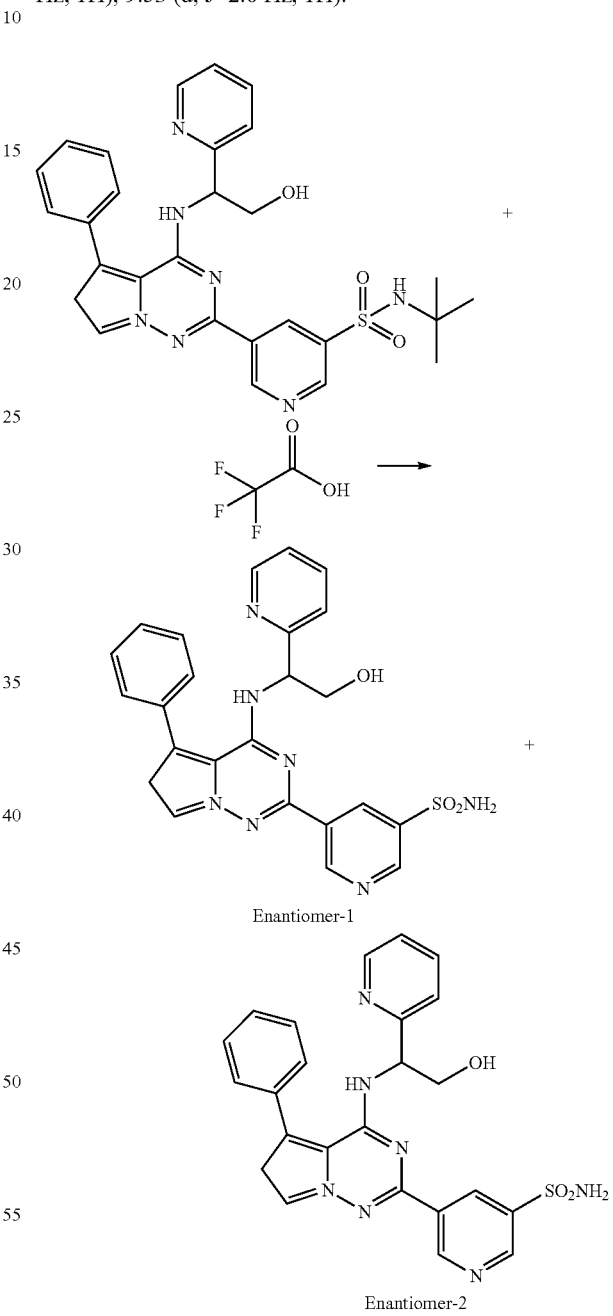

N-(tert-Butyl)-5-(4-((2-hydroxy-1-(pyridin-2-yl)ethyl)amino)-5-phenylpyrrolo[2,1-f][1,2,4]triazin-2-yl)pyridine-3-sulfonamide (0.300 g, 0.552 mmol) was converted to 5-(4-((2-hydroxy-1-(pyridin-2-yl)ethyl)amino)-5-phenylpyrrolo[2,1-f][1,2,4]triazin-2-yl)pyridine-3-sulfonamide using TFA (4.34 mL, 56.3 mmol) at room temperature for 12 h. The volatile components were removed under reduced pressure.

The residue was basified with 10% NaHCO₃ solution and extracted with EtOAc (2×50 mL). The combined organic layer was dried over Na₂SO₄, filtered and concentrated under reduced pressure. The resulting residue purified by chiral preparative HPLC (Condition B-92 as described in general methods) to afford 5-(4-((2-hydroxy-1-(pyridin-2-yl)ethyl) amino)-5-phenylpyrrolo[2,1-f][1,2,4]triazin-2-yl)pyridine-3-sulfonamide (enantiomer-1, 50.0 mg, 18.6%) and 5-(4-((2-hydroxy-1-(pyridin-2-yl)ethyl)amino)-5-phenylpyrrolo[2,1-f][1,2,4]triazin-2-yl)pyridine-3-sulfonamide (enantiomer-2, 45.0 mg, 16.7%).

Enantiomer-1: LCMS Condition B-13: retention time 1.92 min, [M+1]=488.0. HPLC Condition B-104: retention time 7.24 min, purity 100.0%. ¹H NMR (400 MHz, DMSO-d₆) δ ppm 3.75-3.91 (m, 2H), 4.98 (t, J=5.5 Hz, 1H), 5.56 (d, J=6.7 Hz, 1H), 6.87 (d, J=2.8 Hz, 1H), 7.25-7.39 (m, 2H), 7.45-7.57 (m, 4H), 7.59-7.68 (m, 2H), 7.74-7.81 (m, 3H), 7.97 (d, J=2.7 Hz, 1H), 8.36-8.45 (m, 1H), 8.90 (t, J=2.1 Hz, 1H), 9.07 (d, J=2.3 Hz, 1H), 9.54 (d, J=2.0 Hz, 1H).

Enantiomer-2: LCMS Condition B-13: retention time 1.92 min, [M+1]488.0. HPLC Condition B-104: retention time 8.42 min, purity 97.85%. ¹H NMR (400 MHz, DMSO-d₆) δ ppm 3.75-3.91 (m, 2H), 4.98 (t, J=5.5 Hz, 1H), 5.56 (d, J=6.7 Hz, 1H), 6.87 (d, J=2.8 Hz, 1H), 7.25-7.39 (m, 2H), 7.45-7.57 (m, 4H), 7.59-7.68 (m, 2H), 7.74-7.81 (m, 3H), 7.97 (d, J=2.7 Hz, 1H), 8.36-8.45 (m, 1H), 8.90 (t, J=2.1 Hz, 1H), 9.07 (d, J=2.3 Hz, 1H), 9.54 (d, J=2.0 Hz, 1H).

Example 34 tert-Butyl 1-(5-phenyl-4-(pyridin-2-ylmethylamino) pyrrolo[1,2-f][1,2,4]triazin-2-yl)cyclopropylcarbamate

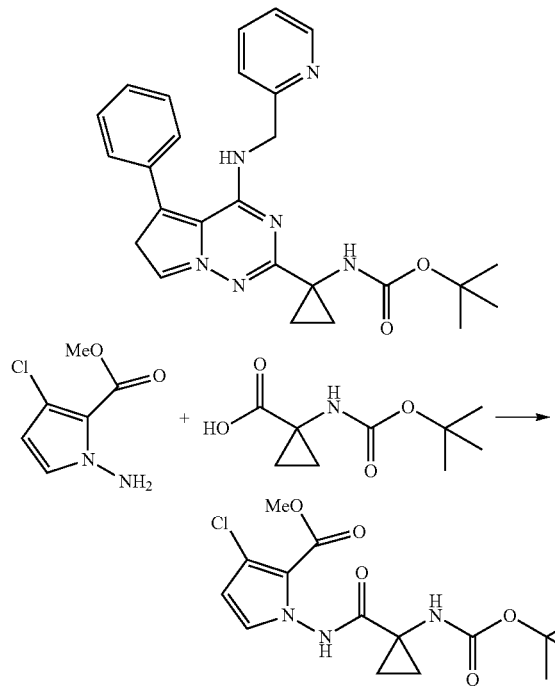

To a stirred solution of methyl 1-amino-3-chloro-1H-pyrrole-2-carboxylate (1.50 g, 8.59 mmol) in DCM (50 mL) was added 1-(((tert-butoxycarbonyl)amino) cyclopropanecarboxylic acid (2.59 g, 12.9 mmol), HOBT (1.58 g, 10.3 mmol), 1-(3-dimethylaminopropyl)-3-ethylcarbodiimidehydrochloride (2.47 g, 12.9 mmol) and DIPEA (3.00 mL, 17.2 mmol) at room temperature. The reaction mixture was stirred at room temperature for 12 h then concentrated under reduced pressure. The residue was dissolved in ethyl acetate (100 mL) and washed with water (2×30 mL). The combined organic layers were dried over Na₂SO₄, filtered and concentrated under reduced pressure. The resulting residue was purified by CombiFlash ISCO (REDISEP®, SiO₂, 12 g, 50% EtOAc/petroleum ether) to give methyl 1-(1-((tert-butoxycarbonyl) amino)cyclopropanecarboxamido)-3-chloro-1H-pyrrole-2-carboxylate (950 mg, 30.9%) as a white solid. LCMS Condition B-16: retention time 0.87 min, [M+1]=358.1. ¹H NMR (300 MHz, DMSO-d₆) δ ppm 1.01-1.06 (m, 2H), 1.30-1.38 (m, 2H), 1.41 (s, 9H), 3.74 (s, 3H), 6.27 (s, 1H), 6.99 (d, J=2.4 Hz, 1H), 7.46 (d, J=2.4 Hz, 1H), 11.08 (s, 1H).

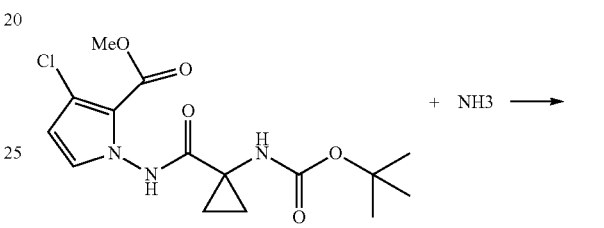

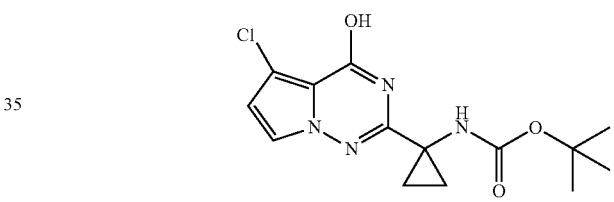

A stirred solution of methyl 1-(1-((tert-butoxycarbonyl) amino)cyclopropanecarboxamido)-3-chloro-1H-pyrrole-2-carboxylate (500 mg, 1.40 mmol) in water (12 mL) was purged with NH₃ gas for 5 minutes. The sealed pressure tube was heated at 110° C. for 12 h. The reaction mixture was dissolved in EtOAc (100 mL) and washed with water (50 mL). The organic layer was separated, dried over Na₂SO₄ and concentrated under reduced pressure. The residue was purified using CombiFlash ISCO (REDISEP®, SiO₂, 12 g, 50% EtOAc/petroleum ether) to give tert-butyl (1-(5-chloro-4-hydroxypyrrolo[2,1-f][1,2,4]triazin-2-yl)cyclopropyl)carbamate (210 mg, 46.3%) as a off-white solid. LCMS Condition B-16: retention time 0.91 min, [M+1]=325.1. ¹H NMR (300 MHz, DMSO-d₆) δ ppm 1.06-1.10 (m, 2H), 1.37-1.45 (m, 2H), 1.41 (s, 9H), 6.57 (d, J=2.4 Hz, 1H), 7.31 (br s, 1H), 7.51 (d, J=2.4 Hz, 1H), 11.32 (br s, 1H).

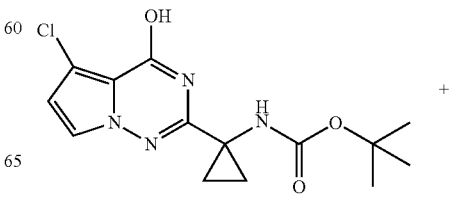

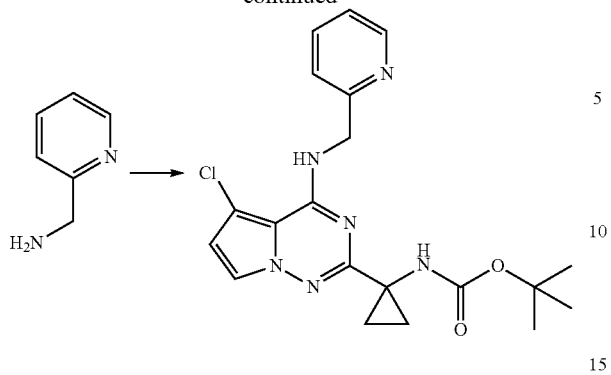
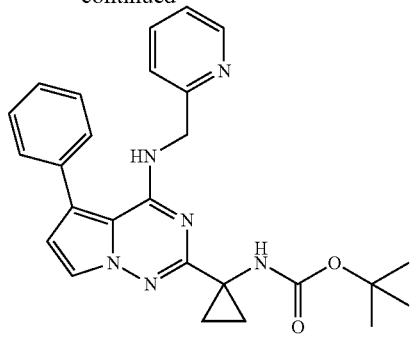

To a stirred solution of tert-butyl (1-(5-chloro-4-hydroxy-pyrrolo[2,1-f][1,2,4]triazin-2-yl)cyclopropyl)carbamate (500 mg, 1.54 mmol) in acetonitrile (50 mL) was added BOP (1.02 g, 2.31 mmol), DBU (0.464 mL, 3.08 mmol) and the reaction mixture was stirred at RT for 1 h. Pyridin-2-ylmethanamine (166 mg, 1.54 mmol) was added to the reaction mixture and stirred for 12 h. The reaction mixture was concentrated under reduced pressure. The residue was dissolved in ethyl acetate (100 mL) and washed water (2×30 mL). The organic layer was separated, dried over $Na_2SO_4$, filtered and concentrated under reduced pressure. The resulting residue was purified by CombiFlash ISCO (REDISEP®, $SiO_2$, 12 g, 10% MeOH/$CHCl_3$) to give tert-butyl (1-(5-chloro-4-((pyridin-2-ylmethyl)amino)pyrrolo[2,1-f][1,2,4]triazin-2-yl)cyclopropyl)carbamate (320 mg, 50.1%) as a pale yellow solid. LCMS Condition B-16: retention time 1.06 min, [M+1]=415.2. $^1$H NMR (300 MHz, DMSO-$d_6$) δ ppm 0.89-0.92 (m, 2H), 1.15-1.17 (m, 2H), 1.38 (s, 9H), 4.75 (d, J=5.7 Hz, 2H), 6.69 (d, J=2.7 Hz, 1H), 7.25-7.33 (m, 3H), 7.52-7.56 (m, 1H), 7.73-7.76 (m, 1H), 7.96-7.98 (m, 1H), 8.53 (d, J=5.2 Hz, 1H).

To a stirred solution of tert-butyl (1-(5-chloro-4-((pyridin-2-ylmethyl)amino) PP-156 pyrrolo[2,1-f][1,2,4]triazin-2-yl)cyclopropyl)carbamate (200 mg, 0.482 mmol) in dioxane (6 mL) and water (2 mL) was added 2-(dicyclohexylphosphino)-2',4',6'-triisopropylbiphenyl (68.9 mg, 0.145 mmol), phenylboronic acid (70.5 mg, 0.578 mmol), $K_2CO_3$ (200 mg, 1.45 mmol) and the reaction mixture purged with $N_2$ gas for 5 minutes. Pd(OAc)$_2$ (10.8 mg, 0.0480 mmol) was added and the resulting mixture stirred at 95° C. for 12 h. The reaction mixture was allowed to cool to ambient temperature, filtered through a pad of CELITE® and the filter cake was washed with EtOAc (2×25 mL). The filtrate was concentrated under reduced pressure. The residue was purified using CombiFlash ISCO (REDISEP®, $SiO_2$, 12 g, 50% EtOAc/petroleum ether) to give tert-butyl (1-(5-phenyl-4-((pyridin-2-ylmethyl) amino)pyrrolo[2,1-f][1,2,4]triazin-2-yl)cyclopropyl)carbamate (165 mg, 75.0%) as white solid. LCMS Condition B-34: retention time 2.54 min, [M+1]=457.0. HPLC Condition B-31: retention time 8.72 min, Purity 97.86%. $^1$H NMR (400 MHz, DMSO-$d_6$) δ ppm 0.95-1.02 (m, 2H), 1.29-1.35 (m, 2H), 1.41 (s, 9H), 4.67 (d, J=4.8 Hz, 2H), 6.67 (d, J=2.6 Hz, 1H), 6.97 (t, J=4.9 Hz, 1H), 7.26 (dd, J=6.7 Hz, J=5.0 Hz, 1H), 7.34 (d, J=7.8 Hz, 1H), 7.37-7.45 (m, 2H), 7.47-7.56 (m, 4H), 7.61 (d, J=2.4 Hz, 1H), 7.71-7.79 (m, 1H), 8.35-8.41 (m, 1H).

Example 35

Methyl 1-(5-phenyl-4-(pyridin-2-ylmethylamino) pyrrolo[1,2-f][1,2,4]triazin-2-yl)cyclopropylcarbamate

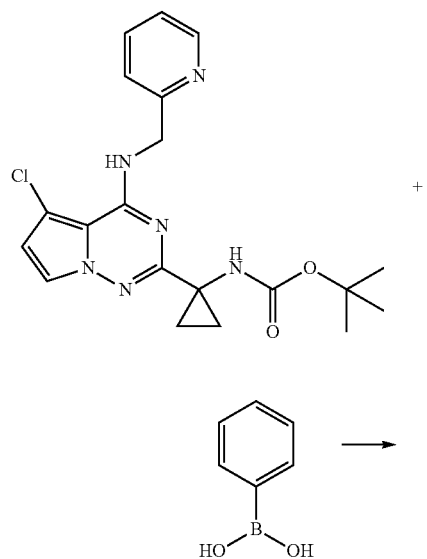

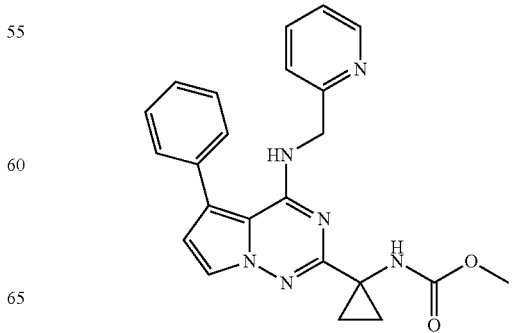

-continued

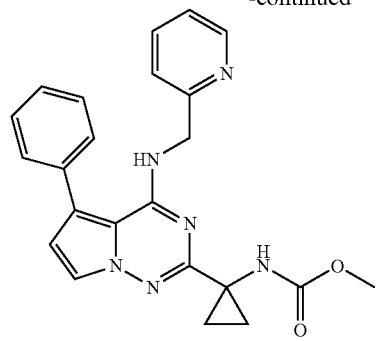

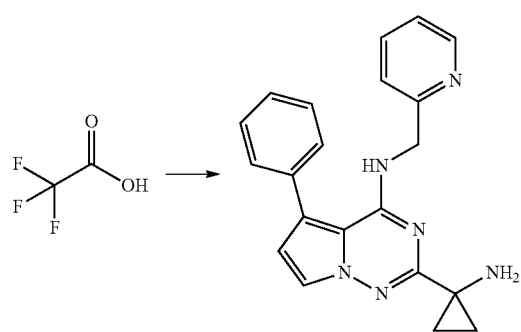

To a stirred solution of tert-butyl (1-(5-phenyl-4-((pyridin-2-ylmethyl)amino) pyrrolo[2,1-f][1,2,4]triazin-2-yl)cyclopropyl)carbamate (200 mg, 0.438 mmol) in DCM (15 mL) was added TFA (0.169 mL, 2.19 mmol) and the reaction mixture was stirred at RT for 5 h then concentrated under reduced pressure. The residue was dissolved in (100 mL) and washed with 10% NaHCO₃ solution (2×30 mL). The combined organic portion was dried over Na₂SO₄ and concentrated under reduced pressure. The residue was purified using CombiFlash ISCO (REDISEP®, SiO₂, 12 g, 50% EtOAc/petroleum ether) to give 2-(1-aminocyclopropyl)-5-phenyl-N-(pyridin-2-ylmethyl)pyrrolo[2,1-f][1,2,4]triazin-4-amine (120 mg, 77.0%) as brown solid. LCMS Condition B-41: retention time 0.62 min, [M+1]=357.1. $^1$H NMR (300 MHz, DMSO-d$_6$) δ ppm 0.80-0.87 (m, 2H), 1.13-1.18 (m, 2H), 4.68 (d, J=4.8 Hz, 2H), 6.68 (d, J=2.7 Hz, 1H), 7.02 (s, 1H), 7.22-7.30 (m, 1H), 7.35 (d, J=7.8 Hz, 1H), 7.41-7.58 (m, 5H), 7.68-7.80 (m, 2H), 8.34-8.40 (m, 1H).

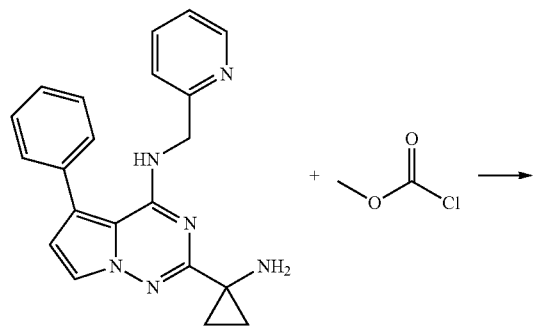

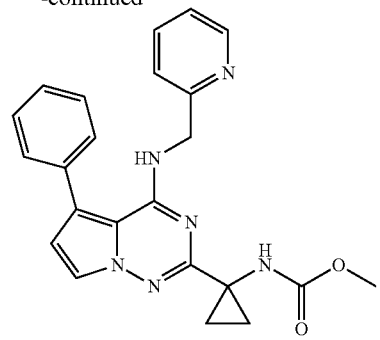

To a stirred solution of 2-(1-aminocyclopropyl)-5-phenyl-N-(pyridin-2-ylmethyl)pyrrolo[2,1-f][1,2,4]triazin-4-amine (60.0 mg, 0.168 mmol) in DCM (10 mL) was added pyridine (0.0270 mL, 0.337 mmol) followed by methyl chloroformate (0.0140 mL, 0.185 mmol) and the reaction mixture stirred at RT for 2 h then concentrated under reduced pressure. The residue was dissolved in ethyl acetate (100 mL) and washed water (2×30 mL). The organic layer was separated, dried over Na₂SO₄, filtered and concentrated under reduced pressure. The residue was purified by preparative HPLC (Condition B-93 as described in general methods) to give methyl (1-(5-phenyl-4-((pyridin-2-ylmethyl)amino)pyrrolo[2,1-f][1,2,4]triazin-2-yl)cyclopropyl)carbamate (21.0 mg, 30.1%) as white solid. LCMS Condition B-34: retention time 2.29 min, [M+1]=415.0. HPLC Condition B-31: retention time 7.09 min, Purity 99.15%. $^1$H NMR (400 MHz, DMSO-d$_6$) δ ppm 0.99-1.06 (m, 2H), 1.34-1.41 (m, 2H), 3.54 (s, 3H), 4.67 (d, J=4.8 Hz, 2H), 6.68 (d, J=2.7 Hz, 1H), 7.00 (s, 1H), 7.27 (ddd, J=7.5 Hz, J=4.9 Hz, J=1.1 Hz, 1H), 7.35 (d, J=7.9 Hz, 1H), 7.39-7.45 (m, 1H), 7.48-7.57 (m, 4H), 7.70 (d, J=2.7 Hz, 1H), 7.73-7.80 (m, 2H), 8.36-8.41 (m, 1H).

Example 36

N-(1-(5-Phenyl-4-(pyridin-2-ylmethylamino)pyrrolo[1,2-f][1,2,4]triazin-2-yl)cyclopropyl)acetamide

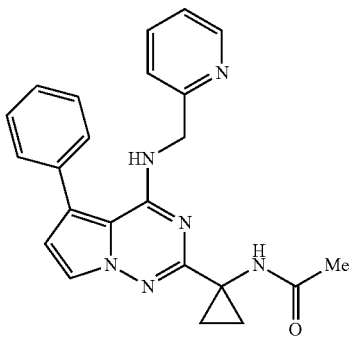

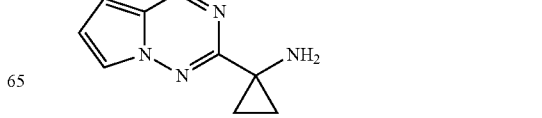

133

-continued

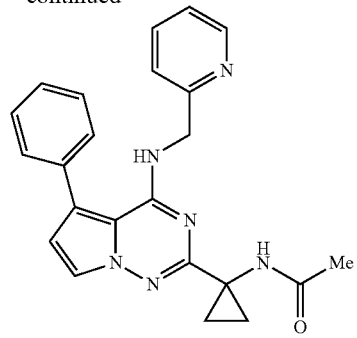

To a stirred solution of 2-(1-aminocyclopropyl)-5-phenyl-N-(pyridin-2-ylmethyl)pyrrolo[2,1-f][1,2,4]triazin-4-amine (60.0 mg, 0.168 mmol)) in DCM (15 mL) was added pyridine (0.0200 mL, 0.253 mmol) followed by acetyl chloride (0.0140 mL, 0.202 mmol) and the reaction mixture stirred at RT for 2 h then concentrated under reduced pressure. The residue was dissolved in ethyl acetate (100 mL) and washed with water (2×30 mL). The combined organic layer was dried over $Na_2SO_4$, filtered and concentrated under reduced pressure. The residue was purified by preparative HPLC (Condition B-111 as described in general methods) to give N-(1-(5-phenyl-4-((pyridin-2-ylmethyl)amino)pyrrolo[2,1-f][1,2,4]triazin-2-yl)cyclopropyl)acetamide (25.0 mg, 37.3%) as white solid. LCMS Condition B-34: retention time 2.14 min, [M+1]=399.0. HPLC Condition B-31: retention time 6.09 min, Purity 99.83%. $^1$H NMR (400 MHz, DMSO-$d_6$) δ ppm 0.93-1.01 (m, 2H), 1.35-1.41 (m, 2H), 1.85 (s, 3H), 4.68 (d, J=4.8 Hz, 2H), 6.68 (d, J=2.7 Hz, 1H), 6.99 (t, J=4.9 Hz, 1H), 7.27 (dd, J=6.5 Hz, J=4.9 Hz, 1H), 7.36 (d, J=7.8 Hz, 1H), 7.40-7.48 (m, 1H), 7.48-7.57 (m, 4H), 7.67 (d, J=2.7 Hz, 1H), 7.76 (td, J=7.7 Hz, J=1.7 Hz, 1H), 8.37-8.41 (m, 1H), 8.44 (s, 1H).

Example 37

N-(1-(5-Phenyl-4-(pyridin-2-ylmethylamino)pyrrolo[1,2-f][1,2,4]triazin-2-yl)cyclopropyl)methanesulfonamide

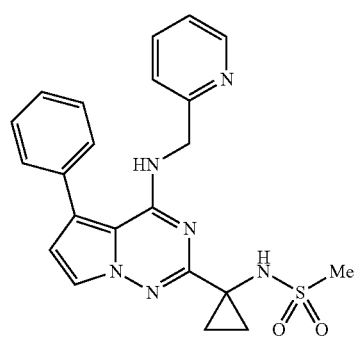

134

-continued

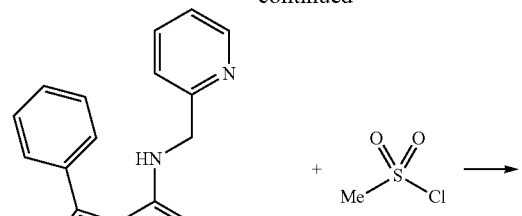

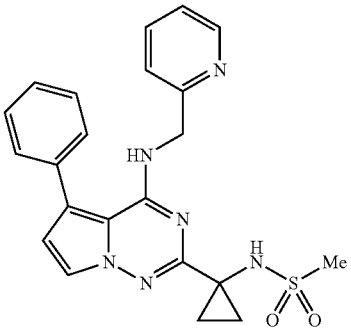

To a stirred solution of 2-(1-aminocyclopropyl)-5-phenyl-N-(pyridin-2-ylmethyl)pyrrolo[2,1-f][1,2,4]triazin-4-amine (60.0 mg, 0.168 mmol)) in DCM (15 mL) was added pyridine (0.0200 mL, 0.253 mmol) followed by methanesulfonylchloride (0.0200 mL, 0.253 mmol) and the reaction stirred at RT for 2 h then concentrated under reduced pressure. The residue was dissolved in ethyl acetate (100 mL) and washed with water (2×30 mL). The organic layer was separated, dried over $Na_2SO_4$, filtered and concentrated under reduced pressure. The residue was purified by preparative HPLC (Condition B-94 as described in general methods) to give N-(1-(5-phenyl-4-((pyridin-2-ylmethyl)amino)pyrrolo[2,1-f][1,2,4]triazin-2-yl)cyclopropyl)methanesulfonamide (26.0 mg, 35.5%) as white solid. LCMS Condition B-34: retention time 2.32 min, [M+1]=435.0. HPLC Condition B-31: retention time 7.72 min, Purity 99.61%. $^1$H NMR (400 MHz, DMSO-$d_6$) δ ppm 1.25-1.31 (m, 2H), 1.36-1.42 (m, 2H), 2.99 (s, 3H), 4.71 (d, J=4.8 Hz, 2H), 6.71 (d, J=2.7 Hz, 1H), 7.07 (t, J=4.8 Hz, 1H), 7.27 (ddd, J=6.8 Hz, J=5.5 Hz, J=1.0 Hz, 1H), 7.36 (d, J=7.8 Hz, 1H), 7.41-7.45 (m, 1H), 7.47-7.57 (m, 4H), 7.72-7.77 (m, 2H), 8.06 (s, 1H), 8.35-8.40 (m, 1H).

Example 38

2-(5-(5-Phenyl-4-(pyridin-2-ylmethylamino)pyrrolo[1,2-f][1,2,4]triazin-2-yl)pyridin-3-yl)ethanesulfonamide

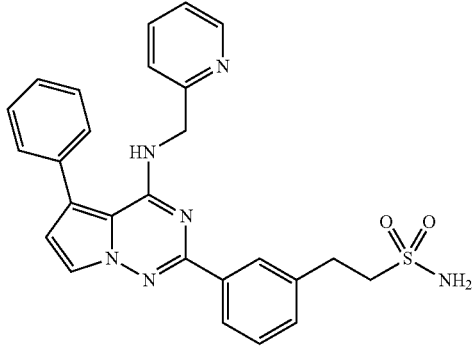

-continued

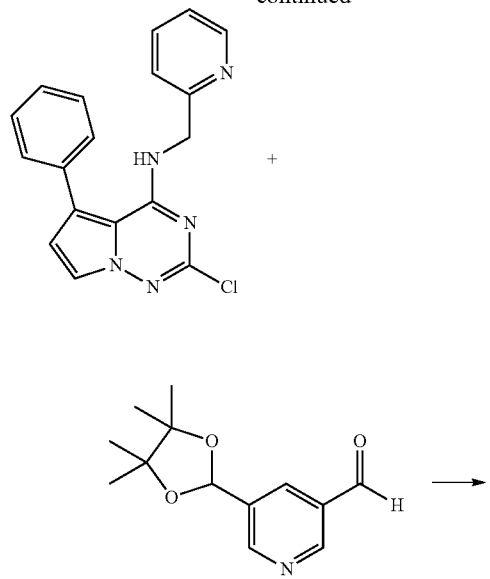

+

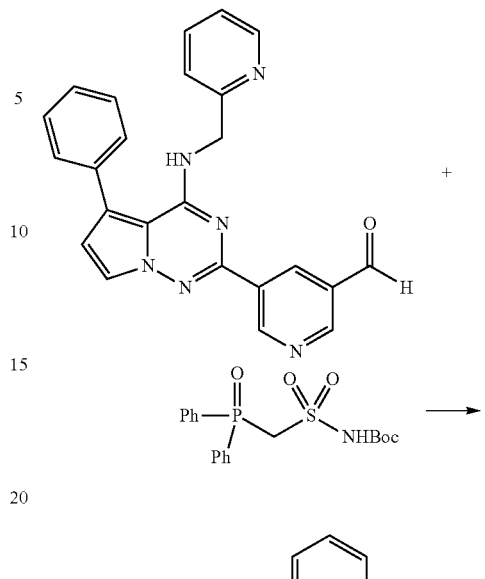

+

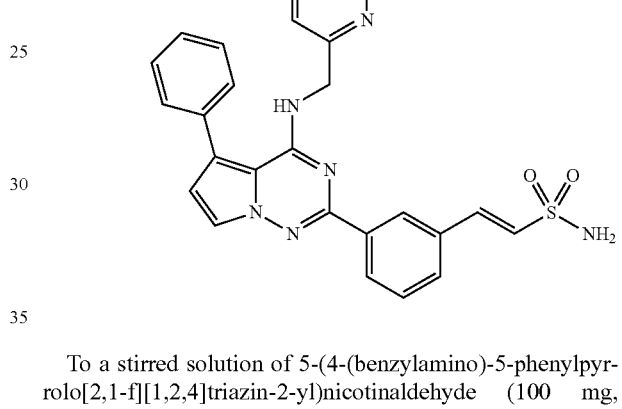

To a stirred solution of N-benzyl-2-chloro-5-phenylpyrrolo[2,1-f][1,2,4]triazin-4-amine (100 mg, 0.299 mmol) in dioxane/water (10/2 mL) was added 5-(4,4,5,5-tetramethyl-1,3,2-dioxaborolan-2-yl)nicotinaldehyde (69.6 mg, 0.299 mmol), K$_2$CO$_3$ (124 mg, 0.896 mmol) and the reaction mixture purged with N$_2$ for 5 min. PdCl$_2$(dppf) (219 mg, 0.299 mmol) was added to the reaction mixture and heated at 95° C. for 12 h. The reaction mixture was allowed to cool to ambient temperature, filtered through a pad of CELITE® and the filter cake was washed with EtOAc (2×25 mL). The filtrate was concentrated under reduced pressure. The residue was purified using CombiFlash ISCO (REDISEP®, SiO$_2$, 12 g, 50% EtOAc/petroleum ether) to give 5-(5-phenyl-4-((pyridin-2-ylmethyl)amino)pyrrolo[2,1-f][1,2,4]triazin-2-yl)nicotinaldehyde (71.0 mg, 58.7%) as brown solid. LCMS Condition B-41: retention time 0.79 min, [M+1]=407.1. $^1$H NMR (300 MHz, DMSO-d$_6$) δ ppm: 4.94 (d, J=4.6 Hz, 2H), 6.84 (d, J=2.7 Hz, 1H), 7.25-7.32 (m, 1H), 7.42 (t, J=4.5 Hz, 1H), 7.45-7.63 (m, 6H), 7.79 (td, J=7.7 Hz, J=1.8 Hz, 1H), 7.94 (d, J=2.7 Hz, 1H), 8.38 (td, J=2.4 Hz, J=0.9 Hz, 1H), 8.93 (t, J=2.1 Hz, 1H), 9.17 (d, J=2.0 Hz, 1H), 9.64 (d, J=2.2 Hz, 1H), 10.23 (s, 1H).

To a stirred solution of 5-(4-(benzylamino)-5-phenylpyrrolo[2,1-f][1,2,4]triazin-2-yl)nicotinaldehyde (100 mg, 0.247 mmol) in DMF (3 mL) was added NaH (11.8 mg, 0.493 mmol) followed by tert-butyl((diphenylphosphoryl)methyl)sulfonylcarbamate (98.0 mg, 0.247 mmol) and the reaction mixture stirred at RT for 12 h then concentrated under reduced pressure. The residue was purified using CombiFlash ISCO (REDISEP®, SiO$_2$, 12 g, 50% EtOAc/petroleum ether) to give (E)-N-(tert-butyl)-2-(5-(5-phenyl-4-((pyridin-2-ylmethyl)amino)pyrrolo[2,1-f][1,2,4]triazin-2-yl)pyridin-3-yl)ethenesulfonamide (55.0 mg, 38.3%) as off-white solid. LCMS Condition B-41: retention time 0.85 min, [M+1]=584.2.

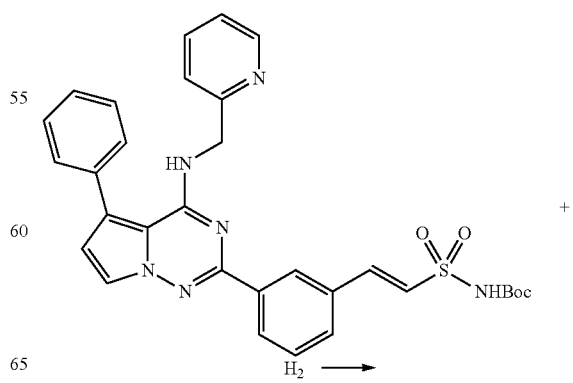

+

H$_2$ →

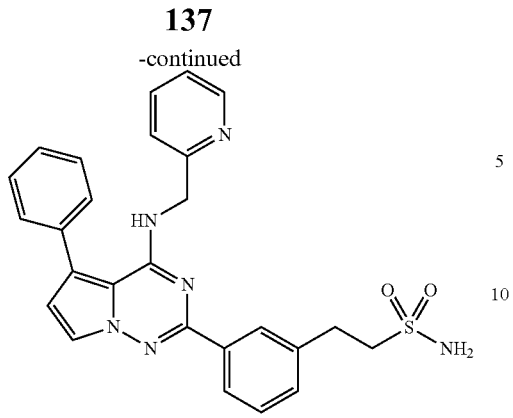

To a stirred solution of (E)-tert-butyl (2-(5-(5-phenyl-4-((pyridin-2-ylmethyl)amino)pyrrolo[2,1-f][1,2,4]triazin-2-yl)pyridin-3-yl)vinyl)sulfonylcarbamate (100 mg, 0.171 mmol) in EtOAc (20 mL) was added 10% Pd/C (36.5 mg, 0.343 mmol) and the reaction mixture stirred for 12 h at RT under the $H_2$ atmosphere using a bladder. The reaction mixture was filtered through a pad of CELITE® and the filtrate was treated with TFA (1 mL) then stirred at RT for 4 h. The volatile components were removed under reduced pressure. The resulting residue was dissolved in DCM (100 mL) and washed with 10% $NaHCO_3$ (50 mL). The organic layer was separated, dried over $Na_2SO_4$, filtered and concentrated under reduced pressure. The residue was purified by preparative HPLC (Condition B-95 as described in general methods) to give 2-(5-(5-phenyl-4-((pyridin-2-ylmethyl)amino)pyrrolo[2,1-f][1,2,4]triazin-2-yl)pyridin-3-yl)ethanesulfonamide (15.0 mg, 18.0%). LCMS Condition B-83: retention time 0.995 min, [M+1]=486.0, Purity: 96.17%. $^1$H NMR (400 MHz, $CD_3OD$) δ ppm 3.24-3.30 (m, 2H), 3.42-3.52 (m, 2H), 4.90-4.93 (m, 2H), 6.77 (d, J=2.7 Hz, 1H), 7.30 (dd, J=7.0 Hz, J=5.3 Hz, 1H), 7.43-7.48 (m, 2H), 7.49-7.56 (m, 2H), 7.58-7.63 (m, 2H), 7.76 (d, J=2.7 Hz, 1H), 7.80 (td, J=7.7 Hz, J=1.8 Hz, 1H), 8.46 (d, J=4.2 Hz, 1H), 8.50-8.56 (m, 2H), 9.25 (d, J=2.0 Hz, 1H).

Example 39

2-(Difluoromethyl)-5-(5-phenyl-4-(pyridin-2-ylmethylamino)pyrrolo[1,2-f][1,2,4]triazin-2-yl)pyridine-3-sulfonamide

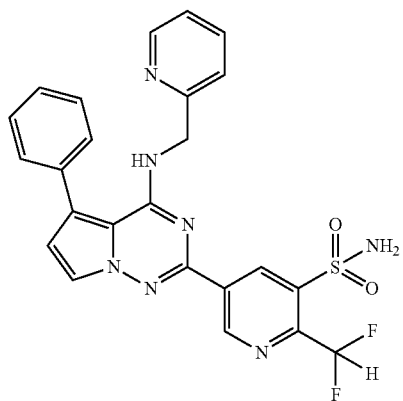

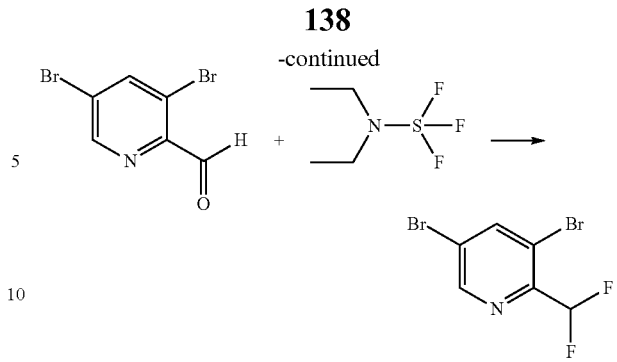

To a solution of 3,5-dibromopicolinaldehyde (3.00 g, 11.3 mmol) in DCM (60 mL) was added DAST (2.99 mL, 22.6 mmol) at 0° C. The reaction mixture was stirred for 1 h then slowly quenched by the addition of $NaHCO_3$ (100 mL) and extracted with EtOAc (200 mL). The organic layer was washed with brine (50 mL), dried over $Na_2SO_4$, filtered, and concentrated under reduced pressure. The residue was purified by CombiFlash Isco (REDISEP®, $SiO_2$, 40 g, 0-15% EtOAC/petroleum ether) to obtain 3,5-dibromo-2-(difluoromethyl)pyridine (3.00 g, 92.0%) as a pale yellow liquid. LCMS Condition B-78: retention time 2.11 min, [M+2]=288.2. $^1$H NMR (400 MHz, DMSO-$d_6$) δ ppm: 7.15 (t, J=52.8 Hz, 1H), 8.68 (dd, J=0.8 Hz, 2.0 Hz, 1H), 8.85 (d, J=2.0 Hz, 1H).

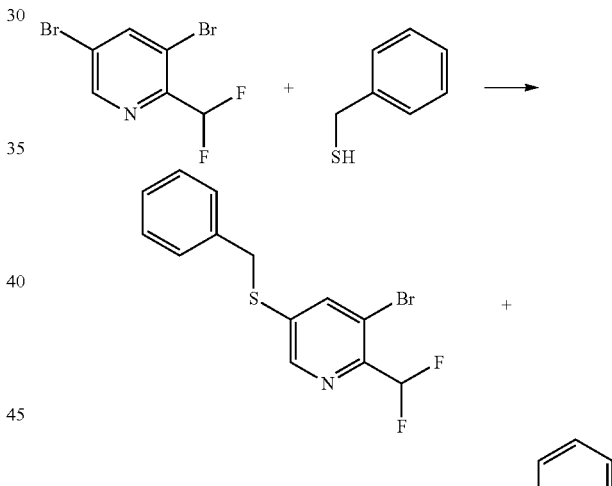

To a solution of 3,5-dibromo-2-(difluoromethyl)pyridine (3.00 g, 10.5 mmol) in DMF (100 mL) was added $K_2CO_3$ (1.45 g, 10.5 mmol) at 0° C. Phenylmethanethiol (1.30 g, 10.5 mmol) in DMF (50 mL) was added through addition funnel over a period of 0.5 h and the reaction mixture was stirred at ambient temperature for 14 h. The reaction mixture was dissolved in EtOAc (300 mL) and washed with ice cold water (2×150 mL). The organic phase was separated, dried over $Na_2SO_4$, filtered and concentrated under reduced pressure. The residue was purified by CombiFlash Isco (REDISEP®, SiO₂, 12 g, 0-13% EtOAc/petroleum ether) to obtain a mixture of both regio-isomers. Both regio-isomers were separated by preparative HPLC (Condition B-16 described in general methods) to obtain 5-(benzylthio)-3-bromo-2-(difluoromethyl)pyridine (0.700 g, 20.3%) as a colorless liquid and 3-(benzylthio)-5-bromo-2-(difluoromethyl)pyridine (0.900 g, 26.1%) as a pale yellow liquid.

5-(Benzylthio)-3-bromo-2-(difluoromethyl)pyridine: LCMS Condition B-78: retention time 2.34 min, [M+2]=330.0. ¹H NMR (400 MHz, CDCl₃) δ ppm: 4.19 (s, 2H), 6.83 (t, J=54.0 Hz, 1H), 7.28-7.34 (m, 5H), 7.76 (dd, J=1.2 Hz, J=2.0 Hz, 1H), 8.45 (d, J=2.0 Hz, 1H).

3-(Benzylthio)-5-bromo-2-(difluoromethyl)pyridine: LCMS Condition B-78: retention time 2.33 min, [M+2]=330.0. ¹H NMR (400 MHz, CDCl₃) δ ppm: 4.10 (s, 2H), 6.87 (t, J=54.0 Hz, 1H), 7.21-7.23 (m, 2H), 7.28-7.33 (m, 3H), 7.74 (dd, J=1.2 Hz, J=2.0 Hz, 1H), 8.56 (d, J=2.0 Hz, 1H).

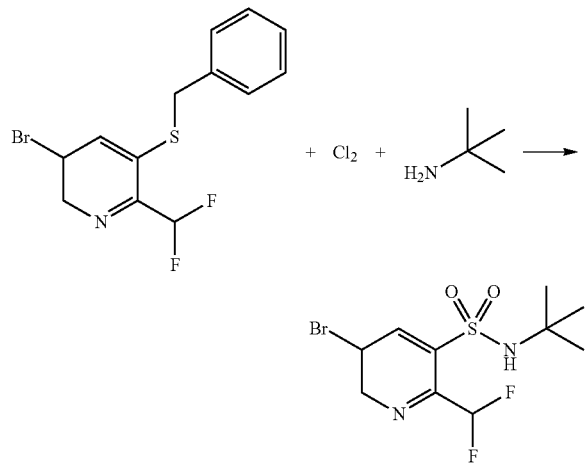

3-(Benzylthio)-5-bromo-2-(difluoromethyl)pyridine (0.900 g, 2.73 mmol) was dissolved in CCl₄ (75 mL) and water (15 mL) and the resulting bi-phasic solution was cooled to 0-5° C. Cl₂ gas was slowly purged through the reaction mixture for 5 minutes and was allowed to stir at room temperature for 30 minutes. The reaction mixture was diluted with water (10 mL) and extracted with CCl₄ (100 mL). The organic layer was separated, dried over Na₂SO₄, filtered, and concentrated under reduced pressure. The resulting residue was dissolved in dry THF (5 mL) and slowly added to 2-methylpropan-2-amine (5.00 mL, 2.73 mmol) at 0-5° C. The reaction mixture was heated in a sealed tube at 60° C. for 6 h, allowed to cool to ambient temperature and diluted with EtOAc (300 mL). The solution was transferred to a separation funnel and washed with water (50 mL) followed by brine solution (25 mL). The organic layer was dried over Na₂SO₄, filtered, and concentrated under reduced pressure. The resulting residue was purified by CombiFlash Isco (REDISEP®, SiO₂, 40 g, 0-15% EtOAc/petroleum ether) to obtain 5-bromo-N-(tert-butyl)-2-(difluoromethyl)pyridine-3-sulfonamide (0.80 g, 85%) as a brown liquid. LCMS Condition B-81: retention time 2.19 min, [M+2]=345.0. ¹H NMR (400 MHz, DMSO-d₆) δ ppm: 1.15 (s, 9H), 7.59 (t, J=52.8 Hz, 1H), 8.25 (br s, 1H), 8.54 (dd, J=0.8 Hz, J=2.0 Hz, 1H), 9.12 (d, J=2.0 Hz, 1H).

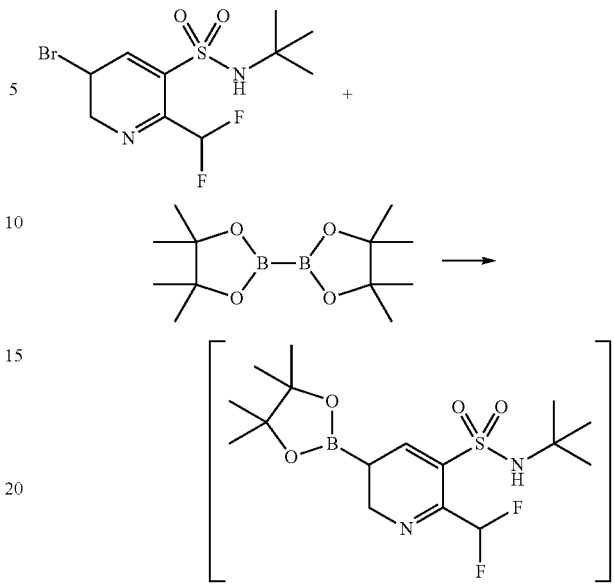

To a solution of 5-bromo-N-(tert-butyl)-2-(difluoromethyl)pyridine-3-sulfonamide (0.750 g, 2.19 mmol) and bis(pinacolato)diboron (0.832 g, 3.28 mmol) in 1,4-dioxane (2 mL) at ambient temperature was added KOAc (0.643 g, 6.56 mmol). The reaction mixture was purged with nitrogen gas for 10 min. PdCl₂(dppf)-CH₂Cl₂ (0.178 g, 0.219 mmol) was added and nitrogen purging was continued for further 10 min. The resulting mixture was stirred at 100° C. for 1 h under microwave irradiation. The reaction mixture was allowed to cool to ambient temperature, filtered through CELITE® and the filter cake was washed with EtOAc (2×50 mL). The filtrate was concentrated under reduced pressure to obtain N-(tert-butyl)-2-(difluoromethyl)-5-(4,4,5,5-tetramethyl-1,3,2-dioxaborolan-2-yl)pyridine-3-sulfonamide (0.810 g). The residue was taken to the next step without further purification. LCMS Condition B-81: retention time 1.68 min, [M+1]=309.0.

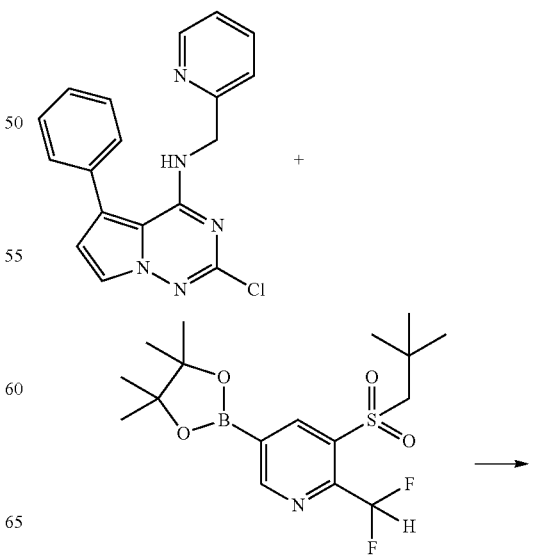

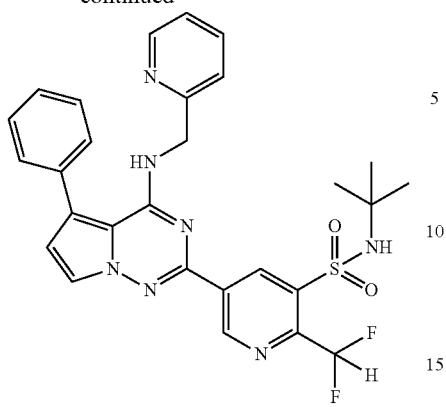

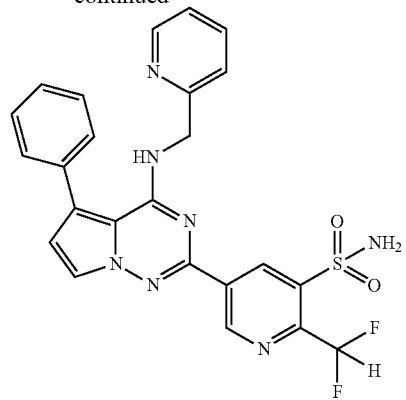

To a solution of 2-chloro-5-phenyl-N-(pyridin-2-ylmethyl)pyrrolo[2,1-f][1,2,4]triazin-4-amine (0.500 g, 1.49 mmol) and N-(tert-butyl)-2-(difluoromethyl)-5-(4,4,5,5-tetramethyl-1,3,2-dioxaborolan-2-yl)pyridine-3-sulfonamide (0.697 g, 1.79 mmol) in 1,4-dioxane (5 mL) and water (1 mL) was added $K_2CO_3$ (0.412 g, 2.98 mmol). The reaction mixture was purged with nitrogen gas for 10 min. Then $PdCl2$ (dppf)-$CH_2Cl_2$ (0.122 g, 0.149 mmol) was added and heated at 100° C. for 1 h in micro wave. The reaction mixture was allowed to cool to ambient temperature. The reaction mixture was filtered through CELITE® bed and the bed was washed with EtOAc (2×50 mL). The filtrate was diluted with water (50 mL) and extracted with EtOAc (100 mL). The combined organic extracts were dried over anhydrous $Na_2SO_4$, filtered and concentrated under reduced pressure. The resulting residue was purified by CombiFlash (REDISEP®, silica gel, 40 g, 40% EtOAc/hexanes) to obtain N-(tert-butyl)-2-(difluoromethyl)-5-(5-phenyl-4-((pyridin-2-ylmethyl)amino)pyrrolo[2,1-f][1,2,4]triazin-2-yl)pyridine-3-sulfonamide (0.600 g, 71.5% yield) as a pale yellow solid. LCMS Condition B-83: retention time 1.84 min, [M+1]=564.0. $^1$H NMR (400 MHz, $CD_3OD$) δ ppm 1.26 (s, 9H), 4.94 (s, 2H), 6.81 (d, J=2.8 Hz, 1H), 7.27-7.31 (m, 1H), 7.44-7.55 (m, 3H), 7.59-7.63 (m, 4H), 7.77-7.82 (m, 2H), 8.43 (d, J=4.4 Hz, 1H), 9.19 (dd, J=2.0 Hz, J=1.2 Hz, 1H), 9.64 (d, J=2.0 Hz, 1H).

N-(tert-Butyl)-2-(difluoromethyl)-5-(5-phenyl-4-((pyridin-2-ylmethyl)amino) pyrrolo[2,1-f][1,2,4]triazin-2-yl)pyridine-3-sulfonamide (0.520 g, 0.923 mmol) was dissolved in $CH_2Cl_2$ (4 mL). Then TFA (1.0 0 mL, 13.0 mmol) was added and stirred at RT for 16 h. The volatile components were removed under reduced pressure and the resulting residue was diluted with 10% $NaHCO_3$ (25 mL). The reaction mixture was extracted with EtOAc (2×25 mL). The combined organic extracts were dried over anhydrous $Na_2SO_4$, filtered and concentrated under reduced pressure. The resulting residue was purified by preparative HPLC (Condition B-96 as described in general methods) to afford 2-(difluoromethyl)-5-(5-phenyl-4-((pyridin-2-ylmethyl)amino)pyrrolo[2,1-f][1,2,4]triazin-2-yl)pyridine-3-sulfonamide (0.140 g, 29.9%) as a pale yellow solid. LCMS Condition B-78: retention time 2.29 min, [M+1]=508.2. HPLC Condition B-31: retention time 8.65 min, purity 98.6%. $^1$H NMR (400 MHz, DMSO-$d_6$) δ ppm 4.95 (d, J=4.8 Hz, 2H), 6.87 (d, J=2.8 Hz, 1H), 7.28-7.62 (m, 9H), 7.75-7.82 (m, 1H), 7.99 (d, J=2.4 Hz, 1H), 8.17 (s, 2H), 8.38-8.40 (m, 1H), 9.09 (d, J=1.6 Hz, 1H), 9.67 (d, J=2.0 Hz, 1H).

Example 40

2-Methoxy-5-(5-phenyl-4-(5H-pyrrolo[3,4-b]pyridin-6(7H)-yl)pyrrolo[1,2-f][1,2,4]triazin-2-yl)pyridine-3-sulfonamide

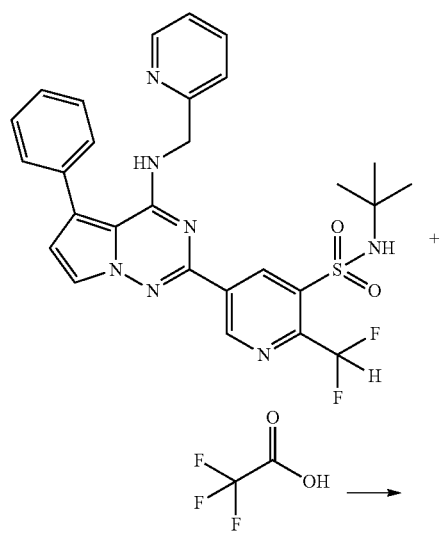

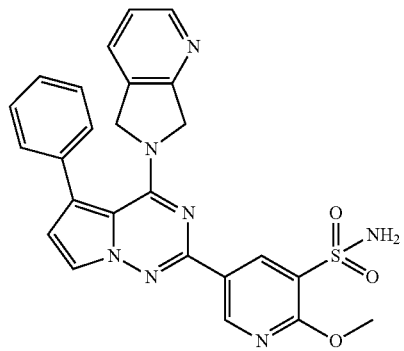

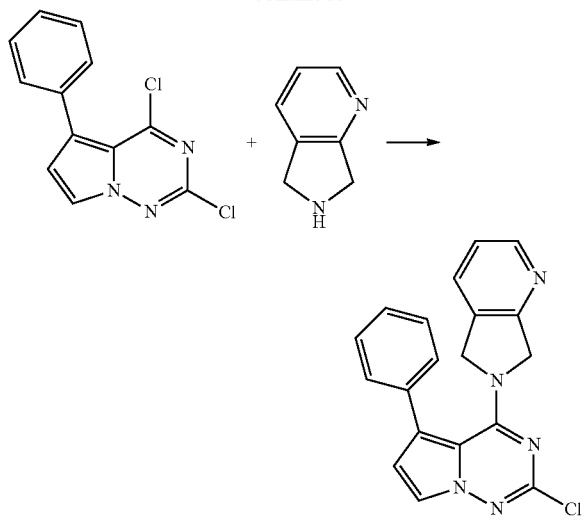

2,4-Dichloro-5-phenylpyrrolo[2,1-f][1,2,4]triazine (50.0 mg, 0.189 mmol) was dissolved in THF (3 mL) and then DIPEA (0.0990 mL, 0.568 mmol) was added, followed by the addition of 6,7-dihydro-5H-pyrrolo[3,4-b]pyridine (0.0270 g, 0.227 mmol). The reaction mixture was stirred at room temperature for 12 h. The reaction mixture was concentrated under reduced pressure and water (5 mL) was added to the resulting residue. The aqueous solution was extracted with EtOAc (2×25 mL). The organic layer was separated, dried over anhydrous sodium sulfate, filtered and concentrated under reduced pressure. The residue was purified by Combi-Flash (REDISEP®, silica gel, 12 g, 30% EA/petroleum ether) to afford 2-chloro-5-phenyl-4-(5H-pyrrolo[3,4-b]pyridin-6 (7H)-yl)pyrrolo[2,1-f][1,2,4]triazine (29.0 mg, 44.0%) as a brown solid. LCMS Condition B-79: retention time 1.70 min, [M+1]=348.0. $^1$H NMR (400 MHz, DMSO-d$_6$) δ ppm 4.38 (br s, 2H), 4.84 (br s, 2H), 6.80 (d, J=2.8 Hz, 1H), 7.25 (dd, J=7.7 Hz, J=4.9 Hz, 1H), 7.35-7.54 (m, 5H), 7.64 (br s, 1H), 7.90 (d, J=2.7 Hz, 1H), 8.34 (d, J=4.3 Hz, 1H).

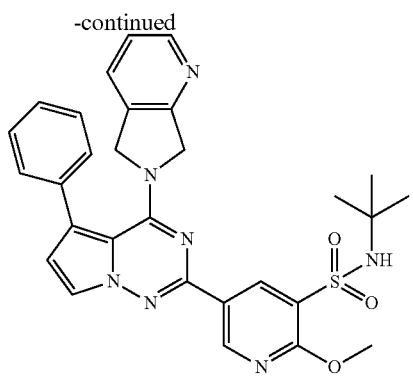

To a solution of 2-chloro-5-phenyl-4-(5H-pyrrolo[3,4-b] pyridin-6(7H)-yl)pyrrolo[2,1-f][1,2,4]triazine (30.0 mg, 0.0860 mmol) and N-(tert-butyl)-2-methoxy-5-(4,4,5,5-tetramethyl-1,3,2-dioxaborolan-2-yl)pyridine-3-sulfonamide (48.0 mg, 0.129 mmol) in 1,4-dioxane (3 mL) and water (0.5 mL) was added K$_2$CO$_3$ (24.0 mg, 0.173 mmol). The reaction mixture was purged with nitrogen gas for 10 min. PdCl$_2$ (dppf)-CH$_2$Cl$_2$ (7.04 mg, 8.63 µmol) was added and the reaction mixture heated at 100° C. for 12 h. The reaction mixture was allowed to cool to ambient temperature then filtered through CELITE® bed and the bed was washed with EtOAc (2×20 mL). The filtrate was diluted with water (20 mL) and extracted with EtOAc (3×15 mL). The combined organic extracts were dried over anhydrous Na$_2$SO$_4$, filtered and concentrated under reduced pressure. The resulting residue was purified by preparative HPLC (Condition B-97 as described in general methods) to obtain N-(tert-butyl)-2-methoxy-5-(5-phenyl-4-(5H-pyrrolo[3,4-b]pyridin-6(7H)-yl)pyrrolo[2,1-f] [1,2,4]triazin-2-yl)pyridine-3-sulfonamide (17.0 mg, 35.5%) as a pale yellow solid. LCMS Condition B-83: retention time 1.91 min, [M+1]=556.0. $^1$H NMR (400 MHz, DMSO-d$_6$) δ ppm 1.19 (s, 9H), 3.74 (s, 3H), 3.74 (br s, 2H), 3.74 (br s, 2H), 6.83 (d, J=2.7 Hz, 1H), 6.90 (s, 1H), 7.25 (dd, J=7.7 Hz, J=4.9 Hz, 1 H), 7.43-7.54 (m, 5H), 7.51 (d, J=1.7 Hz, 1H), 8.00 (d, J=2.7 Hz, 1H), 8.37 (d, J=3.6 Hz, 1H), 8.82 (d, J=2.6 Hz, 1H), 8.96 (d, J=2.6 Hz, 1H).

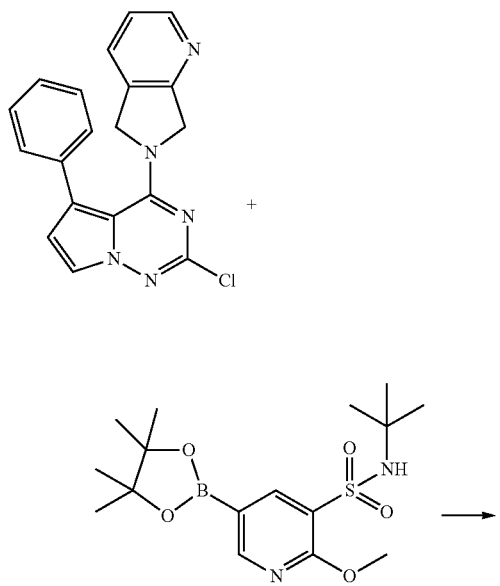

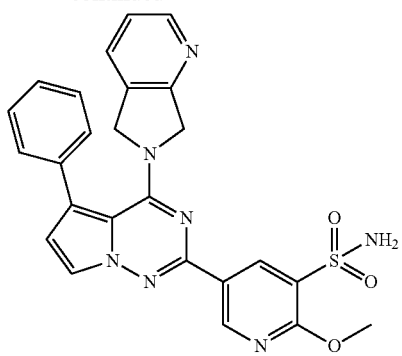

N-(tert-Butyl)-2-methoxy-5-(5-phenyl-4-(5H-pyrrolo[3,4-b]pyridin-6(7H)-yl)pyrrolo[2,1-f][1,2,4]triazin-2-yl)pyridine-3-sulfonamide (0.180 g, 0.324 mmol) was dissolved in TFA (2.00 mL, 26.0 mmol) and heated at 70° C. for 2 h. The volatile components were removed under reduced pressure and resulting residue was diluted with saturated NaHCO$_3$ (30 mL). The reaction mixture was extracted with EtOAc (3×50 mL). The combined organic extracts were dried over anhydrous Na$_2$SO$_4$, filtered and concentrated under reduced pressure. The resulting residue was purified by preparative HPLC (Condition B-98 as described in general methods) to afford 2-methoxy-5-(5-phenyl-4-(5H-pyrrolo[3,4-b]pyridin-6(7H)-yl)pyrrolo[2,1-f][1,2,4]triazin-2-yl)pyridine-3-sulfonamide (32.0 mg, 19.8%) as off-white solid. LCMS Condition B-22: retention time 1.93 min, [M+1]=500.2. HPLC Condition B-31: retention time 9.01 min, purity 97.4%. $^1$H NMR (400 MHz, DMSO-d$_6$) δ ppm 3.74 (s, 3H), 4.57 (br s, 2H), 4.89 (br s, 2H), 6.83 (d, J=2.7 Hz, 1H), 7.09 (br s, 2H), 7.26 (dd, J=7.8 Hz, J=4.9 Hz, 1H), 7.37-7.43 (m, 1H), 7.44-7.55 (m, 4H), 7.61 (d, J=6.0 Hz, 1H), 7.99 (d, J=2.8 Hz, 1H), 8.38 (d, J=5.1 Hz, 1H), 8.80 (d, J=2.6 Hz, 1H), 8.96 (d, J=2.5 Hz, 1H).

Example 41

2-Isopropoxy-5-(5-phenyl-4-((pyridin-2-ylmethyl)amino)pyrrolo[2,1-f][1,2,4]triazin-2-yl)pyridine-3-sulfonamide

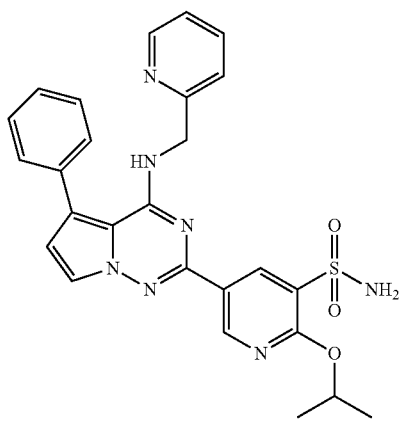

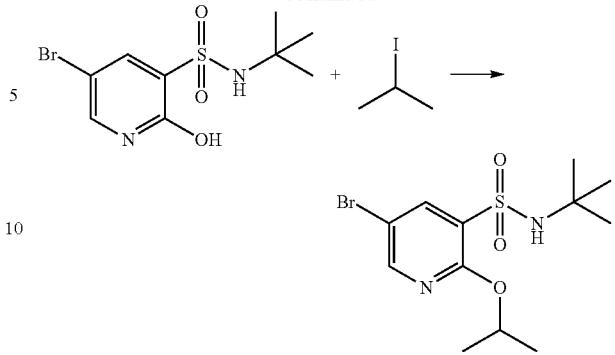

To a solution of 5-bromo-N-(tert-butyl)-2-hydroxypyridine-3-sulfonamide (1.50 g, 4.85 mmol) in DMF (40 mL) was added 2-iodopropane (0.825 g, 4.85 mmol) followed by K$_2$CO$_3$ (1.34 g, 9.70 mmol) at RT. The reaction mixture was heated to 100° C. for 14 h. The reaction mixture was allowed to cool and the volatile components were removed under reduced pressure. The residue was diluted with cold water (150 mL) and extracted into ethyl acetate (2×100 mL). The combined organic layer was dried over sodium sulfate, filtered and evaporated under reduced pressure and the residue was purified by CombiFlash (REDISEP®, silica gel, 24 g, 50% EtOAc/petroleum ether) to give 5-bromo-N-(tert-butyl)-2-isopropoxypyridine-3-sulfonamide (0.660 g, 37.7%) as a white solid. LCMS Condition B-22: retention time 1.92 min, [M+1]=351.0. $^1$H NMR (300 MHz, DMSO-d$_6$) δ ppm 1.13 (s, 9H), 1.35 (d, J=6.8 Hz, 6H), 5.06 (dt, J=13.6 Hz, J=6.8 Hz, 1H), 6.96 (s, 1H), 8.00 (d, J=2.6 Hz, 1H), 8.36 (d, J=2.6 Hz, 1H).

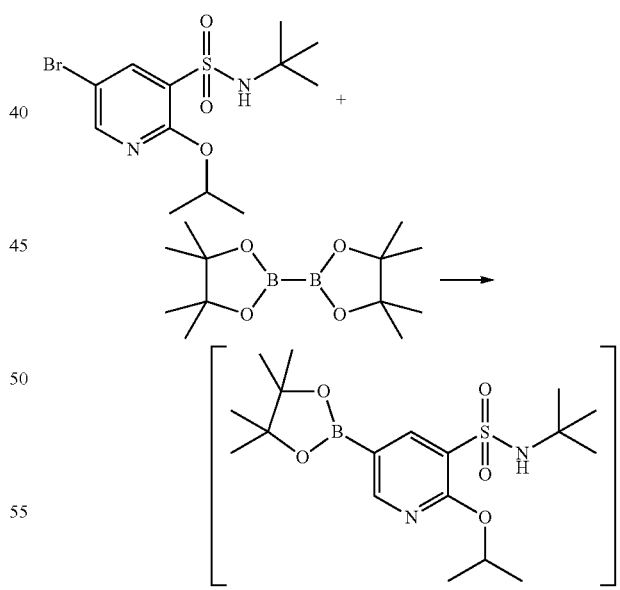

A solution of 5-bromo-N-(tert-butyl)-2-isopropoxypyridine-3-sulfonamide (0.400 g, 1.14 mmol), bis(pinacolato)diboron (0.434 g, 1.71 mmol) and KOAc (0.335 g, 3.42 mmol) in 1,4-dioxane (15 mL) was purged with nitrogen gas for 30 min. PdCl$_2$(dppf)-CH$_2$Cl$_2$ (46.0 mg, 0.0570 mmol) was added and the reaction mixture heated at 100° C. in a sealed tube for 12 h. The cooled reaction mixture was filtered through the CELITE® and washed with ethyl acetate (20 mL). The filtrate was evaporated under reduced pressure to a residue (0.350 g) as a black solid which was used in the next step without purification. LCMS Condition B-84: retention time 2.14 min, [M+1]=399.6.

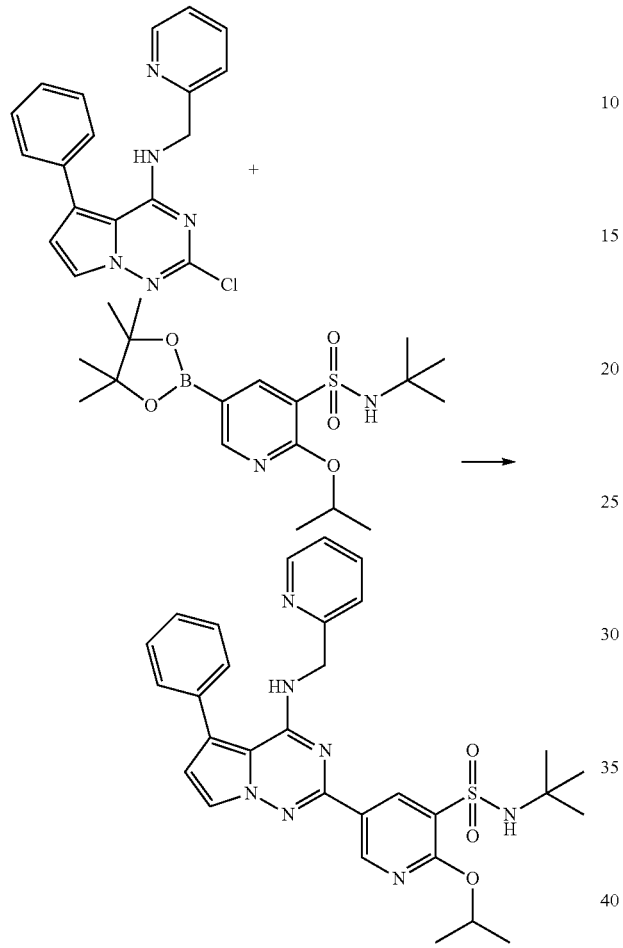

A solution of 2-chloro-5-phenyl-N-(pyridin-2-ylmethyl)pyrrolo[2,1-f][1,2,4]triazin-4-amine (50.0 mg, 0.149 mmol), N-(tert-butyl)-2-isopropoxy-5-(4,4,5,5-tetramethyl-1,3,2-dioxaborolan-2-yl)pyridine-3-sulfonamide (89.0 mg, 0.223 mmol), $K_2CO_3$ (62.0 mg, 0.447 mmol) in 1,4-dioxane (20 mL) and water (6 mL) was purged with nitrogen gas for 10 min. $PdCl_2(dppf)$-$CH_2Cl_2$ (6.08 mg, 7.45 mol) was added and the reaction mixture purged with nitrogen gas for further 5 min then heated to 100° C. for 12 h. The cooled reaction mixture was filtered through the CELITE® and washed with ethyl acetate (20 mL). The filtrate was washed with brine solution (10 mL). The organic layer was dried over sodium sulfate, filtered and evaporated under reduced pressure to give a residue that was purified by preparative HPLC (Condition B-91 as described in general methods) to give N-(tert-butyl)-2-isopropoxy-5-(5-phenyl-4-((pyridin-2-ylmethyl)amino)pyrrolo[2,1-f][1,2,4]triazin-2-yl)pyridine-3-sulfonamide (13.0 mg, 15.1%) as a pale yellow solid. LCMS Condition B-79: retention time 2.39 min, [M+1]=572.2. $^1H$ NMR (400 MHz, DMSO-$d_6$) δ ppm 1.15 (s, 9H), 1.41 (d, J=6.5 Hz, 6H), 4.88 (d, J=5.0 Hz, 2H), 5.13 (quintet, J=6.7 Hz, 1H), 6.78 (d, J=2.5 Hz, 1H), 6.89 (s, 1H), 7.28 (t, J=5.5 Hz, 2H), 7.42-7.49 (m, 2H), 7.50-7.62 (m, 4H), 7.74-7.81 (m, 1H), 7.92 (d, J=2.5 Hz, 1H), 8.40-8.45 (m, 1H), 8.66 (d, J=2.5 Hz, 1H), 8.75 (d, J=2.5 Hz, 1H).

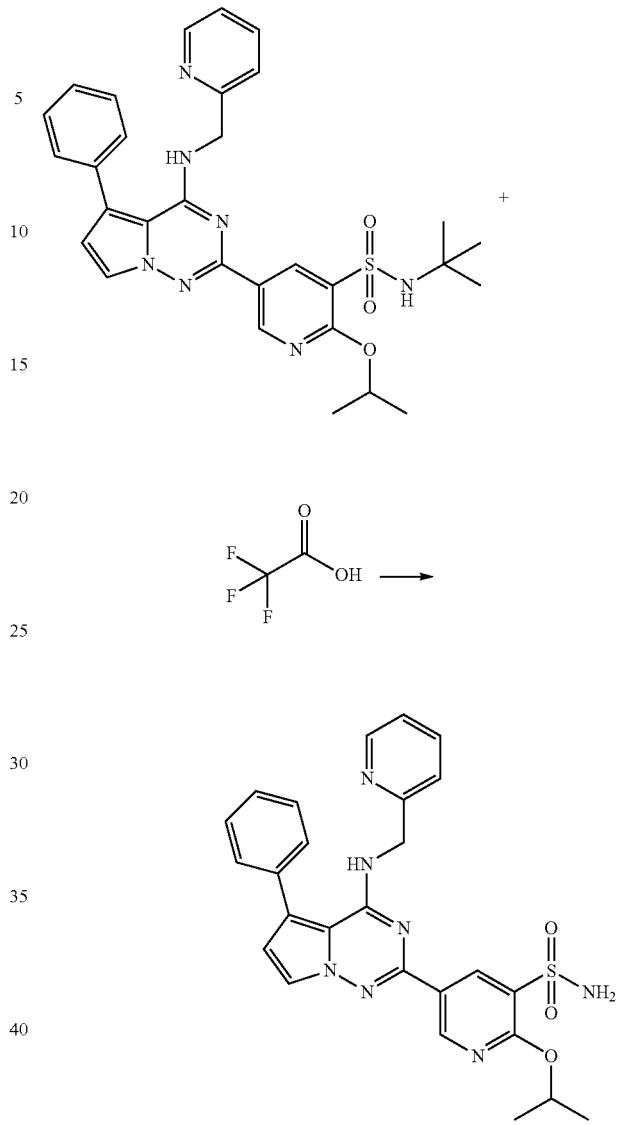

N-(tert-Butyl)-2-isopropoxy-5-(5-phenyl-4-((pyridin-2-ylmethyl)amino)pyrrolo[2,1-f][1,2,4]triazin-2-yl)pyridine-3-sulfonamide (0.175 g, 0.306 mmol) in TFA (30 mL) was stirred at RT for 12 h. TFA was removed under reduced pressure and reaction mixture was diluted with 10% $NaHCO_3$ (50 mL). The reaction mixture was extracted with EtOAc (3×30 mL). The combined organic extracts were dried over anhydrous $Na_2SO_4$, filtered and concentrated under reduced pressure to give a residue which was purified by preparative HPLC (Condition B-99 as described in general methods) to afford 2-isopropoxy-5-(5-phenyl-4-((pyridin-2-ylmethyl)amino)pyrrolo[2,1-f][1,2,4]triazin-2-yl)pyridine-3-sulfonamide (65.0 mg, 40.8%) as a white solid. LCMS Condition B-39: retention time 2.32 min, [M+1]=516.2. HPLC Condition B-5: retention time 8.21 min, purity 99.29%. $^1H$ NMR (400 MHz, DMSO-$d_6$) δ ppm 1.42 (d, J=7.1 Hz, 6H), 4.88 (d, J=4.5 Hz, 2H), 5.14 (quintet, J=6.8 Hz, 1H), 6.77 (d, J=3.1 Hz, 1H), 7.08 (s, 2H), 7.24-7.31 (m, 2H), 7.42-7.49 (m, 2H), 7.50-7.62 (m, 4H), 7.77 (td, J=7.7 Hz, J=1.8 Hz, 1H), 7.90 (d, J=2.5 Hz, 1H), 8.42 (dt, J=5.1 Hz, J=1.2 Hz, 1H), 8.65 (d, J=2.5 Hz, 1H), 8.73 (d, J=2.5 Hz, 1H).

Example 42

N-(6-(5-Phenyl-4-(pyridin-2-ylmethylamino)pyrrolo[1,2-f][1,2,4]triazin-2-yl)pyrazin-2-yl)acetamide

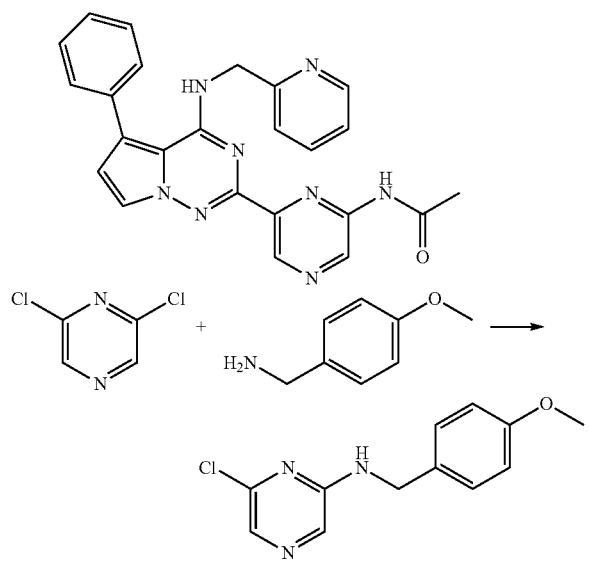

To a solution of 2,6-dichloropyrazine (4.00 g, 26.8 mmol) and 4-methoxybenzylamine (7.02 mL, 53.7 mmol) in DMF (30 mL) was added K$_2$CO$_3$ (7.42 g, 53.7 mmol) at RT and the reaction mixture was stirred for 12 h. The reaction mixture was diluted with cold water (100 mL) and extracted into ethyl acetate (2×50 mL). The combined organic layer was dried over sodium sulfate, filtered and evaporated under reduced pressure to give a residue that was purified by CombiFlash (REDISEP®, silica gel, 24 g, 25% EtOAc/petroleum ether) to give 6-chloro-N-(4-methoxybenzyl)pyrazin-2-amine (5.00 g, 74.6%). $^1$H NMR (400 MHz, DMSO-d$_6$) δ ppm 3.31 (s, 3H), 4.37 (d, J=6.0 Hz, 2H), 6.87-6.93 (m, 2H), 7.24-7.31 (m, 2H), 7.70 (s, 1H), 7.90 (s, 1H), 7.95 (t, J=5.5 Hz, 1H).

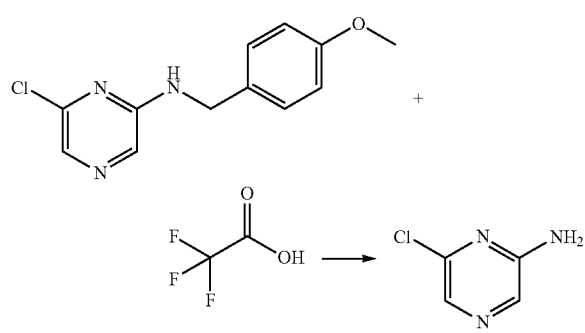

6-Chloro-N-(4-methoxybenzyl)pyrazin-2-amine (5.00 g, 20.0 mmol) was dissolved in TFA (25 mL) and the reaction mixture heated for 2 h at 60° C. TFA was removed under reduced pressure and reaction mixture was diluted with 10% sodium bicarbonate solution (100 mL) extracted with ethyl acetate (3×30 mL). The combined organic extracts were dried over sodium sulfate, filtered and evaporated under reduced pressure to give a residue which was purified by CombiFlash (REDISEP®, silica gel, 24 g, 35% EtOAc/petroleum ether) to give 6-chloropyrazin-2-amine (2.00 g, 77.0%). LCMS Condition B-39: retention time 0.230 min, [M+1]=130.2. $^1$H NMR (400 MHz, DMSO-d$_6$) δ ppm 6.91 (br s, 2H), 7.71 (s, 1H), 7.81 (s, 1H).

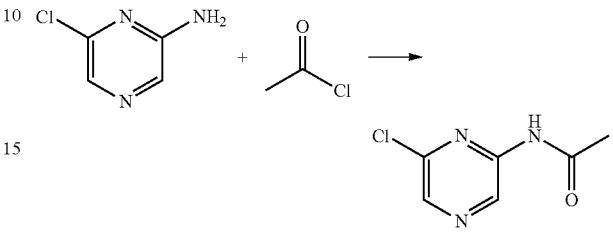

To a solution of 6-chloropyrazin-2-amine (1.00 g, 7.72 mmol) in DCM (20 mL) was added acetyl chloride (0.659 mL, 9.26 mmol) at RT and the reaction mixture was stirred for 1 h. The reaction mixture was diluted with water (100 mL) and extracted with DCM (2×100 mL). The combined organic layer was dried over sodium sulfate, filtered and evaporated under reduced pressure to give a residue which was purified by CombiFlash (REDISEP®, silica gel, 12 g, 25% EtOAc/petroleum ether) to give N-(6-chloropyrazin-2-yl)acetamide (0.700 g, 52.9%). LCMS Condition B-39: retention time 1.67 min, [M+1]=170.0. $^1$H NMR (400 MHz, DMSO-d$_6$) δ ppm 2.14 (s, 3H), 8.47 (s, 1H), 9.29 (s, 1H), 11.09 (br s, 1H).

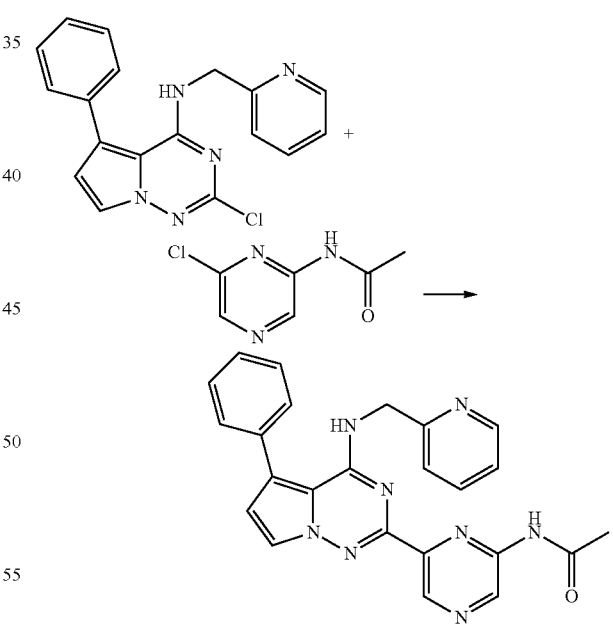

A solution of N-(6-chloropyrazin-2-yl)acetamide (77.0 mg, 0.447 mmol) and hexamethylditin (0.124 mL, 0.596 mmol) in 1,4-dioxane (15 mL) was purged with argon gas for 30 min. Pd(Ph$_3$P)$_4$ (34.0 mg, 0.0300 mmol) was added and the reaction mixture was heated at 100° C. for 1 h. Then the reaction mixture was allowed to cool to RT and then 2-chloro-5-phenyl-N-(pyridin-2-ylmethyl)pyrrolo[2,1-f][1,2,4]triazin-4-amine (0.100 g, 0.298 mmol) was added followed by LiCl (13.0 mg, 0.298 mmol). The reaction mixture was heated at 100° C. for 12 h. The cooled reaction mixture was filtered through the CELITE® and washed with ethyl acetate (10 mL). The filtrate was evaporated under reduced pressure to give a residue which was purified by preparative TLC plate (40% ethylacetate/petroleum ether) then further purified by preparative HPLC (Condition B-100 as described in general methods) to give N-(6-(5-phenyl-4-((pyridin-2-ylmethyl)amino)pyrrolo[2,1-f][1,2,4]triazin-2-yl)pyrazin-2-yl)acetamide (20.0 mg, 15.4%). LCMS Condition B-34: retention time 2.27 min, [M+1]=437.0. HPLC Condition B-5: retention time 6.86 min, purity 97.45%. $^1$H NMR (400 MHz, DMSO-$d_6$) δ ppm 2.18 (s, 3H), 4.93 (d, J=4.5 Hz, 2H), 6.85-6.88 (m, 1H), 7.29 (ddd, J=7.5 Hz, J=5.0 Hz, J=1.0 Hz, 1H), 7.38 (t, J=4.5 Hz, 1H), 7.46-7.50 (m, 2H), 7.52-7.57 (m, 2H), 7.58-7.63 (m, 2H), 7.79 (td, J=7.7 Hz, J=1.8 Hz, 1H), 7.89 (d, J=2.5 Hz, 1H), 8.39 (td, J=2.5 Hz, J=1.0 Hz, 1H), 9.17 (s, 1H), 9.43 (s, 1H), 11.15 (s, 1H).

Example 43

(±)-2-(5-Phenyl-4-(pyridin-2-ylmethylamino)pyrrolo[1,2-f][1,2,4]triazin-2-yl)cyclopropanecarbonitrile

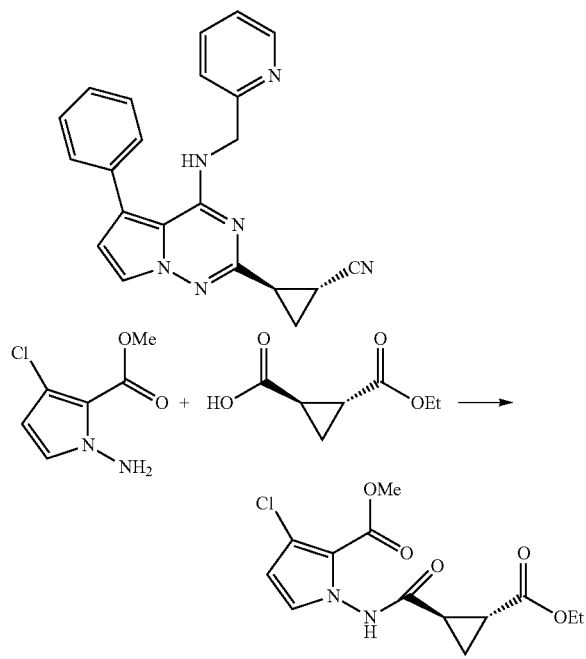

To a solution of methyl 1-amino-3-chloro-1H-pyrrole-2-carboxylate (2.00 g, 11.5 mmol) in DCM (40 mL) was added 1-propanephosphonic acid cyclic anhydride in ethyl acetate (13.6 mL, 22.9 mmol). The reaction mixture was cooled to 0° C. and DIPEA (6.00 mL, 34.4 mmol) was added and stirred at 0° C. for 5 minutes. (±)-2-(Ethoxycarbonyl)cyclopropanecarboxylic acid (1.99 g, 12.6 mmol) was added and the resulting mixture stirred at RT for 12 h. The reaction mixture was diluted with DCM (100 mL) and washed with water (50 mL). The aqueous layer was extracted with DCM (2×50 mL). The combined organic extracts were dried over sodium sulfate, filtered and concentrated under reduced pressure to afford a residue which was taken for the next step without further purification. LCMS Condition B-40: retention time 0.83 min, [M+1]=315.1. $^1$H NMR (400 MHz, DMSO-$d_6$) δ ppm 1.22 (t, J=7.2 Hz, 3H), 1.32-1.39 (m, 2H), 1.95-2.01 (m, 1H), 2.20-2.26 (m, 1H), 3.75 (s, 3H), 4.13 (q, J=7.2 Hz, 2H), 6.30 (d, J=2.8 Hz, 1H), 7.20 (d, J=2.8 Hz, 1H), 11.68 (s, 1H).

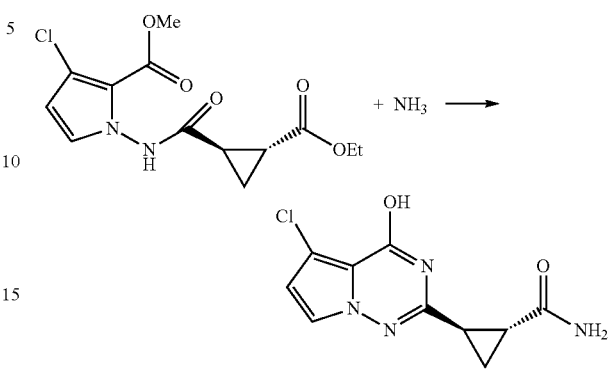

A solution of (±)-methyl 3-chloro-1-(-2-(ethoxycarbonyl)cyclopropanecarboxamido)-1H-pyrrole-2-carboxylate (3.80 g, 12.1 mmol) in MeOH (100 mL) was purged ammonia gas at −40° C. for 5 min. The resulting mixture was heated in a miniclave at 120° C. for 12 h. The reaction mixture was allowed to cool to RT and the volatile components were removed under reduce pressure. Cold methanol (25 mL) was added to the residue and the resulting precipitate was filtered and dried under high vacuum to afforded (±)-2-(5-chloro-4-oxo-3,4-dihydropyrrolo[2,1-f][1,2,4]triazin-2-yl)cyclopropanecarboxamide (1.13 g, 25.8%) as off-white solid. LCMS Condition B-40: retention time 0.62 min, [M+1]=254.9. $^1$H NMR (400 MHz, DMSO-$d_6$) δ ppm 1.26-1.37 (m, 2H), 2.14-2.22 (m, 2H), 6.56 (d, J=3.2 Hz, 1H), 7.48 (d, J=3.2 Hz, 1H), 7.75 (br s, 2H), 11.92 (br s, 1H).

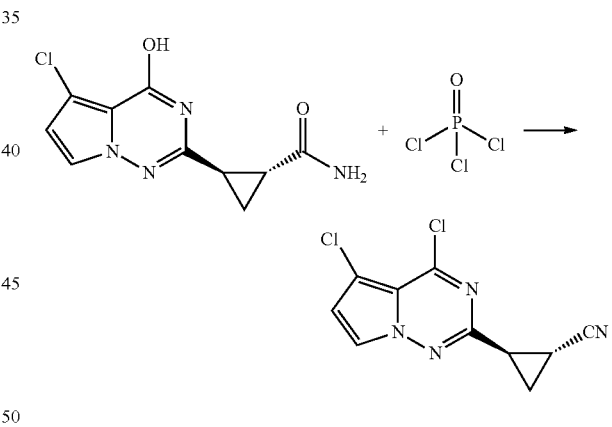

To a suspension of (±)-2-(5-chloro-4-hydroxypyrrolo[2,1-f][1,2,4]triazin-2-yl)cyclopropanecarboxamide (80.0 mg, 0.317 mmol) in toluene (4 mL) was added DIPEA (0.111 mL, 0.633 mmol) followed by POCl$_3$ (0.177 mL, 1.90 mmol). The reaction mixture was heated at 125° C. in a sealed tube for 24 hours. The volatile components were evaporated under reduced pressure and cold water (10 mL) was added to the resulting residue. The reaction mixture was basified with 10% sodium bicarbonate and extracted with EtOAc (2×50 mL). The combined organic extracts was washed with brine (10 mL), dried over Na$_2$SO$_4$, filtered and concentrated under reduced pressure to obtain a residue (60.0 mg, 71.0%) which was taken for the next step without purification. LCMS Condition B-39: retention time 2.53 min, [M+1]=253.0. $^1$H NMR (300 MHz, CDCl$_3$) δ ppm 1.63-1.77 (m, 2H), 2.08-2.15 (m, 1H), 2.68-2.75 (m, 1H), 6.86 (d, J=3.6 Hz, 1H), 7.69 (d, J=4.0 Hz, 1H).

153

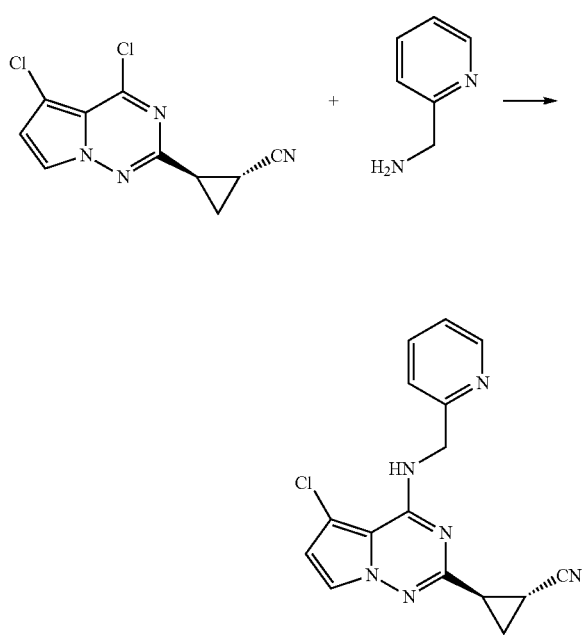

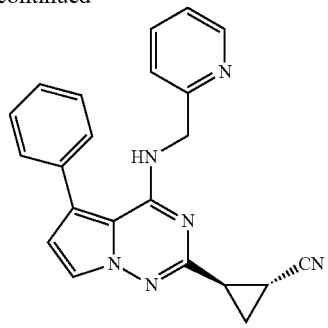

To a solution of (±)-2-(4,5-dichloropyrrolo[2,1-f][1,2,4]triazin-2-yl)cyclopropanecarbonitrile (60.0 mg, 0.237 mmol) in THF (1 mL) was added 2-(aminomethyl)pyridine (0.0290 mL, 0.284 mmol) followed by DIPEA (0.124 mL, 0.711 mmol). The reaction mixture was stirred at RT for 1 hour. The reaction mixture was quenched with water (10 mL) and extracted with EtOAc (2×25 mL). The combined organic extracts was washed with brine (25 mL), dried over $Na_2SO_4$, filtered and concentrated under reduced pressure. The residue was purified by CombiFlash (REDISEP®, silica gel, 4 g, 10% EtOAc/petroleum ether) to afford (±)-2-(5-chloro-4-((pyridin-2-ylmethyl)amino)pyrrolo[2,1-f][1,2,4]triazin-2-yl)cyclopropanecarbonitrile (50.0 mg, 59.1%) as off-white solid. LCMS Condition B-41: retention time 0.67 min, [M+1]=325.0. $^1$H NMR (400 MHz, DMSO-$d_6$) δ ppm 1.30-1.34 (m, 1H), 1.48-1.51 (m, 1H), 1.92-1.96 (m, 1H), 2.45-2.49 (m, 1H), 4.76 (t, J=4.8 Hz, 2H), 6.72 (d, J=2.8 Hz, 1H), 7.29 (q, J=4.8 Hz, 1H), 7.35 (d, J=8.0 Hz, 1H), 7.68 (d, J=2.8 Hz, 1H), 7.77 (q, J=2.0 Hz, 1H), 8.14 (s, 1H), 8.53 (dd, J=1.2 Hz, J=3.2 Hz, 1H).

154

-continued

To a stirred solution of (±)-2-(5-chloro-4-((pyridin-2-ylmethyl)amino)pyrrolo[2,1-f][1,2,4]triazin-2-yl)cyclopropanecarbonitrile (50.0 mg, 0.154 mmol) and phenylboronic acid (22.5 mg, 0.185 mmol) in a mixture of 1,4-dioxane (3 mL) and water (0.6 mL) was added 2-(dicyclohexylphosphino)-2',4',6'-triisopropylbiphenyl (14.7 mg, 0.0310 mmol), $Pd(OAc)_2$ (3.46 mg, 0.0150 mmol) followed by $K_2CO_3$ (63.8 mg, 0.462 mmol). The resulting suspension was purged with $N_2$ gas for 5 minutes then heated at 100° C. in a sealed tube for 12 h. The reaction mixture was allowed to cool to RT and water (10 mL) was added. The reaction mixture was extracted with EtOAc (2×25 mL) and the combined organic extracts washed with brine (10 mL), dried over $Na_2SO_4$, filtered and concentrated under reduced pressure. The residue was purified by preparative HPLC (Condition B-101 as described in general methods) to afforded (±)-2-(5-phenyl-4-((pyridin-2-ylmethyl)amino)pyrrolo[2,1-f][1,2,4]triazin-2-yl)cyclopropanecarbonitrile (25.0 mg, 43.9%) as white solid. LCMS Condition B-34: retention time 2.44 min, [M+1]=367.0. HPLC Condition B-5: retention time 8.52 min, purity 99.03%. $^1$H NMR (400 MHz, DMSO-$d_6$) δ ppm 1.53-1.59 (m, 2H), 2.11-2.16 (m, 1H), 2.56-2.61 (m, 1H), 4.69 (d, J=4.8 Hz, 2H), 6.71 (d, J=2.8 Hz, 1H), 7.18 (t, J=4.4 Hz, 1H), 7.27 (t, J=5.2 Hz, 1H), 7.36 (d, J=7.6 Hz, 1H), 7.42-7.53 (m, 5H), 7.73-7.78 (m, 2H), 8.35 (td, J=1.2 Hz, J=4.0 Hz, 1H).

Example 44

(±)-2-(5-Phenyl-4-(pyridin-2-ylmethylamino)pyrrolo[1,2-f][1,2,4]triazin-2-yl)cyclopropanecarboxamide

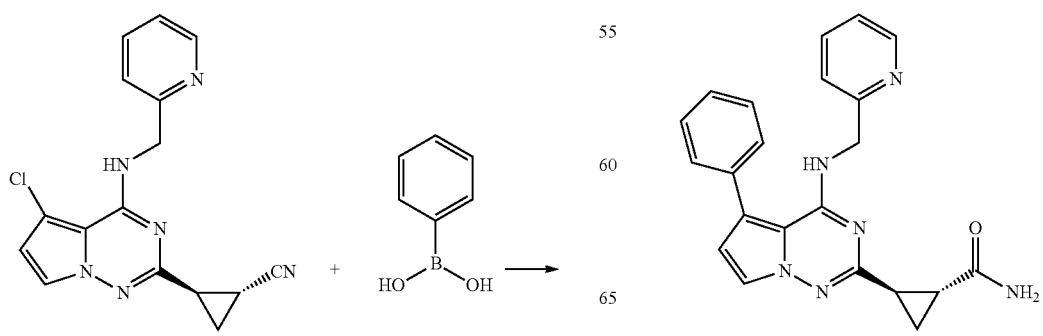

-continued

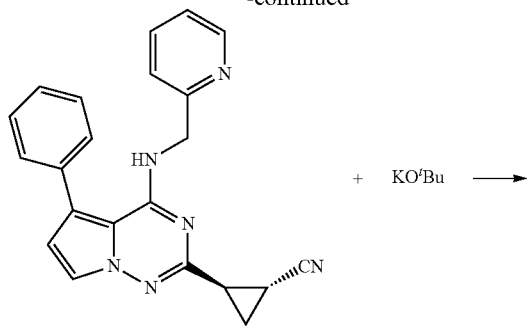

+ KOᵗBu ⟶

To a solution of (±)-2-(5-phenyl-4-((pyridin-2-ylmethyl) amino)pyrrolo[2,1-f][1,2,4]triazin-2-yl)cyclopropanecarbonitrile (550 mg, 1.50 mmol) in t-butanol (30 mL) was added KOtBu (842 mg, 7.51 mmol). The reaction mixture was heated to reflux at 90° C. for 12 h. t-Butanol was evaporated under reduced pressure and water (25 mL) was added to the reaction mixture. The aqueous layer was acidified with aqueous citric acid solution and extracted with DCM (3×50 mL). The combined organic extracts were washed with brine (25 mL), dried over sodium sulfate and concentrated. The residue was purified by preparative HPLC (Condition B-108 as described in general methods) to obtain (±)-2-(5-phenyl-4-((pyridin-2-ylmethyl)amino)pyrrolo[2,1-f][1,2,4]triazin-2-yl)cyclopropanecarboxamide (130 mg, 22.0%) which was resolved by chiral HPLC (Condition B-109 as described in general methods) to obtain enantiomer-1 (42 mg) and enantiomer-2 (46 mg).

Enantiomer-1: LCMS Condition B-78: retention time 1.85 min, [M+1]=385.0. HPLC Condition B-110: retention time 4.05 min, purity 100.0%. ¹H NMR (400 MHz, DMSO-$d_6$) δ ppm 1.23-1.25 (m, 1H), 1.29-1.34 (m, 1H), 2.11-2.18 (m, 2H), 4.64-4.78 (m, 2H), 7.68 (d, J=2.8 Hz, 1H), 6.94 (br s, 1H), 7.11 (t, J=4.8 Hz, 1H), 7.28 (dt, J=1.6 Hz, J=6.0 Hz, 1H), 7.37-7.54 (m, 6H), 7.65 (br s, 1H), 7.69 (d, J=2.4 Hz, 1H), 7.77 (dt, J=1.6 Hz, J=7.6 Hz, 1H), 7.77 (td, J=0.8 Hz, J=4.8 Hz, 1H).

Enantiomer-2: LCMS Condition B-78: retention time 1.85 min, [M+1]=385.0. HPLC Condition B-110: retention time 4.85 min, purity 98.90%. ¹H NMR (400 MHz, DMSO-$d_6$) δ ppm 1.23-1.25 (m, 1H), 1.29-1.34 (m, 1H), 2.11-2.18 (m, 2H), 4.64-4.78 (m, 2H), 7.68 (d, J=2.8 Hz, 1H), 6.94 (br s, 1H), 7.11 (t, J=4.8 Hz, 1H), 7.28 (dt, J=1.6 Hz, J=6.0 Hz, 1H), 7.37-7.54 (m, 6H), 7.65 (br s, 1H), 7.69 (d, J=2.4 Hz, 1H), 7.77 (dt, J=1.6 Hz, J=7.6 Hz, 1H), 7.77 (td, J=0.8 Hz, J=4.8 Hz, 1H).

Example 45

Methyl 2-(5-(4-(benzylamino)-5-phenylpyrrolo[2,1-f][1,2,4]triazin-2-yl)nicotinamido)-3-sulfamoylpropanoate

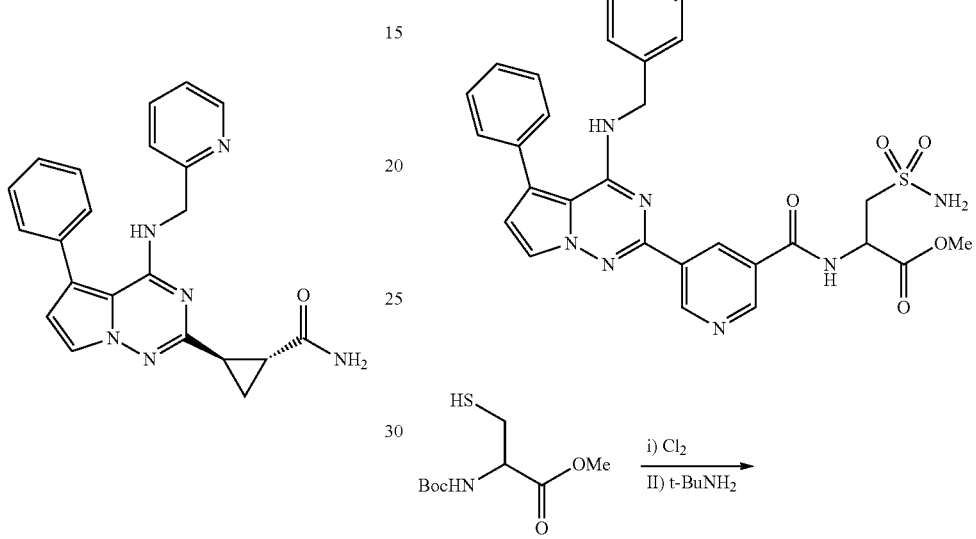

Methyl 2-((tert-butoxycarbonyl)amino)-3-mercaptopropanoate (1.00 g, 4.25 mmol) was dissolved in DCM (15 mL) and cooled to 0° C. Chlorine gas was purged (1 bladder) through the reaction mixture for 30 minutes and the reaction mixture stirred at room temperature for an additional 30 minutes. The reaction mixture was diluted with water (50 mL) and extracted with DCM (2×100 mL). The combined organic layer was dried over sodium sulfate, filtered and concentrated under reduced pressure to obtain a residue. tert-Butylamine (2.25 mL, 21.3 mmol) was added to the residue in THF (10 mL) and the reaction mixture was stirred at room temperature for 12 h. The reaction mixture was quenched by the addition of water (50 mL) and the solution extracted with ethyl acetate (2×50 mL). The combined organic layer was dried over sodium sulfate, filtered and concentrated under reduced pressure. The residue was purified by CombiFlash (REDISEP®, silica gel, 24 g, 30% EtOAc/petroleum ether) to afford methyl 2-((tert-butoxycarbonyl)amino)-3-(N-(tert-butyl)sulfamoyl) propanoate (0.300 g, 20.9%). ¹H NMR (400 MHz, DMSO-$d_6$) δ ppm 1.19-1.29 (m, 9H), 1.34-1.44 (m, 9H), 3.36-3.47 (m, 2H), 3.66 (s, 3H), 4.44 (d, J=3.8 Hz, 1H), 6.99 (s, 1H), 7.32 (d, J=8.0 Hz, 1H).

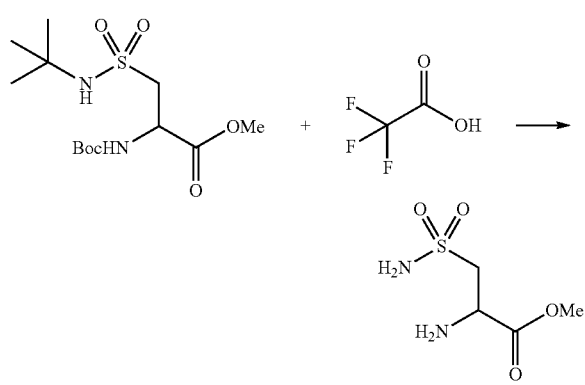

TFA (1 mL, 11.0 mmol) was added to methyl 2-((tert-butoxycarbonyl)amino)-3-(N-(tert-butyl)sulfamoyl)propanoate (30.0 mg, 0.0890 mmol) and the reaction mixture was stirred at room temperature for 12 h. TFA was removed under reduced pressure and the reaction mixture was diluted with 10% sodium bicarbonate solution (20 mL) then extracted with DCM (3×30 mL). The combined organic extracts were dried over sodium sulfate, filtered and evaporated under reduced pressure to give a residue (15.0 mg) which was taken onto the next step as such without further purification. LCMS Condition B-39: retention time 0.30 min, [M+1]=182.2.

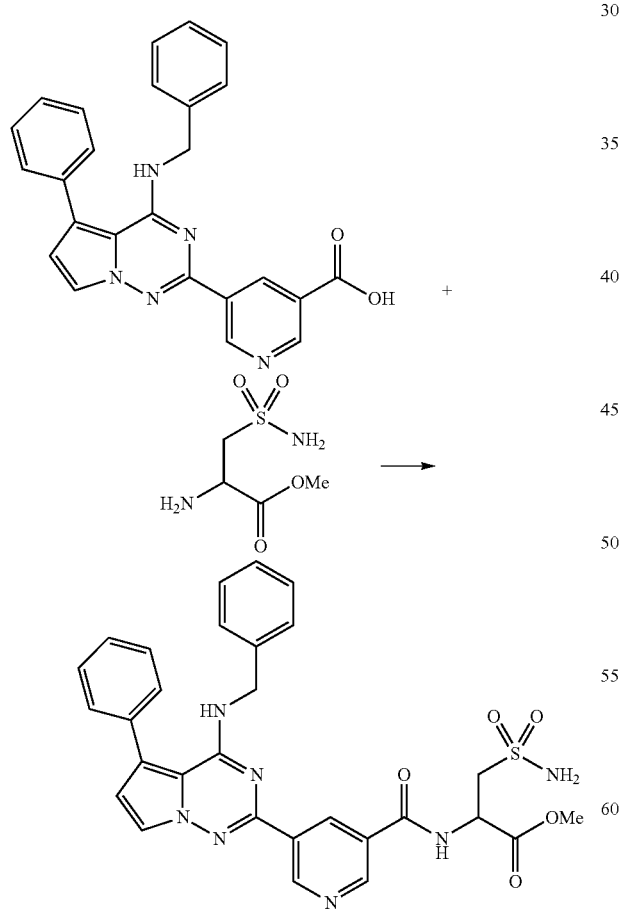

To a solution of 5-(4-(benzylamino)-5-phenylpyrrolo[2,1-f][1,2,4]triazin-2-yl)nicotinic acid (50.0 mg, 0.119 mmol) in DMF (1 mL) was added DMAP (22.0 mg, 0.178 mmol) followed by HATU (68.0 mg, 0.178 mmol) and the reaction mixture stirred for 10 minutes at room temperature. Methyl 2-amino-3-sulfamoylpropanoate (10.8 mg, 0.0590 mmol) was added and the reaction mixture stirred at room temperature for 14 h. The reaction mixture was concentrated under reduced pressure and water (10 mL) was added to the resulting residue and the solution extracted with DCM (2×25 mL). The combined organic layer was dried over sodium sulfate, filtered and concentrated under reduced pressure. The residue was purified by preparative HPLC (Condition B-102 as described in general methods) to obtain (methyl 2-(5-(4-(benzylamino)-5-phenylpyrrolo[2,1-f][1,2,4]triazin-2-yl)nicotinamido)-3-sulfamoylpropanoate (10.0 mg, 27.6%). LCMS Condition B-19: retention time 2.11 min, [M+1]=586.1. HPLC Condition B-30: retention time 11.20 min, Purity 98.0%. $^1$H NMR (400 MHz, DMSO-$d_6$) δ ppm 3.65 (d, J=6.3 Hz, 2H), 3.71 (s, 3H), 4.84 (d, J=5.8 Hz, 2H), 4.93 (d, J=7.1 Hz, 1H), 6.72 (t, J=5.6 Hz, 1H), 6.83 (d, J=2.8 Hz, 1H), 7.08 (br s, 2H), 7.21-7.29 (m, 1H), 7.31-7.42 (m, 5H), 7.44-7.52 (m, 2H), 7.53-7.57 (m, 2H), 7.93 (d, J=2.8 Hz, 1H), 8.95 (t, J=2.1 Hz, 1H), 9.09 (d, J=2.1 Hz, 1H), 9.44 (d, J=7.8 Hz, 1H), 9.50 (d, J=2.1 Hz, 1H).

Example 46

((5-(5-Phenyl-4-((pyrimidin-2-ylmethyl)amino)pyrrolo[2,1-f][1,2,4]triazin-2-yl)pyridin-3-yl)sulfonyl)phosphoramidic acid

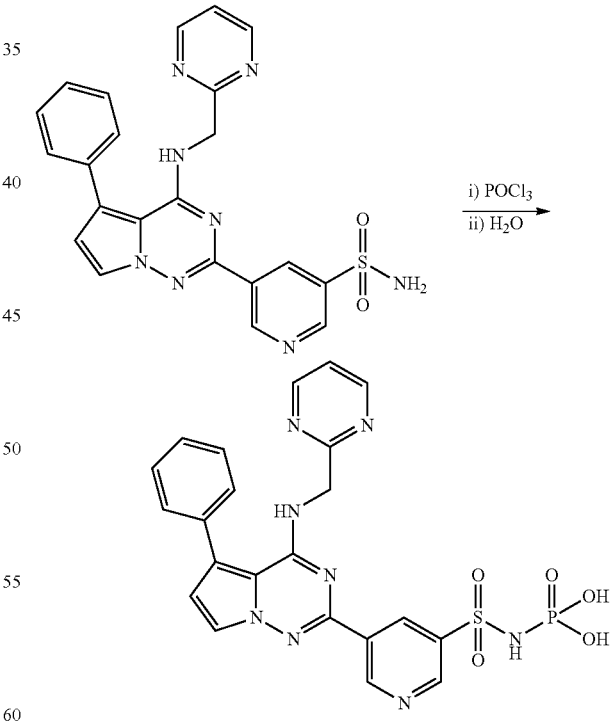

To a solution of 5-(5-phenyl-4-((pyrimidin-2-ylmethyl)amino)pyrrolo[2,1-f][1,2,4]triazin-2-yl)pyridine-3-sulfonamide (0.100 g, 0.218 mmol) in DCM (15 mL) was added DIPEA (0.0760 mL, 0.436 mmol) at 0° C. and mixture was stirred for 10 min. Then POCl$_3$ (0.0810 mL, 0.872 mmol) was added at 0° C. and mixture was allowed to stir for 2 h. The reaction mixture was evaporated under reduced pressure, water (100 mL) was added to the residue at 0° C. and stirred for 8 h while warming to RT. The resulting precipitate was filtered and washed with acetone (10 mL). The precipitate was purified by preparative HPLC (Condition B-112 as described in general methods) to give ((5-(5-phenyl-4-((pyrimidin-2-ylmethyl)amino)pyrrolo[2,1-f][1,2,4]triazin-2-yl)pyridin-3-yl)sulfonyl)phosphoramidic acid (45.0 mg, 36.8%) as a white solid. LCMS Condition B-13: retention time 1.76 min, [M+1]=539.2. HPLC Condition B-107: retention time 6.13 purity 96.31%. $^1$H NMR (400 MHz, DMSO-d$_6$) δ ppm 5.02 (d, J=4.5 Hz, 2H) 6.81-6.88 (m, 1H), 7.26 (t, J=4.5 Hz, 1H), 7.42 (t, J=4.8 Hz, 1H), 7.45-7.51 (m, 1H), 7.53-7.61 (m, 2H), 7.62-7.68 (m, 2H), 7.95-8.00 (m, 1H), 8.74 (d, J=5.1 Hz, 2H), 8.84-8.88 (m, 1H), 9.08 (d, J=2.1 Hz, 1H), 9.33 (d, J=2.1 Hz, 1H).

Examples 47-185

Examples 47-185 were synthesized via the procedures described above for Examples 1-46. HPLC/MS data for each compound was collected using method mentioned in the table, and the molecular mass determined by MS (ES) by the formula m/z. The retention time, MS, and proton NMR data for Examples 47-185 are listed in Table 1.

TABLE 1

| Ex. No. | Structure | Name | $^1$H NMR | LC/MS Rt (min) Condition [M + 1] |
|---|---|---|---|---|
| 47 | 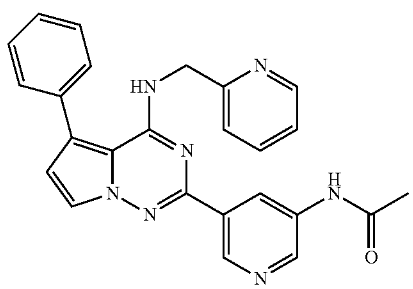 [SMILES: CC(=O)Nc1cncc(-c2nc(NCc3ccccn3)c3c(-c4ccccc4)ccn3n2)c1] | N-(5-(5-phenyl-4-(pyridin-2-ylmethylamino)pyrrolo[1,2-f][1,2,4]triazin-2-yl)pyridin-3-yl)acetamide | $^1$H NMR (400 MHz, DMSO-d$_6$) δ ppm: 2.12 (s, 3 H), 4.91 (d, J = 4.4 Hz, 2 H), 6.81 (d, J = 2.8 Hz, 1 H), 7.27-7.30 (m, 2 H), 7.32-7.55 (m, 6 H), 7.58-7.81 (m, 1 H), 7.90 (d, J = 2.4 Hz, 1 H), 8.38-8.39 (m, 1 H), 8.81 (t, J = 6.8 Hz, 1 H), 8.86 (d, J = 2.4 Hz, 1 H), 9.08 (d, J = 2.0 Hz, 1 H), 10.29 (m, 1 H). | 2.02 B-39 436.2 |
| 48 | 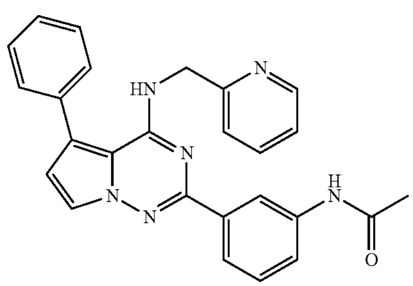 [SMILES: CC(=O)Nc1cccc(-c2nc(NCc3ccccn3)c3c(-c4ccccc4)ccn3n2)c1] | N-(3-(5-phenyl-4-(pyridin-2-ylmethylamino)pyrrolo[1,2-f][1,2,4]triazin-2-yl)phenyl)acetamide | $^1$H NMR (400 MHz, DMSO-d$_6$) δ ppm: 2.07 (s, 3 H), 4.91 (d, J = 4.4 Hz, 2 H), 6.79 (d, J = 2.8 Hz, 1 H), 7.21 (t, J = 4.8 Hz, 1 H), 7.29 (dd, J = 5.2, J = 6.8 Hz, 1 H), 7.38-7.60 (m, 7 H), 7.76-7.81 (m, 2 H), 7.85 (d, J = 2.8 Hz, 1 H), –7.94-7.97 (m, 2 H), 8.12-8.23 (m, 2 H). | 2.12 B-12 434.8 |
| 49 | 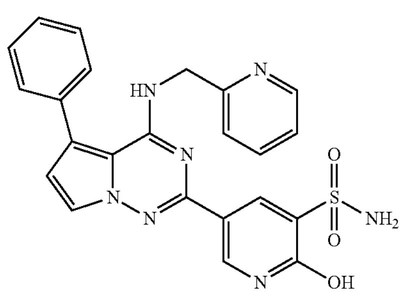 [SMILES: NS(=O)(=O)c1cc(-c2nc(NCc3ccccn3)c3c(-c4ccccc4)ccn3n2)cnc1O] | 2-hydroxy-5-(5-phenyl-4-(pyridin-2-ylmethylamino)pyrrolo[1,2-f][1,2,4]triazin-2-yl)pyridine-3-sulfonamide | $^1$H NMR (400 MHz, DMSO-d$_6$): δ 4.86 (d, J = 4.8 Hz, 2H), 6.75 (d, J = 2.8 Hz, 1H), 7.04 (s, 2H), 7.26-7.29 (m, 2H), 7.42-7.58 (m, 6H), 7.75-7.80 (m, 1H), 7.88 (d, J = 2.8 Hz, 1 H), 8.38 (t, J = 4.4 Hz, 1 H), 8.45 (d, J = 2.4 Hz, 1 H), 8.76 (d, J = 2.4 Hz, 1 H), 12.69 (s, 1 H). | 1.83 B-14 437.2 |
| 50 | 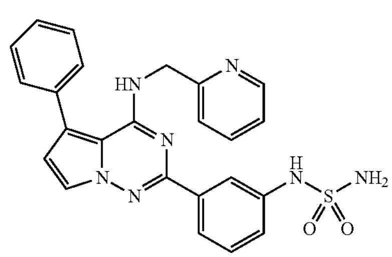 [SMILES: NS(=O)(=O)Nc1cccc(-c2nc(NCc3ccccn3)c3c(-c4ccccc4)ccn3n2)c1] | 1-(3-(5-phenyl-4-(pyridin-2-ylmethylamino)pyrrolo[1,2-f][1,2,4]triazin-2-yl)phenyl)sulfonylurea | $^1$H NMR (400 MHz, DMSO-d$_6$) δ ppm: 4.91 (d, J = 4.8 Hz, 2 H), 6.79 (d, J = 2.8 Hz, 1 H), 7.12-7.61 (m, 11 H), 7.77-7.7.91 (m, 3 H), 8.14 (dd, J = 2.0 Hz, J = 3.6 Hz, 1 H), 8.38-8.40 (m, 1 H), 9.60 (s, 1 H). | 1.58 B-42 472.2 |

TABLE 1-continued

| Ex. No. | Structure | Name | ¹H NMR | LC/MS Rt (min) Condition [M + 1] |
|---|---|---|---|---|
| 51 | 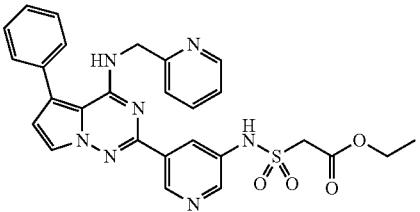 [SMILES: CCOC(=O)CS(=O)(=O)Nc1cncc(-c2nc(NCc3ccccn3)c3c(-c4ccccc4)ccn3n2)c1] | ethyl 2-(N-(5-(5-phenyl-4-(pyridin-2-ylmethylamino) pyrrolo[1,2-f][1,2,4] triazin-2-yl)pyridin-3-yl)sulfamoyl)acetate | ¹H NMR (400 MHz, DMSO-d$_6$) δ ppm: 1.15 (t, J = 7.2 Hz, 3 H), 4.08 (q J = 7.2, 2 H), 4.91 (d, J = 4.4 Hz, 2 H), 6.82 (d, J = 2.8 Hz, 1 H), 7.27-7.32 (m, 4 H), 7.45-7.48 (m, 3 H), 7.53 (t, J = 7.6 Hz, 2 H), 7.58 (d, J = 6.8- Hz, 2 H), 7.77-7.80 (m, 2 H), 7.91 (d, J = 2.8 Hz, 1 H), 10.59 (br s, 1 H). | 1.70 B-42 444.2 |
| 52 | 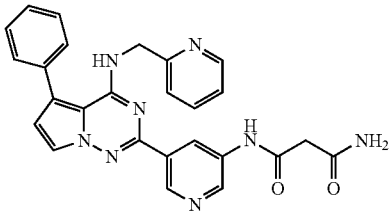 [SMILES: NC(=O)CC(=O)Nc1cncc(-c2nc(NCc3ccccn3)c3c(-c4ccccc4)ccn3n2)c1] | N1-(5-(5-phenyl-4-(pyridin-2-ylmethylamino) pyrrolo[1,2-f][1,2,4] triazin-2-yl)pyridin-3-yl)malonamide | ¹H NMR (400 MHz, DMSO-d$_6$) δ ppm: 3.30 (d, J = 5.6 Hz, 2 H), 4.92 (d, J = 4.8 Hz, 2 H), 6.82 (d, J = 2.8 Hz, 1 H), 7.16 (s, 1 H), 7.28-7.32 (m, 2 H), 7.47-7.61 (m, 7 H), 7.77 (dd, J = 1.6 Hz, J = 7.6 Hz, 1 H), 7.92 (d, J = 2.4 Hz, 1 H), 8.32-8.39 (m, 1 H), 8.84-8.87 (m, 2 H), −9.11 (d, J = 1.6 Hz, 1 H), 9.51 (br s, 1 H). | 1.43 B-42 479.2 |
| 53 | 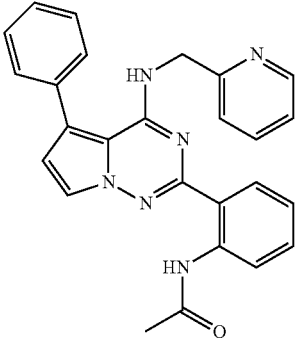 [SMILES: CC(=O)Nc1ccccc1-c1nc(NCc2ccccn2)c2c(-c3ccccc3)ccn2n1] | N-(2-(5-phenyl-4-(pyridin-2-ylmethylamino) pyrrolo[1,2-f][1,2,4] triazin-2-yl)phenyl) acetamide | ¹H NMR (400 MHz, DMSO-d$_6$) δ ppm: 2.19 (s, 3 H), 4.90 (d, J = 4.4 Hz, 2 H), 6.80 (d, J = 2.8 Hz, 1 H), 7.13-7.62 (m, 11 H), 7.77 (dt, J = 2.0 Hz, J = 7.6 Hz, 1 H), 7.97 (d, J = 2.8 Hz, 1 H), 8.19 (dd, J = 1.6 Hz, J = 8.0 Hz, 1 H), 8.36-8.43 (m, 2 H). | 1.90 B-42 435.2 |
| 54 | 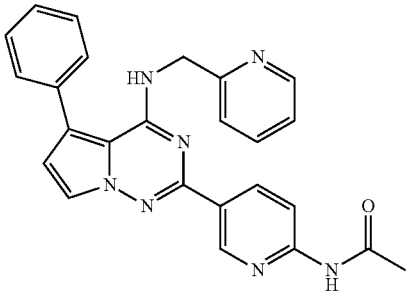 [SMILES: CC(=O)Nc1ccc(-c2nc(NCc3ccccn3)c3c(-c4ccccc4)ccn3n2)cn1] | N-(5-(5-phenyl-4-(pyridin-2-ylmethylamino) pyrrolo[1,2-f][1,2,4] triazin-2-yl)pyridin-2-yl)acetamide | ¹H NMR (400 MHz, DMSO-d$_6$) δ ppm: 2.13 (s, 3 H), 4.92 (d, J = 4.8 Hz, 2 H), 6.81 (d, J = 2.8 Hz, 1 H), 7.28 (t, J = 4.8 Hz, 2 H), 7.44-7.60 (m, 6 H), 7.76 (dt, J = 2.0 Hz, J = 8.0 Hz, 1 H), 7.87 (d, J = 2.8 Hz, 1 H), 8.19 (d, J = 8.8 Hz, 1 H), 8.38 (d, J = 5.2 Hz, 1 H), 8.51 (dd, J = 2.4 Hz, J = 8.8 Hz, 1 H), 9.10 (dd, J = 0.4 Hz, J = 2.4 Hz, 1 H), 10.70 (s, 1 H). | 1.73 B-42 436.2 |
| 55 | 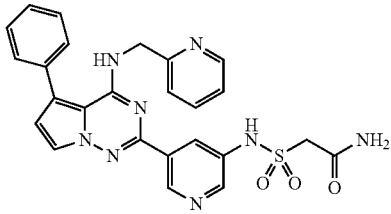 [SMILES: NC(=O)CS(=O)(=O)Nc1cncc(-c2nc(NCc3ccccn3)c3c(-c4ccccc4)ccn3n2)c1] | 2-(N-(5-(5-phenyl-4-(pyridin-2-ylmethylamino) pyrrolo[1,2-f][1,2,4] triazin-2-yl)pyridin-3-yl)sulfamoyl)acetamide | ¹H NMR (400 MHz, DMSO-d$_6$) δ ppm: 4.03 (s, 2 H), 4.91 (d, J = 4.8 Hz, 2H), 6.82 (d, J = 2.8 Hz, 1H), 7.27-7.67 (m, 9 H), 7.67 (br s, 1 H), 7.77 (dt, J = 1.6 Hz, J = 7.6 Hz, 1 H), 7.92 (d, J = 2.8 Hz, 1 H). 8.38 (m, 1 H), 8.45 (t, J = 2.4 Hz, 1H), 8.56 (d, J = 2.4 Hz, 1 H), 9.14 (d, J = 1.6 Hz, 1 H), 10.28 (br s, 1 H). | 1.42 B-43 515.2 |
| 56 | 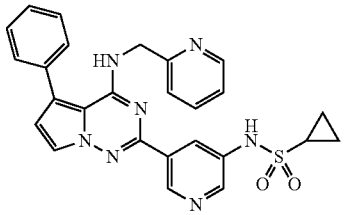 [SMILES: O=S(=O)(Nc1cncc(-c2nc(NCc3ccccn3)c3c(-c4ccccc4)ccn3n2)c1)C1CC1] | N-(5-(5-phenyl-4-(pyridin-2-ylmethylamino) pyrrolo[1,2-f][1,2,4] triazin-2-yl)pyridin-3-yl) cyclopropanesulfonamide | ¹H NMR (400 MHz, DMSO-d$_6$) δ ppm: 0.98 (dd, J = 2.8 Hz, J = 4.4 Hz, 4 H), 2.74 (m, 1 H), 4.91 (d, J = 4.8 Hz, 2 H), 6.83 (d, J = 2.4 Hz, 1H), 7.27-7.33 (m, 2 H), 7.44, −7.60 (m, 6 H), 7.78 (dt, J = 2.0 Hz, J = 7.6 Hz, 1 H), 7.92 (d, J = 2.4 Hz, 1 H). 8.38-8.40 (m, 1 H), 8.47 (dd, J = 2.0 Hz, J = 2.4 Hz, 1H), 8.56 (d, J = 2.8 Hz, 1 H), 9.16 (d, J = 1.6 Hz, 1 H), 10.15 (br s, 1 H). | 1.50 B-43 498.2 |

TABLE 1-continued

| Ex. No. | Structure | Name | ¹H NMR | LC/MS Rt (min) Condition [M + 1] |
|---|---|---|---|---|
| 57 | 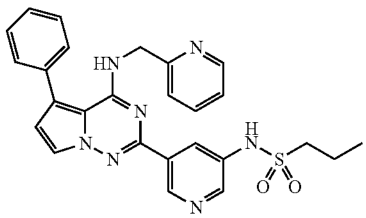 [SMILES: CCCS(=O)(=O)Nc1cncc(-c2nc(NCc3ccccn3)c3c(-c4ccccc4)ccn3n2)c1] | N-(5-(5-phenyl-4-(pyridin-2-ylmethylamino)pyrrolo[1,2-f][1,2,4]triazin-2-yl)pyridin-3-yl)propane-1-sulfonamide | ¹H NMR (400 MHz, DMSO-d₆) δ ppm: 0.97 (t, J = 7.6 Hz, 3 H), 1.71-1.76 (m, 2 H), 3.17-3.20 (m, 2 H), 4.91 (d, J = 4.8 Hz, 2 H), 6.82 (d, J = 2.4 Hz, 1 H), 7.28-7.31 (m, 2 H), 7.45-7.65 (m, 7 H), 7.78 (dt, J = 2.0 Hz, J = 7.6 Hz, 1 H), 7.92 (d, J = 2.8 Hz, 1 H-), 8.39 (dd, J = 1.2 Hz, J = 1.6 Hz, 1 H), 8.40 (dd, J = 0.8 Hz, J = 1.6 Hz, 1 H), 8.53 (d, J = 2.4 Hz, 1 H), 9.13 (d, J = 1.6 Hz, 1 H). | 2.07 B-12 500.5 |
| 58 | 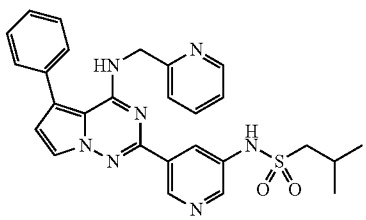 [SMILES: CC(C)CS(=O)(=O)Nc1cncc(-c2nc(NCc3ccccn3)c3c(-c4ccccc4)ccn3n2)c1] | 2-methyl-N-(5-(5-phenyl-4-(pyridin-2-ylmethylamino)pyrrolo[1,2-f][1,2,4]triazin-2-yl)pyridin-3-yl)propane-1-sulfonamide | ¹H NMR (400 MHz, DMSO-d₆) δ ppm: 1.02 (d, J = 6.8 Hz, 6 H), -2.14-2.21 (m, 1 H), 3.08 (d, J = 6.4 Hz, 2 H), 4.91 (d, J = 4.8 Hz, 2 H), 6.82 (d, J = 2.8 Hz, 1 H), 7.27-7.32 (m, 2 H), 7.44-7.61 (m, 7 H), 7.78 (dt, J = 2.0 Hz, J = 7.6 Hz, 1 H), 7.92 (d, J = 2.8 Hz, 1 H), 8.38-8.43 (m, 2 H), 8.52 (d, J = 2.4 Hz, 1 H), 9.13 (d, J = 1.6 Hz, 1 H). | 2.14 B-12 514.5 |
| 59 | 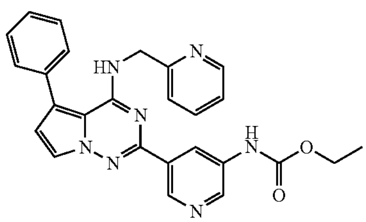 [SMILES: CCOC(=O)Nc1cncc(-c2nc(NCc3ccccn3)c3c(-c4ccccc4)ccn3n2)c1] | ethyl 5-(5-phenyl-4-(pyridin-2-ylmethylamino)pyrrolo[1,2-f][1,2,4]triazin-2-yl)pyridin-3-ylcarbamate | ¹H NMR (400 MHz, DMSO-d₆) δ ppm: 1.29 (t, J = 7.2 Hz, 3 H), 4.19 (q, J = 6.8 Hz, -2 H), 4.91 (d, J = 4.8 Hz, 2 H), 6.81 (d, J = 2.4 Hz, 1H), 7.27-7.33 (m, 2 H), 7.44-, -7.61 (m, 7 H), 7.76 (dt, J = 1.6 Hz, J = 7.6 Hz, 1 H), 8.38 -8.40 (m, 1 H), 8.73-8.75 (m, 2 H), 9.05 (d, J = 1.6 Hz, 1 H), 9.98 (br s, 1 H). | 2.07 B-14 466.2 |
| 60 | 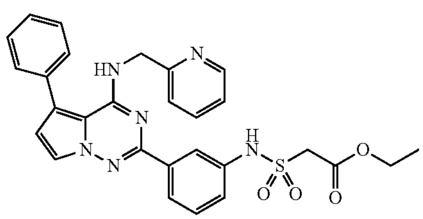 [SMILES: CCOC(=O)CS(=O)(=O)Nc1cccc(-c2nc(NCc3ccccn3)c3c(-c4ccccc4)ccn3n2)c1] | ethyl 2-(N-(3-(5-phenyl-4-(pyridin-2-ylmethylamino)pyrrolo[1,2-f][1,2,4]triazin-2-yl)phenyl)sulfamoyl)acetate | ¹H NMR (400 MHz, DMSO-d₆) δ ppm: 1.16 (t, J = 6.8 Hz, 3 H), 2.09 (q, J = 7.2 Hz, 2 H), 4.24 (s, 2 H), 4.91 (d, J = 4.4 Hz, 2 H), 6.82 (d, J = 2.8 Hz, 1 H), 7.21-7.60 (m, 11 H), 7.78 (dt, J = 2.0 Hz, J = 7.6 Hz, 1 H), 7.86 (d, J = 2.4 Hz, 1 H), 8.04 (dd, J = 1.2 Hz, J = 2.4 Hz, 1 H), 8.22 (t, J = 1.6 Hz, 1 H), 8.39 (d, J = 4.0 Hz, 1 H). | 2.16 B-39 543.2 |
| 61 | 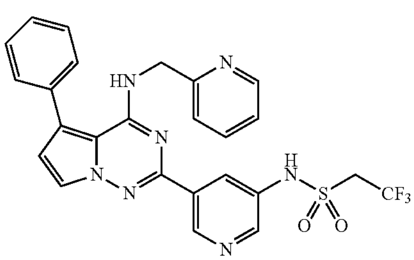 [SMILES: O=S(=O)(CC(F)(F)F)Nc1cncc(-c2nc(NCc3ccccn3)c3c(-c4ccccc4)ccn3n2)c1] | 2,2,2-trifluoro-N-(5-(5-phenyl-4-(pyridin-2-ylmethylamino)pyrrolo[1,2-f][1,2,4]triazin-2-yl)pyridin-3-yl)ethanesulfonamide | ¹H NMR (400 MHz, DMSO-d₆) δ ppm: 4.66 (q J = 9.6 Hz, 2 H), 4.92 (d, J = 4.8 Hz, 2 H), 6.82 (d, J = 2.4 Hz, 1 H), 7.27-7.60 (m, 8H), 7.76-7.81 (m, 1 H), 7.92 (d, J = 2.4 Hz, 1 H), 8.39-8.55 (m, 3 H), 9.18 (d, J = 1.6 Hz, 1 H), 10.83 (br s, 1 H). | 2.03 B-39 540.2 |
| 62 | 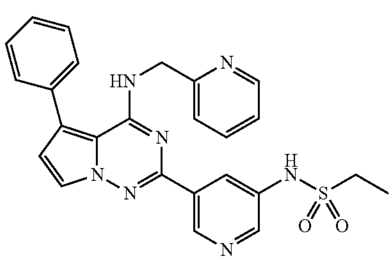 [SMILES: CCS(=O)(=O)Nc1cncc(-c2nc(NCc3ccccn3)c3c(-c4ccccc4)ccn3n2)c1] | N-(5-(5-phenyl-4-(pyridin-2-ylmethylamino)pyrrolo[1,2-f][1,2,4]triazin-2-yl)pyridin-3-yl)ethanesulfonamide | ¹H NMR (400 MHz, DMSO-d₆) δ ppm: 1.21 (t, J = 7.2 Hz, 3 H), 3.09 (q, J = 7.2 Hz, 2 H), 4.91 (d, J = 4.8 Hz, 2 H), 6.81 (d, J = 2.8 Hz, 1 H), 7.27-7.30 (m, 2 H), 7.44, -7.60 (m, 7 H), 7.76 (dt, J = 2.0 Hz, J = 7.6 Hz, 1 H), 7.90 (d, J = 2.8 Hz, 1 H), 8.33-8.42 (m, 3 H), 8.97 (br s, 1 H). | 1.85 B-43 486.2 |

TABLE 1-continued

| Ex. No. | Structure | Name | ¹H NMR | LC/MS Rt (min) Condition [M + 1] |
|---|---|---|---|---|
| 63 | 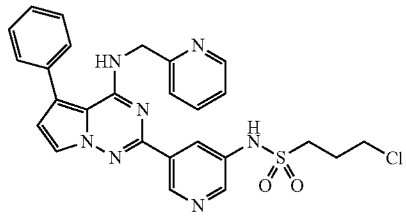 [SMILES: O=S(=O)(CCCCl)Nc1cncc(-c2nc(NCc3ccccn3)c3c(-c4ccccc4)ccn3n2)c1] | 3-chloro-N-(5-(5-phenyl-4-(pyridin-2-ylmethylamino)pyrrolo[1,2-f][1,2,4]triazin-2-yl)pyridin-3-yl)propane-1-sulfonamide | ¹H NMR (400 MHz, DMSO-d₆) δ ppm: 2.14-2.18 (m, 2H), 3.26-2.36 (m, 2H), 3.74 (t, J = 6.4 Hz, 2 H), 4.91 (d, J = 4.8 Hz, 2 H), 6.82 (d, J = 2.8 Hz, 1 H), 7.29 (t, J = 6.4 Hz, 2 H), 7.45-7.60 (m, 6 H), 7.78 (dt, J = 2.0 Hz, J = 7.6 Hz, 1 H), 7.91 (d, J = 2.0 Hz, 1 H), 8.38-8.39 (m, 1 H), 8.72 (d, J = 2.4 Hz, 1 H), 8.77 (t, J = 2.0 Hz, 1 H), 9.04 (d, J = 1.6 Hz, 1H), 9.92 (br s, 1 H). | 1.99 B-43 533.0 |
| 64 | 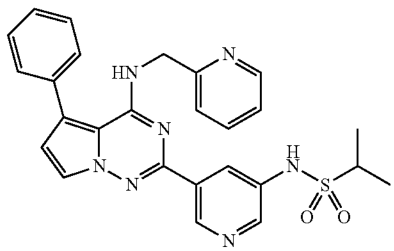 [SMILES: CC(C)S(=O)(=O)Nc1cncc(-c2nc(NCc3ccccn3)c3c(-c4ccccc4)ccn3n2)c1] | N-(5-(5-phenyl-4-(pyridin-2-ylmethylamino)pyrrolo[1,2-f][1,2,4]triazin-2-yl)pyridin-3-yl)propane-2-sulfonamide | ¹H NMR (400 MHz, DMSO-d₆) δ ppm: 1.20 (d, J = 6.8 Hz, 6 H), 4.91 (d, J = 4.8 Hz, 2 H), 6.81 (d, J = 2.8 Hz, 1 H), 7.29 (dd, J = 5.2 Hz, J = 8.0 Hz, 2 H), 7.45-7.60 (m, 7 H), 7.78 (dt, J = 2.0 Hz, J = 7.6 Hz, 1 H), 7.92 (d, J = 2.4 Hz, 1 H), 8.40 (dd, J = 4.0 Hz, J = 14.4 Hz, 2 H), 8.50 (s, 1 H), 9.06 (br s, 1 H), 10.15 (br s, 1 H). | 1.95 B-43 500.2 |
| 65 | 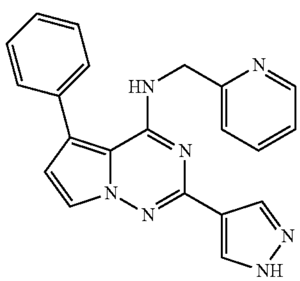 [SMILES: c1ccc(-c2ccn3nc(-c4cn[nH]c4)nc(NCc4ccccn4)c23)cc1] | 5-phenyl-2-(1H-pyrazol-4-yl)-N-(pyridin-2-ylmethyl)pyrrolo[1,2-f][1,2,4]triazin-4-amine | ¹H NMR (400 MHz, DMSO-d₆) δ ppm: 4.98 (m, 2 H), 6.81 (m, 1 H), 6.67 (t, J = 5.7 Hz, 1 H), 6.80 (d, J = 2.7- Hz, 1 H), 7.16 (m, 1 H), 7.28 (t, J = 1.2 Hz, 1 H), 7.42-7.59 (m, 7 H), 7.82 (m, 2 H), 8.32 (br s, 1 H). | 2.05 B-12 368.2 |
| 66 | 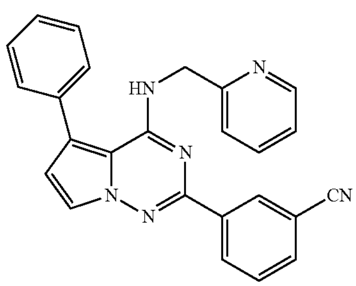 [SMILES: N#Cc1cccc(-c2nc(NCc3ccccn3)c3c(-c4ccccc4)ccn3n2)c1] | 3-(5-phenyl-4-(pyridin-2-ylmethylamino)pyrrolo[1,2-f][1,2,4]triazin-2-yl)benzonitrile | ¹H NMR (400 MHz, DMSO-d₆) δ ppm: 4.92 (d, J = 4.4 Hz, 2 H), 6.82 (d, J = 2.7 Hz, 1 H), 7.29 (t, J = 4.8 Hz, 1 H), 7.36 (t, J = 4.8 Hz, 1 H), 7.47-7.60 (m, 6 H), 7.70-7.78 (m, 2 H), 7.79 (d, J = 2.7 Hz, 1 H), 8.96 (dd, J = 2.0 Hz, J = 4.2 Hz, 1 H), 8.38 (m, 1 H), 8.56 (m, 2 H). | 2.30 B-12 403.2 |
| 67 | 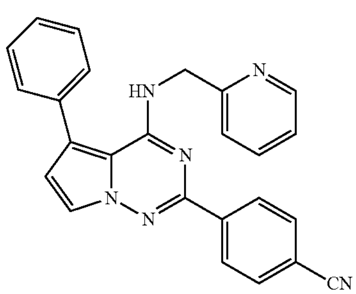 [SMILES: N#Cc1ccc(-c2nc(NCc3ccccn3)c3c(-c4ccccc4)ccn3n2)cc1] | 4-(5-phenyl-4-(pyridin-2-ylmethylamino)pyrrolo[1,2-f][1,2,4]triazin-2-yl)benzonitrile | ¹H NMR (400 MHz, DMSO-d₆) δ ppm: 4.92 (d, J = 4.4 Hz, 2 H), 6.84 (d, J = 2.8 Hz, 1 H), 7.36 (m, 1 H), 7.46 (t, J = 4.8 Hz, 1 H), 7.48-7.60 (m, 6 H), 7.77 (m, 1 H), 7.79 (d, J = 2.7 Hz, 1 H), 7.91-7.95 (m, 2 H), 8.38-8.45 (m, 3 H). | 2.30 B-12 403.2 |

TABLE 1-continued

| Ex. No. | Structure | Name | ¹H NMR | LC/MS Rt (min) Condition [M + 1] |
|---|---|---|---|---|
| 68 | 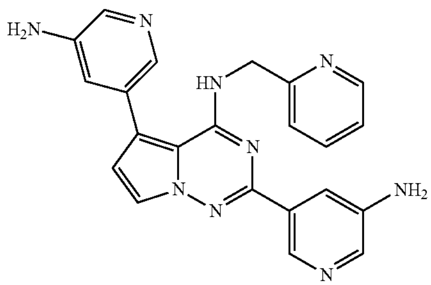 [SMILES: Nc1cncc(-c2nc(NCc3ccccn3)c3c(-c4cncc(N)c4)ccn3n2)c1] | 5,5'-(4-(pyridin-2-ylmethylamino)pyrrolo[1,2-f][1,2,4]triazine-2-,5-diyl)dipyridin-3-amine | ¹H NMR (400 MHz, DMSO-$d_6$) δ ppm: 4.90 (d, J = 4.4 Hz, 2 H), 5.46 (br s, 4 H), 6.76 (d, J = 2.8 Hz, 1 H), 7.06 (d, J = 2.0 Hz, 1 H), 7.36 (m, 1 H), 7.37 (t, J = 4.8 Hz, 1 H), 7.43-7.45 (m, 1 H), 7.72-7.80 (m, 2 H), 7.79 (d, J = 2.7 Hz, 1 H), 7.80-7.89 (m, 3 H), 8.43 (d, J = 2.8 Hz, 1 H) 8.53 (d, J = 2.2 Hz, 1 H). | 1.81 B-12 410.2 |
| 69 | 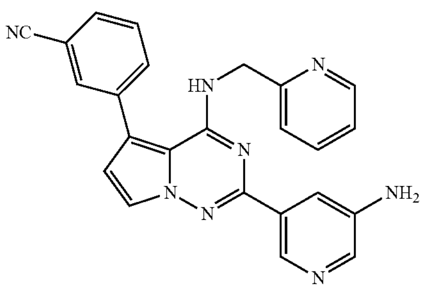 [SMILES: N#Cc1cccc(-c2ccn3nc(-c4cncc(N)c4)nc(NCc4ccccn4)c23)c1] | 3-(2-(5-aminopyridin-3-yl)-4-(pyridin-2-ylmethylamino)pyrrolo[1,2-f][1,2,4]triazin-5-yl)benzonitrile | ¹H NMR (400 MHz, DMSO-$d_6$) δ ppm: 4.91 (d, J = 4.0 Hz, 2 H), 5.46 (br s, 2 H), 6.88 (d, J = 2.7 Hz, 1 H), 7.28-7.38 (m, 2 H), 7.47 (t, J = 2.0 Hz, 1 H), 7.50-7.71 (m, 4 H), 7.73-7.79 (m, 2 H), 7.94 (d, J = 2.7 Hz, 1 H), 8.06 (br s, 1 H), 8.35 (d, J = 2.4 Hz, 1 H), −8.46 (d, J = 2.8 Hz, 1 H). | 2.01 B-12 419.2 |
| 70 | 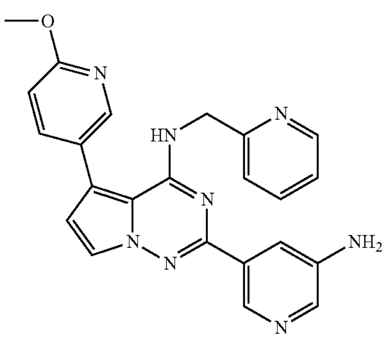 [SMILES: COc1ccc(-c2ccn3nc(-c4cncc(N)c4)nc(NCc4ccccn4)c23)cn1] | 2-(5-aminopyridin-3-yl)-5-(6-methoxypyridin-3-yl)-N-(pyridin-2-ylmethyl)pyrrolo[1,2-f][1,2,4]triazin-4-amine | ¹H NMR (400 MHz, DMSO-$d_6$) δ ppm: 3.94 (s, 3 H), 4.88 (d, J = 4.8 Hz, 2 H), 5.47 (br s, 2 H), 6.78 (d, J = 2.7 Hz, 1 H), 6.95 (t, J = 2.4 Hz, 1 H), 7.27-7.30 (m, 2 H), 7.43 (t, J = 2.8 Hz, 1 H), 7.71-7.86 (m, 5 H), 7.99 (d, J = 2.7 Hz, 1 H), 8.35 (d, J = 2.6 Hz, 1 H), 8.52 (s, 1 H). | 2.01 B-12 425.2 |
| 71 | 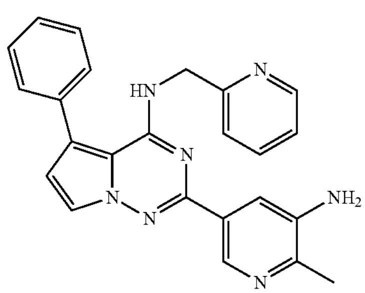 [SMILES: Cc1ncc(-c2nc(NCc3ccccn3)c3c(-c4ccccc4)ccn3n2)cc1N] | 2-(5-amino-6-methylpyridin-3-yl)-5-phenyl-N-(pyridin-2-ylmethyl)pyrrolo[1,2-f][1,2,4]triazin-4-amine | ¹H NMR (400 MHz, DMSO-$d_6$) δ ppm: 2.53 (s, 3 H), 4.91 (d, J = 4.4 Hz, 2 H), 5.19 (s, 2 H), 6.78 (d, J = 2.7 Hz, 1 H), 7.19 (t, J = 4.8 Hz, 1 H-), 7.28 (t, J = 5.6 Hz, 1 H), 7.44-7.57 (m, 6 H), 7.76-7.79 (m, 2 H), 7.80 (d, J = 2.7 Hz, 1 H), 8.32-8.38 (m, 1 H), 8.55 (s, 1 H). | 2.16 B-12 408.2 |
| 72 | 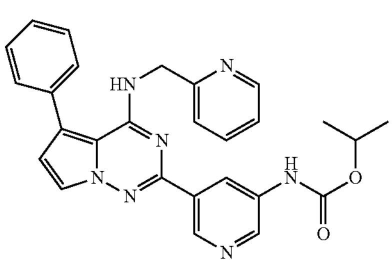 [SMILES: CC(C)OC(=O)Nc1cncc(-c2nc(NCc3ccccn3)c3c(-c4ccccc4)ccn3n2)c1] | isopropyl 5-(5-phenyl-4-(pyridin-2-ylmethylamino)pyrrolo[1,2-f][1,2,4]triazin-2-yl)pyridin-3-ylcarbamate | ¹H NMR (400 MHz, DMSO-$d_6$) δ ppm: 1.29 (d, J = 6.4 Hz, 6 H), 4.91-4.99 (m, 3 H), 6.81 (d, J = 2.8 Hz, 1 H), 7.29 (t, J = 6.4 Hz, 2 H), 7.45-7.60 (m, 6 H), 7.77 (dt, J = 2.0 Hz, J = 7.6 Hz, 1 H), 7.91 (d, J = 2.8 Hz, 1 H), 8.39-8.42 (m, 1 H), 8.72 (d, J = 2.4 Hz, 1 H), 8.76 (t, J = 2.0 Hz, 1 H), 9.04 (d, J = 1.6 Hz, 1 H), 9.92 (br s, 1 H). | 2.01 B-43 480.2 |

TABLE 1-continued

| Ex. No. | Structure | Name | ¹H NMR | LC/MS Rt (min) Condition [M + 1] |
|---|---|---|---|---|
| 73 | 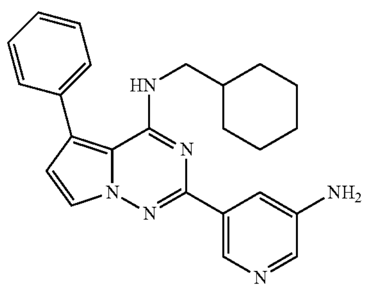 [SMILES: Nc1cncc(-c2nc(NCC3CCCCC3)c3c(-c4ccccc4)ccn3n2)c1] | 2-(5-aminopyridin-3-yl)-N-(cyclohexylmethyl)-5-phenylpyrrolo[1,2-f][1,2,4]triazin-4-amine | ¹H NMR (400 MHz, DMSO-d₆) δ ppm: 0.89-1.24 (m, 5 H), 1.51-1.68 (m, 6 H), 3.45 82 (t, J = 5.6 Hz, 2 H), 5.43 (br s, 2 H), 5.83 (t, J = 6.0 Hz, 1 H), 6.74 (d, J = 2.4 Hz, −1 H), 7.43-7.54 (m, 5 H), 7.74 (dd, J = 2.0 Hz, J = 2.8 Hz, 1 H), −7.80 (d, J = 2.4 Hz, 1 H), 8.01 (d, J = 2.8 Hz, 1 H), 8.59 (d, J = 2.0 Hz, 1 H). | 2.48 B-43 399.2 |
| 74 | 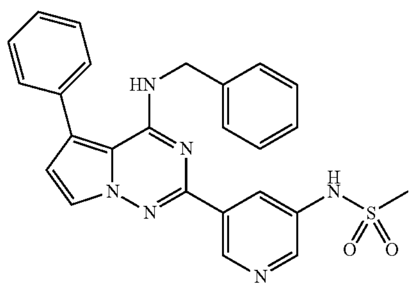 [SMILES: CS(=O)(=O)Nc1cncc(-c2nc(NCc3ccccc3)c3c(-c4ccccc4)ccn3n2)c1] | N-(5-(4-(benzylamino)-5-phenylpyrrolo[1,2-f][1,2,4]triazin-2-yl)pyridin-3-yl)methanesulfonamide | ¹H NMR (400 MHz, DMSO-d₆) δ ppm: −3.09 (s, 3 H), −4.82 (d, J = 6.0 Hz, 2 H), 6.65 (t, J = 5.6 Hz, 1 H), 6.80 (d, J = 2.8 Hz, 1 H), 7.23-7.54 (m, 11 H), 7.89 (d, J = 2.4 Hz, 1 H), 8.52 (d, J = 2.8 Hz, 1 H), 9.12 (d, J = 1.6 Hz, 1 H), 10.09 (br s, 1 H). | 2.36 B-43 471.2 |
| 75 | 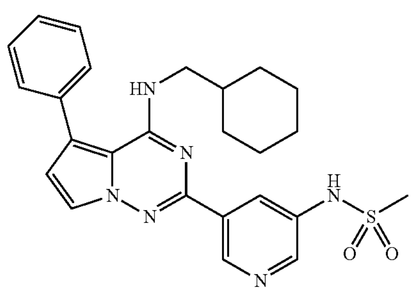 [SMILES: CS(=O)(=O)Nc1cncc(-c2nc(NCC3CCCCC3)c3c(-c4ccccc4)ccn3n2)c1] | N-(5-(4-(cyclohexylmethylamino)-5-phenylpyrrolo[1,2-f][1,2,4]triazin-2-yl)pyridin-3-yl)methanesulfonamide | ¹H NMR (400 MHz, DMSO-d₆) δ ppm: 0.91-1.25 (m, 6 H), 1.56-1.69 (m, 6 H), 3.10 (s, 3 H), 3.46 (t, J = 6.0 Hz, 1 H), 5.97 (t, J = 5.6 Hz, 1 H), 6.78 (d, J = 2.8 Hz, 1 H), 7.44-7.53 (m, 5 H), 7.86 (d, J = 2.8 Hz, 1 H), 8.46 (t, J = 2.4 Hz, 1 H), 8.53 (d, J = 2.8 Hz, 1 H), 9.14 (d, J = 1.6 Hz, 1 H), 10.11 (br s, 1 H). | 2.62 B-43 477.2 |
| 76 | 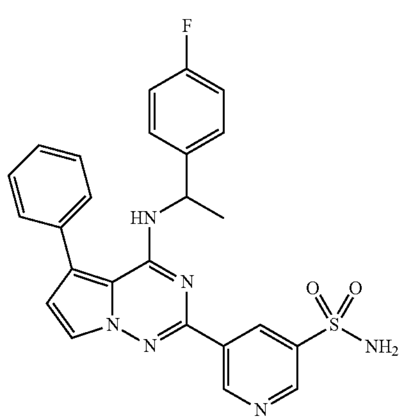 [SMILES: CC(Nc1nc(-c2cncc(S(N)(=O)=O)c2)nn2ccc(-c3ccccc3)c12)c1ccc(F)cc1] | 5-(4-(1-(4-fluorophenyl)ethylamino)-5-phenylpyrrolo[1,2-f][1,2,4]triazin-2-yl)pyridine-3-sulfonamide | ¹H NMR (400 MHz, DMSO-d₆) δ ppm: −1.46 (d, J = 6.8 Hz, 3 H), 5.49 (m, 1 H), 6.30 (d, J = 6.8 Hz, 1 H), 6.86 (t, J = 2.8 Hz, 1 H), 7.12-7.16 (m, 2 H), 7.42-7.60 (m, 7 H), 7.74 (s, 2 H), 7.95 (d, J = 2.8 Hz, 1 H), 8.89 (t, J = 2.0 Hz, 1 H), 9.05 (d, J = 2.4 Hz, 1 H), 9.45 (d, J = 2.0 Hz, 1 H). | 2.08 B-12 488.2 |

TABLE 1-continued

| Ex. No. | Structure | Name | $^1$H NMR | LC/MS Rt (min) Condition [M + 1] |
|---|---|---|---|---|
| 77 | 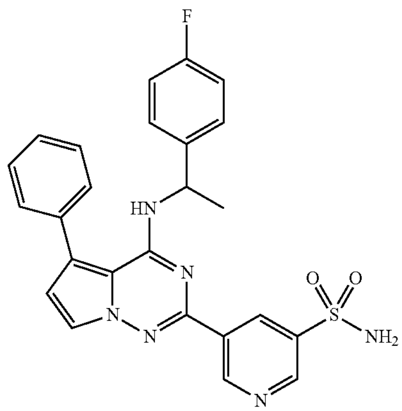 [SMILES: CC(Nc1nc(-c2cncc(S(N)(=O)=O)c2)nn2ccc(-c3ccccc3)c12)c1ccc(F)cc1] | 5-(4-(1-(4-fluorophenyl) ethylamino)-5-phenylpyrrolo[1,2-f][1,2,4]triazin-2-yl)pyridine-3-sulfonamide | $^1$H NMR (400 MHz, DMSO-d$_6$) δ ppm:1.46 (d, J = 6.8 Hz, 3 H), 5.49 (m, 1 H), 6.30 (d, J = 6.8 Hz, 1 H), 6.86 (t, J = 2.8 Hz, 1 H), 7.12-7.16 (m, 2 H), 7.42-7.60 (m, 7 H), 7.74 (s, 2 H), 7.95 (d, J = 2.8 Hz, 1 H), 8.89 (t, J = 2.0 Hz, 1 H), 9.05 (d, J = 2.4 Hz, 1 H), 9.45 (d, J = 2.0 Hz, 1 H). | 2.09 B-12 488.2 |
| 78 | 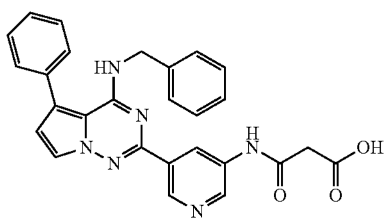 [SMILES: O=C(O)CC(=O)Nc1cncc(-c2nc(NCc3ccccc3)c3c(-c4ccccc4)ccn3n2)c1] | 3-(5-(4-(benzylamino)-5-phenylpyrrolo[1,2-f][1,2,4]triazin-2-yl)pyridin-3-ylamino)-3-oxopropanoic acid | $^1$H NMR (400 MHz, DMSO-d$_6$) δ ppm: 4.81 (d, J = 5.6 Hz, 2 H), 6.66 (t, J = 6.0 Hz, 1 H), 6.80 (d, J = 2.8 Hz, 1 H), 7.24-7.55 (m, 12- H), 7.92 (d, J = 2.8 Hz, 1 H), 8.82 (d, J = 2.4 Hz, 1 H), 8.85 (t, J = 2.0 Hz, 1 H), 9.07 (d, J = 2.0 Hz, 1 H). | 1.88 B-12 478.8 |
| 79 | 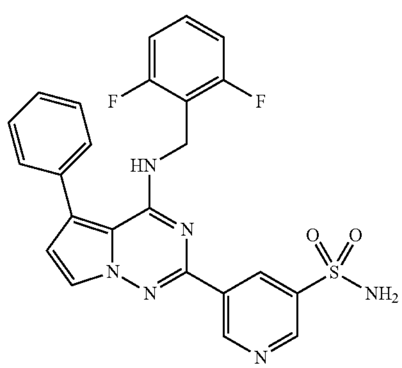 [SMILES: NS(=O)(=O)c1cncc(-c2nc(NCc3c(F)cccc3F)c3c(-c4ccccc4)ccn3n2)c1] | 5-(4-(2,6-difluorobenzylamino)-5-phenylpyrrolo[1,2-f][1,2,4]triazin-2-yl)pyridine-3-sulfonamide | $^1$H NMR (400 MHz, DMSO-d$_6$) δ ppm: 4.90 (d, J = 5.6 Hz, 2 H), 6.65 (t, J = 5.6 Hz, 1 H), 6.83 (d, J = 2.4 Hz, 1 H), 7.12 (t, J = 8.0 Hz, 2 H), 7.38-7.51 (m, 6 H), 7.70 (br s, 2 H), 7.95 (d, J = 2.8 Hz, 1 H), 8.94 (t, J = 2.0 Hz, 1 H), 9.08 (d, J = 2.0 Hz, 1 H), 9.06 (d, J = 2.0 Hz, 1 H). | 2.78 B-26 493.0 |
| 80 | 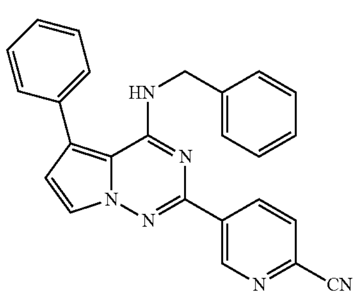 [SMILES: N#Cc1ccc(-c2nc(NCc3ccccc3)c3c(-c4ccccc4)ccn3n2)cn1] | 5-(4-(-benzylamino)-5-phenylpyrrolo[1,2-f][1,2,4]triazin-2-yl)picolinonitrile | $^1$H NMR (400 MHz, DMSO-d$_6$): 4.82 (d, J = 7.6 Hz, 2 H), 6.79 (t, J = 7.6 Hz, 1 H), 6.84 (d, J = 2.8 Hz, 1 H), 7.25-7.31 (m, 1 H), 7.36-7.41 (m, 5 H), 7.44-7.55 (m, 4H), 7.94 (d, J = 3.6 Hz, 1 H), 8.16 (dd, J = 10.8 Hz, J = 1.2 Hz, 1 H), 8.72 (dd, J = 10.8 Hz, J = 2.8 Hz, 1 H), 9.47 (dd, J = 2.8 Hz, J = 0.8 Hz, 1 H). | 2.50 B-12 402.6 |

TABLE 1-continued

| Ex. No. | Structure | Name | $^1$H NMR | LC/MS Rt (min) Condition [M + 1] |
|---|---|---|---|---|
| 81 | 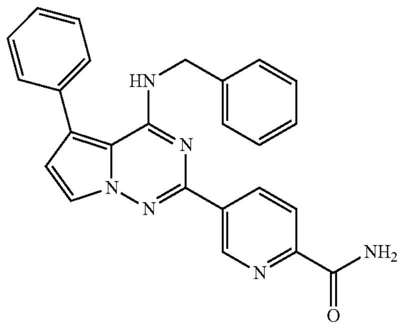 [SMILES: NC(=O)c1ccc(-c2nc(NCc3ccccc3)c3c(-c4ccccc4)ccn3n2)cn1] | 5-(4-(benzylamino)-5-phenylpyrrolo[1,2-f][1,2,4]triazin-2-yl)picolinamide | $^1$H NMR (400 MHz, DMSO-d$_6$): 4.83 (d, J = 5.6 Hz, 2 H), 6.72 (t, J = 5.6 Hz, 1 H), 6.82 (d, J = 2.8 Hz, 1 H), 7.23-7.27 (m, 1 H), 7.32-7.40 (m, 5 H), 7.45-7.49 (m, 2 H), 7.52-7.54 (m, 2 H), 7.70 (br s, 1 H), 7.92 (d, J = 2.4 Hz, 1 H), 8.14 (dd, J = 8.4 Hz, J = 0.8 Hz, 1 H), 8.17 (br s, 1 H), 8.69 (dd, J = 8.4 Hz, J = 2 Hz, 1 H), 9.37 (dd, J = 2.4 Hz, J = 0.8 Hz, 1 H). | 2.25 B-12 420.6 |
| 82 | 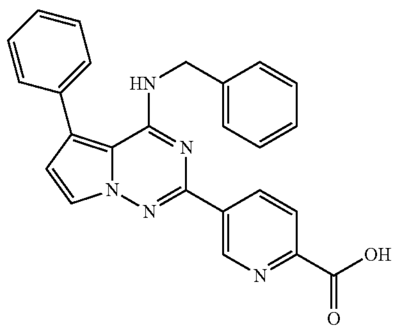 [SMILES: O=C(O)c1ccc(-c2nc(NCc3ccccc3)c3c(-c4ccccc4)ccn3n2)cn1] | 5-(4-(benzylamino)-5-phenylpyrrolo[1,2-f][1,2,4]triazin-2-yl)picolinic acid | $^1$H NMR (400 MHz, DMSO-d$_6$): 4.83 (d, J = 5.6 Hz, 2 H), 6.71 (t, J = 5.6 Hz, 1 H), 6.82 (d, J = 2.8 Hz, 1 H), 7.23-7.27 (m, 1 H), 7.33-7.41 (m, 6 H), 7.45-7.55 (m, 4 H), 7.93 (d, J = 2.8 Hz, 1 H), 8.12-8.14 (m, 1 H), 8.65 (dd, J = 8.4 Hz, J = 2.4 Hz, 1 H), 9.44 (s, 1 H). | 2.49 B-12 422.2 |
| 83 | 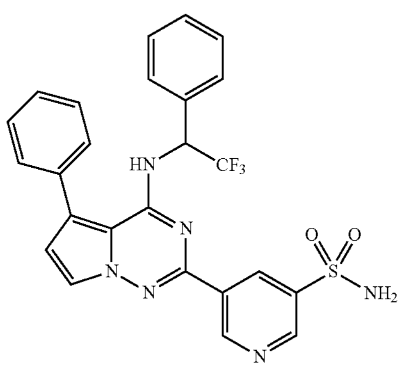 [SMILES: NS(=O)(=O)c1cncc(-c2nc(NC(c3ccccc3)C(F)(F)F)c3c(-c4ccccc4)ccn3n2)c1] | 5-(5-phenyl-4-(2,2,2-trifluoro-1-phenylethylamino)pyrrolo[1,2-f][1,2,4]triazin-2-yl)pyridine-3-sulfonamide | $^1$H NMR (400 MHz, DMSO-d$_6$) δ ppm: 6.59-6.60 (m, 2H), 6.96 (d, J = 2.8 Hz, 1 H), 7.42 (s, 5 H), 7.56-7.62 (m, 6 H), 7.76 (br s, 1 H), 8.08 (d, J = 2.8 Hz, 1 H), 8.94 (t, J = 2.0 Hz, 1 H), 9.09 (d, J = 2.0 Hz, 1 H), –9.68 (d, J = 1.6 Hz, 1 H). | 2.16 B-12 525.2 |
| 84 | 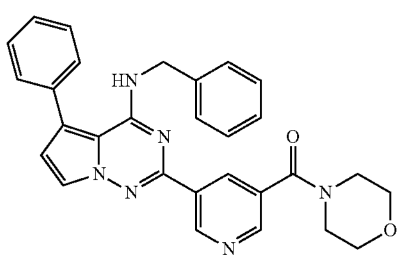 [SMILES: O=C(c1cncc(-c2nc(NCc3ccccc3)c3c(-c4ccccc4)ccn3n2)c1)N1CCOCC1] | (5-(4-(benzylamino)-5-phenylpyrrolo[1,2-f][1,2,4]triazin-2-yl)pyridin-3-yl)(morpholino)methanone | $^1$H NMR (400 MHz, DMSO-d$_6$) δ ppm: –3.27-3.67 (m, 8 H), 4.81 (d, J = 5.6 Hz, 1 H), 6.71 (t, J = 6.0 Hz, 1 H), 6.81 (d, J = 2.8 Hz, 1 H), 7.23-7.54 (m, 11 H), 7.90 (d, J = 2.8 Hz, 1 H), 8.48 (t, J = 2.0 Hz, 1 H), 8.70 (d, J = 2.0 Hz, 1 H), 9.40 (d, J = 2.0 Hz, 1 H). | 1.88 B-44 490.6 |
| 85 | 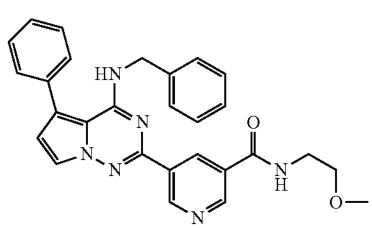 [SMILES: COCCNC(=O)c1cncc(-c2nc(NCc3ccccc3)c3c(-c4ccccc4)ccn3n2)c1] | 5-(4-(benzylamino)-5-phenylpyrrolo[1,2-f][1,2,4]triazin-2-yl)-N-(2-methoxyethyl)nicotinamide | $^1$H NMR (400 MHz, DMSO-d$_6$) δ ppm: 3.30 (s, 3 H), 3.49-3.52 (m, 4 H), 4.85 (d, J = 5.6 Hz, 2 H), 6.72 (t, J = 5.6 Hz, 1 H), 6.83 (d, J = 2.8 Hz, 1 H), 7.26-7.56 (m, 10 H), 7.93 (d, J = 2.4 Hz, 1 H), 8.93 (t, J = 2.0 Hz, 2 H), 9.08 (d, J = 2.4 Hz, 1 H), 9.46 (d, J = 2.0 Hz, 1 H). | 1.89 B-44 478.6 |

TABLE 1-continued

| Ex. No. | Structure | Name | ¹H NMR | LC/MS Rt (min) Condition [M + 1] |
|---|---|---|---|---|
| 86 | 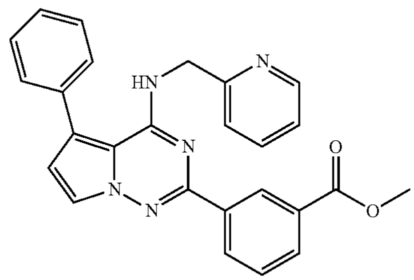 [SMILES: COC(=O)c1cccc(-c2nc(NCc3ccccn3)c3c(-c4ccccc4)ccn3n2)c1] | methyl 3-(5-phenyl-4-(pyridin-2-ylmethylamino)pyrrolo[1,2-f][1,2,4]triazin-2-yl)benzoate | ¹H NMR (400 MHz, DMSO-d₆) δ ppm: 3.92 (s, 3 H), −4.92 (d, J = 4.8 Hz, 1 H), 6.82 (d, J = 2.8 Hz, 1 H), 7.28-7.79 (m, 8 H), 7.81-7.95 (m, 3 H), 8.06 (m, 2 H), 8.53-8.55 (m, 1 H), 8.84 (t, J = 1.6 Hz, 1 H), 8.85 (br s, 1 H). | 2.20 B-44 435.4 |
| 87 | 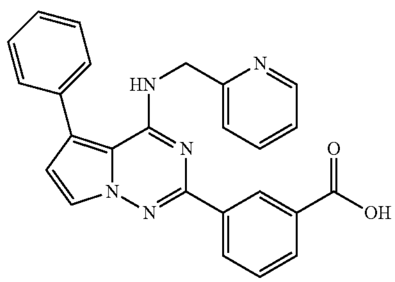 [SMILES: O=C(O)c1cccc(-c2nc(NCc3ccccn3)c3c(-c4ccccc4)ccn3n2)c1] | 3-(5-phenyl-4-(pyridin-2-ylmethylamino)pyrrolo[1,2-f][1,2,4]triazin-2-yl)benzoic acid | ¹H NMR (400 MHz, DMSO-d₆) δ ppm: 4.92 (d, J = 4.4 Hz, 2 H), 6.81 (d, J = 2.8 Hz, 1 H), 7.27 (dd, J = 0.8 Hz, J = 6.0 Hz, 2 H), 7.29-7.62 (m, 8 H), 7.64 (br s, 1 H), 8.37 (m, 1 H), 8.38 (dd, J = 0.8 Hz, J = 1.2 Hz, 1 H), 8.51 (m, 1 H), 8.84 (t, J = 1.6 Hz, 1 H), 13.1-13.2 (br s, 1 H). | 1.81 B-29 421.1 |
| 88 | 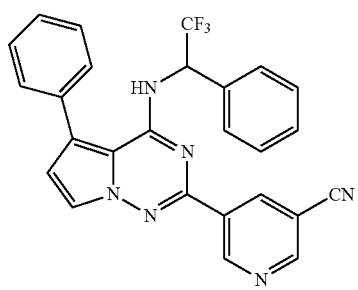 [SMILES: N#Cc1cncc(-c2nc(NC(c3ccccc3)C(F)(F)F)c3c(-c4ccccc4)ccn3n2)c1] | 5-(5-phenyl-4-(-2-,2,2-trifluoro-1-phenylethylamino)pyrrolo[1,2-f][1,2,4]triazin-2-yl)nicotinonitrile | ¹H NMR (400 MHz, DMSO-d₆) δ ppm: 6.52 (d, J = 8.1 Hz, 1H), 6.72 (m, 1 H), 6.94 (d, J = 2.8 Hz, 1 H), 7.40-7.41 (m, 5 H), 7.54-7.63 (m, 5 H), 8.02 (d, J = 2.8 Hz, 1 H), 9.05 (t, J = 2.0 Hz, 1 H), −9.14 (d, J = 2.0 Hz, 1 H), 9.67 (d, J = 2.0 Hz, 1 H). | 2.44 B-45 470.9 |
| 89 | 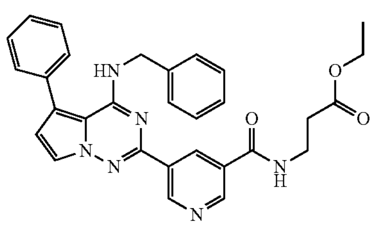 [SMILES: CCOC(=O)CCNC(=O)c1cncc(-c2nc(NCc3ccccc3)c3c(-c4ccccc4)ccn3n2)c1] | ethyl 3-(5-(4-(benzylamino)-5-phenylpyrrolo[1,2-f][1,2,4]triazin-2-yl)nicotinamido)propanoate | ¹H NMR (400 MHz, DMSO-d₆) δ ppm: 1.18 (t, J = 7.2 Hz, 3 H), 2.63 (t, J = 7.2 Hz, 2 H), 3.56 (dd, J = 6.8 Hz, J = 6.8 Hz, 2H), 4.09 (q, J = 7.2 Hz, 2 H), 4.83 (d, J = 5.6 Hz, 2 H) 6.72 (t, J = 5.6 Hz, 1 H), 6.82 (d, J = 2.8 Hz, 1 H), 7.21-7.55 (m, 10 H), 7.92 (d, J = 2.8 Hz, 1 H), 8.90 (t, J = 2.8 Hz, 1 H), 8.95 (t, J = 5.6 Hz, 1 H), 9.05 (d, J = 2.0 Hz, 1 H), 9.46 (d, J = 2.0 Hz, 1 H). | 2.20 B-45 518.9 |
| 90 | 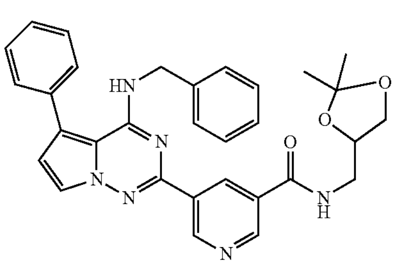 [SMILES: CC1(C)OCC(CNC(=O)c2cncc(-c3nc(NCc4ccccc4)c4c(-c5ccccc5)ccn4n3)c2)O1] | 5-(4-(benzylamino)-5-phenylpyrrolo[1,2-f][1,2,4]triazin-2-yl)-N-((2,2-dimethyl-1,3-dioxolan-4-yl)methyl)nicotinamide | ¹H NMR (400 MHz, DMSO-d₆) δ ppm: 1.26 (s, 3 H), 1.35 (s, 3 H), 3.39-3.45 (m, 2 H), 3.72 (dd, J = 5.6 Hz, J = 8.4 Hz, 1 H), 4.01 (dd, J = 6.4 Hz, J = 8.4 Hz, 1 H), 4.24 (m, 1 H), 4.82 (d, J = 5.6 Hz, 2 H) 6.68 (t, J = 5.6 Hz, 1 H), 6.80 (d, J = 2.8 Hz, 1 H), 7.21-7.53 (m, 10 H), 7.91 (d, J = 2.8 Hz, 1 H), 8.91 (t, J = 2.8 Hz, 1 H), 8.96 (t, J = 5.6 Hz, 1 H), 9.05 (d, J = 2.0 Hz, 1 H), 9.44 (d, J = 2.0 Hz, 1H). | 2.21 B-45 533.0 |

TABLE 1-continued

| Ex. No. | Structure | Name | $^1$H NMR | LC/MS Rt (min) Condition [M + 1] |
|---|---|---|---|---|
| 91 | 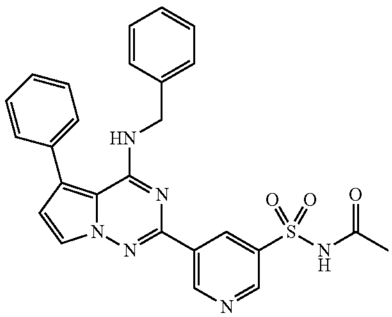 [SMILES: CC(=O)NS(=O)(=O)c1cncc(-c2nc(NCc3ccccc3)c3c(-c4ccccc4)ccn3n2)c1] | N-(5-(4-(benzylamino)-5-phenylpyrrolo[1,2-f][1,2,4]triazin-2-yl)pyridin-3-ylsulfonyl)acetamide | $^1$H NMR (400 MHz, MeOH-d$_4$) δ ppm: 1.89 (s, 3 H), −4.80 (d, J = 5.6 Hz, 2 H), 6.78 (t, J = 5.6 Hz, 1 H), 6.81 (d, J = 2.8 Hz, 1 H), 7.23-7.54 (m, 9 H), 7.97 (d, J = 2.8 Hz, 1 H), 8.96 (t, J = 2.0 Hz, 1 H), 9.06 (d, J = 2.4 Hz, 1 H), 9.53 (d, J = 2.0 Hz, 1 H). | 2.47 B-45 499.2 |
| 92 | 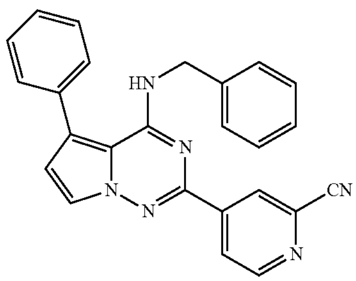 [SMILES: N#Cc1cc(-c2nc(NCc3ccccc3)c3c(-c4ccccc4)ccn3n2)ccn1] | 4-(4-(benzylamino)-5-phenylpyrrolo[1,2-f][1,2,4]triazin-2-yl)picolinonitrile | $^1$H NMR (400 MHz, DMSO-d$_6$) δ ppm: 4.80 (d, J = 5.6 Hz, 2 H), 6.78 (t, J = 5.6 Hz, 1 H), 6.80 (d, J = 2.8 Hz, 1 H), 7.24-7.54 (m, 10 H), 7.94 (d, J = 2.8 Hz, 1 H), 8.40 (dd, J = 1.6 Hz, J = 4.8 Hz, 1 H), 8.59 (dd, J = 0.8 Hz, J = 1.6 Hz, 1 H), 8.87 (dd, J = 0.8 Hz, J = 5.2 Hz, 1 H). | 3.17 B-45 401.4 |
| 93 | 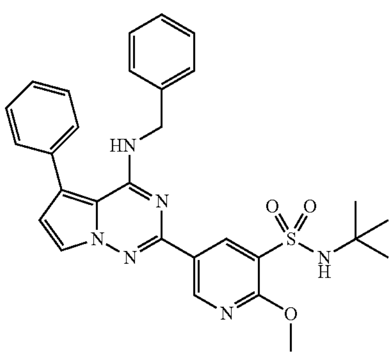 [SMILES: COc1ncc(-c2nc(NCc3ccccc3)c3c(-c4ccccc4)ccn3n2)cc1S(=O)(=O)NC(C)(C)C] | 5-(4-(benzylamino)-5-phenylpyrrolo[1,2-f][1,2,4]triazin-2-yl)-N-tert-butyl-2-methoxypyridine-3-sulfonamide | $^1$H NMR (400 MHz, CD$_3$OD-d$_4$): 1.28 (s, 9 H), 3.75 (s, 3 H), 4.79 (d, J = 5.6 Hz, 2 H), 6.70 (d, J = 2.8 Hz, 1 H), 7.27-7.28 (m, 1 H), 7.35-7.39 (m, 4 H), 7.43-7.46 (m, 2 H), 7.49-7.52 (m, 3 H), 7.70 (d, J = 2.8 Hz, 1 H), 8.80 (d, J = 2.8 Hz, 1 H), 9.01 (d, J = 2.8 Hz, 1 H). | 1.33 B-27 543.2 |
| 94 | 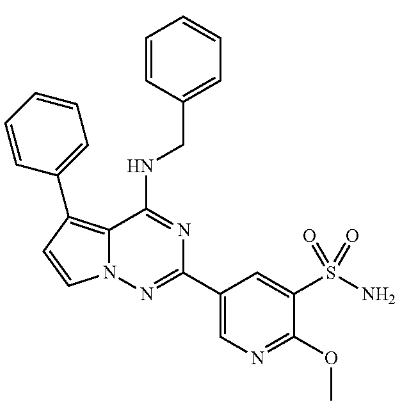 [SMILES: COc1ncc(-c2nc(NCc3ccccc3)c3c(-c4ccccc4)ccn3n2)cc1S(N)(=O)=O] | 5-(4-(benzylamino)-5-phenylpyrrolo[1,2-f][1,2,4]triazin-2-yl)-2-methoxypyridine-3-sulfonamide | $^1$H NMR (300 MHz, -DMSO-d$_6$) δ 3.67 (s, 3H), 4.80 (d, J = 5.7 Hz, 2H), 6.60 (t, J = 5.7 Hz, 1H), 6.74 (d, J = 2.7 Hz, −1H), 7.05 (br s, 2H), 7.23-7.25 (m, 1 H), 7.26-7.53 (m, 9 H), 7.86 (d, J = 2.7 Hz, 1H), 8.72 (d, J = 2.8 Hz, 1 H), 8.83 (d, J = 2.8 Hz, 1 H). | 2.15 B-21 487.2 |

TABLE 1-continued

| Ex. No. | Structure | Name | ¹H NMR | LC/MS Rt (min) Condition [M + 1] |
|---|---|---|---|---|
| 95 | 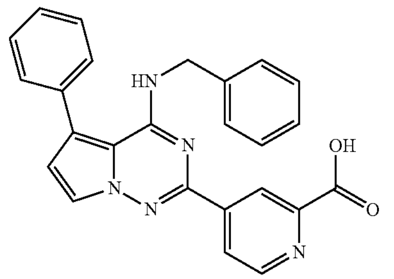 [SMILES: O=C(O)c1cc(-c2nc(NCc3ccccc3)c3c(-c4ccccc4)ccn3n2)ccn1] | 4-(4-(benzylamino)-5-phenylpyrrolo[1,2-f][1,2,4]triazin-2-yl)picolinic acid | ¹H NMR (400 MHz, DMSO-d$_6$) δ ppm: 4.82 (d, J = 6.0 Hz, 2 H), 6.72 (t, J = 6.0 Hz, 1 H), 6.84 (d, J = 2.8 Hz, −1 H), 7.25-7.71 (m, 9H), 7.71 (d, J = 2.0 Hz, 1 H), 7.98 (d, J = 2.8 Hz, 1 H), 8.17 (d, J = 2.0 Hz, 1 H), 8.30 (dd, J = 1.6 Hz, J = 5.2 Hz, 1 H), 8.75 (dd, J = 0.8 Hz, J = 5.2 Hz, 1 H), 8.44 (t, J = 0.8 Hz, 1 H). | 2.34 B-12 421.2 |
| 96 | 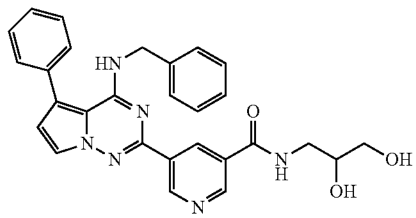 [SMILES: O=C(NCC(O)CO)c1cncc(-c2nc(NCc3ccccc3)c3c(-c4ccccc4)ccn3n2)c1] | 5-(4-(benzylamino)-5-phenylpyrrolo[1,2-f][1,2,4]triazin-2-yl)-N-(2,3-dihydroxypropyl)nicotinamide | ¹H NMR (400 MHz, DMSO-d$_6$) δ ppm: 3.22-3.28 (m, 1 H), 3.39 (t, J = 5.2 Hz, 1 H), 3.43-3.49 (m, 1 H), 3.70 (m, 1 H), 4.59 (t, J = 5.6 Hz, 1 H), 4.83 (m, 2 H), 4.84 (d, J = 5.6 Hz, 2 H), 6.77 (t, J = 5.6 Hz, 1 H), 6.86 (d, J = 2.8 Hz, 1 H), 7.24-7.54 (m, 11 H), 7.94 (d, J = 2.8 Hz, 1 H), 8.41 (dd, J = 1.6, J = 4.8 Hz, 1 H), 8.59 (q, J = 0.8 Hz, 1 H), 8.88 (dd, J = 0.8, J = 5.2 Hz, 1 H). | 1.98 B-12 495.2 |
| 97 | 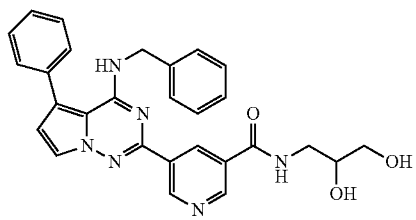 [SMILES: O=C(NCC(O)CO)c1cncc(-c2nc(NCc3ccccc3)c3c(-c4ccccc4)ccn3n2)c1] | 5-(4-(benzylamino)-5-phenylpyrrolo[1,2-f][1,2,4]triazin-2-yl)-N-(2,3-dihydroxypropyl)nicotinamide | ¹H NMR (400 MHz, DMSO-d$_6$) δ ppm: 3.22-3.28 (m, 1 H), 3.39 (t, J = 5.2 Hz, 1 H), 3.43-3.49 (m, 1 H), 3.70 (m, 1 H), 4.59 (t, J = 5.6 Hz, 1 H), 4.83 (m, 2 H), 4.84 (d, J = 5.6 Hz, 2 H), 6.77 (t, J = 5.6 Hz, 1 H), 6.86 (d, J = 2.8 Hz, 1 H), 7.24-7.54 (m, 11 H), 7.94 (d, J = 2.8 Hz, 1 H), 8.41 (dd, J = 1.6, J = 4.8 Hz, 1 H), 8.59 (q, J = 0.8 Hz, 1 H), 8.88 (dd, J = 0.8, J = 5.2 Hz, 1 H). | 1.98 B-12 495.2 |
| 98 | 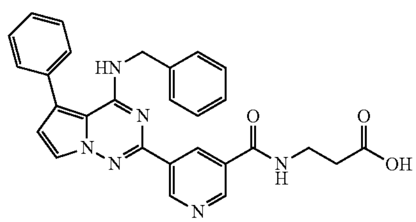 [SMILES: O=C(O)CCNC(=O)c1cncc(-c2nc(NCc3ccccc3)c3c(-c4ccccc4)ccn3n2)c1] | 3-(5-(4-(benzylamino)-5-phenylpyrrolo[1,2-f][1,2,4]triazin-2-yl)nicotinamido)propanoic acid | ¹H NMR (400 MHz, DMSO-d$_6$) δ ppm: −2.56 (t, J = 7.2 Hz, 2 H), 3.51 (q, J = 7.2 Hz, 2 H), 4.82 (d, J = 5.6 Hz, 2 H), 6.70 (t, J = 5.6 Hz, 1 H), 6.81 (d, J = 2.8 Hz, 1 H), 7.23-7.55 (m, 10 H), 7.93 (d, J = 2.8 Hz, 1 H), 8.90-8.95 (m, 3 H), 9.05 (d, J = 2.0 Hz, 1 H), 9.57 (d, J = 2.0 Hz, 1 H). | 1.85 B-45 493.2 |
| 99 | 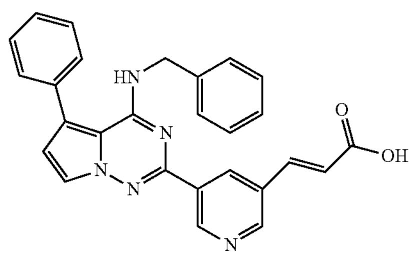 [SMILES: O=C(O)/C=C/c1cncc(-c2nc(NCc3ccccc3)c3c(-c4ccccc4)ccn3n2)c1] | (E)-3-(5-(4-(benzylamino)-5-phenylpyrrolo[1,2-f][1,2,4]triazin-2-yl)pyridin-3-yl)acrylic acid | ¹H NMR (400 MHz, DMSO-d$_6$) δ ppm: 4.84 (d, J = 4.0 Hz, 2 H), 6.71-6.75 (m, 2 H), 6.82 (d, J = 2.8 Hz, 1 H), 7.24- (m, 1 H), 7.25-7.53 (m, 8 H), 7.71-7.75 (m, 1 H), 7.92 (d, J = 2.8 Hz, 1 H), 8.65 (t, J = 2.8 Hz, 1 H), 8.91 (s, 1 H), 8.95 (d, J = 2.6 Hz, 1 H), 9.32 (d, J = 2.0 Hz, 1 H), 10.12 (br s, 1 H). | 1.98 B-45 448.2 |
| 100 | 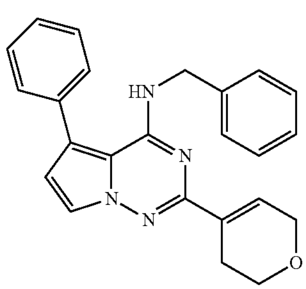 [SMILES: C1=C(c2nc(NCc3ccccc3)c3c(-c4ccccc4)ccn3n2)CCOC1] | N-benzyl-2-(3,6-dihydro-2H-pyran-4-yl)-5-phenylpyrrolo[1,2-f][1,2,4]triazin-4-amine | ¹H NMR (400 MHz, DMSO-d$_6$) δ ppm: 3.78 (t, J = 7.2 Hz, 2 H), 4.26 (m, 4 H), 4.72 (d, J = 5.7 Hz, 2 H), 6.34 (t, J = 5.4 Hz, 1 H), 6.71 (d, J = 2.7 Hz, 1 H), 7.03 (m, 1 H), 7.25-7.22-7.43 (m, 10 H), 7.88 (d, J = 2.7 Hz, −1 H). | 2.44 B-45 483.2 |

TABLE 1-continued

| Ex. No. | Structure | Name | ¹H NMR | LC/MS Rt (min) Condition [M + 1] |
|---|---|---|---|---|
| 101 | 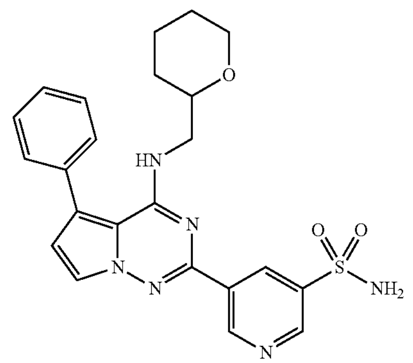 [SMILES: NS(=O)(=O)c1cncc(-c2nc(NCC3CCCCO3)c3c(-c4ccccc4)ccn3n2)c1] | 5-(5-phenyl-4-((tetrahydro-2H-pyran-2-yl)methylamino)pyrrolo[1,2-f][1,2,4]triazin-2-yl)pyridine-3-sulfonamide | ¹H NMR (400 MHz, DMSO-d₆) δ ppm: 1.22-1.78 (m, 5 H), 3.17-3.49 (m, 4 H), 3.76-3.87 (m, 2 H), 6.26 (br s, 1 H), 6.81 (d, J = 2.4 Hz, 1 H), 7.43 (q, J = 4.4 Hz, 1 H), 7.50-7.58 (m, 6 H), 7.73 (d, J = 2.8 Hz, 1 H), 8.92 (t, J = 2.0 Hz, 1 H), 9.05 (d, J = 2.4 Hz, 1 H), 9.57 (d, J = 2.0 Hz, 1 H). | 2.23 B-12 465.2 |
| 102 | 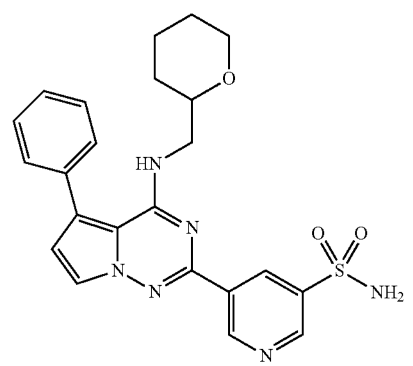 [SMILES: NS(=O)(=O)c1cncc(-c2nc(NCC3CCCCO3)c3c(-c4ccccc4)ccn3n2)c1] | 5-(5-phenyl-4-((tetrahydro-2H-pyran-2-yl)methylamino)pyrrolo[1,2-f][1,2,4]triazin-2-yl)pyridine-3-sulfonamide | ¹H NMR (400 MHz, DMSO-d₆) δ ppm: 1.22-1.78 (m, 5 H), 3.17-3.49 (m, 4 H), 3.76-3.87 (m, 2 H), 6.26 (br s, 1 H), 6.81 (d, J = 2.4 Hz, 1 H), 7.43 (q, J = 4.4 Hz, 1 H), 7.50-7.58 (m, 6 H), 7.73 (d, J = 2.8 Hz, 1 H), 8.92 (t, J = 2.0 Hz, 1 H), 9.05 (d, J = 2.4 Hz, 1 H), 9.57 (d, J = 2.0 Hz, 1 H). | 2.23 B-12 465.2 |
| 103 | 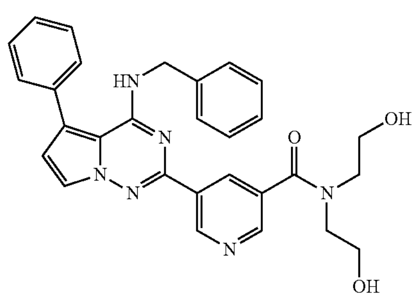 [SMILES: O=C(c1cncc(-c2nc(NCc3ccccc3)c3c(-c4ccccc4)ccn3n2)c1)N(CCO)CCO] | 5-(4-(benzylamino)-5-phenylpyrrolo[1,2-f][1,2,4]triazin-2-yl)-N,N-bis(2-hydroxyethyl)nicotinamide | ¹H NMR (400 MHz, DMSO-d₆) δ ppm: 3.36-3.38 (m, 8 H), 4.82 (d, J = 5.6 Hz, 2 H), 4.86 (t, J = 4.8 Hz, 2 H) 6.70 (t, J = 5.6 Hz, 1 H), 6.81 (d, J = 2.8 Hz, 1 H), 7.32-7.55 (m, 10 H), 7.91 (d, J = 2.8 Hz, 1 H), 8.50 (t, J = 2.0 Hz, 1 H), 8.69 (d, J = 2.0 Hz, 1 H), 9.37 (d, J = 2.0 Hz, 1 H). | 1.94 B-12 509.2 |
| 104 | 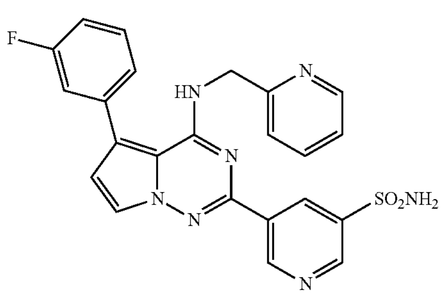 [SMILES: NS(=O)(=O)c1cncc(-c2nc(NCc3ccccn3)c3c(-c4cccc(F)c4)ccn3n2)c1] | 5-(5-(3-fluorophenyl)-4-(pyridin-2-ylmethylamino)pyrrolo[1,2-f][1,2,4]triazin-2-yl)pyridine-3-sulfonamide | ¹H NMR (400 MHz, DMSO-d₆) δ ppm: 4.96 (d, J = 4.4 Hz, 2 H), 6.91 (d, J = 2.8 Hz, 1 H), 7.29-7.58 (m, 7 H), 7.75 (s, 1 H), 7.78-7.82 (m, 2 H), 7.97 (d, J = 4.0 Hz, 1 H), 8.34 (t, J = 2.0 Hz, 1 H), 9.07 (d, J = 2.0 Hz, 1 H), 9.58 (d, J = 2.0 Hz, 1 H), 9.60 (d, J = 2.0 Hz, 1 H). | 1.93 B-22 474.0 |

TABLE 1-continued

| Ex. No. | Structure | Name | ¹H NMR | LC/MS Rt (min) Condition [M + 1] |
|---|---|---|---|---|
| 105 | 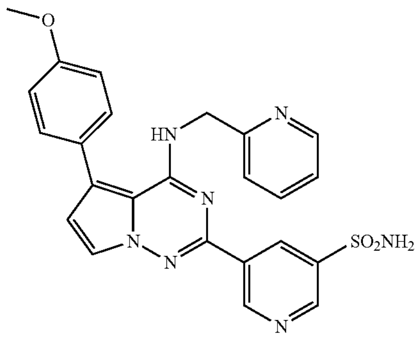 [SMILES: COc1ccc(-c2ccn3nc(-c4cncc(S(N)(=O)=O)c4)nc(NCc4ccccn4)c23)cc1] | 5-(5-(4-methoxyphenyl)-4-(pyridin-2-ylmethylamino)pyrrolo[1,2-f][1,2,4]triazin-2-yl)pyridine-3-sulfonamide | ¹H NMR (400 MHz, DMSO-$d_6$) δ ppm: −4.09 (s, 3 H), 4.94 (d, J = 4.4 Hz, 2 H), 6.78 (d, J = 2.8 Hz, 1 H), 7.10 (d, J = 8.8 Hz, 2 H), 7.28-7.37 (m, 4 H), 7.77-7.81 (m, 2 H), 8.38 (d, J = 4.4 Hz, 1 H), 8.92 (t, J = 2.0 Hz, 1 H), 9.05 (d, J = 2.0 Hz, 1 H), 9.55 (d, J = 2.0 Hz, 1 H). | 2.14 B-17 486.0 |
| 106 | 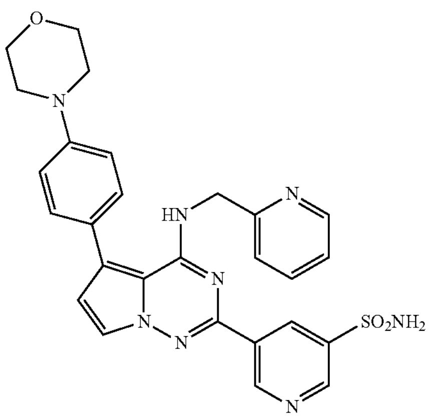 [SMILES: NS(=O)(=O)c1cncc(-c2nc(NCc3ccccn3)c3c(-c4ccc(N5CCOCC5)cc4)ccn3n2)c1] | 5-(5-(4-morpholinophenyl)-4-(pyridin-2-ylmethylamino)pyrrolo[1,2-f][1,2,4]triazin-2-yl)pyridine-3-sulfonamide | ¹H NMR (400 MHz, DMSO-$d_6$) δ ppm: 3.21 (t, J = 4.8 Hz, 4 H), 3.80 (t, J = 5.2 Hz, 4 H), 4.95 (d, J = 4.8 Hz, 2 H), 6.77 (d, J = 2.4 Hz, 1 H), 7.10 (d, J = 8.4 Hz, 2 H), 7.29-7.49 (m, 5 H), 7.77 (m, 3 H), 7.91 (d, J = 2.4 Hz, 1 H), 8.41 (d, J = 4.0 Hz, 1 H), 8.92 (t, J = 2.0 Hz, 1 H), 9.05 (d, J = 2.0 Hz, 1 H), 9.55 (d, J = 2.0 Hz, 1 H). | 0.70 B-47 543.0 |
| 107 | 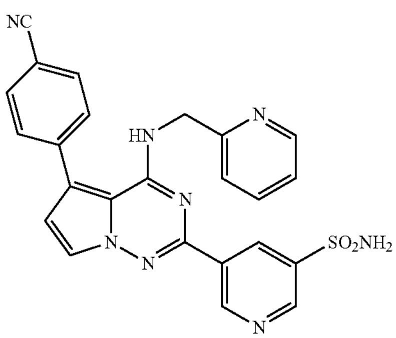 [SMILES: N#Cc1ccc(-c2ccn3nc(-c4cncc(S(N)(=O)=O)c4)nc(NCc4ccccn4)c23)cc1] | 5-(5-(-4-cyanophenyl)-4-(pyridin-2-ylmethylamino)pyrrolo[1,2-f][1,2,4]triazin-2-yl)pyridine-3-sulfonamide | ¹H NMR (400 MHz, DMSO-$d_6$) δ ppm: 4.94 (d, J = 4.8 Hz, 2 H), 6.96 (d, J = 2.4 Hz, 1 H), 7.31 (dd, J = 6.0 Hz, J = 7.6, 1 H), 7.50 (m, 2 H), 7.74 (m, 8 H), 8.41 (t, J = 4.4 Hz, 1 H), 8.91 (t, J = 2.0 Hz, 1 H), 9.06 (d, J = 2.0 Hz, 1 H), 9.50 (d, J = 2.0 Hz, 1 H). | 1.97 B-17 483.0 |
| 108 | 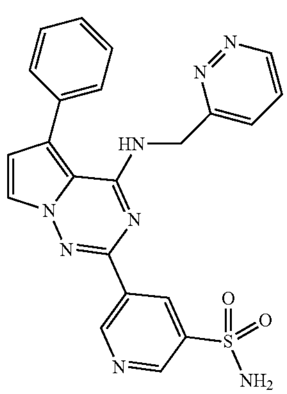 [SMILES: NS(=O)(=O)c1cncc(-c2nc(NCc3cccnn3)c3c(-c4ccccc4)ccn3n2)c1] | 5-(5-phenyl-4-(pyridazin-3-ylmethylamino)pyrrolo[1,2-f][1,2,4]triazin-2-yl)pyridine-3-sulfonamide | ¹H NMR (400 MHz, DMSO-$d_6$) δ ppm: 5.14 (d, J = 4.8 Hz, 2 H), 6.88 (d, J = 2.8 Hz, 1 H), 7.35 (t, J = 5.6 Hz, 1 H), 7.41-7.78 (m, 9 H), 7.98 (d, J = 2.8 Hz, 1 H), 8.87 (dd, J = 2.4 Hz, J = 2.0 Hz, 1 H), 9.04 (d, J = 2.0 Hz, 1 H), 9.13 (dd, J = 2.0 Hz, J = 1.6 Hz, 1 H), 9.44 (d, J = 1.6 Hz, 1 H). | 1.59 B-23 457.2 |

TABLE 1-continued

| Ex. No. | Structure | Name | ¹H NMR | LC/MS Rt (min) Condition [M + 1] |
|---|---|---|---|---|
| 109 | 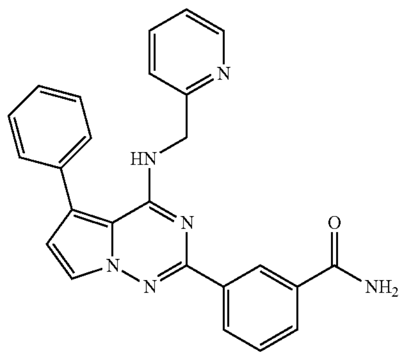 [SMILES: NC(=O)c1cccc(-c2nc(NCc3ccccn3)c3c(-c4ccccc4)ccn3n2)c1] | 3-(5-phenyl-4-(pyridin-2-ylmethylamino)pyrrolo[1,2-f][1,2,4]triazin-2-yl)benzamide | ¹H NMR (400 MHz, DMSO-$d_6$) δ ppm: 4.95 (d, J = 4.4 Hz, 2 H), 6.81 (d, J = 2.8 Hz, 1 H), 7.21-7.52 (m, 10 H), 7.89 (t, J = 1.7 Hz, 1 H), 7.91 (d, J = 2.8 Hz, 1 H) 7.95 (m, 1 H), 8.12 (s, 1 H) 8.42 (m, 2 H), 8.75 (s, 1 H). | 2.22 B-12 421.2 |
| 110 | 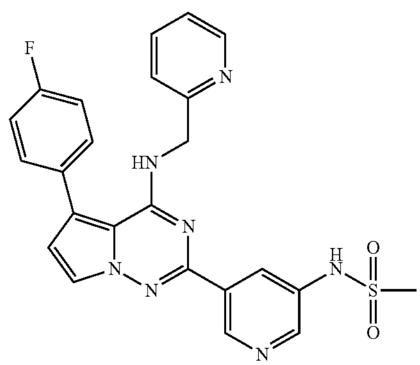 [SMILES: CS(=O)(=O)Nc1cncc(-c2nc(NCc3ccccn3)c3c(-c4ccc(F)cc4)ccn3n2)c1] | N-(5-(5-(4-fluorophenyl)-4-(pyridin-2-ylmethylamino)pyrrolo[1,2-f][1,2,4]triazin-2-yl)pyridin-3-yl)methanesulfonamide | ¹H NMR (400 MHz, DMSO-$d_6$) δ ppm: 2.81 (s, 3 H), 4.89 (d, J = 4.0 Hz, 2 H), 6.78 (d, J = 2.7 Hz, 1 H), 7.21 (t, J = 3.8 Hz, 1 H), 7.30-7.49 (m, 3 H), 7.59 (m, 1 H), 7.60-7.63 (m, 3 H), 7.76 (t, J = 2.8 Hz, 1 H), 7.89 (d, J = 2.7 Hz, 1 H), 8.16 (s, 1 H), 9.24 (d, J = 2.2 Hz, 1 H), 9.39 (d, J = 2.8 Hz, 1 H), 9.77 (br s, 1H). | 2.20 B-12 490.2 |
| 111 | 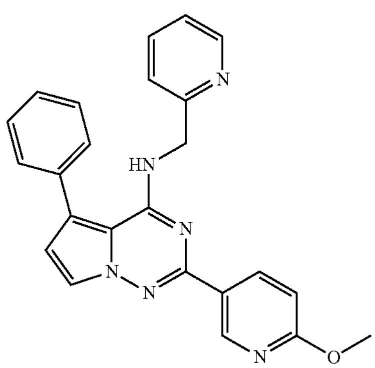 [SMILES: COc1ccc(-c2nc(NCc3ccccn3)c3c(-c4ccccc4)ccn3n2)cn1] | 2-(6-methoxypyridin-3-yl)-5-phenyl-N-(pyridin-2-ylmethyl)pyrrolo[1,2-f][1,2,4]triazin-4-amine | ¹H NMR (400 MHz, DMSO-$d_6$) δ ppm: 3.91 (s, 3 H), 4.91 (d, J = 4.4 Hz, 2 H), 6.78 (d, J = 2.7 Hz, 1 H), −6.94 (m, 1 H), 7.28-7.30 (m, 2 H), 7.48-7.59 (m, 6 H), 7.78 (t, J = 4.0 Hz, 1 H), 7.86 (d, J = 2.7 Hz, 1 H), 8.36-845 (m, 2 H), 9.02 (s, 1 H). | 2.64 B-12 409.2 |
| 112 | 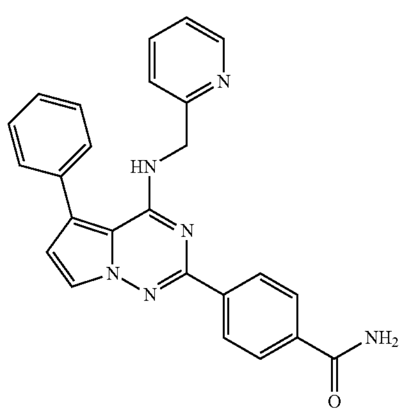 [SMILES: NC(=O)c1ccc(-c2nc(NCc3ccccn3)c3c(-c4ccccc4)ccn3n2)cc1] | 4-(5-phenyl-4-(pyridin-2-ylmethylamino)pyrrolo[1,2-f][1,2,4]triazin-2-yl)benzamide | ¹H NMR (400 MHz, DMSO-$d_6$) δ ppm: 4.94 (d, J = 4.4 Hz, 2 H), 6.82 (d, J = 2.8 Hz, 1 H), 7.28 (t, J = 4.0 Hz, 1 H), 7.29-7.53 (m, 7 H), 7.78 (t, J = 1.2 Hz, 1 H), 7.89 (d, J = 2.7 Hz, 1 H), 7.91-8.05 (m, 4 H), 8.32-8.42 (m, 3 H). | 2.22 B-12 421.2 |

TABLE 1-continued

| Ex. No. | Structure | Name | ¹H NMR | LC/MS Rt (min) Condition [M + 1] |
|---|---|---|---|---|
| 113 | 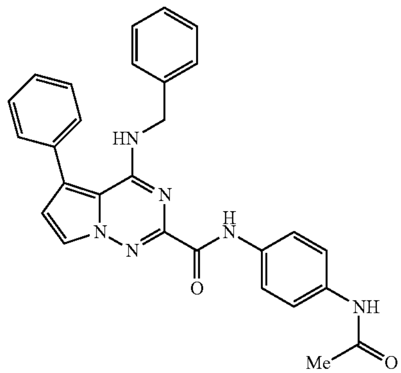 [SMILES: CC(=O)Nc1ccc(NC(=O)c2nc(NCc3ccccc3)c3c(-c4ccccc4)ccn3n2)cc1] | N-(4-acetamidophenyl)-4-(benzylamino)-5-phenylpyrrolo[1,2-f][1,2,4]triazine-2-carboxamide | ¹H NMR (400 MHz, DMSO-d₆) δ ppm: 2.04 (s, 3 H), 4.86 (d, J = 5.6 Hz, 2 H), 6.75 (t, J = 5.5 Hz, 1 H), 6.89 (d, J = 2.8 Hz, 1 H), 7.23-7.29 (m, 1 H), 7.30-7.40 (m, 5 H), 7.43-7.50 (m, 2 H), 7.51-7.61 (m, 4 H), 7.65-7.72 (m, 2 H), 7.97 (d, J = 2.8 Hz, 1 H), 9.95 (s, 1 H), 10.17 (s, 1 H). | 1.88 B-79 476.5 |
| 114 | 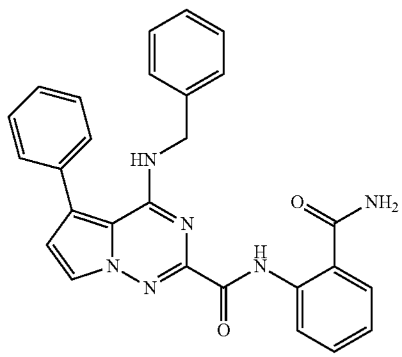 [SMILES: NC(=O)c1ccccc1NC(=O)c1nc(NCc2ccccc2)c2c(-c3ccccc3)ccn2n1] | 4-(benzylamino)-N-(2-carbamoylphenyl)-5-phenylpyrrolo[1,2-f][1,2,4]triazine-2-carboxamide | ¹H NMR (400 MHz, DMSO-d₆) δ ppm: 5.03 (d, J = 5.8 Hz, 2 H), 6.65 (t, J = 5.9 Hz, 1 H), 6.89 (d, J = 2.8 Hz, 1 H), 7.17-7.27 (m, 2 H), 7.31-7.36 (m, 2 H), 7.38-7.53 (m, 7 H), 7.55-7.61 (m, 1 H), 7.72 (br s, 1 H), -7.84 (dd, J = 7.9 Hz, J = 1.4 Hz, 1 H), 7.99 (d, J = 2.8 Hz, 1 H), 8.28 (br s, 1 H), 8.76 (dd, J = 8.4 Hz, J = 1.0 Hz, 1 H), 13.29 (s, 1 H). | 1.95 B-79 462.5 |
| 115 | 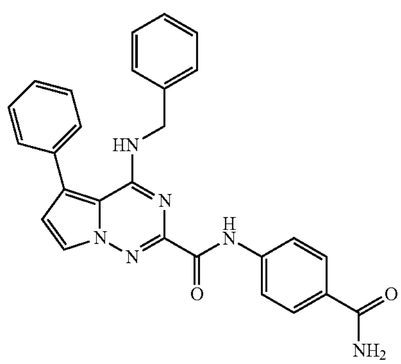 [SMILES: NC(=O)c1ccc(NC(=O)c2nc(NCc3ccccc3)c3c(-c4ccccc4)ccn3n2)cc1] | 4-(benzylamino)-N-(4-carbamoylphenyl)-5-phenylpyrrolo[1,2-f][1,2,4]triazine-2-carboxamide | ¹H NMR (400 MHz, DMSO-d₆) δ ppm: 4.87 (d, J = 5.7 Hz, 2 H), 6.78 (s, 1 H), 6.90 (d, J = 2.8 Hz, 1 H), 7.23-7.32 (m, 1 H), 7.32-7.42 (m, 6 H), 7.44-7.50 (m, 2 H), 7.51-7.56 (m, 2 H), 7.83-7.94 (m, 5 H), 7.99 (d, J = 2.8 Hz, 1 H), 10.42 (s, 1 H). | 1.78 B-79 462.5 |
| 116 | 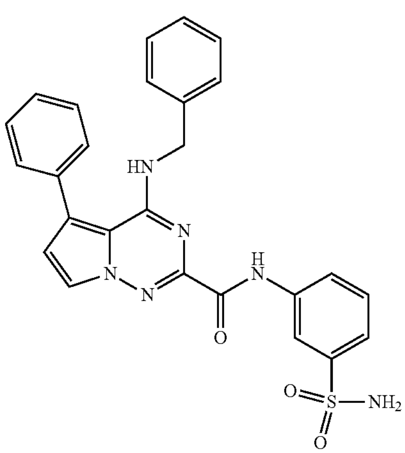 [SMILES: NS(=O)(=O)c1cccc(NC(=O)c2nc(NCc3ccccc3)c3c(-c4ccccc4)ccn3n2)c1] | 4-(benzylamino)-5-phenyl-N-(3-sulfamoylphenyl)pyrrolo[1,2-f][1,2,4]triazine-2-carboxamide | ¹H NMR (400 MHz, DMSO-d₆) δ ppm: 4.88 (d, J = 5.7 Hz, 2 H), 6.77 (t, J = 5.5 Hz, 1 H), 6.90 (d, J = 2.8 Hz, 1 H), 7.22-7.29 (m, 1 H), 7.32-7.50 (m, 9 H), 7.51-7.56 (m, 2 H), 7.58-7.64 (m, 2 H), 7.94 (dt, J = 6.6 Hz, J = 2.4 Hz, 1 H), 7.99 (d, J = 2.8 Hz, 1 H), 8.36-8.41 (m, 1 H), 10.54 (s, 1 H). | 1.88 B-79 498.5 |

| Ex. No. | Structure | Name | ¹H NMR | LC/MS Rt (min) Condition [M + 1] |
|---|---|---|---|---|
| 117 | 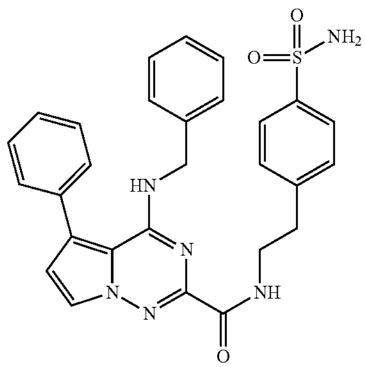 [SMILES: NS(=O)(=O)c1ccc(CCNC(=O)c2nc(NCc3ccccc3)c3c(-c4ccccc4)ccn3n2)cc1] | 4-(benzylamino)-5-phenyl-N-(4-sulfamoylphenethyl)pyrrolo[1,2-f][1,2,4]triazine-2-carboxamide | ¹H NMR (400 MHz, DMSO-d₆) δ ppm: 2.93 (t, J = 7.1 Hz, 2 H), 3.51-3.59 (m, 2 H), 4.80 (d, J = 5.5 Hz, 2 H), 6.60 (t, J = 5.8 Hz, 1 H), 6.84 (d, J = 2.8 Hz, 1 H), 7.22-7.31 (m, 3 H), 7.32-7.39 (m, 5 H), 7.40-7.53 (m, 6 H), 7.71-7.77 (m, 2 H), 7.91 (d, J = 2.8 Hz, 1 H), 8.64 (t, J = 5.9 Hz, 1 H). | 1.76 B-79 526.6 |
| 118 | 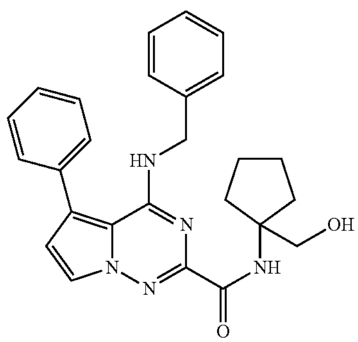 [SMILES: O=C(NC1(CO)CCCC1)c1nc(NCc2ccccc2)c2c(-c3ccccc3)ccn2n1] | 4-(benzylamino)-N-(1-(hydroxymethyl)cyclopentyl)-5-phenylpyrrolo[1,2-f][1,2,4]triazine-2-carboxamide | ¹H NMR (400 MHz, DMSO-d₆) δ ppm: 1.52-1.60 (m, 2 H), 1.63-1.76 (m, 4 H), 1.88-2.00 (m, 2 H), 3.52 (d, J = 5.5 Hz, 2 H), 4.69 (d, J = 5.5 Hz, 2 H), 5.05 (t, J = 5.5 Hz, 1 H), 6.80 (t, J = 5.8 Hz, 1 H), 6.83 (d, J = 2.8 Hz, 1 H), 7.23-7.30 (m, 1 H), 7.31-7.42 (m, 5 H), 7.44-7.54 (m, 4 H), 7.89-7.94 (d, J = 2.4 Hz, 1 H), 8.03 (s, 1 H). | 1.98 B-79 441.5 |
| 119 | 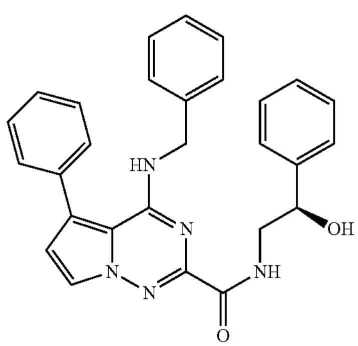 [SMILES: O=C(NC[C@H](O)c1ccccc1)c1nc(NCc2ccccc2)c2c(-c3ccccc3)ccn2n1] | (R)-4-(benzylamino)-N-(2-hydroxy-2-phenylethyl)-5-phenylpyrrolo[1,2-f][1,2,4]triazine-2-carboxamide | ¹H NMR (400 MHz, DMSO-d₆) δ ppm: 3.36-3.48 (m, 1 H), 3.50-3.58 (m, 1 H), 4.70-4.76 (m, 2 H), 4.77-4.83 (m, 1 H), 5.65 (d, J = 4.5 Hz, 1 H), 6.66 (t, J = 5.8 Hz, 1 H), 6.85 (d, J = 3.0 Hz, 1 H), 7.20-7.53 (m, 15 H), 7.92 (d, J = 3.0 Hz, 1 H), 8.44 (t, J = 6.0 Hz, 1 H). | 1.95 B-79 463.5 |
| 120 | 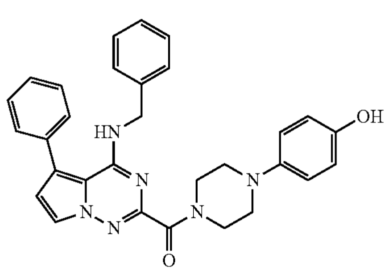 [SMILES: O=C(c1nc(NCc2ccccc2)c2c(-c3ccccc3)ccn2n1)N1CCN(c2ccc(O)cc2)CC1] | (4-(benzylamino)-5-phenylpyrrolo[1,2-f][1,2,4]triazin-2-yl)(4-(4-hydroxyphenyl)piperazin-1-yl)methanone | ¹H NMR (400 MHz, DMSO-d₆) δ ppm: 2.73-2.79 (m, 2 H), 2.98 (dd, J = 5.8 Hz, J = 3.8 Hz, 2 H), 3.36-3.42 (m, 3 H), 3.69-3.74 (m, 2 H), 4.68 (d, J = 6.0 Hz, 2 H), 6.64-6.82 (m, 5 H), 7.26-7.54 (m, 10 H), 7.82-7.86 (m, 1 H), 8.89 (s, 1 H). | 1.86 B-79 504.6 |

TABLE 1-continued

| Ex. No. | Structure | Name | ¹H NMR | LC/MS Rt (min) Condition [M + 1] |
|---|---|---|---|---|
| 121 | 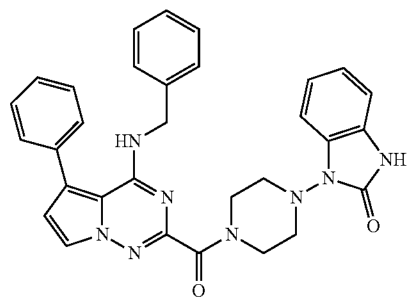 [SMILES: O=C(c1nc(NCc2ccccc2)c2c(-c3ccccc3)ccn2n1)N1CCN(n2c(=O)[nH]c3ccccc32)CC1] | 1-(1-(4-(benzylamino)-5-phenylpyrrolo[1,2-f][1,2,4]triazine-2-carbonyl)piperidin-4-yl)-1H-benzo[d]imidazol-2(3H)-one | ¹H NMR (400 MHz, DMSO-d₆) δ ppm: 1.56 (d, J = 10.5 Hz, 1 H), 1.82 (d, J = 11.1 Hz, 1 H), 2.27 (td, J = 12.8 Hz, J = 4.5 Hz, 2 H), 2.88-2.98 (m, 1 H), 3.12-3.23 (m, 1 H), 3.66-3.74 (m, 1 H), 4.41-4.51 (m, 1 H), 4.60 (d, J = 13.1 Hz, 1 H), 4.70 (dd, J = 5.8 Hz, J = 1.8 Hz, 2 H), 6.65 (t, J = 5.8 Hz, 1 H), 6.79-6.82 (m, 1 H), 6.94-7.00 (m, 3 H), 7.14-7.29 (m, 6 H), 7.34-7.53 (m, 5 H), 7.86 (d, J = 2.5 Hz, 1 H), 10.87 (s, 1 H). | 1.89 B-79 543.6 |
| 122 | 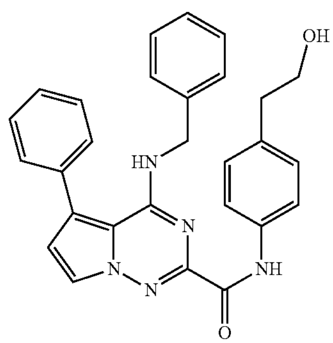 [SMILES: O=C(Nc1ccc(CCO)cc1)c1nc(NCc2ccccc2)c2c(-c3ccccc3)ccn2n1] | 4-(benzylamino)-N-(4-(2-hydroxyethyl)phenyl)-5-phenylpyrrolo[1,2-f][1,2,4]triazine-2-carboxamide | ¹H NMR (400 MHz, DMSO-d₆) δ ppm: 2.71 (t, J = 7.3 Hz, 2 H), 3.60 (td, J = 7.1 Hz, J = 5.5 Hz, 2 H), 4.62-4.66 (m, 1 H), 4.86 (d, J = 5.5 Hz, 2 H), 6.77 (t, J = 5.5 Hz, 1 H), 6.89 (d, J = 2.5 Hz, 1 H) 7.20-7.29 (m, 3 H), 7.32-7.42 (m, 5 H), 7.45-7.50 (m, 2 H), 7.51-7.56 (m, 2 H), 7.64-7.69 (m, 2 H), 7.97 (d, J = 2.5 Hz, 1 H), 10.15 (s, 1 H). | 1.96 B-79 463.5 |
| 123 | 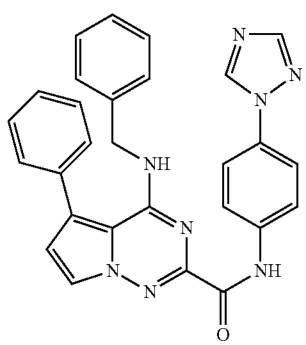 [SMILES: O=C(Nc1ccc(-n2cncn2)cc1)c1nc(NCc2ccccc2)c2c(-c3ccccc3)ccn2n1] | N-(4-(1H-1,2,4-triazol-1-yl)phenyl)-4-(benzylamino)-5-phenylpyrrolo[1,2-f][1,2,4]triazine-2-carboxamide | ¹H NMR (400 MHz, DMSO-d₆) δ ppm: 4.89 (d, J = 5.5 Hz, 2 H), 6.77 (t, J = 5.8 Hz, 1 H), 6.90 (d, J = 2.5 Hz, 1 H), 7.24-7.30 (m, 1 H), 7.32-7.42 (m, 5 H), 7.44-7.49 (m, 2 H), 7.51-7.56 (m, 2 H), 7.86-7.91 (m, 2 H), 7.96-8.02 (m, 3 H), 8.24 (s, 1 H), 9.27 (s, 1 H), 10.47 (s, 1 H). | 1.99 B-79 486.5 |
| 124 | 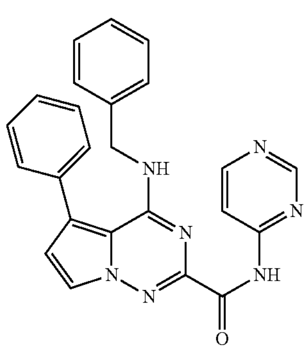 [SMILES: O=C(Nc1ccncn1)c1nc(NCc2ccccc2)c2c(-c3ccccc3)ccn2n1] | 4-(benzylamino)-5-phenyl-N-(pyrimidin-4-yl)pyrrolo[1,2-f][1,2,4]triazine-2-carboxamide | ¹H NMR (400 MHz, DMSO-d₆) δ ppm: 4.79 (d, J = 5.5 Hz, 2 H), 6.93 (d, J = 3.0 Hz, 1 H), 6.98 (t, J = 5.5 Hz, 1 H), 7.23-7.29 (m, 1 H), 7.32-7.45 (m, 5 H), 7.45-7.56 (m, 4 H), 8.02-8.05 (m, 1 H), 8.22 (dd, J = 5.8 Hz, J = 1.3 Hz, 1 H), 8.80 (d, J = 6.0 Hz, 1 H), 9.01 (d, J = 1.5 Hz, 1 H), 10.54 (br s, 1 H). | 2.01 B-79 421.5 |

TABLE 1-continued

| Ex. No. | Structure | Name | ¹H NMR | LC/MS Rt (min) Condition [M + 1] |
|---|---|---|---|---|
| 125 | 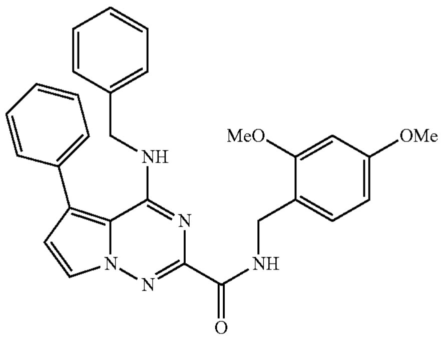 [SMILES: COc1ccc(CNC(=O)c2nc(NCc3ccccc3)c3c(-c4ccccc4)ccn3n2)c(OC)c1] | 4-(benzylamino)-N-(2,4-dimethoxybenzyl)-5-phenylpyrrolo[1,2-f][1,2,4]triazine-2-carboxamide | ¹H NMR (400 MHz, DMSO-$d_6$) δ ppm: 3.75 (s, 3 H), 3.80 (s, 3 H), 4.38 (d, J = 6.0 Hz, 2 H), 4.78 (d, J = 5.5 Hz, 2 H), 6.48 (dd, J = 8.5 Hz, J = 2.5 Hz, 1 H), 6.58 (d, J = 2.0 Hz, 1 H), 6.67 (t, J = 5.8 Hz, 1 H), 6.85 (d, J = 3.0 Hz, 1 H), 7.08 (d, J = 8.5 Hz, 1 H), 7.21-7.41 (m, 6 H), 7.42-7.54 (m, 4 H), 7.93 (d, J = 3.0 Hz, 1 H), 8.76 (t, J = 6.3 Hz, 1 H). | 2.19 B-79 493.6 |
| 126 | 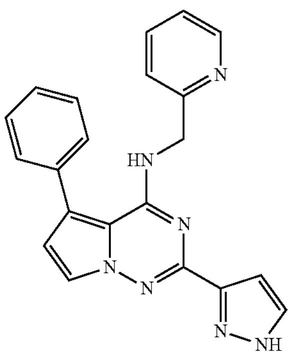 [SMILES: c1ccc(-c2ccn3nc(-c4cc[nH]n4)nc(NCc4ccccn4)c23)cc1] | 5-pheny l-2-(1H-pyrazol-3-yl)-N-(pyridin-2-ylmethyl)pyrrolo[1,2-f][1,2,4]triazin-4-amine | ¹H NMR (400 MHz, DMSO-$d_6$) δ ppm: 4.97 (br s, 2 H), 6.77 (br s, 1 H), 6.81 (d, J = 2.0 Hz, 1 H), 7.17 (br s, 1 H), 7.29 (dd, J = 6.7 Hz, J = 5.1 Hz, 1 H), 7.41-7.48 (m, 2 H), 7.50-7.55 (m, 2 H), 7.56-7.58 (m, 2 H), 7.58-7.60 (m, 1 H), 7.74-7.84 (m, 2 H), 8.39 (d, J = 4.1 Hz, 1 H), 13.52 (br s, 1 H). | 2.27 B-34 368.0 |
| 127 | 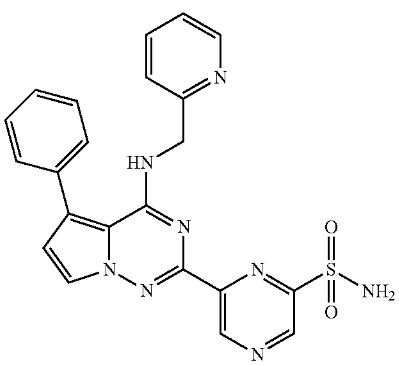 [SMILES: NS(=O)(=O)c1cncc(-c2nc(NCc3ccccn3)c3c(-c4ccccc4)ccn3n2)n1] | 6-(5-phenyl-4-(pyridin-2-ylmethylamino)pyrrolo[1,2-f][1,2,4]triazin-2-yl)pyrazine-2-sulfonamide | ¹H NMR (400 MHz, DMSO-$d_6$) δ ppm: 4.96 (d, J = 4.6 Hz, 2 H), 6.91 (d, J = 2.7 Hz, 1 H), 7.30 (d, J = 1.6 Hz, 1 H), 7.43-7.64 (m, 7 H), 7.79 (dd, J = 7.7 Hz, J = 1.8 Hz, 1 H), 7.90 (s, 2 H), 8.00 (d, J = 2.7 Hz, 1 H), 8.35-8.44 (m, 1 H), 9.23 (d, J = 0.4 Hz, 1 H), 9.68 (d, J = 0.4 Hz, 1 H). | 2.23 B-34 459.0 |
| 128 | 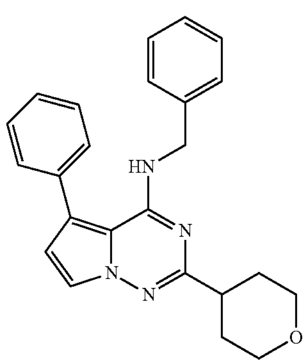 [SMILES: c1ccc(CNc2nc(C3CCOCC3)nn3ccc(-c4ccccc4)c23)cc1] | N-benzyl-5-phenyl-2-(tetrahydro-2H-pyran-4-yl)pyrrolo[1,2-f][1,2,4]triazin-4-amine | ¹H NMR (400 MHz, DMSO-$d_6$) δ ppm: 1.76-1.84 (m, 4 H), 2.78 (s, 1 H), 3.39-3.48 (m, 2 H), 3.92 (dt, J = 11.0 Hz, J = 3.1 Hz, 2 H), 4.68 (d, J = 5.1 Hz, 2 H), 6.34 (s, 1 H), 6.68 (d, J = 2.7 Hz, 1 H), 7.26 (dd, J = 6.1 Hz, J = 2.5 Hz, 1 H), 7.29-7.39 (m, 5 H), 7.41-7.51 (m, 4 H), 7.71 (d, J = 2.6 Hz, 1 H). | 2.52 B-82 385.0 |

TABLE 1-continued

| Ex. No. | Structure | Name | ¹H NMR | LC/MS Rt (min) Condition [M + 1] |
|---|---|---|---|---|
| 129 | 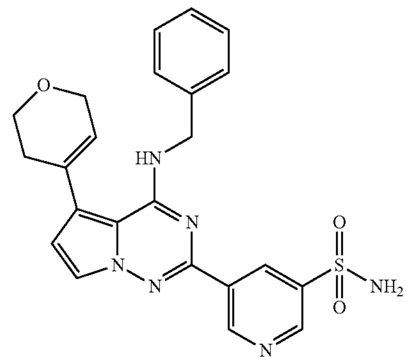 [SMILES: NS(=O)(=O)c1cncc(-c2nc(NCc3ccccc3)c3c(C4=CCOCC4)ccn3n2)c1] | 5-(4-(benzylamino)-5-(3,6-dihydro-2H-pyran-4-yl)pyrrolo[2,1-f][1,2,4]triazin-2-yl)pyridine-3-sulfonamide | ¹H NMR (400 MHz, DMSO-$d_6$) δ ppm: 2.49-2.50 (obscured, 2 H), 3.86 (t, J = 5.4 Hz, 2 H), 4.18 (d, J = 2.6 Hz, 2 H), 4.92 (d, J = 5.7 Hz, 2 H), 5.86 (s, 1 H), 6.80 (d, J = 2.8 Hz, 1 H), 7.24-7.32 (m, 2 H), 7.35-7.41 (m, 2 H), 7.48 (d, J = 7.0 Hz, 2 H), 7.74 (s, 2 H), 7.85 (d, J = 2.8 Hz, 1 H), 8.92 (t, J = 2.1 Hz, 1 H), 9.05 (d, J = 1.8 Hz, 1 H), 9.51 (s, 1 H). | 2.13 B-82 463.0 |
| 130 | 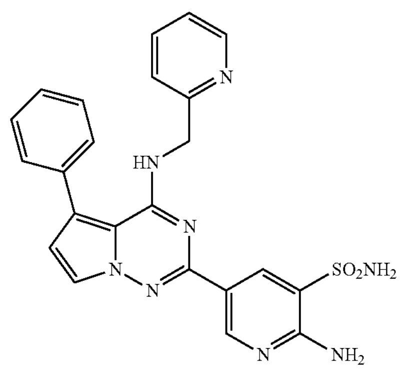 [SMILES: Nc1ncc(-c2nc(NCc3ccccn3)c3c(-c4ccccc4)ccn3n2)cc1S(N)(=O)=O] | 2-amino-5-(5-phenyl-4-((pyridin-2-ylmethyl)amino)pyrrolo[2,1-f][1,2,4]triazin-2-yl)pyridine-3-sulfonamide | ¹H NMR (400 MHz, DMSO-$d_6$) δ ppm: 4.89 (d, J = 4.7 Hz, 2 H), 6.76 (d, J = 2.7 Hz, 1 H), 6.89 (br s, 2 H), 7.23 (t, J = 4.7 Hz, 1 H), 7.26-7.30 (m, 1 H), 7.43-7.48 (m, 2 H), 7.49-7.55 (m, 2 H), 7.56-7.60 (m, 4 H), 7.78 (td, J = 7.7 Hz, J = 1.8 Hz, 1 H), 7.85 (d, J = 2.70 Hz, 1 H), 8.37-8.41 (m, 1 H), 8.69 (d, J = 2.2 Hz, 1 H), 9.00 (d, J = 2.3 Hz, 1 H). | 1.77 B-79 473.0 |
| 131 | 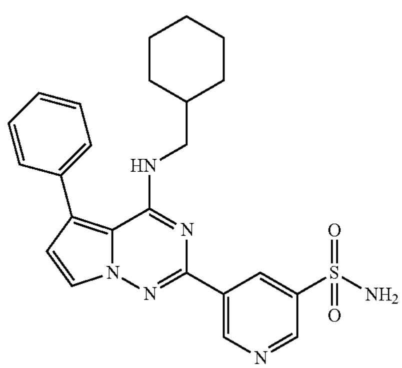 [SMILES: NS(=O)(=O)c1cncc(-c2nc(NCC3CCCCC3)c3c(-c4ccccc4)ccn3n2)c1] | 5-(4-((cyclohexylmethyl)amino)-5-phenylpyrrolo[2,1-f][1,2,4]triazin-2-yl)pyridine-3-sulfonamide | ¹H NMR (400 MHz, DMSO-$d_6$) δ ppm: 0.81-1.04 (m, 2 H), 1.06-1.29 (m, 3 H), 1.48-1.76 (m, 6 H), 3.49 (t, J = 5.8 Hz, 2 H), 6.04 (t, J = 5.5 Hz, 1 H), 6.82 (d, J = 3.0 Hz, 1 H), 7.42-7.60 (m, 5 H), 7.72 (br s, 2 H), 7.92 (d, J = 2.5 Hz, 1 H), 8.89-8.97 (m, 1 H), 9.07 (d, J = 2.0 Hz, 1 H), 9.57 (d, J = 2.0 Hz, 1 H). | 2.26 B-85 462.9 |
| 132 | 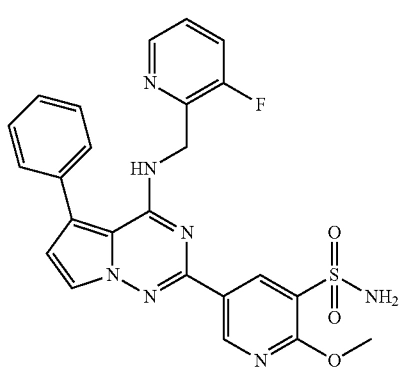 [SMILES: COc1ncc(-c2nc(NCc3ncccc3F)c3c(-c4ccccc4)ccn3n2)cc1S(N)(=O)=O] | 5-(4-(((3-fluoropyridin-2-yl)methyl)amino)-5-phenylpyrrolo[2,1-f][1,2,4]triazin-2-yl)-2-methoxypyridine-3-sulfonamide | ¹H NMR (400 MHz, DMSO-$d_6$) δ ppm: 3.71 (s, 3 H), 4.98 (d, J = 4.0 Hz, 2 H), 6.76-6.80 (m, 1 H), 7.08 (br s, 2 H), 7.28 (s, 1 H), 7.40-7.62 (m, 6 H), 7.77 (t, J = 9.0 Hz, 1 H), 7.87-7.91 (m, 1 H), 8.25 (d, J = 4.5 Hz, 1 H), 8.79 (s, 1 H), 8.89 (s, 1 H). | 2.13 B-82 506.2 |

TABLE 1-continued

| Ex. No. | Structure | Name | ¹H NMR | LC/MS Rt (min) Condition [M + 1] |
|---|---|---|---|---|
| 133 | 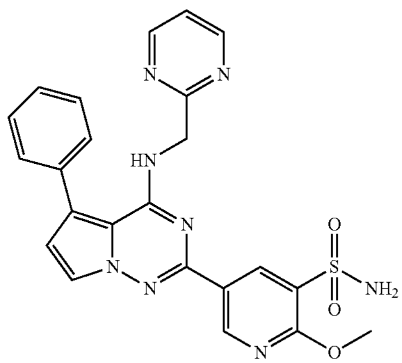 [SMILES: COc1ncc(-c2nc(NCc3ncccn3)c3c(-c4ccccc4)ccn3n2)cc1S(N)(=O)=O] | 2-methoxy-5-(5-phenyl-4-((pyrimidin-2-ylmethyl)amino)pyrrolo[2,1-f][1,2,4]triazin-2-yl)pyridine-3-sulfonamide | ¹H NMR (400 MHz, DMSO-d₆) δ ppm: 3.70 (s, 3 H), 5.01 (d, J = 4.5 Hz, 2 H), 6.79 (d, J = 3.0 Hz, 1 H), 7.07 (br s, 2 H), 7.23 (t, J = 4.5 Hz, 1 H), 7.40-7.50 (m, 2 H), 7.52-7.64 (m, 4 H), 7.87-7.90 (m, 1 H), 8.72-8.78 (m, 3 H), 8.86 (d, J = 2.5 Hz, 1 H). | 1.90 B-13 489.2 |
| 134 | 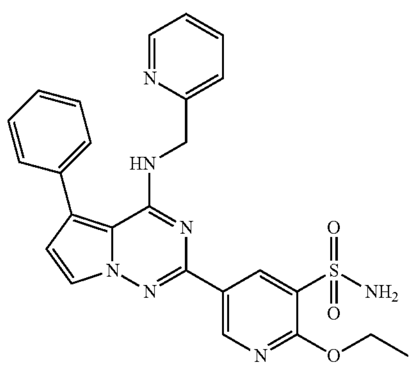 [SMILES: CCOc1ncc(-c2nc(NCc3ccccn3)c3c(-c4ccccc4)ccn3n2)cc1S(N)(=O)=O] | 2-ethoxy-5-(5-phenyl-4-((pyridin-2-ylmethyl)amino)pyrrolo[2,1-f][1,2,4]triazin-2-yl)pyridine-3-sulfonamide | ¹H NMR (400 MHz, DMSO-d₆) δ ppm: 1.35 (t, J = 7.0 Hz, 3 H), 4.17 (q, J = 7.0 Hz, 2 H), 4.94 (d, J = 5.0 Hz, 2 H), 6.78 (d, J = 2.5 Hz, 1 H), 7.08 (s, 2 H), 7.26 (t, J = 5.0 Hz, 1 H), 7.36-7.42 (m, 1 H), 7.43-7.49 (m, 1 H), 7.50-7.62 (m, 5 H), 7.87-7.94 (m, 2 H), 8.47 (d, J = 5.5 Hz, 1 H), 8.73 (d, J = 2.5 Hz, 1 H), 8.78 (d, J = 2.5 Hz, 1 H). | 1.95 B-78 502.2 |
| 135 | 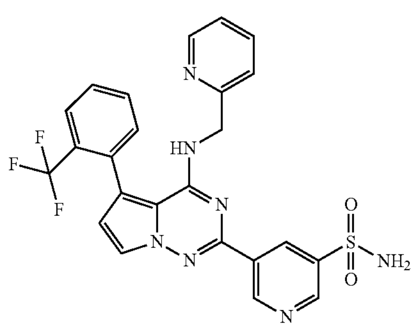 [SMILES: NS(=O)(=O)c1cncc(-c2nc(NCc3ccccn3)c3c(-c4ccccc4C(F)(F)F)ccn3n2)c1] | 5-(4-((pyridin-2-ylmethyl)amino)-5-(2-(trifluoromethyl)phenyl)pyrrolo[2,1-f][1,2,4]triazin-2-yl)pyridine-3-sulfonamide | ¹H NMR (400 MHz, DMSO-d₆) δ ppm: 4.75-4.90 (m, 2 H), 6.78 (d, J = 2.0 Hz, 1 H), 7.01 (t, J = 4.3 Hz, 1 H), 7.26 (ddd, J = 6.9 Hz, J = 5.7 Hz, J = 1.0 Hz, 1 H), 7.39 (d, J = 8.0 Hz, 1 H), 7.60-7.69 (m, 1 H), 7.71-7.86 (m, 5 H), 7.92-8.02 (m, 2 H), 8.20-8.25 (m, 1 H), 8.94 (t, J = 2.0 Hz, 1 H), 9.08 (d, J = 2.0 Hz, 1 H), 9.59 (d, J = 2.0 Hz, 1 H). | 2.31 B-81 526.0 |
| 136 | 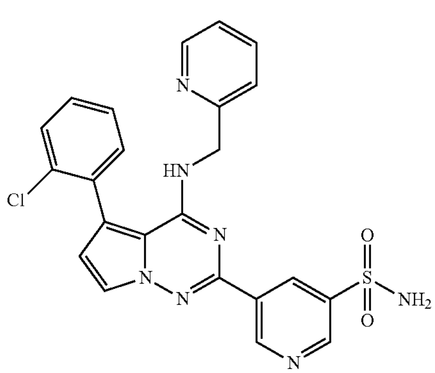 [SMILES: NS(=O)(=O)c1cncc(-c2nc(NCc3ccccn3)c3c(-c4ccccc4Cl)ccn3n2)c1] | 5-(5-(2-chlorophenyl)-4-((pyridin-2-ylmethyl)amino)pyrrolo[2,1-f][1,2,4]triazin-2-yl)pyridine-3-sulfonamide | ¹H NMR (400 MHz, DMSO-d₆) δ ppm: 4.87 (d, J = 4.0 Hz, 2 H), 6.81 (d, J = 2.5 Hz, 1 H), 7.21-7.31 (m, 2 H), 7.44 (d, J = 8.0 Hz, 1 H), 7.47-7.54 (m, 1 H), 7.56-7.62 (m, 2 H), 7.66-7.81 (m, 4 H), 7.97 (d, J = 3.0 Hz, 1 H), 8.28 (d, J = 4.0 Hz, 1 H), 8.94 (t, J = 2.3 Hz, 1 H), 9.07 (d, J = 2.5 Hz, 1 H), 9.59 (d, J = 2.0 Hz, 1 H). | 2.27 B-81 492.0 |

TABLE 1-continued

| Ex. No. | Structure | Name | ¹H NMR | LC/MS Rt (min) Condition [M + 1] |
|---|---|---|---|---|
| 137 | 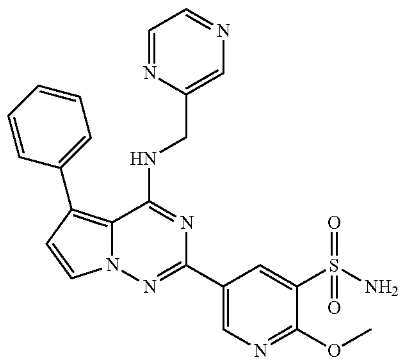 [SMILES: COc1ncc(-c2nc(NCc3cnccn3)c3c(-c4ccccc4)ccn3n2)cc1S(N)(=O)=O] | 2-methoxy-5-(5-phenyl-4-((pyrazin-2-ylmethyl)amino)pyrrolo[2,1-f][1,2,4]triazin-2-yl)pyridine-3-sulfonamide | ¹H NMR (400 MHz, DMSO-d₆) δ ppm: 3.68 (s, 3 H), 4.99 (d, J = 3.5 Hz, 2 H), 6.76-6.79 (m, 1 H), 7.06 (br s, 3 H), 7.42-7.47 (m, 1 H), 7.49-7.54 (m, 2 H), 7.55-7.60 (m, 2 H), 7.87-7.90 (m, 1 H), 8.52-8.55 (m, 2 H), 8.73 (d, J = 2.5 Hz, 1 H), 8.76 (d, J = 1.5 Hz, 1 H), 8.79 (d, J = 2.5 Hz, 1 H). | 2.05 B-78 489.2 |
| 138 | 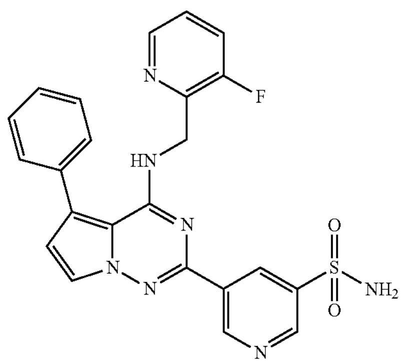 [SMILES: NS(=O)(=O)c1cncc(-c2nc(NCc3ncccc3F)c3c(-c4ccccc4)ccn3n2)c1] | 5-(4-(((3-fluoropyridin-2-yl)methyl)amino)-5-phenylpyrrolo[2,1-f][1,2,4]triazin-2-yl)pyridine-3-sulfonamide | ¹H NMR (400 MHz, DMSO-d₆) δ ppm: 5.01 (d, J = 3.6 Hz, 2 H), 6.87 (d, J = 2.7 Hz, 1 H), 7.35-7.47 (m, 2 H), 7.47-7.67 (m, 5 H), 7.72-7.82 (m, 3 H), 7.98 (d, J = 2.7 Hz, 1 H), 8.24 (d, J = 4.7 Hz, 1 H), 8.95 (t, J = 2.1 Hz, 1 H), 9.08 (d, J = 2.2 Hz, 1 H), 9.59 (d, J = 2.0 Hz, 1 H). | 2.23 B-80 476.0 |
| 139 | 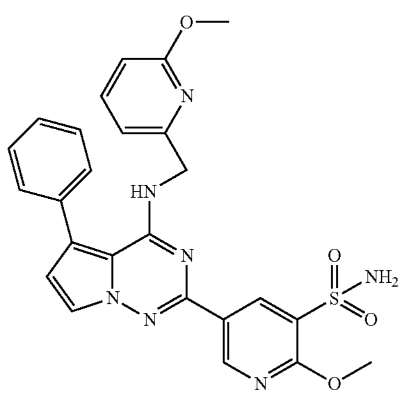 [SMILES: COc1cccc(CNc2nc(-c3cnc(OC)c(S(N)(=O)=O)c3)nn3ccc(-c4ccccc4)c23)n1] | 2-methoxy-5-(4-(((6-methoxypyridin-2-yl)methyl)amino)-5-phenylpyrrolo[2,1-f][1,2,4]triazin-2-yl)pyridine-3-sulfonamide | ¹H NMR (400 MHz, DMSO-d₆) δ ppm: 3.55 (s, 3 H), 3.70 (s, 3 H), 4.88 (d, J = 5.2 Hz, 2 H), 6.69 (d, J = 8.2 Hz, 1 H), 6.75-6.82 (m, 2 H), 7.03-7.10 (m, 3 H), 7.41 (d, J = 7.4 Hz, 1 H), 7.44-7.51 (m, 2 H), 7.55-7.60 (m, 2 H), 7.69 (dd, J = 8.2 Hz, J = 7.3 Hz, 1 H), 7.89 (d, J = 2.7 Hz, 1 H), 8.77 (d, J = 2.6 Hz, 1 H), 8.86 (d, J = 2.6 Hz, 1 H). | 1.89 B-79 518.0 |
| 140 | 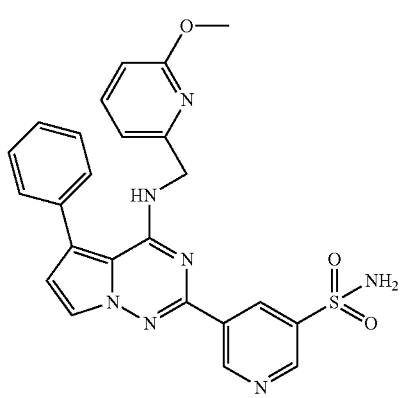 [SMILES: COc1cccc(CNc2nc(-c3cncc(S(N)(=O)=O)c3)nn3ccc(-c4ccccc4)c23)n1] | 5-(4-(((6-methoxypyridin-2-yl)methyl)amino)-5-phenylpyrrolo[2,1-f][1,2,4]triazin-2-yl)pyridine-3-sulfonamide | ¹H NMR (400 MHz, DMSO-d₆) δ ppm: 3.56 (s, 3 H), 4.90 (d, J = 5.2 Hz, 2 H), 6.68 (d, J = 8.2 Hz, 1 H), 6.85 (d, J = 2.8 Hz, 1 H), 6.96 (t, J = 5.2 Hz, 1 H), 7.07 (d, J = 7.2 Hz, 1 H), 7.38-7.45 (m, 1 H), 7.46-7.53 (m, 2 H), 7.58-7.63 (m, 2 H), 7.68 (dd, J = 8.2 Hz, J = 7.3 Hz, 1 H), 7.75 (s, 2 H), 7.97 (d, J = 2.70 Hz, 1 H), 8.94 (t, J = 2.1 Hz, 1 H), 9.07 (d, J = 2.2 Hz, 1 H), 9.58 (d, J = 2.0 Hz, 1 H). | 2.08 B-86 488.2 |

TABLE 1-continued

| Ex. No. | Structure | Name | $^1$H NMR | LC/MS Rt (min) Condition [M + 1] |
|---|---|---|---|---|
| 141 | 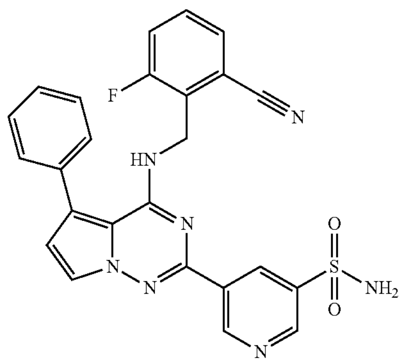 [SMILES: N#Cc1cccc(F)c1CNc1nc(-c2cncc(S(N)(=O)=O)c2)nn2ccc(-c3ccccc3)c12] | 5-(4-((2-cyano-6-fluorobenzyl)amino)-5-phenylpyrrolo[2,1-f][1,2,4]triazin-2-yl)pyridine-3-sulfonamide | $^1$H NMR (400 MHz, DMSO-d$_6$) δ ppm: 5.02 (d, J = 5.6 Hz, 2 H), 6.85-6.89 (m, 2 H), 7.41 (d, J = 7.3 Hz, 1 H), 7.44-7.50 (m, 2 H), 7.54-7.61 (m, 4 H), 7.68-7.77 (m, 3 H), 7.98 (d, J = 2.8 Hz, 1 H), 8.88 (t, J = 2.1 Hz, 1 H), 9.07 (d, J = 2.3 Hz, 1 H), 9.56 (d, J = 2.0 Hz, 1 H). | 1.86 B-83 500.0 |
| 142 | 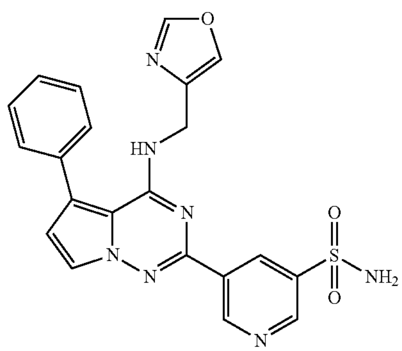 [SMILES: NS(=O)(=O)c1cncc(-c2nc(NCc3cocn3)c3c(-c4ccccc4)ccn3n2)c1] | 5-(4-((oxazol-4-ylmethyl)amino)-5-phenylpyrrolo[2,1-f][1,2,4]triazin-2-yl)pyridine-3-sulfonamide | $^1$H NMR (400 MHz, DMSO-d$_6$) δ ppm: 4.78 (d, J = 3.4 Hz, 2 H), 6.60 (br s, 1 H), 6.85 (d, J = 2.6 Hz, 1H), 7.42 (d, J = 7.2 Hz, 1 H), 7.50 (t, J = 7.5 Hz, 2 H), 7.53-7.58 (m, 2 H), 7.73 (br s, 2 H), 7.97 (d, J = 2.6 Hz, 1 H), 8.06 (s, 1 H), 8.35 (s, 1 H), 9.07 (d, J = 2.0 Hz, 1 H), 9.59 (d, J = 1.4 Hz, 1 H), 8.95 (s, 1 H). | 2.59 B-87 448.0 |
| 143 | 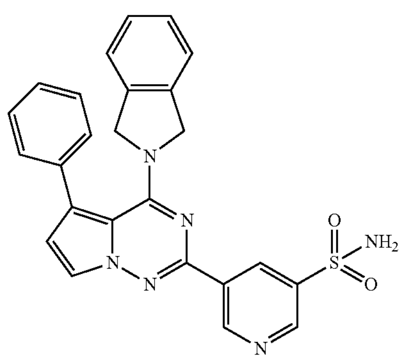 [SMILES: NS(=O)(=O)c1cncc(-c2nc(N3Cc4ccccc4C3)c3c(-c4ccccc4)ccn3n2)c1] | 5-(4-(isoindolin-2-yl)-5-phenylpyrrolo[2,1-f][1,2,4]triazin-2-yl)pyridine-3-sulfonamide | $^1$H NMR (400 MHz, DMSO-d$_6$) δ ppm: 4.737 (br s, 4 H), 6.89 (d, J = 2.8 Hz, 1 H), 7.12 (br s, 2 H), 7.24 (dd, J = 5.52 Hz, J = 3.2 Hz, 2 H), 7.37-7.57 (m, 5 H), 7.78 (s, 2 H), 8.04 (d, J = 2.7 Hz, 1 H), 8.97 (t, J = 2.1 Hz, 1 H), 9.09 (d, J = 2.3 Hz, 1 H), 9.66 (d, J = 2.0 Hz, 1 H). | 2.31 B-80 469.0 |
| 144 | 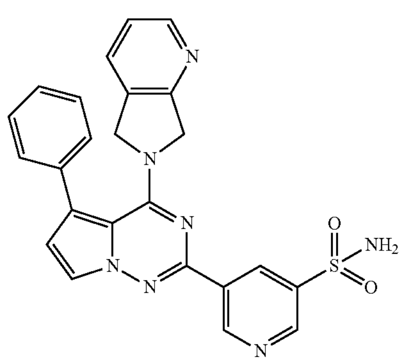 [SMILES: NS(=O)(=O)c1cncc(-c2nc(N3Cc4cccnc4C3)c3c(-c4ccccc4)ccn3n2)c1] | 5-(4-(5,7-dihydro-6H-pyrrolo[3,4-b]pyridin-6-yl)-5-phenylpyrrolo[2,1-f][1,2,4]triazin-2-yl)pyridine-3-sulfonamide | $^1$H NMR (400 MHz, DMSO-d$_6$) δ ppm: 4.55 (s, 2 H), 4.97 (s, 2 H), 6.91 (d, J = 2.8 Hz, 1 H), 7.26 (dd, J = 7.6 Hz, J = 5.0 Hz, 1 H), 7.43 (d, J = 7.2 Hz, 1 H), 7.48 (t, J = 7.4 Hz, 2 H), 7.51-7.57 (m, 2 H), 7.672 (s, 1 H), 7.78 (s, 2 H), 8.06 (d, J = 2.7 Hz, 1 H), 8.37 (d, J = 4.7 Hz, 1 H), 8.98 (t, J = 2.1 Hz, 1 H), 9.09 (d, J = 2.2 Hz, 1 H), 9.66 (d, J = 1.9 Hz, 1 H). | 2.10 B-80 470.0 |

TABLE 1-continued

| Ex. No. | Structure | Name | $^1$H NMR | LC/MS Rt (min) Condition [M + 1] |
|---|---|---|---|---|
| 145 | 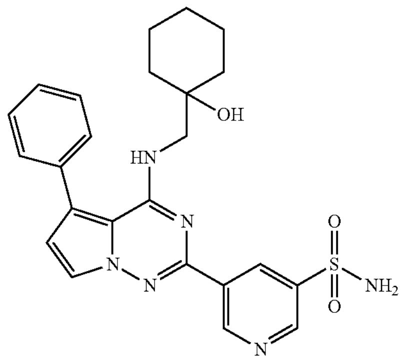 [SMILES: NS(=O)(=O)c1cncc(-c2nc(NCC3(O)CCCCC3)c3c(-c4ccccc4)ccn3n2)c1] | 5-(4-((1-hydroxycyclohexyl)methylamino)-5-phenylpyrrolo[1,2-f][1,2,4]triazin-2-yl)pyridine-3-sulfonamide | $^1$H NMR (400 MHz, DMSO-d$_6$) δ ppm: 1.21-1.46 (m, 8 H), 1.54 (t, J = 8.8 Hz, 2 H), 3.63 (d, J = 5.2 Hz, 2 H), 4.40 (s, 1 H), 6.28 (t, J = 5.5 Hz, 1 H), 6.82 (d, J = 3.0 Hz, 1 H), 7.39-7.46 (m, 1 H), 7.49-7.60 (m, 4 H), 7.75 (s, 2 H), 7.93 (d, J = 3.0 Hz, 1 H), 8.94 (t, J = 2.0 Hz, 1 H), 9.07 (d, J = 2.0 Hz, 1 H), 9.59 (d, J = 2.0 Hz, 1 H). | 2.29 B-80 479.2 |
| 146 | 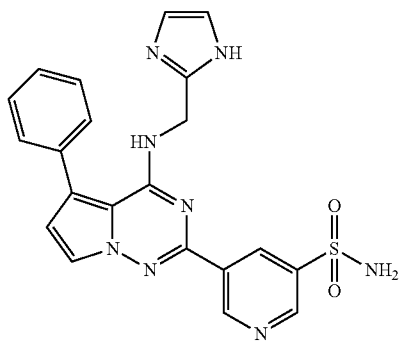 [SMILES: NS(=O)(=O)c1cncc(-c2nc(NCc3ncc[nH]3)c3c(-c4ccccc4)ccn3n2)c1] | 5-(4-((1H-imidazol-2-yl)methylamino)-5-phenylpyrrolo[1,2-f][1,2,4]triazin-2-yl)pyridine-3-sulfonamide | $^1$H NMR (400 MHz, DMSO-d$_6$) δ ppm: 4.87 (d, J = 5.0 Hz, 2 H), 6.80-7.00 (m, 4 H), 7.38-7.44 (m, 1 H), 7.46-7.52 (m, 2 H), 7.57-7.62 (m, 2 H), 7.74 (s, 2 H), 7.98 (d, J = 3.0 Hz, 1 H), 8.94 (t, J = 2.0 Hz, 1 H), 9.07 (d, J = 2.0 Hz, 1 H), 9.57 (d, J = 2.0 Hz, 1 H), 11.94 (br s, 1 H). | 1.92 B-80 447.2 |
| 147 | 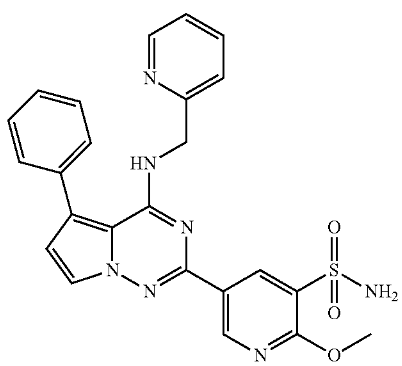 [SMILES: COc1ncc(-c2nc(NCc3ccccn3)c3c(-c4ccccc4)ccn3n2)cc1S(N)(=O)=O] | 2-methoxy-5-(5-phenyl-4-(pyridin-2-ylmethylamino)pyrrolo[1,2-f][1,2,4]triazin-2-yl)pyridine-3-sulfonamide | $^1$H NMR (400 MHz, DMSO-d$_6$) δ ppm: 3.70 (s, 3 H), 4.92 (d, J = 5.0 Hz, 2 H), 6.77 (d, J = 2.5 Hz, 1 H), 7.08 (br s, 2 H), 7.29 (td, J = 7.8 Hz, J = 5.0 Hz, 2 H), 7.43-7.63 (m, 6 H), 7.80 (td, J = 7.7 Hz, J = 1.8 Hz, 1 H), 7.88 (d, J = 2.5 Hz, 1 H), 8.40 (d, J = 4.0 Hz, 1 H), 8.78 (d, J = 2.5 Hz, 1 H), 8.87 (d, J = 2.51 Hz, 1 H). | 2.02 B-82 488.2 |
| 148 | 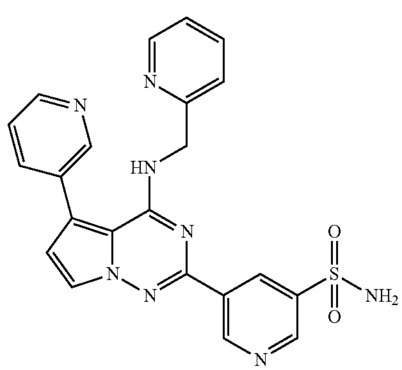 [SMILES: NS(=O)(=O)c1cncc(-c2nc(NCc3ccccn3)c3c(-c4cccnc4)ccn3n2)c1] | 5-(4-(pyridin-2-ylmethylamino)-5-(pyridin-3-yl)pyrrolo[1,2-f][1,2,4]triazin-2-yl)pyridine-3-sulfonamide | $^1$H NMR (400 MHz, DMSO-d$_6$) δ ppm: 4.93 (d, J = 3.0 Hz, 2 H), 6.94 (d, J = 2.5 Hz, 1 H), 7.29 (dd, J = 6.5 Hz, J = 5.0 Hz, 1 H), 7.46-7.59 (m, 3 H), 7.69-7.82 (m, 3 H), 7.99-8.04 (m, 2 H), 8.38-8.41 (m, 1 H), 8.67 (dd, J = 4.5 Hz, J = 1.5 Hz, 1 H), 8.80-8.82 (m, 1 H), 8.91-8.94 (m, 1 H), 9.06 (d, J = 2.0 Hz, 1 H), 9.54 (d, J = 2.0 Hz, 1 H). | 1.95 B-39 459.8 |

TABLE 1-continued

| Ex. No. | Structure | Name | ¹H NMR | LC/MS Rt (min) Condition [M + 1] |
|---|---|---|---|---|
| 149 | 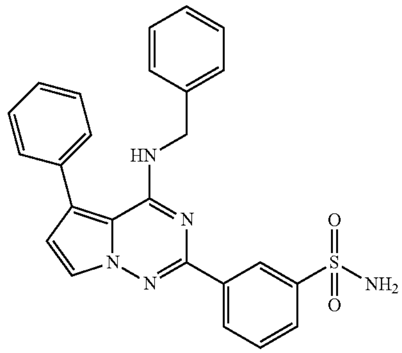 [SMILES: NS(=O)(=O)c1cccc(-c2nc(NCc3ccccc3)c3c(-c4ccccc4)ccn3n2)c1] | 3-(4-(benzylamino)-5-phenylpyrrolo[1,2-f][1,2,4]triazin-2-yl)benzenesulfonamide | ¹H NMR (400 MHz, DMSO-d$_6$) δ ppm: 4.83 (d, J = 6.0 Hz, 2 H), 6.63 (t, J = 5.5 Hz, 1 H), 6.78-6.83 (m, 1 H), 7.21-7.29 (m, 1 H), 7.32-7.43 (m, 5 H), 7.43-7.48 (m, 4 H), 7.50-7.56 (m, 2 H), 7.69 (t, J = 8.0 Hz, 1 H), 7.89-7.95 (m, 2 H), 8.45 (dt, J = 7.9 Hz, J = 1.3 Hz, 1 H), 8.75 (t, J = 1.8 Hz, 1 H). | 2.47 B-34 456.0 |
| 150 | 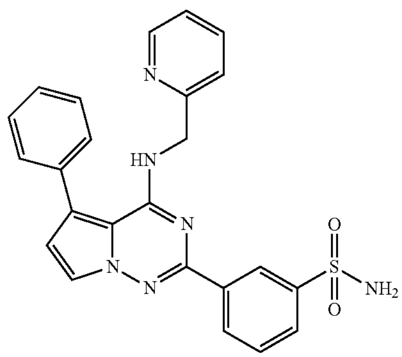 [SMILES: NS(=O)(=O)c1cccc(-c2nc(NCc3ccccn3)c3c(-c4ccccc4)ccn3n2)c1] | 3-(5-phenyl-4-(pyridin-2-ylmethylamino)pyrrolo[1,2-f][1,2,4]triazin-2-yl)benzenesulfonamide | ¹H NMR (400 MHz, DMSO-d$_6$) δ ppm: 4.93 (d, J = 4.5 Hz, 2 H), 6.82 (d, J = 3.0 Hz, 1 H), 7.25-7.34 (m, 2 H), 7.43-7.56 (m, 6 H), 7.56-7.62 (m, 2H), 7.71 (t, J = 7.8 Hz, 1 H), 7.79 (td, J = 7.7 Hz, J = 1.8 Hz, 1 H), 7.90-7.96 (m, 2 H), 8.36-8.40 (m, 1 H), 8.48 (dt, J = 7.9 Hz, J = 1.3 Hz, 1 H), 8.74 (t, J = 1.5 Hz, 1 H). | 2.35 B-34 457.0 |
| 151 | 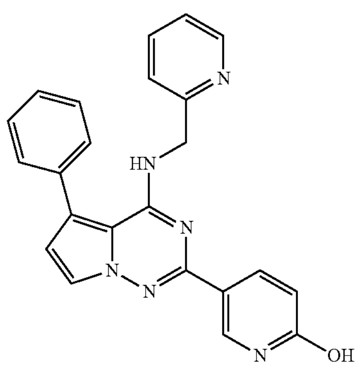 [SMILES: Oc1ccc(-c2nc(NCc3ccccn3)c3c(-c4ccccc4)ccn3n2)cn1] | 5-(5-phenyl-4-((pyridin-2-ylmethyl)amino)pyrrolo[2,1-f][1,2,4]triazin-2-yl)pyridin-2-ol | ¹H NMR (400 MHz, DMSO-d$_6$) δ ppm: 4.84 (d, J = 4.8 Hz, 2 H), 6.42 (d, J = 7.6 Hz, 1 H), 6.73 (d, J = 2.8 Hz, 1 H), 7.22-7.57 (m, 8 H), 7.75-7.79 (m, 2 H), 8.16-8.19 (m, 2 H), 8.38 (d, J = 4.4 Hz, 1 H), 11.88 (s, 1 H). | 2.12 B-80 395.0 |
| 152 | 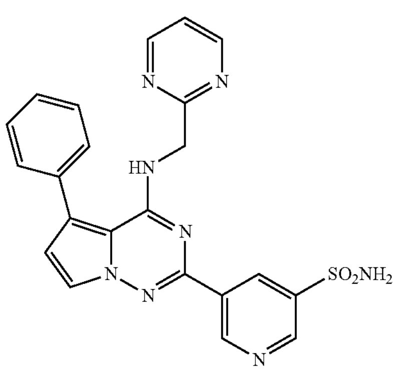 [SMILES: NS(=O)(=O)c1cncc(-c2nc(NCc3ncccn3)c3c(-c4ccccc4)ccn3n2)c1] | 5-(5-phenyl-4-((pyrimidin-2-ylmethyl)amino)pyrrolo[2,1-f][1,2,4]triazin-2-yl)pyridine-3-sulfonamide | ¹H NMR (400 MHz, DMSO-d$_6$) δ ppm: 5.02 (d, J = 4.8 Hz, 2 H), 6.86 (d, J = 2.8 Hz, 1 H), 7.31 (t, J = 4.4 Hz, 1 H), 7.41-7.64 (m, 6 H), 7.74 (s, 2 H), 7.97 (d, J = 2.8 Hz, 1 H), 8.73 (d, J = 4.8 Hz, 2 H), 8.91 (t, J = 2.0 Hz, 1 H), 9.05 (d, J = 2.4 Hz, 1 H), 9.51 (d, J = 2.0 Hz, 1 H). | 2.27 B-81 459.2 |

TABLE 1-continued

| Ex. No. | Structure | Name | ¹H NMR | LC/MS Rt (min) Condition [M + 1] |
|---|---|---|---|---|
| 153 | 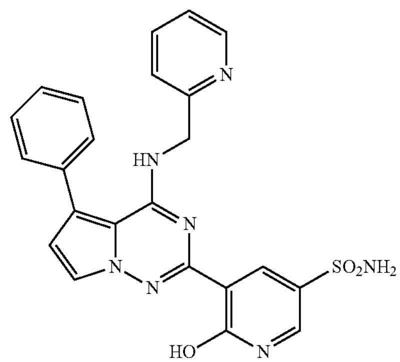 [SMILES: NS(=O)(=O)c1cnc(O)c(-c2nc(NCc3ccccn3)c3c(-c4ccccc4)ccn3n2)c1] | 6-hydroxy-5-(5-phenyl-4-((pyridin-2-ylmethyl)amino)pyrrolo[2,1-f][1,2,4]triazin-2-yl)pyridine-3-sulfonamide | ¹H NMR (400 MHz, DMSO-$d_6$) δ ppm: 4.79 (s, 2 H), 6.80 (s, 1 H), 7.22-7.58 (m, 10 H), 7.75-7.89 (m, 3 H), 8.19 (s, 1 H), 8.35 (d, J = 4.8 Hz, 1 H), 12.28 (s, 1 H). | 1.47 B-79 474.0 |
| 154 | 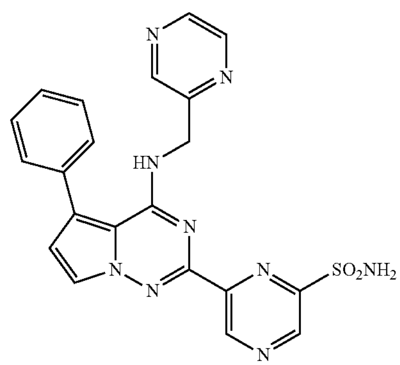 [SMILES: NS(=O)(=O)c1cncc(-c2nc(NCc3cnccn3)c3c(-c4ccccc4)ccn3n2)n1] | 6-(5-phenyl-4-((pyrazin-2-ylmethyl)amino)pyrrolo[2,1-f][1,2,4]triazin-2-yl)pyrazine-2-sulfonamide | ¹H NMR (400 MHz, DMSO-$d_6$) δ ppm: 5.02 (d, J = 4.8 Hz, 2 H), 6.91 (d, J = 2.8 Hz, 1 H), 7.24 (t, J = 5.2 Hz, 1 H), 7.44-7.62 (m, 5 H), 7.86 (br s, 2 H), 8.00 (d, J = 2.4 Hz, 1 H), 8.51-8.54 (m, 2 H), 8.84 (d, J = 1.6 Hz, 1 H), 9.21 (s, 1 H), 9.61 (s, 1 H). | 2.00 B-78 460.2 |
| 155 | 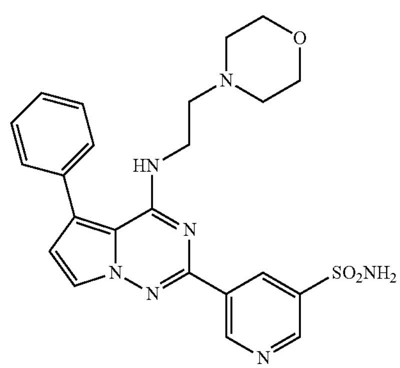 [SMILES: NS(=O)(=O)c1cncc(-c2nc(NCCN3CCOCC3)c3c(-c4ccccc4)ccn3n2)c1] | 5-(4-((2-morpholinoethyl)amino)-5-phenylpyrrolo[2,1-f][1,2,4]triazin-2-yl)pyridine-3-sulfonamide | ¹H NMR (400 MHz, DMSO-$d_6$) δ ppm: 2.28 (br s, 4 H), 2.52 (q, J = 6.0 Hz, 2 H), 3.35 (br s, 4 H), 3.73 (q, J = 5.2 Hz, 2 H), 6.47 (t, J = 4.8 Hz, 1 H), 6.80 (d, J = 2.8 Hz, 1 H), 7.43-7.56 (m, 5 H), 7.73 (br s, 2 H), 7.92 (d, J = 2.8 Hz, 1 H), 8.94 (t, J = 2.4 Hz, 1 H), 9.06 (d, J = 2.4 Hz, 1 H), 9.59 (d, J = 2.0 Hz, 1 H). | 1.65 B-79 480.0 |
| 156 | 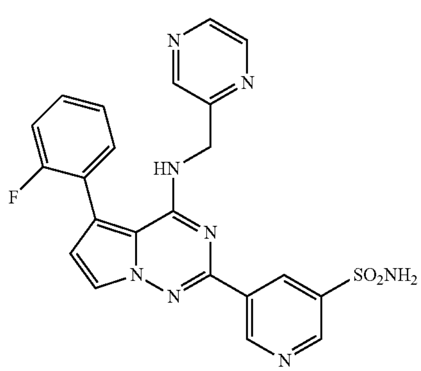 [SMILES: NS(=O)(=O)c1cncc(-c2nc(NCc3cnccn3)c3c(-c4ccccc4F)ccn3n2)c1] | 5-(5-(2-fluorophenyl)-4-((pyrazin-2-ylmethyl)amino)pyrrolo[2,1-f][1,2,4]triazin-2-yl)pyridine-3-sulfonamide | ¹H NMR (400 MHz, DMSO-$d_6$) δ ppm: 4.98 (s, 2 H), 6.85 (d, J = 2.4 Hz, 1 H), 7.23 (br s, 1 H), 7.33-7.41 (m, 2 H), 7.51-7.59 (m, 2 H), 7.71 (br s, 2 H), 7.99 (d, J = 2.8 Hz, 1 H), 8.49 (t, J = 1.6 Hz, 1 H), 8.53 (d, J = 2.4 Hz, 1 H), 8.74 (d, J = 1.2 Hz, 1 H), 8.88 (d, J = 2.0 Hz, 1 H), 9.05 (d, J = 2.0 Hz, 1 H), 9.50 (d, J = 2.0 Hz, 1 H). | 2.18 B-81 477.0 |

TABLE 1-continued

| Ex. No. | Structure | Name | ¹H NMR | LC/MS Rt (min) Condition [M + 1] |
|---|---|---|---|---|
| 157 | 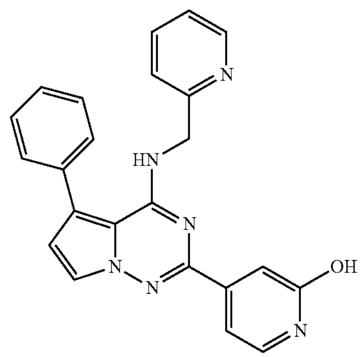 [SMILES: Oc1cc(-c2nc(NCc3ccccn3)c3c(-c4ccccc4)ccn3n2)ccn1] | 4-(5-phenyl-4-((pyridin-2-ylmethyl)amino)pyrrolo[2,1-f][1,2,4]triazin-2-yl)pyridin-2-ol | ¹H NMR (400 MHz, DMSO-$d_6$) δ ppm: 4.89 (d, J = 4.8 Hz, 2 H), 6.84 (d, J = 2.8 Hz, 1 H), 6.94 (dd, J = 1.6 Hz, J = 5.2 Hz, 1 H), 7.22 (d, J = 1.2 Hz, 1 H), 7.27-7.30 (m, 1 H), 7.34 (t, J = 4.8 Hz, 1 H), 7.43-7.59 (m, 7 H), 7.78 (dt, J = 2.0 Hz, J = 7.6 Hz, 1 H), 7.90 (d, J = 2.8 Hz, 1 H), 8.36 (dd, J = 0.8 Hz, J = 3.2 Hz, 1 H), 11.73 (br s, 1 H). | 2.10 B-80 393.0 [M-l] |
| 158 | 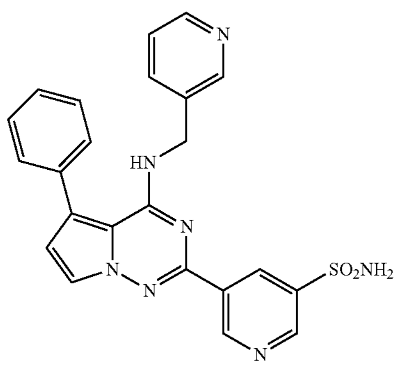 [SMILES: NS(=O)(=O)c1cncc(-c2nc(NCc3cccnc3)c3c(-c4ccccc4)ccn3n2)c1] | 5-(5-phenyl-4-(pyridin-3-ylmethylamino)pyrrolo[1,2-f][1,2,4]triazin-2-yl)pyridine-3-sulfonamide | ¹H NMR (400 MHz, DMSO-$d_6$) δ ppm: 4.86 (d, J = 6.0 Hz, 2 H), 6.81-6.86 (m, 1 H), 6.96 (t, J = 5.8 Hz, 1 H), 7.34-7.43 (m, 2 H), 7.45-7.62 (m, 4 H), 7.69-7.79 (m, 2 H), 7.80-7.85 (m, 1 H), 7.93-8.02 (m, 1 H), 8.46 (dd, J = 4.8 Hz, J = 1.8 Hz, 1 H), 8.65 (d, J = 1.5 Hz, 1 H), 8.86-8.98 (m, 1 H), 9.06 (d, J = 2.0 Hz, 1 H), 9.52 (d, J = 2.0 Hz, 1 H). | 2.01 B-78 458.0 |
| 159 | 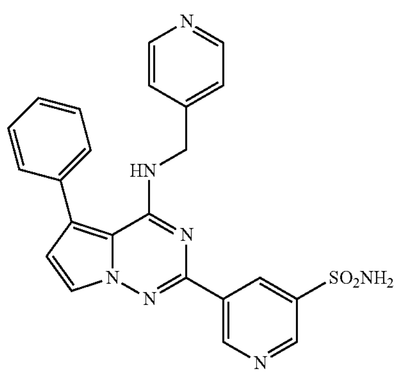 [SMILES: NS(=O)(=O)c1cncc(-c2nc(NCc3ccncc3)c3c(-c4ccccc4)ccn3n2)c1] | 3-(5-phenyl-4-(pyridin-4-ylmethylamino)pyrrolo[1,2-f][1,2,4]triazin-2-yl)benzenesulfonamide | ¹H NMR (400 MHz, DMSO-$d_6$) δ ppm: 4.85 (d, J = 6.0 Hz, 2 H), 6.80-6.87 (m, 1 H), 7.03 (t, J = 6.0 Hz, 1 H), 7.35-7.44 (m, 3 H), 7.45-7.53 (m, 2 H), 7.57-7.62 (m, 2 H), 7.72 (br s, 2 H), 7.93-8.00 (m, 1 H), 8.44-8.55 (m, 2 H), 8.84-8.90 (m, 1 H), 9.00-9.08 (m, 1 H), 9.43 (d, J = 2.0 Hz, 1 H). | 1.98 B-78 458.0 |
| 160 | 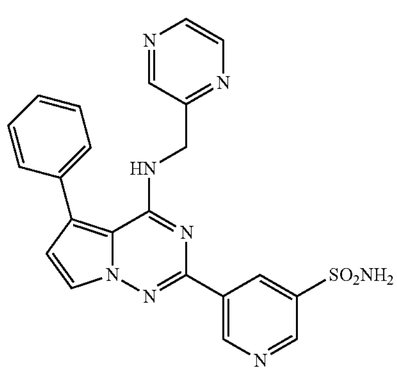 [SMILES: NS(=O)(=O)c1cncc(-c2nc(NCc3cnccn3)c3c(-c4ccccc4)ccn3n2)c1] | 5-(5-phenyl-4-(pyrazin-2-ylmethylamino)pyrrolo[1,2-f][1,2,4]triazin-2-yl)pyridine-3-sulfonamide | ¹H NMR (400 MHz, DMSO-$d_6$) δ ppm: 5.03 (d, J = 5.0 Hz, 2 H), 6.87 (d, J = 3.0 Hz, 1 H), 7.21 (t, J = 5.0 Hz, 1 H), 7.43-7.48 (m, 1 H), 7.51-7.57 (m, 2 H), 7.58-7.64 (m, 2 H), 7.73 (s, 2 H), 7.98 (d, J = 2.5 Hz, 1 H), 8.49-8.56 (m, 2 H), 8.78 (d, J = 1.5 Hz, 1 H), 8.89-8.92 (m, 1 H), 9.06 (d, J = 2.0 Hz, 1 H), 9.52 (d, J = 2.0 Hz, 1 H). | 1.56 B-79 459.0 |

TABLE 1-continued

| Ex. No. | Structure | Name | ¹H NMR | LC/MS Rt (min) Condition [M + 1] |
|---|---|---|---|---|
| 161 | 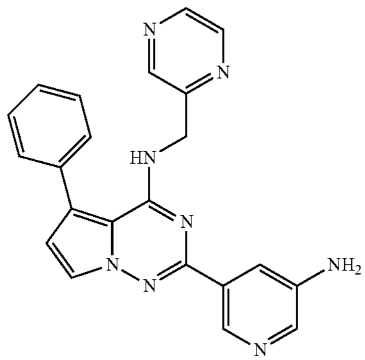 [SMILES: Nc1cncc(-c2nc(NCc3cnccn3)c3c(-c4ccccc4)ccn3n2)c1] | 2-(5-aminopyridin-3-yl)-5-phenyl-N-(pyrazin-2-ylmethyl)pyrrolo[1,2-f][1,2,4]triazin-4-amine | ¹H NMR (400 MHz, DMSO-d₆) δ ppm: 4.98 (s, 2 H), 5.45 (s, 2 H), 6.75-6.84 (m, 1 H), 7.03 (t, J = 5.3 Hz, 1 H), 7.39-7.47 (m, 1 H), 7.49-7.56 (m, 2 H), 7.57-7.62 (m, 2 H), 7.69-7.74 (m, 1 H), 7.86 (d, J = 2.5 Hz, 1 H), 8.00 (d, J = 3.0 Hz, 1 H), 8.47-8.57 (m, 3 H), 8.73-8.81 (m, 1 H). | 1.54 B-79 395.0 |
| 162 | 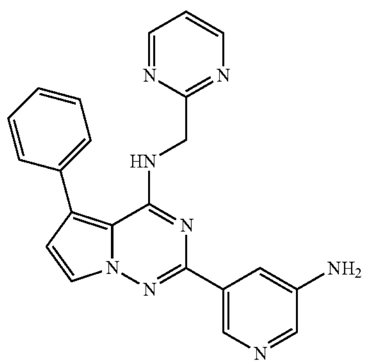 [SMILES: Nc1cncc(-c2nc(NCc3ncccn3)c3c(-c4ccccc4)ccn3n2)c1] | 2-(5-aminopyridin-3-yl)-5-phenyl-N-(pyrimidin-2-ylmethyl)pyrrolo[2,1-f][1,2,4]triazin-4-amine | ¹H NMR (400 MHz, DMSO-d₆) δ ppm: 5.00 (d, J = 4.5 Hz, 2 H), 5.47 (br s, 2 H), 6.78-6.85 (m, 1 H), 7.16 (t, J = 4.5 Hz, 1 H), 7.39-7.50 (m, 2 H), 7.51-7.59 (m, 2 H), 7.59-7.65 (m, 2 H), 7.75 (d, J = 1.5 Hz, 1 H), 7.83-7.90 (m, 1 H), 8.00 (d, J = 2.5 Hz, 1 H), 8.55 (d, J = 1.5 Hz, 1 H), 8.74 (d, J = 5.0 Hz, 2 H). | 1.34 B-83 395.0 |
| 163 | 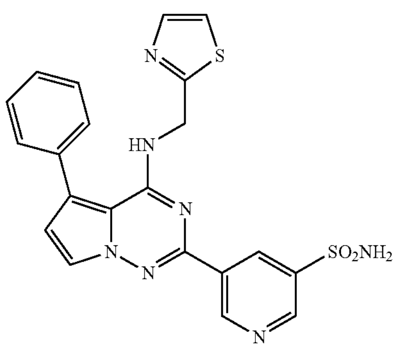 [SMILES: NS(=O)(=O)c1cncc(-c2nc(NCc3nccs3)c3c(-c4ccccc4)ccn3n2)c1] | 5-(5-phenyl-4-((thiazol-2-ylmethyl)amino)pyrrolo[2,1-f][1,2,4]triazin-2-yl)pyridine-3-sulfonamide | ¹H NMR (400 MHz, DMSO-d₆) δ ppm: 5.16 (s, 2 H), 6.88 (d, J = 2.8 Hz, 1 H), 7.42 (s, 1 H), 7.50-7.54 (m, 1 H), 7.55-7.60 (m, 4 H), 7.62 (d, J = 3.3 Hz, 1 H), 7.74 (d, J = 3.3 Hz, 3 H), 8.00 (d, J = 2.8 Hz, 1 H), 8.93 (t, J = 2.1 Hz, 1 H), 9.06 (d, J = 2.2 Hz, 1 H), 9.55 (d, J = 2.0 Hz, 1 H). | 2.18 B-81 464.0 |
| 164 | 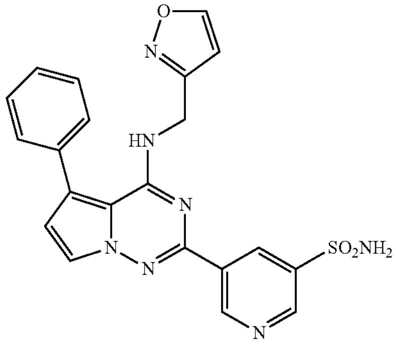 [SMILES: NS(=O)(=O)c1cncc(-c2nc(NCc3ccon3)c3c(-c4ccccc4)ccn3n2)c1] | 5-(4-((oxazol-4-ylmethyl)amino)-5-phenylpyrrolo[2,1-f][1,2,4]triazin-2-yl)pyridine-3-sulfonamide | ¹H NMR (400 MHz, DMSO-d₆) δ ppm: 4.94 (br s, 2 H), 6.61 (d, J = 1.5 Hz, 1 H), 6.86 (d, J = 2.8 Hz, 1 H), 6.96 (br s, 1 H), 7.39-7.46 (m, 1 H), 7.48-7.59 (m, 4 H), 7.71 (br s, 2 H), 7.98 (d, J = 2.8 Hz, 1 H), 8.84 (d, J = 1.8 Hz, 1 H), 8.91 (t, J = 2.1 Hz, 1 H), 9.06 (d, J = 2.3 Hz, 1 H), 9.54 (d, J = 2.0 Hz, 1 H). | 2.16 B-81 448.0 |

TABLE 1-continued

| Ex. No. | Structure | Name | $^1$H NMR | LC/MS Rt (min) Condition [M + 1] |
|---|---|---|---|---|
| 165 | 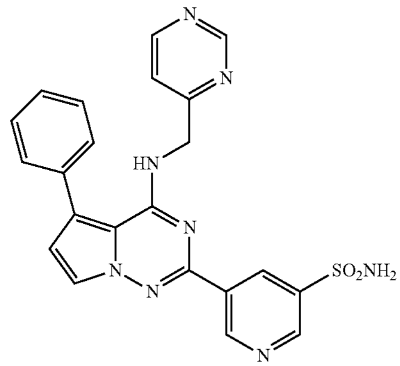 [SMILES: NS(=O)(=O)c1cncc(-c2nc(NCc3ccncn3)c3c(-c4ccccc4)ccn3n2)c1] | 5-(5-phenyl-4-((pyrimidin-4-ylmethyl)amino)pyrrolo[2,1-f][1,2,4]triazin-2-yl)pyridine-3-sulfonamide | $^1$H NMR (400 MHz, DMSO-$d_6$) δ ppm: 4.95 (d, J = 4.8 Hz, 2 H), 6.88 (d, J = 2.7 Hz, 1 H), 7.27 (s, 1 H), 7.48 (d, J = 7.3 Hz, 1 H), 7.52-7.64 (m, 5 H), 7.72 (br s, 2 H), 7.98 (d, J = 2.7 Hz, 1 H), 8.73 (d, J = 5.3 Hz, 1 H), 8.86 (t, J = 2.1 Hz, 1 H), 9.05 (dd, J = 4.9 Hz, J = 1.8 Hz, 2 H), 9.46 (d, J = 2.0 Hz, 1 H). | 2.07 B-81 459.2 |
| 166 | 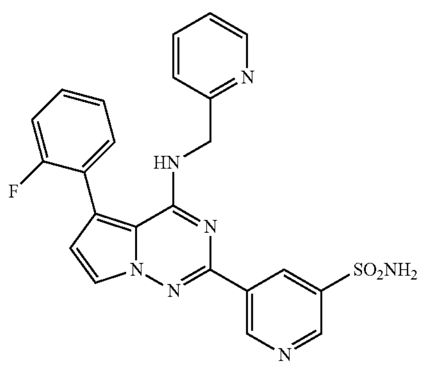 [SMILES: NS(=O)(=O)c1cncc(-c2nc(NCc3ccccn3)c3c(-c4ccccc4F)ccn3n2)c1] | 5-(5-(2-fluorophenyl)-4-((pyridin-2-ylmethyl)amino)pyrrolo[2,1-f][1,2,4]triazin-2-yl)pyridine-3-sulfonamide | $^1$H NMR (400 MHz, DMSO-$d_6$) δ ppm: 4.90 (d, J = 4.3 Hz, 2 H), 6.85 (d, J = 2.0 Hz, 1 H), 7.28 (d, J = 1.5 Hz, 1 H), 7.34-7.48 (m, 4 H), 7.55-7.61 (m, 2 H), 7.68-7.84 (m, 3 H), 7.98 (d, J = 2.8 Hz, 1 H), 8.32-8.36 (m, 1 H), 8.93 (t, J = 2.1 Hz, 1 H), 9.06 (d, J = 2.3 Hz, 1 H), 9.57 (d, J = 2.0 Hz, 1 H). | 2.22 B-81 476.0 |
| 167 | 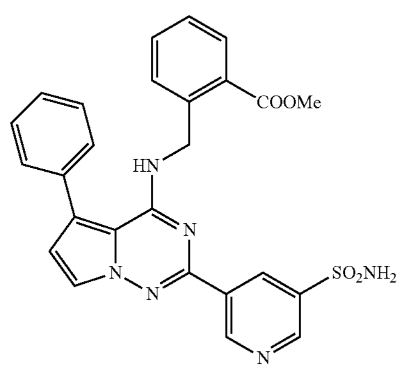 [SMILES: COC(=O)c1ccccc1CNc1nc(-c2cncc(S(N)(=O)=O)c2)nn2ccc(-c3ccccc3)c12] | methyl 2-(((5-phenyl-2-(5-sulfamoylpyridin-3-yl)pyrrolo[2,1-f][1,2,4]triazin-4-yl)amino)methyl)benzoate | $^1$H NMR (400 MHz, DMSO-$d_6$) δ ppm: 3.73 (s, 3 H), 5.09 (d, J = 6.5 Hz, 2 H), 6.80 (d, J = 3.0 Hz, 1 H), 6.93-6.94 (m, 1 H), 7.40-7.53 (m, 6 H), 7.60 (td, J = 1.5 Hz, J = 1.5 Hz, 1 H), 7.71 (d, J = 7.0 Hz, 1 H), 7.77 (s, 2 H), 7.91-7.96 (m, 2 H), 8.97-9.01 (m, 1 H), 9.09 (d, J = 2.0 Hz, 1 H), 9.59 (d, J = 2.0 Hz, 1 H). | 2.02 B-79 515.0 |
| 168 | 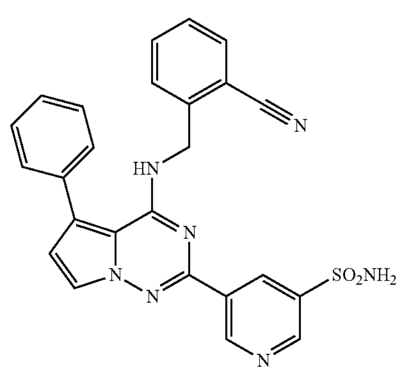 [SMILES: N#Cc1ccccc1CNc1nc(-c2cncc(S(N)(=O)=O)c2)nn2ccc(-c3ccccc3)c12] | 5-(4-((2-cyanobenzyl)amino)-5-phenylpyrrolo[2,1-f][1,2,4]triazin-2-yl)pyridine-3-sulfonamide | $^1$H NMR (400 MHz, DMSO-$d_6$) δ ppm: 5.00 (d, J = 4.5 Hz, 2 H), 6.87 (s, 1 H), 7.09-7.00 (m, 1 H), 7.43-7.36 (m, 1 H), 7.52-7.45 (m, 3 H), 7.62-7.57 (m, 2 H), 7.74-7.63 (m, 4 H), 7.86 (d, J = 7.0 Hz, 1 H), 7.99 (s, 1 H), 8.87 (d, J = 2.0 Hz, 1 H), 9.05 (s, 1 H), 9.45 (d, J = 2.0 Hz, 1 H). | 2.26 B-81 482.0 |

TABLE 1-continued

| Ex. No. | Structure | Name | ¹H NMR | LC/MS Rt (min) Condition [M + 1] |
|---|---|---|---|---|
| 169 | 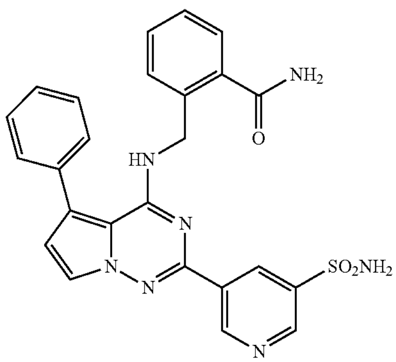 [SMILES: NC(=O)c1ccccc1CNc1nc(-c2cncc(S(N)(=O)=O)c2)nn2ccc(-c3ccccc3)c12] | 2-(((5-phenyl-2-(5-sulfamoylpyridin-3-yl)pyrrolo[2,1-f][1,2,4]triazin-4-yl)amino)methyl)benzamide | ¹H NMR (400 MHz, MD₃OD) δ ppm: 5.02 (s, 2 H), 6.74 (d, J = 3.0 Hz, 1 H), 7.31-7.42 (m, 2 H), 7.46-7.53 (m, 5 H), 7.55-7.65 (m, 2 H), 7.75 (d, J = 2.5 Hz, 1 H), 9.09 (s, 1 H), 9.15 (s, 1 H), 9.60 (s, 1 H). | 1.52 B-79 500.0 |
| 170 | Enatiomer-1 | 5-(5-phenyl-4-((5,6,7,8-tetrahydroquinolin-8-yl)amino)pyrrolo[2,1-f][1,2,4]triazin-2-yl)pyridine-3-sulfonamide | ¹H NMR (400 MHz, DMSO-d₆) δ ppm: 1.64-1.75 (m, 1 H), 1.86-2.09 (m, 2 H), 2.72-2.89 (m, 3 H), 5.27-5.43 (m, 1 H), 6.85 (d, J = 2.8 Hz, 1 H), 7.07 (d, J = 5.5 Hz, 1 H), 7.25-7.28 (m, 2 H), 7.31-7.39 (m, 2 H), 7.42-7.50 (m, 3 H), 7.55-7.63 (m, 2 H), 7.98 (d, J = 2.7 Hz, 1 H), 8.33 (dd, J = 4.6 Hz, J = 1.5 Hz, 1 H), 8.97 (t, J = 2.1 Hz, 1 H), 9.08 (d, J = 2.3 Hz, 1 H), 9.59 (d, J = 2.0 Hz, 1 H). | 2.67 B-81 498.0 Chiral HPLC: (B-105 7.90 min) |
| 171 | Enatiomer-2 | 5-(5-phenyl-4-((5,6,7,8-tetrahydroquinolin-8-yl)amino)pyrrolo[2,1-f][1,2,4]triazin-2-yl)pyridine-3-sulfonamide | ¹H NMR (400 MHz, DMSO-d₆) δ ppm: 1.64-1.75 (m, 1 H), 1.86-2.09 (m, 2 H), 2.72-2.89 (m, 3 H), 5.27-5.43 (m, 1 H), 6.85 (d, J = 2.8 Hz, 1 H), 7.07 (d, J = 5.5 Hz, 1 H), 7.25-7.28 (m, 2 H), 7.31-7.39 (m, 2 H), 7.42-7.50 (m, 3 H), 7.55-7.63 (m, 2 H), 7.98 (d, J = 2.7 Hz, 1 H), 8.33 (dd, J = 4.6 Hz, J = 1.5 Hz, 1 H), 8.97 (t, J = 2.1 Hz, 1 H), 9.08 (d, J = 2.3 Hz, 1 H), 9.59 (d, J = 2.0 Hz, 1 H). | 2.61 B-81 498.0 Chiral HPLC: (B-106 15.5 min) |

TABLE 1-continued

| Ex. No. | Structure | Name | $^1$H NMR | LC/MS Rt (min) Condition [M + 1] |
|---|---|---|---|---|
| 172 | 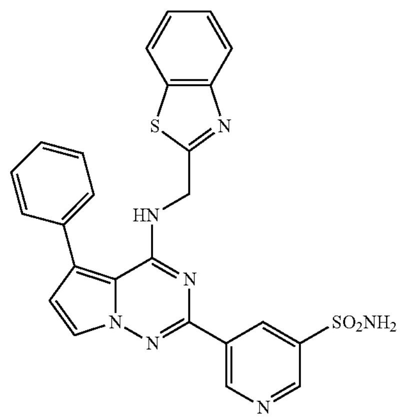 [SMILES: NS(=O)(=O)c1cncc(-c2nc(NCc3nc4ccccc4s3)c3c(-c4ccccc4)ccn3n2)c1] | 5-(4-((benzo[d]thiazol-2-ylmethyl)amino)-5-phenylpyrrolo[2,1-f][1,2,4]triazin-2-yl)pyridine-3-sulfonamide | $^1$H NMR (400 MHz, DMSO-d$_6$) δ ppm: 5.29 (d, J = 5.7 Hz, 2 H), 6.91 (d, J = 2.7 Hz, 1 H), 7.38-7.56 (m, 6 H), 7.59-7.65 (m, 2 H), 7.73 (s, 2 H), 7.92-7.98 (m, 1 H), 8.03-8.10 (m, 2 H), 8.94 (t, J = 2.1 Hz, 1 H), 9.05 (d, J = 2.3 Hz, 1 H), 9.56 (d, J = 2.0 Hz, 1 H). | 1.93 B-79 514.0 |
| 173 | 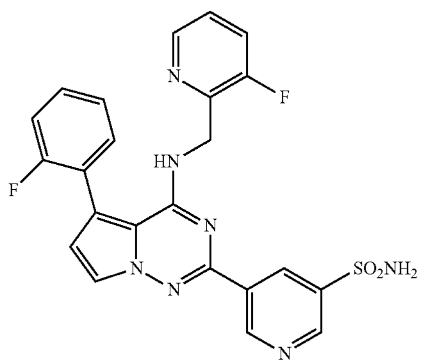 [SMILES: NS(=O)(=O)c1cncc(-c2nc(NCc3ncccc3F)c3c(-c4ccccc4F)ccn3n2)c1] | 5-(5-(2-fluorophenyl)-4-(((3-fluoropyridin-2-yl)methyl)amino)pyrrolo[2,1-f][1,2,4]triazin-2-yl)pyridine-3-sulfonamide | $^1$H NMR (400 MHz, DMSO-d$_6$) δ ppm: 4.96 (d, J = 3.8 Hz, 2 H), 6.87 (dd, J = 2.7 Hz, J = 0.7 Hz, 1 H), 7.28-7.49 (m, 4 H), 7.56-7.64 (m, 2 H), 7.71-7.82 (m, 3 H), 8.00 (d, J = 2.7 Hz, 1 H), 8.18 (dt, J = 4.7 Hz, J = 1.4 Hz, 1 H), 8.95 (t, J = 2.1 Hz, 1 H), 9.09 (d, J = 2.3 Hz, 1 H), 9.60 (d, J = 1.9 Hz, 1 H). | 1.75 B-79 494.0 |
| 174 | 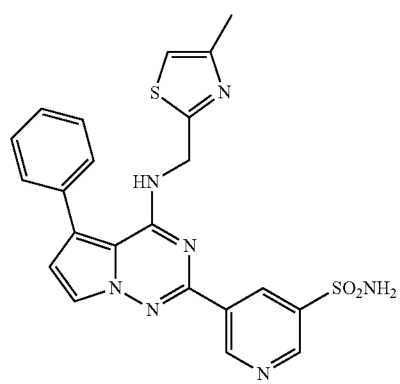 [SMILES: Cc1csc(CNc2nc(-c3cncc(S(N)(=O)=O)c3)nn3ccc(-c4ccccc4)c23)n1] | 5-(4-(((4-methylthiazol-2-yl)methyl)amino)-5-phenylpyrrolo[2,1-f][1,2,4]triazin-2-yl)pyridine-3-sulfonamide | $^1$H NMR (400 MHz, DMSO-d$_6$) δ ppm: 2.33 (d, J = 1.0 Hz, 3 H), 5.10 (d, J = 5.5 Hz, 2 H), 6.87 (d, J = 2.8 Hz, 1 H), 7.15 (d, J = 1.0 Hz, 1 H), 7.22 (s, 1 H), 7.44 (d, J = 7.2 Hz, 1 H), 7.48-7.61 (m, 4 H), 7.74 (s, 2 H), 8.00 (d, J = 2.8 Hz, 1 H), 8.94 (t, J = 2.1 Hz, 1 H), 9.07 (d, J = 2.3 Hz, 1 H), 9.58 (d, J = 2.0 Hz, 1 H). | 1.66 B-83 478.0 |
| 175 | 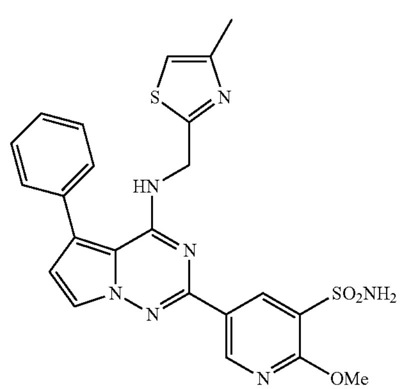 [SMILES: COc1ncc(-c2nc(NCc3nc(C)cs3)c3c(-c4ccccc4)ccn3n2)cc1S(N)(=O)=O] | 2-methoxy-5-(4-(((4-methylthiazol-2-yl)methyl)amino)-5-phenylpyrrolo[2,1-f][1,2,4]triazin-2-yl)pyridine-3-sulfonamide | $^1$H NMR (400 MHz, DMSO-d$_6$) δ ppm: 2.34 (d, J = 1.0 Hz, 3 H), 3.69 (s, 3 H), 5.10 (d, J = 5.6 Hz, 2 H), 6.79 (d, J = 2.7 Hz, 1 H), 6.94-7.23 (m, 4 H), 7.43 (d, J = 7.2 Hz, 1 H), 7.45-7.62 (m, 4 H), 7.92 (d, J = 2.7 Hz, 1 H), 8.77 (d, J = 2.6 Hz, 1 H), 8.90 (d, J = 2.5 Hz, 1 H). | 1.63 B-79 509.0 |

TABLE 1-continued

| Ex. No. | Structure | Name | ¹H NMR | LC/MS Rt (min) Condition [M + 1] |
|---|---|---|---|---|
| 176 | 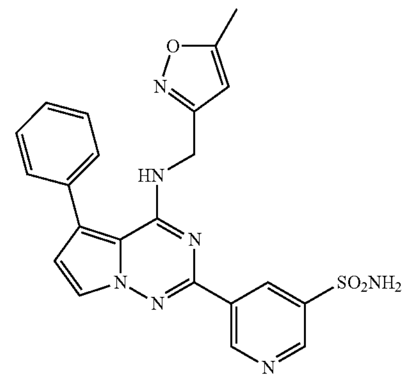 [SMILES: Cc1cc(CNc2nc(-c3cncc(S(N)(=O)=O)c3)nn3ccc(-c4ccccc4)c23)no1] | 5-(4-(((5-methylisoxazol-3-yl)methyl)amino)-5-phenylpyrrolo[2,1-f][1,2,4]triazin-2-yl)pyridine-3-sulfonamide | ¹H NMR (400 MHz, DMSO-d₆) δ ppm: 2.37 (s, 3 H), 4.87 (d, J = 5.5 Hz, 2 H), 6.25 (d, J = 1.0 Hz, 1 H), 6.87 (d, J = 2.5 Hz, 1 H), 6.91 (t, J = 5.5 Hz, 1 H), 7.40-7.46 (m, 1 H), 7.49-7.59 (m, 4 H), 7.74 (s, 2 H), 7.99 (d, J = 3.0 Hz, 1 H), 8.91-8.95 (m, 1 H), 9.07 (d, J = 2.5 Hz, 1 H), 9.57 (d, J = 2.0 Hz, 1 H). | 1.98 B-86 462.2 |
| 177 | 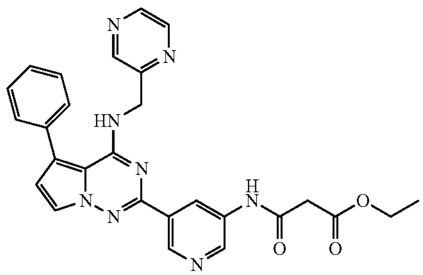 [SMILES: CCOC(=O)CC(=O)Nc1cncc(-c2nc(NCc3cnccn3)c3c(-c4ccccc4)ccn3n2)c1] | ethyl 3-oxo-3-((5-(5-phenyl-4-((pyrazin-2-ylmethyl)amino)pyrrolo[2,1-f][1,2,4]triazin-2-yl)pyridin-3-yl)amino)propanoate | ¹H NMR (400 MHz, DMSO-d₆) δ ppm: 1.24 (t, J = 7.1 Hz, 3 H), 3.55 (s, 2 H), 4.16 (q, J = 7.1 Hz, 2 H), 5.00 (d, J = 5.1 Hz, 2 H), 6.84 (d, J = 2.8 Hz, 1 H), 7.13 (s, 1 H), 7.42-7.49 (m, 1 H), 7.51-7.65 (m, 4 H), 7.94 (d, J = 2.7 Hz, 1 H), 8.49-8.58 (m, 2 H), 8.72-8.88 (m, 3 H), 9.07 (d, J = 1.3 Hz, 1 H), 10.57 (s, 1 H). | 1.71 B-79 509.0 |
| 178 | 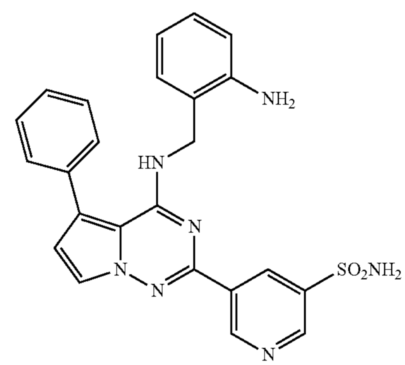 [SMILES: Nc1ccccc1CNc1nc(-c2cncc(S(N)(=O)=O)c2)nn2ccc(-c3ccccc3)c12] | 5-(4-((2-aminobenzyl)amino)-5-phenylpyrrolo[2,1-f][1,2,4]triazin-2-yl)pyridine-3-sulfonamide | ¹H NMR (400 MHz, DMSO-d₆) δ ppm: 4.72 (d, J = 5.6 Hz, 2 H), 5.13 (s, 2 H), 6.49-6.54 (m, 2 H), 6.66 (dd, J = 0.8 Hz, J = 8.0 Hz, 1 H), 6.82 (d, J = 2.8 Hz, 1 H), 6.98 (dt, J = 1.6 Hz, J = 8.8 Hz, 1 H), 7.11 (dd, J = 1.2 Hz, J = 7.6 Hz, 1 H), 7.35-7.53 (m, 5 H), 7.50 (s, 2 H), 7.93 (d, J = 2.8 Hz, 1 H), 8.99 (dd, J = 2.0 Hz, J = 2.4 Hz, 1 H), 9.08 (d, J = 2.4 Hz, 1 H), 9.63 (d, J = 2.0 Hz, 1 H). | 1.81 B-79 472.0 |
| 179 | 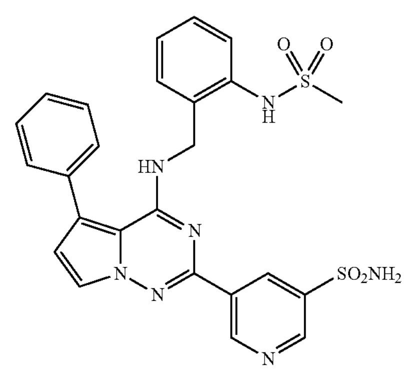 [SMILES: CS(=O)(=O)Nc1ccccc1CNc1nc(-c2cncc(S(N)(=O)=O)c2)nn2ccc(-c3ccccc3)c12] | 5-(4-((2-(methylsulfonamido)benzyl)amino)-5-phenylpyrrolo[2,1-f][1,2,4]triazin-2-yl)pyridine-3-sulfonamide | ¹H NMR (400 MHz, DMSO-d₆) δ ppm: 2.95 (s, 3 H), 4.99 (d, J = 5.6 Hz, 2 H), 6.67 (t, J = 5.6 Hz, 1 H), 6.83 (d, J = 2.8 Hz, 1 H), 7.23-7.38 (m, 4 H), 7.42-7.53 (m, 5 H), 7.72 (s, 2 H), 7.96 (d, J = 2.8 Hz, 1 H), 8.93 (t, J = 2.0 Hz, 1 H), 9.06 (d, J = 2.0 Hz, 1 H), 9.25 (br s, 1 H), 9.55 (d, J = 2.0 Hz, 1 H). | 1.72 B-79 550.0 |

TABLE 1-continued

| Ex. No. | Structure | Name | $^1$H NMR | LC/MS Rt (min) Condition [M + 1] |
|---|---|---|---|---|
| 180 | 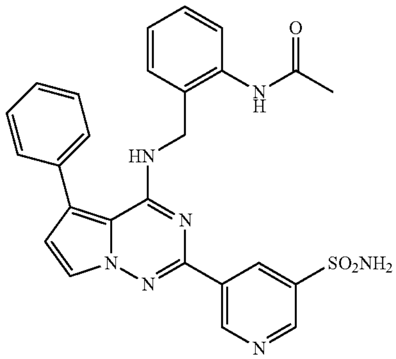 [SMILES: CC(=O)Nc1ccccc1CNc1nc(-c2cncc(S(N)(=O)=O)c2)nn2ccc(-c3ccccc3)c12] | N-(2-(((5-phenyl-2-(5-sulfamoylpyridin-3-yl)pyrrolo[2,1-f][1,2,4]triazin-4-yl)amino)methyl)phenyl)acetamide | $^1$H NMR (400 MHz, DMSO-d$_6$) δ ppm: 1.94 (s, 3 H), 4.85 (d, J = 5.6 Hz, 2 H), 6.61 (dd, J = 5.6 Hz, J = 6.0 Hz, 1 H), 6.82 (d, J = 2.8 Hz, 1 H), 7.15 -7.27 (m, 2 H), 7.35-7.52 (m, 7 H), 7.73 (br s, 2 H), 7.95 (d, J = 2.8 Hz, 1 H), 8.95 (t, J = 2.0 Hz, 1 H), 9.06 (d, J = 2.0 Hz, 1 H), 9.51 (s, 1 H), 9.57 (d, J = 2.0 Hz, 1 H). | 1.64 B-79 514.0 |
| 181 | 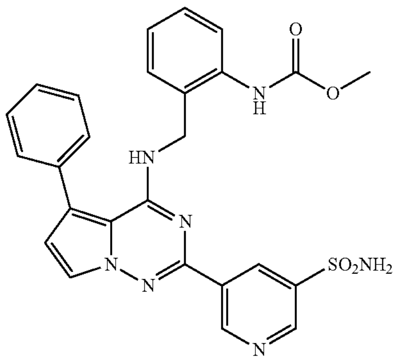 [SMILES: COC(=O)Nc1ccccc1CNc1nc(-c2cncc(S(N)(=O)=O)c2)nn2ccc(-c3ccccc3)c12] | methyl (2-(((5-phenyl-2-(5-sulfamoylpyridin-3-yl)pyrrolo[2,1-f][1,2,4]triazin-4-yl)amino)methyl)phenyl)carbamate | $^1$H NMR (400 MHz, DMSO-d$_6$) δ ppm: 3.53 (s, 3 H), 4.88 (d, J = 6.0 Hz, 2 H), 6.62 (dd, J = 5.6 Hz, J = 6.0 Hz, 1 H), 6.82 (d, J = 2.8 Hz, 1 H), 7.13 (dt, J = 1.2 Hz, J = 7.6 Hz, 1 H), 7.26 (dt, J = 1.2 Hz, J = 8.0 Hz, 1 H), 7.35-7.50 (m, 7 H), 7.73 (s, 2 H), 7.96 (d, J = 2.8 Hz, 1 H), 8.95 (t, J = 2.0 Hz, 1 H), 9.06 (d, J = 2.0 Hz, 1 H), 9.10 (s, 1 H), 9.59 (d, J = 2.0 Hz, 1 H). | 1.81 B-79 530.0 |
| 182 | 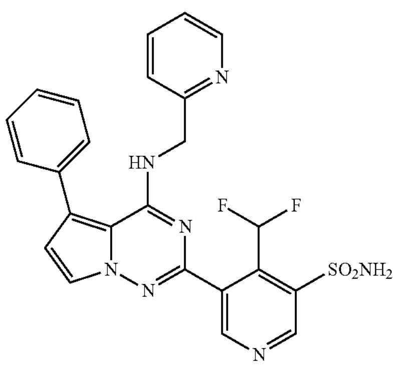 [SMILES: NS(=O)(=O)c1cncc(-c2nc(NCc3ccccn3)c3c(-c4ccccc4)ccn3n2)c1C(F)F] | 4-(difluoromethyl)-5-(5-phenyl-4-((pyridin-2-ylmethyl)amino)pyrrolo[2,1-f][1,2,4]triazin-2-yl)pyridine-3-sulfonamide | $^1$H NMR (400 MHz, DMSO-d$_6$) δ ppm: 4.76 (d, J = 4.8 Hz, 2 H), 6.83 (d, J = 2.4 Hz, 1 H), 7.26-7.78 (m, 10 H), 7.87 (d, J = 2.4 Hz, 1 H), 7.95-8.03 (br s, 2 H), 8.33-8.35 (m, 1 H), 9.06 (s, 1 H), 9.25 (s, 1 H). | 2.20 B-78 508.2 |
| 183 | 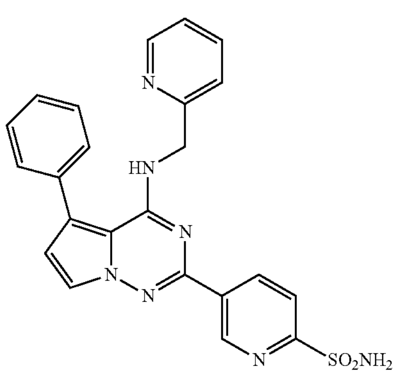 [SMILES: NS(=O)(=O)c1ccc(-c2nc(NCc3ccccn3)c3c(-c4ccccc4)ccn3n2)cn1] | 5-(5-phenyl-4-((pyridin-2-ylmethyl)amino)pyrrolo[2,1-f][1,2,4]triazin-2-yl)pyridine-2-sulfonamide | $^1$H NMR (400 MHz, DMSO-d$_6$) δ ppm: 4.95 (d, J = 4.5 Hz, 2 H), 6.86 (d, J = 2.5 Hz, 1 H), 7.26-7.34 (m, 1 H), 7.40 (br s, 1 H), 7.45-7.63 (m, 8 H), 7.80 (td, J = 7.7 Hz, J = 1.8 Hz, 1 H), 7.96 (d, J = 3.0 Hz, 1 H), 8.07 (d, J = 7.5 Hz, 1 H), 8.40 (d, J = 4.0 Hz, 1 H), 8.80 (dd, J = 8.3 Hz, J = 2.3 Hz, 1 H), 9.46 (d, J = 1.5 Hz, 1 H). | 1.77 B-79 458.0 |

TABLE 1-continued

| Ex. No. | Structure | Name | ¹H NMR | LC/MS Rt (min) Condition [M + 1] |
|---|---|---|---|---|
| 184 | 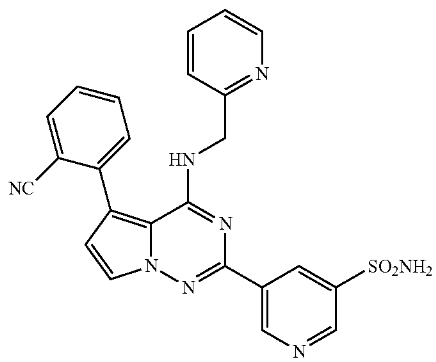 [SMILES: N#Cc1ccccc1-c1ccn2nc(-c3cncc(S(N)(=O)=O)c3)nc(NCc3ccccn3)c12] | 5-(5-(2-cyanophenyl)-4-((pyridin-2-ylmethyl)amino)pyrrolo[2,1-f][1,2,4]triazin-2-yl)pyridine-3-sulfonamide | ¹H NMR (400 MHz, DMSO-$d_6$) δ ppm: 4.90 (br s, 2 H), 6.96 (d, J = 2.8 Hz, 1 H), 7.26-7.29 (m, 1 H), 7.36 (br s, 1 H), 7.47 (d, J = 8.0 Hz, 1 H), 7.69-7.87 (m, 6 H), 8.02-8.05 (m, 2 H), 8.31-8.33 (m, 1 H), 8.93 (dd, J = 2.0 Hz, J = 2.4 Hz, 1 H), 9.07 (d, J = 2.4 Hz, 1 H), 9.56 (d, J = 2.0 Hz, 1 H). | 2.20 B-81 483.0 |
| 185 | 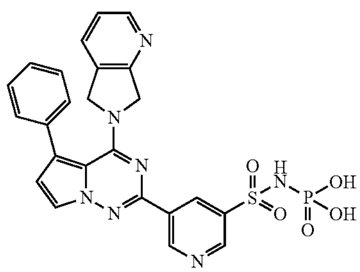 [SMILES: O=P(O)(O)NS(=O)(=O)c1cncc(-c2nc(N3Cc4cccnc4C3)c3c(-c4ccccc4)ccn3n2)c1] | 5-(5-phenyl-4-(5H-pyrrolo[3,4-b]pyridin-6(7H)-yl)pyrrolo[1,2-f][1,2,4]triazin-2-yl)pyridin-3-ylsulfonylphosphoramidic acid | ¹H NMR (300 MHz, DMSO-$d_6$) δ ppm: 4.84 (s, 2 H), 5.00 (s, 2 H), 6.86 (d, J = 2.8 Hz, 2 H), 7.25 (dd, J = 7.6 Hz, J = 4.9 Hz, 2 H), 7.39-7.54 (m, 6 H), 7.55 (d, J = 1.6 Hz, 1 H), 8.04 (d, J = 2.7 Hz, 1 H), 8.35 (d, J = 4.7 Hz, 1 H), 8.94-8.98 (m, 1 H), 9.09 (d, J = 1.8 Hz, 1 H), 9.48 (d, J = 1.9 Hz, 1 H). | 1.93 B-81 550.2 |

UTILITY

In general, compounds of the present invention, such as particular compounds disclosed in the preceding examples, have been shown to inhibit the $K_v1$ subfamily of voltage-gated $K^+$ channels (for example, by displaying % inhibition values ≥14%, preferably ≥30%, more preferably ≥40%, even more preferably ≥50%, at 0.3 micromolar concentration in an assay such as those set forth below). By displaying activity as inhibitors of the $K_v1$ subfamily of voltage-gated $K^+$ channels, compounds of the present invention are expected to be useful in the treatment of human diseases associated with the $K_v1$ subfamily of voltage-gated $K^+$ channels.

Assays to determine the degree of activity of a compound as an $I_{Kur}$ inhibitor are well known in the art and are described in references such as *J. Gen. Physiol.*, 101(4):513-543 (April 1993), and *Br. J. Pharmacol.*, 115(2):267-274 (May 1995).

Assays to determine the degree of activity of a compound as an inhibitor of other members of the $K_v1$ subfamily are also well known in the art. For example, inhibition of $K_v1.1$, $K_v1.2$ and $K_v1.3$ can be measured using procedures described by Grissmer, S. et al., *Mol. Pharmacol.*, 45(6):1227-1234 (June 1994); inhibition of $K_v1.4$ can be measured using procedures described by Petersen, K. R. et al., *Pflugers Arch.*, 437(3):381-392 (February 1999); inhibition of $K_v1.6$ can be measured using procedures described by Bowlby, M. R. et al., *J. Neurophysiol.* 73(6):2221-2229 (June 1995); and inhibition of $K_v1.7$ can be measured using procedures described by Kalman, K. et al., *J. Biol. Chem.*, 273(10):5851-5857 (Mar. 6, 1998).

The Examples, as shown in Table 2, were assayed for block of $I_{Kur}$ current in patch clamped mammalian L-929 cells which were injected with human $K_v1.5$ mRNA and stably expressed $I_{Kur}$ protein (as described in the references described below). Inhibition data at 0.3 mM concentration for the Examples are shown in Table 2.

1. Synders, D. J. et al., "A rapidly activating and slowly inactivating potassium channel cloned from human heart: functional analysis after stable mammalian cell culture expression", *J. Gen. Physiol.*, 101:513-543 (1993).
2. Zhou, Z. et al., "Block of HERG potassium channels by the antihistamine astemizole and its metabolites desmethylastemizole and norastemizole", *J. Cardiovasc. Electrophysiol.*, 10(6):836-843 (1999).

TABLE 2

| Example No. | KV1_5% Inh L929 @0.3 μM |
|---|---|
| 1 | 96.51 |
| 2 | 98.51 |
| 3 | 94.07 |
| 4 | 97.34 |
| 5 | 98.46 |
| 6 | 91.69 |
| 7 | 97.77 |
| 8 | 97.49 |
| 8 | 95.79 |
| 9 | 98.44 |
| 10 | 85.97 |
| 11 | 93.42 |
| 12 | 88.20 |
| 13 | 95.89 |
| 14 | 95.03 |
| 14 | 90.60 |
| 15 | 95.51 |
| 16 | 91.10 |
| 17 | 92.44 |
| 18 | 40.90 |
| 18 | 47.37 |
| 19 | 91.34 |
| 20 | 96.56 |

TABLE 2-continued

| Example No. | KV1_5% Inh L929 @0.3 µM |
|---|---|
| 21 | 93.21 |
| 21 | 96.63 |
| 22 | 95.08 |
| 23 | 91.59 |
| 24 | 63.49 |
| 25 | 96.85 |
| 26 | 94.45 |
| 27 | 93.18 |
| 28 | 97.52 |
| 30 | 96.31 |
| 31 | 98.59 |
| 32 | 99.28 |
| 33 | 87.82 |
| 33 | 95.01 |
| 34 | 97.27 |
| 35 | 92.85 |
| 36 | 46.01 |
| 37 | 98.60 |
| 38 | 97.45 |
| 39 | 97.08 |
| 40 | 40.39 |
| 41 | 95.08 |
| 42 | 99.37 |
| 43 | 98.58 |
| 44 | 98.77 |
| 45 | 90.13 |
| 46 | (prodrug) |
| 47 | 94.85 |
| 48 | 96.58 |
| 49 | 84.92 |
| 50 | 97.75 |
| 51 | 88.19 |
| 52 | 96.12 |
| 53 | 98.09 |
| 54 | 90.24 |
| 55 | 20.62 |
| 56 | 93.75 |
| 57 | 95.45 |
| 58 | 96.07 |
| 59 | 96.97 |
| 60 | 97.63 |
| 61 | 89.95 |
| 62 | 97.90 |
| 63 | 97.75 |
| 64 | 97.57 |
| 65 | 97.73 |
| 66 | 89.17 |
| 67 | 97.79 |
| 68 | 28.12 |
| 69 | 80.28 |
| 70 | 85.44 |
| 71 | 89.08 |
| 72 | 95.51 |
| 73 | 88.31 |
| 74 | 96.72 |
| 75 | 90.89 |
| 76 | 93.76 |
| 77 | 95.70 |
| 78 | 22.89 |
| 79 | 95.98 |
| 80 | 96.88 |
| 81 | 96.97 |
| 82 | 17.63 |
| 83 | 89.79 |
| 84 | 85.88 |
| 85 | 96.35 |
| 86 | 86.29 |
| 87 | 90.96 |
| 88 | 27.22 |
| 89 | 97.02 |
| 90 | 96.05 |
| 91 | 61.67 |
| 92 | 88.19 |
| 93 | 41.02 |
| 94 | 95.75 |
| 95 | 98.08 |
| 96 | 95.70 |
| 97 | 96.86 |
| 98 | 55.34 |
| 99 | 92.22 |
| 100 | 96.93 |
| 101 | 93.63 |
| 102 | 98.89 |
| 103 | 72.17 |
| 104 | 95.68 |
| 105 | 89.34 |
| 106 | 15.97 |
| 107 | 15.60 |
| 108 | 71.95 |
| 109 | 98.22 |
| 110 | 81.42 |
| 111 | 97.02 |
| 112 | 98.95 |
| 113 | 88.42 |
| 114 | 35.18 |
| 115 | 90.00 |
| 116 | 89.40 |
| 117 | 86.58 |
| 118 | 45.03 |
| 119 | 67.53 |
| 120 | 48.96 |
| 121 | 38.74 |
| 122 | 75.78 |
| 123 | 63.55 |
| 124 | 86.43 |
| 125 | 88.67 |
| 126 | 98.54 |
| 127 | 99.27 |
| 128 | 95.43 |
| 129 | 93.80 |
| 130 | 97.64 |
| 131 | 83.91 |
| 134 | 95.04 |
| 135 | 98.49 |
| 136 | 98.67 |
| 137 | 82.88 |
| 138 | 96.17 |
| 139 | 98.54 |
| 140 | 99.13 |
| 141 | 87.71 |
| 142 | 97.20 |
| 143 | 93.80 |
| 144 | 98.98 |
| 145 | 62.46 |
| 146 | 78.73 |
| 147 | 97.31 |
| 148 | 84.81 |
| 149 | 95.84 |
| 150 | 97.48 |
| 151 | 94.23 |
| 152 | 97.26 |
| 153 | 79.91 |
| 154 | 89.47 |
| 155 | 30.16 |
| 156 | 98.45 |
| 157 | 94.46 |
| 158 | 92.01 |
| 159 | 89.98 |
| 160 | 94.65 |
| 161 | 97.94 |
| 162 | 95.58 |
| 163 | 97.55 |
| 164 | 96.45 |
| 165 | 90.30 |
| 166 | 97.96 |
| 167 | 89.85 |
| 168 | 86.75 |
| 169 | 62.17 |
| 170 | 96.42 |
| 171 | 97.64 |
| 172 | 84.33 |
| 173 | 98.68 |
| 174 | 97.20 |
| 175 | 97.07 |

TABLE 2-continued

| Example No. | KV1_5% Inh L929 @0.3 μM |
|---|---|
| 176 | 96.05 |
| 177 | 96.72 |
| 178 | 99.16 |
| 179 | 90.06 |
| 180 | 36.93 |
| 181 | 96.01 |
| 182 | 93.74 |
| 183 | 97.83 |
| 184 | 80.90 |
| 185 | Prodrug |

Examples 46 and 185 are prodrugs. Prodrugs prepared as described had significantly increased solubility at pH 7 and demonstrated an improved profile with respect to pH dependent solubility. Prodrugs would be expected to cleave to the respective parent compound with $K_v1.5$ activity on oral dosing. Therefore, Examples 46 and 185, and other prodrugs, may be useful in the inhibition of potassium channel function and may be useful in the treatment and prevention of arrhythmia, $I_{Kur}$-associated disorders, and other disorders mediated by ion channel function, by providing the active compounds which have been shown to be an inhibitor of potassium channel function.

Compounds within the scope of the present invention inhibit the $K_v1$ subfamily of voltage-gated $K^+$ channels, and as such are believed to be useful in the treatment and/or prevention of various disorders: cardiac arrhythmias, including supraventricular arrhythmias, atrial arrhythmias, atrial flutter, atrial fibrillation, complications of cardiac ischemia, and use as heart rate control agents, including maintaining normal sinus rhythm; angina pectoris including relief of Prinzmetal's symptoms, vasospastic symptoms and variant symptoms; gastrointestinal disorders including reflux esophagitis, functional dyspepsia, motility disorders (including constipation and diarrhea), and irritable bowel syndrome; disorders of vascular and visceral smooth muscle including asthma, chronic obstructive pulmonary disease, adult respiratory distress syndrome, peripheral vascular disease (including intermittent claudication), venous insufficiency, impotence, cerebral and coronary spasm and Raynaud's disease; inflammatory and immunological disease including inflammatory bowel disease, rheumatoid arthritis, graft rejection, asthma. chronic obstructive pulmonary disease, cystic fibrosis and atherosclerosis; cell proliferative disorders including restenosis and cancer (including leukemia); disorders of the auditory system; disorders of the visual system including macular degeneration and cataracts; diabetes including diabetic retinopathy, diabetic nephropathy and diabetic neuropathy; muscle disease including myotonia and wasting; peripheral neuropathy; cognitive disorders; migraine; memory loss including Alzheimer's and dementia; CNS mediated motor dysfunction including Parkinson's disease, and ataxia; epilepsy; and other ion channel mediated disorders.

As inhibitors of the $K_v1$ subfamily of voltage-gated $K^+$ channels compounds of the present invention are believed to be useful to treat a variety of further disorders including resistance by transplantation of organs or tissue, graft-versus-host diseases brought about by medulla ossium transplantation, rheumatoid arthritis, systemic lupus erythematosus, Hashimoto's thyroiditis, multiple sclerosis, myasthenia gravis, type I diabetes uveitis, juvenile-onset or recent-onset diabetes mellitus, posterior uveitis, allergic encephalomyelitis, glomerulonephritis, infectious diseases caused by pathogenic microorganisms, inflammatory and hyperproliferative skin diseases, psoriasis, atopical dermatitis, contact dermatitis, eczematous dermatitises, seborrhoeic dermatitis, Lichen planus, Pemphigus, bullous pemphigoid, Epidermolysis bullosa, urticaria, angioedemas, vasculitides, erythemas, cutaneous eosinophilias, Lupus erythematosus, acne, Alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer Scleritis, Graves' ophthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns and leukotriene B4-mediated diseases, Coeliaz diseases, proctitis, eosinophilic gastroenteritis, mastocytosis, Crohn's disease, ulcerative colitis, migraine, rhinitis, eczema, interstitial nephritis, Good-pasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, arteriosclerosis, atherosclerosis, aortitis syndrome, polyarteritis nodosa, myocardosis, scleroderma, Wegener's granuloma, Sjögren's syndrome, adiposis, eosinophilic fascitis, lesions of gingiva, periodontium, alveolar bone, substantia osses dentis, glomerulonephritis, male pattern alopecia or alopecia senilis by preventing epilation or providing hair germination and/or promoting hair generation and hair growth, muscular dystrophy; Pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis, pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenis, metastatis of carcinoma and hypobaropathy, disease caused by histamine or leukotriene-C4 release, Behcet's disease, autoimmune hepatitis, primary biliary cirrhosis sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augention of chemotherapeutic effect, cytomegalovirus infection, HCMV infection, AIDS, cancer, senile dementia, trauma, and chronic bacterial infection.

The compounds of the present invention are suspected antiarrhythmic agents which are useful in the prevention and treatment (including partial alleviation or cure) of arrhythmias. As inhibitors of $K_v1.5$, compounds within the scope of the present invention are particularly useful in the selective prevention and treatment of supraventricular arrhythmias such as atrial fibrillation, and atrial flutter. By "selective prevention and treatment of supraventricular arrhythmias" is meant the prevention or treatment of supraventricular arrhythmias wherein the ratio of the prolongation of the atrial effective refractory period to the prolongation of the ventricular effective refractory period is greater than 1:1. This ratio can also be greater than 4:1, even greater than 10:1. In addition, the ratio may be such that prolongation of the atrial effective refractory response period is achieved without significantly detectable prolongation of the ventricular effective refractory period.

In addition, the compounds within the scope of the present invention block $I_{Kur}$, and thus may be useful in the prevention and treatment of all $I_{Kur}$-associated conditions. An "$I_{Kur}$-associated condition" is a disorder which may be prevented, partially alleviated or cured by the administration of an $I_{Kur}$ blocker. The $K_v1.5$ gene is known to be expressed in stomach tissue, intestinal/colon tissue, the pulmonary artery, and pancreatic beta cells. Thus, administration of an $I_{Kur}$ blocker can provide useful treatment for disorders such as: reflux esophagitis, functional dyspepsia, constipation, asthma, and diabetes. Additionally, $K_v1.5$ is known to be expressed in the anterior pituitary. Thus, administration of an $I_{Kur}$ blocker can stimulate growth hormone secretion. $I_{Ku}$ inhibitors can additionally be useful in cell proliferative disorders such as leukemia, and autoimmune diseases such as rheumatoid arthritis and transplant rejection.

The present invention thus provides methods for the prevention or treatment of one or more of the aforementioned disorders, comprising the step of administering to a subject in need thereof an effective amount of at least one compound of the formula (I), (Ia), or compounds exemplified in the examples. Other therapeutic agents such as those described below may be employed with the inventive compounds in the present methods. In the methods of the present invention, such other therapeutic agent(s) may be administered prior to, simultaneously with or following the administration of the compound(s) of the present invention.

DOSAGE AND FORMULATION

The present invention also provides pharmaceutical compositions comprising at least one of the compounds of the formula (I), (Ia), or compounds exemplified in the examples, or salts thereof capable of preventing or treating one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the formula (I), (Ia), or compounds exemplified in the examples, may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents.

The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. In the case where the compounds of formula (I), (Ia), or compounds exemplified in the examples, are being administered to prevent or treat arrhythmias, the compounds may be administered to achieve chemical conversion to normal sinus rhythm, or may optionally be used in conjunction with electrical cardioconversion.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of formula (I), (Ia), or compounds exemplified in the examples, may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (AVICEL®) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders, including: other antiarrhythmic agents such as Class I agents (e.g., propafenone), Class II agents (e.g., carvadiol and propranolol), Class III agents (e.g., sotalol, dofetilide, amiodarone, azimilide and ibutilide), Class IV agents (e.g., diltiazem and verapamil), 5HT antagonists (e.g., sulamserod, serraline and tropsetron), and dronedarone; calcium channel blockers (both L-type and T-type) such as diltiazem, verapamil, nifedipine, amlodipine and mybefradil; Cyclooxygenase inhibitors (i.e., COX-1 and/or COX-2 inhibitors) such as aspirin, indomethacin, ibuprofen, piroxicam, naproxen, CELEBREX®, VIOXX® and NSAIDs; anti-platelet agents such as GPIIb/IIIa blockers (e.g., abciximab, eptifibatide and tirofiban), P2Y12 antagonists (e.g., clopidogrel, cangrelor, ticlopidine and CS-747), P2Y1 antagonists, thromboxane receptor antagonists (e.g., ifetroban), aspirin, and PDE-III inhibitors (e.g., dipyridamole) with or without aspirin; diuretics such as chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone; anti-hypertensive agents such as alpha adrenergic blockers, beta adrenergic blockers, calcium channel blockers, diuretics, renin inhibitors, ACE inhibitors, (e.g., captopril, zofenopril, fosinopril, enalapril, ceranopril, cilazopril, delapril, pentopril, quinapril, ramipril, lisinopril), A II antagonists (e.g., losartan, irbesartan, valsartan), ET antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), nitrates, and combinations of such anti-hypertensive agents; anti-thrombotic/thrombolytic agents such as tissue plasminogen activator (tPA), recombinant tPA, tenecteplase (TNK), lanoteplase (nPA), factor VIIa inhibitors, factor Xa inhibitors (such as razaxaban), XIa inhibitors, thrombin inhibitors (e.g., hirudin and argatroban), PAI-1 inhibitors (i.e., inactivators of tissue plasminogen activator inhibitors), α2-antiplasmin inhibitors, streptokinase, urokinase, prourokinase, anisoylated plasminogen streptokinase activator complex, and animal or salivary gland plasminogen activators; anticoagulants such as warfarin and heparins (including unfractionated and low molecular weight heparins such as enoxaparin and dalteparin); HMG-CoA reductase inhibitors such as pravastatin lovastatin, atorvastatin, simvastatin, NK-104 (a.k.a. itavastatin, or nisvastatin or nisbastatin) and ZD-4522 (a.k.a. rosuvastatin, or atavastatin or visastatin); other cholesterol/lipid lowering agents such as squalene synthetase inhibitors, fibrates, and bile acid sequestrants (e.g., QUESTRAN®); antiproliferative agents such as cyclosporin A, TAXOL®, FK 506, and adriamycin; antitumor agents such as TAXOL®, adriamycin, epothilones, cisplatin and carboplatin; anti-diabetic agents such as biguanides (e.g., metformin), glucosidase inhibitors (e.g., acarbose), insulins, meglitinides (e.g., repaglinide), sulfonylureas (e.g., glimepiride, glyburide and glipizide), biguanide/glyburide combinations (i.e., GLUCOVANCE®), thiozolidinediones (e.g., troglitazone, rosiglitazone and pioglitazone), PPAR-gamma agonists, aP2 inhibitors, and DP4 inhibitors; thyroid mimetics (including thyroid receptor antagonists) (e.g., thyrotropin, polythyroid, KB-130015, and dronedarone); Mineralocorticoid receptor antagonists such as spironolactone and eplerinone; growth hormone secretagogues; anti-osteoporosis agents (e.g., alendronate and raloxifene); hormone replacement therapy agents such as estrogen (including conjugated estrogens in premarin), and estradiol; antidepressants such as nefazodone and sertraline; antianxiety agents such as diazepam, lorazepam, buspirone, and hydroxyzine pamoate; oral contraceptives; anti-ulcer and gastroesophageal reflux disease agents such as famotidine, ranitidine, and omeprazole; anti-obesity agents such as orlistat; cardiac glycosides including digitalis and ouabain; phosphodiesterase inhibitors including PDE III inhibitors (e.g., cilostazol), and PDE V inhibitors (e.g., sildenafil); protein tyrosine kinase inhibitors; steroidal anti-inflammatory agents such as prednisone, and dexamethasone; and other anti-inflammatory agents such as ENBREL®. The combinations can be co-formulated or in the form of kits packaged to provide appropriate dosages for co-administration.

The above other therapeutic agents, when employed in combination with the compounds of the present invention, may be used, for example, in those amounts indicated in the *Physicians' Desk Reference* (PDR) or as otherwise determined by one of ordinary skill in the art.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

While this invention has been described with an emphasis upon particular embodiments, it will be obvious to those of ordinary skill in the art that variations in the particular compounds and methods may be used and that it is intended that the invention may be practiced otherwise than as specifically described herein. Accordingly, this invention includes all modifications encompassed within the spirit and scope of the invention as defined by the claims that follow.

What is claimed is:

1. A compound of formula I

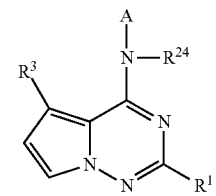

or an enantiomer, diastereomer, tautomer, or salt thereof wherein:

A is —(CH$_2$)$_m$—R$^2$, —CH(R$^{26}$)—R$^2$, —(CH$_2$)$_{n-1}$—O—R$^2$, —(CH$_2$)$_{n-1}$—NR$^{25}$—R$^2$, —CH(R$^{26}$)—CO$_2$—R$^2$, or —(CH$_2$)$_{n-1}$—NR$^{25}$—CO$_2$—R$^2$;

R$^1$ is C$_{1-10}$ alkyl substituted with 1-2 —OH, haloC$_{1-10}$ alkyl, C$_{2-12}$ alkenyl, C$_{3-10}$ cycloalkyl, wherein the cycloalkyl may be substituted with 0-2 R$^{13}$; or R$^1$ is

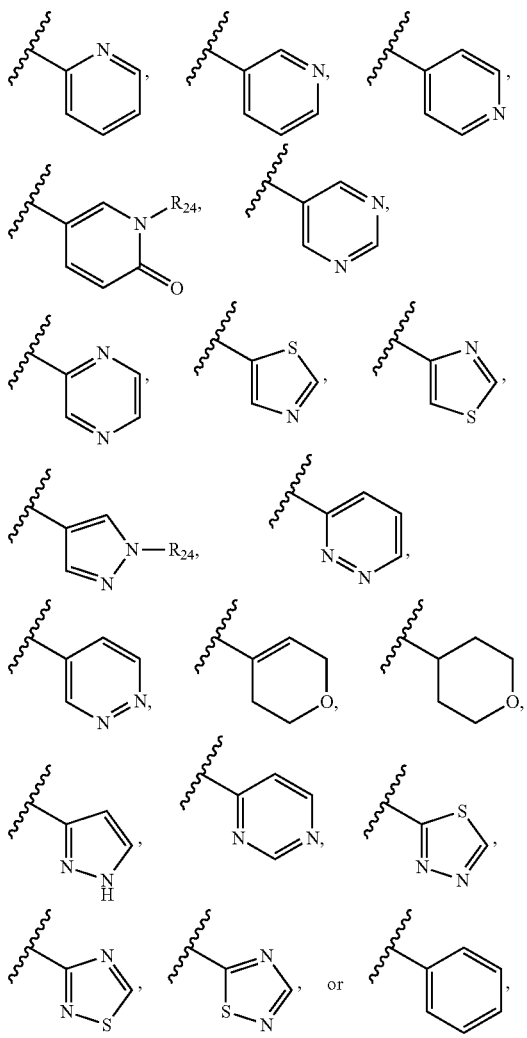

any of which may be substituted with 0-2 R$^{13}$;

R$^2$ is phenyl, cyclopentyl, cyclohexyl, pyridinyl, pyrazinyl, pyridazinyl, pyrimidinyl, piperidinyl, pyridinone, pyrrolidinyl, tetrahydropyran, or thiazolyl, any of which are substituted with 0-2 R$^{2a}$;

R$^{2a}$, at each occurrence, is independently H, —OH, F, Cl, Br, I, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —CN, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_n$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, —NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$ or —NCOR$^{14}$, wherein the alkyl, cycloalkyl, alkenyl, alkoxy, aryl, heteroaryl and heterocyclyl may be substituted with 0-2 R$^{14a}$, and the heteroaryl and heterocyclyl consist of carbon atoms and 1, 2, 3, or 4 heteroatoms independently selected from the group consisting of N, S, or O;

R$^3$ is phenyl, pyridinyl, pyrimidinyl, or dihydropyran, tetrahydropyran any of which may be substituted with 0-1 R$^{3a}$;

R$^{3a}$ is halo, CN, NH$_2$, —O—C$_{1-3}$alkyl, or morpholinyl;

R$^{13}$, at each occurrence, is independently H, F, Cl, Br, I, CN, C$_{1-10}$ alkyl, C$_{1-10}$ alkoxy, haloC$_{1-10}$ alkyl, C$_{3-10}$ cycloalkyl, C$_{2-12}$ alkenyl, C$_{2-12}$ alkynyl, C$_{6-10}$aryl, a 4- to 12-membered heteroaryl, a 4- to 12-membered heterocyclyl, a 4- to 12-membered heteroaryl-C$_{1-10}$ alkyl, —NO$_2$, —(CH$_2$)$_m$—SO$_2$R$^{14}$, —NR$^{14}$SO$_2$R$^{14}$, =O, —CONR$^{14}$R$^{14}$, —(CH$_2$)$_m$—SO$_2$NR$^{14}$R$^{14}$, —(CH$_2$)$_m$—NR$^{14}$SO$_2$R$^{14}$, —(CH$_2$)$_n$—NR$^{14}$SO$_2$NR$^{14}$R$^{14}$, —NR$^{14}$SO$_2$NR$^{14}$R$^{14}$, —CO$_2$NR$^{14}$R$^{14}$, —NR$^{14}$CO$_2$NR$^{14}$R$^{14}$, —NR$^{14}$COR$^{14}$, —SO$_2$NR$^{14}$COR$^{14}$, —SO$_2$NR$^{14}$CONR$^{14}$R$^{14}$, —NR$^{14}$CO$_2$R$^{14}$, —CO$_2$R$^{14}$, NR$^{14}$R$^{14}$, —NR$^{14}$CONR$^{14}$R$^{14}$, —C(=NOR$^{14}$)NR$^{14}$R$^{14}$, —CONR$^{14}$OR$^{14}$ or —NCOR$^{14}$, OR$^{14}$, wherein the alkyl, cycloalkyl, alkenyl, alkoxy, aryl, heteroaryl and heterocyclyl may be substituted with 0-2 R$^{14a}$, and the heteroaryl and heterocyclyl consist of carbon atoms and 1, 2, 3, or 4 heteroatoms independently selected from the group consisting of N, S, or O;

R$^{14}$, at each occurrence, is independently selected from hydrogen, C$_{1-10}$ alkyl, C$_{3-10}$ cycloalkyl, C$_{6-10}$ aryl, a 4- to 12-membered heteroaryl or a 4- to 12-membered heterocyclyl, wherein the alkyl, cycloalkyl, aryl, heteroaryl and heterocyclyl may be substituted with 0-3 R$^{14a}$ and the heteroaryl and heterocyclyl consist of carbon atoms and 1, 2, 3, or 4 heteroatoms independently selected from the group consisting of N, S, or O; or alternatively, two R$^{14}$'s are taken together with the atoms to which they are attached to form a heterocyclic ring, wherein the cyclic ring may be substituted with 0-1 R$^{14a}$ and optionally contain 1, 2, 3, or 4 heteroatoms independently selected from the group consisting of N, S, or O;

R$^{14a}$, at each occurrence, is independently selected from F, Cl, Br, I, C$_{1-10}$ alkyl, haloC$_{1-10}$alkyl, C$_{6-10}$aryl, C$_{3-10}$cycloalkyl, a 4- to 12-membered heteroaryl, a 4- to 12-membered heterocyclyl, —CN, —NO$_2$, —CO$_2$R$_{26}$, —CO$_2$NR$_{24}$R$_{24}$, —OCF$_3$, —OR$_{25}$, =O, —CONR$^{24}$R$^{24}$, —COR$^{24}$, —SO$_2$R$^{24}$, —NR$^{24}$R$^{24}$, —NR$^{24}$CO$_2$R$^{24}$, —SO$_2$NR$^{24}$R$^{24}$, or C$_{6-10}$aryl C$_{1-10}$alkyl, wherein the heteroaryl and heterocyclyl consist of carbon atoms and 1, 2, 3, or 4 heteroatoms independently selected from the group consisting of N, S, or O;

R$^{24}$, at each occurrence, is independently selected from hydrogen, C$_{1-10}$alkyl, C$_{3-6}$cycloalkyl, or phenyl; or R$^{25}$, at each occurrence, is independently selected from hydrogen, C$_{1-10}$alkyl, C$_{3-6}$cycloalkyl, or phenyl;

R$_{26}$, at each occurrence, is independently selected from hydrogen, C$_{1-10}$alkyl, C$_{3-6}$cycloalkyl, or phenyl;

m is 0 to 4;

n is 0 to 4; or n-1 is 2 to 4.

2. The compound of claim 1, wherein:
one of $R^1$ or $R^{1a}$ is $C_{1-10}$ alkyl substituted with 1-2 —OH, haloC$_{1-10}$ alkyl, $C_{3-10}$ cycloalkyl, wherein the cycloalkyl may be substituted with 0-2 $R^{13}$; or

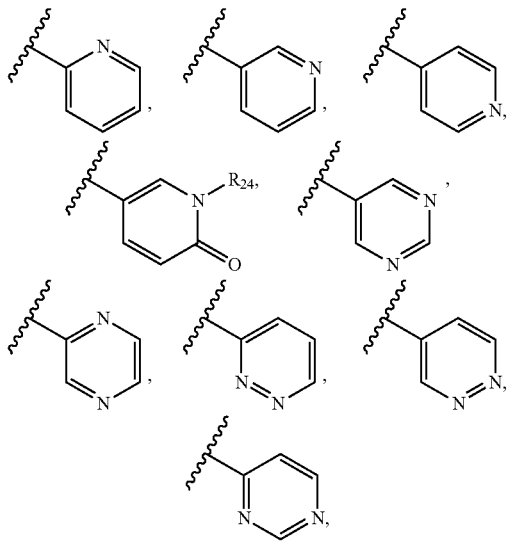

or

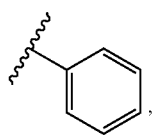, any of which may be substituted with 0-2 $R^{13}$.

3. The compound, of claim 2, wherein:
$R^{13}$, at each occurrence, is independently H, —OH, F, Cl, Br, I, $C_{1-6}$ alkyl, $C_{1-6}$ alkoxy, haloC$_{1-6}$ alkyl, $C_{3-6}$ cycloalkyl, phenyl, a 4- to 12-membered heteroaryl, wherein the heteroaryl is selected from tetrazolyl, —CN, —NO$_2$, —(CH$_2$)$_m$—SO$_2$R$^{14}$, —NR$^{14}$SO$_2$R$^{14}$, —CONR$^{14}$R$^{14}$, —(CH$_2$)$_m$—SO$_2$NR$^{14}$R$^{14}$, —NR$^{14}$CO$_2$NR$^{14}$R$^{14}$, —NR$^{14}$CO$_2$NR$^{14b}$R$^{14b}$, —NR$^{14}$COR$^{14}$, —NR$^{14}$CO$_2$R$^{14}$, —CO$_2$R$^{14}$, or —NR$^{14}$R$^{14}$, wherein the alkyl, cycloalkyl, phenyl, and heteroaryl may be substituted with 0-2 $R^{14a}$, and the heteroaryl and heterocyclyl consist of carbon atoms and 1, 2, 3, or 4 heteroatoms independently selected from the group consisting of N, S, or O;
$R^{14}$, at each occurrence, is independently selected from hydrogen, $C_{1-6}$ alkyl, $C_{3-6}$ cycloalkyl, phenyl, wherein the alkyl, cycloalkyl, and phenyl, may be substituted with 0-3 $R^{14a}$; or
alternatively, two $R^{14b}$'s are taken together with the atoms to which they are attached to form a cyclic ring, wherein the cyclic ring is morpholinyl, piperidinyl, or piperazinyl, and may be substituted with 0-1 $C_{1-6}$alkyl;
$R^{14a}$, at each occurrence, is independently selected from F, Cl, Br, I, $C_{1-6}$ alkyl, haloC$_{1-6}$alkyl, phenyl, $C_{3-6}$cycloalkyl.

4. The compound of claim 3, wherein:
A is —(CH$_2$)$_m$—R$^2$, —CH(R$^{26}$)—R$_2$, —(CH$_2$)$_{n-1}$—O— R$_2$, —(CH$_2$)$_{n-1}$—NR$^{25}$—R$_2$, —CH(R$^{26}$)—CO$_2$—R$^2$, or —(CH$_2$)$_{n-1}$—NR$^{25}$—CO$_2$—R$^2$;

$R^2$ is phenyl, pyridinyl, pyrazinyl, pyrimidinyl, piperidinyl, or pyridinone, any of which are substituted with 0-2 $R^{2a}$; or
$R^{2a}$, at each occurrence, is independently H, —OH, F, $C_{1-6}$ alkyl, $C_{1-6}$ alkoxy, 6-SO$_2$NR$^{14}$R$^{14}$.

5. The compound of claim 4, wherein:
$R^1$ is $C_{1-10}$ alkyl substituted with 1-2 —OH, haloC$_{1-10}$ alkyl, $C_{3-10}$ cycloalkyl, wherein the cycloalkyl may be substituted with 0-1 $R^{13}$; or
$R^1$ is

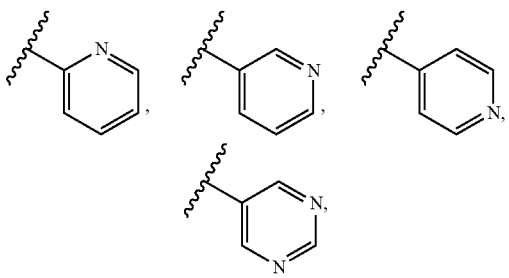

or

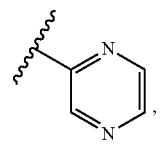, or

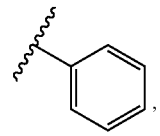, any of which may be substituted with 0-2 $R^{13}$.

6. The compound of claim 5, wherein:
$R^{13}$, at each occurrence, is independently H, $C_{1-6}$ alkyl, a 4- to 12-membered heteroaryl, wherein the heteroaryl is, selected from tetrazolyl, —CN, —NR$^{14}$SO$_2$R$^{14}$, —CONR$^{14}$R$^{14}$, —SO$_2$NR$^{14}$R$^{14}$, —NR$^{14}$CO$_2$NR$^{14}$R$^{14}$, —NR$^{14}$CO$_2$NR$^{14b}$R$^{14b}$, —NR$^{14}$COR$^{14}$, —CO$_2$R$^{14}$, or —NR$^{14}$R$^{14}$, wherein the alkyl, and heteroaryl may be substituted with 0-2 $R^{14a}$;
$R^{14}$, at each occurrence, is independently selected from hydrogen, $C_{1-6}$ alkyl, $C_{3-6}$ cycloalkyl, phenyl, wherein the alkyl, cycloalkyl, and phenyl, may be substituted with 0-3 $R^{14a}$; or
two $R^{14b}$'s are taken together with the atoms to which they are attached to form a cyclic ring, wherein the cyclic ring is morpholinyl, and may be substituted with 0-1 $C_{1-6}$alkyl;
$R^{14a}$, at each occurrence, is independently selected from F, Cl, Br, I, $C_{1-6}$ alkyl, haloC$_{1-6}$alkyl, phenyl, $C_{3-6}$cycloalkyl.

7. The compound of claim 6, wherein:

A is —(CH$_2$)—R$^2$;

R$^2$ is phenyl,

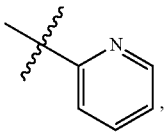

or

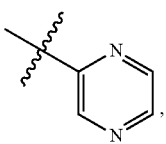 [SMILES: *c1cnccn1]

any of which are substituted with 0-1 R$^{2a}$; or

R$^{2a}$, at each occurrence, is independently H, —OH, F, C$_{1-6}$ alkyl, C$_{1-6}$ alkoxy, C$_{1-6}$ haloalkoxy, or SO$_2$NR$^{14}$R$^{14}$.

8. The compound of claim 7, wherein:

R$^3$ is phenyl.

9. The compound of claim 8, wherein:

R$^{24}$, at each occurrence, is independently selected from hydrogen, C$_{1-6}$alkyl, C$_{3-6}$cycloalkyl, or phenyl; or R$^{25}$, at each occurrence, is independently selected from hydrogen, C$_{1-6}$alkyl, C$_{3-6}$cycloalkyl, or phenyl; or R$_{26}$, at each occurrence, is independently selected from hydrogen, C$_{1-6}$alkyl, C$_{3-6}$cycloalkyl, or phenyl.

10. The compound of claim 9, wherein:

R$^{13}$, at each occurrence, is independently H, —CN, —NHSO$_2$R$^{14}$, —CONH$_2$, —SO$_2$NR$^{14}$R$^{14}$, —NHCO$_2$NR$^{14b}$R$^{14b}$, —NHCOR$^{14}$, or —NH$_2$;

R$^{14}$, at each occurrence, is independently selected from hydrogen, or methyl.

11. A compound, enantiomer, diastereomer, or salt thereof, selected from:

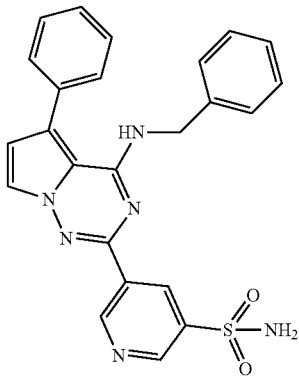

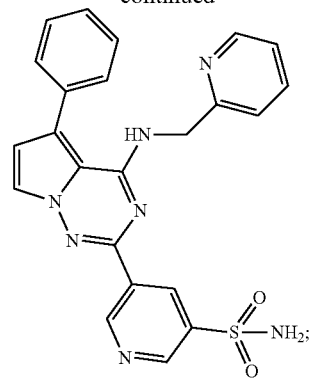

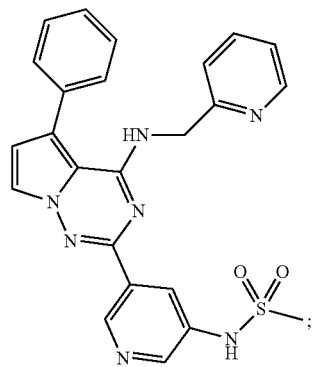

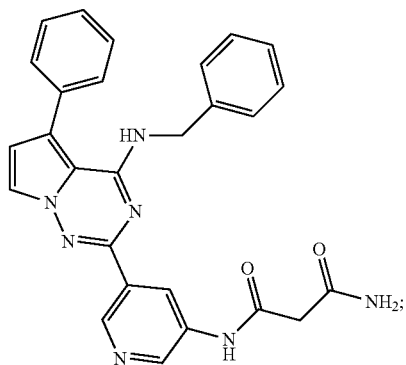

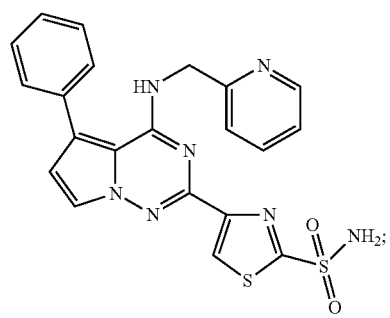

239
-continued
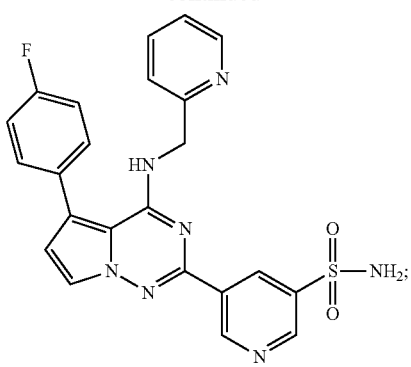
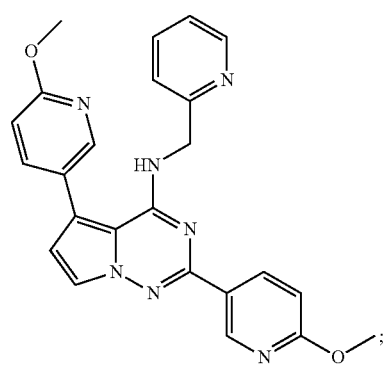
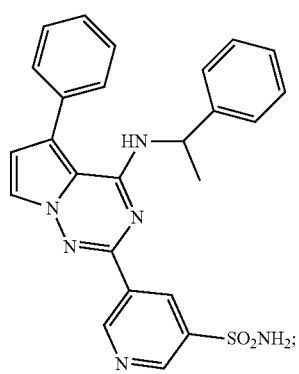
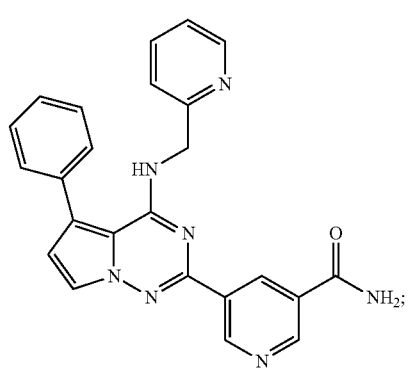
240
-continued
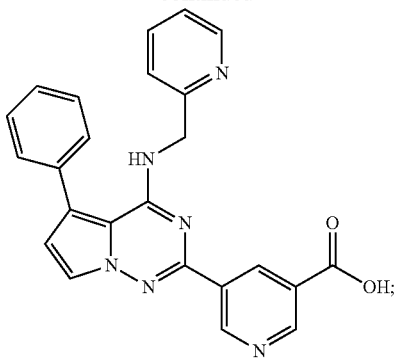
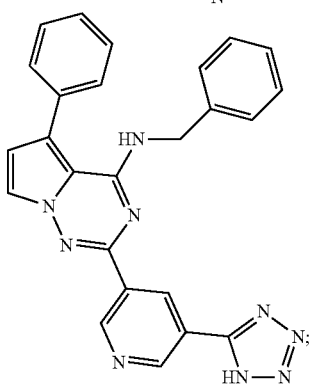
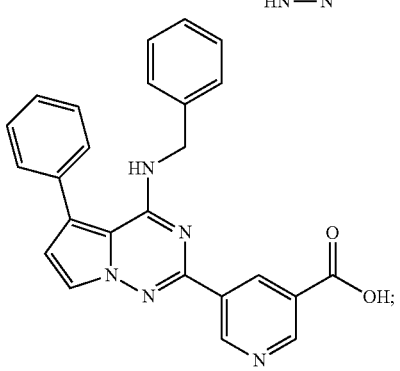
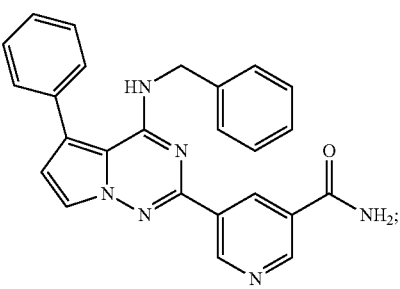
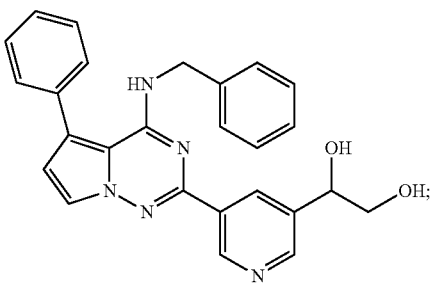

241
-continued
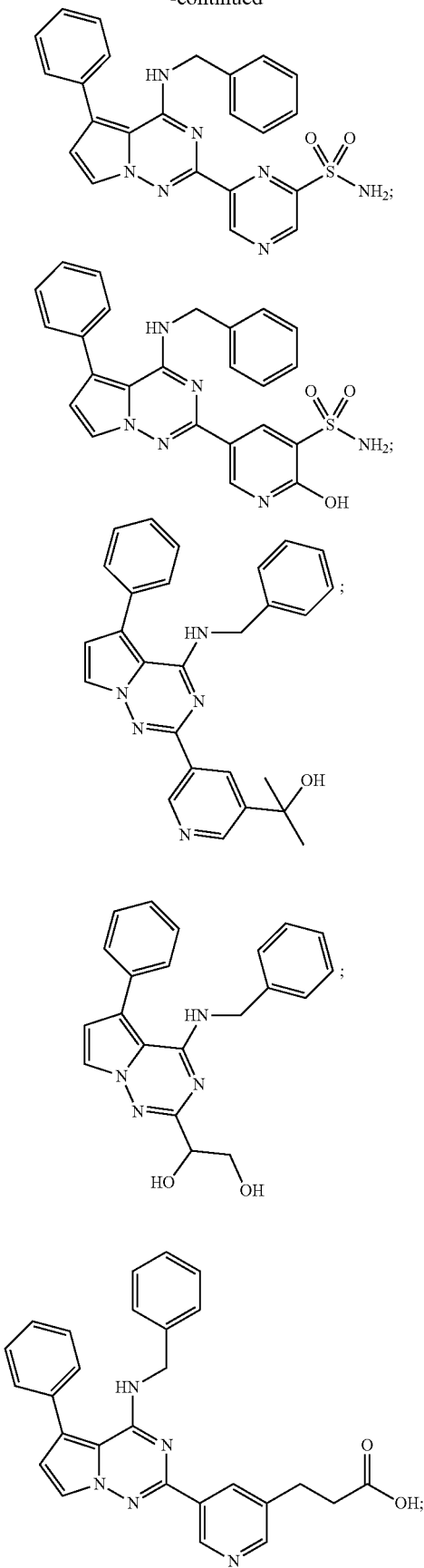
242
-continued
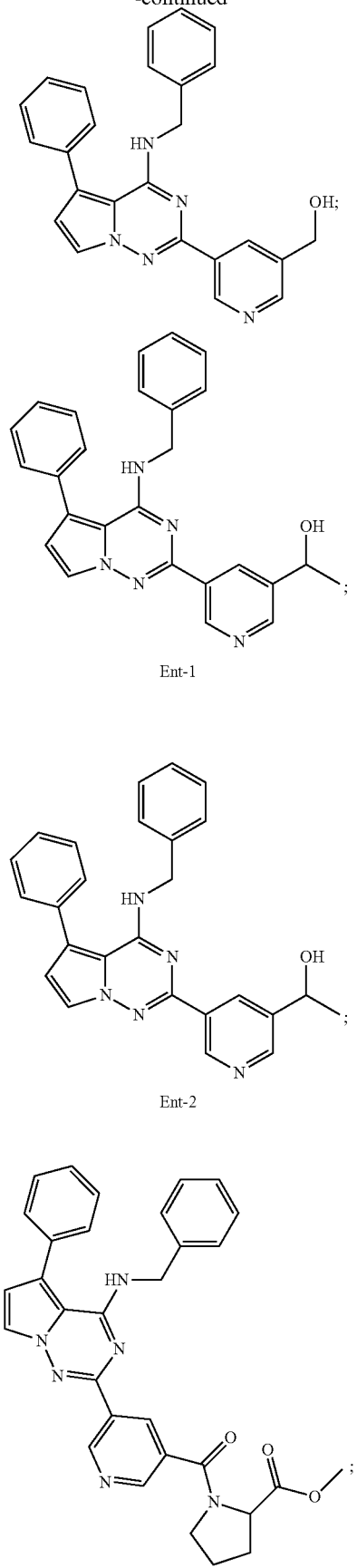

243
-continued
244
-continued
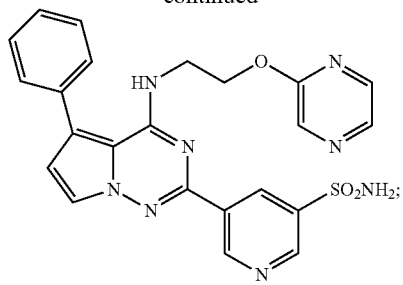
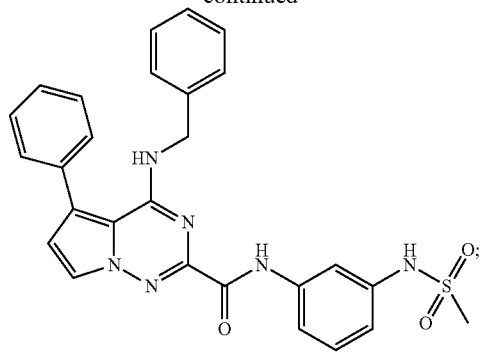
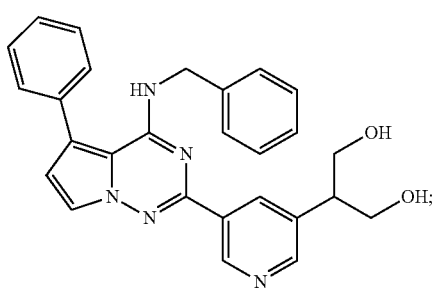
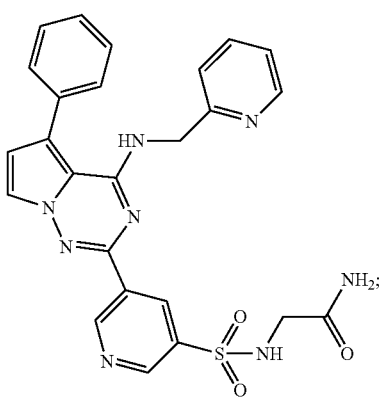
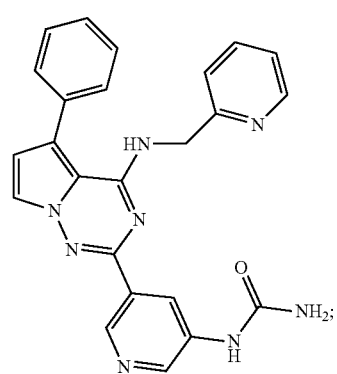
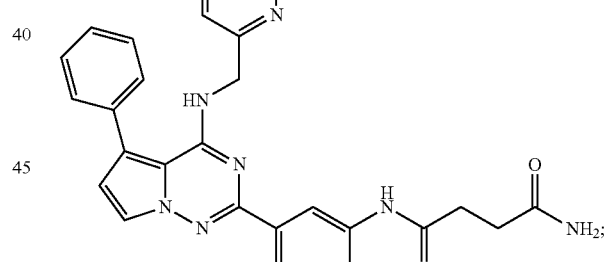
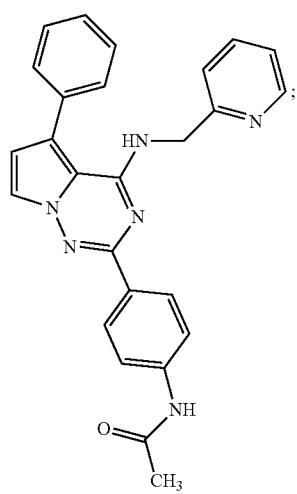
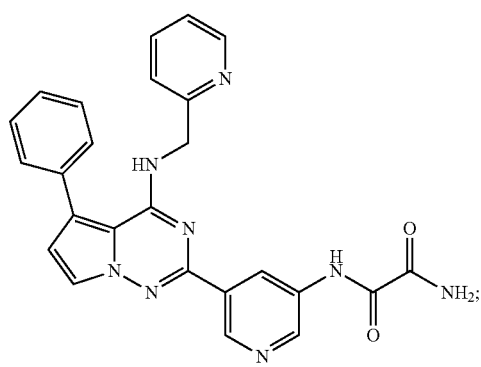

245
-continued
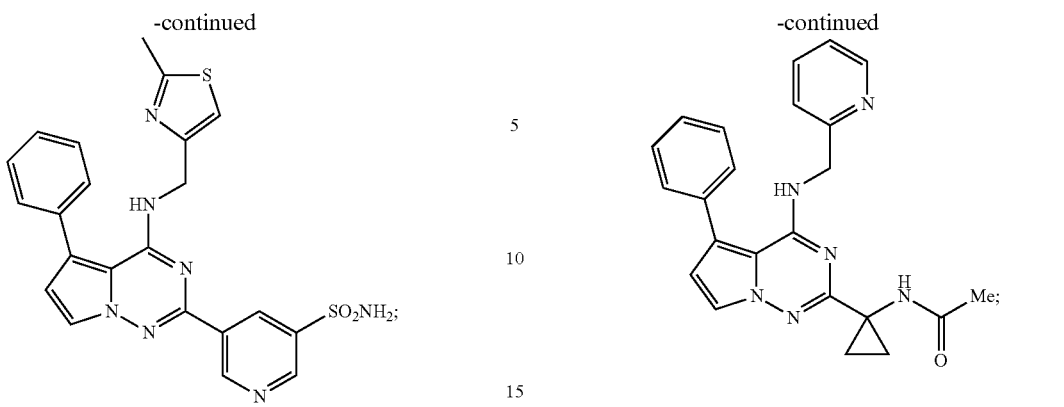
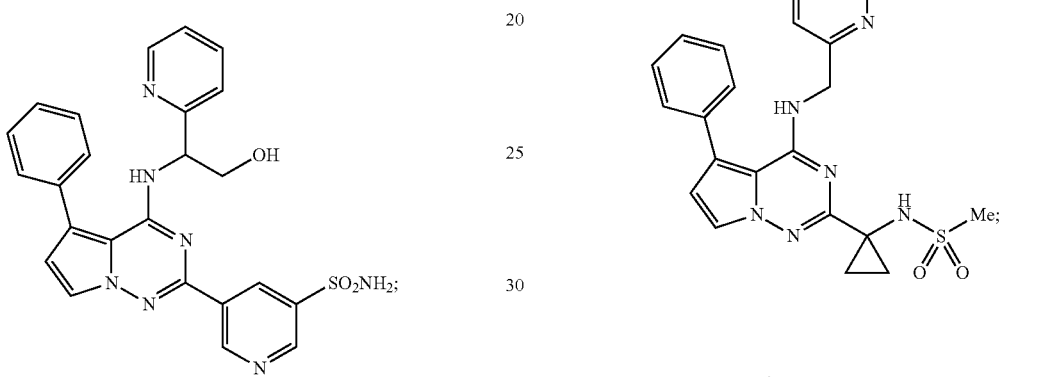
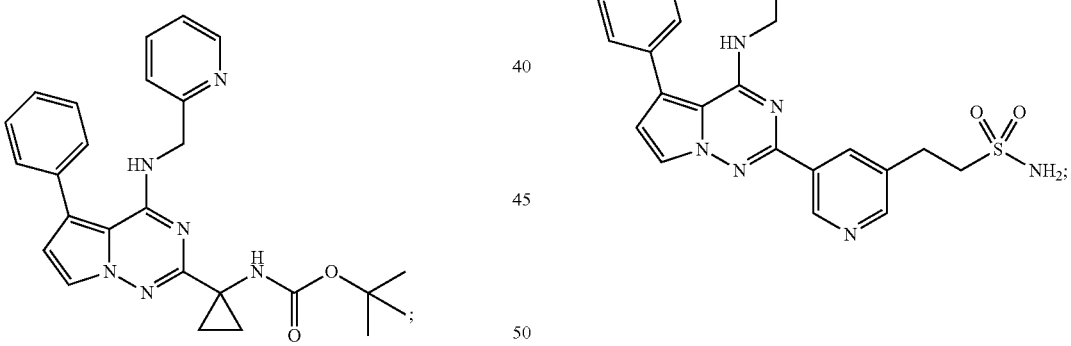
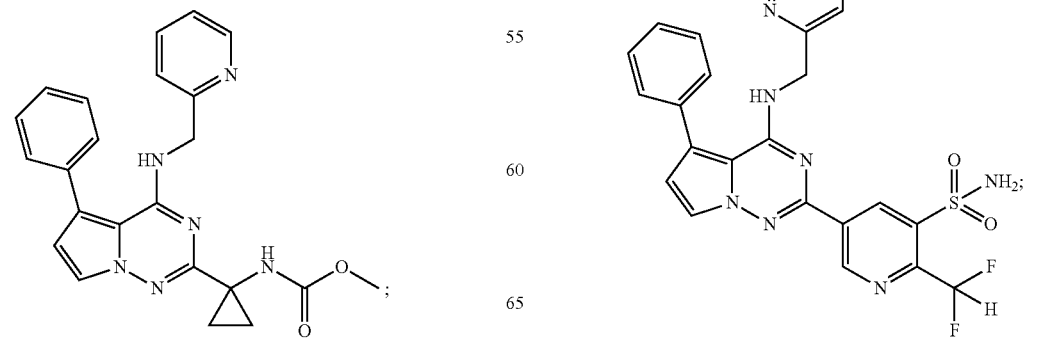
246
-continued
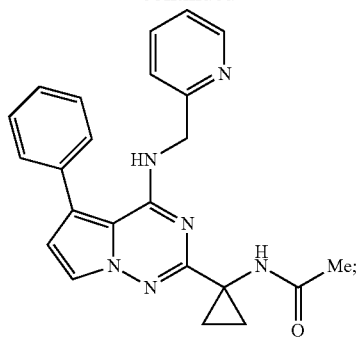
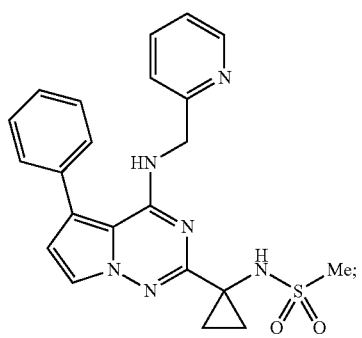
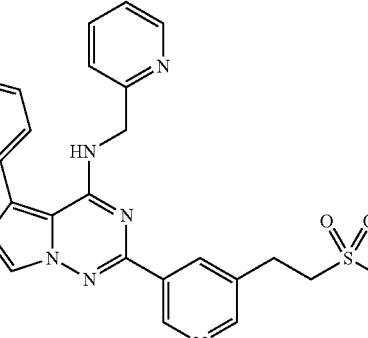
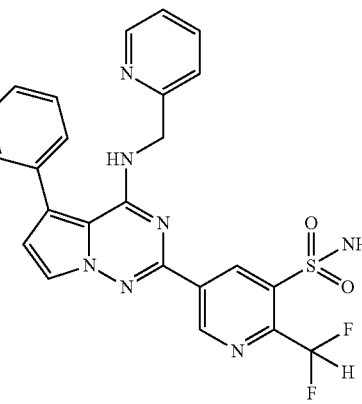

247
-continued
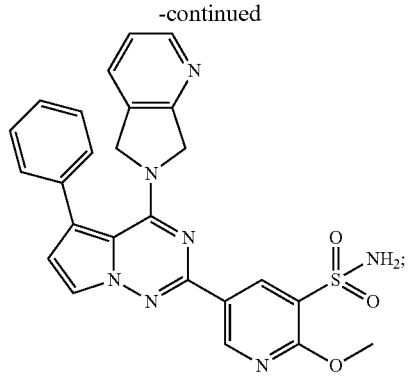
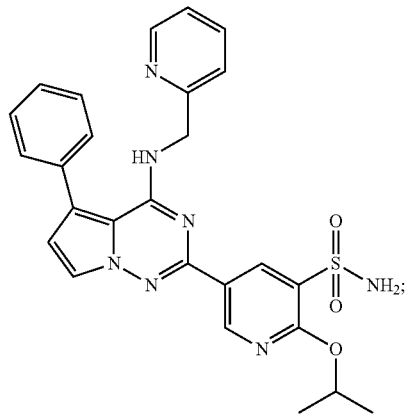
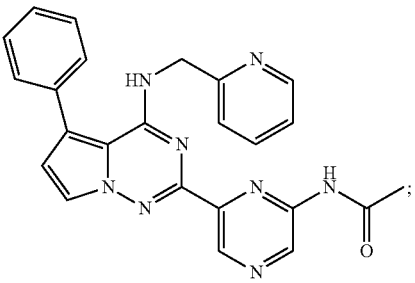
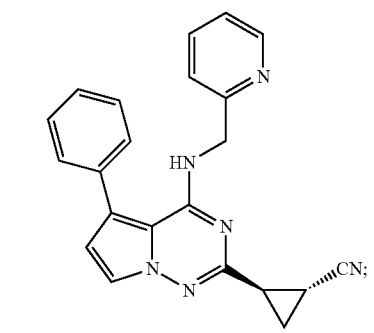
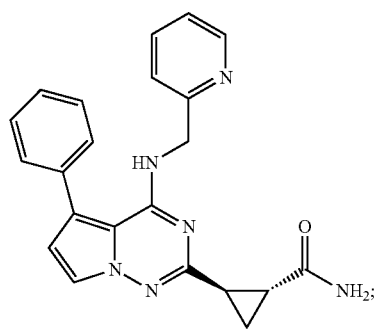
248
-continued
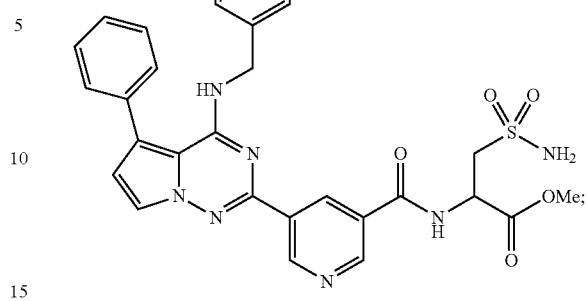
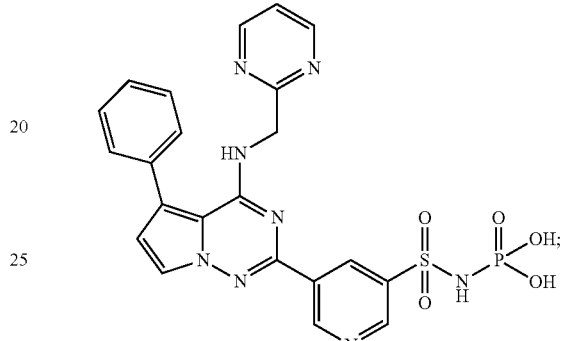
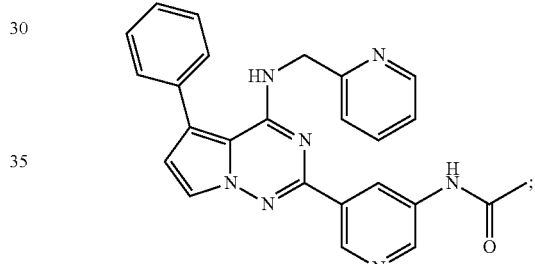
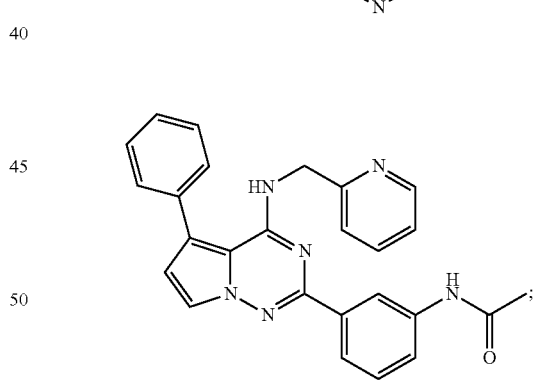
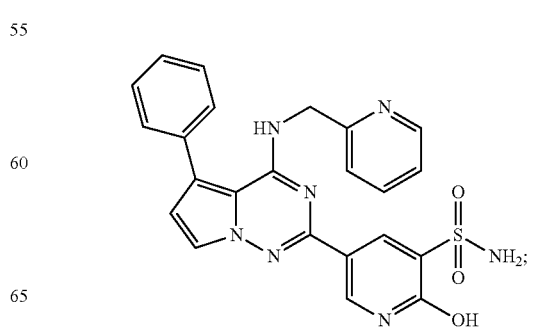

249
-continued
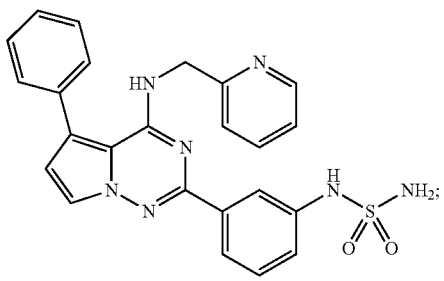
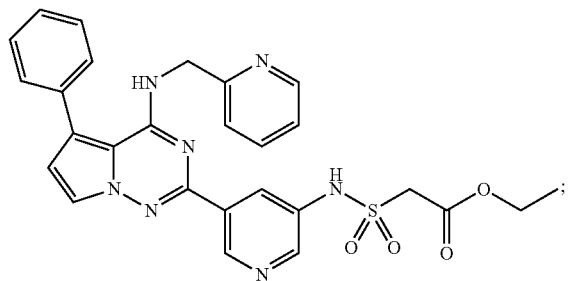
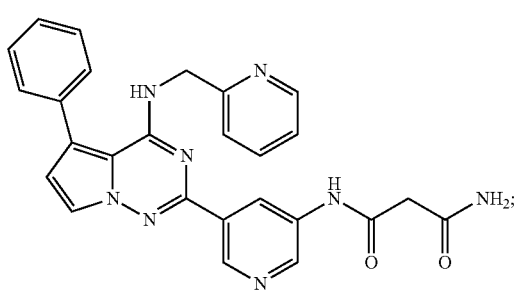
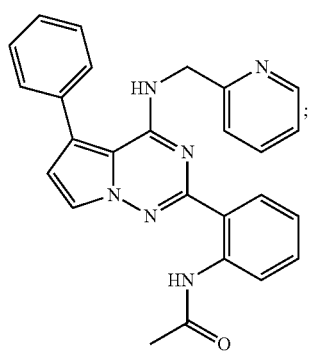
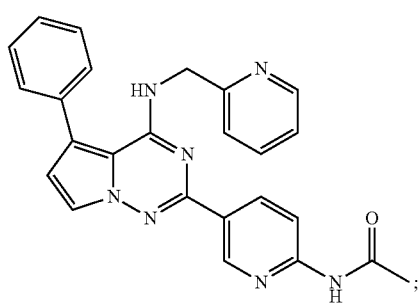
250
-continued
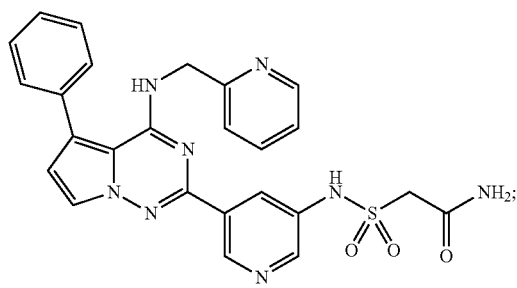
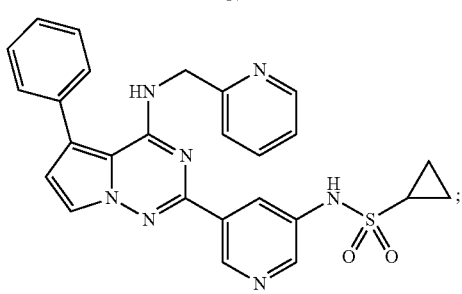
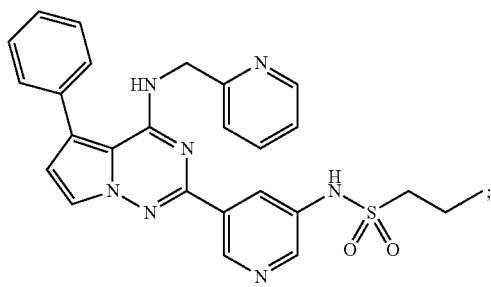
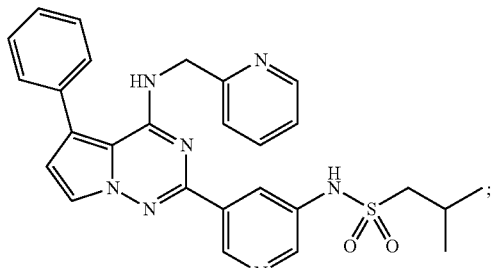
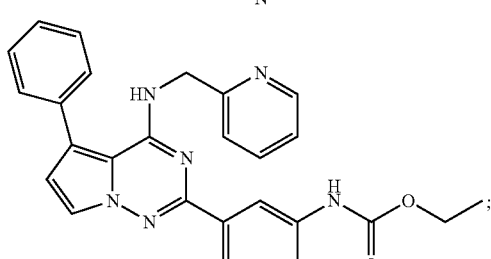
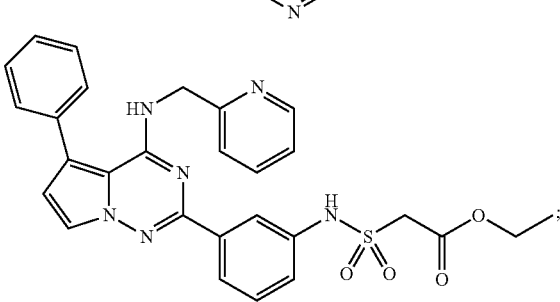

251
-continued
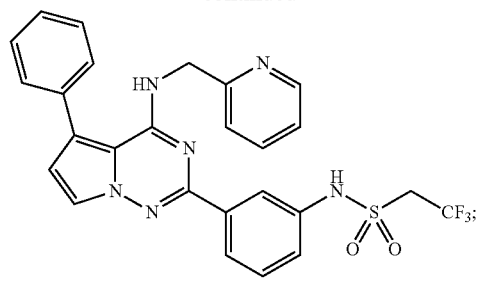
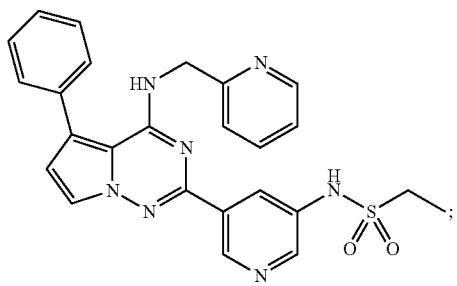
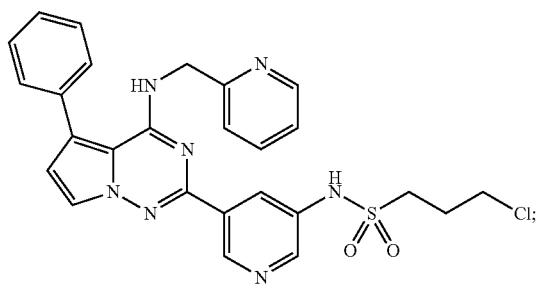
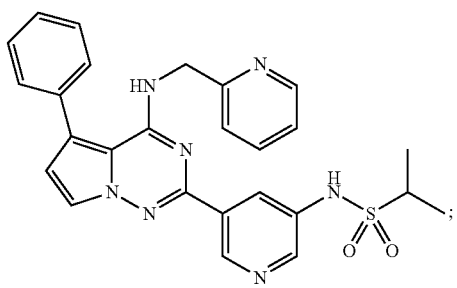
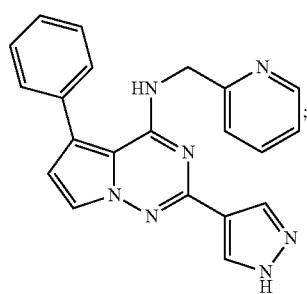
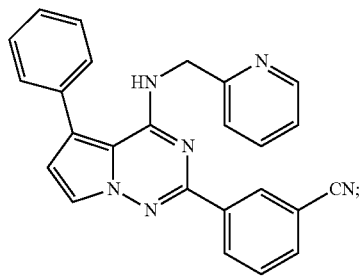
252
-continued
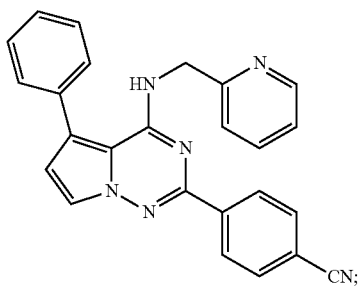
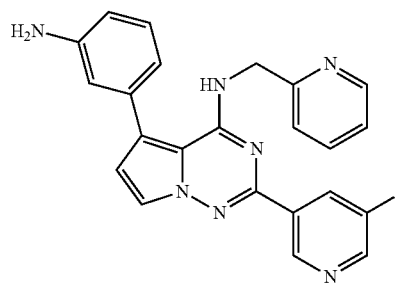
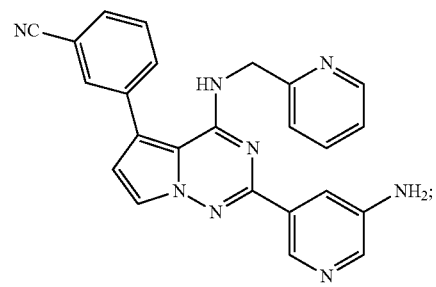
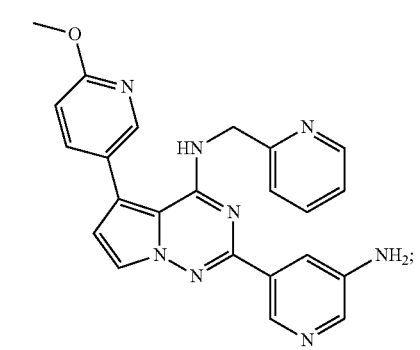
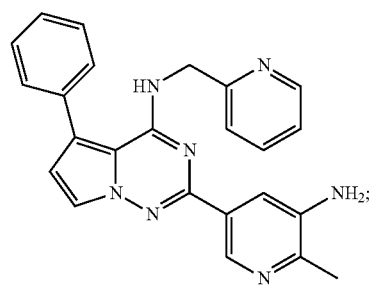

253
-continued
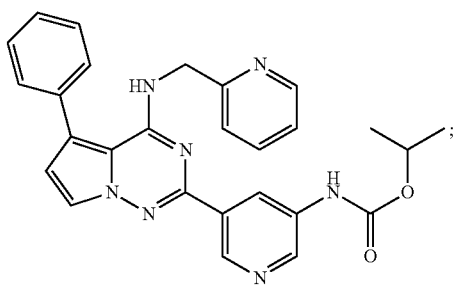
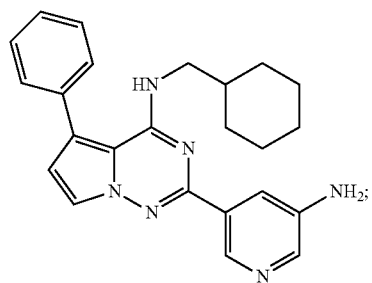
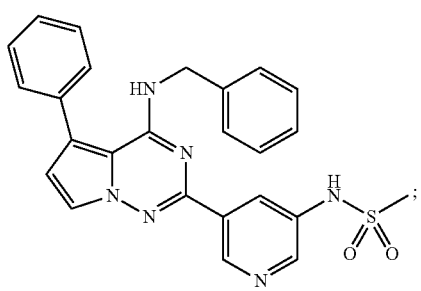
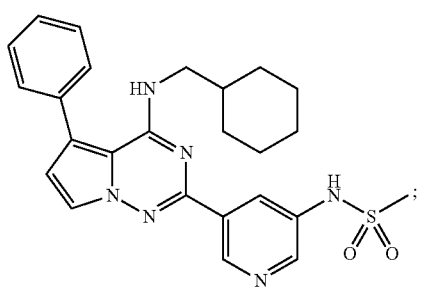
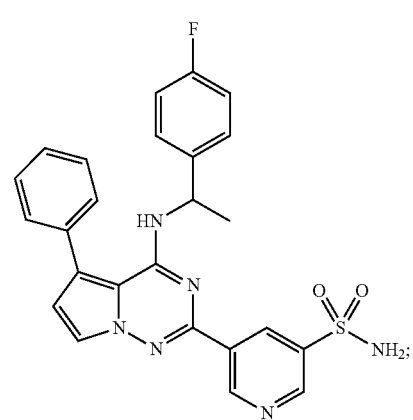
254
-continued
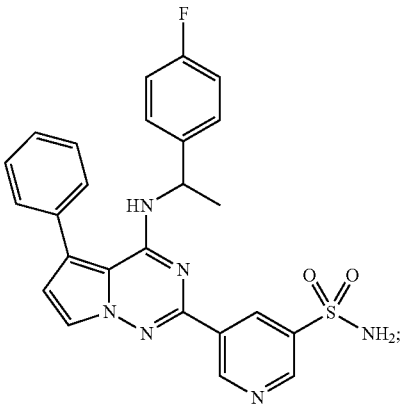
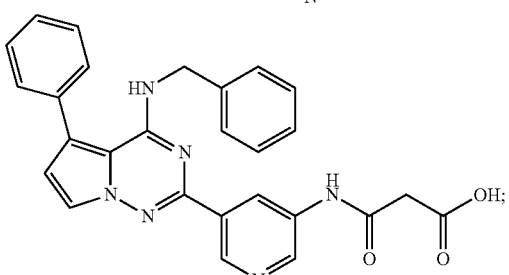
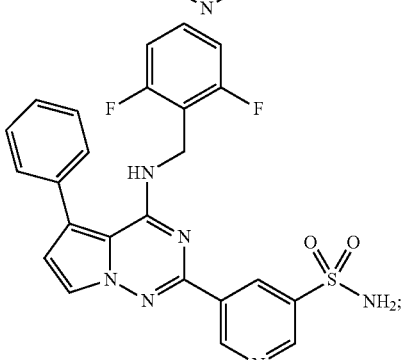
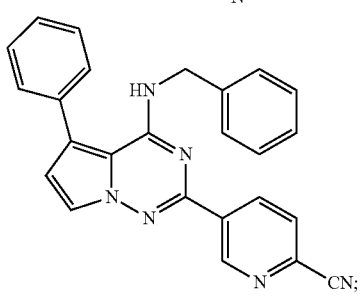
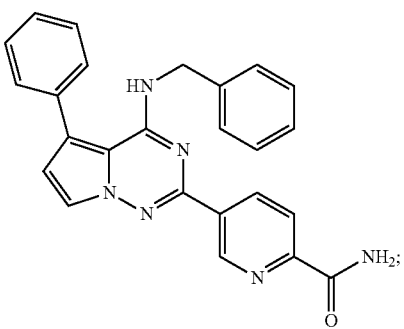

255
-continued
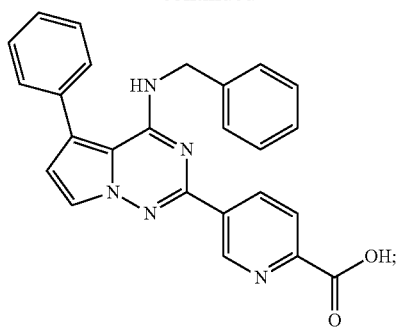
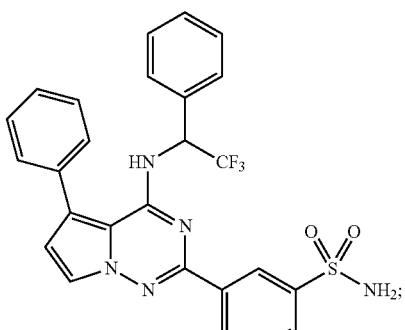
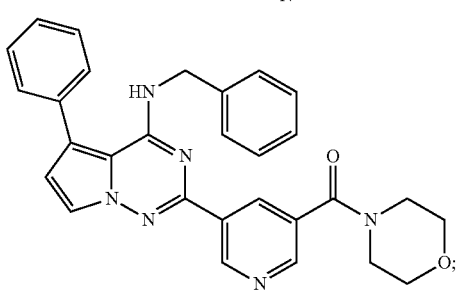
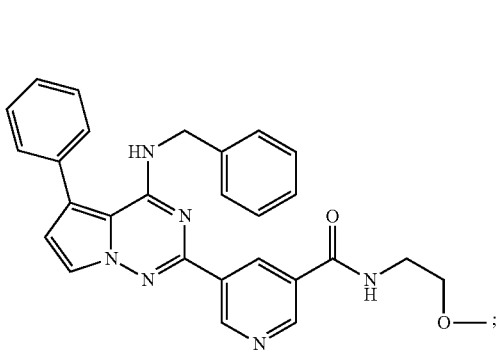
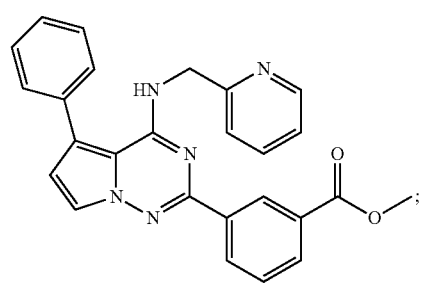
256
-continued
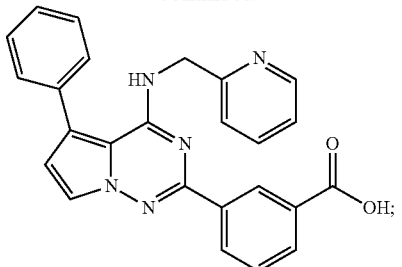
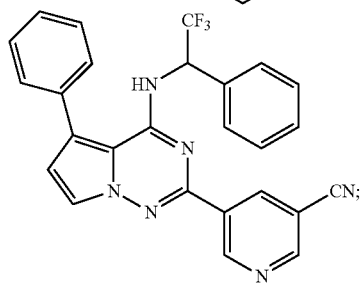
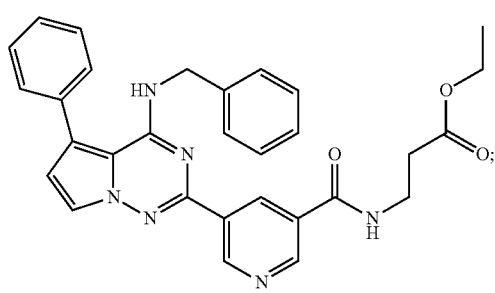
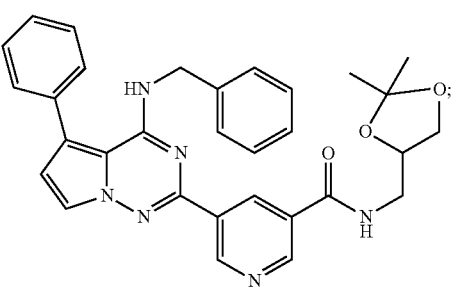
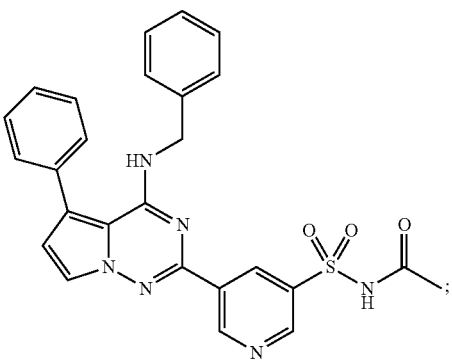

257
-continued
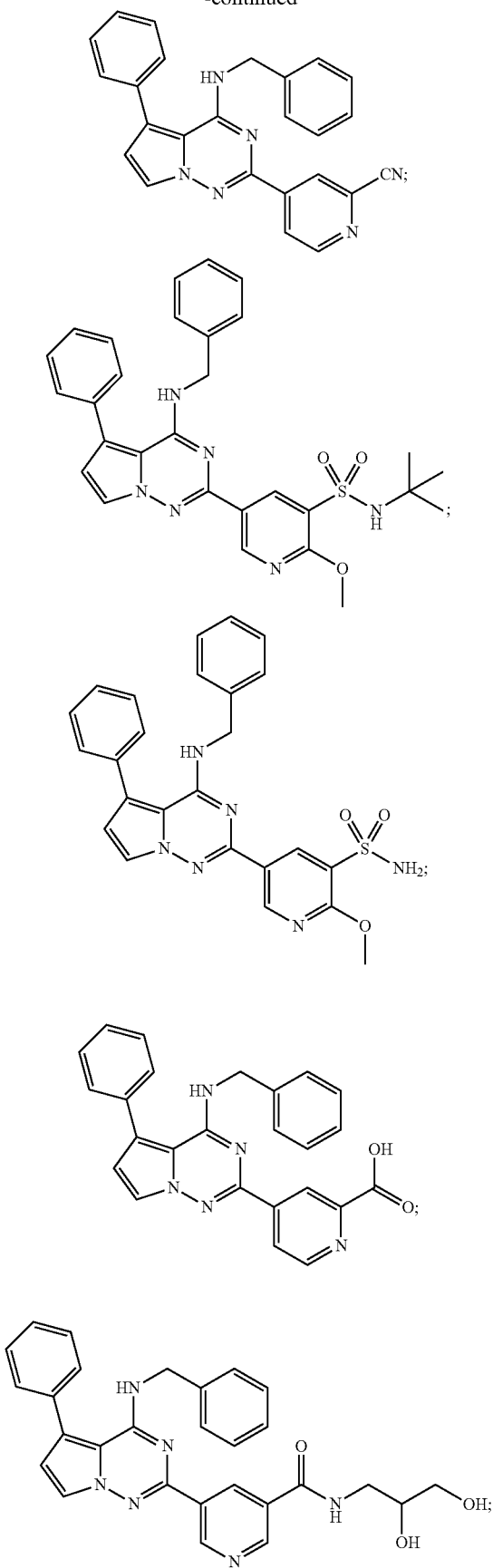
258
-continued
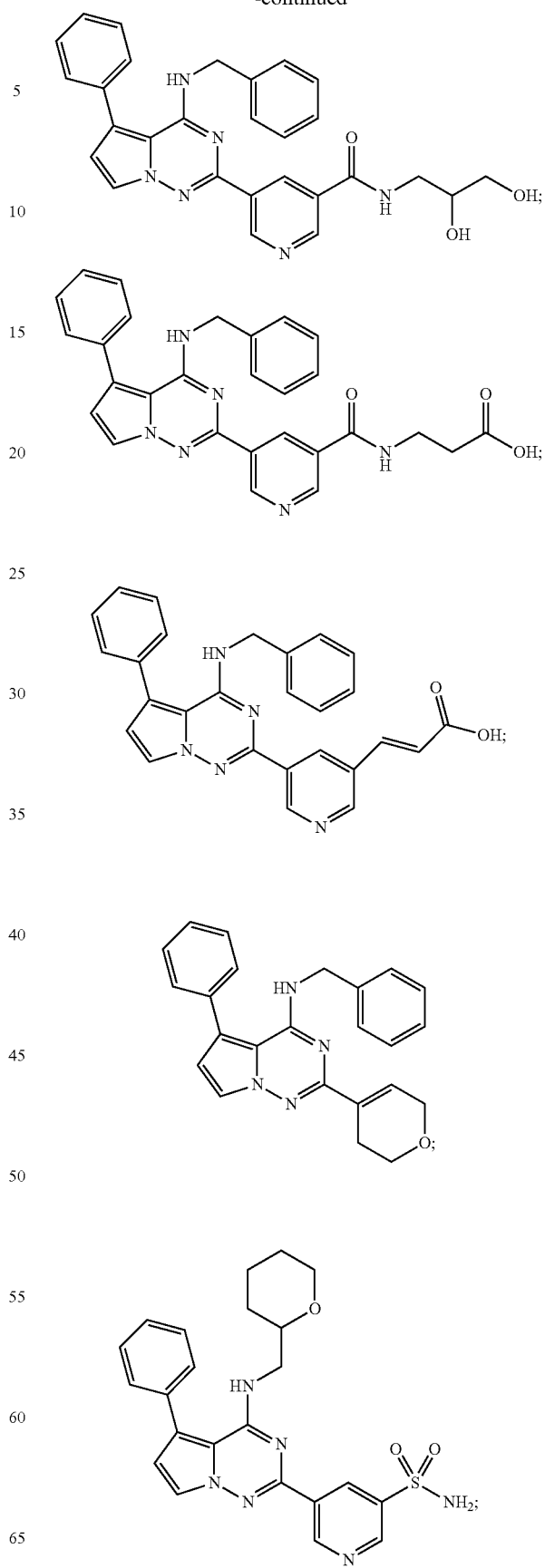

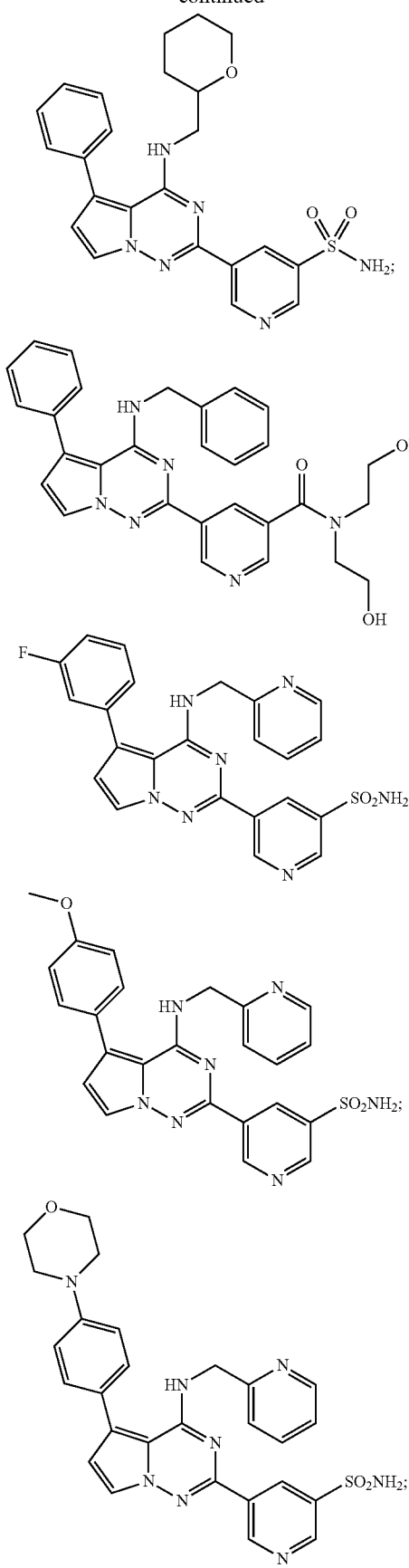
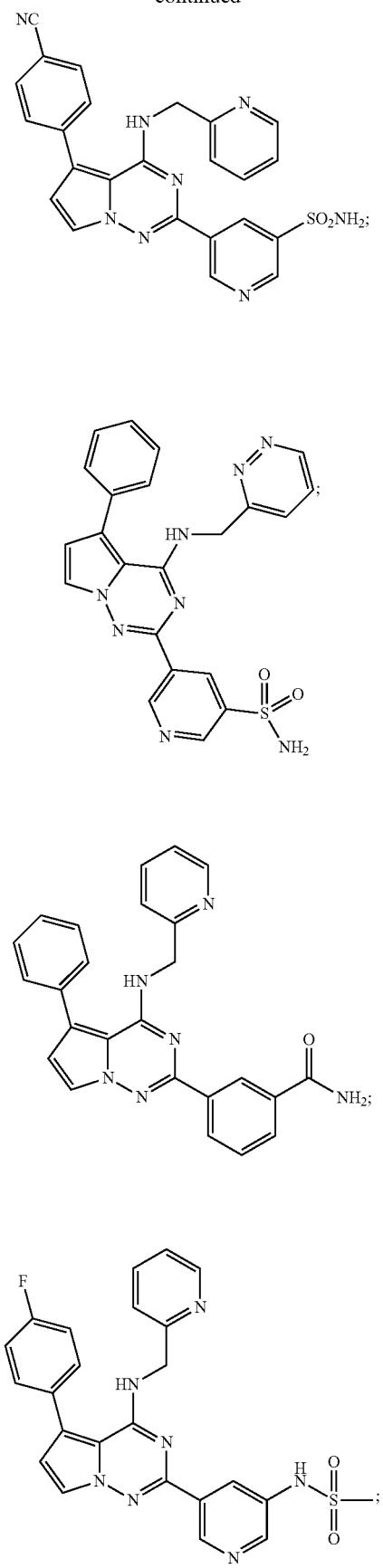

261
-continued
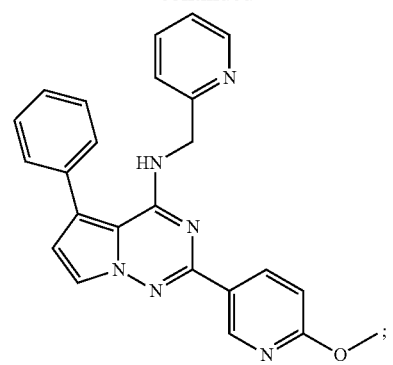
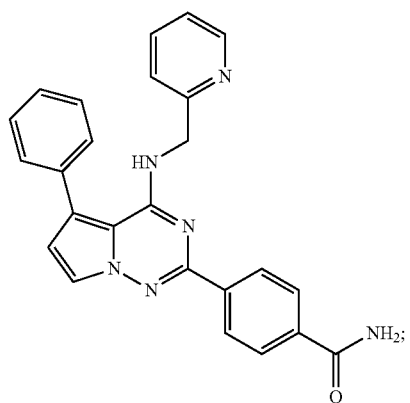
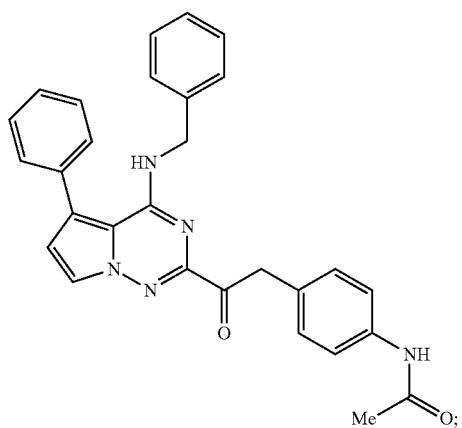
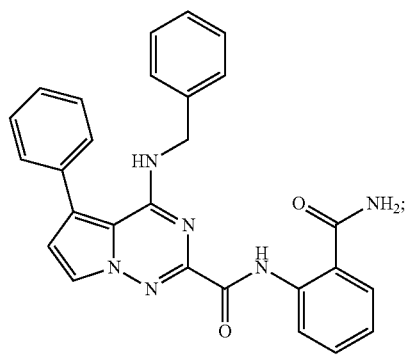
262
-continued
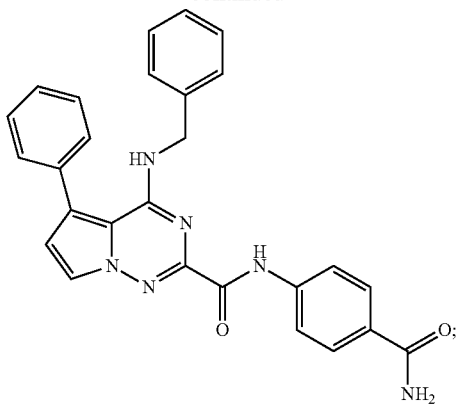
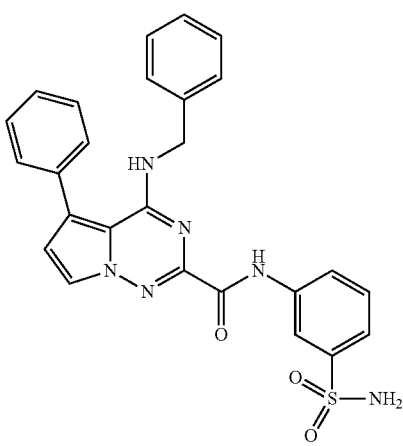
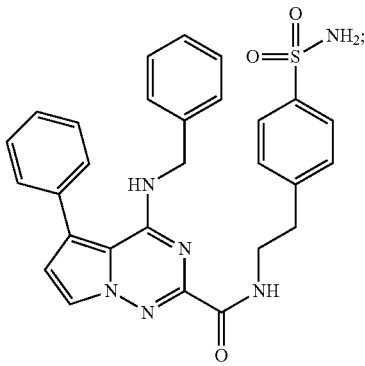
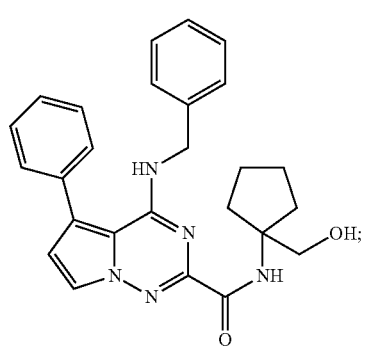

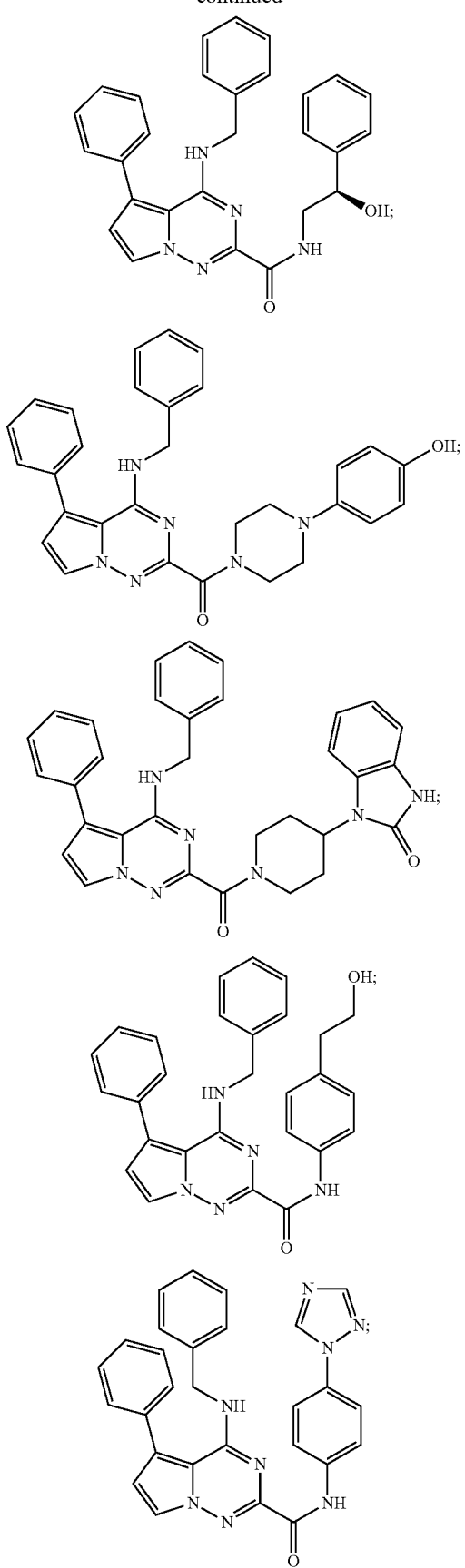
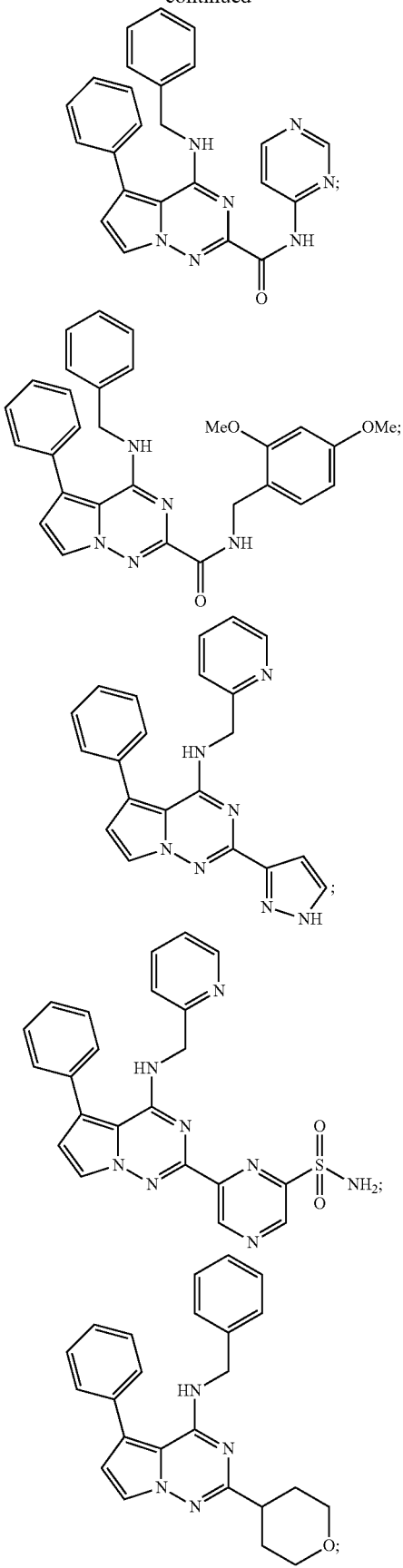

265
-continued
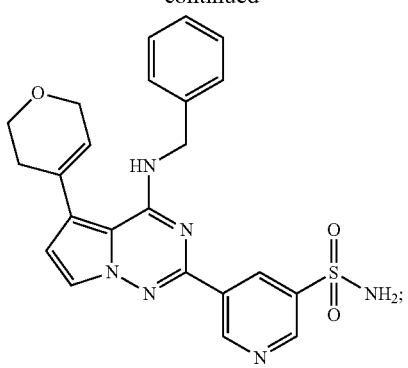
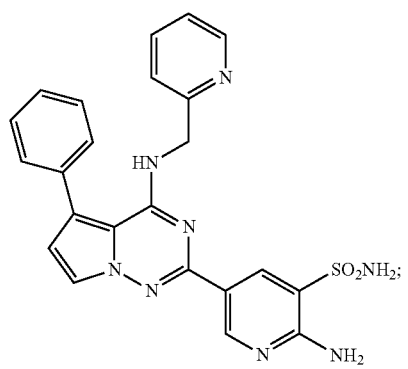
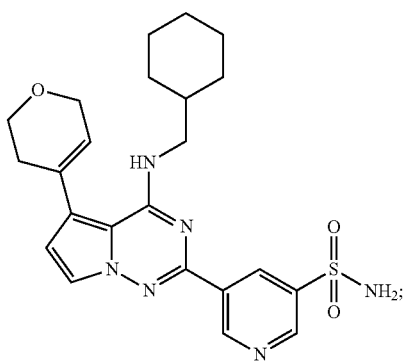
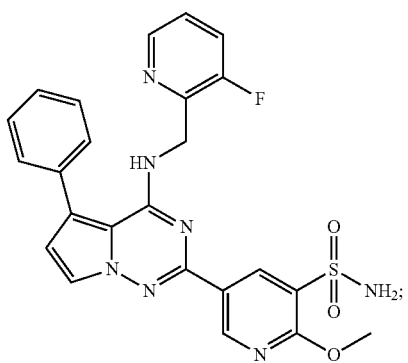
266
-continued
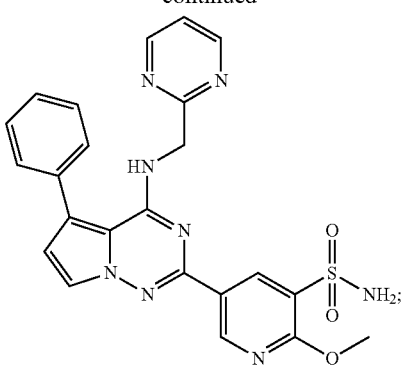
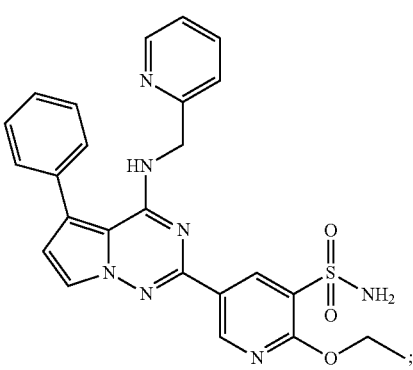
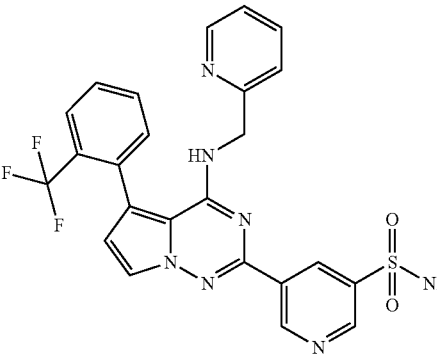
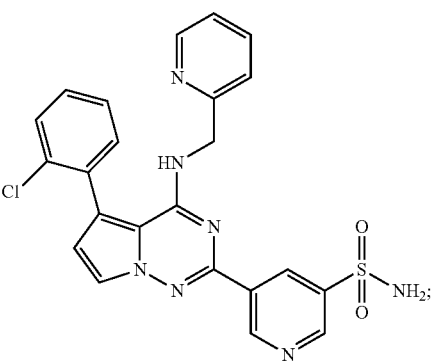

267
-continued
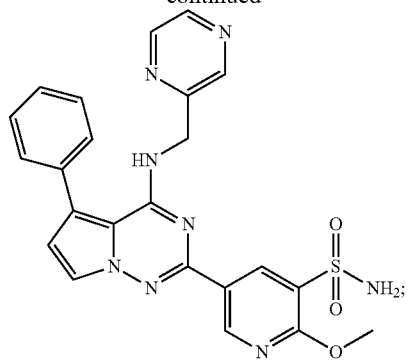
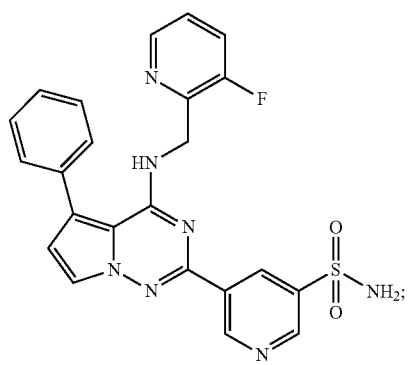
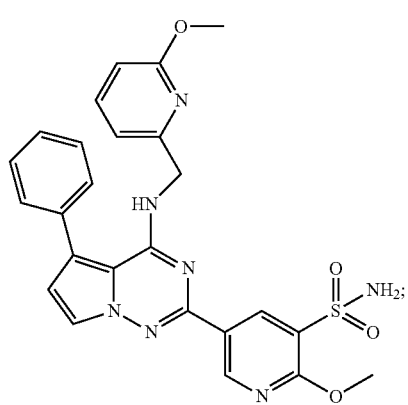
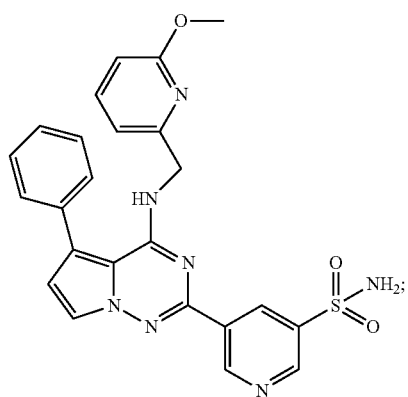
268
-continued
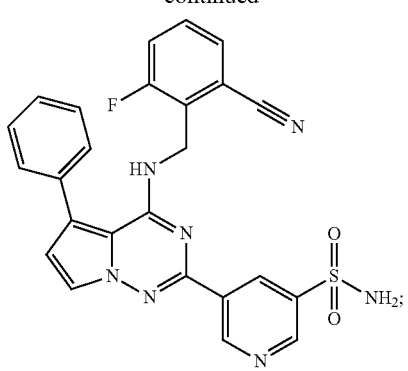
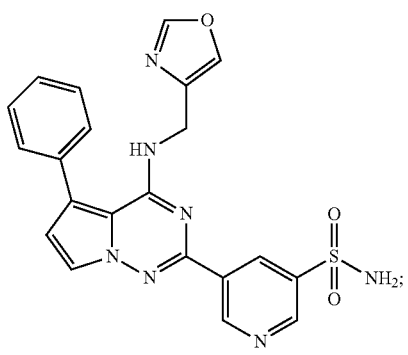
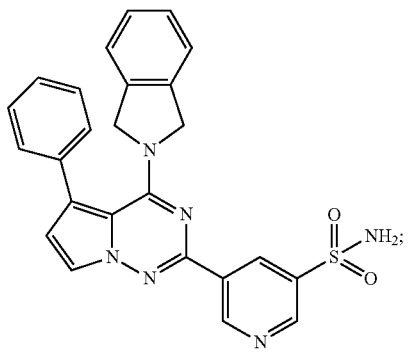
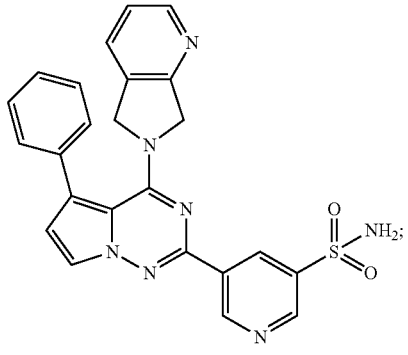

269
-continued
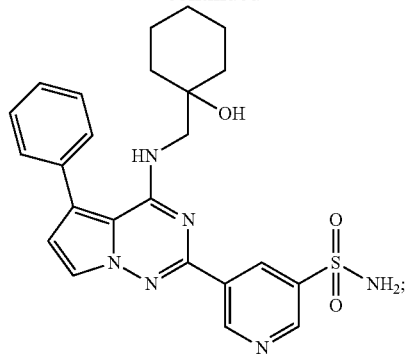
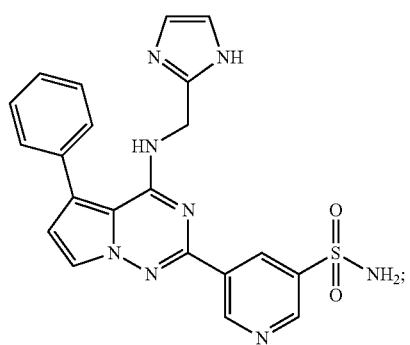
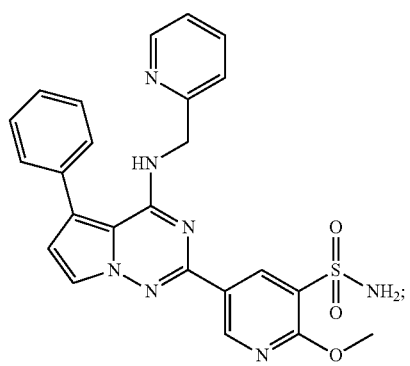
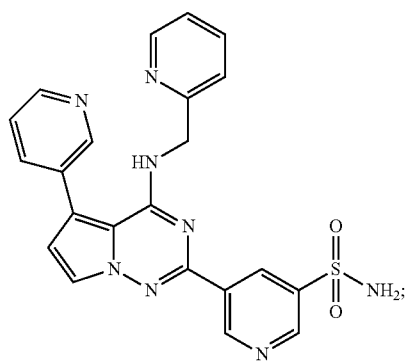
270
-continued
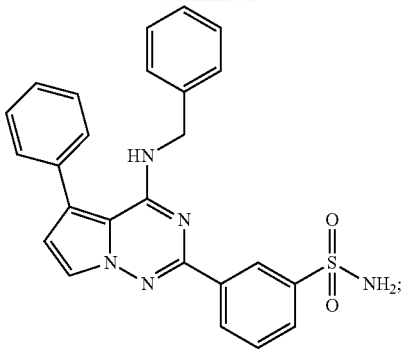
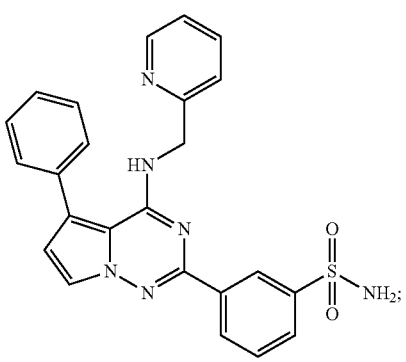
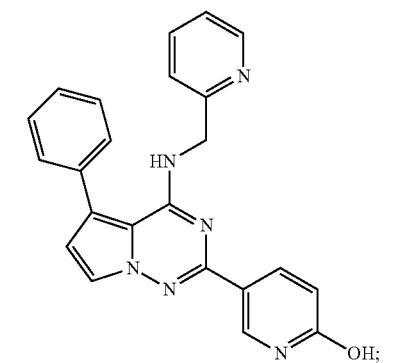
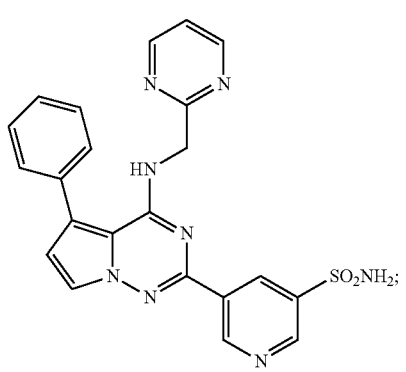

-continued
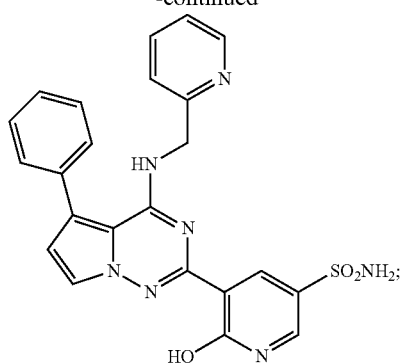
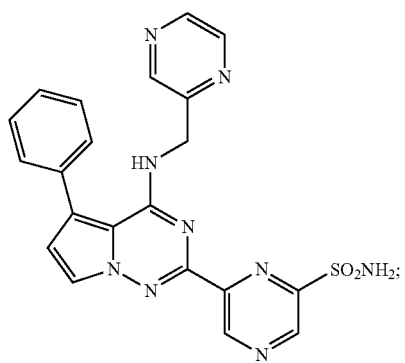
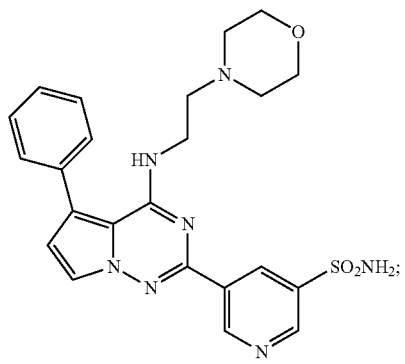
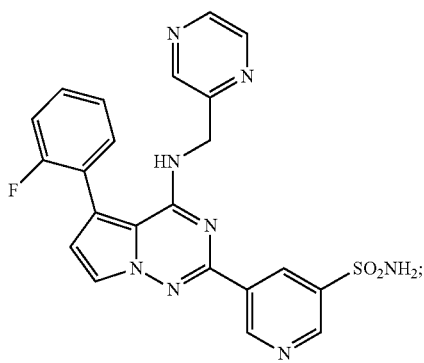
-continued
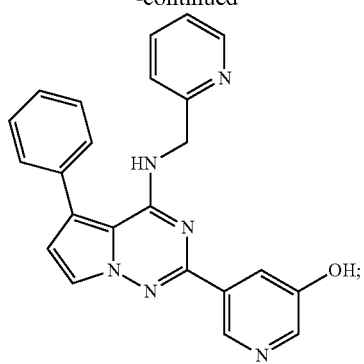
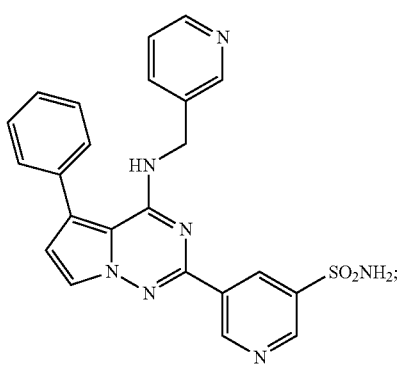
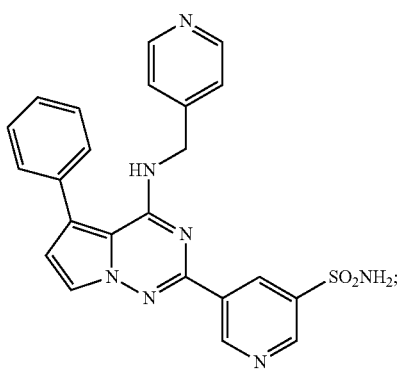
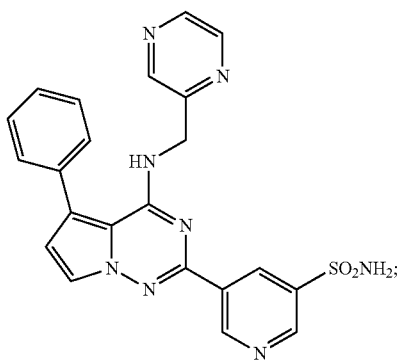

273
-continued
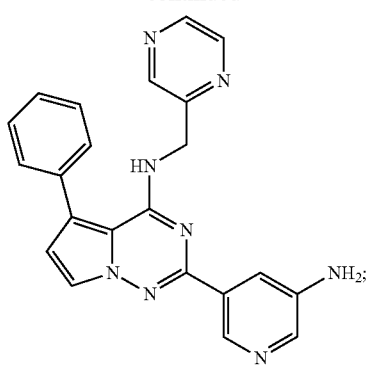
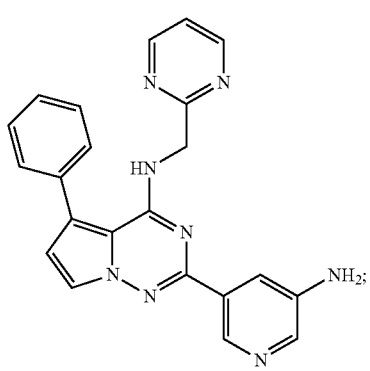
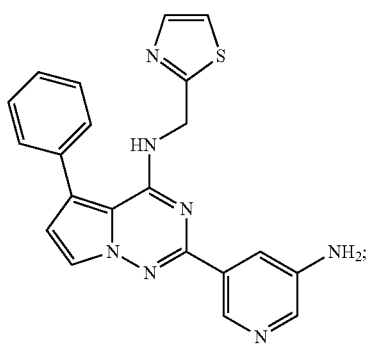
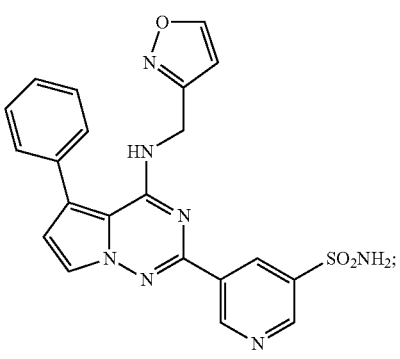
274
-continued
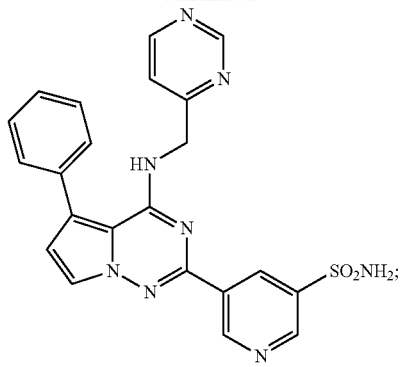
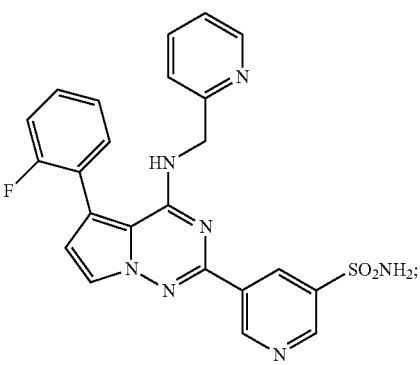
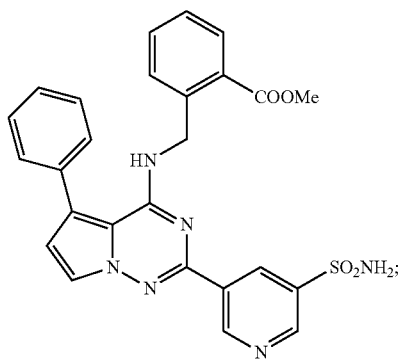
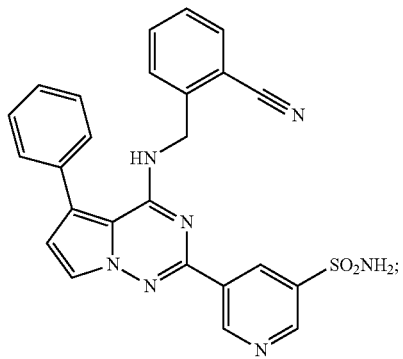

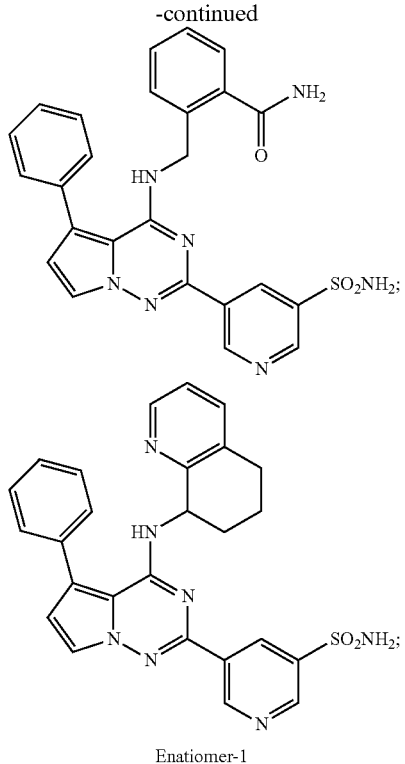
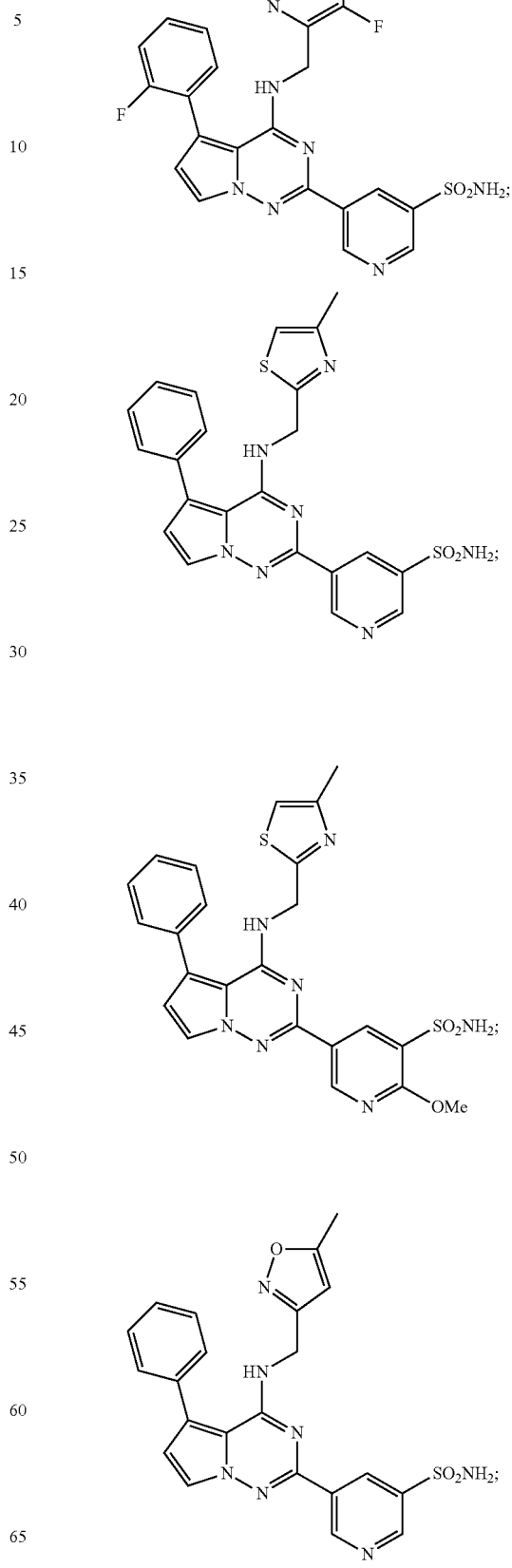

277
-continued
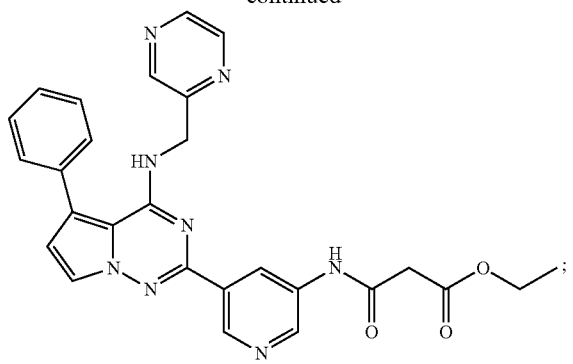
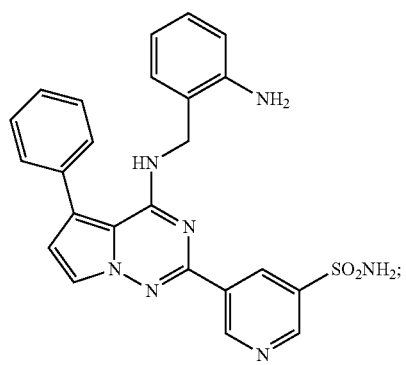
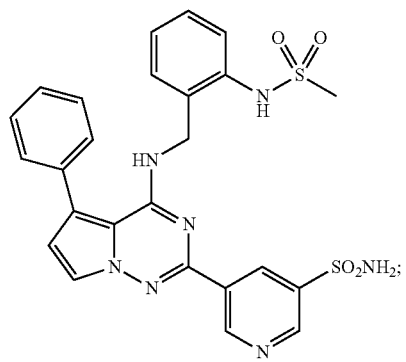
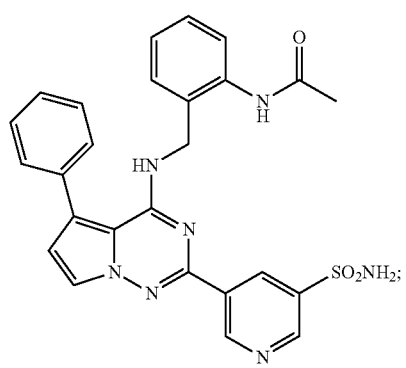
278
-continued
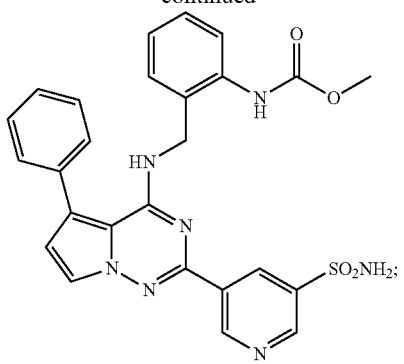
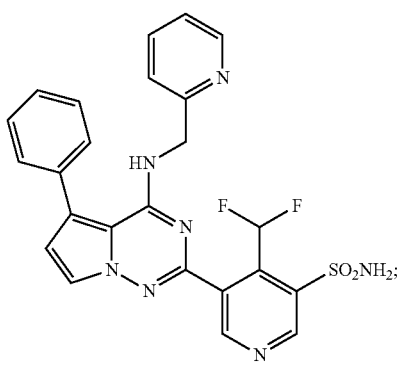
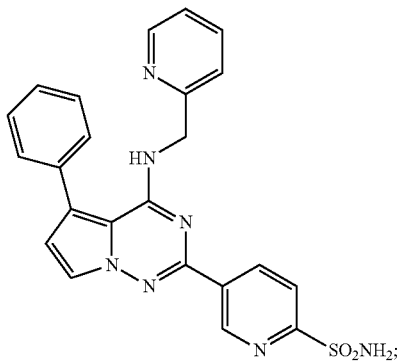
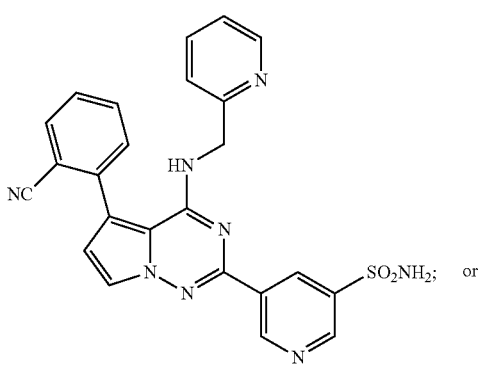 or -continued

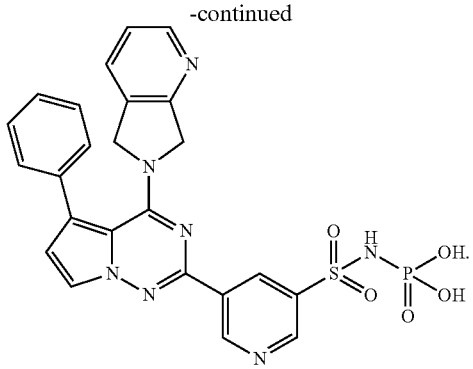

12. A pharmaceutical composition comprising a therapeutically effective amount of one or more compound of claim 1.

13. The pharmaceutical composition of claim 12, further comprising at least one other therapeutic agent.

14. A method of treating arrhythmia comprising administering to a patient in need thereof an effective amount of one or more compound of claim 1.

15. A method of controlling heart rate comprising administering to a patient in need thereof an effective amount of one or more compound of claim 1.

16. A pharmaceutical composition comprising a therapeutically effective amount of one or more compound of claim 11.

17. The pharmaceutical composition of claim 16, further comprising at least one other therapeutic agent.

18. A method of treating arrhythmia comprising administering to a patient in need thereof an effective amount of one or more compound of claim 11.

19. A method of controlling heart rate comprising administering to a patient in need thereof an effective amount of one or more compound of claim 11.

* * * * *